US007615379B2

(12) United States Patent
Raitano et al.

(10) Patent No.: US 7,615,379 B2
(45) **Date of Patent: *Nov. 10, 2009**

(54) NUCLEIC ACID AND CORRESPONDING PROTEIN ENTITLED 193P1E1B USEFUL IN TREATMENT AND DETECTION OF CANCER

(75) Inventors: Arthur B. Raitano, Los Angeles, CA (US); Pia M. Challita-Eid, Encino, CA (US); Mary Faris, Los Angeles, CA (US); Rene S. Hubert, Los Angeles, CA (US); Wangmao Ge, Culver City, CA (US); Aya Jakobovits, Beverly Hills, CA (US)

(73) Assignee: Agensys, Inc., Santa Monica, CA (US)

( * ) Notice: Subject to any disclaimer, the term of this patent is extended or adjusted under 35 U.S.C. 154(b) by 437 days.

This patent is subject to a terminal disclaimer.

(21) Appl. No.: 10/313,972

(22) Filed: Dec. 6, 2002

(65) Prior Publication Data

US 2004/0102407 A1 May 27, 2004

(51) Int. Cl.
*G01N 33/4844* (2006.01)

(52) U.S. Cl. ...................... 436/501; 436/518; 435/7.23

(58) Field of Classification Search ...................... None
See application file for complete search history.

(56) References Cited

U.S. PATENT DOCUMENTS 5,643,778 A * 7/1997 Nishikura ................... 435/227
5,840,839 A 11/1998 Wang et al.

FOREIGN PATENT DOCUMENTS

| | | |
|---|---|---|
| EP | 1 308 459 | 5/2003 |
| WO | WO98/39446 A2 | 9/1998 |
| WO | WO98/45435 A2 | 10/1998 |
| WO | WO99/06548 A2 | 2/1999 |
| WO | WO99/31236 A2 | 6/1999 |
| WO | WO99/38972 A2 | 8/1999 |
| WO | WO99/58675 A2 | 11/1999 |
| WO | WO00/18916 A2 | 4/2000 |
| WO | WO00/21991 A1 | 4/2000 |
| WO | WO-01/12811 | 2/2001 |
| WO | WO01/22920 A2 | 4/2001 |
| WO | WO01/42302 A1 | 6/2001 |
| WO | WO01/42451 A2 | 6/2001 |
| WO | WO01/60860 A2 | 8/2001 |
| WO | WO-01/90157 | 11/2001 |
| WO | WO02/29086 A2 | 4/2002 |
| WO | WO02/40718 A2 | 5/2002 |
| WO | WO02/48337 A2 | 6/2002 |
| WO | WO02/074961 | 9/2002 |
| WO | WO02/085298 | 10/2002 |
| WO | WO-2004/028479 | 4/2004 |

OTHER PUBLICATIONS

Thai et al., (Adv Immunol. 2005;86:113-36, abstract only).*
Greenbaum et al. (Genome Biology, 2003, vol. 4, Issue 9, pp. 117.1-117.8).*
You et al., Neoplasia. Jun. 2007; 9(6): 464-470.*
Alberts et al., Molecular Biology of the Cell, 3rd Edition (1994) p. 465.
Boon, Adv. Can. Res. (1992) 58:177-210.
Bork, Genome Research (2000) 10:398-400.
Bork et al., Trends in Genetics (1996) 12:425-427.
Bowie et al., Science (1990) 247:1306-1310.
Brenner, Trends in Genetics (1999) 15:132-133.
Broder et al., Curr. Opin. Biotechnol. (2000) 11(6):581-585.
Bussenmakers et al., Cancer Res. (1999) 59:5975-5979.
Curti, Crit. Rev. in Oncology/Hematology (1993) 14:29-39.
Doerks et al., Trends in Genetics (1998) 14:248-250.
Ezzell, J. NIH Res. (1995) 7:46-49.
Fu et al., EMBO Journal (1996) 15:4392-4401.
Gura, Science (1997) 278:1041-1042.
Jain, Sci. Am. (1994) 271:58-65.
Lauritzsen et al., International Journal of Cancer (1998) 78:216-222.
McClean and Hill, Eur. J. of Cancer (1993) 29A:2243-2248.
NCBI Accession No. BC013418 (Sep. 4, 2001).
Sarma et al., Journal of Experimental Medicine (1999) 189:811-820.
Scott et al., Nature Genetics (1999) 21:440-443.
Shantz and Pegg, Int. J. of Biochem. and Cell Biol. (1999) 31:107-122.
Sherman et al., Critical Reviews in Immunol. (1998) 18(1-2):47-54.
Skolnick et al., Trends in Biotech. (2000) 18:34-39.
Smith et al., Nature Biotechnology (1997) 15:1222-1223.
Spitler, Cancer Biotherapy (1995) 10:1-3.
Wang et al., J. Biol. Chem. (1997) 272(35):22227-22235.
Benjamini and Leskowitz, Immunology: A Short Course, Second Edition, John Wiley & Sons, Inc. (1993) Ch. 3, pp. 37-45.
International Search Report for PCT/US02/39274, mailed on Oct. 6, 2004, 3 pages.
Ota et al., Nat. Genet. (2004) 36(1):40-45.
Shibata et al., Genome Res. (2000) 10(11):1757-1771.
Database EMBL, EBI accession No. EMBL:BC013418 (2001).
Database EMBL, EBI accession No. EMBL:BG392826 (2001).
Database EMBL, EBI accession No. EMBL:AL561096 (2001).
Database EMBL, EBI accession No. EMBL:AL519504 (2001).
Database EMBL, EBI accession No. EMBL:AK090584 (2002).
Supplementary Partial European Search Report for EP 02797238.9, mailed Oct. 12, 2007, 7 pages.
Hubert et al., PNAS USA (1999) 96(25):14523-14528.
Japanese Office Action for Application No. 2003-551277, mailed on Feb. 15, 2008, 7 pages.
Klein et al., Nature Medicine (1997) 3(4):402-408.
Office Action for European Patent Application No. EP 02 797 238.9, mailed on Jun. 13, 2008, 11 pages.

* cited by examiner

*Primary Examiner*—Misook Yu
(74) *Attorney, Agent, or Firm*—Morrison & Foerster LLP

(57) ABSTRACT

A novel gene 0193P1E1B (also designated 193P1E1B) and its encoded protein, and variants thereof, are described wherein 193P1E1B exhibits tissue specific expression in normal adult tissue, and is aberrantly expressed in the cancers listed in Table I. Consequently, 193P1E1B provides a diagnostic, prognostic, prophylactic and/or therapeutic target for cancer. The 193P1E1B gene or fragment thereof, or its encoded protein, or variants thereof, or a fragment thereof, can be used to elicit a humoral or cellular immune response; antibodies or T cells reactive with 193P1E1B can be used in active or passive immunization.

2 Claims, 49 Drawing Sheets

FIGURE 1: 193P1E1B SSH SEQUENCE OF 227 NUCLEOTIDES (SEQ ID NO: 1)

```
  1 GATCCACTGG AATTTCAGTT TTCTTTGTTG CTGACATCTC GGATGTTCTG TCCATGTTTA
 61 GGGAACCTTT TACTGGGTGG CACTGCTTTA ATTGCTATTG GAGTAGCTAG GTTTGAGTTG
121 TATTTTGATA GAAGCTGGAG AATATCTTCT GGAATTTTAG TTACTTCTGG AGGGGGNAGG
181 TTCTGAGCAG ATTCTCATAA GAAGAAATCG TAGGTGAAAG AGGGATC
```

Figure 2:

Figure 2A. The cDNA (SEQ ID NO: 2) and amino acid sequence (SEQ ID NO: 3) of 193P1E1B v.1. The start methionine is underlined. The open reading frame extends from nucleic acid 805-2043 including the stop codon.

```
   1 tatcatctgtgactgaggaaatccctatcttcctatcagactaatgaaaccacaggacag
  61 caattagacttttaagtattgggggtttagagctctagatattcgatatgcagactact
 121 catgtttgtttgttttaataaagactggtccaaaggctcattttcacacaagctacagtt
 181 tttcagttccaggaccaggtaaagatggtcagctccgtgatccataaaatccaagggtga
 241 cgactcaggattaggaccatttcttggtgacattgagatggtcgagctggtccgcaatga
 301 atctatgcgggggaacttggaagtggcggccgcctttatggcctcgaaggcctccctcc
 361 tgcgcaccgcggcgtggccgcgctcctgctcccgggtcatgtagggcatgctcagccagt
 421 aatggttctccgcctcgatctccaggcggcggatcatgttctgcttggcgcgcaacgaca
 481 cgaaccgcggccgccggtgcttcccgatccactgacggccgggaatgcggccgcgccaga
 541 ggagcgcagtcaggaacatggtgcctgccgcgctgctcaagactctgcgtctccgcggcc
 601 gccagcagacgccgtggcgtaagcgcacccgtctcgcggggtctccgggggcctcggcga
 661 gagacttcggctctcgcgagagaggactgcgcctgcgcagagccgaggacgcgtccggcg
 721 ccgagattcaaactagtggcgggaggctgtgagctgagcggtggggtctgcgtacgcctg
   1                          M  D  P  I  R  S  F  C  G  K  L  R
 781 gagtccttccccgctgtgctcagcATGGACCCTATCCGGAGCTTCTGCGGGAAGCTGCGG
  13 S  L  A  S  T  L  D  C  E  T  A  R  L  Q  R  A  L  D  G  E
 841 TCTCTGGCCAGCACGCTGGACTGCGAGACGGCCCGGCTGCAGCGAGCGCTGGACGGAGAG
  33 E  S  D  F  E  D  Y  P  M  R  I  L  Y  D  L  H  S  E  V  Q
 901 GAAAGCGACTTTGAAGATTATCCAATGAGAATTTTATATGACCTTCATTCAGAAGTTCAG
  53 T  L  K  D  D  V  N  I  L  L  D  K  A  R  L  E  N  Q  E  G
 961 ACTCTAAAGGATGATGTTAATATTCTTCTTGATAAAGCAAGATTGGAAAATCAAGAAGGC
  73 I  D  F  I  K  A  T  K  V  L  M  E  K  N  S  M  D  I  M  K
1021 ATTGATTTCATAAAGGCAACAAAAGTACTAATGGAAAAAAATTCAATGGATATTATGAAA
  93 I  R  E  Y  F  Q  K  Y  G  Y  S  P  R  V  K  K  N  S  V  H
1081 ATAAGAGAGTATTTCCAGAAGTATGGATATAGTCCACGTGTCAAGAAAAATTCAGTACAC
 113 E  Q  E  A  I  N  S  D  P  E  L  S  N  C  E  N  F  Q  K  T
1141 GAGCAAGAAGCCATTAACTCTGACCCAGAGTTGTCTAATTGTGAAAATTTTCAGAAGACT
 133 D  V  K  D  D  L  S  D  P  P  V  A  S  S  C  I  S  E  K  S
1201 GATGTGAAAGATGATCTGTCTGATCCTCCTGTTGCAAGCAGTTGTATTTCTGAGAAGTCT
 153 P  R  S  P  Q  L  S  D  F  G  L  E  R  Y  I  V  S  Q  V  L
1261 CCACGTAGTCCACAACTTTCAGATTTTGGACTTGAGCGGTACATCGTATCCCAAGTTCTA
 173 P  N  P  P  Q  A  V  N  N  Y  K  E  E  P  V  I  V  T  P  P
1321 CCAAACCCTCCACAGGCAGTGAACAACTATAAGGAAGAGCCCGTAATTGTAACCCCACCT
 193 T  K  Q  S  L  V  K  V  L  K  T  P  K  C  A  L  K  M  D  D
1381 ACCAAACAATCACTAGTAAAAGTACTAAAAACTCCAAAATGTGCACTAAAAATGGATGAT
 213 F  E  C  V  T  P  K  L  E  H  F  G  I  S  E  Y  T  M  C  L
1441 TTTGAGTGTGTAACTCCTAAATTAGAACACTTTGGTATCTCTGAATATACTATGTGTTTA
 233 N  E  D  Y  T  M  G  L  K  N  A  R  N  N  K  S  E  E  A  I
```

Figure 2A-2

```
1501 AATGAAGATTACACAATGGGACTTAAAAATGCGAGGAATAATAAAAGTGAGGAGGCCATA
 253 D  T  E  S  R  L  N  D  N  V  F  A  T  P  S  P  I  I  Q  Q
1561 GATACAGAATCCAGGCTCAATGATAATGTTTTTGCCACTCCCAGCCCCATCATCCAGCAG
 273 L  E  K  S  D  A  E  Y  T  N  S  P  L  V  P  T  F  C  T  P
1621 TTGGAAAAAAGTGATGCCGAATATACCAACTCTCCTTTGGTACCTACATTCTGTACTCCT
 293 G  L  K  I  P  S  T  K  N  S  I  A  L  V  S  T  N  Y  P  L
1681 GGTTTGAAAATTCCATCTACAAAGAACAGCATAGCTTTGGTATCCACAAATTACCCATTA
 313 S  K  T  N  S  S  S  N  D  L  E  V  E  D  R  T  S  L  V  L
1741 TCAAAAACAAATAGTTCATCAAATGATTTGGAAGTTGAAGATCGTACTTCGTTGGTTTTA
 333 N  S  D  T  C  F  E  N  L  T  D  P  S  S  P  T  I  S  S  Y
1801 AATTCAGACACATGCTTTGAGAATTTAACAGATCCCTCTTCACCTACGATTTCTTCTTAT
 353 E  N  L  L  R  T  P  T  P  P  E  V  T  K  I  P  E  D  I  L
1861 GAGAATCTGCTCAGAACACCTACACCTCCAGAAGTAACTAAAATTCCAGAAGATATTCTC
 373 Q  L  L  S  K  Y  N  S  N  L  A  T  P  I  A  I  K  A  V  P
1921 CAGCTTTTATCAAAATACAACTCAAACCTAGCTACTCCAATAGCAATTAAAGCAGTGCCA
 393 P  S  K  R  F  L  K  H  G  Q  N  I  R  D  V  S  N  K  E  N
1981 CCCAGTAAAAGGTTCCTTAAACATGGACAGAACATCCGAGATGTCAGCAACAAAGAAAAC
 413 *
2041 TGAaattccagtggatctatccaacacagaaactgaacaaaatgagatgaaagccgagct
2101 ggaccgattttaacattcacattgccctgcctctgtccccctttaaacgttgacccattt
2161 taaagacaaacatgaacattaacatcataatatgctttttatgaagtttcaataaggttt
2221 aaccttagtcttgttgacatgtagcccagtcattcactctttaaggactattagtgtttc
2281 attgatactaaattacccagcttaatcaacagaatggtttaagtagtaccaggaagtagg
2341 acaagtaatttcaaaaatataaaggtgtttgctactcagatgaggccgcccctgaccttc
2401 tggccagagagacattgctgccagccagctctgccttcccatcatctcctttcaggaccg
2461 tcccacaccttttacttgctcagtgctgtctgaagatgcagttgctgtttgcaaacaaca
2521 ggaacaccagttaaactaattaggaaacagagggagatttccaggcctgggtaactatat
2581 actgtgaccattggcggttgagaccggtcttcaaccagtggaaccccgaactctgctgtc
2641 agggtgtggacttcggtgctcttccaagttttcacctgggggggggagctaacccccctat
2701 gttcacgccttctattcccattggcgctgaactcttaaggtcactctggtcgcttgtgac
2761 cccgtaaccctgatgtacccctctaaaaggtgaggggc
```

Figure 2B. The cDNA (SEQ ID NO: 4) and amino acid sequence (SEQ ID NO: 5) of 193P1E1B v.2. The start methionine is underlined. The open reading frame extends from nucleic acid 805-2043 including the stop codon.

```
  1 tatcatctgtgactgaggaaatccctatcttcctatcagactaatgaaaccacagggcag
 61 caattagacttttaagtattggggggtttagagctctagatattcgatatgcagactact
121 catgtttgtttgttttaataaagactggtccaaaggctcattttcacacaagctacagtt
181 tttcagttccaggaccaggtaaagatggtcagctccgtgatccataaaatccaagggtga
```

Figure 2B-2

```
 241 cgactcaggattaggaccatttcttggtgacattgagatggtcgagctggtccgcaatga
 301 atctatgcgggggaacttggaagtggcggccgcctttatggcctcgaaggcctccctcc
 361 tgcgcaccgcggcgtggccgcgctcctgctcccgggtcatgtagggcatgctcagccagt
 421 aatggttctccgcctcgatctccaggcggcggatcatgttctgcttggcgcgcaacgaca
 481 cgaaccgcggccgccggtgcttcccgatccactgacggccgggaatgcggccgcgccaga
 541 ggagcgcagtcaggaacatggtgcctgccgcgctgctcaagactctgcgtctccgcggcc
 601 gccagcagacgccgtggcgtaagcgcacccgtctcgcggggtctccgggggcctcggcga
 661 gagacttcggctctcgcgagagaggactgcgcctgcgcagagccgaggacgcgtccggcg
 721 ccgagattcaaactagtggcgggaggctgtgagctgagcggtggggtctgcgtacgcctg
   1                            M  D  P  I  R  S  F  C  G  K  L  R
 781 gagtccttccccgctgtgctcagcATGGACCCTATCCGGAGCTTCTGCGGGAAGCTGCGG
  13 S  L  A  S  T  L  D  C  E  T  A  R  L  Q  R  A  L  D  G  E
 841 TCTCTGGCCAGCACGCTGGACTGCGAGACGGCCCGGCTGCAGCGAGCGCTGGACGGAGAG
  33 E  S  D  F  E  D  Y  P  M  R  I  L  Y  D  L  H  S  E  V  Q
 901 GAAAGCGACTTTGAAGATTATCCAATGAGAATTTTATATGACCTTCATTCAGAAGTTCAG
  53 T  L  K  D  D  V  N  I  L  L  D  K  A  R  L  E  N  Q  E  G
 961 ACTCTAAAGGATGATGTTAATATTCTTCTTGATAAAGCAAGATTGGAAAATCAAGAAGGC
  73 I  D  F  I  K  A  T  K  V  L  M  E  K  N  S  M  D  I  M  K
1021 ATTGATTTCATAAAGGCAACAAAAGTACTAATGGAAAAAAATTCAATGGATATTATGAAA
  93 I  R  E  Y  F  Q  K  Y  G  Y  S  P  R  V  K  K  N  S  V  H
1081 ATAAGAGAGTATTTCCAGAAGTATGGATATAGTCCACGTGTCAAGAAAAATTCAGTACAC
 113 E  Q  E  A  I  N  S  D  P  E  L  S  N  C  E  N  F  Q  K  T
1141 GAGCAAGAAGCCATTAACTCTGACCCAGAGTTGTCTAATTGTGAAAATTTTCAGAAGACT
 133 D  V  K  D  D  L  S  D  P  P  V  A  S  S  C  I  S  E  K  S
1201 GATGTGAAAGATGATCTGTCTGATCCTCCTGTTGCAAGCAGTTGTATTTCTGAGAAGTCT
 153 P  R  S  P  Q  L  S  D  F  G  L  E  R  Y  I  V  S  Q  V  L
1261 CCACGTAGTCCACAACTTTCAGATTTTGGACTTGAGCGGTACATCGTATCCCAAGTTCTA
 173 P  N  P  P  Q  A  V  N  N  Y  K  E  E  P  V  I  V  T  P  P
1321 CCAAACCCTCCACAGGCAGTGAACAACTATAAGGAAGAGCCCGTAATTGTAACCCCACCT
 193 T  K  Q  S  L  V  K  V  L  K  T  P  K  C  A  L  K  M  D  D
1381 ACCAAACAATCACTAGTAAAAGTACTAAAAACTCCAAAATGTGCACTAAAAATGGATGAT
 213 F  E  C  V  T  P  K  L  E  H  F  G  I  S  E  Y  T  M  C  L
1441 TTTGAGTGTGTAACTCCTAAATTAGAACACTTTGGTATCTCTGAATATACTATGTGTTTA
 233 N  E  D  Y  T  M  G  L  K  N  A  R  N  N  K  S  E  E  A  I
1501 AATGAAGATTACACAATGGGACTTAAAAATGCGAGGAATAATAAAAGTGAGGAGGCCATA
 253 D  T  E  S  R  L  N  D  N  V  F  A  T  P  S  P  I  I  Q  Q
1561 GATACAGAATCCAGGCTCAATGATAATGTTTTTGCCACTCCCAGCCCCATCATCCAGCAG
 273 L  E  K  S  D  A  E  Y  T  N  S  P  L  V  P  T  F  C  T  P
1621 TTGGAAAAAAGTGATGCCGAATATACCAACTCTCCTTTGGTACCTACATTCTGTACTCCT
 293 G  L  K  I  P  S  T  K  N  S  I  A  L  V  S  T  N  Y  P  L
1681 GGTTTGAAAATTCCATCTACAAAGAACAGCATAGCTTTGGTATCCACAAATTACCCATTA
```

Figure 2B-3

```
 313 S  K  T  N  S  S  S  N  D  L  E  V  E  D  R  T  S  L  V  L
1741 TCAAAAACAAATAGTTCATCAAATGATTTGGAAGTTGAAGATCGTACTTCGTTGGTTTTA
 333 N  S  D  T  C  F  E  N  L  T  D  P  S  S  P  T  I  S  S  Y
1801 AATTCAGACACATGCTTTGAGAATTTAACAGATCCCTCTTCACCTACGATTTCTTCTTAT
 353 E  N  L  L  R  T  P  T  P  P  E  V  T  K  I  P  E  D  I  L
1861 GAGAATCTGCTCAGAACACCTACACCTCCAGAAGTAACTAAAATTCCAGAAGATATTCTC
 373 Q  L  L  S  K  Y  N  S  N  L  A  T  P  I  A  I  K  A  V  P
1921 CAGCTTTTATCAAAATACAACTCAAACCTAGCTACTCCAATAGCAATTAAAGCAGTGCCA
 393 P  S  K  R  F  L  K  H  G  Q  N  I  R  D  V  S  N  K  E  N
1981 CCCAGTAAAAGGTTCCTTAAACATGGACAGAACATCCGAGATGTCAGCAACAAAGAAAAC
 413 *
2041 TGAaattccagtggatctatccaacacagaaactgaacaaaatgagatgaaagccgagct
2101 ggaccgattttaacattcacattgccctgcctctgtccccctttaaacgttgacccattt
2161 taaagacaaacatgaacattaacatcataatatgctttttatgaagtttcaataaggttt
2221 aaccttagtcttgttgacatgtagcccagtcattcactctttaaggactattagtgtttc
2281 attgatactaaattacccagcttaatcaacagaatggtttaagtagtaccaggaagtagg
2341 acaagtaatttcaaaaatataaaggtgtttgctactcagatgaggccgcccctgaccttc
2401 tggccagagagacattgctgccagccagctctgccttcccatcatctcctttcaggaccg
2461 tcccacaccttttacttgctcagtgctgtctgaagatgcagttgctgtttgcaaacaaca
2521 ggaacaccagttaaactaattaggaaacagagggagatttccaggcctgggtaactatat
2581 actgtgaccattggcggttgagaccggtcttcaaccagtggaaccccgaactctgctgtc
2641 agggtgtggacttcggtgctcttccaagttttcacctgggggggggagctaaccccctat
2701 gttcacgccttctattcccattggcgctgaactcttaaggtcactctggtcgcttgtgac
2761 cccgtaaccctgatgtacccctctaaaaggtgaggggc
```

Figure 2C. The cDNA (SEQ ID NO: 6) and amino acid sequence (SEQ ID NO: 7) of 193P1E1B v.3. The start methionine is underlined. The open reading frame extends from nucleic acid 805-2043 including the stop codon.

```
   1 tatcatctgtgactgaggaaatccctatcttcctatcagactaatgaaaccacaggacag
  61 caattagacttttaagtattgggggtttagagctctagatattcgatatgcagactact
 121 catgtttgtttgttttaataaagactggtccaaaggctcattttcacacaagctacagtt
 181 tttcagttccaggaccaggtaaagatggtcagctccgtgatccataaaatccaagggtga
 241 cgactcaggattaggaccatttcttggtgacattgagatggtcgagctggtccgcaatga
 301 atctatgcgggggggaacttggaagtggcggccgcctttatggcctcgaaggcctccctcc
 361 tgcgcaccgcggcgtggccgcgctcctgctcccgggtcatgtagggcatgctcagccagt
 421 aatggttctccgcctcgatctccaggcggcggatcatgttctgcttggcgcgcaacgaca
 481 cgaaccgcggccgccggtgcttcccgatccactgacggccgggaatgcggccgcgccaga
 541 ggagcgcagtcaggaacatggtgcctgccgcgctgctcaagactctgcgtctccgcggcc
 601 gccagcagacgccgtggcgtaagcgcacccgtctcgcggggtctccgggggcctcggcga
 661 gagacttcggctctcgcgagagaggactgcgcctgcgcagagccgaggacgcgtccggcg
```

Figure 2C-2

```
 721 ccgagattcaaactagtggcgggaggctgtgagctgagcggtggggtctgcgtacgcctg
   1                               M  D  P  I  R  S  F  C  G  K  L  R
 781 gagtccttcccggctgtgctcagcATGGACCCTATCCGGAGCTTCTGCGGGAAGCTGCGG
  13 S  L  A  S  T  L  D  C  E  T  A  R  L  Q  R  A  L  D  G  E
 841 TCTCTGGCCAGCACGCTGGACTGCGAGACGGCCCGGCTGCAGCGAGCGCTGGACGGAGAG
  33 E  S  D  F  E  D  Y  P  M  R  I  L  Y  D  L  H  S  E  V  Q
 901 GAAAGCGACTTTGAAGATTATCCAATGAGAATTTTATATGACCTTCATTCAGAAGTTCAG
  53 T  L  K  D  D  V  N  I  L  L  D  K  A  R  L  E  N  Q  E  G
 961 ACTCTAAAGGATGATGTTAATATTCTTCTTGATAAAGCAAGATTGGAAAATCAAGAAGGC
  73 I  D  F  I  K  A  T  K  V  L  M  E  K  N  S  M  D  I  M  K
1021 ATTGATTTCATAAAGGCAACAAAAGTACTAATGGAAAAAAATTCAATGGATATTATGAAA
  93 I  R  E  Y  F  Q  K  Y  G  Y  S  P  R  V  K  K  N  S  V  H
1081 ATAAGAGAGTATTTCCAGAAGTATGGATATAGTCCACGTGTCAAGAAAAATTCAGTACAC
 113 E  Q  E  A  I  N  S  D  P  E  L  S  N  C  E  N  F  Q  K  T
1141 GAGCAAGAAGCCATTAACTCTGACCCAGAGTTGTCTAATTGTGAAAATTTTCAGAAGACT
 133 D  V  K  D  D  L  S  D  P  P  V  A  S  S  C  I  S  E  K  S
1201 GATGTGAAAGATGATCTGTCTGATCCTCCTGTTGCAAGCAGTTGTATTTCTGAGAAGTCT
 153 P  R  S  P  Q  L  S  D  F  G  L  E  R  Y  I  V  S  Q  V  L
1261 CCACGTAGTCCACAACTTTCAGATTTTGGACTTGAGCGGTACATCGTATCCCAAGTTCTA
 173 P  N  P  P  Q  A  V  N  N  Y  K  E  E  P  V  I  V  T  P  P
1321 CCAAACCCTCCACAGGCAGTGAACAACTATAAGGAAGAGCCCGTAATTGTAACCCCACCT
 193 T  K  Q  S  L  V  K  V  L  K  T  P  K  C  A  L  K  M  D  D
1381 ACCAAACAATCACTAGTAAAAGTACTAAAAACTCCAAAATGTGCACTAAAAATGGATGAT
 213 F  E  C  V  T  P  K  L  E  H  F  G  I  S  E  Y  T  M  C  L
1441 TTTGAGTGTGTAACTCCTAAATTAGAACACTTTGGTATCTCTGAATATACTATGTGTTTA
 233 N  E  D  Y  T  M  G  L  K  N  A  R  N  N  K  S  E  E  A  I
1501 AATGAAGATTACACAATGGGACTTAAAAATGCGAGGAATAATAAAAGTGAGGAGGCCATA
 253 D  T  E  S  R  L  N  D  N  V  F  A  T  P  S  P  I  I  Q  Q
1561 GATACAGAATCCAGGCTCAATGATAATGTTTTTGCCACTCCCAGCCCCATCATCCAGCAG
 273 L  E  K  S  D  A  E  Y  T  N  S  P  L  V  P  T  F  C  T  P
1621 TTGGAAAAAAGTGATGCCGAATATACCAACTCTCCTTTGGTACCTACATTCTGTACTCCT
 293 G  L  K  I  P  S  T  K  N  S  I  A  L  V  S  T  N  Y  P  L
1681 GGTTTGAAAATTCCATCTACAAAGAACAGCATAGCTTTGGTATCCACAAATTACCCATTA
 313 S  K  T  N  S  S  S  N  D  L  E  V  E  D  R  T  S  L  V  L
1741 TCAAAAACAAATAGTTCATCAAATGATTTGGAAGTTGAAGATCGTACTTCGTTGGTTTTA
 333 N  S  D  T  C  F  E  N  L  T  D  P  S  S  P  T  I  S  S  Y
1801 AATTCAGACACATGCTTTGAGAATTTAACAGATCCCTCTTCACCTACGATTTCTTCTTAT
 353 E  N  L  L  R  T  P  T  P  P  E  V  T  K  I  P  E  D  I  L
1861 GAGAATCTGCTCAGAACACCTACACCTCCAGAAGTAACTAAAATTCCAGAAGATATTCTC
 373 Q  L  L  S  K  Y  N  S  N  L  A  T  P  I  A  I  K  A  V  P
1921 CAGCTTTTATCAAAATACAACTCAAACCTAGCTACTCCAATAGCAATTAAAGCAGTGCCA
```

Figure 2C-3

```
 393 P  S  K  R  F  L  K  H  G  Q  N  I  R  D  V  S  N  K  E  N
1981 CCCAGTAAAAGGTTCCTTAAACATGGACAGAACATCCGAGATGTCAGCAACAAAGAAAAC
 413 *
2041 TGAaattccagtggatctatccaacacagaaactgaacaaaatgagatgaaagccgagct
2101 ggaccgattttaacattcacattgccctgcctctgtcccccttaaacgttgacccattt
2161 taaagacaaacatgaacattaacatcataatatgctttttatgaagtttcaataaggttt
2221 aaccttagtcttgttgacatgtagcccagtcattcactctttaaggactattagtgtttc
2281 attgatactaaattacccagcttaatcaacagaatggtttaagtagtaccaggaagtagg
2341 acaagtaatttcaaaaatataaaggtgtttgctactcagatgaggccgcccctgaccttc
2401 tggccagagagacattgctgccagccagctctgccttcccatcatctcctttcaggaccg
2461 tcccacacctttttacttgctcagtgctgtctgaagatgcagttgctgtttgcaaacaaca
2521 ggaacaccagttaaactaattaggaaacagagggagatttccaggcctgggtaactatat
2581 actgtgaccattggcggttgagaccggtcttcaaccagtggaaccccgaactctgctgtc
2641 agggtgtggacttcggtgctcttccaagttttcacctgggggggggagctaacccccctat
2701 gttcacgccttctattcccattggcgctgaactcttaaggtcactctggtcgcttgtgac
2761 cccgtaaccctgatgtacccctctaaaaggtgaggggc
```

Figure 2D. The cDNA (SEQ ID NO: 8) and amino acid sequence (SEQ ID NO: 9) of 193P1E1B v.4. The start methionine is underlined. The open reading frame extends from nucleic acid 805-2043 including the stop codon.

```
   1 tatcatctgtgactgaggaaatccctatcttcctatcagactaatgaaaccacaggacag
  61 caattagacttttaagtattgggggggtttagagctctagatattcgatatgcagactact
 121 catgtttgtttgttttaataaagactggtccaaaggctcattttcacacaagctacagtt
 181 tttcagttccaggaccaggtaaagatggtcagctccgtgatccataaaatccaagggtga
 241 cgactcaggattaggaccatttcttggtgacattgagatggtcgagctggtccgcaatga
 301 atctatgcgggggaacttggaagtggcggccgcctttatggcctcgaaggcctccctcc
 361 tgcgcaccgcggcgtggccgcgctcctgctcccgggtcatgtagggcatgctcagccagt
 421 aatggttctccgcctcgatctccaggcggcggatcatgttctgcttggcgcgcaacgaca
 481 cgaaccgcggccgccggtgcttcccgatccactgacggccgggaatgcggccgcgccaga
 541 ggagcgcagtcaggaacatggtgcctgccgcgctgctcaagactctgcgtctccgcggcc
 601 gccagcagacgccgtggcgtaagcgcacccgtctcgcggggtctccgggggcctcggcga
 661 gagacttcggctctcgcgagagaggactgcgcctgcgcagagccgaggacgcgtccggcg
 721 ccgagattcaaactagtggcgggaggctgtgagctgagcggtggggtctgcgtacgcctg
   1                        M  D  P  I  R  S  F  C  G  K  L  R
 781 gagtccttccccgctgtgctcagaATGGACCCTATCCGGAGCTTCTGCGGGAAGCTGCGG
  13 S  L  A  S  T  L  D  C  E  T  A  R  L  Q  R  A  L  D  G  E
 841 TCTCTGGCCAGCACGCTGGACTGCGAGACGGCCCGGCTGCAGCGAGCGCTGGACGGAGAG
  33 E  S  D  F  E  D  Y  P  M  R  I  L  Y  D  L  H  S  E  V  Q
 901 GAAAGCGACTTTGAAGATTATCCAATGAGAATTTTATATGACCTTCATTCAGAAGTTCAG
  53 T  L  K  D  D  V  N  I  L  L  D  K  A  R  L  E  N  Q  E  G
```

Figure 2D-2

```
 961 ACTCTAAAGGATGATGTTAATATTCTTCTTGATAAAGCAAGATTGGAAAATCAAGAAGGC
  73 I  D  F  I  K  A  T  K  V  L  M  E  K  N  S  M  D  I  M  K
1021 ATTGATTTCATAAAGGCAACAAAAGTACTAATGGAAAAAAATTCAATGGATATTATGAAA
  93 I  R  E  Y  F  Q  K  Y  G  Y  S  P  R  V  K  K  N  S  V  H
1081 ATAAGAGAGTATTTCCAGAAGTATGGATATAGTCCACGTGTCAAGAAAAATTCAGTACAC
 113 E  Q  E  A  I  N  S  D  P  E  L  S  N  C  E  N  F  Q  K  T
1141 GAGCAAGAAGCCATTAACTCTGACCCAGAGTTGTCTAATTGTGAAAATTTTCAGAAGACT
 133 D  V  K  D  D  L  S  D  P  P  V  A  S  S  C  I  S  E  K  S
1201 GATGTGAAAGATGATCTGTCTGATCCTCCTGTTGCAAGCAGTTGTATTTCTGAGAAGTCT
 153 P  R  S  P  Q  L  S  D  F  G  L  E  R  Y  I  V  S  Q  V  L
1261 CCACGTAGTCCACAACTTTCAGATTTTGGACTTGAGCGGTACATCGTATCCCAAGTTCTA
 173 P  N  P  P  Q  A  V  N  N  Y  K  E  E  P  V  I  V  T  P  P
1321 CCAAACCCTCCACAGGCAGTGAACAACTATAAGGAAGAGCCCGTAATTGTAACCCCACCT
 193 T  K  Q  S  L  V  K  V  L  K  T  P  K  C  A  L  K  M  D  D
1381 ACCAAACAATCACTAGTAAAAGTACTAAAAACTCCAAAATGTGCACTAAAAATGGATGAT
 213 F  E  C  V  T  P  K  L  E  H  F  G  I  S  E  Y  T  M  C  L
1441 TTTGAGTGTGTAACTCCTAAATTAGAACACTTTGGTATCTCTGAATATACTATGTGTTTA
 233 N  E  D  Y  T  M  G  L  K  N  A  R  N  N  K  S  E  E  A  I
1501 AATGAAGATTACACAATGGGACTTAAAAATGCGAGGAATAATAAAAGTGAGGAGGCCATA
 253 D  T  E  S  R  L  N  D  N  V  F  A  T  P  S  P  I  I  Q  Q
1561 GATACAGAATCCAGGCTCAATGATAATGTTTTTGCCACTCCCAGCCCCATCATCCAGCAG
 273 L  E  K  S  D  A  E  Y  T  N  S  P  L  V  P  T  F  C  T  P
1621 TTGGAAAAAAGTGATGCCGAATATACCAACTCTCCTTTGGTACCTACATTCTGTACTCCT
 293 G  L  K  I  P  S  T  K  N  S  I  A  L  V  S  T  N  Y  P  L
1681 GGTTTGAAAATTCCATCTACAAAGAACAGCATAGCTTTGGTATCCACAAATTACCCATTA
 313 S  K  T  N  S  S  S  N  D  L  E  V  E  D  R  T  S  L  V  L
1741 TCAAAAACAAATAGTTCATCAAATGATTTGGAAGTTGAAGATCGTACTTCGTTGGTTTTA
 333 N  S  D  T  C  F  E  N  L  T  D  P  S  S  P  T  I  S  S  Y
1801 AATTCAGACACATGCTTTGAGAATTTAACAGATCCCTCTTCACCTACGATTTCTTCTTAT
 353 E  N  L  L  R  T  P  T  P  P  E  V  T  K  I  P  E  D  I  L
1861 GAGAATCTGCTCAGAACACCTACACCTCCAGAAGTAACTAAAATTCCAGAAGATATTCTC
 373 Q  L  L  S  K  Y  N  S  N  L  A  T  P  I  A  I  K  A  V  P
1921 CAGCTTTTATCAAAATACAACTCAAACCTAGCTACTCCAATAGCAATTAAAGCAGTGCCA
 393 P  S  K  R  F  L  K  H  G  Q  N  I  R  D  V  S  N  K  E  N
1981 CCCAGTAAAAGGTTCCTTAAACATGGACAGAACATCCGAGATGTCAGCAACAAAGAAAAC
 413 *
2041 TGAaattccagtggatctatccaacacagaaactgaacaaaatgagatgaaagccgagct
2101 ggaccgattttaacattcacattgccctgcctctgtccccctttaaacgttgacccattt
2161 taaagacaaacatgaacattaacatcataatatgctttttatgaagtttcaataaggttt
2221 aaccttagtcttgttgacatgtagcccagtcattcactctttaaggactattagtgtttc
2281 attgatactaaattacccagcttaatcaacagaatggtttaagtagtaccaggaagtagg
```

Figure 2D-3

```
2341 acaagtaatttcaaaaatataaaggtgtttgctactcagatgaggccgcccctgaccttc
2401 tggccagagagacattgctgccagccagctctgccttcccatcatctcctttcaggaccg
2461 tcccacaccttttacttgctcagtgctgtctgaagatgcagttgctgtttgcaaacaaca
2521 ggaacaccagttaaactaattaggaaacagagggagatttccaggcctgggtaactatat
2581 actgtgaccattggcggttgagaccggtcttcaaccagtggaaccccgaactctgctgtc
2641 agggtgtggacttcggtgctcttccaagttttcacctgggggggggagctaacccctat
2701 gttcacgccttctattcccattggcgctgaactcttaaggtcactctggtcgcttgtgac
2761 cccgtaaccctgatgtacccctctaaaaggtgaggggc
```

Figure 2E. The cDNA (SEQ ID NO: 10) and amino acid sequence (SEQ ID NO: 11) of 193P1E1B v.5. The start methionine is underlined. The open reading frame extends from nucleic acid 805-2043 including the stop codon.

```
   1 tatcatctgtgactgaggaaatccctatcttcctatcagactaatgaaaccacaggacag
  61 caattagacttttaagtattgggggggtttagagctctagatattcgatatgcagactact
 121 catgtttgtttgttttaataaagactggtccaaaggctcattttcacacaagctacagtt
 181 tttcagttccaggaccaggtaaagatggtcagctccgtgatccataaaatccaagggtga
 241 cgactcaggattaggaccatttcttggtgacattgagatggtcgagctggtccgcaatga
 301 atctatgcggggggaacttggaagtggcggccgcctttatggcctcgaaggcctccctcc
 361 tgcgcaccgcggcgtggccgcgctcctgctcccgggtcatgtagggcatgctcagccagt
 421 aatggttctccgcctcgatctccaggcggcggatcatgttctgcttggcgcgcaacgaca
 481 cgaaccgcggccgccggtgcttcccgatccactgacggccgggaatgcggccgcgccaga
 541 ggagcgcagtcaggaacatggtgcctgccgcgctgctcaagactctgcgtctccgcggcc
 601 gccagcagacgccgtggcgtaagcgcacccgtctcgcggggtctccgggggcctcggcga
 661 gagacttcggctctcgcgagagaggactgcgcctgcgcagagccgaggacgcgtccggcg
 721 ccgagattcaaactagtggcgggaggctgtgagctgagcggtggggtctgcgtacgcctg
   1                           M  D  P  I  R  S  F  C  G  K  L  R
 781 gagtccttccccgctgtgctcagcATGGACCCTATCCGGAGCTTCTGCGGGAAGCTGCGG
  13 S  L  A  S  T  L  D  C  E  T  A  R  L  Q  R  A  L  D  G  E
 841 TCTCTGGCCAGCACGCTGGACTGCGAGACGGCCCGGCTGCAGCGAGCGCTGGACGGAGAG
  33 E  S  D  F  E  D  Y  P  M  R  I  L  Y  D  L  H  S  E  V  Q
 901 GAAAGCGACTTTGAAGATTATCCAATGAGAATTTTATATGACCTTCATTCAGAAGTTCAG
  53 T  L  K  D  D  V  N  I  L  L  D  K  A  R  L  E  N  Q  E  G
 961 ACTCTAAAGGATGATGTTAATATTCTTCTTGATAAAGCAAGATTGGAAAATCAAGAAGGC
  73 I  D  F  I  K  A  T  K  V  L  M  E  K  N  S  M  D  I  M  K
1021 ATTGATTTCATAAAGGCAACAAAAGTACTAATGGAAAAAAATTCAATGGATATTATGAAA
  93 I  R  E  Y  F  Q  K  Y  G  Y  S  P  R  V  K  K  N  S  V  H
1081 ATAAGAGAGTATTTCCAGAAGTATGGATATAGTCCACGTGTCAAGAAAAATTCAGTACAC
 113 E  Q  E  A  I  N  S  D  P  E  L  S  N  C  E  N  F  Q  K  T
1141 GAGCAAGAAGCCATTAACTCTGACCCAGAGTTGTCTAATTGTGAAAATTTTCAGAAGACT
 133 D  V  K  D  D  L  S  D  P  P  V  A  S  S  C  I  S  G  K  S
```

Figure 2E-2

1201 GATGTGAAAGATGATCTGTCTGATCCTCCTGTTGCAAGCAGTTGTATTTCTGGGAAGTCT

153 P R S P Q L S D F G L E R Y I V S Q V L

1261 CCACGTAGTCCACAACTTTCAGATTTTGGACTTGAGCGGTACATCGTATCCCAAGTTCTA

173 P N P P Q A V N N Y K E E P V I V T P P

1321 CCAAACCCTCCACAGGCAGTGAACAACTATAAGGAAGAGCCCGTAATTGTAACCCCACCT

193 T K Q S L V K V L K T P K C A L K M D D

1381 ACCAAACAATCACTAGTAAAAGTACTAAAAACTCCAAAATGTGCACTAAAAATGGATGAT

213 F E C V T P K L E H F G I S E Y T M C L

1441 TTTGAGTGTGTAACTCCTAAATTAGAACACTTTGGTATCTCTGAATATACTATGTGTTTA

233 N E D Y T M G L K N A R N N K S E E A I

1501 AATGAAGATTACACAATGGGACTTAAAAATGCGAGGAATAATAAAAGTGAGGAGGCCATA

253 D T E S R L N D N V F A T P S P I I Q Q

1561 GATACAGAATCCAGGCTCAATGATAATGTTTTTGCCACTCCCAGCCCCATCATCCAGCAG

273 L E K S D A E Y T N S P L V P T F C T P

1621 TTGGAAAAAAGTGATGCCGAATATACCAACTCTCCTTTGGTACCTACATTCTGTACTCCT

293 G L K I P S T K N S I A L V S T N Y P L

1681 GGTTTGAAAATTCCATCTACAAAGAACAGCATAGCTTTGGTATCCACAAATTACCCATTA

313 S K T N S S S N D L E V E D R T S L V L

1741 TCAAAAACAAATAGTTCATCAAATGATTTGGAAGTTGAAGATCGTACTTCGTTGGTTTTA

333 N S D T C F E N L T D P S S P T I S S Y

1801 AATTCAGACACATGCTTTGAGAATTTAACAGATCCCTCTTCACCTACGATTTCTTCTTAT

353 E N L L R T P T P P E V T K I P E D I L

1861 GAGAATCTGCTCAGAACACCTACACCTCCAGAAGTAACTAAAATTCCAGAAGATATTCTC

373 Q L L S K Y N S N L A T P I A I K A V P

1921 CAGCTTTTATCAAAATACAACTCAAACCTAGCTACTCCAATAGCAATTAAAGCAGTGCCA

393 P S K R F L K H G Q N I R D V S N K E N

1981 CCCAGTAAAAGGTTCCTTAAACATGGACAGAACATCCGAGATGTCAGCAACAAAGAAAAC

413 *

2041 TGAaattccagtggatctatccaacacagaaactgaacaaaatgagatgaaagccgagct 2101 ggaccgattttaacattcacattgccctgcctctgtccccctttaaacgttgacccattt 2161 taaagacaaacatgaacattaacatcataatatgctttttatgaagtttcaataaggttt 2221 aaccttagtcttgttgacatgtagcccagtcattcactctttaaggactattagtgtttc 2281 attgatactaaattacccagcttaatcaacagaatggtttaagtagtaccaggaagtagg 2341 acaagtaatttcaaaaatataaaggtgtttgctactcagatgaggccgcccctgaccttc 2401 tggccagagagacattgctgccagccagctctgccttcccatcatctcctttcaggaccg 2461 tcccacaccttttacttgctcagtgctgtctgaagatgcagttgctgtttgcaaacaaca 2521 ggaacaccagttaaactaattaggaaacagagggagatttccaggcctgggtaactatat 2581 actgtgaccattggcggttgagaccggtcttcaaccagtggaaccccgaactctgctgtc 2641 agggtgtggacttcggtgctcttccaagttttcacctgggggggggagctaaccccctat 2701 gttcacgccttctattcccattggcgctgaactcttaaggtcactctggtcgcttgtgac 2761 cccgtaaccctgatgtacccctctaaaaggtgaggggc

Figure 2F. The cDNA (SEQ ID NO: 12) and amino acid sequence (SEQ ID NO: 13) of 193P1E1B v.6. The start methionine is underlined. The open reading frame extends from nucleic acid 805-2043 including the stop codon.

1 tatcatctgtgactgaggaaatccctatcttcctatcagactaatgaaaccacaggacag
61 caattagacttttaagtattgggggtttagagctctagatattcgatatgcagactact
121 catgtttgtttgttttaataaagactggtccaaaggctcattttcacacaagctacagtt
181 tttcagttccaggaccaggtaaagatggtcagctccgtgatccataaaatccaagggtga
241 cgactcaggattaggaccatttcttggtgacattgagatggtcgagctggtccgcaatga
301 atctatgcgggggggaacttggaagtggcggccgcctttatggcctcgaaggcctccctcc
361 tgcgcaccgcggcgtggccgcgctcctgctcccgggtcatgtagggcatgctcagccagt
421 aatggttctccgcctcgatctccaggcggcggatcatgttctgcttggcgcgcaacgaca
481 cgaaccgcggccgccggtgcttcccgatccactgacggccgggaatgcggccgcgccaga
541 ggagcgcagtcaggaacatggtgcctgccgcgctgctcaagactctgcgtctccgcggcc
601 gccagcagacgccgtggcgtaagcgcacccgtctcgcggggtctccgggggcctcggcga
661 gagacttcggctctcgcgagagaggactgcgcctgcgcagagccgaggacgcgtccggcg
721 ccgagattcaaactagtggcgggaggctgtgagctgagcggtggggtctgcgtacgcctg
1 M D P I R S F C G K L R
781 gagtccttccccgctgtgctcagcATGGACCCTATCCGGAGCTTCTGCGGGAAGCTGCGG
13 S L A S T L D C E T A R L Q R A L D G E
841 TCTCTGGCCAGCACGCTGGACTGCGAGACGGCCCGGCTGCAGCGAGCGCTGGACGGAGAG
33 E S D F E D Y P M R I L Y D L H S E V Q
901 GAAAGCGACTTTGAAGATTATCCAATGAGAATTTTATATGACCTTCATTCAGAAGTTCAG
53 T L K D D V N I L L D K A R L E N Q E G
961 ACTCTAAAGGATGATGTTAATATTCTTCTTGATAAAGCAAGATTGGAAAATCAAGAAGGC
73 I D F I K A T K V L M E K N S M D I M K
1021 ATTGATTTCATAAAGGCAACAAAAGTACTAATGGAAAAAAATTCAATGGATATTATGAAA
93 I R E Y F Q K Y G Y S P R V K K N S V H
1081 ATAAGAGAGTATTTCCAGAAGTATGGATATAGTCCACGTGTCAAGAAAAATTCAGTACAC
113 E Q E A I N S D P E L S N C E N F Q K T
1141 GAGCAAGAAGCCATTAACTCTGACCCAGAGTTGTCTAATTGTGAAAATTTTCAGAAGACT
133 D V K D D L S D P P V A S S C I S E K S
1201 GATGTGAAAGATGATCTGTCTGATCCTCCTGTTGCAAGCAGTTGTATTTCTGAGAAGTCT
153 P R S P Q L S D F G L E R Y I V S Q V L
1261 CCACGTAGTCCACAACTTTCAGATTTTGGACTTGAGCGGTACATCGTATCCCAAGTTCTA
173 P N P P Q A V N N Y K E E P V I V T P P
1321 CCAAACCCTCCACAGGCAGTGAACAACTATAAGGAAGAGCCCGTAATTGTAACCCCACCT
193 T K Q S L V K V L K T P K C A L K M D D
1381 ACCAAACAATCACTAGTAAAAGTACTAAAAACTCCAAAATGTGCACTAAAAATGGATGAT
213 F E C V T P K L E H F G I S E Y T M C L
1441 TTTGAGTGTGTAACTCCTAAATTAGAACACTTTGGTATCTCTGAATATACTATGTGTTTA
233 N E D Y T M G L K N A R N N K S E E A I

Figure 2F-2

```
1501 AATGAAGATTACACAATGGGACTTAAAAATGCGAGGAATAATAAAAGTGAGGAGGCCATA
 253 D  A  E  S  R  L  N  D  N  V  F  A  T  P  S  P  I  I  Q  Q
1561 GATGCAGAATCCAGGCTCAATGATAATGTTTTTGCCACTCCCAGCCCCATCATCCAGCAG
 273 L  E  K  S  D  A  E  Y  T  N  S  P  L  V  P  T  F  C  T  P
1621 TTGGAAAAAAGTGATGCCGAATATACCAACTCTCCTTTGGTACCTACATTCTGTACTCCT
 293 G  L  K  I  P  S  T  K  N  S  I  A  L  V  S  T  N  Y  P  L
1681 GGTTTGAAAATTCCATCTACAAAGAACAGCATAGCTTTGGTATCCACAAATTACCCATTA
 313 S  K  T  N  S  S  S  N  D  L  E  V  E  D  R  T  S  L  V  L
1741 TCAAAAACAAATAGTTCATCAAATGATTTGGAAGTTGAAGATCGTACTTCGTTGGTTTTA
 333 N  S  D  T  C  F  E  N  L  T  D  P  S  S  P  T  I  S  S  Y
1801 AATTCAGACACATGCTTTGAGAATTTAACAGATCCCTCTTCACCTACGATTTCTTCTTAT
 353 E  N  L  L  R  T  P  T  P  P  E  V  T  K  I  P  E  D  I  L
1861 GAGAATCTGCTCAGAACACCTACACCTCCAGAAGTAACTAAAATTCCAGAAGATATTCTC
 373 Q  L  L  S  K  Y  N  S  N  L  A  T  P  I  A  I  K  A  V  P
1921 CAGCTTTTATCAAAATACAACTCAAACCTAGCTACTCCAATAGCAATTAAAGCAGTGCCA
 393 P  S  K  R  F  L  K  H  G  Q  N  I  R  D  V  S  N  K  E  N
1981 CCCAGTAAAAGGTTCCTTAAACATGGACAGAACATCCGAGATGTCAGCAACAAAGAAAAC
 413 *
2041 TGAaattccagtggatctatccaacacagaaactgaacaaaatgagatgaaagccgagct
2101 ggaccgattttaacattcacattgccctgcctctgtcccccttttaaacgttgacccattt
2161 taaagacaaacatgaacattaacatcataatatgctttttatgaagtttcaataaggttt
2221 aaccttagtcttgttgacatgtagcccagtcattcactctttaaggactattagtgtttc
2281 attgatactaaattacccagcttaatcaacagaatggtttaagtagtaccaggaagtagg
2341 acaagtaatttcaaaaatataaaggtgtttgctactcagatgaggccgcccctgaccttc
2401 tggccagagagacattgctgccagccagctctgccttcccatcatctcctttcaggaccg
2461 tcccacaccttttacttgctcagtgctgtctgaagatgcagttgctgtttgcaaacaaca
2521 ggaacaccagttaaactaattaggaaacagagggagatttccaggcctgggtaactatat
2581 actgtgaccattggcggttgagaccggtcttcaaccagtggaaccccgaactctgctgtc
2641 agggtgtggacttcggtgctcttccaagttttcacctggggggggggagctaacccccctat
2701 gttcacgccttctattcccattggcgctgaactcttaaggtcactctggtcgcttgtgac
2761 cccgtaaccctgatgtacccctctaaaaggtgaggggc
```

Figure 2G. The cDNA (SEQ ID NO: 14) and amino acid sequence (SEQ ID NO: 15) of 193P1E1B v.7. The start methionine is underlined. The open reading frame extends from nucleic acid 805-2043 including the stop codon.

```
  1 tatcatctgtgactgaggaaatccctatcttcctatcagactaatgaaaccacaggacag
 61 caattagacttttaagtattggggggtttagagctctagatattcgatatgcagactact
121 catgtttgtttgttttaataaagactggtccaaaggctcattttcacacaagctacagtt
181 tttcagttccaggaccaggtaaagatggtcagctccgtgatccataaaatccaagggtga
241 cgactcaggattaggaccatttcttggtgacattgagatggtcgagctggtccgcaatga
301 atctatgcggggggaacttggaagtggcggccgcctttatggcctcgaaggcctccctcc
```

Figure 2G-2

```
 361 tgcgcaccgcggcgtggccgcgctcctgctcccgggtcatgtagggcatgctcagccagt
 421 aatggttctccgcctcgatctccaggcggcggatcatgttctgcttggcgcgcaacgaca
 481 cgaaccgcggccgccggtgcttcccgatccactgacggccgggaatgcggccgcgccaga
 541 ggagcgcagtcaggaacatggtgcctgccgcgctgctcaagactctgcgtctccgcggcc
 601 gccagcagacgccgtggcgtaagcgcacccgtctcgcggggtctccgggggcctcggcga
 661 gagacttcggctctcgcgagagaggactgcgcctgcgcagagccgaggacgcgtccggcg
 721 ccgagattcaaactagtggcgggaggctgtgagctgagcggtggggtctgcgtacgcctg
   1                            M  D  P  I  R  S  F  C  G  K  L  R
 781 gagtccttccccgctgtgctcagcATGGACCCTATCCGGAGCTTCTGCGGGAAGCTGCGG
  13 S  L  A  S  T  L  D  C  E  T  A  R  L  Q  R  A  L  D  G  E
 841 TCTCTGGCCAGCACGCTGGACTGCGAGACGGCCCGGCTGCAGCGAGCGCTGGACGGAGAG
  33 E  S  D  F  E  D  Y  P  M  R  I  L  Y  D  L  H  S  E  V  Q
 901 GAAAGCGACTTTGAAGATTATCCAATGAGAATTTTATATGACCTTCATTCAGAAGTTCAG
  53 T  L  K  D  D  V  N  I  L  L  D  K  A  R  L  E  N  Q  E  G
 961 ACTCTAAAGGATGATGTTAATATTCTTCTTGATAAAGCAAGATTGGAAAATCAAGAAGGC
  73 I  D  F  I  K  A  T  K  V  L  M  E  K  N  S  M  D  I  M  K
1021 ATTGATTTCATAAAGGCAACAAAAGTACTAATGGAAAAAAATTCAATGGATATTATGAAA
  93 I  R  E  Y  F  Q  K  Y  G  Y  S  P  R  V  K  K  N  S  V  H
1081 ATAAGAGAGTATTTCCAGAAGTATGGATATAGTCCACGTGTCAAGAAAAATTCAGTACAC
 113 E  Q  E  A  I  N  S  D  P  E  L  S  N  C  E  N  F  Q  K  T
1141 GAGCAAGAAGCCATTAACTCTGACCCAGAGTTGTCTAATTGTGAAAATTTTCAGAAGACT
 133 D  V  K  D  D  L  S  D  P  P  V  A  S  S  C  I  S  E  K  S
1201 GATGTGAAAGATGATCTGTCTGATCCTCCTGTTGCAAGCAGTTGTATTTCTGAGAAGTCT
 153 P  R  S  P  Q  L  S  D  F  G  L  E  R  Y  I  V  S  Q  V  L
1261 CCACGTAGTCCACAACTTTCAGATTTTGGACTTGAGCGGTACATCGTATCCCAAGTTCTA
 173 P  N  P  P  Q  A  V  N  N  Y  K  E  E  P  V  I  V  T  P  P
1321 CCAAACCCTCCACAGGCAGTGAACAACTATAAGGAAGAGCCCGTAATTGTAACCCCACCT
 193 T  K  Q  S  L  V  K  V  L  K  T  P  K  C  A  L  K  M  D  D
1381 ACCAAACAATCACTAGTAAAAGTACTAAAAACTCCAAAATGTGCACTAAAAATGGATGAT
 213 F  E  C  V  T  P  K  L  E  H  F  G  I  S  E  Y  T  M  C  L
1441 TTTGAGTGTGTAACTCCTAAATTAGAACACTTTGGTATCTCTGAATATACTATGTGTTTA
 233 N  E  D  Y  T  M  G  L  K  N  A  R  N  N  K  S  E  E  A  I
1501 AATGAAGATTACACAATGGGACTTAAAAATGCGAGGAATAATAAAAGTGAGGAGGCCATA
 253 D  T  E  S  R  L  N  D  N  V  F  A  T  P  S  P  I  I  Q  Q
1561 GATACAGAATCCAGGCTCAATGATAATGTTTTTGCCACTCCCAGCCCCATCATCCAGCAG
 273 L  E  K  S  D  A  E  Y  T  N  S  P  L  V  P  T  F  C  T  P
1621 TTGGAAAAAAGTGATGCCGAATATACCAACTCTCCTTTGGTACCTACATTCTGTACTCCT
 293 G  L  K  I  P  S  T  K  N  S  I  A  L  V  S  T  N  Y  P  L
1681 GGTTTGAAAATTCCATCTACAAAGAACAGCATAGCTTTGGTATCCACAAATTACCCATTA
 313 S  K  T  N  S  S  S  N  D  L  E  V  E  D  R  T  S  L  V  L
1741 TCAAAAACAAATAGTTCATCAAATGATTTGGAAGTTGAAGATCGTACTTCGTTGGTTTTA
```

Figure 2G-3

```
 333 N   S   D   T   C   F   E   N   L   T   D   P   S   S   P   T   I   S   S   Y
1801 AATTCAGACACATGCTTTGAGAATTTAACAGATCCCTCTTCACCTACGATTTCTTCTTAT
 353 E   N   L   L   R   T   P   T   P   P   E   V   T   K   I   P   E   D   I   L
1861 GAGAATCTGCTCAGAACACCTACACCTCCAGAAGTAACTAAAATTCCAGAAGATATTCTC
 373 Q   L   L   S   K   Y   N   S   N   L   A   T   P   I   A   I   K   A   V   P
1921 CAGCTTTTATCAAAATACAACTCAAACCTAGCTACTCCAATAGCAATTAAAGCAGTGCCA
 393 P   S   K   R   F   L   K   H   G   Q   N   I   R   D   V   S   N   K   E   N
1981 CCCAGTAAAAGGTTCCTTAAACATGGACAGAACATCCGAGATGTCAGCAACAAAGAAAAC
 413 *
2041 TGAaattccagtggatctatccaacacagaaactgaacaaaatgagatgaaagccgagct
2101 ggaccgattttaacattcacattgccctgcctctgtcccccttttaaacgttgacccattt
2161 taaagacaaacatgaacattaacatcataatatgctttttatgaagtttcaataaggttt
2221 aaccttagtcttgttgacatgtagcccagtcattcactctttaaggattattagtgtttc
2281 attgatactaaattacccagcttaatcaacagaatggtttaagtagtaccaggaagtagg
2341 acaagtaatttcaaaaatataaaggtgtttgctactcagatgaggccgcccctgaccttc
2401 tggccagagagacattgctgccagccagctctgccttcccatcatctcctttcaggaccg
2461 tcccacaccttttacttgctcagtgctgtctgaagatgcagttgctgtttgcaaacaaca
2521 ggaacaccagttaaactaattaggaaacagagggagatttccaggcctgggtaactatat
2581 actgtgaccattggcggttgagaccggtcttcaaccagtggaaccccgaactctgctgtc
2641 agggtgtggacttcggtgctcttccaagttttcacctgggggggggagctaacccccctat
2701 gttcacgccttctattcccattggcgctgaactcttaaggtcactctggtcgcttgtgac
2761 cccgtaaccctgatgtacccctctaaaaggtgaggggc
```

Figure 2H. The cDNA (SEQ ID NO: 16) and amino acid sequence (SEQ ID NO: 17) of 193P1E1B v.8. The start methionine is underlined. The open reading frame extends from nucleic acid 805-2043 including the stop codon.

```
   1 tatcatctgtgactgaggaaatccctatcttcctatcagactaatgaaaccacaggacag
  61 caattagacttttaagtattgggggtttagagctctagatattcgatatgcagactact
 121 catgtttgtttgttttaataaagactggtccaaaggctcattttcacacaagctacagtt
 181 tttcagttccaggaccaggtaaagatggtcagctccgtgatccataaaatccaagggtga
 241 cgactcaggattaggaccatttcttggtgacattgagatggtcgagctggtccgcaatga
 301 atctatgcgggggaacttggaagtggcggccgcctttatggcctcgaaggcctccctcc
 361 tgcgcaccgcggcgtggccgcgctcctgctcccgggtcatgtagggcatgctcagccagt
 421 aatggttctccgcctcgatctccaggcggcggatcatgttctgcttggcgcgcaacgaca
 481 cgaaccgcggccgccggtgcttcccgatccactgacggccgggaatgcggccgcgccaga
 541 ggagcgcagtcaggaacatggtgcctgccgcgctgctcaagactctgcgtctccgcggcc
 601 gccagcagacgccgtggcgtaagcgcacccgtctcgcggggtctccgggggcctcggcga
 661 gagacttcggctctcgcgagagaggactgcgcctgcgcagagccgaggacgcgtccggcg
 721 ccgagattcaaactagtggcgggaggctgtgagctgagcggtggggtctgcgtacgcctg
   1                            M   D   P   I   R   S   F   C   G   K   L   R
 781 gagtccttccccgctgtgctcagcATGGACCCTATCCGGAGCTTCTGCGGGAAGCTGCGG
```

Figure 2H-2

```
  13 S   L   A   S   T   L   D   C   E   T   A   R   L   Q   R   A   L   D   G   E
 841 TCTCTGGCCAGCACGCTGGACTGCGAGACGGCCCGGCTGCAGCGAGCGCTGGACGGAGAG
  33 E   S   D   F   E   D   Y   P   M   R   I   L   Y   D   L   H   S   E   V   Q
 901 GAAAGCGACTTTGAAGATTATCCAATGAGAATTTTATATGACCTTCATTCAGAAGTTCAG
  53 T   L   K   D   D   V   N   I   L   L   D   K   A   R   L   E   N   Q   E   G
 961 ACTCTAAAGGATGATGTTAATATTCTTCTTGATAAAGCAAGATTGGAAAATCAAGAAGGC
  73 I   D   F   I   K   A   T   K   V   L   M   E   K   N   S   M   D   I   M   K
1021 ATTGATTTCATAAAGGCAACAAAAGTACTAATGGAAAAAAATTCAATGGATATTATGAAA
  93 I   R   E   Y   F   Q   K   Y   G   Y   S   P   R   V   K   K   N   S   V   H
1081 ATAAGAGAGTATTTCCAGAAGTATGGATATAGTCCACGTGTCAAGAAAAATTCAGTACAC
 113 E   Q   E   A   I   N   S   D   P   E   L   S   N   C   E   N   F   Q   K   T
1141 GAGCAAGAAGCCATTAACTCTGACCCAGAGTTGTCTAATTGTGAAAATTTTCAGAAGACT
 133 D   V   K   D   D   L   S   D   P   P   V   A   S   S   C   I   S   E   K   S
1201 GATGTGAAAGATGATCTGTCTGATCCTCCTGTTGCAAGCAGTTGTATTTCTGAGAAGTCT
 153 P   R   S   P   Q   L   S   D   F   G   L   E   R   Y   I   V   S   Q   V   L
1261 CCACGTAGTCCACAACTTTCAGATTTTGGACTTGAGCGGTACATCGTATCCCAAGTTCTA
 173 P   N   P   P   Q   A   V   N   N   Y   K   E   E   P   V   I   V   T   P   P
1321 CCAAACCCTCCACAGGCAGTGAACAACTATAAGGAAGAGCCCGTAATTGTAACCCCACCT
 193 T   K   Q   S   L   V   K   V   L   K   T   P   K   C   A   L   K   M   D   D
1381 ACCAAACAATCACTAGTAAAAGTACTAAAAACTCCAAAATGTGCACTAAAAATGGATGAT
 213 F   E   C   V   T   P   K   L   E   H   F   G   I   S   E   Y   T   M   C   L
1441 TTTGAGTGTGTAACTCCTAAATTAGAACACTTTGGTATCTCTGAATATACTATGTGTTTA
 233 N   E   D   Y   T   M   G   L   K   N   A   R   N   N   K   S   E   E   A   I
1501 AATGAAGATTACACAATGGGACTTAAAAATGCGAGGAATAATAAAAGTGAGGAGGCCATA
 253 D   T   E   S   R   L   N   D   N   V   F   A   T   P   S   P   I   I   Q   Q
1561 GATACAGAATCCAGGCTCAATGATAATGTTTTTGCCACTCCCAGCCCCATCATCCAGCAG
 273 L   E   K   S   D   A   E   Y   T   N   S   P   L   V   P   T   F   C   T   P
1621 TTGGAAAAAAGTGATGCCGAATATACCAACTCTCCTTTGGTACCTACATTCTGTACTCCT
 293 G   L   K   I   P   S   T   K   N   S   I   A   L   V   S   T   N   Y   P   L
1681 GGTTTGAAAATTCCATCTACAAAGAACAGCATAGCTTTGGTATCCACAAATTACCCATTA
 313 S   K   T   N   S   S   S   N   D   L   E   V   E   D   R   T   S   L   V   L
1741 TCAAAAACAAATAGTTCATCAAATGATTTGGAAGTTGAAGATCGTACTTCGTTGGTTTTA
 333 N   S   D   T   C   F   E   N   L   T   D   P   S   S   P   T   I   S   S   Y
1801 AATTCAGACACATGCTTTGAGAATTTAACAGATCCCTCTTCACCTACGATTTCTTCTTAT
 353 E   N   L   L   R   T   P   T   P   P   E   V   T   K   I   P   E   D   I   L
1861 GAGAATCTGCTCAGAACACCTACACCTCCAGAAGTAACTAAAATTCCAGAAGATATTCTC
 373 Q   L   L   S   K   Y   N   S   N   L   A   T   P   I   A   I   K   A   V   P
1921 CAGCTTTTATCAAAATACAACTCAAACCTAGCTACTCCAATAGCAATTAAAGCAGTGCCA
 393 P   S   K   R   F   L   K   H   G   Q   N   I   R   D   V   S   N   K   E   N
1981 CCCAGTAAAAGGTTCCTTAAACATGGACAGAACATCCGAGATGTCAGCAACAAAGAAAAC
 413 *
```

Figure 2H-3

```
2041 TGAaattccagtggatctatccaacacagaaactgaacaaaatgagatgaaagccgagct
2101 ggaccgattttaacattcacattgccctgcctctgtcccccttttaaacgttgacccattt
2161 taaagacaaacatgaacattaacatcataatatgctttttatgaagtttcaataaggttt
2221 aaccttagtcttgttgacatgtagcccagtcattcactctttaaggactattagtgtttc
2281 attgatactaaattacccagcttaatcaacagaatggtttaagtagtaccaggaagtagg
2341 acaagtaatttcaaaaatataaaggtgtttgctactcagatgaggctgcccctgaccttc
2401 tggccagagagacattgctgccagccagctctgccttcccatcatctcctttcaggaccg
2461 tcccacaccttttacttgctcagtgctgtctgaagatgcagttgctgtttgcaaacaaca
2521 ggaacaccagttaaactaattaggaaacagagggagatttccaggcctgggtaactatat
2581 actgtgaccattggcggttgagaccggtcttcaaccagtggaaccccgaactctgctgtc
2641 agggtgtggacttcggtgctcttccaagttttcacctgggggggggagctaaccccctat
2701 gttcacgccttctattcccattggcgctgaactcttaaggtcactctggtcgcttgtgac
2761 cccgtaaccctgatgtacccctctaaaaggtgaggggc
```

Figure 2I. The cDNA (SEQ ID NO: 18) and amino acid sequence (SEQ ID NO: 19) of 193P1E1B v.9. The start methionine is underlined. The open reading frame extends from nucleic acid 989-1981 including the stop codon.

```
   1 tatcatctgtgactgaggaaatccctatcttcctatcagactaatgaaaccacaggacag
  61 caattagacttttaagtattgggggggtttagagctctagatattcgatatgcagactact
 121 catgtttgtttgttttaataaagactggtccaaaggctcattttcacacaagctacagtt
 181 tttcagttccaggaccaggtaaagatggtcagctccgtgatccataaaatccaagggtga
 241 cgactcaggattaggaccatttcttggtgacattgagatggtcgagctggtccgcaatga
 301 atctatgcgggggggaacttggaagtggcggccgcctttatggcctcgaaggcctccctcc
 361 tgcgcaccgcggcgtggccgcgctcctgctcccgggtcatgtagggcatgctcagccagt
 421 aatggttctccgcctcgatctccaggcggcggatcatgttctgcttggcgcgcaacgaca
 481 cgaaccgcggccgccggtgcttcccgatccactgacggccgggaatgcggccgcgccaga
 541 ggagcgcagtcaggaacatggtgcctgccgcgctgctcaagactctgcgtctccgcggcc
 601 gccagcagacgccgtggcgtaagcgcacccgtctcgcggggtctccgggggcctcggcga
 661 gagacttcggctctcgcgagagaggactgcgcctgcgcagagccgaggacgcgtccggcg
 721 ccgagattcaaactagtggcgggaggctgtgagctgagcggtggggtctgcgtacgcctg
 781 gagtccttccccgctgtgctcagcatggaccctatccggagcttctgcgggaagctgcgg
 841 tctctggccagcacgctggactgcgagacggcccggctgcagcgagcgctggacggagag
 901 gaaagcggatgatgttaatattcttcttgataaagcaagattggaaaatcaagaaggcat
   1                                M  E  K  N  S  M  D  I  M  K  I
 961 tgatttcataaaggcaacaaaagtactaATGGAAAAAAATTCAATGGATATTATGAAAAT
  12  R  E  Y  F  Q  K  Y  G  Y  S  P  R  V  K  K  N  S  V  H  E
1021 AAGAGAGTATTTCCAGAAGTATGGATATAGTCCACGTGTCAAGAAAAAATTCAGTACACGA
  32  Q  E  A  I  N  S  D  P  E  L  S  N  C  E  N  F  Q  K  T  D
1081 GCAAGAAGCCATTAACTCTGACCCAGAGTTGTCTAATTGTGAAAATTTTCAGAAGACTGA
  52  V  K  D  D  L  S  D  P  P  V  A  S  S  C  I  S  E  K  S  P
```

Figure 2I-2

```
1141 TGTGAAAGATGATCTGTCTGATCCTCCTGTTGCAAGCAGTTGTATTTCTGAGAAGTCTCC
  72  R  S  P  Q  L  S  D  F  G  L  E  R  Y  I  V  S  Q  V  L  P
1201 ACGTAGTCCACAACTTTCAGATTTTGGACTTGAGCGGTACATCGTATCCCAAGTTCTACC
  92  N  P  P  Q  A  V  N  N  Y  K  E  E  P  V  I  V  T  P  P  T
1261 AAACCCTCCACAGGCAGTGAACAACTATAAGGAAGAGCCCGTAATTGTAACCCCACCTAC
 112  K  Q  S  L  V  K  V  L  K  T  P  K  C  A  L  K  M  D  D  F
1321 CAAACAATCACTAGTAAAAGTACTAAAAACTCCAAAATGTGCACTAAAAATGGATGATTT
 132  E  C  V  T  P  K  L  E  H  F  G  I  S  E  Y  T  M  C  L  N
1381 TGAGTGTGTAACTCCTAAATTAGAACACTTTGGTATCTCTGAATATACTATGTGTTTAAA
 152  E  D  Y  T  M  G  L  K  N  A  R  N  N  K  S  E  E  A  I  D
1441 TGAAGATTACACAATGGGACTTAAAAATGCGAGGAATAATAAAAGTGAGGAGGCCATAGA
 172  T  E  S  R  L  N  D  N  V  F  A  T  P  S  P  I  I  Q  Q  L
1501 TACAGAATCCAGGCTCAATGATAATGTTTTTGCCACTCCCAGCCCCATCATCCAGCAGTT
 192  E  K  S  D  A  E  Y  T  N  S  P  L  V  P  T  F  C  T  P  G
1561 GGAAAAAAGTGATGCCGAATATACCAACTCTCCTTTGGTACCTACATTCTGTACTCCTGG
 212  L  K  I  P  S  T  K  N  S  I  A  L  V  S  T  N  Y  P  L  S
1621 TTTGAAAATTCCATCTACAAAGAACAGCATAGCTTTGGTATCCACAAATTACCCATTATC
 232  K  T  N  S  S  S  N  D  L  E  V  E  D  R  T  S  L  V  L  N
1681 AAAAACAAATAGTTCATCAAATGATTTGGAAGTTGAAGATCGTACTTCGTTGGTTTTAAA
 252  S  D  T  C  F  E  N  L  T  D  P  S  S  P  T  I  S  S  Y  E
1741 TTCAGACACATGCTTTGAGAATTTAACAGATCCCTCTTCACCTACGATTTCTTCTTATGA
 272  N  L  L  R  T  P  T  P  P  E  V  T  K  I  P  E  D  I  L  Q
1801 GAATCTGCTCAGAACACCTACACCTCCAGAAGTAACTAAAATTCCAGAAGATATTCTCCA
 292  L  L  S  K  Y  N  S  N  L  A  T  P  I  A  I  K  A  V  P  P
1861 GCTTTTATCAAAATACAACTCAAACCTAGCTACTCCAATAGCAATTAAAGCAGTGCCACC
 312  S  K  R  F  L  K  H  G  Q  N  I  R  D  V  S  N  K  E  N  *
1921 CAGTAAAAGGTTCCTTAAACATGGACAGAACATCCGAGATGTCAGCAACAAAGAAAACTG
1981 Aaattccagtggatctatccaacacagaaactgaacaaaatgagatgaaagccgagctgg
2041 accgattttaacattcacattgccctgcctctgtcccccttttaaacgttgacccatttta
2101 aagacaaacatgaacattaacatcataatatgctttttatgaagtttcaataaggtttaa
2161 ccttagtcttgttgacatgtagcccagtcattcactctttaaggactattagtgtttcat
2221 tgatactaaattacccagcttaatcaacagaatggtttaagtagtaccaggaagtaggac
2281 aagtaatttcaaaaatataaaggtgtttgctactcagatgaggccgcccctgaccttctg
2341 gccagagagacattgctgccagccagctctgccttcccatcatctcctttcaggaccgtc
2401 ccacaccttttacttgctcagtgctgtctgaagatgcagttgctgtttgcaaacaacagg
2461 aacaccagttaaactaattaggaaacagagggagatttccaggcctgggtaactatatac
2521 tgtgaccattggcggttgagaccggtcttcaaccagtggaaccccgaactctgctgtcag
2581 ggtgtggacttcggtgctcttccaagttttcacctgggggggggagctaacccctatgt
2641 tcacgccttctattcccattggcgctgaactcttaaggtcactctggtcgcttgtgaccc
2701 cgtaaccctgatgtacccctctaaaaggtgaggggc
```

Figure 2J. The cDNA (SEQ ID NO: 20) and amino acid sequence (SEQ ID NO: 21) of 193P1E1B v.10. The start methionine is underlined. The open reading frame extends from nucleic acid 805-1971 including the stop codon.

```
   1 tatcatctgtgactgaggaaatccctatcttcctatcagactaatgaaaccacaggacag
  61 caattagacttttaagtattgggggtttagagctctagatattcgatatgcagactact
 121 catgtttgtttgttttaataaagactggtccaaaggctcattttcacacaagctacagtt
 181 tttcagttccaggaccaggtaaagatggtcagctccgtgatccataaaatccaagggtga
 241 cgactcaggattaggaccatttcttggtgacattgagatggtcgagctggtccgcaatga
 301 atctatgcgggggaacttggaagtggcggccgcctttatggcctcgaaggcctccctcc
 361 tgcgcaccgcggcgtggccgcgctcctgctcccgggtcatgtagggcatgctcagccagt
 421 aatggttctccgcctcgatctccaggcggcggatcatgttctgcttggcgcgcaacgaca
 481 cgaaccgcggccgccggtgcttcccgatccactgacggccgggaatgcggccgcgccaga
 541 ggagcgcagtcaggaacatggtgcctgccgcgctgctcaagactctgcgtctccgcggcc
 601 gccagcagacgccgtggcgtaagcgcacccgtctcgcggggtctccgggggcctcggcga
 661 gagacttcggctctcgcgagagaggactgcgcctgcgcagagccgaggacgcgtccggcg
 721 ccgagattcaaactagtggcgggaggctgtgagctgagcggtggggtctgcgtacgcctg
   1                         M  D  P  I  R  S  F  C  G  K  L  R
 781 gagtccttccccgctgtgctcagcATGGACCCTATCCGGAGCTTCTGCGGGAAGCTGCGG
  13 S  L  A  S  T  L  D  C  E  T  A  R  L  Q  R  A  L  D  G  E
 841 TCTCTGGCCAGCACGCTGGACTGCGAGACGGCCCGGCTGCAGCGAGCGCTGGACGGAGAG
  33 E  S  D  F  E  D  Y  P  M  R  I  L  Y  D  L  H  S  E  V  Q
 901 GAAAGCGACTTTGAAGATTATCCAATGAGAATTTTATATGACCTTCATTCAGAAGTTCAG
  53 T  L  K  D  D  V  N  I  L  L  D  K  A  R  L  E  N  Q  E  G
 961 ACTCTAAAGGATGATGTTAATATTCTTCTTGATAAAGCAAGATTGGAAAATCAAGAAGGC
  73 I  D  F  I  K  A  T  K  V  L  M  E  K  N  S  M  D  I  M  K
1021 ATTGATTTCATAAAGGCAACAAAAGTACTAATGGAAAAAAATTCAATGGATATTATGAAA
  93 I  R  E  Y  F  Q  K  Y  G  Y  S  P  R  V  K  K  N  S  V  H
1081 ATAAGAGAGTATTTCCAGAAGTATGGATATAGTCCACGTGTCAAGAAAAATTCAGTACAC
 113 E  Q  E  A  I  N  S  D  P  E  L  S  N  C  E  N  F  Q  K  T
1141 GAGCAAGAAGCCATTAACTCTGACCCAGAGTTGTCTAATTGTGAAAATTTTCAGAAGACT
 133 D  V  K  D  D  L  S  D  P  P  V  A  S  S  C  I  S  E  K  S
1201 GATGTGAAAGATGATCTGTCTGATCCTCCTGTTGCAAGCAGTTGTATTTCTGAGAAGTCT
 153 P  R  S  P  Q  L  S  D  F  G  L  E  R  Y  I  V  S  Q  V  L
1261 CCACGTAGTCCACAACTTTCAGATTTTGGACTTGAGCGGTACATCGTATCCCAAGTTCTA
 173 P  N  P  P  Q  A  V  N  N  Y  K  E  E  P  V  I  V  T  P  P
1321 CCAAACCCTCCACAGGCAGTGAACAACTATAAGGAAGAGCCCGTAATTGTAACCCCACCT
 193 T  K  Q  S  L  V  K  V  L  K  T  P  K  C  A  L  K  M  D  D
1381 ACCAAACAATCACTAGTAAAAGTACTAAAAACTCCAAAATGTGCACTAAAAATGGATGAT
 213 F  E  C  V  T  P  K  L  E  H  F  G  I  S  E  Y  T  M  C  L
1441 TTTGAGTGTGTAACTCCTAAATTAGAACACTTTGGTATCTCTGAATATACTATGTGTTTA
 233 N  E  D  Y  T  M  G  L  K  N  A  R  N  N  K  S  E  E  A  I
1501 AATGAAGATTACACAATGGGACTTAAAAATGCGAGGAATAATAAAAGTGAGGAGGCCATA
```

Figure 2J-2

```
 253 D  T  E  S  R  L  N  D  N  V  F  A  T  P  S  P  I  I  Q  Q
1561 GATACAGAATCCAGGCTCAATGATAATGTTTTTGCCACTCCCAGCCCCATCATCCAGCAG
 273 L  E  K  S  D  A  E  Y  T  N  S  P  L  V  P  T  F  C  T  P
1621 TTGGAAAAAAGTGATGCCGAATATACCAACTCTCCTTTGGTACCTACATTCTGTACTCCT
 293 G  L  K  I  P  S  T  K  N  S  I  A  L  V  S  T  N  Y  P  L
1681 GGTTTGAAAATTCCATCTACAAAGAACAGCATAGCTTTGGTATCCACAAATTACCCATTA
 313 S  K  T  N  S  S  S  N  D  L  E  V  E  D  R  T  S  L  V  L
1741 TCAAAAACAAATAGTTCATCAAATGATTTGGAAGTTGAAGATCGTACTTCGTTGGTTTTA
 333 N  S  D  T  C  F  E  N  L  T  D  P  S  S  P  T  I  S  S  Y
1801 AATTCAGACACATGCTTTGAGAATTTAACAGATCCCTCTTCACCTACGATTTCTTCTTAT
 353 E  N  L  L  R  T  P  T  P  P  E  V  T  K  I  P  E  D  I  L
1861 GAGAATCTGCTCAGAACACCTACACCTCCAGAAGTAACTAAAATTCCAGAAGATATTCTC
 373 Q  K  F  Q  W  I  Y  P  T  Q  K  L  N  K  M  R  *
1921 CAGAAATTCCAGTGGATCTATCCAACACAGAAACTGAACAAAATGAGATGAaagccgagc
1981 tggaccgattttaacattcacattgccctgcctctgtcccccttaaacgttgacccatt
2041 ttaaagacaaacatgaacattaacatcataatatgctttttatgaagtttcaataaggtt
2101 taaccttagtcttgttgacatgtagcccagtcattcactctttaaggactattagtgttt
2161 cattgatactaaattacccagcttaatcaacagaatggtttaagtagtaccaggaagtag
2221 gacaagtaatttcaaaaatataaaggtgtttgctactcagatgaggccgcccctgacctt
2281 ctggccagagagacattgctgccagccagctctgccttcccatcatctcctttcaggacc
2341 gtcccacaccttttacttgctcagtgctgtctgaagatgcagttgctgtttgcaaacaac
2401 aggaacaccagttaaactaattaggaaacagagggagatttccaggcctgggtaactata
2461 tactgtgaccattggcggttgagaccggtcttcaaccagtggaaccccgaactctgctgt
2521 cagggtgtggacttcggtgctcttccaagttttcacctgggggggggagctaacccccta
2581 tgttcacgccttctattcccattggcgctgaactcttaaggtcactctggtcgcttgtga
2641 ccccgtaaccctgatgtacccctctaaaaggtgaggggc
```

Figure 2K. The cDNA (SEQ ID NO: 22) and amino acid sequence (SEQ ID NO: 23) of 193P1E1B v.11. The start methionine is underlined. The open reading frame extends from nucleic acid 989-1909 including the stop codon.

```
   1 tatcatctgtgactgaggaaatccctatcttcctatcagactaatgaaaccacaggacag
  61 caattagacttttaagtattgggggtttagagctctagatattcgatatgcagactact
 121 catgtttgtttgttttaataaagactggtccaaaggctcattttcacacaagctacagtt
 181 tttcagttccaggaccaggtaaagatggtcagctccgtgatccataaaatccaagggtga
 241 cgactcaggattaggaccatttcttggtgacattgagatggtcgagctggtccgcaatga
 301 atctatgcgggggaacttggaagtggcggccgcctttatggcctcgaaggcctccctcc
 361 tgcgcaccgcggcgtggccgcgctcctgctcccgggtcatgtagggcatgctcagccagt
 421 aatggttctccgcctcgatctccaggcggcggatcatgttctgcttggcgcgcaacgaca
 481 cgaaccgcggccgccggtgcttcccgatccactgacggccgggaatgcggccgcgccaga
 541 ggagcgcagtcaggaacatggtgcctgccgcgctgctcaagactctgcgtctccgcggcc
```

Figure 2K-2

```
 601 gccagcagacgccgtggcgtaagcgcacccgtctcgcggggtctccgggggcctcggcga
 661 gagacttcggctctcgcgagagaggactgcgcctgcgcagagccgaggacgcgtccggcg
 721 ccgagattcaaactagtggcgggaggctgtgagctgagcggtggggtctgcgtacgcctg
 781 gagtccttccccgctgtgctcagcatggaccctatccggagcttctgcgggaagctgcgg
 841 tctctggccagcacgctggactgcgagacggcccggctgcagcgagcgctggacggagag
 901 gaaagcggatgatgttaatattcttcttgataaagcaagattggaaaatcaagaaggcat
   1                              M  E  K  N  S  M  D  I  M  K  I
 961 tgatttcataaaggcaacaaaagtactaATGGAAAAAAATTCAATGGATATTATGAAAAT
  12  R  E  Y  F  Q  K  Y  G  Y  S  P  R  V  K  K  N  S  V  H  E
1021 AAGAGAGTATTTCCAGAAGTATGGATATAGTCCACGTGTCAAGAAAAATTCAGTACACGA
  32  Q  E  A  I  N  S  D  P  E  L  S  N  C  E  N  F  Q  K  T  D
1081 GCAAGAAGCCATTAACTCTGACCCAGAGTTGTCTAATTGTGAAAATTTTCAGAAGACTGA
  52  V  K  D  D  L  S  D  P  P  V  A  S  S  C  I  S  G  K  S  P
1141 TGTGAAAGATGATCTGTCTGATCCTCCTGTTGCAAGCAGTTGTATTTCTGGGAAGTCTCC
  72  R  S  P  Q  L  S  D  F  G  L  E  R  Y  I  V  S  Q  V  L  P
1201 ACGTAGTCCACAACTTTCAGATTTTGGACTTGAGCGGTACATCGTATCCCAAGTTCTACC
  92  N  P  P  Q  A  V  N  N  Y  K  E  E  P  V  I  V  T  P  P  T
1261 AAACCCTCCACAGGCAGTGAACAACTATAAGGAAGAGCCCGTAATTGTAACCCCACCTAC
 112  K  Q  S  L  V  K  V  L  K  T  P  K  C  A  L  K  M  D  D  F
1321 CAAACAATCACTAGTAAAAGTACTAAAAACTCCAAAATGTGCACTAAAAATGGATGATTT
 132  E  C  V  T  P  K  L  E  H  F  G  I  S  E  Y  T  M  C  L  N
1381 TGAGTGTGTAACTCCTAAATTAGAACACTTTGGTATCTCTGAATATACTATGTGTTTAAA
 152  E  D  Y  T  M  G  L  K  N  A  R  N  N  K  S  E  E  A  I  D
1441 TGAAGATTACACAATGGGACTTAAAAATGCGAGGAATAATAAAAGTGAGGAGGCCATAGA
 172  T  E  S  R  L  N  D  N  V  F  A  T  P  S  P  I  I  Q  Q  L
1501 TACAGAATCCAGGCTCAATGATAATGTTTTTGCCACTCCCAGCCCCATCATCCAGCAGTT
 192  E  K  S  D  A  E  Y  T  N  S  P  L  V  P  T  F  C  T  P  G
1561 GGAAAAAAGTGATGCCGAATATACCAACTCTCCTTTGGTACCTACATTCTGTACTCCTGG
 212  L  K  I  P  S  T  K  N  S  I  A  L  V  S  T  N  Y  P  L  S
1621 TTTGAAAATTCCATCTACAAAGAACAGCATAGCTTTGGTATCCACAAATTACCCATTATC
 232  K  T  N  S  S  S  N  D  L  E  V  E  D  R  T  S  L  V  L  N
1681 AAAAACAAATAGTTCATCAAATGATTTGGAAGTTGAAGATCGTACTTCGTTGGTTTTAAA
 252  S  D  T  C  F  E  N  L  T  D  P  S  S  P  T  I  S  S  Y  E
1741 TTCAGACACATGCTTTGAGAATTTAACAGATCCCTCTTCACCTACGATTTCTTCTTATGA
 272  N  L  L  R  T  P  T  P  P  E  V  T  K  I  P  E  D  I  L  Q
1801 GAATCTGCTCAGAACACCTACACCTCCAGAAGTAACTAAAATTCCAGAAGATATTCTCCA
 292  K  F  Q  W  I  Y  P  T  Q  K  L  N  K  M  R  *
1861 GAAATTCCAGTGGATCTATCCAACACAGAAACTGAACAAAATGAGATGAaagccgagctg
1921 gaccgattttaacattcacattgccctgcctctgtcccccttttaaacgttgacccatttt
1981 aaagacaaacatgaacattaacatcataatatgctttttatgaagtttcaataaggttta
2041 accttagtcttgttgacatgtagcccagtcattcactctttaaggactattagtgtttca
```

Figure 2K-3

```
2101 ttgatactaaattacccagcttaatcaacagaatggtttaagtagtaccaggaagtagga
2161 caagtaatttcaaaaatataaaggtgtttgctactcagatgaggccgcccctgaccttct
2221 ggccagagagacattgctgccagccagctctgccttcccatcatctcctttcaggaccgt
2281 cccacaccttttacttgctcagtgctgtctgaagatgcagttgctgtttgcaaacaacag
2341 gaacaccagttaaactaattaggaaacagagggagatttccaggcctgggtaactatata
2401 ctgtgaccattggcggttgagaccggtcttcaaccagtggaaccccgaactctgctgtca
2461 gggtgtggacttcggtgctcttccaagttttcacctgggggggggagctaacccccctatg
2521 ttcacgccttctattcccattggcgctgaactcttaaggtcactctggtcgcttgtgacc
2581 ccgtaaccctgatgtacccctctaaaaggtgaggggc
```

Figure 2L. The cDNA (SEQ ID NO: 24) and amino acid sequence (SEQ ID NO: 25) of 193P1E1B v.12. The start methionine is underlined. The open reading frame extends from nucleic acid 805-1026 including the stop codon.

```
   1 tatcatctgtgactgaggaaatccctatcttcctatcagactaatgaaaccacaggacag
  61 caattagacttttaagtattgggggtttagagctctagatattcgatatgcagactact
 121 catgtttgtttgttttaataaagactggtccaaaggctcattttcacacaagctacagtt
 181 tttcagttccaggaccaggtaaagatggtcagctccgtgatccataaaatccaagggtga
 241 cgactcaggattaggaccatttcttggtgacattgagatggtcgagctggtccgcaatga
 301 atctatgcgggggggaacttggaagtggcggccgcctttatggcctcgaaggcctccctcc
 361 tgcgcaccgcggcgtggccgcgctcctgctcccgggtcatgtagggcatgctcagccagt
 421 aatggttctccgcctcgatctccaggcggcggatcatgttctgcttggcgcgcaacgaca
 481 cgaaccgcggccgccggtgcttcccgatccactgacggccgggaatgcggccgcgccaga
 541 ggagcgcagtcaggaacatggtgcctgccgcgctgctcaagactctgcgtctccgcggcc
 601 gccagcagacgccgtggcgtaagcgcacccgtctcgcggggtctccgggggcctcggcga
 661 gagacttcggctctcgcgagagaggactgcgcctgcgcagagccgaggacgcgtccggcg
 721 ccgagattcaaactagtggcgggaggctgtgagctgagcggtggggtctgcgtacgcctg
   1                         M  D  P  I  R  S  F  C  G  K  L  R
 781 gagtccttccccgctgtgctcagcATGGACCCTATCCGGAGCTTCTGCGGGAAGCTGCGG
  13 S  L  A  S  T  L  D  C  E  T  A  R  L  Q  R  A  L  D  G  E
 841 TCTCTGGCCAGCACGCTGGACTGCGAGACGGCCCGGCTGCAGCGAGCGCTGGACGGAGAG
  33 E  S  L  L  S  K  Y  N  S  N  L  A  T  P  I  A  I  K  A  V
 901 GAAAGCCTTTTATCAAAATACAACTCAAACCTAGCTACTCCAATAGCAATTAAAGCAGTG
  53 P  P  S  K  R  F  L  K  H  G  Q  N  I  R  D  V  S  N  K  E
 961 CCACCCAGTAAAAGGTTCCTTAAACATGGACAGAACATCCGAGATGTCAGCAACAAAGAA
  73 N  *
1021 AACTGAaattccagtggatctatccaacacagaaactgaacaaaatgagatgaaagccga
1081 gctggaccgattttaacattcacattgccctgcctctgtcccccctttaaacgttgaccca
1141 ttttaaagacaaacatgaacattaacatcataatatgctttttatgaagtttcaataagg
1201 tttaaccttagtcttgttgacatgtagcccagtcattcactctttaaggactattagtgt
1261 ttcattgatactaaattacccagcttaatcaacagaatggtttaagtagtaccaggaagt
```

Figure 2L-2

```
1321 aggacaagtaatttcaaaaatataaaggtgtttgctactcagatgaggccgcccctgacc
1381 ttctggccagagagacattgctgccagccagctctgccttcccatcatctcctttcagga
1441 ccgtcccacaccttttacttgctcagtgctgtctgaagatgcagttgctgtttgcaaaca
1501 acaggaacaccagttaaactaattaggaaacagagggagatttccaggcctgggtaacta
1561 tatactgtgaccattggcggttgagaccggtcttcaaccagtggaaccccgaactctgct
1621 gtcagggtgtggacttcggtgctcttccaagttttcacctgggggggggagctaaccccc
1681 tatgttcacgccttctattcccattggcgctgaactcttaaggtcactctggtcgcttgt
1741 gaccccgtaaccctgatgtacccctctaaaaggtgaggggc
```

Figure 2M. The cDNA (SEQ ID NO: 26) and amino acid sequence (SEQ ID NO: 27) of 193P1E1B v.13. The start methionine is underlined. The open reading frame extends from nucleic acid 952-2070 including the stop codon.

```
   1 tatcatctgtgactgaggaaatccctatcttcctatcagactaatgaaaccacaggacag
  61 caattagacttttaagtattgggggtttagagctctagatattcgatatgcagactact
 121 catgtttgtttgttttaataaagactggtccaaaggctcattttcacacaagctacagtt
 181 tttcagttccaggaccaggtaaagatggtcagctccgtgatccataaaatccaagggtga
 241 cgactcaggattaggaccatttcttggtgacattgagatggtcgagctggtccgcaatga
 301 atctatgcgggggaacttggaagtggcggccgcctttatggcctcgaaggcctccctcc
 361 tgcgcaccgcggcgtggccgcgctcctgctcccgggtcatgtagggcatgctcagccagt
 421 aatggttctccgcctcgatctccaggcggcggatcatgttctgcttggcgcgcaacgaca
 481 cgaaccgcggccgccggtgcttcccgatccactgacggccgggaatgcggccgcgccaga
 541 ggagcgcagtcaggaacatggtgcctgccgcgctgctcaagactctgcgtctccgcggcc
 601 gccagcagacgccgtggcgtaagcgcacccgtctcgcggggtctccgggggcctcggcga
 661 gagacttcggctctcgcgagagaggactgcgcctgcgcagagccgaggacgcgtccggcg
 721 ccgagattcaaactagtggcgggaggctgtgagctgagcggtggggtctgcgtacgcctg
 781 gagtccttccccgctgtgctcagcatggaccctatccggagcttctgcgggaagctgcgg
 841 tctctggccagcacgctggactgcgagacggcccggctgcagcgagcgctggacggagag
   1                                                        M  R  I
 901 gaaagcggtgcgtgaggcgggcggccagggcacgactttgaagattatccaATGAGAATT
   4 L  Y  D  L  H  S  E  V  Q  T  L  K  D  D  V  N  I  L  L  D
 961 TTATATGACCTTCATTCAGAAGTTCAGACTCTAAAGGATGATGTTAATATTCTTCTTGAT
  24 K  A  R  L  E  N  Q  E  G  I  D  F  I  K  A  T  K  V  L  M
1021 AAAGCAAGATTGGAAAATCAAGAAGGCATTGATTTCATAAAGGCAACAAAAGTACTAATG
  44 E  K  N  S  M  D  I  M  K  I  R  E  Y  F  Q  K  Y  G  Y  S
1081 GAAAAAAATTCAATGGATATTATGAAAATAAGAGAGTATTTCCAGAAGTATGGATATAGT
  64 P  R  V  K  K  N  S  V  H  E  Q  E  A  I  N  S  D  P  E  L
1141 CCACGTGTCAAGAAAAATTCAGTACACGAGCAAGAAGCCATTAACTCTGACCCAGAGTTG
  84 S  N  C  E  N  F  Q  K  T  D  V  K  D  D  L  S  D  P  P  V
1201 TCTAATTGTGAAAATTTTCAGAAGACTGATGTGAAAGATGATCTGTCTGATCCTCCTGTT
 104 A  S  S  C  I  S  G  K  S  P  R  S  P  Q  L  S  D  F  G  L
```

Figure 2M-2

```
1261 GCAAGCAGTTGTATTTCTGGGAAGTCTCCACGTAGTCCACAACTTTCAGATTTTGGACTT
 124 E  R  Y  I  V  S  Q  V  L  P  N  P  P  Q  A  V  N  N  Y  K
1321 GAGCGGTACATCGTATCCCAAGTTCTACCAAACCCTCCACAGGCAGTGAACAACTATAAG
 144 E  E  P  V  I  V  T  P  P  T  K  Q  S  L  V  K  V  L  K  T
1381 GAAGAGCCCGTAATTGTAACCCCACCTACCAAACAATCACTAGTAAAAGTACTAAAAACT
 164 P  K  C  A  L  K  M  D  D  F  E  C  V  T  P  K  L  E  H  F
1441 CCAAAATGTGCACTAAAAATGGATGATTTTGAGTGTGTAACTCCTAAATTAGAACACTTT
 184 G  I  S  E  Y  T  M  C  L  N  E  D  Y  T  M  G  L  K  N  A
1501 GGTATCTCTGAATATACTATGTGTTTAAATGAAGATTACACAATGGGACTTAAAAATGCG
 204 R  N  N  K  S  E  E  A  I  D  T  E  S  R  L  N  D  N  V  F
1561 AGGAATAATAAAAGTGAGGAGGCCATAGATACAGAATCCAGGCTCAATGATAATGTTTTT
 224 A  T  P  S  P  I  I  Q  Q  L  E  K  S  D  A  E  Y  T  N  S
1621 GCCACTCCCAGCCCCATCATCCAGCAGTTGGAAAAAAGTGATGCCGAATATACCAACTCT
 244 P  L  V  P  T  F  C  T  P  G  L  K  I  P  S  T  K  N  S  I
1681 CCTTTGGTACCTACATTCTGTACTCCTGGTTTGAAAATTCCATCTACAAAGAACAGCATA
 264 A  L  V  S  T  N  Y  P  L  S  K  T  N  S  S  S  N  D  L  E
1741 GCTTTGGTATCCACAAATTACCCATTATCAAAAACAAATAGTTCATCAAATGATTTGGAA
 284 V  E  D  R  T  S  L  V  L  N  S  D  T  C  F  E  N  L  T  D
1801 GTTGAAGATCGTACTTCGTTGGTTTTAAATTCAGACACATGCTTTGAGAATTTAACAGAT
 304 P  S  S  P  T  I  S  S  Y  E  N  L  L  R  T  P  T  P  P  E
1861 CCCTCTTCACCTACGATTTCTTCTTATGAGAATCTGCTCAGAACACCTACACCTCCAGAA
 324 V  T  K  I  P  E  D  I  L  Q  L  L  S  K  Y  N  S  N  L  A
1921 GTAACTAAAATTCCAGAAGATATTCTCCAGCTTTTATCAAAATACAACTCAAACCTAGCT
 344 T  P  I  A  I  K  A  V  P  P  S  K  R  F  L  K  H  G  Q  N
1981 ACTCCAATAGCAATTAAAGCAGTGCCACCCAGTAAAAGGTTCCTTAAACATGGACAGAAC
 364 I  R  D  V  S  N  K  E  N  *
2041 ATCCGAGATGTCAGCAACAAAGAAAACTGAaattccagtggatctatccaacacagaaac
2101 tgaacaaaatgagatgaaagccgagctggaccgattttaacattcacattgccctgcctc
2161 tgtccccctttaaacgttgacccatttttaaagacaaacatgaacattaacatcataatat
2221 gctttttatgaagtttcaataaggtttaaccttagtcttgttgacatgtagcccagtcat
2281 tcactctttaaggactattagtgtttcattgatactaaattacccagcttaatcaacaga
2341 atggtttaagtagtaccaggaagtaggacaagtaatttcaaaaatataaaggtgtttgct
2401 actcagatgaggccgcccctgaccttctggccagagagacattgctgccagccagctctg
2461 ccttcccatcatctcctttcaggaccgtcccacaccttttacttgctcagtgctgtctga
2521 agatgcagttgctgtttgcaaacaacaggaacaccagttaaactaattaggaaacagagg
2581 gagatttccaggcctgggtaactatatactgtgaccattggcggttgagaccggtcttca
2641 accagtggaaccccgaactctgctgtcagggtgtggacttcggtgctcttccaagttttc
2701 acctgggggggggagctaacccccctatgttcacgccttctattcccattggcgctgaact
2761 cttaaggtcactctggtcgcttgtgaccccgtaaccctgatgtacccctctaaaaggtga
2821 ggggc
```

Figure 3:

Figure 3A. Amino acid sequence of 193P1E1B v.1 (SEQ ID NO: 28). The 193P1E1B v.1 protein has 412 amino acids.

```
  1 MDPIRSFCGK LRSLASTLDC ETARLQRALD GEESDFEDYP MRILYDLHSE VQTLKDDVNI
 61 LLDKARLENQ EGIDFIKATK VLMEKNSMDI MKIREYFQKY GYSPRVKKNS VHEQEAINSD
121 PELSNCENFQ KTDVKDDLSD PPVASSCISG KSPRSPQLSD FGLERYIVSQ VLPNPPQAVN
181 NYKEEPVIVT PPTKQSLVKV LKTPKCALKM DDFECVTPKL EHFGISEYTM CLNEDYTMGL
241 KNARNNKSEE AIDTESRLND NVFATPSPII QQLEKSDAEY TNSPLVPTFC TPGLKIPSTK
301 NSIALVSTNY PLSKTNSSSN DLEVEDRTSL VLNSDTCFEN LTDPSSPTIS SYENLLRTPT
361 PPEVTKIPED ILQLLSKYNS NLATPIAIKA VPPSKRFLKH GQNIRDVSNK EN
```

Figure 3B. Amino acid sequence of 193P1E1B v.5 (SEQ ID NO: 29). The 193P1E1B v.5 protein has 412 amino acids.

```
  1 MDPIRSFCGK LRSLASTLDC ETARLQRALD GEESDFEDYP MRILYDLHSE VQTLKDDVNI
 61 LLDKARLENQ EGIDFIKATK VLMEKNSMDI MKIREYFQKY GYSPRVKKNS VHEQEAINSD
121 PELSNCENFQ KTDVKDDLSD PPVASSCISE KSPRSPQLSD FGLERYIVSQ VLPNPPQAVN
181 NYKEEPVIVT PPTKQSLVKV LKTPKCALKM DDFECVTPKL EHFGISEYTM CLNEDYTMGL
241 KNARNNKSEE AIDTESRLND NVFATPSPII QQLEKSDAEY TNSPLVPTFC TPGLKIPSTK
301 NSIALVSTNY PLSKTNSSSN DLEVEDRTSL VLNSDTCFEN LTDPSSPTIS SYENLLRTPT
361 PPEVTKIPED ILQLLSKYNS NLATPIAIKA VPPSKRFLKH GQNIRDVSNK EN
```

Figure 3C. Amino acid sequence of 193P1E1B v.6 (SEQ ID NO: 30). The 193P1E1B v.6 protein has 412 amino acids.

```
  1 MDPIRSFCGK LRSLASTLDC ETARLQRALD GEESDFEDYP MRILYDLHSE VQTLKDDVNI
 61 LLDKARLENQ EGIDFIKATK VLMEKNSMDI MKIREYFQKY GYSPRVKKNS VHEQEAINSD
121 PELSNCENFQ KTDVKDDLSD PPVASSCISG KSPRSPQLSD FGLERYIVSQ VLPNPPQAVN
181 NYKEEPVIVT PPTKQSLVKV LKTPKCALKM DDFECVTPKL EHFGISEYTM CLNEDYTMGL
241 KNARNNKSEE AIDAESRLND NVFATPSPII QQLEKSDAEY TNSPLVPTFC TPGLKIPSTK
301 NSIALVSTNY PLSKTNSSSN DLEVEDRTSL VLNSDTCFEN LTDPSSPTIS SYENLLRTPT
361 PPEVTKIPED ILQLLSKYNS NLATPIAIKA VPPSKRFLKH GQNIRDVSNK EN
```

Figure 3D. Amino acid sequence of 193P1E1B v.9 (SEQ ID NO: 31). The 193P1E1B v.9 protein has 330 amino acids.

```
  1 MEKNSMDIMK IREYFQKYGY SPRVKKNSVH EQEAINSDPE LSNCENFQKT DVKDDLSDPP
 61 VASSCISEKS PRSPQLSDFG LERYIVSQVL PNPPQAVNNY KEEPVIVTPP TKQSLVKVLK
121 TPKCALKMDD FECVTPKLEH FGISEYTMCL NEDYTMGLKN ARNNKSEEAI DTESRLNDNV
181 FATPSPIIQQ LEKSDAEYTN SPLVPTFCTP GLKIPSTKNS IALVSTNYPL SKTNSSSNDL
241 EVEDRTSLVL NSDTCFENLT DPSSPTISSY ENLLRTPTPP EVTKIPEDIL QLLSKYNSNL
301 ATPIAIKAVP PSKRFLKHGQ NIRDVSNKEN
```

Figure 3E. Amino acid sequence of 193P1E1B v.10 (SEQ ID NO: 32). The 193P1E1B v.10 protein has 388 amino acids.

```
  1 MDPIRSFCGK LRSLASTLDC ETARLQRALD GEESDFEDYP MRILYDLHSE VQTLKDDVNI
 61 LLDKARLENQ EGIDFIKATK VLMEKNSMDI MKIREYFQKY GYSPRVKKNS VHEQEAINSD
121 PELSNCENFQ KTDVKDDLSD PPVASSCISE KSPRSPQLSD FGLERYIVSQ VLPNPPQAVN
181 NYKEEPVIVT PPTKQSLVKV LKTPKCALKM DDFECVTPKL EHFGISEYTM CLNEDYTMGL
241 KNARNNKSEE AIDTESRLND NVFATPSPII QQLEKSDAEY TNSPLVPTFC TPGLKIPSTK
301 NSIALVSTNY PLSKTNSSSN DLEVEDRTSL VLNSDTCFEN LTDPSSPTIS SYENLLRTPT
361 PPEVTKIPED ILQKFQWIYP TQKLNKMR
```

Figure 3F. Amino acid sequence of 193P1E1B v.11 (SEQ ID NO: 33). The 193P1E1B v.11 protein has 308 amino acids.

```
  1 MEKNSMDIMK IREYFQKYGY SPRVKKNSVH EQEAINSDPE LSNCENFQKT DVKDDLSDPP
 61 VASSCISGKS PRSPQLSDFG LERYIVSQVL PNPPQAVNNY KEEPVIVTPP TKQSLVKVLK
121 TPKCALKMDD FECVTPKLEH FGISEYTMCL NEDYTMGLKN ARNNKSEEAI DTESRLNDNV
181 FATPSPIIQQ LEKSDAEYTN SPLVPTFCTP GLKIPSTKNS IALVSTNYPL SKTNSSSNDL
241 EVEDRTSLVL NSDTCFENLT DPSSPTISSY ENLLRTPTPP EVTKIPEDIL QKFQWIYPTQ
301 KLNKMR
```

Figure 3G. Amino acid sequence of 193P1E1B v.12 (SEQ ID NO: 34). The 193P1E1B v.12 protein has 73 amino acids.

```
  1 MDPIRSFCGK LRSLASTLDC ETARLQRALD GEESLLSKYN SNLATPIAIK AVPPSKRFLK
 61 HGQNIRDVSN KEN
```

Figure 3H. Amino acid sequence of 193P1E1B v.13 (SEQ ID NO: 35). The 193P1E1B v.13 protein has 372 amino acids.

```
  1 MRILYDLHSE VQTLKDDVNI LLDKARLENQ EGIDFIKATK VLMEKNSMDI MKIREYFQKY
 61 GYSPRVKKNS VHEQEAINSD PELSNCENFQ KTDVKDDLSD PPVASSCISG KSPRSPQLSD
121 FGLERYIVSQ VLPNPPQAVN NYKEEPVIVT PPTKQSLVKV LKTPKCALKM DDFECVTPKL
181 EHFGISEYTM CLNEDYTMGL KNARNNKSEE AIDTESRLND NVFATPSPII QQLEKSDAEY
241 TNSPLVPTFC TPGLKIPSTK NSIALVSTNY PLSKTNSSSN DLEVEDRTSL VLNSDTCFEN
301 LTDPSSPTIS SYENLLRTPT PPEVTKIPED ILQLLSKYNS NLATPIAIKA VPPSKRFLKH
361 GQNIRDVSNK EN
```

Figure 4:

Figures 4A-D: Alignment of 193P1E1B variants with the human un-named protein gi 21748775

4A) Alignment of 193P1E1B v.1 (SEQ ID NO: 36) with gi 2178775 (SEQ ID NO: 37)

```
Identities = 372/373 (99%), Positives = 372/373 (99%)

Query: 1   MDPIRSFCGKLRSLASTLDCETARLQRALDGEESDFEDYPMRILYDLHSEVQTLKDDVNI 60
            MDPIRSFCGKLRSLASTLDCETARLQRALDGEESDFEDYPMRILYDLHSEVQTLKDDVNI
Sbjct: 1   MDPIRSFCGKLRSLASTLDCETARLQRALDGEESDFEDYPMRILYDLHSEVQTLKDDVNI 60

Query: 61  LLDKARLENQEGIDFIKATKVLMEKNSMDIMKIREYFQKYGYSPRVKKNSVHEQEAINSD 120
            LLDKARLENQEGIDFIKATKVLMEKNSMDIMKIREYFQKYGYSPRVKKNSVHEQEAINSD
Sbjct: 61  LLDKARLENQEGIDFIKATKVLMEKNSMDIMKIREYFQKYGYSPRVKKNSVHEQEAINSD 120

Query: 121 PELSNCENFQKTDVKDDLSDPPVASSCISGKSPRSPQLSDFGLERYIVSQVLPNPPQAVN 180
            PELSNCENFQKTDVKDDLSDPPVASSCIS KSPRSPQLSDFGLERYIVSQVLPNPPQAVN
Sbjct: 121 PELSNCENFQKTDVKDDLSDPPVASSCISEKSPRSPQLSDFGLERYIVSQVLPNPPQAVN 180

Query: 181 NYKEEPVIVTPPTKQSLVKVLKTPKCALKMDDFECVTPKLEHFGISEYTMCLNEDYTMGL 240
            NYKEEPVIVTPPTKQSLVKVLKTPKCALKMDDFECVTPKLEHFGISEYTMCLNEDYTMGL
Sbjct: 181 NYKEEPVIVTPPTKQSLVKVLKTPKCALKMDDFECVTPKLEHFGISEYTMCLNEDYTMGL 240

Query: 241 KNARNNKSEEAIDTESRLNDNVFATPSPIIQQLEKSDAEYTNSPLVPTFCTPGLKIPSTK 300
            KNARNNKSEEAIDTESRLNDNVFATPSPIIQQLEKSDAEYTNSPLVPTFCTPGLKIPSTK
Sbjct: 241 KNARNNKSEEAIDTESRLNDNVFATPSPIIQQLEKSDAEYTNSPLVPTFCTPGLKIPSTK 300

Query: 301 NSIALVSTNYPLSKTNSSSNDLEVEDRTSLVLNSDTCFENLTDPSSPTISSYENLLRTPT 360
            NSIALVSTNYPLSKTNSSSNDLEVEDRTSLVLNSDTCFENLTDPSSPTISSYENLLRTPT
Sbjct: 301 NSIALVSTNYPLSKTNSSSNDLEVEDRTSLVLNSDTCFENLTDPSSPTISSYENLLRTPT 360

Query: 361 PPEVTKIPEDILQ 373
            PPEVTKIPEDILQ
Sbjct: 361 PPEVTKIPEDILQ 373
```

4B) Alignment of 193P1E1B v.5 (SEQ ID NO: 38) with gi 2178775 (SEQ ID NO: 39)

```
Identities = 372/373 (100%), Positives = 372/373 (100%)

Query: 1   MDPIRSFCGKLRSLASTLDCETARLQRALDGEESDFEDYPMRILYDLHSEVQTLKDDVNI 60
            MDPIRSFCGKLRSLASTLDCETARLQRALDGEESDFEDYPMRILYDLHSEVQTLKDDVNI
Sbjct: 1   MDPIRSFCGKLRSLASTLDCETARLQRALDGEESDFEDYPMRILYDLHSEVQTLKDDVNI 60

Query: 61  LLDKARLENQEGIDFIKATKVLMEKNSMDIMKIREYFQKYGYSPRVKKNSVHEQEAINSD 120
            LLDKARLENQEGIDFIKATKVLMEKNSMDIMKIREYFQKYGYSPRVKKNSVHEQEAINSD
Sbjct: 61  LLDKARLENQEGIDFIKATKVLMEKNSMDIMKIREYFQKYGYSPRVKKNSVHEQEAINSD 120

Query: 121 PELSNCENFQKTDVKDDLSDPPVASSCISEKSPRSPQLSDFGLERYIVSQVLPNPPQAVN 180
            PELSNCENFQKTDVKDDLSDPPVASSCISEKSPRSPQLSDFGLERYIVSQVLPNPPQAVN
Sbjct: 121 PELSNCENFQKTDVKDDLSDPPVASSCISEKSPRSPQLSDFGLERYIVSQVLPNPPQAVN 180

Query: 181 NYKEEPVIVTPPTKQSLVKVLKTPKCALKMDDFECVTPKLEHFGISEYTMCLNEDYTMGL 240
            NYKEEPVIVTPPTKQSLVKVLKTPKCALKMDDFECVTPKLEHFGISEYTMCLNEDYTMGL
Sbjct: 181 NYKEEPVIVTPPTKQSLVKVLKTPKCALKMDDFECVTPKLEHFGISEYTMCLNEDYTMGL 240

Query: 241 KNARNNKSEEAIDTESRLNDNVFATPSPIIQQLEKSDAEYTNSPLVPTFCTPGLKIPSTK 300
            KNARNNKSEEAIDTESRLNDNVFATPSPIIQQLEKSDAEYTNSPLVPTFCTPGLKIPSTK
Sbjct: 241 KNARNNKSEEAIDTESRLNDNVFATPSPIIQQLEKSDAEYTNSPLVPTFCTPGLKIPSTK 300

Query: 301 NSIALVSTNYPLSKTNSSSNDLEVEDRTSLVLNSDTCFENLTDPSSPTISSYENLLRTPT 360
            NSIALVSTNYPLSKTNSSSNDLEVEDRTSLVLNSDTCFENLTDPSSPTISSYENLLRTPT
Sbjct: 301 NSIALVSTNYPLSKTNSSSNDLEVEDRTSLVLNSDTCFENLTDPSSPTISSYENLLRTPT 360

Query: 361 PPEVTKIPEDILQ 373
            PPEVTKIPEDILQ
Sbjct: 361 PPEVTKIPEDILQ 373
```

4C) Alignment of 193P1E1B v.11 (SEQ ID NO: 40) with gi 2178775 (SEQ ID NO: 41)

```
Identities = 388/388 (100%), Positives = 388/388 (100%)

Query: 1   MDPIRSFCGKLRSLASTLDCETARLQRALDGEESDFEDYPMRILYDLHSEVQTLKDDVNI 60
           MDPIRSFCGKLRSLASTLDCETARLQRALDGEESDFEDYPMRILYDLHSEVQTLKDDVNI
Sbjct: 1   MDPIRSFCGKLRSLASTLDCETARLQRALDGEESDFEDYPMRILYDLHSEVQTLKDDVNI 60

Query: 61  LLDKARLENQEGIDFIKATKVLMEKNSMDIMKIREYFQKYGYSPRVKKNSVHEQEAINSD 120
           LLDKARLENQEGIDFIKATKVLMEKNSMDIMKIREYFQKYGYSPRVKKNSVHEQEAINSD
Sbjct: 61  LLDKARLENQEGIDFIKATKVLMEKNSMDIMKIREYFQKYGYSPRVKKNSVHEQEAINSD 120

Query: 121 PELSNCENFQKTDVKDDLSDPPVASSCISEKSPRSPQLSDFGLERYIVSQVLPNPPQAVN 180
           PELSNCENFQKTDVKDDLSDPPVASSCISEKSPRSPQLSDFGLERYIVSQVLPNPPQAVN
Sbjct: 121 PELSNCENFQKTDVKDDLSDPPVASSCISEKSPRSPQLSDFGLERYIVSQVLPNPPQAVN 180

Query: 181 NYKEEPVIVTPPTKQSLVKVLKTPKCALKMDDFECVTPKLEHFGISEYTMCLNEDYIMGL 240
           NYKEEPVIVTPPTKQSLVKVLKTPKCALKMDDFECVTPKLEHFGISEYTMCLNEDYIMGL
Sbjct: 181 NYKEEPVIVTPPTKQSLVKVLKTPKCALKMDDFECVTPKLEHFGISEYTMCLNEDYIMGL 240

Query: 241 KNARNNKSEEAIDTESRLNDNVFATPSPIIQQLEKSDAEYTNSPLVPTFCTPGLKIPSTK 300
           KNARNNKSEEAIDTESRLNDNVFATPSPIIQQLEKSDAEYTNSPLVPTFCTPGLKIPSTK
Sbjct: 241 KNARNNKSEEAIDTESRLNDNVFATPSPIIQQLEKSDAEYTNSPLVPTFCTPGLKIPSTK 300

Query: 301 NSIALVSTNYPLSKTNSSSNDLEVEDRTSLVLNSDTCFENLTDPSSPTISSYENLLRTPT 360
           NSIALVSTNYPLSKTNSSSNDLEVEDRTSLVLNSDTCFENLTDPSSPTISSYENLLRTPT
Sbjct: 301 NSIALVSTNYPLSKTNSSSNDLEVEDRTSLVLNSDTCFENLTDPSSPTISSYENLLRTPT 360

Query: 361 PPEVTKIPEDILQKFQWIYPTQKLNKMR 388
           PPEVTKIPEDILQKFQWIYPTQKLNKMR
Sbjct: 361 PPEVTKIPEDILQKFQWIYPTQKLNKMR 388
```

4D) Alignment of 193P1E1B v.12 (SEQ ID NO: 42) with gi 2178775 (SEQ ID NO: 43)

```
Identities = 35/39 (89%), Positives = 35/39 (89%)

Query: 1  MDPIRSFCGKLRSLASTLDCETARLQRALDGEESLLSKY 39
          MDPIRSFCGKLRSLASTLDCETARLQRALDGEES    Y
Sbjct: 1  MDPIRSFCGKLRSLASTLDCETARLQRALDGEESDFEDY 39
```

**Figure 4E: Alignment of 193P1E1B v.1 (SEQ ID NO: 44) with *E coli* arginine repressor (SEQ ID NO: 45)**

```
Identities = 15/49 (30%), Positives = 28/49 (57%), Gaps = 2/49 (4%)

Query: 58  VNILLDKARLENQEGIDFIKA--TKVLMEKNSMDIMKIREYFQKYGYSP 104
           + +L+D+ R+ N   +  I    T +++ KN  D +++  YFQ+Y Y P
Sbjct: 111 IGVLIDRIRIHNPHILGCIAGDDTILILSKNKEDALEVNNYFQQYLYHP 159
```

Figure 4F: Alignment of 193P1E1B v.1 (SEQ ID NO: 46) with human adenosine deaminase (SEQ ID NO: 47)

```
Identities = 38/143 (26%), Positives = 58/143 (40%), Gaps = 30/143 (20%)

Query: 18  LDCETARLQRALDGEESDFEDYPMRIL--------------YDLHSEVQTLKDDVNILLD 63
           +DC ++  Q     E S ++D   RIL              +DL  ++ T K ++N +L
Sbjct: 123 VDCLSSHFQ-----ELSIYQDQEQRILKFLEELGEGKATTAHDLSGKLGTPKKEINRVL- 176

Query: 64  KARLENQEGIDFIKATKVLMEKNSMDIMKIREYFQKYGYSPRVKKNSVHEQEAINSDPEL 123
                        K  K+  E  +  + KI    Q +    V +   H Q A NSDP L
Sbjct: 177 ---------YSLAKKGKLQKEAGIPPLWKIAVSTQAWNQHSGVVRPDGHSQGAPNSDPSL 227

Query: 124 SNCENFQKTDVKDDLSDPPVASS 146
              E+   T V +DL +P +A S
Sbjct: 228 EP-EDRNSTSVSEDLLEPFIAVS 249
```

Figure 4G: Clustal Alignment of 193P1E1B protein variants (SEQ ID NOS: 3, 11, 13, 19, 21, 23, 25, and 27)

Variants v.1, v.5 and v.6 differ from each other by one amino acid each, with corresponding SNP location shown in red.

```
v.1             MDPIRSFCGKLRSLASTLDCETARLQRALDGEESDFEDYPMRILYDLHSEVQTLKDDVNI
v.5             MDPIRSFCGKLRSLASTLDCETARLQRALDGEESDFEDYPMRILYDLHSEVQTLKDDVNI
v.6             MDPIRSFCGKLRSLASTLDCETARLQRALDGEESDFEDYPMRILYDLHSEVQTLKDDVNI
v.9             ------------------------------------------------------------
v.10            MDPIRSFCGKLRSLASTLDCETARLQRALDGEESDFEDYPMRILYDLHSEVQTLKDDVNI
v.11            ------------------------------------------------------------
v.12            MDPIRSFCGKLRSLASTLDCETARLQRALDGEES--------------------------
v.13            ----------------------------------------MRILYDLHSEVQTLKDDVNI

v.1             LLDKARLENQEGIDFIKATKVLMEKNSMDIMKIREYFQKYGYSPRVKKNSVHEQEAINSD
v.5             LLDKARLENQEGIDFIKATKVLMEKNSMDIMKIREYFQKYGYSPRVKKNSVHEQEAINSD
v.6             LLDKARLENQEGIDFIKATKVLMEKNSMDIMKIREYFQKYGYSPRVKKNSVHEQEAINSD
v.9             ----------------------MEKNSMDIMKIREYFQKYGYSPRVKKNSVHEQEAINSD
v.10            LLDKARLENQEGIDFIKATKVLMEKNSMDIMKIREYFQKYGYSPRVKKNSVHEQEAINSD
v.11            ----------------------MEKNSMDIMKIREYFQKYGYSPRVKKNSVHEQEAINSD
v.12            ------------------------------------------------------------
v.13            LLDKARLENQEGIDFIKATKVLMEKNSMDIMKIREYFQKYGYSPRVKKNSVHEQEAINSD

v.1             PELSNCENFQKTDVKDDLSDPPVASSCISGKSPRSPQLSDFGLERYIVSQVLPNPPQAVN
v.5             PELSNCENFQKTDVKDDLSDPPVASSCISEKSPRSPQLSDFGLERYIVSQVLPNPPQAVN
v.6             PELSNCENFQKTDVKDDLSDPPVASSCISGKSPRSPQLSDFGLERYIVSQVLPNPPQAVN
v.9             PELSNCENFQKTDVKDDLSDPPVASSCISEKSPRSPQLSDFGLERYIVSQVLPNPPQAVN
v.10            PELSNCENFQKTDVKDDLSDPPVASSCISEKSPRSPQLSDFGLERYIVSQVLPNPPQAVN
v.11            PELSNCENFQKTDVKDDLSDPPVASSCISGKSPRSPQLSDFGLERYIVSQVLPNPPQAVN
v.12            ------------------------------------------------------------
v.13            PELSNCENFQKTDVKDDLSDPPVASSCISGKSPRSPQLSDFGLERYIVSQVLPNPPQAVN
                                   **  : .    . . : : .   *:* : .:    .    *

v.1             NYKEEPVIVTPPTKQSLVKVLKTPKCALKMDDFECVTPKLEHFGISEYTMCLNEDYTMGL
v.5             NYKEEPVIVTPPTKQSLVKVLKTPKCALKMDDFECVTPKLEHFGISEYTMCLNEDYTMGL
v.6             NYKEEPVIVTPPTKQSLVKVLKTPKCALKMDDFECVTPKLEHFGISEYTMCLNEDYTMGL
v.9             NYKEEPVIVTPPTKQSLVKVLKTPKCALKMDDFECVTPKLEHFGISEYTMCLNEDYTMGL
v.10            NYKEEPVIVTPPTKQSLVKVLKTPKCALKMDDFECVTPKLEHFGISEYTMCLNEDYTMGL
v.11            NYKEEPVIVTPPTKQSLVKVLKTPKCALKMDDFECVTPKLEHFGISEYTMCLNEDYTMGL
v.12            ------------------------------------------------------------
v.13            NYKEEPVIVTPPTKQSLVKVLKTPKCALKMDDFECVTPKLEHFGISEYTMCLNEDYTMGL
                  .  .: ..**:*: * :  :  . : * :

v.1             KNARNNKSEEAIDTESRLNDNVFATPSPIIQQLEKSDAEYTNSPLVPTFCTPGLKIPSTK
v.5             KNARNNKSEEAIDTESRLNDNVFATPSPIIQQLEKSDAEYTNSPLVPTFCTPGLKIPSTK
v.6             KNARNNKSEEAIDAESRLNDNVFATPSPIIQQLEKSDAEYTNSPLVPTFCTPGLKIPSTK
v.9             KNARNNKSEEAIDTESRLNDNVFATPSPIIQQLEKSDAEYTNSPLVPTFCTPGLKIPSTK
v.10            KNARNNKSEEAIDTESRLNDNVFATPSPIIQQLEKSDAEYTNSPLVPTFCTPGLKIPSTK
v.11            KNARNNKSEEAIDTESRLNDNVFATPSPIIQQLEKSDAEYTNSPLVPTFCTPGLKIPSTK
v.12            ------------------------------------------------------------
v.13            KNARNNKSEEAIDTESRLNDNVFATPSPIIQQLEKSDAEYTNSPLVPTFCTPGLKIPSTK

v.1             NSIALVSTNYPLSKTNSSSNDLEVEDRTSLVLNSDTCFENLTDPSSPTISSYENLLRTPT
v.5             NSIALVSTNYPLSKTNSSSNDLEVEDRTSLVLNSDTCFENLTDPSSPTISSYENLLRTPT
v.6             NSIALVSTNYPLSKTNSSSNDLEVEDRTSLVLNSDTCFENLTDPSSPTISSYENLLRTPT
v.9             NSIALVSTNYPLSKTNSSSNDLEVEDRTSLVLNSDTCFENLTDPSSPTISSYENLLRTPT
v.10            NSIALVSTNYPLSKTNSSSNDLEVEDRTSLVLNSDTCFENLTDPSSPTISSYENLLRTPT
v.11            NSIALVSTNYPLSKTNSSSNDLEVEDRTSLVLNSDTCFENLTDPSSPTISSYENLLRTPT
v.12            ------------------------------------------------------------
v.13            NSIALVSTNYPLSKTNSSSNDLEVEDRTSLVLNSDTCFENLTDPSSPTISSYENLLRTPT

v.1             PPEVTKIPEDILQLLSKYNSNLATPIAIKAVPPSKRFLKHGQNIRDVSNKEN
v.5             PPEVTKIPEDILQLLSKYNSNLATPIAIKAVPPSKRFLKHGQNIRDVSNKEN
v.6             PPEVTKIPEDILQLLSKYNSNLATPIAIKAVPPSKRFLKHGQNIRDVSNKEN
v.9             PPEVTKIPEDILQLLSKYNSNLATPIAIKAVPPSKRFLKHGQNIRDVSNKEN
v.10            PPEVTKIPEDILQKF-------------QWIYPTQKLNKMR-----------
```

Figure 4G-2

```
v.11          PPEVTKIPEDILQKF-------------QWIYPTQKLNKMR-----------
v.12          -------------LLSKYNSNLATPIAIKAVPPSKRFLKHGQNIRDVSNKEN
v.13          PPEVTKIPEDILQLLSKYNSNLATPIAIKAVPPSKRFLKHGQNIRDVSNKEN
```

Figure 5: 193P1E1B Hydrophilicity profile
(Hopp T.P., Woods K.R., 1981.
Proc. Natl. Acad. Sci. U.S.A. 78:3824-3828)
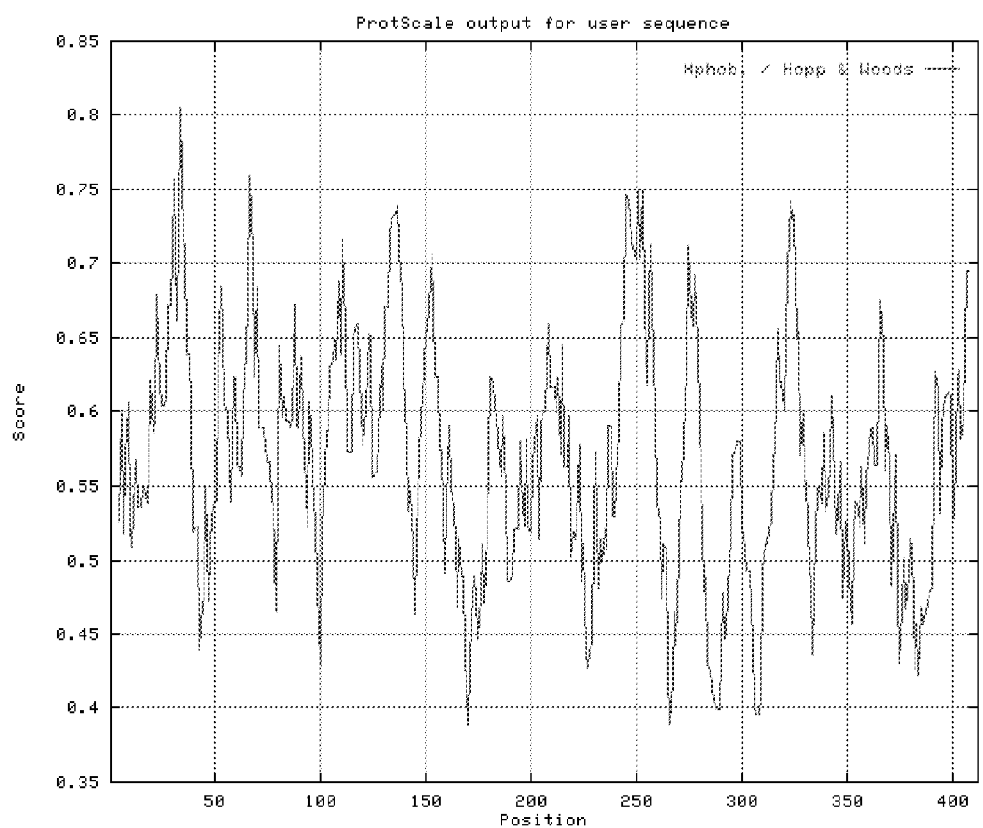

Figure 6: 193P1E1B Hydropathicity Profile
(Kyte J., Doolittle R.F., 1982. J. Mol. Biol. 157:105-132)
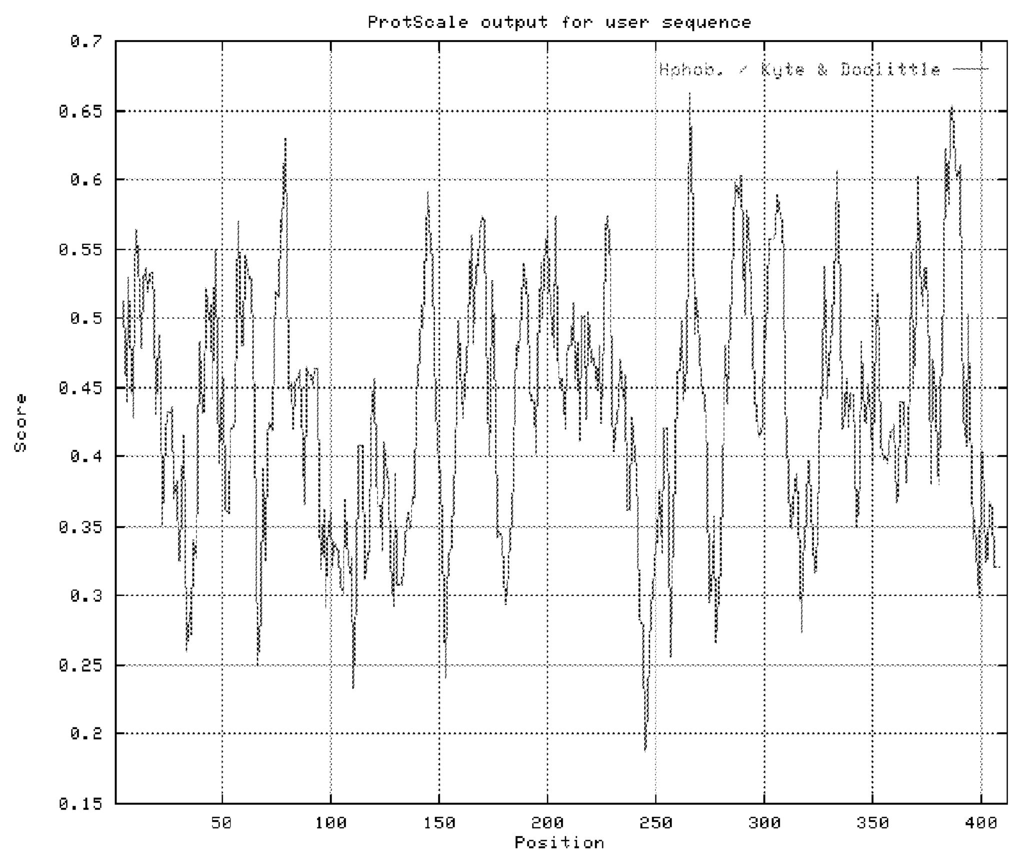

Figure 7: 193P1E1B % Accessible Residues Profile
(Janin J., 1979. Nature 277:491-492)
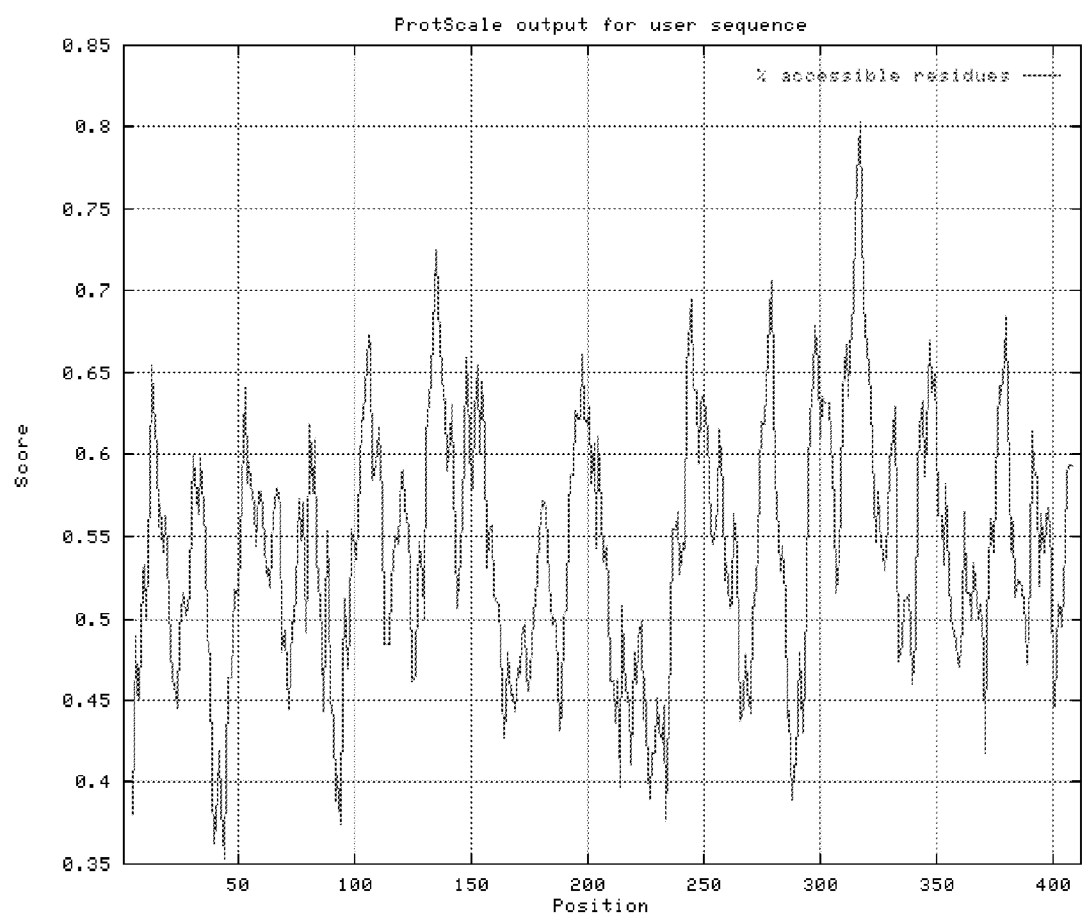

Figure 8: 193P1E1B Average Flexibility Profile
(Bhaskaran R., Ponnuswamy P.K., 1988.
Int. J. Pept. Protein Res. 32:242-255)
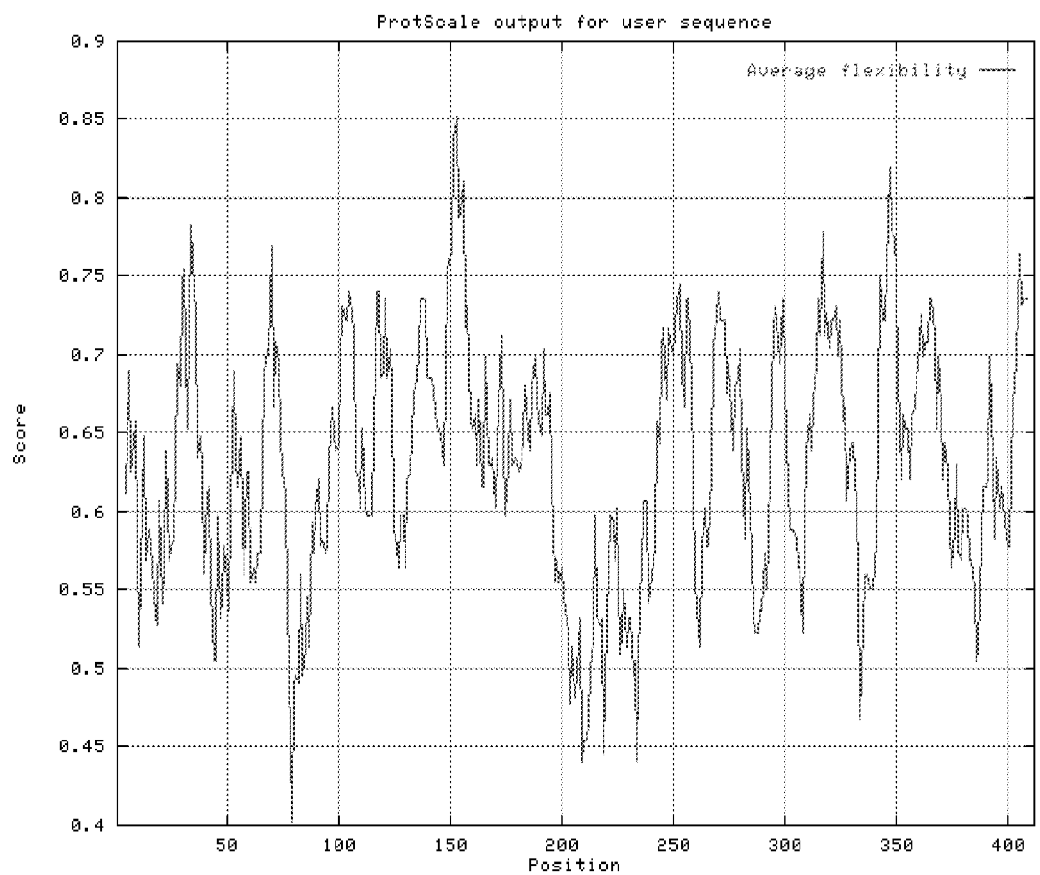

Figure 9: 193P1E1B Beta-turn Profile
(Deleage, G., Roux B. 1987. Protein Engineering 1:289-294)
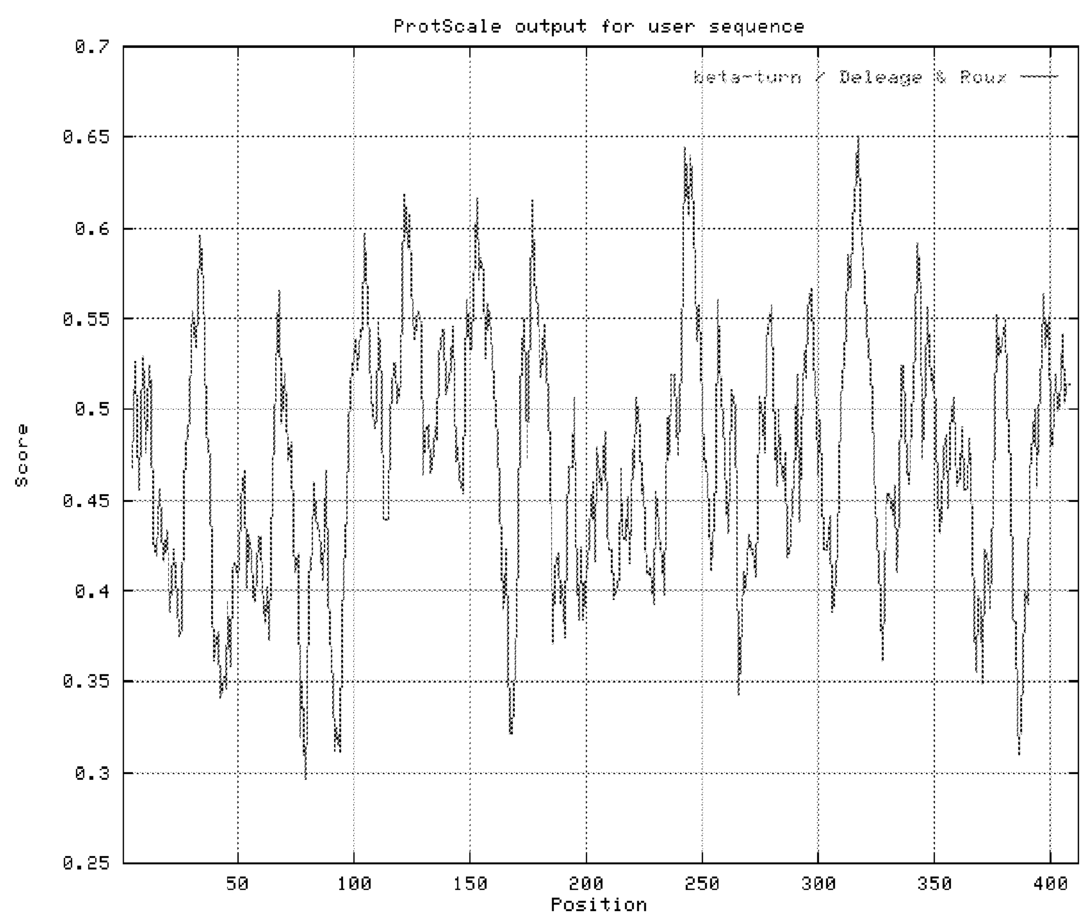

Figure 13: 193P1E1B secondary structure

```
        10        20        30        40        50        60        70
         |         |         |         |         |         |         |
MDPIRSFCGKLRSLASTLDCETARLQRALDGEESDFEDYPMRILYDLHSEVQTLKDDVNILLDKARLENQ
ccchhhhhchchhhhhhchhhhhhhhhhhccccchhhhhhhhhhhhhhhhhhhhhhhhhhhhhhchhchh
EGIDFIKATKVLMEKNSMDIMKIREYFQKYGYSPRVKKNSVHEQEAINSDPELSNCENFQKTDVKDDLSD
cchhhhhhhhhhhhccchhhhhhhhhhhhccccccccccccccccccccccccccccccccccccccccc
PPVASSCISEKSPRSPQLSDFGLERYIVSQVLPNPPQAVNNYKEEPVIVTPPTKQSLVKVLKTPKCALKM
cccccccccccccccccccccccchhehheccccccccccccccceeeecccccccEEEEEcccccceeec
DDFECVTPKLEHFGISEYTMCLNEDYTMGLKNARNNKSEEAIDTESRLNDNVFATPSPIIQQLEKSDAEY
ccccccccccccccceeeeeecccchcccccccccccchhhhhhhhhhccccccccchhhhecccccccc
TNSPLVPTFCTPGLKIPSTKNSIALVSTNYPLSKTNSSSNDLEVEDRTSLVLNSDTCFENLTDPSSPTIS
ccccccccccccccccccccceeeeeeccccccccccccccceeeccceeeeeeccchccccccccccccc
SYENLLRTPTPPEVTKIPEDILQLLSKYNSNLATPIAIKAVPPSKRFLKHGQNIRDVSNKEN
chhhhccccccccccchhhhhhhhhhhhhcccccceeeecccccchchhcccccceccccccc
```

h: Alpha helix 29.13%
c: Random coil 60.92%
e: Extended strand 9.95%

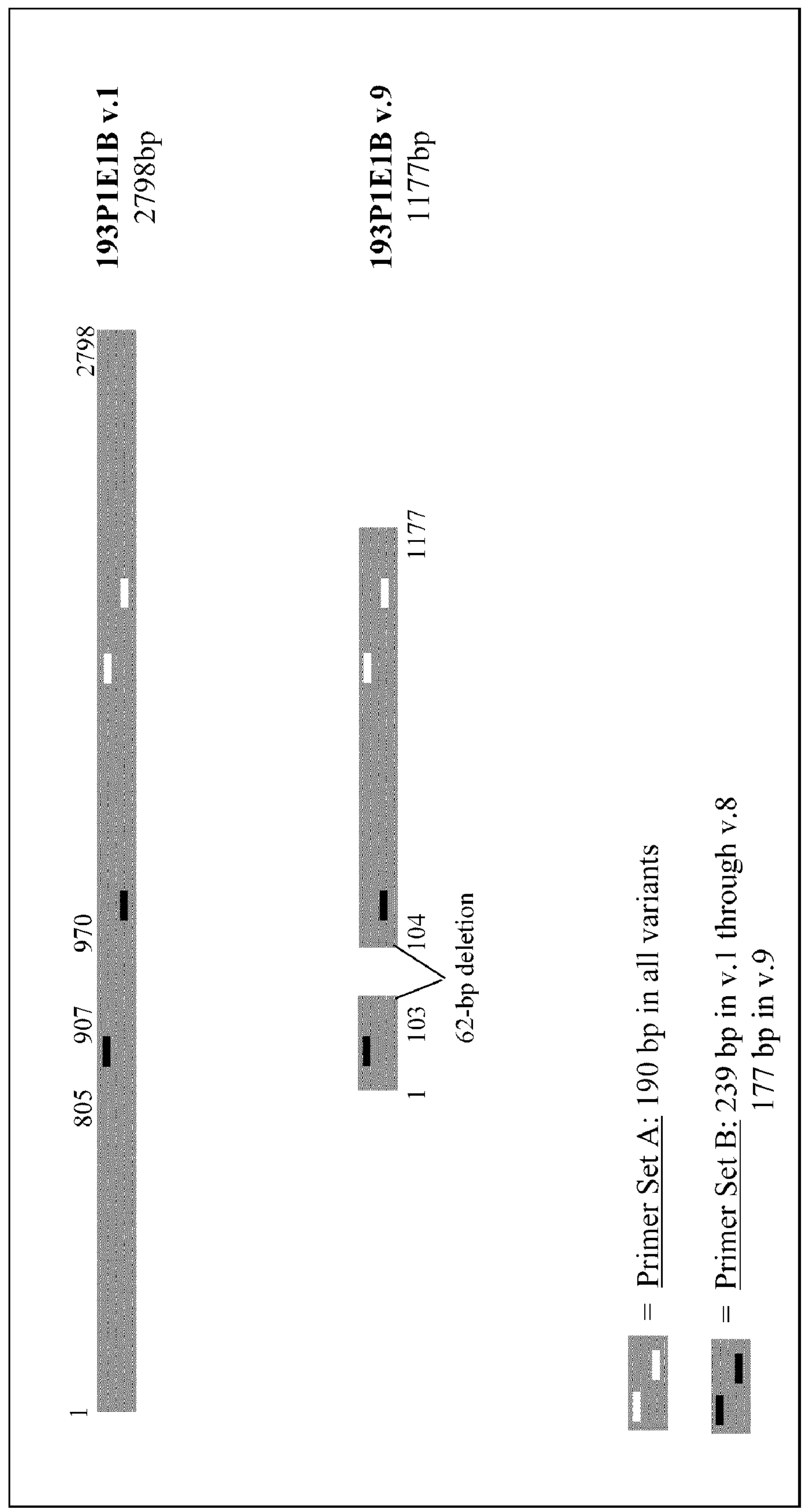
Figure 14A: Schematic Diagram Depicting
Location of the PCR primers
193P1E1B v.1
2798bp
1
805
907
970
2798
193P1E1B v.9
1177bp
1
103
104
1177
62-bp deletion
= Primer Set A: 190 bp in all variants
= Primer Set B: 239 bp in v.1 through v.8
177 bp in v.9

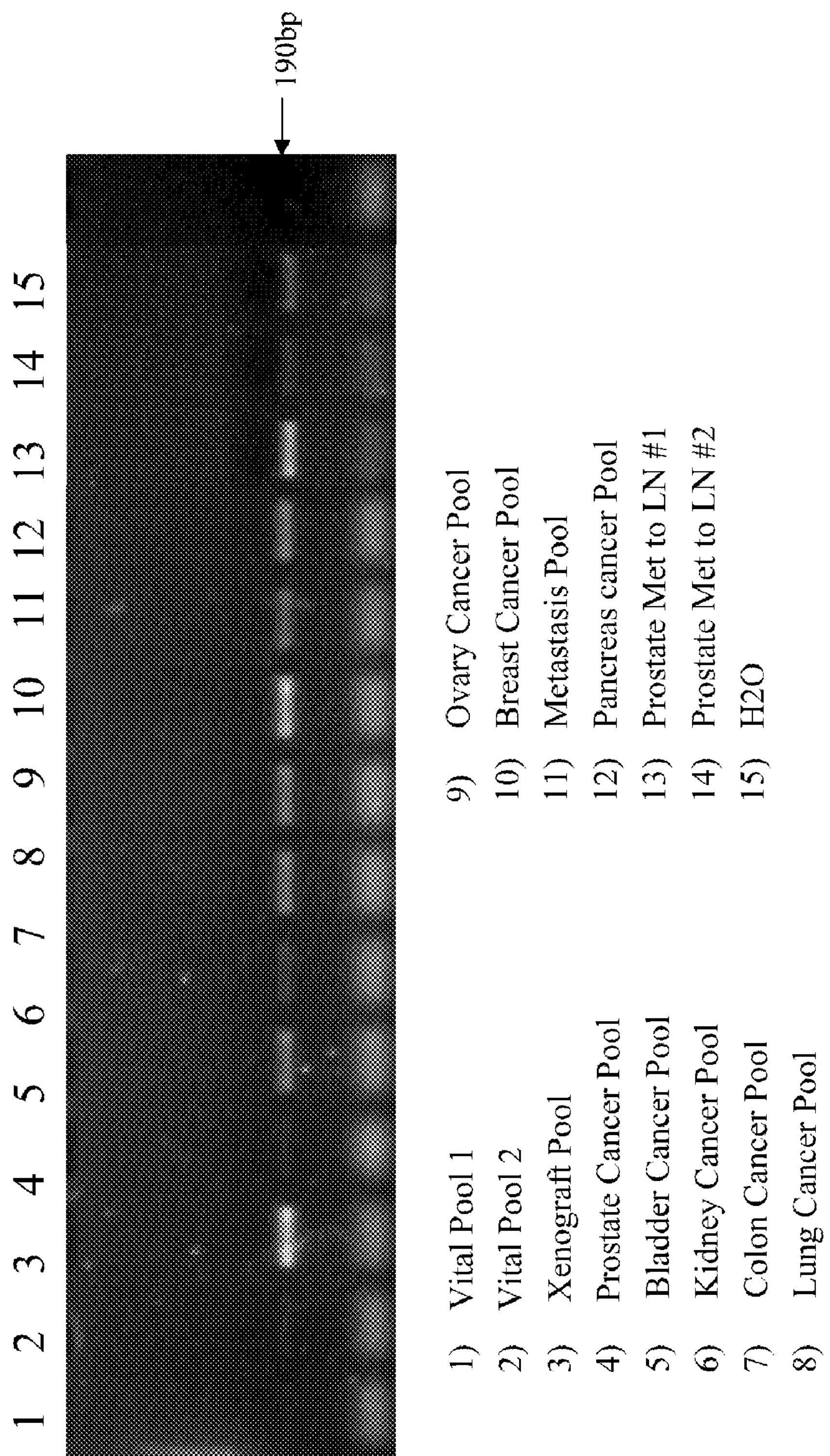
Figure 14B: Expression of 193P1E1B
by RT-PCR using Primer Set A
1 2 3 4 5 6 7 8 9 10 11 12 13 14 15
190bp
1) Vital Pool 1
2) Vital Pool 2
3) Xenograft Pool
4) Prostate Cancer Pool
5) Bladder Cancer Pool
6) Kidney Cancer Pool
7) Colon Cancer Pool
8) Lung Cancer Pool
9) Ovary Cancer Pool
10) Breast Cancer Pool
11) Metastasis Pool
12) Pancreas cancer Pool
13) Prostate Met to LN #1
14) Prostate Met to LN #2
15) H2O

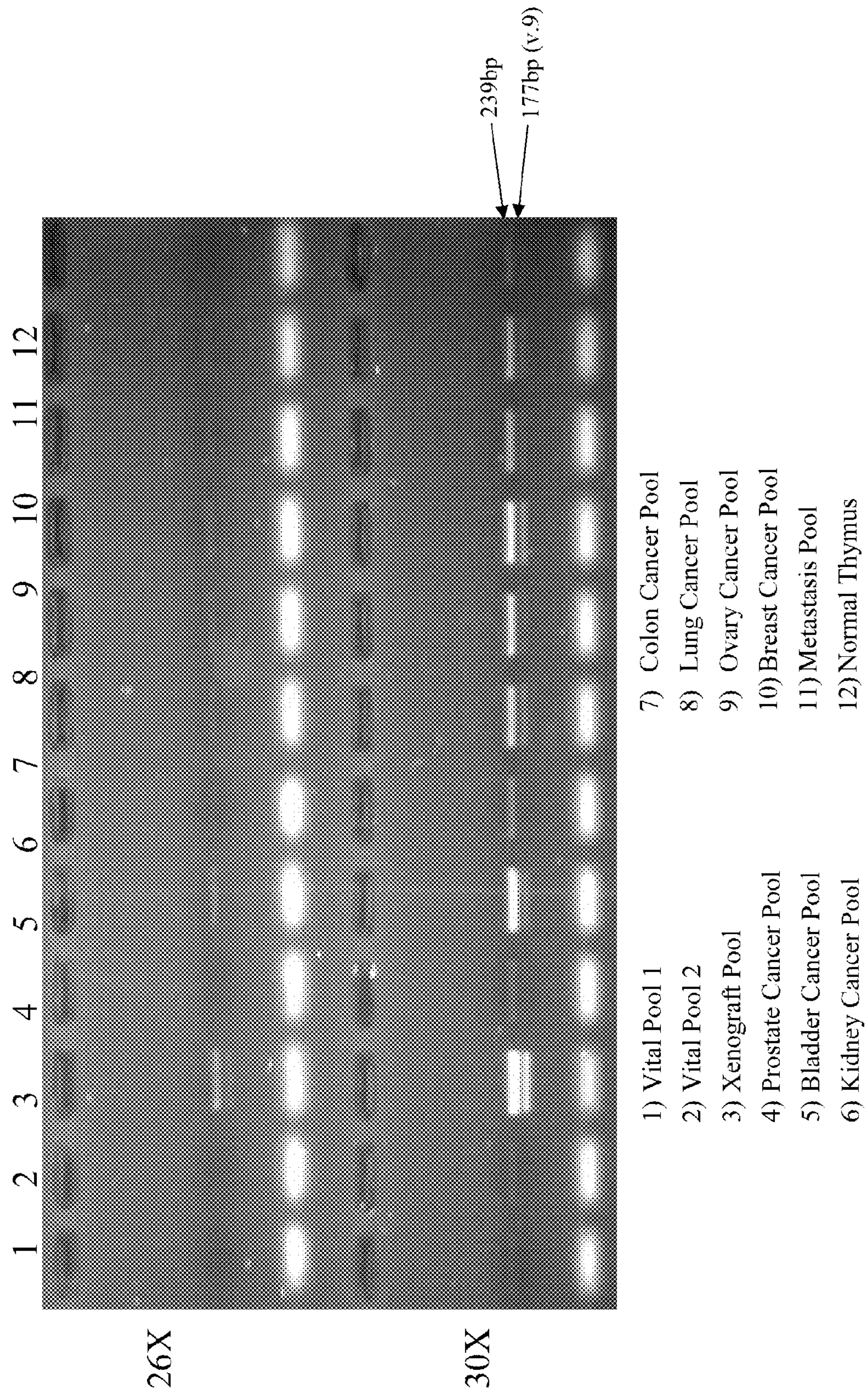
Figure 14C: Expression of 193P1E1B by RT-PCR using Primer Set B

Figure 15: Expression of 193P1E1B in Normal Tissues
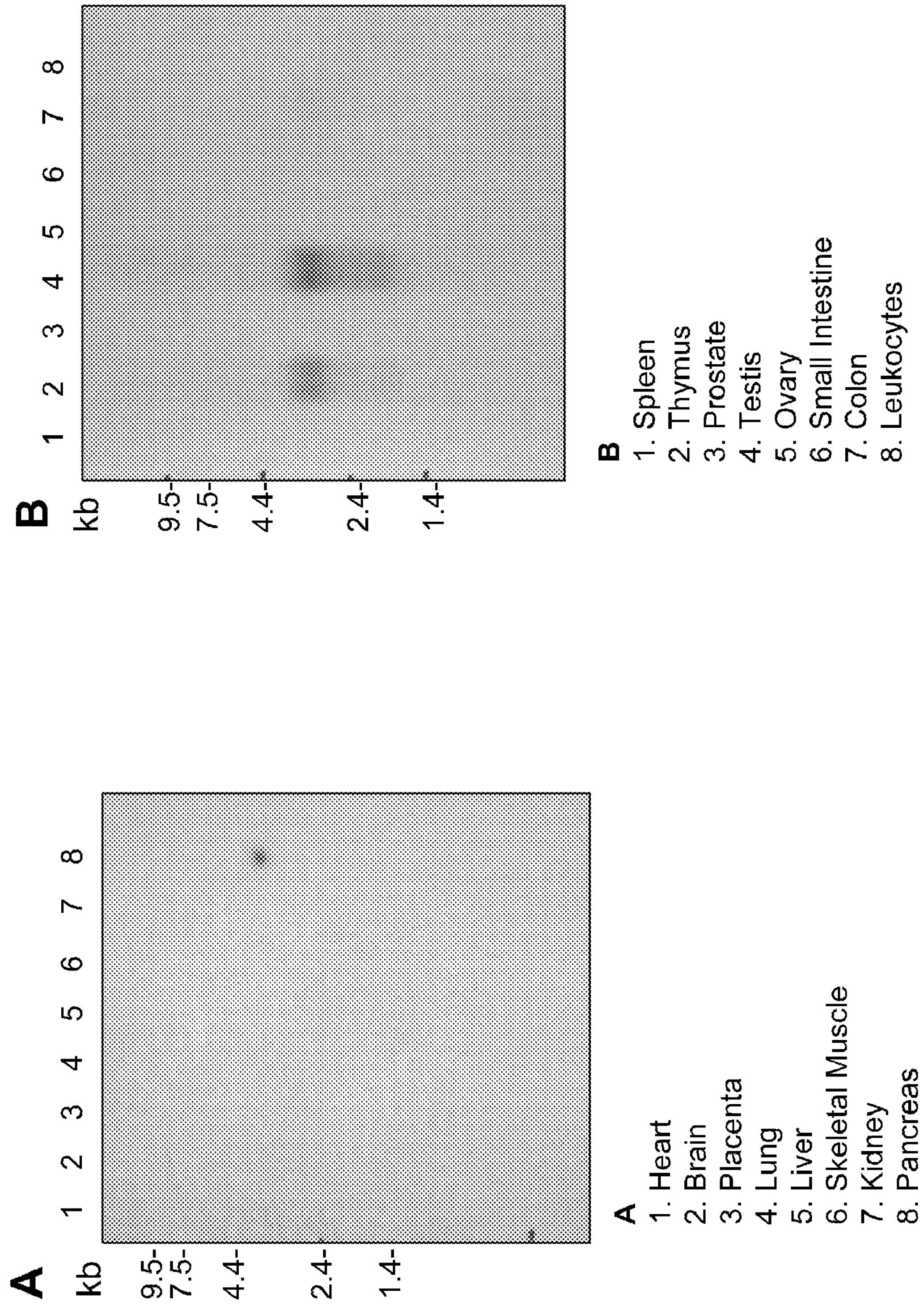

Figure 16: Expression of 193P1E1B in Prostate Cancer Xenografts
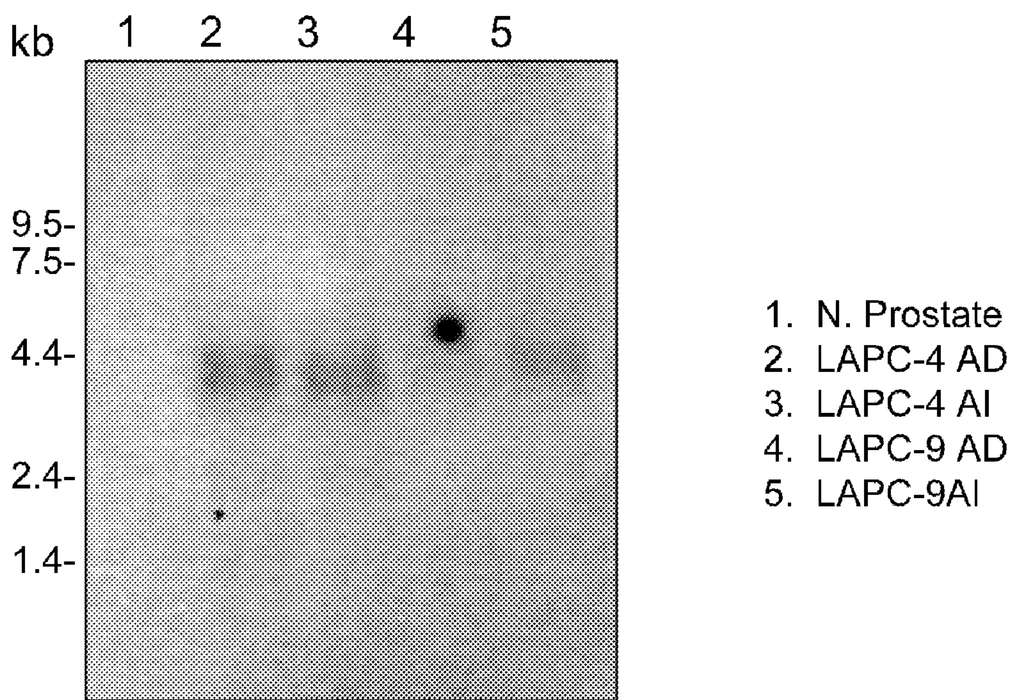

Figure 17: Expression of 193P1E1B in Human Patient Cancer Specimens
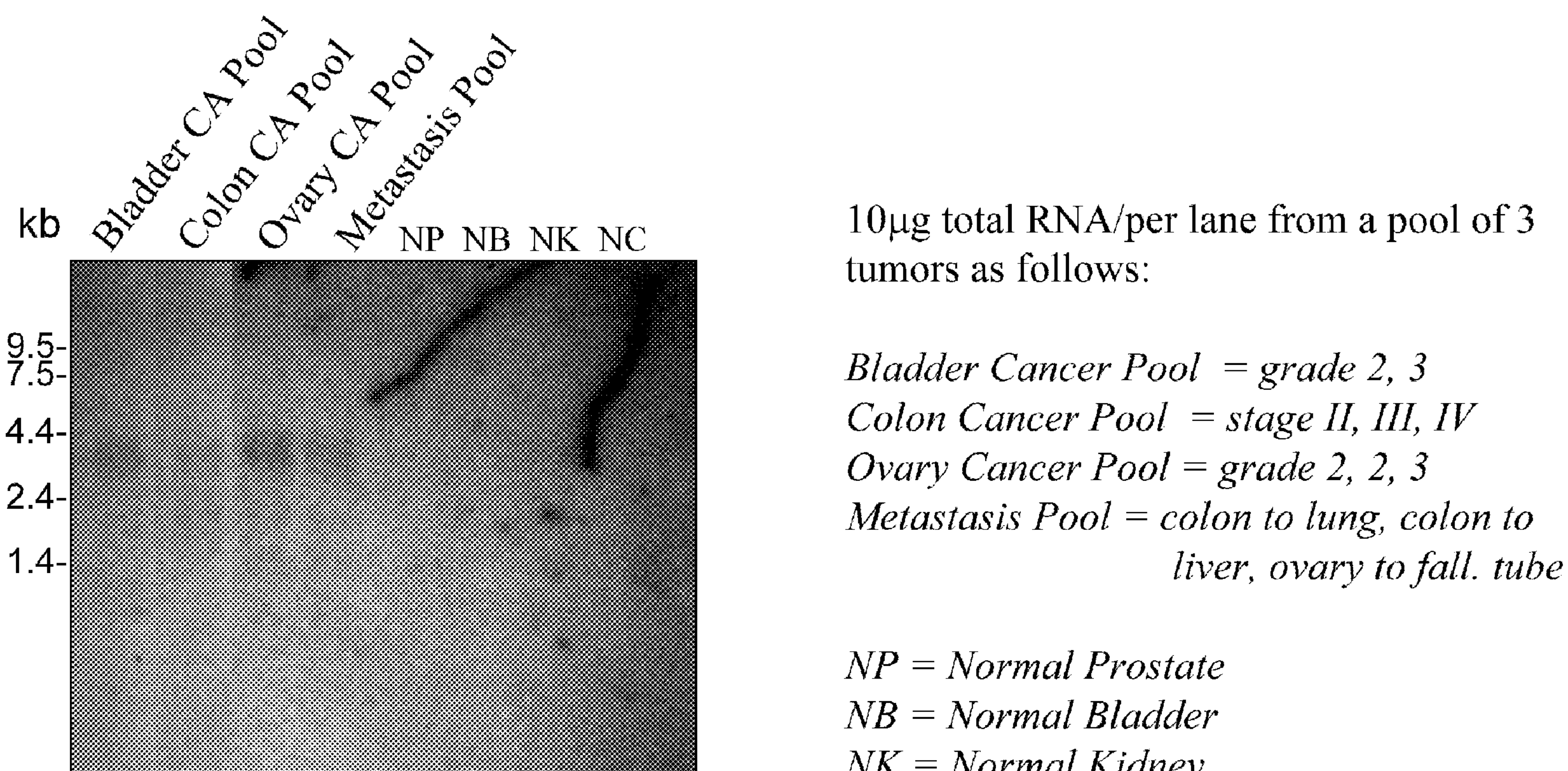
10μg total RNA/per lane from a pool of 3 tumors as follows:
*Bladder Cancer Pool = grade 2, 3*
*Colon Cancer Pool = stage II, III, IV*
*Ovary Cancer Pool = grade 2, 2, 3*
*Metastasis Pool = colon to lung, colon to liver, ovary to fall. tube*
*NP = Normal Prostate*
*NB = Normal Bladder*
*NK = Normal Kidney*
*NC = Normal Colon*

Figure 18: Expression of 193P1E1B in Bladder Cancer Patient Specimens
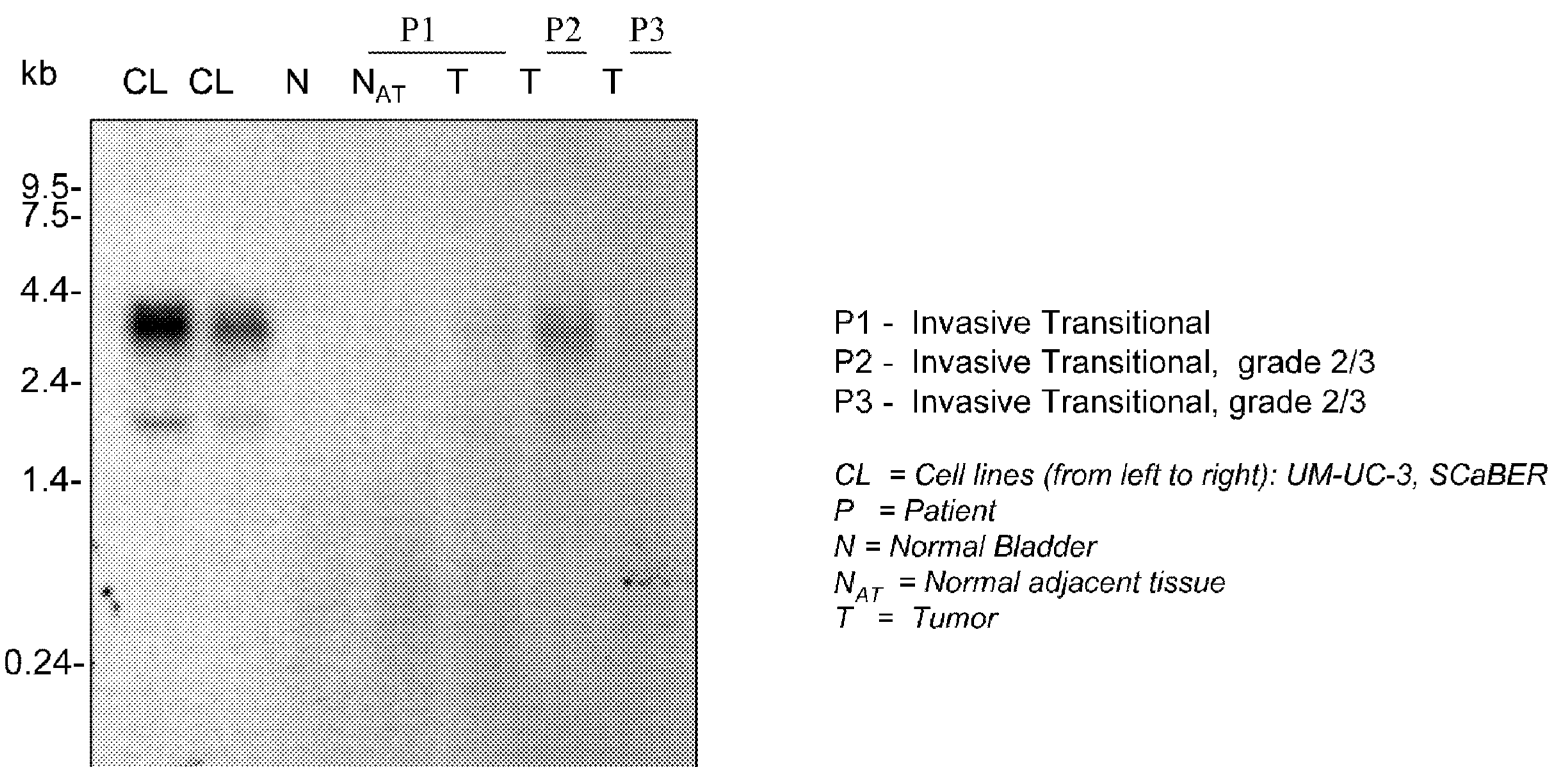

Figure 19: Expression of 193P1E1B in Cancer Metastasis Patient Specimens
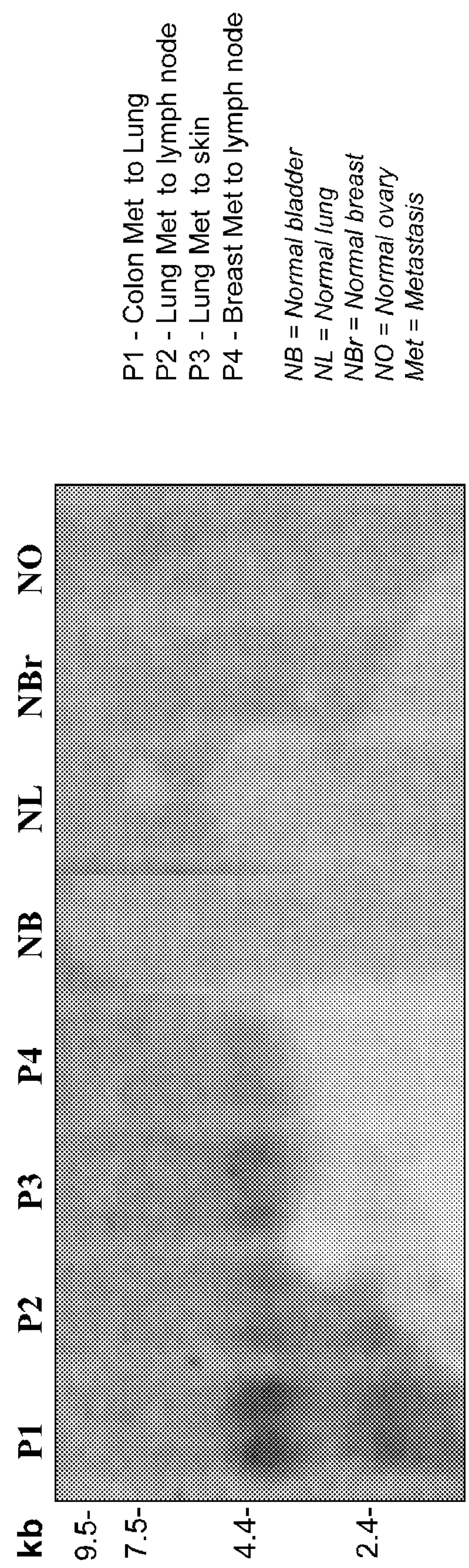
P1 - Colon Met to Lung
P2 - Lung Met to lymph node
P3 - Lung Met to skin
P4 - Breast Met to lymph node
*NB = Normal bladder*
*NL = Normal lung*
*NBr = Normal breast*
*NO = Normal ovary*
*Met = Metastasis*

Figure 20: Expression of 193P1E1B in Pancreas, Ovary and Testis Cancer Patient Specimens
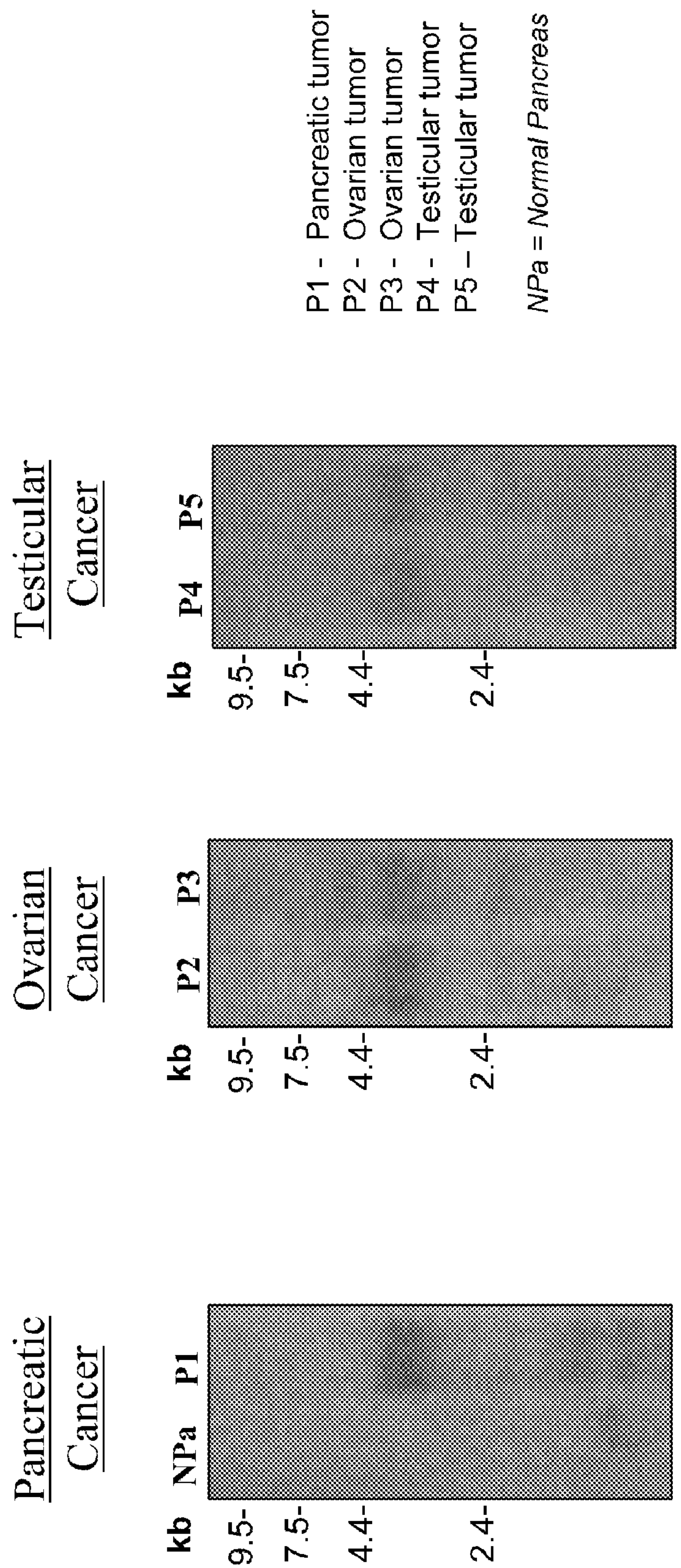

Figure 21: Expression of 193P1E1B in Normal versus Patient Cancer Specimens
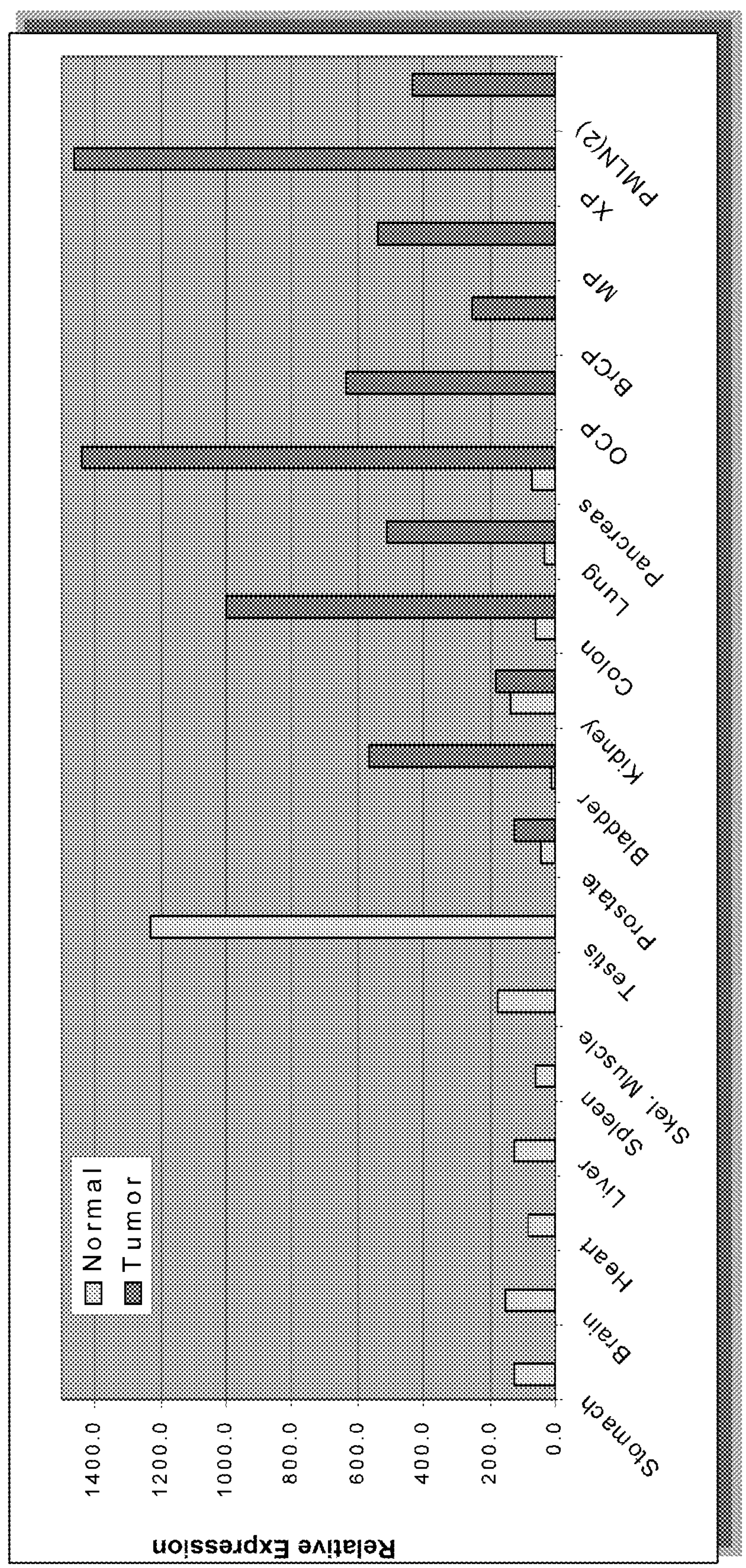

Figure 22: 193P1E1B Expression in Uterus, Melanoma and Bone Cancer Patient Specimens

A.

| Sample | Expression |
|---|---|
| Normal Uterus | |
| 1 | |
| 2 | |
| 3 | |
| 4 | |
| 5 | |
| 6 | |
| 7 | |
| 8 | |
| 9 | |
| 10 | |
| 11 | |
| 12 | |
| % Positive | 83.3% |

B.

| Tumor type | Diagnosis | Grade/Stage | Expression |
|---|---|---|---|
| Bone T | Storiform-Pleomorphic | Grade III-IV | |
| Melanoma | | ND | |
| Melanoma | Melanoma from Toes | T4bN1M0 (III) | |

| | |
|---|---|
| No expression | |
| Low expression | |
| High expression | |

*ND = not determined*

SEQUENCE LISTING

<160> NUMBER OF SEQ ID NOS: 259

<210> SEQ ID NO 1
<211> LENGTH: 227
<212> TYPE: DNA
<213> ORGANISM: Homo sapiens
<220> FEATURE:
<221> NAME/KEY: misc_feature
<222> LOCATION: 177
<223> OTHER INFORMATION: n = A,T,C or G

<400> SEQUENCE: 1

```
gatccactgg aatttcagtt ttctttgttg ctgacatctc ggatgttctg tccatgttta     60

gggaaccttt tactgggtgg cactgcttta attgctattg gagtagctag gtttgagttg    120

tattttgata gaagctggag aatatcttct ggaattttag ttacttctgg agggggnagg    180

ttctgagcag attctcataa gaagaaatcg taggtgaaag agggatc                  227
```

<210> SEQ ID NO 2
<211> LENGTH: 2798
<212> TYPE: DNA
<213> ORGANISM: Homo sapiens
<220> FEATURE:
<221> NAME/KEY: CDS
<222> LOCATION: (805)...(2043)

<400> SEQUENCE: 2

```
tatcatctgt gactgaggaa atccctatct tcctatcaga ctaatgaaac cacaggacag     60

caattagact tttaagtatt ggggggttta gagctctaga tattcgatat gcagactact    120

catgtttgtt tgttttaata aagactggtc caaaggctca ttttcacaca agctacagtt    180

tttcagttcc aggaccaggt aaagatggtc agctccgtga tccataaaat ccaagggtga    240

cgactcagga ttaggaccat ttcttggtga cattgagatg gtcgagctgg tccgcaatga    300

atctatgcgg ggggaacttg gaagtggcgg ccgcctttat ggcctcgaag gcctccctcc    360

tgcgcaccgc ggcgtggccg cgctcctgct cccgggtcat gtagggcatg ctcagccagt    420

aatggttctc cgcctcgatc tccaggcggc ggatcatgtt ctgcttggcg cgcaacgaca    480

cgaaccgcgg ccgccggtgc ttcccgatcc actgacggcc gggaatgcgg ccgcgccaga    540

ggagcgcagt caggaacatg gtgcctgccg cgctgctcaa gactctgcgt ctccgcggcc    600

gccagcagac gccgtggcgt aagcgcaccc gtctcgcggg gtctccgggg gcctcggcga    660

gagacttcgg ctctcgcgag agaggactgc gcctgcgcag agccgaggac gcgtccggcg    720

ccgagattca aactagtggc gggaggctgt gagctgagcg gtggggtctg cgtacgcctg    780

gagtccttcc ccgctgtgct cagc atg gac cct atc cgg agc ttc tgc ggg       831
                           Met Asp Pro Ile Arg Ser Phe Cys Gly
                            1               5

aag ctg cgg tct ctg gcc agc acg ctg gac tgc gag acg gcc cgg ctg      879
Lys Leu Arg Ser Leu Ala Ser Thr Leu Asp Cys Glu Thr Ala Arg Leu
 10                  15                  20                  25

cag cga gcg ctg gac gga gag gaa agc gac ttt gaa gat tat cca atg      927
Gln Arg Ala Leu Asp Gly Glu Glu Ser Asp Phe Glu Asp Tyr Pro Met
                 30                  35                  40

aga att tta tat gac ctt cat tca gaa gtt cag act cta aag gat gat      975
Arg Ile Leu Tyr Asp Leu His Ser Glu Val Gln Thr Leu Lys Asp Asp
             45                  50                  55

gtt aat att ctt ctt gat aaa gca aga ttg gaa aat caa gaa ggc att     1023
Val Asn Ile Leu Leu Asp Lys Ala Arg Leu Glu Asn Gln Glu Gly Ile
```

-continued

```
        60                  65                  70

gat ttc ata aag gca aca aaa gta cta atg gaa aaa aat tca atg gat     1071
Asp Phe Ile Lys Ala Thr Lys Val Leu Met Glu Lys Asn Ser Met Asp
     75                  80                  85

att atg aaa ata aga gag tat ttc cag aag tat gga tat agt cca cgt     1119
Ile Met Lys Ile Arg Glu Tyr Phe Gln Lys Tyr Gly Tyr Ser Pro Arg
 90                  95                 100                 105

gtc aag aaa aat tca gta cac gag caa gaa gcc att aac tct gac cca     1167
Val Lys Lys Asn Ser Val His Glu Gln Glu Ala Ile Asn Ser Asp Pro
                110                 115                 120

gag ttg tct aat tgt gaa aat ttt cag aag act gat gtg aaa gat gat     1215
Glu Leu Ser Asn Cys Glu Asn Phe Gln Lys Thr Asp Val Lys Asp Asp
            125                 130                 135

ctg tct gat cct cct gtt gca agc agt tgt att tct gag aag tct cca     1263
Leu Ser Asp Pro Pro Val Ala Ser Ser Cys Ile Ser Glu Lys Ser Pro
        140                 145                 150

cgt agt cca caa ctt tca gat ttt gga ctt gag cgg tac atc gta tcc     1311
Arg Ser Pro Gln Leu Ser Asp Phe Gly Leu Glu Arg Tyr Ile Val Ser
    155                 160                 165

caa gtt cta cca aac cct cca cag gca gtg aac aac tat aag gaa gag     1359
Gln Val Leu Pro Asn Pro Pro Gln Ala Val Asn Asn Tyr Lys Glu Glu
170                 175                 180                 185

ccc gta att gta acc cca cct acc aaa caa tca cta gta aaa gta cta     1407
Pro Val Ile Val Thr Pro Pro Thr Lys Gln Ser Leu Val Lys Val Leu
                190                 195                 200

aaa act cca aaa tgt gca cta aaa atg gat gat ttt gag tgt gta act     1455
Lys Thr Pro Lys Cys Ala Leu Lys Met Asp Asp Phe Glu Cys Val Thr
            205                 210                 215

cct aaa tta gaa cac ttt ggt atc tct gaa tat act atg tgt tta aat     1503
Pro Lys Leu Glu His Phe Gly Ile Ser Glu Tyr Thr Met Cys Leu Asn
        220                 225                 230

gaa gat tac aca atg gga ctt aaa aat gcg agg aat aat aaa agt gag     1551
Glu Asp Tyr Thr Met Gly Leu Lys Asn Ala Arg Asn Asn Lys Ser Glu
    235                 240                 245

gag gcc ata gat aca gaa tcc agg ctc aat gat aat gtt ttt gcc act     1599
Glu Ala Ile Asp Thr Glu Ser Arg Leu Asn Asp Asn Val Phe Ala Thr
250                 255                 260                 265

ccc agc ccc atc atc cag cag ttg gaa aaa agt gat gcc gaa tat acc     1647
Pro Ser Pro Ile Ile Gln Gln Leu Glu Lys Ser Asp Ala Glu Tyr Thr
                270                 275                 280

aac tct cct ttg gta cct aca ttc tgt act cct ggt ttg aaa att cca     1695
Asn Ser Pro Leu Val Pro Thr Phe Cys Thr Pro Gly Leu Lys Ile Pro
            285                 290                 295

tct aca aag aac agc ata gct ttg gta tcc aca aat tac cca tta tca     1743
Ser Thr Lys Asn Ser Ile Ala Leu Val Ser Thr Asn Tyr Pro Leu Ser
        300                 305                 310

aaa aca aat agt tca tca aat gat ttg gaa gtt gaa gat cgt act tcg     1791
Lys Thr Asn Ser Ser Ser Asn Asp Leu Glu Val Glu Asp Arg Thr Ser
    315                 320                 325

ttg gtt tta aat tca gac aca tgc ttt gag aat tta aca gat ccc tct     1839
Leu Val Leu Asn Ser Asp Thr Cys Phe Glu Asn Leu Thr Asp Pro Ser
330                 335                 340                 345

tca cct acg att tct tct tat gag aat ctg ctc aga aca cct aca cct     1887
Ser Pro Thr Ile Ser Ser Tyr Glu Asn Leu Leu Arg Thr Pro Thr Pro
                350                 355                 360

cca gaa gta act aaa att cca gaa gat att ctc cag ctt tta tca aaa     1935
Pro Glu Val Thr Lys Ile Pro Glu Asp Ile Leu Gln Leu Leu Ser Lys
            365                 370                 375

tac aac tca aac cta gct act cca ata gca att aaa gca gtg cca ccc     1983
```

-continued

```
Tyr Asn Ser Asn Leu Ala Thr Pro Ile Ala Ile Lys Ala Val Pro Pro
        380                 385                 390

agt aaa agg ttc ctt aaa cat gga cag aac atc cga gat gtc agc aac     2031
Ser Lys Arg Phe Leu Lys His Gly Gln Asn Ile Arg Asp Val Ser Asn
    395                 400                 405

aaa gaa aac tga aattccagtg gatctatcca acacagaaac tgaacaaaat         2083
Lys Glu Asn
410

gagatgaaag ccgagctgga ccgattttaa cattcacatt gccctgcctc tgtccccctt   2143

taaacgttga cccattttaa agacaaacat gaacattaac atcataatat gctttttatg   2203

aagtttcaat aaggtttaac cttagtcttg ttgacatgta gcccagtcat tcactcttta   2263

aggactatta gtgtttcatt gatactaaat tacccagctt aatcaacaga atggtttaag   2323

tagtaccagg aagtaggaca agtaatttca aaaatataaa ggtgtttgct actcagatga   2383

ggccgcccct gaccttctgg ccagagagac attgctgcca gccagctctg ccttcccatc   2443

atctcctttc aggaccgtcc cacacctttt acttgctcag tgctgtctga agatgcagtt   2503

gctgtttgca aacaacagga acaccagtta aactaattag gaaacagagg gagatttcca   2563

ggcctgggta actatatact gtgaccattg gcggttgaga ccggtcttca accagtggaa   2623

ccccgaactc tgctgtcagg gtgtggactt cggtgctctt ccaagttttc acctgggggg   2683

gggagctaac cccctatgtt cacgccttct attcccattg gcgctgaact cttaaggtca   2743

ctctggtcgc ttgtgacccc gtaaccctga tgtacccctc taaaaggtga ggggc        2798


<210> SEQ ID NO 3
<211> LENGTH: 412
<212> TYPE: PRT
<213> ORGANISM: Homo sapiens

<400> SEQUENCE: 3

Met Asp Pro Ile Arg Ser Phe Cys Gly Lys Leu Arg Ser Leu Ala Ser
 1               5                  10                  15

Thr Leu Asp Cys Glu Thr Ala Arg Leu Gln Arg Ala Leu Asp Gly Glu
            20                  25                  30

Glu Ser Asp Phe Glu Asp Tyr Pro Met Arg Ile Leu Tyr Asp Leu His
        35                  40                  45

Ser Glu Val Gln Thr Leu Lys Asp Asp Val Asn Ile Leu Leu Asp Lys
    50                  55                  60

Ala Arg Leu Glu Asn Gln Glu Gly Ile Asp Phe Ile Lys Ala Thr Lys
65                  70                  75                  80

Val Leu Met Glu Lys Asn Ser Met Asp Ile Met Lys Ile Arg Glu Tyr
                85                  90                  95

Phe Gln Lys Tyr Gly Tyr Ser Pro Arg Val Lys Lys Asn Ser Val His
            100                 105                 110

Glu Gln Glu Ala Ile Asn Ser Asp Pro Glu Leu Ser Asn Cys Glu Asn
        115                 120                 125

Phe Gln Lys Thr Asp Val Lys Asp Asp Leu Ser Asp Pro Pro Val Ala
    130                 135                 140

Ser Ser Cys Ile Ser Glu Lys Ser Pro Arg Ser Pro Gln Leu Ser Asp
145                 150                 155                 160

Phe Gly Leu Glu Arg Tyr Ile Val Ser Gln Val Leu Pro Asn Pro Pro
                165                 170                 175

Gln Ala Val Asn Asn Tyr Lys Glu Glu Pro Val Ile Val Thr Pro Pro
            180                 185                 190
```

```
Thr Lys Gln Ser Leu Val Lys Val Leu Lys Thr Pro Lys Cys Ala Leu
        195                 200                 205

Lys Met Asp Asp Phe Glu Cys Val Thr Pro Lys Leu Glu His Phe Gly
    210                 215                 220

Ile Ser Glu Tyr Thr Met Cys Leu Asn Glu Asp Tyr Thr Met Gly Leu
225                 230                 235                 240

Lys Asn Ala Arg Asn Asn Lys Ser Glu Glu Ala Ile Asp Thr Glu Ser
                245                 250                 255

Arg Leu Asn Asp Asn Val Phe Ala Thr Pro Ser Pro Ile Ile Gln Gln
            260                 265                 270

Leu Glu Lys Ser Asp Ala Glu Tyr Thr Asn Ser Pro Leu Val Pro Thr
        275                 280                 285

Phe Cys Thr Pro Gly Leu Lys Ile Pro Ser Thr Lys Asn Ser Ile Ala
    290                 295                 300

Leu Val Ser Thr Asn Tyr Pro Leu Ser Lys Thr Asn Ser Ser Ser Asn
305                 310                 315                 320

Asp Leu Glu Val Glu Asp Arg Thr Ser Leu Val Leu Asn Ser Asp Thr
                325                 330                 335

Cys Phe Glu Asn Leu Thr Asp Pro Ser Ser Pro Thr Ile Ser Ser Tyr
            340                 345                 350

Glu Asn Leu Leu Arg Thr Pro Thr Pro Pro Glu Val Thr Lys Ile Pro
        355                 360                 365

Glu Asp Ile Leu Gln Leu Leu Ser Lys Tyr Asn Ser Asn Leu Ala Thr
    370                 375                 380

Pro Ile Ala Ile Lys Ala Val Pro Pro Ser Lys Arg Phe Leu Lys His
385                 390                 395                 400

Gly Gln Asn Ile Arg Asp Val Ser Asn Lys Glu Asn
                405                 410


<210> SEQ ID NO 4
<211> LENGTH: 2798
<212> TYPE: DNA
<213> ORGANISM: Homo sapiens
<220> FEATURE:
<221> NAME/KEY: CDS
<222> LOCATION: (805)...(2043)

<400> SEQUENCE: 4

tatcatctgt gactgaggaa atccctatct tcctatcaga ctaatgaaac cacagggcag      60

caattagact tttaagtatt ggggggttta gagctctaga tattcgatat gcagactact     120

catgtttgtt tgttttaata aagactggtc caaaggctca ttttcacaca agctacagtt     180

tttcagttcc aggaccaggt aaagatggtc agctccgtga tccataaaat ccaagggtga     240

cgactcagga ttaggaccat ttcttggtga cattgagatg gtcgagctgg tccgcaatga     300

atctatgcgg ggggaacttg gaagtggcgg ccgcctttat ggcctcgaag gcctccctcc     360

tgcgcaccgc ggcgtggccg cgctcctgct cccgggtcat gtagggcatg ctcagccagt     420

aatggttctc cgcctcgatc tccaggcggc ggatcatgtt ctgcttggcg cgcaacgaca     480

cgaaccgcgg ccgccggtgc ttcccgatcc actgacggcc gggaatgcgg ccgcgccaga     540

ggagcgcagt caggaacatg gtgcctgccg cgctgctcaa gactctgcgt ctccgcggcc     600

gccagcagac gccgtggcgt aagcgcaccc gtctcgcggg gtctccgggg gcctcggcga     660

gagacttcgg ctctcgcgag agaggactgc gcctgcgcag agccgaggac gcgtccggcg     720

ccgagattca aactagtggc gggaggctgt gagctgagcg gtggggtctg cgtacgcctg     780
```

-continued

```
gagtccttcc ccgctgtgct cagc atg gac cct atc cgg agc ttc tgc ggg      831
                           Met Asp Pro Ile Arg Ser Phe Cys Gly
                            1               5

aag ctg cgg tct ctg gcc agc acg ctg gac tgc gag acg gcc cgg ctg      879
Lys Leu Arg Ser Leu Ala Ser Thr Leu Asp Cys Glu Thr Ala Arg Leu
 10                  15                  20                  25

cag cga gcg ctg gac gga gag gaa agc gac ttt gaa gat tat cca atg      927
Gln Arg Ala Leu Asp Gly Glu Glu Ser Asp Phe Glu Asp Tyr Pro Met
                 30                  35                  40

aga att tta tat gac ctt cat tca gaa gtt cag act cta aag gat gat      975
Arg Ile Leu Tyr Asp Leu His Ser Glu Val Gln Thr Leu Lys Asp Asp
             45                  50                  55

gtt aat att ctt ctt gat aaa gca aga ttg gaa aat caa gaa ggc att     1023
Val Asn Ile Leu Leu Asp Lys Ala Arg Leu Glu Asn Gln Glu Gly Ile
         60                  65                  70

gat ttc ata aag gca aca aaa gta cta atg gaa aaa aat tca atg gat     1071
Asp Phe Ile Lys Ala Thr Lys Val Leu Met Glu Lys Asn Ser Met Asp
     75                  80                  85

att atg aaa ata aga gag tat ttc cag aag tat gga tat agt cca cgt     1119
Ile Met Lys Ile Arg Glu Tyr Phe Gln Lys Tyr Gly Tyr Ser Pro Arg
 90                  95                 100                 105

gtc aag aaa aat tca gta cac gag caa gaa gcc att aac tct gac cca     1167
Val Lys Lys Asn Ser Val His Glu Gln Glu Ala Ile Asn Ser Asp Pro
                110                 115                 120

gag ttg tct aat tgt gaa aat ttt cag aag act gat gtg aaa gat gat     1215
Glu Leu Ser Asn Cys Glu Asn Phe Gln Lys Thr Asp Val Lys Asp Asp
            125                 130                 135

ctg tct gat cct cct gtt gca agc agt tgt att tct gag aag tct cca     1263
Leu Ser Asp Pro Pro Val Ala Ser Ser Cys Ile Ser Glu Lys Ser Pro
        140                 145                 150

cgt agt cca caa ctt tca gat ttt gga ctt gag cgg tac atc gta tcc     1311
Arg Ser Pro Gln Leu Ser Asp Phe Gly Leu Glu Arg Tyr Ile Val Ser
    155                 160                 165

caa gtt cta cca aac cct cca cag gca gtg aac aac tat aag gaa gag     1359
Gln Val Leu Pro Asn Pro Pro Gln Ala Val Asn Asn Tyr Lys Glu Glu
170                 175                 180                 185

ccc gta att gta acc cca cct acc aaa caa tca cta gta aaa gta cta     1407
Pro Val Ile Val Thr Pro Pro Thr Lys Gln Ser Leu Val Lys Val Leu
                190                 195                 200

aaa act cca aaa tgt gca cta aaa atg gat gat ttt gag tgt gta act     1455
Lys Thr Pro Lys Cys Ala Leu Lys Met Asp Asp Phe Glu Cys Val Thr
            205                 210                 215

cct aaa tta gaa cac ttt ggt atc tct gaa tat act atg tgt tta aat     1503
Pro Lys Leu Glu His Phe Gly Ile Ser Glu Tyr Thr Met Cys Leu Asn
        220                 225                 230

gaa gat tac aca atg gga ctt aaa aat gcg agg aat aat aaa agt gag     1551
Glu Asp Tyr Thr Met Gly Leu Lys Asn Ala Arg Asn Asn Lys Ser Glu
    235                 240                 245

gag gcc ata gat aca gaa tcc agg ctc aat gat aat gtt ttt gcc act     1599
Glu Ala Ile Asp Thr Glu Ser Arg Leu Asn Asp Asn Val Phe Ala Thr
250                 255                 260                 265

ccc agc ccc atc atc cag cag ttg gaa aaa agt gat gcc gaa tat acc     1647
Pro Ser Pro Ile Ile Gln Gln Leu Glu Lys Ser Asp Ala Glu Tyr Thr
                270                 275                 280

aac tct cct ttg gta cct aca ttc tgt act cct ggt ttg aaa att cca     1695
Asn Ser Pro Leu Val Pro Thr Phe Cys Thr Pro Gly Leu Lys Ile Pro
            285                 290                 295

tct aca aag aac agc ata gct ttg gta tcc aca aat tac cca tta tca     1743
Ser Thr Lys Asn Ser Ile Ala Leu Val Ser Thr Asn Tyr Pro Leu Ser
        300                 305                 310
```

-continued

```
aaa aca aat agt tca tca aat gat ttg gaa gtt gaa gat cgt act tcg     1791
Lys Thr Asn Ser Ser Ser Asn Asp Leu Glu Val Glu Asp Arg Thr Ser
    315                 320                 325

ttg gtt tta aat tca gac aca tgc ttt gag aat tta aca gat ccc tct     1839
Leu Val Leu Asn Ser Asp Thr Cys Phe Glu Asn Leu Thr Asp Pro Ser
330                 335                 340                 345

tca cct acg att tct tct tat gag aat ctg ctc aga aca cct aca cct     1887
Ser Pro Thr Ile Ser Ser Tyr Glu Asn Leu Leu Arg Thr Pro Thr Pro
                350                 355                 360

cca gaa gta act aaa att cca gaa gat att ctc cag ctt tta tca aaa     1935
Pro Glu Val Thr Lys Ile Pro Glu Asp Ile Leu Gln Leu Leu Ser Lys
            365                 370                 375

tac aac tca aac cta gct act cca ata gca att aaa gca gtg cca ccc     1983
Tyr Asn Ser Asn Leu Ala Thr Pro Ile Ala Ile Lys Ala Val Pro Pro
        380                 385                 390

agt aaa agg ttc ctt aaa cat gga cag aac atc cga gat gtc agc aac     2031
Ser Lys Arg Phe Leu Lys His Gly Gln Asn Ile Arg Asp Val Ser Asn
    395                 400                 405

aaa gaa aac tga aattccagtg gatctatcca acacagaaac tgaacaaaat         2083
Lys Glu Asn
410

gagatgaaag ccgagctgga ccgattttaa cattcacatt gccctgcctc tgtcccccttt   2143

taaacgttga cccattttaa agacaaacat gaacattaac atcataatat gctttttatg   2203

aagtttcaat aaggtttaac cttagtcttg ttgacatgta gcccagtcat tcactcttta   2263

aggactatta gtgtttcatt gatactaaat tacccagctt aatcaacaga atggtttaag   2323

tagtaccagg aagtaggaca agtaatttca aaaatataaa ggtgtttgct actcagatga   2383

ggccgcccct gaccttctgg ccagagagac attgctgcca gccagctctg ccttcccatc   2443

atctcctttc aggaccgtcc cacacctttt acttgctcag tgctgtctga agatgcagtt   2503

gctgtttgca aacaacagga acaccagtta aactaattag gaaacagagg gagatttcca   2563

ggcctgggta actatatact gtgaccattg gcggttgaga ccggtcttca accagtggaa   2623

ccccgaactc tgctgtcagg gtgtggactt cggtgctctt ccaagttttc acctgggggg   2683

gggagctaac cccctatgtt cacgccttct attcccattg gcgctgaact cttaaggtca   2743

ctctggtcgc ttgtgacccc gtaaccctga tgtacccctc taaaaggtga ggggc        2798


<210> SEQ ID NO 5
<211> LENGTH: 412
<212> TYPE: PRT
<213> ORGANISM: Homo sapiens

<400> SEQUENCE: 5

Met Asp Pro Ile Arg Ser Phe Cys Gly Lys Leu Arg Ser Leu Ala Ser
 1               5                  10                  15

Thr Leu Asp Cys Glu Thr Ala Arg Leu Gln Arg Ala Leu Asp Gly Glu
            20                  25                  30

Glu Ser Asp Phe Glu Asp Tyr Pro Met Arg Ile Leu Tyr Asp Leu His
        35                  40                  45

Ser Glu Val Gln Thr Leu Lys Asp Asp Val Asn Ile Leu Leu Asp Lys
    50                  55                  60

Ala Arg Leu Glu Asn Gln Glu Gly Ile Asp Phe Ile Lys Ala Thr Lys
65                  70                  75                  80

Val Leu Met Glu Lys Asn Ser Met Asp Ile Met Lys Ile Arg Glu Tyr
                85                  90                  95
```

-continued

```
Phe Gln Lys Tyr Gly Tyr Ser Pro Arg Val Lys Lys Asn Ser Val His
            100                 105                 110

Glu Gln Glu Ala Ile Asn Ser Asp Pro Glu Leu Ser Asn Cys Glu Asn
        115                 120                 125

Phe Gln Lys Thr Asp Val Lys Asp Asp Leu Ser Asp Pro Pro Val Ala
    130                 135                 140

Ser Ser Cys Ile Ser Glu Lys Ser Pro Arg Ser Pro Gln Leu Ser Asp
145                 150                 155                 160

Phe Gly Leu Glu Arg Tyr Ile Val Ser Gln Val Leu Pro Asn Pro Pro
                165                 170                 175

Gln Ala Val Asn Asn Tyr Lys Glu Glu Pro Val Ile Val Thr Pro Pro
            180                 185                 190

Thr Lys Gln Ser Leu Val Lys Val Leu Lys Thr Pro Lys Cys Ala Leu
        195                 200                 205

Lys Met Asp Asp Phe Glu Cys Val Thr Pro Lys Leu Glu His Phe Gly
    210                 215                 220

Ile Ser Glu Tyr Thr Met Cys Leu Asn Glu Asp Tyr Thr Met Gly Leu
225                 230                 235                 240

Lys Asn Ala Arg Asn Asn Lys Ser Glu Glu Ala Ile Asp Thr Glu Ser
                245                 250                 255

Arg Leu Asn Asp Asn Val Phe Ala Thr Pro Ser Pro Ile Ile Gln Gln
            260                 265                 270

Leu Glu Lys Ser Asp Ala Glu Tyr Thr Asn Ser Pro Leu Val Pro Thr
        275                 280                 285

Phe Cys Thr Pro Gly Leu Lys Ile Pro Ser Thr Lys Asn Ser Ile Ala
    290                 295                 300

Leu Val Ser Thr Asn Tyr Pro Leu Ser Lys Thr Asn Ser Ser Ser Asn
305                 310                 315                 320

Asp Leu Glu Val Glu Asp Arg Thr Ser Leu Val Leu Asn Ser Asp Thr
                325                 330                 335

Cys Phe Glu Asn Leu Thr Asp Pro Ser Ser Pro Thr Ile Ser Ser Tyr
            340                 345                 350

Glu Asn Leu Leu Arg Thr Pro Thr Pro Pro Glu Val Thr Lys Ile Pro
        355                 360                 365

Glu Asp Ile Leu Gln Leu Leu Ser Lys Tyr Asn Ser Asn Leu Ala Thr
    370                 375                 380

Pro Ile Ala Ile Lys Ala Val Pro Pro Ser Lys Arg Phe Leu Lys His
385                 390                 395                 400

Gly Gln Asn Ile Arg Asp Val Ser Asn Lys Glu Asn
                405                 410
```

<210> SEQ ID NO 6
<211> LENGTH: 2798
<212> TYPE: DNA
<213> ORGANISM: Homo sapiens
<220> FEATURE:
<221> NAME/KEY: CDS
<222> LOCATION: (805)...(2043)

<400> SEQUENCE: 6

```
tatcatctgt gactgaggaa atccctatct tcctatcaga ctaatgaaac cacaggacag      60

caattagact tttaagtatt ggggggttta gagctctaga tattcgatat gcagactact     120

catgtttgtt tgttttaata aagactggtc caaaggctca ttttcacaca agctacagtt     180

tttcagttcc aggaccaggt aaagatggtc agctccgtga tccataaaat ccaagggtga     240
```

-continued

```
cgactcagga ttaggaccat ttcttggtga cattgagatg gtcgagctgg tccgcaatga    300

atctatgcgg ggggaacttg gaagtggcgg ccgcctttat ggcctcgaag gcctccctcc    360

tgcgcaccgc ggcgtggccg cgctcctgct cccgggtcat gtagggcatg ctcagccagt    420

aatggttctc cgcctcgatc tccaggcggc ggatcatgtt ctgcttggcg cgcaacgaca    480

cgaaccgcgg ccgccggtgc ttcccgatcc actgacggcc gggaatgcgg ccgcgccaga    540

ggagcgcagt caggaacatg gtgcctgccg cgctgctcaa gactctgcgt ctccgcggcc    600

gccagcagac gccgtggcgt aagcgcaccc gtctcgcggg gtctccgggg gcctcggcga    660

gagacttcgg ctctcgcgag agaggactgc gcctgcgcag agccgaggac gcgtccggcg    720

ccgagattca aactagtggc gggaggctgt gagctgagcg gtggggtctg cgtacgcctg    780

gagtccttcc cggctgtgct cagc atg gac cct atc cgg agc ttc tgc ggg      831
                           Met Asp Pro Ile Arg Ser Phe Cys Gly
                            1               5

aag ctg cgg tct ctg gcc agc acg ctg gac tgc gag acg gcc cgg ctg      879
Lys Leu Arg Ser Leu Ala Ser Thr Leu Asp Cys Glu Thr Ala Arg Leu
 10                  15                  20                  25

cag cga gcg ctg gac gga gag gaa agc gac ttt gaa gat tat cca atg      927
Gln Arg Ala Leu Asp Gly Glu Glu Ser Asp Phe Glu Asp Tyr Pro Met
                 30                  35                  40

aga att tta tat gac ctt cat tca gaa gtt cag act cta aag gat gat      975
Arg Ile Leu Tyr Asp Leu His Ser Glu Val Gln Thr Leu Lys Asp Asp
             45                  50                  55

gtt aat att ctt ctt gat aaa gca aga ttg gaa aat caa gaa ggc att     1023
Val Asn Ile Leu Leu Asp Lys Ala Arg Leu Glu Asn Gln Glu Gly Ile
         60                  65                  70

gat ttc ata aag gca aca aaa gta cta atg gaa aaa aat tca atg gat     1071
Asp Phe Ile Lys Ala Thr Lys Val Leu Met Glu Lys Asn Ser Met Asp
     75                  80                  85

att atg aaa ata aga gag tat ttc cag aag tat gga tat agt cca cgt     1119
Ile Met Lys Ile Arg Glu Tyr Phe Gln Lys Tyr Gly Tyr Ser Pro Arg
 90                  95                 100                 105

gtc aag aaa aat tca gta cac gag caa gaa gcc att aac tct gac cca     1167
Val Lys Lys Asn Ser Val His Glu Gln Glu Ala Ile Asn Ser Asp Pro
                110                 115                 120

gag ttg tct aat tgt gaa aat ttt cag aag act gat gtg aaa gat gat     1215
Glu Leu Ser Asn Cys Glu Asn Phe Gln Lys Thr Asp Val Lys Asp Asp
            125                 130                 135

ctg tct gat cct cct gtt gca agc agt tgt att tct gag aag tct cca     1263
Leu Ser Asp Pro Pro Val Ala Ser Ser Cys Ile Ser Glu Lys Ser Pro
        140                 145                 150

cgt agt cca caa ctt tca gat ttt gga ctt gag cgg tac atc gta tcc     1311
Arg Ser Pro Gln Leu Ser Asp Phe Gly Leu Glu Arg Tyr Ile Val Ser
    155                 160                 165

caa gtt cta cca aac cct cca cag gca gtg aac aac tat aag gaa gag     1359
Gln Val Leu Pro Asn Pro Pro Gln Ala Val Asn Asn Tyr Lys Glu Glu
170                 175                 180                 185

ccc gta att gta acc cca cct acc aaa caa tca cta gta aaa gta cta     1407
Pro Val Ile Val Thr Pro Pro Thr Lys Gln Ser Leu Val Lys Val Leu
                190                 195                 200

aaa act cca aaa tgt gca cta aaa atg gat gat ttt gag tgt gta act     1455
Lys Thr Pro Lys Cys Ala Leu Lys Met Asp Asp Phe Glu Cys Val Thr
            205                 210                 215

cct aaa tta gaa cac ttt ggt atc tct gaa tat act atg tgt tta aat     1503
Pro Lys Leu Glu His Phe Gly Ile Ser Glu Tyr Thr Met Cys Leu Asn
        220                 225                 230

gaa gat tac aca atg gga ctt aaa aat gcg agg aat aat aaa agt gag     1551
```

-continued

```
Glu Asp Tyr Thr Met Gly Leu Lys Asn Ala Arg Asn Asn Lys Ser Glu
    235                 240                 245

gag gcc ata gat aca gaa tcc agg ctc aat gat aat gtt ttt gcc act      1599
Glu Ala Ile Asp Thr Glu Ser Arg Leu Asn Asp Asn Val Phe Ala Thr
250                 255                 260                 265

ccc agc ccc atc atc cag cag ttg gaa aaa agt gat gcc gaa tat acc      1647
Pro Ser Pro Ile Ile Gln Gln Leu Glu Lys Ser Asp Ala Glu Tyr Thr
                270                 275                 280

aac tct cct ttg gta cct aca ttc tgt act cct ggt ttg aaa att cca      1695
Asn Ser Pro Leu Val Pro Thr Phe Cys Thr Pro Gly Leu Lys Ile Pro
            285                 290                 295

tct aca aag aac agc ata gct ttg gta tcc aca aat tac cca tta tca      1743
Ser Thr Lys Asn Ser Ile Ala Leu Val Ser Thr Asn Tyr Pro Leu Ser
        300                 305                 310

aaa aca aat agt tca tca aat gat ttg gaa gtt gaa gat cgt act tcg      1791
Lys Thr Asn Ser Ser Ser Asn Asp Leu Glu Val Glu Asp Arg Thr Ser
    315                 320                 325

ttg gtt tta aat tca gac aca tgc ttt gag aat tta aca gat ccc tct      1839
Leu Val Leu Asn Ser Asp Thr Cys Phe Glu Asn Leu Thr Asp Pro Ser
330                 335                 340                 345

tca cct acg att tct tct tat gag aat ctg ctc aga aca cct aca cct      1887
Ser Pro Thr Ile Ser Ser Tyr Glu Asn Leu Leu Arg Thr Pro Thr Pro
                350                 355                 360

cca gaa gta act aaa att cca gaa gat att ctc cag ctt tta tca aaa      1935
Pro Glu Val Thr Lys Ile Pro Glu Asp Ile Leu Gln Leu Leu Ser Lys
            365                 370                 375

tac aac tca aac cta gct act cca ata gca att aaa gca gtg cca ccc      1983
Tyr Asn Ser Asn Leu Ala Thr Pro Ile Ala Ile Lys Ala Val Pro Pro
        380                 385                 390

agt aaa agg ttc ctt aaa cat gga cag aac atc cga gat gtc agc aac      2031
Ser Lys Arg Phe Leu Lys His Gly Gln Asn Ile Arg Asp Val Ser Asn
    395                 400                 405

aaa gaa aac tga aattccagtg gatctatcca acacagaaac tgaacaaaat          2083
Lys Glu Asn
410

gagatgaaag ccgagctgga ccgattttaa cattcacatt gccctgcctc tgtcccctt    2143

taaacgttga cccattttaa agacaaacat gaacattaac atcataatat gctttttatg   2203

aagtttcaat aaggtttaac cttagtcttg ttgacatgta gcccagtcat tcactcttta   2263

aggactatta gtgtttcatt gatactaaat tacccagctt aatcaacaga atggtttaag   2323

tagtaccagg aagtaggaca agtaatttca aaaatataaa ggtgtttgct actcagatga   2383

ggccgcccct gaccttctgg ccagagagac attgctgcca gccagctctg ccttcccatc   2443

atctcctttc aggaccgtcc cacacctttt acttgctcag tgctgtctga agatgcagtt   2503

gctgtttgca aacaacagga acaccagtta aactaattag gaaacagagg gagatttcca   2563

ggcctgggta actatatact gtgaccattg gcggttgaga ccggtcttca accagtggaa   2623

ccccgaactc tgctgtcagg gtgtggactt cggtgctctt ccaagttttc acctgggggg   2683

gggagctaac cccctatgtt cacgccttct attcccattg gcgctgaact cttaaggtca   2743

ctctggtcgc ttgtgacccc gtaaccctga tgtacccctc taaaaggtga ggggc         2798


<210> SEQ ID NO 7
<211> LENGTH: 412
<212> TYPE: PRT
<213> ORGANISM: Homo sapiens

<400> SEQUENCE: 7
```

-continued

```
Met Asp Pro Ile Arg Ser Phe Cys Gly Lys Leu Arg Ser Leu Ala Ser
1               5                   10                  15

Thr Leu Asp Cys Glu Thr Ala Arg Leu Gln Arg Ala Leu Asp Gly Glu
            20                  25                  30

Glu Ser Asp Phe Glu Asp Tyr Pro Met Arg Ile Leu Tyr Asp Leu His
        35                  40                  45

Ser Glu Val Gln Thr Leu Lys Asp Asp Val Asn Ile Leu Leu Asp Lys
    50                  55                  60

Ala Arg Leu Glu Asn Gln Glu Gly Ile Asp Phe Ile Lys Ala Thr Lys
65                  70                  75                  80

Val Leu Met Glu Lys Asn Ser Met Asp Ile Met Lys Ile Arg Glu Tyr
                85                  90                  95

Phe Gln Lys Tyr Gly Tyr Ser Pro Arg Val Lys Lys Asn Ser Val His
            100                 105                 110

Glu Gln Glu Ala Ile Asn Ser Asp Pro Glu Leu Ser Asn Cys Glu Asn
        115                 120                 125

Phe Gln Lys Thr Asp Val Lys Asp Asp Leu Ser Asp Pro Pro Val Ala
    130                 135                 140

Ser Ser Cys Ile Ser Glu Lys Ser Pro Arg Ser Pro Gln Leu Ser Asp
145                 150                 155                 160

Phe Gly Leu Glu Arg Tyr Ile Val Ser Gln Val Leu Pro Asn Pro Pro
                165                 170                 175

Gln Ala Val Asn Asn Tyr Lys Glu Glu Pro Val Ile Val Thr Pro Pro
            180                 185                 190

Thr Lys Gln Ser Leu Val Lys Val Leu Lys Thr Pro Lys Cys Ala Leu
        195                 200                 205

Lys Met Asp Asp Phe Glu Cys Val Thr Pro Lys Leu Glu His Phe Gly
    210                 215                 220

Ile Ser Glu Tyr Thr Met Cys Leu Asn Glu Asp Tyr Thr Met Gly Leu
225                 230                 235                 240

Lys Asn Ala Arg Asn Asn Lys Ser Glu Glu Ala Ile Asp Thr Glu Ser
                245                 250                 255

Arg Leu Asn Asp Asn Val Phe Ala Thr Pro Ser Pro Ile Ile Gln Gln
            260                 265                 270

Leu Glu Lys Ser Asp Ala Glu Tyr Thr Asn Ser Pro Leu Val Pro Thr
        275                 280                 285

Phe Cys Thr Pro Gly Leu Lys Ile Pro Ser Thr Lys Asn Ser Ile Ala
    290                 295                 300

Leu Val Ser Thr Asn Tyr Pro Leu Ser Lys Thr Asn Ser Ser Ser Asn
305                 310                 315                 320

Asp Leu Glu Val Glu Asp Arg Thr Ser Leu Val Leu Asn Ser Asp Thr
                325                 330                 335

Cys Phe Glu Asn Leu Thr Asp Pro Ser Ser Pro Thr Ile Ser Ser Tyr
            340                 345                 350

Glu Asn Leu Leu Arg Thr Pro Thr Pro Pro Glu Val Thr Lys Ile Pro
        355                 360                 365

Glu Asp Ile Leu Gln Leu Leu Ser Lys Tyr Asn Ser Asn Leu Ala Thr
    370                 375                 380

Pro Ile Ala Ile Lys Ala Val Pro Pro Ser Lys Arg Phe Leu Lys His
385                 390                 395                 400

Gly Gln Asn Ile Arg Asp Val Ser Asn Lys Glu Asn
                405                 410
```

-continued

```
<210> SEQ ID NO 8
<211> LENGTH: 2798
<212> TYPE: DNA
<213> ORGANISM: Homo sapiens
<220> FEATURE:
<221> NAME/KEY: CDS
<222> LOCATION: (805)...(2043)

<400> SEQUENCE: 8

tatcatctgt gactgaggaa atccctatct tcctatcaga ctaatgaaac cacaggacag     60

caattagact tttaagtatt ggggggttta gagctctaga tattcgatat gcagactact    120

catgtttgtt tgttttaata aagactggtc caaaggctca ttttcacaca agctacagtt    180

tttcagttcc aggaccaggt aaagatggtc agctccgtga tccataaaat ccaagggtga    240

cgactcagga ttaggaccat ttcttggtga cattgagatg gtcgagctgg tccgcaatga    300

atctatgcgg ggggaacttg gaagtggcgg ccgcctttat ggcctcgaag gcctccctcc    360

tgcgcaccgc ggcgtggccg cgctcctgct cccgggtcat gtagggcatg ctcagccagt    420

aatggttctc cgcctcgatc tccaggcggc ggatcatgtt ctgcttggcg cgcaacgaca    480

cgaaccgcgg ccgccggtgc ttcccgatcc actgacggcc gggaatgcgg ccgcgccaga    540

ggagcgcagt caggaacatg gtgcctgccg cgctgctcaa gactctgcgt ctccgcggcc    600

gccagcagac gccgtggcgt aagcgcaccc gtctcgcggg gtctccgggg gcctcggcga    660

gagacttcgg ctctcgcgag agaggactgc gcctgcgcag agccgaggac gcgtccggcg    720

ccgagattca aactagtggc gggaggctgt gagctgagcg gtggggtctg cgtacgcctg    780

gagtccttcc ccgctgtgct caga atg gac cct atc cgg agc ttc tgc ggg       831
                           Met Asp Pro Ile Arg Ser Phe Cys Gly
                            1               5

aag ctg cgg tct ctg gcc agc acg ctg gac tgc gag acg gcc cgg ctg      879
Lys Leu Arg Ser Leu Ala Ser Thr Leu Asp Cys Glu Thr Ala Arg Leu
 10                  15                  20                  25

cag cga gcg ctg gac gga gag gaa agc gac ttt gaa gat tat cca atg      927
Gln Arg Ala Leu Asp Gly Glu Glu Ser Asp Phe Glu Asp Tyr Pro Met
                 30                  35                  40

aga att tta tat gac ctt cat tca gaa gtt cag act cta aag gat gat      975
Arg Ile Leu Tyr Asp Leu His Ser Glu Val Gln Thr Leu Lys Asp Asp
             45                  50                  55

gtt aat att ctt ctt gat aaa gca aga ttg gaa aat caa gaa ggc att     1023
Val Asn Ile Leu Leu Asp Lys Ala Arg Leu Glu Asn Gln Glu Gly Ile
         60                  65                  70

gat ttc ata aag gca aca aaa gta cta atg gaa aaa aat tca atg gat     1071
Asp Phe Ile Lys Ala Thr Lys Val Leu Met Glu Lys Asn Ser Met Asp
     75                  80                  85

att atg aaa ata aga gag tat ttc cag aag tat gga tat agt cca cgt     1119
Ile Met Lys Ile Arg Glu Tyr Phe Gln Lys Tyr Gly Tyr Ser Pro Arg
 90                  95                 100                 105

gtc aag aaa aat tca gta cac gag caa gaa gcc att aac tct gac cca     1167
Val Lys Lys Asn Ser Val His Glu Gln Glu Ala Ile Asn Ser Asp Pro
                110                 115                 120

gag ttg tct aat tgt gaa aat ttt cag aag act gat gtg aaa gat gat     1215
Glu Leu Ser Asn Cys Glu Asn Phe Gln Lys Thr Asp Val Lys Asp Asp
            125                 130                 135

ctg tct gat cct cct gtt gca agc agt tgt att tct gag aag tct cca     1263
Leu Ser Asp Pro Pro Val Ala Ser Ser Cys Ile Ser Glu Lys Ser Pro
        140                 145                 150

cgt agt cca caa ctt tca gat ttt gga ctt gag cgg tac atc gta tcc     1311
Arg Ser Pro Gln Leu Ser Asp Phe Gly Leu Glu Arg Tyr Ile Val Ser
    155                 160                 165
```

-continued

```
caa gtt cta cca aac cct cca cag gca gtg aac aac tat aag gaa gag     1359
Gln Val Leu Pro Asn Pro Pro Gln Ala Val Asn Asn Tyr Lys Glu Glu
170                 175                 180                 185

ccc gta att gta acc cca cct acc aaa caa tca cta gta aaa gta cta     1407
Pro Val Ile Val Thr Pro Pro Thr Lys Gln Ser Leu Val Lys Val Leu
                190                 195                 200

aaa act cca aaa tgt gca cta aaa atg gat gat ttt gag tgt gta act     1455
Lys Thr Pro Lys Cys Ala Leu Lys Met Asp Asp Phe Glu Cys Val Thr
            205                 210                 215

cct aaa tta gaa cac ttt ggt atc tct gaa tat act atg tgt tta aat     1503
Pro Lys Leu Glu His Phe Gly Ile Ser Glu Tyr Thr Met Cys Leu Asn
        220                 225                 230

gaa gat tac aca atg gga ctt aaa aat gcg agg aat aat aaa agt gag     1551
Glu Asp Tyr Thr Met Gly Leu Lys Asn Ala Arg Asn Asn Lys Ser Glu
    235                 240                 245

gag gcc ata gat aca gaa tcc agg ctc aat gat aat gtt ttt gcc act     1599
Glu Ala Ile Asp Thr Glu Ser Arg Leu Asn Asp Asn Val Phe Ala Thr
250                 255                 260                 265

ccc agc ccc atc atc cag cag ttg gaa aaa agt gat gcc gaa tat acc     1647
Pro Ser Pro Ile Ile Gln Gln Leu Glu Lys Ser Asp Ala Glu Tyr Thr
                270                 275                 280

aac tct cct ttg gta cct aca ttc tgt act cct ggt ttg aaa att cca     1695
Asn Ser Pro Leu Val Pro Thr Phe Cys Thr Pro Gly Leu Lys Ile Pro
            285                 290                 295

tct aca aag aac agc ata gct ttg gta tcc aca aat tac cca tta tca     1743
Ser Thr Lys Asn Ser Ile Ala Leu Val Ser Thr Asn Tyr Pro Leu Ser
        300                 305                 310

aaa aca aat agt tca tca aat gat ttg gaa gtt gaa gat cgt act tcg     1791
Lys Thr Asn Ser Ser Ser Asn Asp Leu Glu Val Glu Asp Arg Thr Ser
    315                 320                 325

ttg gtt tta aat tca gac aca tgc ttt gag aat tta aca gat ccc tct     1839
Leu Val Leu Asn Ser Asp Thr Cys Phe Glu Asn Leu Thr Asp Pro Ser
330                 335                 340                 345

tca cct acg att tct tct tat gag aat ctg ctc aga aca cct aca cct     1887
Ser Pro Thr Ile Ser Ser Tyr Glu Asn Leu Leu Arg Thr Pro Thr Pro
                350                 355                 360

cca gaa gta act aaa att cca gaa gat att ctc cag ctt tta tca aaa     1935
Pro Glu Val Thr Lys Ile Pro Glu Asp Ile Leu Gln Leu Leu Ser Lys
            365                 370                 375

tac aac tca aac cta gct act cca ata gca att aaa gca gtg cca ccc     1983
Tyr Asn Ser Asn Leu Ala Thr Pro Ile Ala Ile Lys Ala Val Pro Pro
        380                 385                 390

agt aaa agg ttc ctt aaa cat gga cag aac atc cga gat gtc agc aac     2031
Ser Lys Arg Phe Leu Lys His Gly Gln Asn Ile Arg Asp Val Ser Asn
    395                 400                 405

aaa gaa aac tga aattccagtg gatctatcca acacagaaac tgaacaaaat         2083
Lys Glu Asn
410

gagatgaaag ccgagctgga ccgattttaa cattcacatt gccctgcctc tgtcccctt    2143

taaacgttga cccattttaa agacaaacat gaacattaac atcataatat gctttttatg   2203

aagtttcaat aaggtttaac cttagtcttg ttgacatgta gcccagtcat tcactcttta   2263

aggactatta gtgtttcatt gatactaaat tacccagctt aatcaacaga atggtttaag   2323

tagtaccagg aagtaggaca agtaatttca aaaatataaa ggtgtttgct actcagatga   2383

ggccgcccct gaccttctgg ccagagagac attgctgcca gccagctctg ccttcccatc   2443

atctcctttc aggaccgtcc cacacctttt acttgctcag tgctgtctga agatgcagtt   2503
```

-continued

```
gctgtttgca aacaacagga acaccagtta aactaattag gaaacagagg gagatttcca   2563

ggcctgggta actatatact gtgaccattg gcggttgaga ccggtcttca accagtggaa   2623

ccccgaactc tgctgtcagg gtgtggactt cggtgctctt ccaagttttc acctgggggg   2683

gggagctaac cccctatgtt cacgccttct attcccattg gcgctgaact cttaaggtca   2743

ctctggtcgc ttgtgacccc gtaaccctga tgtacccctc taaaaggtga ggggc        2798


<210> SEQ ID NO 9
<211> LENGTH: 412
<212> TYPE: PRT
<213> ORGANISM: Homo sapiens

<400> SEQUENCE: 9

Met Asp Pro Ile Arg Ser Phe Cys Gly Lys Leu Arg Ser Leu Ala Ser
 1               5                  10                  15

Thr Leu Asp Cys Glu Thr Ala Arg Leu Gln Arg Ala Leu Asp Gly Glu
            20                  25                  30

Glu Ser Asp Phe Glu Asp Tyr Pro Met Arg Ile Leu Tyr Asp Leu His
        35                  40                  45

Ser Glu Val Gln Thr Leu Lys Asp Asp Val Asn Ile Leu Leu Asp Lys
    50                  55                  60

Ala Arg Leu Glu Asn Gln Glu Gly Ile Asp Phe Ile Lys Ala Thr Lys
65                  70                  75                  80

Val Leu Met Glu Lys Asn Ser Met Asp Ile Met Lys Ile Arg Glu Tyr
                85                  90                  95

Phe Gln Lys Tyr Gly Tyr Ser Pro Arg Val Lys Lys Asn Ser Val His
            100                 105                 110

Glu Gln Glu Ala Ile Asn Ser Asp Pro Glu Leu Ser Asn Cys Glu Asn
        115                 120                 125

Phe Gln Lys Thr Asp Val Lys Asp Asp Leu Ser Asp Pro Pro Val Ala
    130                 135                 140

Ser Ser Cys Ile Ser Glu Lys Ser Pro Arg Ser Pro Gln Leu Ser Asp
145                 150                 155                 160

Phe Gly Leu Glu Arg Tyr Ile Val Ser Gln Val Leu Pro Asn Pro Pro
                165                 170                 175

Gln Ala Val Asn Asn Tyr Lys Glu Glu Pro Val Ile Val Thr Pro Pro
            180                 185                 190

Thr Lys Gln Ser Leu Val Lys Val Leu Lys Thr Pro Lys Cys Ala Leu
        195                 200                 205

Lys Met Asp Asp Phe Glu Cys Val Thr Pro Lys Leu Glu His Phe Gly
    210                 215                 220

Ile Ser Glu Tyr Thr Met Cys Leu Asn Glu Asp Tyr Thr Met Gly Leu
225                 230                 235                 240

Lys Asn Ala Arg Asn Asn Lys Ser Glu Glu Ala Ile Asp Thr Glu Ser
                245                 250                 255

Arg Leu Asn Asp Asn Val Phe Ala Thr Pro Ser Pro Ile Ile Gln Gln
            260                 265                 270

Leu Glu Lys Ser Asp Ala Glu Tyr Thr Asn Ser Pro Leu Val Pro Thr
        275                 280                 285

Phe Cys Thr Pro Gly Leu Lys Ile Pro Ser Thr Lys Asn Ser Ile Ala
    290                 295                 300

Leu Val Ser Thr Asn Tyr Pro Leu Ser Lys Thr Asn Ser Ser Ser Asn
305                 310                 315                 320

Asp Leu Glu Val Glu Asp Arg Thr Ser Leu Val Leu Asn Ser Asp Thr
```

-continued

```
                325                 330                 335

Cys Phe Glu Asn Leu Thr Asp Pro Ser Ser Pro Thr Ile Ser Ser Tyr
            340                 345                 350

Glu Asn Leu Leu Arg Thr Pro Thr Pro Pro Glu Val Thr Lys Ile Pro
        355                 360                 365

Glu Asp Ile Leu Gln Leu Leu Ser Lys Tyr Asn Ser Asn Leu Ala Thr
    370                 375                 380

Pro Ile Ala Ile Lys Ala Val Pro Pro Ser Lys Arg Phe Leu Lys His
385                 390                 395                 400

Gly Gln Asn Ile Arg Asp Val Ser Asn Lys Glu Asn
                405                 410


<210> SEQ ID NO 10
<211> LENGTH: 2798
<212> TYPE: DNA
<213> ORGANISM: Homo sapiens
<220> FEATURE:
<221> NAME/KEY: CDS
<222> LOCATION: (805)...(2043)

<400> SEQUENCE: 10

tatcatctgt gactgaggaa atccctatct tcctatcaga ctaatgaaac cacaggacag     60

caattagact tttaagtatt ggggggttta gagctctaga tattcgatat gcagactact    120

catgtttgtt tgttttaata aagactggtc caaaggctca ttttcacaca agctacagtt    180

tttcagttcc aggaccaggt aaagatggtc agctccgtga tccataaaat ccaagggtga    240

cgactcagga ttaggaccat ttcttggtga cattgagatg gtcgagctgg tccgcaatga    300

atctatgcgg ggggaacttg gaagtggcgg ccgcctttat ggcctcgaag gcctccctcc    360

tgcgcaccgc ggcgtggccg cgctcctgct cccgggtcat gtagggcatg ctcagccagt    420

aatggttctc cgcctcgatc tccaggcggc ggatcatgtt ctgcttggcg cgcaacgaca    480

cgaaccgcgg ccgccggtgc ttcccgatcc actgacggcc gggaatgcgg ccgcgccaga    540

ggagcgcagt caggaacatg gtgcctgccg cgctgctcaa gactctgcgt ctccgcggcc    600

gccagcagac gccgtggcgt aagcgcaccc gtctcgcggg gtctccgggg gcctcggcga    660

gagacttcgg ctctcgcgag agaggactgc gcctgcgcag agccgaggac gcgtccggcg    720

ccgagattca aactagtggc gggaggctgt gagctgagcg gtggggtctg cgtacgcctg    780

gagtccttcc ccgctgtgct cagc atg gac cct atc cgg agc ttc tgc ggg       831
                           Met Asp Pro Ile Arg Ser Phe Cys Gly
                            1               5

aag ctg cgg tct ctg gcc agc acg ctg gac tgc gag acg gcc cgg ctg      879
Lys Leu Arg Ser Leu Ala Ser Thr Leu Asp Cys Glu Thr Ala Arg Leu
 10                  15                  20                  25

cag cga gcg ctg gac gga gag gaa agc gac ttt gaa gat tat cca atg      927
Gln Arg Ala Leu Asp Gly Glu Glu Ser Asp Phe Glu Asp Tyr Pro Met
                 30                  35                  40

aga att tta tat gac ctt cat tca gaa gtt cag act cta aag gat gat      975
Arg Ile Leu Tyr Asp Leu His Ser Glu Val Gln Thr Leu Lys Asp Asp
             45                  50                  55

gtt aat att ctt ctt gat aaa gca aga ttg gaa aat caa gaa ggc att     1023
Val Asn Ile Leu Leu Asp Lys Ala Arg Leu Glu Asn Gln Glu Gly Ile
         60                  65                  70

gat ttc ata aag gca aca aaa gta cta atg gaa aaa aat tca atg gat     1071
Asp Phe Ile Lys Ala Thr Lys Val Leu Met Glu Lys Asn Ser Met Asp
     75                  80                  85

att atg aaa ata aga gag tat ttc cag aag tat gga tat agt cca cgt     1119
```

-continued

```
Ile Met Lys Ile Arg Glu Tyr Phe Gln Lys Tyr Gly Tyr Ser Pro Arg
 90                  95                 100                 105

gtc aag aaa aat tca gta cac gag caa gaa gcc att aac tct gac cca     1167
Val Lys Lys Asn Ser Val His Glu Gln Glu Ala Ile Asn Ser Asp Pro
                110                 115                 120

gag ttg tct aat tgt gaa aat ttt cag aag act gat gtg aaa gat gat     1215
Glu Leu Ser Asn Cys Glu Asn Phe Gln Lys Thr Asp Val Lys Asp Asp
            125                 130                 135

ctg tct gat cct cct gtt gca agc agt tgt att tct ggg aag tct cca     1263
Leu Ser Asp Pro Pro Val Ala Ser Ser Cys Ile Ser Gly Lys Ser Pro
        140                 145                 150

cgt agt cca caa ctt tca gat ttt gga ctt gag cgg tac atc gta tcc     1311
Arg Ser Pro Gln Leu Ser Asp Phe Gly Leu Glu Arg Tyr Ile Val Ser
    155                 160                 165

caa gtt cta cca aac cct cca cag gca gtg aac aac tat aag gaa gag     1359
Gln Val Leu Pro Asn Pro Pro Gln Ala Val Asn Asn Tyr Lys Glu Glu
170                 175                 180                 185

ccc gta att gta acc cca cct acc aaa caa tca cta gta aaa gta cta     1407
Pro Val Ile Val Thr Pro Pro Thr Lys Gln Ser Leu Val Lys Val Leu
                190                 195                 200

aaa act cca aaa tgt gca cta aaa atg gat gat ttt gag tgt gta act     1455
Lys Thr Pro Lys Cys Ala Leu Lys Met Asp Asp Phe Glu Cys Val Thr
            205                 210                 215

cct aaa tta gaa cac ttt ggt atc tct gaa tat act atg tgt tta aat     1503
Pro Lys Leu Glu His Phe Gly Ile Ser Glu Tyr Thr Met Cys Leu Asn
        220                 225                 230

gaa gat tac aca atg gga ctt aaa aat gcg agg aat aat aaa agt gag     1551
Glu Asp Tyr Thr Met Gly Leu Lys Asn Ala Arg Asn Asn Lys Ser Glu
    235                 240                 245

gag gcc ata gat aca gaa tcc agg ctc aat gat aat gtt ttt gcc act     1599
Glu Ala Ile Asp Thr Glu Ser Arg Leu Asn Asp Asn Val Phe Ala Thr
250                 255                 260                 265

ccc agc ccc atc atc cag cag ttg gaa aaa agt gat gcc gaa tat acc     1647
Pro Ser Pro Ile Ile Gln Gln Leu Glu Lys Ser Asp Ala Glu Tyr Thr
                270                 275                 280

aac tct cct ttg gta cct aca ttc tgt act cct ggt ttg aaa att cca     1695
Asn Ser Pro Leu Val Pro Thr Phe Cys Thr Pro Gly Leu Lys Ile Pro
            285                 290                 295

tct aca aag aac agc ata gct ttg gta tcc aca aat tac cca tta tca     1743
Ser Thr Lys Asn Ser Ile Ala Leu Val Ser Thr Asn Tyr Pro Leu Ser
        300                 305                 310

aaa aca aat agt tca tca aat gat ttg gaa gtt gaa gat cgt act tcg     1791
Lys Thr Asn Ser Ser Ser Asn Asp Leu Glu Val Glu Asp Arg Thr Ser
    315                 320                 325

ttg gtt tta aat tca gac aca tgc ttt gag aat tta aca gat ccc tct     1839
Leu Val Leu Asn Ser Asp Thr Cys Phe Glu Asn Leu Thr Asp Pro Ser
330                 335                 340                 345

tca cct acg att tct tct tat gag aat ctg ctc aga aca cct aca cct     1887
Ser Pro Thr Ile Ser Ser Tyr Glu Asn Leu Leu Arg Thr Pro Thr Pro
                350                 355                 360

cca gaa gta act aaa att cca gaa gat att ctc cag ctt tta tca aaa     1935
Pro Glu Val Thr Lys Ile Pro Glu Asp Ile Leu Gln Leu Leu Ser Lys
            365                 370                 375

tac aac tca aac cta gct act cca ata gca att aaa gca gtg cca ccc     1983
Tyr Asn Ser Asn Leu Ala Thr Pro Ile Ala Ile Lys Ala Val Pro Pro
        380                 385                 390

agt aaa agg ttc ctt aaa cat gga cag aac atc cga gat gtc agc aac     2031
Ser Lys Arg Phe Leu Lys His Gly Gln Asn Ile Arg Asp Val Ser Asn
    395                 400                 405
```

-continued

```
aaa gaa aac tga aattccagtg gatctatcca acacagaaac tgaacaaaat        2083
Lys Glu Asn
410

gagatgaaag ccgagctgga ccgattttaa cattcacatt gccctgcctc tgtccccctt   2143

taaacgttga cccattttaa agacaaacat gaacattaac atcataatat gctttttatg   2203

aagtttcaat aaggtttaac cttagtcttg ttgacatgta gcccagtcat tcactcttta   2263

aggactatta gtgtttcatt gatactaaat tacccagctt aatcaacaga atggtttaag   2323

tagtaccagg aagtaggaca agtaatttca aaaatataaa ggtgtttgct actcagatga   2383

ggccgcccct gaccttctgg ccagagagac attgctgcca gccagctctg ccttcccatc   2443

atctcctttc aggaccgtcc cacacctttt acttgctcag tgctgtctga agatgcagtt   2503

gctgtttgca aacaacagga acaccagtta aactaattag gaaacagagg gagatttcca   2563

ggcctgggta actatatact gtgaccattg gcggttgaga ccggtcttca accagtggaa   2623

ccccgaactc tgctgtcagg gtgtggactt cggtgctctt ccaagttttc acctgggggg   2683

gggagctaac cccctatgtt cacgccttct attcccattg gcgctgaact cttaaggtca   2743

ctctggtcgc ttgtgacccc gtaaccctga tgtacccctc taaaaggtga ggggc        2798


<210> SEQ ID NO 11
<211> LENGTH: 412
<212> TYPE: PRT
<213> ORGANISM: Homo sapiens

<400> SEQUENCE: 11

Met Asp Pro Ile Arg Ser Phe Cys Gly Lys Leu Arg Ser Leu Ala Ser
 1               5                  10                  15

Thr Leu Asp Cys Glu Thr Ala Arg Leu Gln Arg Ala Leu Asp Gly Glu
            20                  25                  30

Glu Ser Asp Phe Glu Asp Tyr Pro Met Arg Ile Leu Tyr Asp Leu His
        35                  40                  45

Ser Glu Val Gln Thr Leu Lys Asp Asp Val Asn Ile Leu Leu Asp Lys
    50                  55                  60

Ala Arg Leu Glu Asn Gln Glu Gly Ile Asp Phe Ile Lys Ala Thr Lys
65                  70                  75                  80

Val Leu Met Glu Lys Asn Ser Met Asp Ile Met Lys Ile Arg Glu Tyr
                85                  90                  95

Phe Gln Lys Tyr Gly Tyr Ser Pro Arg Val Lys Lys Asn Ser Val His
            100                 105                 110

Glu Gln Glu Ala Ile Asn Ser Asp Pro Glu Leu Ser Asn Cys Glu Asn
        115                 120                 125

Phe Gln Lys Thr Asp Val Lys Asp Asp Leu Ser Asp Pro Pro Val Ala
    130                 135                 140

Ser Ser Cys Ile Ser Gly Lys Ser Pro Arg Ser Pro Gln Leu Ser Asp
145                 150                 155                 160

Phe Gly Leu Glu Arg Tyr Ile Val Ser Gln Val Leu Pro Asn Pro Pro
                165                 170                 175

Gln Ala Val Asn Asn Tyr Lys Glu Glu Pro Val Ile Val Thr Pro Pro
            180                 185                 190

Thr Lys Gln Ser Leu Val Lys Val Leu Lys Thr Pro Lys Cys Ala Leu
        195                 200                 205

Lys Met Asp Asp Phe Glu Cys Val Thr Pro Lys Leu Glu His Phe Gly
    210                 215                 220

Ile Ser Glu Tyr Thr Met Cys Leu Asn Glu Asp Tyr Thr Met Gly Leu
```

-continued

```
225                 230                 235                 240

Lys Asn Ala Arg Asn Asn Lys Ser Glu Glu Ala Ile Asp Thr Glu Ser
                245                 250                 255

Arg Leu Asn Asp Asn Val Phe Ala Thr Pro Ser Pro Ile Ile Gln Gln
            260                 265                 270

Leu Glu Lys Ser Asp Ala Glu Tyr Thr Asn Ser Pro Leu Val Pro Thr
        275                 280                 285

Phe Cys Thr Pro Gly Leu Lys Ile Pro Ser Thr Lys Asn Ser Ile Ala
    290                 295                 300

Leu Val Ser Thr Asn Tyr Pro Leu Ser Lys Thr Asn Ser Ser Ser Asn
305                 310                 315                 320

Asp Leu Glu Val Glu Asp Arg Thr Ser Leu Val Leu Asn Ser Asp Thr
                325                 330                 335

Cys Phe Glu Asn Leu Thr Asp Pro Ser Ser Pro Thr Ile Ser Ser Tyr
            340                 345                 350

Glu Asn Leu Leu Arg Thr Pro Thr Pro Pro Glu Val Thr Lys Ile Pro
        355                 360                 365

Glu Asp Ile Leu Gln Leu Leu Ser Lys Tyr Asn Ser Asn Leu Ala Thr
    370                 375                 380

Pro Ile Ala Ile Lys Ala Val Pro Pro Ser Lys Arg Phe Leu Lys His
385                 390                 395                 400

Gly Gln Asn Ile Arg Asp Val Ser Asn Lys Glu Asn
                405                 410


<210> SEQ ID NO 12
<211> LENGTH: 2798
<212> TYPE: DNA
<213> ORGANISM: Homo sapiens
<220> FEATURE:
<221> NAME/KEY: CDS
<222> LOCATION: (805)...(2043)

<400> SEQUENCE: 12

tatcatctgt gactgaggaa atccctatct tcctatcaga ctaatgaaac cacaggacag      60

caattagact tttaagtatt ggggggttta gagctctaga tattcgatat gcagactact     120

catgtttgtt tgttttaata aagactggtc caaaggctca ttttcacaca agctacagtt     180

tttcagttcc aggaccaggt aaagatggtc agctccgtga tccataaaat ccaagggtga     240

cgactcagga ttaggaccat ttcttggtga cattgagatg gtcgagctgg tccgcaatga     300

atctatgcgg ggggaacttg gaagtggcgg ccgcctttat ggcctcgaag gcctccctcc     360

tgcgcaccgc ggcgtggccg cgctcctgct cccgggtcat gtagggcatg ctcagccagt     420

aatggttctc cgcctcgatc tccaggcggc ggatcatgtt ctgcttggcg cgcaacgaca     480

cgaaccgcgg ccgccggtgc ttcccgatcc actgacggcc gggaatgcgg ccgcgccaga     540

ggagcgcagt caggaacatg gtgcctgccg cgctgctcaa gactctgcgt ctccgcggcc     600

gccagcagac gccgtggcgt aagcgcaccc gtctcgcggg gtctccgggg gcctcggcga     660

gagacttcgg ctctcgcgag agaggactgc gcctgcgcag agccgaggac gcgtccggcg     720

ccgagattca aactagtggc gggaggctgt gagctgagcg gtggggtctg cgtacgcctg     780

gagtccttcc ccgctgtgct cagc atg gac cct atc cgg agc ttc tgc ggg        831
                           Met Asp Pro Ile Arg Ser Phe Cys Gly
                            1               5

aag ctg cgg tct ctg gcc agc acg ctg gac tgc gag acg gcc cgg ctg       879
Lys Leu Arg Ser Leu Ala Ser Thr Leu Asp Cys Glu Thr Ala Arg Leu
 10                 15                  20                  25
```

-continued

```
cag cga gcg ctg gac gga gag gaa agc gac ttt gaa gat tat cca atg      927
Gln Arg Ala Leu Asp Gly Glu Glu Ser Asp Phe Glu Asp Tyr Pro Met
                 30                  35                  40

aga att tta tat gac ctt cat tca gaa gtt cag act cta aag gat gat      975
Arg Ile Leu Tyr Asp Leu His Ser Glu Val Gln Thr Leu Lys Asp Asp
             45                  50                  55

gtt aat att ctt ctt gat aaa gca aga ttg gaa aat caa gaa ggc att     1023
Val Asn Ile Leu Leu Asp Lys Ala Arg Leu Glu Asn Gln Glu Gly Ile
         60                  65                  70

gat ttc ata aag gca aca aaa gta cta atg gaa aaa aat tca atg gat     1071
Asp Phe Ile Lys Ala Thr Lys Val Leu Met Glu Lys Asn Ser Met Asp
     75                  80                  85

att atg aaa ata aga gag tat ttc cag aag tat gga tat agt cca cgt     1119
Ile Met Lys Ile Arg Glu Tyr Phe Gln Lys Tyr Gly Tyr Ser Pro Arg
 90                  95                 100                 105

gtc aag aaa aat tca gta cac gag caa gaa gcc att aac tct gac cca     1167
Val Lys Lys Asn Ser Val His Glu Gln Glu Ala Ile Asn Ser Asp Pro
                110                 115                 120

gag ttg tct aat tgt gaa aat ttt cag aag act gat gtg aaa gat gat     1215
Glu Leu Ser Asn Cys Glu Asn Phe Gln Lys Thr Asp Val Lys Asp Asp
            125                 130                 135

ctg tct gat cct cct gtt gca agc agt tgt att tct gag aag tct cca     1263
Leu Ser Asp Pro Pro Val Ala Ser Ser Cys Ile Ser Glu Lys Ser Pro
        140                 145                 150

cgt agt cca caa ctt tca gat ttt gga ctt gag cgg tac atc gta tcc     1311
Arg Ser Pro Gln Leu Ser Asp Phe Gly Leu Glu Arg Tyr Ile Val Ser
    155                 160                 165

caa gtt cta cca aac cct cca cag gca gtg aac aac tat aag gaa gag     1359
Gln Val Leu Pro Asn Pro Pro Gln Ala Val Asn Asn Tyr Lys Glu Glu
170                 175                 180                 185

ccc gta att gta acc cca cct acc aaa caa tca cta gta aaa gta cta     1407
Pro Val Ile Val Thr Pro Pro Thr Lys Gln Ser Leu Val Lys Val Leu
                190                 195                 200

aaa act cca aaa tgt gca cta aaa atg gat gat ttt gag tgt gta act     1455
Lys Thr Pro Lys Cys Ala Leu Lys Met Asp Asp Phe Glu Cys Val Thr
            205                 210                 215

cct aaa tta gaa cac ttt ggt atc tct gaa tat act atg tgt tta aat     1503
Pro Lys Leu Glu His Phe Gly Ile Ser Glu Tyr Thr Met Cys Leu Asn
        220                 225                 230

gaa gat tac aca atg gga ctt aaa aat gcg agg aat aat aaa agt gag     1551
Glu Asp Tyr Thr Met Gly Leu Lys Asn Ala Arg Asn Asn Lys Ser Glu
    235                 240                 245

gag gcc ata gat gca gaa tcc agg ctc aat gat aat gtt ttt gcc act     1599
Glu Ala Ile Asp Ala Glu Ser Arg Leu Asn Asp Asn Val Phe Ala Thr
250                 255                 260                 265

ccc agc ccc atc atc cag cag ttg gaa aaa agt gat gcc gaa tat acc     1647
Pro Ser Pro Ile Ile Gln Gln Leu Glu Lys Ser Asp Ala Glu Tyr Thr
                270                 275                 280

aac tct cct ttg gta cct aca ttc tgt act cct ggt ttg aaa att cca     1695
Asn Ser Pro Leu Val Pro Thr Phe Cys Thr Pro Gly Leu Lys Ile Pro
            285                 290                 295

tct aca aag aac agc ata gct ttg gta tcc aca aat tac cca tta tca     1743
Ser Thr Lys Asn Ser Ile Ala Leu Val Ser Thr Asn Tyr Pro Leu Ser
        300                 305                 310

aaa aca aat agt tca tca aat gat ttg gaa gtt gaa gat cgt act tcg     1791
Lys Thr Asn Ser Ser Ser Asn Asp Leu Glu Val Glu Asp Arg Thr Ser
    315                 320                 325

ttg gtt tta aat tca gac aca tgc ttt gag aat tta aca gat ccc tct     1839
Leu Val Leu Asn Ser Asp Thr Cys Phe Glu Asn Leu Thr Asp Pro Ser
```

-continued

```
330                 335                 340                 345

tca cct acg att tct tct tat gag aat ctg ctc aga aca cct aca cct     1887
Ser Pro Thr Ile Ser Ser Tyr Glu Asn Leu Leu Arg Thr Pro Thr Pro
                350                 355                 360

cca gaa gta act aaa att cca gaa gat att ctc cag ctt tta tca aaa     1935
Pro Glu Val Thr Lys Ile Pro Glu Asp Ile Leu Gln Leu Leu Ser Lys
            365                 370                 375

tac aac tca aac cta gct act cca ata gca att aaa gca gtg cca ccc     1983
Tyr Asn Ser Asn Leu Ala Thr Pro Ile Ala Ile Lys Ala Val Pro Pro
        380                 385                 390

agt aaa agg ttc ctt aaa cat gga cag aac atc cga gat gtc agc aac     2031
Ser Lys Arg Phe Leu Lys His Gly Gln Asn Ile Arg Asp Val Ser Asn
    395                 400                 405

aaa gaa aac tga aattccagtg gatctatcca acacagaaac tgaacaaaat         2083
Lys Glu Asn
410

gagatgaaag ccgagctgga ccgattttaa cattcacatt gccctgcctc tgtcccctt   2143

taaacgttga cccattttaa agacaaacat gaacattaac atcataatat gctttttatg   2203

aagtttcaat aaggtttaac cttagtcttg ttgacatgta gcccagtcat tcactcttta   2263

aggactatta gtgtttcatt gatactaaat tacccagctt aatcaacaga atggtttaag   2323

tagtaccagg aagtaggaca agtaatttca aaaatataaa ggtgtttgct actcagatga   2383

ggccgcccct gaccttctgg ccagagagac attgctgcca gccagctctg ccttcccatc   2443

atctcctttc aggaccgtcc cacacctttt acttgctcag tgctgtctga agatgcagtt   2503

gctgtttgca aacaacagga acaccagtta aactaattag gaaacagagg gagatttcca   2563

ggcctgggta actatatact gtgaccattg gcggttgaga ccggtcttca accagtggaa   2623

ccccgaactc tgctgtcagg gtgtggactt cggtgctctt ccaagttttc acctgggggg   2683

gggagctaac cccctatgtt cacgccttct attcccattg gcgctgaact cttaaggtca   2743

ctctggtcgc ttgtgacccc gtaaccctga tgtacccctc taaaaggtga ggggc        2798


<210> SEQ ID NO 13
<211> LENGTH: 412
<212> TYPE: PRT
<213> ORGANISM: Homo sapiens

<400> SEQUENCE: 13

Met Asp Pro Ile Arg Ser Phe Cys Gly Lys Leu Arg Ser Leu Ala Ser
 1               5                  10                  15

Thr Leu Asp Cys Glu Thr Ala Arg Leu Gln Arg Ala Leu Asp Gly Glu
            20                  25                  30

Glu Ser Asp Phe Glu Asp Tyr Pro Met Arg Ile Leu Tyr Asp Leu His
        35                  40                  45

Ser Glu Val Gln Thr Leu Lys Asp Asp Val Asn Ile Leu Leu Asp Lys
    50                  55                  60

Ala Arg Leu Glu Asn Gln Glu Gly Ile Asp Phe Ile Lys Ala Thr Lys
65                  70                  75                  80

Val Leu Met Glu Lys Asn Ser Met Asp Ile Met Lys Ile Arg Glu Tyr
                85                  90                  95

Phe Gln Lys Tyr Gly Tyr Ser Pro Arg Val Lys Lys Asn Ser Val His
            100                 105                 110

Glu Gln Glu Ala Ile Asn Ser Asp Pro Glu Leu Ser Asn Cys Glu Asn
        115                 120                 125

Phe Gln Lys Thr Asp Val Lys Asp Asp Leu Ser Asp Pro Pro Val Ala
```

```
    130                 135                 140

Ser Ser Cys Ile Ser Glu Lys Ser Pro Arg Ser Pro Gln Leu Ser Asp
145                 150                 155                 160

Phe Gly Leu Glu Arg Tyr Ile Val Ser Gln Val Leu Pro Asn Pro Pro
                165                 170                 175

Gln Ala Val Asn Asn Tyr Lys Glu Glu Pro Val Ile Val Thr Pro Pro
            180                 185                 190

Thr Lys Gln Ser Leu Val Lys Val Leu Lys Thr Pro Lys Cys Ala Leu
        195                 200                 205

Lys Met Asp Asp Phe Glu Cys Val Thr Pro Lys Leu Glu His Phe Gly
    210                 215                 220

Ile Ser Glu Tyr Thr Met Cys Leu Asn Glu Asp Tyr Thr Met Gly Leu
225                 230                 235                 240

Lys Asn Ala Arg Asn Asn Lys Ser Glu Glu Ala Ile Asp Ala Glu Ser
                245                 250                 255

Arg Leu Asn Asp Asn Val Phe Ala Thr Pro Ser Pro Ile Ile Gln Gln
            260                 265                 270

Leu Glu Lys Ser Asp Ala Glu Tyr Thr Asn Ser Pro Leu Val Pro Thr
        275                 280                 285

Phe Cys Thr Pro Gly Leu Lys Ile Pro Ser Thr Lys Asn Ser Ile Ala
    290                 295                 300

Leu Val Ser Thr Asn Tyr Pro Leu Ser Lys Thr Asn Ser Ser Ser Asn
305                 310                 315                 320

Asp Leu Glu Val Glu Asp Arg Thr Ser Leu Val Leu Asn Ser Asp Thr
                325                 330                 335

Cys Phe Glu Asn Leu Thr Asp Pro Ser Ser Pro Thr Ile Ser Ser Tyr
            340                 345                 350

Glu Asn Leu Leu Arg Thr Pro Thr Pro Pro Glu Val Thr Lys Ile Pro
        355                 360                 365

Glu Asp Ile Leu Gln Leu Leu Ser Lys Tyr Asn Ser Asn Leu Ala Thr
    370                 375                 380

Pro Ile Ala Ile Lys Ala Val Pro Pro Ser Lys Arg Phe Leu Lys His
385                 390                 395                 400

Gly Gln Asn Ile Arg Asp Val Ser Asn Lys Glu Asn
                405                 410


<210> SEQ ID NO 14
<211> LENGTH: 2798
<212> TYPE: DNA
<213> ORGANISM: Homo sapiens
<220> FEATURE:
<221> NAME/KEY: CDS
<222> LOCATION: (805)...(2043)

<400> SEQUENCE: 14

tatcatctgt gactgaggaa atccctatct tcctatcaga ctaatgaaac cacaggacag      60

caattagact tttaagtatt ggggggttta gagctctaga tattcgatat gcagactact     120

catgtttgtt tgttttaata aagactggtc caaaggctca ttttcacaca agctacagtt     180

tttcagttcc aggaccaggt aaagatggtc agctccgtga tccataaaat ccaagggtga     240

cgactcagga ttaggaccat ttcttggtga cattgagatg gtcgagctgg tccgcaatga     300

atctatgcgg ggggaacttg gaagtggcgg ccgcctttat ggcctcgaag gcctccctcc     360

tgcgcaccgc ggcgtggccg cgctcctgct cccgggtcat gtagggcatg ctcagccagt     420

aatggttctc cgcctcgatc tccaggcggc ggatcatgtt ctgcttggcg cgcaacgaca     480
```

-continued

```
cgaaccgcgg ccgccggtgc ttcccgatcc actgacggcc gggaatgcgg ccgcgccaga    540

ggagcgcagt caggaacatg gtgcctgccg cgctgctcaa gactctgcgt ctccgcggcc    600

gccagcagac gccgtggcgt aagcgcaccc gtctcgcggg gtctccgggg gcctcggcga    660

gagacttcgg ctctcgcgag agaggactgc gcctgcgcag agccgaggac gcgtccggcg    720

ccgagattca aactagtggc gggaggctgt gagctgagcg gtggggtctg cgtacgcctg    780

gagtccttcc ccgctgtgct cagc atg gac cct atc cgg agc ttc tgc ggg       831
                           Met Asp Pro Ile Arg Ser Phe Cys Gly
                            1               5

aag ctg cgg tct ctg gcc agc acg ctg gac tgc gag acg gcc cgg ctg      879
Lys Leu Arg Ser Leu Ala Ser Thr Leu Asp Cys Glu Thr Ala Arg Leu
 10                  15                  20                  25

cag cga gcg ctg gac gga gag gaa agc gac ttt gaa gat tat cca atg      927
Gln Arg Ala Leu Asp Gly Glu Glu Ser Asp Phe Glu Asp Tyr Pro Met
                 30                  35                  40

aga att tta tat gac ctt cat tca gaa gtt cag act cta aag gat gat      975
Arg Ile Leu Tyr Asp Leu His Ser Glu Val Gln Thr Leu Lys Asp Asp
             45                  50                  55

gtt aat att ctt ctt gat aaa gca aga ttg gaa aat caa gaa ggc att     1023
Val Asn Ile Leu Leu Asp Lys Ala Arg Leu Glu Asn Gln Glu Gly Ile
         60                  65                  70

gat ttc ata aag gca aca aaa gta cta atg gaa aaa aat tca atg gat     1071
Asp Phe Ile Lys Ala Thr Lys Val Leu Met Glu Lys Asn Ser Met Asp
     75                  80                  85

att atg aaa ata aga gag tat ttc cag aag tat gga tat agt cca cgt     1119
Ile Met Lys Ile Arg Glu Tyr Phe Gln Lys Tyr Gly Tyr Ser Pro Arg
 90                  95                 100                 105

gtc aag aaa aat tca gta cac gag caa gaa gcc att aac tct gac cca     1167
Val Lys Lys Asn Ser Val His Glu Gln Glu Ala Ile Asn Ser Asp Pro
                110                 115                 120

gag ttg tct aat tgt gaa aat ttt cag aag act gat gtg aaa gat gat     1215
Glu Leu Ser Asn Cys Glu Asn Phe Gln Lys Thr Asp Val Lys Asp Asp
            125                 130                 135

ctg tct gat cct cct gtt gca agc agt tgt att tct gag aag tct cca     1263
Leu Ser Asp Pro Pro Val Ala Ser Ser Cys Ile Ser Glu Lys Ser Pro
        140                 145                 150

cgt agt cca caa ctt tca gat ttt gga ctt gag cgg tac atc gta tcc     1311
Arg Ser Pro Gln Leu Ser Asp Phe Gly Leu Glu Arg Tyr Ile Val Ser
    155                 160                 165

caa gtt cta cca aac cct cca cag gca gtg aac aac tat aag gaa gag     1359
Gln Val Leu Pro Asn Pro Pro Gln Ala Val Asn Asn Tyr Lys Glu Glu
170                 175                 180                 185

ccc gta att gta acc cca cct acc aaa caa tca cta gta aaa gta cta     1407
Pro Val Ile Val Thr Pro Pro Thr Lys Gln Ser Leu Val Lys Val Leu
                190                 195                 200

aaa act cca aaa tgt gca cta aaa atg gat gat ttt gag tgt gta act     1455
Lys Thr Pro Lys Cys Ala Leu Lys Met Asp Asp Phe Glu Cys Val Thr
            205                 210                 215

cct aaa tta gaa cac ttt ggt atc tct gaa tat act atg tgt tta aat     1503
Pro Lys Leu Glu His Phe Gly Ile Ser Glu Tyr Thr Met Cys Leu Asn
        220                 225                 230

gaa gat tac aca atg gga ctt aaa aat gcg agg aat aat aaa agt gag     1551
Glu Asp Tyr Thr Met Gly Leu Lys Asn Ala Arg Asn Asn Lys Ser Glu
    235                 240                 245

gag gcc ata gat aca gaa tcc agg ctc aat gat aat gtt ttt gcc act     1599
Glu Ala Ile Asp Thr Glu Ser Arg Leu Asn Asp Asn Val Phe Ala Thr
250                 255                 260                 265
```

-continued

```
ccc agc ccc atc atc cag cag ttg gaa aaa agt gat gcc gaa tat acc      1647
Pro Ser Pro Ile Ile Gln Gln Leu Glu Lys Ser Asp Ala Glu Tyr Thr
                270                 275                 280

aac tct cct ttg gta cct aca ttc tgt act cct ggt ttg aaa att cca      1695
Asn Ser Pro Leu Val Pro Thr Phe Cys Thr Pro Gly Leu Lys Ile Pro
            285                 290                 295

tct aca aag aac agc ata gct ttg gta tcc aca aat tac cca tta tca      1743
Ser Thr Lys Asn Ser Ile Ala Leu Val Ser Thr Asn Tyr Pro Leu Ser
        300                 305                 310

aaa aca aat agt tca tca aat gat ttg gaa gtt gaa gat cgt act tcg      1791
Lys Thr Asn Ser Ser Ser Asn Asp Leu Glu Val Glu Asp Arg Thr Ser
    315                 320                 325

ttg gtt tta aat tca gac aca tgc ttt gag aat tta aca gat ccc tct      1839
Leu Val Leu Asn Ser Asp Thr Cys Phe Glu Asn Leu Thr Asp Pro Ser
330                 335                 340                 345

tca cct acg att tct tct tat gag aat ctg ctc aga aca cct aca cct      1887
Ser Pro Thr Ile Ser Ser Tyr Glu Asn Leu Leu Arg Thr Pro Thr Pro
                350                 355                 360

cca gaa gta act aaa att cca gaa gat att ctc cag ctt tta tca aaa      1935
Pro Glu Val Thr Lys Ile Pro Glu Asp Ile Leu Gln Leu Leu Ser Lys
            365                 370                 375

tac aac tca aac cta gct act cca ata gca att aaa gca gtg cca ccc      1983
Tyr Asn Ser Asn Leu Ala Thr Pro Ile Ala Ile Lys Ala Val Pro Pro
        380                 385                 390

agt aaa agg ttc ctt aaa cat gga cag aac atc cga gat gtc agc aac      2031
Ser Lys Arg Phe Leu Lys His Gly Gln Asn Ile Arg Asp Val Ser Asn
    395                 400                 405

aaa gaa aac tga aattccagtg gatctatcca acacagaaac tgaacaaaat          2083
Lys Glu Asn
410

gagatgaaag ccgagctgga ccgattttaa cattcacatt gccctgcctc tgtcccctt     2143

taaacgttga cccattttaa agacaaacat gaacattaac atcataatat gctttttatg    2203

aagtttcaat aaggtttaac cttagtcttg ttgacatgta gcccagtcat tcactcttta    2263

aggattatta gtgtttcatt gatactaaat tacccagctt aatcaacaga atggtttaag    2323

tagtaccagg aagtaggaca agtaatttca aaaatataaa ggtgtttgct actcagatga    2383

ggccgcccct gaccttctgg ccagagagac attgctgcca gccagctctg ccttcccatc    2443

atctcctttc aggaccgtcc cacacctttt acttgctcag tgctgtctga agatgcagtt    2503

gctgtttgca aacaacagga acaccagtta aactaattag gaaacagagg gagatttcca    2563

ggcctgggta actatatact gtgaccattg gcggttgaga ccggtcttca accagtggaa    2623

ccccgaactc tgctgtcagg gtgtggactt cggtgctctt ccaagttttc acctgggggg    2683

gggagctaac cccctatgtt cacgccttct attcccattg gcgctgaact cttaaggtca    2743

ctctggtcgc ttgtgacccc gtaaccctga tgtacccctc taaaaggtga ggggc          2798


<210> SEQ ID NO 15
<211> LENGTH: 412
<212> TYPE: PRT
<213> ORGANISM: Homo sapiens

<400> SEQUENCE: 15

Met Asp Pro Ile Arg Ser Phe Cys Gly Lys Leu Arg Ser Leu Ala Ser
 1               5                  10                  15

Thr Leu Asp Cys Glu Thr Ala Arg Leu Gln Arg Ala Leu Asp Gly Glu
            20                  25                  30

Glu Ser Asp Phe Glu Asp Tyr Pro Met Arg Ile Leu Tyr Asp Leu His
```

```
        35                  40                  45

Ser Glu Val Gln Thr Leu Lys Asp Asp Val Asn Ile Leu Leu Asp Lys
    50                  55                  60

Ala Arg Leu Glu Asn Gln Glu Gly Ile Asp Phe Ile Lys Ala Thr Lys
65                  70                  75                  80

Val Leu Met Glu Lys Asn Ser Met Asp Ile Met Lys Ile Arg Glu Tyr
                85                  90                  95

Phe Gln Lys Tyr Gly Tyr Ser Pro Arg Val Lys Lys Asn Ser Val His
            100                 105                 110

Glu Gln Glu Ala Ile Asn Ser Asp Pro Glu Leu Ser Asn Cys Glu Asn
        115                 120                 125

Phe Gln Lys Thr Asp Val Lys Asp Asp Leu Ser Asp Pro Pro Val Ala
    130                 135                 140

Ser Ser Cys Ile Ser Glu Lys Ser Pro Arg Ser Pro Gln Leu Ser Asp
145                 150                 155                 160

Phe Gly Leu Glu Arg Tyr Ile Val Ser Gln Val Leu Pro Asn Pro Pro
                165                 170                 175

Gln Ala Val Asn Asn Tyr Lys Glu Glu Pro Val Ile Val Thr Pro Pro
            180                 185                 190

Thr Lys Gln Ser Leu Val Lys Val Leu Lys Thr Pro Lys Cys Ala Leu
        195                 200                 205

Lys Met Asp Asp Phe Glu Cys Val Thr Pro Lys Leu Glu His Phe Gly
    210                 215                 220

Ile Ser Glu Tyr Thr Met Cys Leu Asn Glu Asp Tyr Thr Met Gly Leu
225                 230                 235                 240

Lys Asn Ala Arg Asn Asn Lys Ser Glu Glu Ala Ile Asp Thr Glu Ser
                245                 250                 255

Arg Leu Asn Asp Asn Val Phe Ala Thr Pro Ser Pro Ile Ile Gln Gln
            260                 265                 270

Leu Glu Lys Ser Asp Ala Glu Tyr Thr Asn Ser Pro Leu Val Pro Thr
        275                 280                 285

Phe Cys Thr Pro Gly Leu Lys Ile Pro Ser Thr Lys Asn Ser Ile Ala
    290                 295                 300

Leu Val Ser Thr Asn Tyr Pro Leu Ser Lys Thr Asn Ser Ser Ser Asn
305                 310                 315                 320

Asp Leu Glu Val Glu Asp Arg Thr Ser Leu Val Leu Asn Ser Asp Thr
                325                 330                 335

Cys Phe Glu Asn Leu Thr Asp Pro Ser Ser Pro Thr Ile Ser Ser Tyr
            340                 345                 350

Glu Asn Leu Leu Arg Thr Pro Thr Pro Pro Glu Val Thr Lys Ile Pro
        355                 360                 365

Glu Asp Ile Leu Gln Leu Leu Ser Lys Tyr Asn Ser Asn Leu Ala Thr
    370                 375                 380

Pro Ile Ala Ile Lys Ala Val Pro Pro Ser Lys Arg Phe Leu Lys His
385                 390                 395                 400

Gly Gln Asn Ile Arg Asp Val Ser Asn Lys Glu Asn
                405                 410
```

<210> SEQ ID NO 16
<211> LENGTH: 2798
<212> TYPE: DNA
<213> ORGANISM: Homo sapiens
<220> FEATURE:
<221> NAME/KEY: CDS
<222> LOCATION: (805)...(2043)

-continued

```
<400> SEQUENCE: 16

tatcatctgt gactgaggaa atccctatct tcctatcaga ctaatgaaac cacaggacag      60

caattagact tttaagtatt ggggggttta gagctctaga tattcgatat gcagactact     120

catgtttgtt tgttttaata aagactggtc caaaggctca ttttcacaca agctacagtt     180

tttcagttcc aggaccaggt aaagatggtc agctccgtga tccataaaat ccaagggtga     240

cgactcagga ttaggaccat ttcttggtga cattgagatg gtcgagctgg tccgcaatga     300

atctatgcgg ggggaacttg gaagtggcgg ccgcctttat ggcctcgaag gcctccctcc     360

tgcgcaccgc ggcgtggccg cgctcctgct cccgggtcat gtagggcatg ctcagccagt     420

aatggttctc cgcctcgatc tccaggcggc ggatcatgtt ctgcttggcg cgcaacgaca     480

cgaaccgcgg ccgccggtgc ttcccgatcc actgacggcc gggaatgcgg ccgcgccaga     540

ggagcgcagt caggaacatg gtgcctgccg cgctgctcaa gactctgcgt ctccgcggcc     600

gccagcagac gccgtggcgt aagcgcaccc gtctcgcggg gtctccgggg gcctcggcga     660

gagacttcgg ctctcgcgag agaggactgc gcctgcgcag agccgaggac gcgtccggcg     720

ccgagattca aactagtggc gggaggctgt gagctgagcg gtggggtctg cgtacgcctg     780

gagtccttcc ccgctgtgct cagc atg gac cct atc cgg agc ttc tgc ggg        831
                           Met Asp Pro Ile Arg Ser Phe Cys Gly
                            1               5

aag ctg cgg tct ctg gcc agc acg ctg gac tgc gag acg gcc cgg ctg       879
Lys Leu Arg Ser Leu Ala Ser Thr Leu Asp Cys Glu Thr Ala Arg Leu
 10                  15                  20                  25

cag cga gcg ctg gac gga gag gaa agc gac ttt gaa gat tat cca atg       927
Gln Arg Ala Leu Asp Gly Glu Glu Ser Asp Phe Glu Asp Tyr Pro Met
                 30                  35                  40

aga att tta tat gac ctt cat tca gaa gtt cag act cta aag gat gat       975
Arg Ile Leu Tyr Asp Leu His Ser Glu Val Gln Thr Leu Lys Asp Asp
             45                  50                  55

gtt aat att ctt ctt gat aaa gca aga ttg gaa aat caa gaa ggc att      1023
Val Asn Ile Leu Leu Asp Lys Ala Arg Leu Glu Asn Gln Glu Gly Ile
         60                  65                  70

gat ttc ata aag gca aca aaa gta cta atg gaa aaa aat tca atg gat      1071
Asp Phe Ile Lys Ala Thr Lys Val Leu Met Glu Lys Asn Ser Met Asp
     75                  80                  85

att atg aaa ata aga gag tat ttc cag aag tat gga tat agt cca cgt      1119
Ile Met Lys Ile Arg Glu Tyr Phe Gln Lys Tyr Gly Tyr Ser Pro Arg
 90                  95                 100                 105

gtc aag aaa aat tca gta cac gag caa gaa gcc att aac tct gac cca      1167
Val Lys Lys Asn Ser Val His Glu Gln Glu Ala Ile Asn Ser Asp Pro
                110                 115                 120

gag ttg tct aat tgt gaa aat ttt cag aag act gat gtg aaa gat gat      1215
Glu Leu Ser Asn Cys Glu Asn Phe Gln Lys Thr Asp Val Lys Asp Asp
            125                 130                 135

ctg tct gat cct cct gtt gca agc agt tgt att tct gag aag tct cca      1263
Leu Ser Asp Pro Pro Val Ala Ser Ser Cys Ile Ser Glu Lys Ser Pro
        140                 145                 150

cgt agt cca caa ctt tca gat ttt gga ctt gag cgg tac atc gta tcc      1311
Arg Ser Pro Gln Leu Ser Asp Phe Gly Leu Glu Arg Tyr Ile Val Ser
    155                 160                 165

caa gtt cta cca aac cct cca cag gca gtg aac aac tat aag gaa gag      1359
Gln Val Leu Pro Asn Pro Pro Gln Ala Val Asn Asn Tyr Lys Glu Glu
170                 175                 180                 185

ccc gta att gta acc cca cct acc aaa caa tca cta gta aaa gta cta      1407
Pro Val Ile Val Thr Pro Pro Thr Lys Gln Ser Leu Val Lys Val Leu
```

-continued

```
                190                 195                 200

aaa act cca aaa tgt gca cta aaa atg gat gat ttt gag tgt gta act     1455
Lys Thr Pro Lys Cys Ala Leu Lys Met Asp Asp Phe Glu Cys Val Thr
            205                 210                 215

cct aaa tta gaa cac ttt ggt atc tct gaa tat act atg tgt tta aat     1503
Pro Lys Leu Glu His Phe Gly Ile Ser Glu Tyr Thr Met Cys Leu Asn
        220                 225                 230

gaa gat tac aca atg gga ctt aaa aat gcg agg aat aat aaa agt gag     1551
Glu Asp Tyr Thr Met Gly Leu Lys Asn Ala Arg Asn Asn Lys Ser Glu
    235                 240                 245

gag gcc ata gat aca gaa tcc agg ctc aat gat aat gtt ttt gcc act     1599
Glu Ala Ile Asp Thr Glu Ser Arg Leu Asn Asp Asn Val Phe Ala Thr
250                 255                 260                 265

ccc agc ccc atc atc cag cag ttg gaa aaa agt gat gcc gaa tat acc     1647
Pro Ser Pro Ile Ile Gln Gln Leu Glu Lys Ser Asp Ala Glu Tyr Thr
                270                 275                 280

aac tct cct ttg gta cct aca ttc tgt act cct ggt ttg aaa att cca     1695
Asn Ser Pro Leu Val Pro Thr Phe Cys Thr Pro Gly Leu Lys Ile Pro
            285                 290                 295

tct aca aag aac agc ata gct ttg gta tcc aca aat tac cca tta tca     1743
Ser Thr Lys Asn Ser Ile Ala Leu Val Ser Thr Asn Tyr Pro Leu Ser
        300                 305                 310

aaa aca aat agt tca tca aat gat ttg gaa gtt gaa gat cgt act tcg     1791
Lys Thr Asn Ser Ser Ser Asn Asp Leu Glu Val Glu Asp Arg Thr Ser
    315                 320                 325

ttg gtt tta aat tca gac aca tgc ttt gag aat tta aca gat ccc tct     1839
Leu Val Leu Asn Ser Asp Thr Cys Phe Glu Asn Leu Thr Asp Pro Ser
330                 335                 340                 345

tca cct acg att tct tct tat gag aat ctg ctc aga aca cct aca cct     1887
Ser Pro Thr Ile Ser Ser Tyr Glu Asn Leu Leu Arg Thr Pro Thr Pro
                350                 355                 360

cca gaa gta act aaa att cca gaa gat att ctc cag ctt tta tca aaa     1935
Pro Glu Val Thr Lys Ile Pro Glu Asp Ile Leu Gln Leu Leu Ser Lys
            365                 370                 375

tac aac tca aac cta gct act cca ata gca att aaa gca gtg cca ccc     1983
Tyr Asn Ser Asn Leu Ala Thr Pro Ile Ala Ile Lys Ala Val Pro Pro
        380                 385                 390

agt aaa agg ttc ctt aaa cat gga cag aac atc cga gat gtc agc aac     2031
Ser Lys Arg Phe Leu Lys His Gly Gln Asn Ile Arg Asp Val Ser Asn
    395                 400                 405

aaa gaa aac tga aattccagtg gatctatcca acacagaaac tgaacaaaat         2083
Lys Glu Asn
410

gagatgaaag ccgagctgga ccgattttaa cattcacatt gccctgcctc tgtcccccttt   2143

taaacgttga cccattttaa agacaaacat gaacattaac atcataatat gctttttatg   2203

aagtttcaat aaggtttaac cttagtcttg ttgacatgta gcccagtcat tcactcttta   2263

aggactatta gtgtttcatt gatactaaat tacccagctt aatcaacaga atggtttaag   2323

tagtaccagg aagtaggaca agtaatttca aaaatataaa ggtgtttgct actcagatga   2383

ggctgcccct gaccttctgg ccagagagac attgctgcca gccagctctg ccttcccatc   2443

atctcctttc aggaccgtcc cacacctttt acttgctcag tgctgtctga agatgcagtt   2503

gctgtttgca aacaacagga acaccagtta aactaattag gaaacagagg gagatttcca   2563

ggcctgggta actatatact gtgaccattg gcggttgaga ccggtcttca accagtggaa   2623

ccccgaactc tgctgtcagg gtgtggactt cggtgctctt ccaagttttc acctgggggg   2683

gggagctaac cccctatgtt cacgccttct attcccattg gcgctgaact cttaaggtca   2743
```

```
ctctggtcgc ttgtgacccc gtaaccctga tgtacccctc taaaaggtga ggggc       2798


<210> SEQ ID NO 17
<211> LENGTH: 412
<212> TYPE: PRT
<213> ORGANISM: Homo sapiens

<400> SEQUENCE: 17

Met Asp Pro Ile Arg Ser Phe Cys Gly Lys Leu Arg Ser Leu Ala Ser
 1               5                  10                  15

Thr Leu Asp Cys Glu Thr Ala Arg Leu Gln Arg Ala Leu Asp Gly Glu
            20                  25                  30

Glu Ser Asp Phe Glu Asp Tyr Pro Met Arg Ile Leu Tyr Asp Leu His
        35                  40                  45

Ser Glu Val Gln Thr Leu Lys Asp Asp Val Asn Ile Leu Leu Asp Lys
    50                  55                  60

Ala Arg Leu Glu Asn Gln Glu Gly Ile Asp Phe Ile Lys Ala Thr Lys
65                  70                  75                  80

Val Leu Met Glu Lys Asn Ser Met Asp Ile Met Lys Ile Arg Glu Tyr
                85                  90                  95

Phe Gln Lys Tyr Gly Tyr Ser Pro Arg Val Lys Lys Asn Ser Val His
            100                 105                 110

Glu Gln Glu Ala Ile Asn Ser Asp Pro Glu Leu Ser Asn Cys Glu Asn
        115                 120                 125

Phe Gln Lys Thr Asp Val Lys Asp Asp Leu Ser Asp Pro Pro Val Ala
    130                 135                 140

Ser Ser Cys Ile Ser Glu Lys Ser Pro Arg Ser Pro Gln Leu Ser Asp
145                 150                 155                 160

Phe Gly Leu Glu Arg Tyr Ile Val Ser Gln Val Leu Pro Asn Pro Pro
                165                 170                 175

Gln Ala Val Asn Asn Tyr Lys Glu Glu Pro Val Ile Val Thr Pro Pro
            180                 185                 190

Thr Lys Gln Ser Leu Val Lys Val Leu Lys Thr Pro Lys Cys Ala Leu
        195                 200                 205

Lys Met Asp Asp Phe Glu Cys Val Thr Pro Lys Leu Glu His Phe Gly
    210                 215                 220

Ile Ser Glu Tyr Thr Met Cys Leu Asn Glu Asp Tyr Thr Met Gly Leu
225                 230                 235                 240

Lys Asn Ala Arg Asn Asn Lys Ser Glu Glu Ala Ile Asp Thr Glu Ser
                245                 250                 255

Arg Leu Asn Asp Asn Val Phe Ala Thr Pro Ser Pro Ile Ile Gln Gln
            260                 265                 270

Leu Glu Lys Ser Asp Ala Glu Tyr Thr Asn Ser Pro Leu Val Pro Thr
        275                 280                 285

Phe Cys Thr Pro Gly Leu Lys Ile Pro Ser Thr Lys Asn Ser Ile Ala
    290                 295                 300

Leu Val Ser Thr Asn Tyr Pro Leu Ser Lys Thr Asn Ser Ser Ser Asn
305                 310                 315                 320

Asp Leu Glu Val Glu Asp Arg Thr Ser Leu Val Leu Asn Ser Asp Thr
                325                 330                 335

Cys Phe Glu Asn Leu Thr Asp Pro Ser Ser Pro Thr Ile Ser Ser Tyr
            340                 345                 350

Glu Asn Leu Leu Arg Thr Pro Thr Pro Pro Glu Val Thr Lys Ile Pro
        355                 360                 365
```

```
Glu Asp Ile Leu Gln Leu Leu Ser Lys Tyr Asn Ser Asn Leu Ala Thr
    370                 375                 380

Pro Ile Ala Ile Lys Ala Val Pro Pro Ser Lys Arg Phe Leu Lys His
385                 390                 395                 400

Gly Gln Asn Ile Arg Asp Val Ser Asn Lys Glu Asn
                405                 410


<210> SEQ ID NO 18
<211> LENGTH: 2736
<212> TYPE: DNA
<213> ORGANISM: Homo sapiens
<220> FEATURE:
<221> NAME/KEY: CDS
<222> LOCATION: (989)...(1981)

<400> SEQUENCE: 18

tatcatctgt gactgaggaa atccctatct tcctatcaga ctaatgaaac cacaggacag      60

caattagact tttaagtatt ggggggttta gagctctaga tattcgatat gcagactact     120

catgtttgtt tgttttaata aagactggtc caaaggctca ttttcacaca agctacagtt     180

tttcagttcc aggaccaggt aaagatggtc agctccgtga tccataaaat ccaagggtga     240

cgactcagga ttaggaccat ttcttggtga cattgagatg gtcgagctgg tccgcaatga     300

atctatgcgg ggggaacttg gaagtggcgg ccgcctttat ggcctcgaag gcctccctcc     360

tgcgcaccgc ggcgtggccg cgctcctgct cccgggtcat gtagggcatg ctcagccagt     420

aatggttctc cgcctcgatc tccaggcggc ggatcatgtt ctgcttggcg cgcaacgaca     480

cgaaccgcgg ccgccggtgc ttcccgatcc actgacggcc gggaatgcgg ccgcgccaga     540

ggagcgcagt caggaacatg gtgcctgccg cgctgctcaa gactctgcgt ctccgcggcc     600

gccagcagac gccgtggcgt aagcgcaccc gtctcgcggg gtctccgggg gcctcggcga     660

gagacttcgg ctctcgcgag agaggactgc gcctgcgcag agccgaggac gcgtccggcg     720

ccgagattca aactagtggc gggaggctgt gagctgagcg gtggggtctg cgtacgcctg     780

gagtccttcc ccgctgtgct cagcatggac cctatccgga gcttctgcgg gaagctgcgg     840

tctctggcca gcacgctgga ctgcgagacg gcccggctgc agcgagcgct ggacggagag     900

gaaagcggat gatgttaata ttcttcttga taaagcaaga ttggaaaatc aagaaggcat     960

tgatttcata aaggcaacaa aagtacta atg gaa aaa aat tca atg gat att      1012
                               Met Glu Lys Asn Ser Met Asp Ile
                                 1               5

atg aaa ata aga gag tat ttc cag aag tat gga tat agt cca cgt gtc     1060
Met Lys Ile Arg Glu Tyr Phe Gln Lys Tyr Gly Tyr Ser Pro Arg Val
     10                  15                  20

aag aaa aat tca gta cac gag caa gaa gcc att aac tct gac cca gag     1108
Lys Lys Asn Ser Val His Glu Gln Glu Ala Ile Asn Ser Asp Pro Glu
 25                  30                  35                  40

ttg tct aat tgt gaa aat ttt cag aag act gat gtg aaa gat gat ctg     1156
Leu Ser Asn Cys Glu Asn Phe Gln Lys Thr Asp Val Lys Asp Asp Leu
                 45                  50                  55

tct gat cct cct gtt gca agc agt tgt att tct gag aag tct cca cgt     1204
Ser Asp Pro Pro Val Ala Ser Ser Cys Ile Ser Glu Lys Ser Pro Arg
             60                  65                  70

agt cca caa ctt tca gat ttt gga ctt gag cgg tac atc gta tcc caa     1252
Ser Pro Gln Leu Ser Asp Phe Gly Leu Glu Arg Tyr Ile Val Ser Gln
         75                  80                  85

gtt cta cca aac cct cca cag gca gtg aac aac tat aag gaa gag ccc     1300
Val Leu Pro Asn Pro Pro Gln Ala Val Asn Asn Tyr Lys Glu Glu Pro
```

-continued

```
     90                  95                  100

gta att gta acc cca cct acc aaa caa tca cta gta aaa gta cta aaa      1348
Val Ile Val Thr Pro Pro Thr Lys Gln Ser Leu Val Lys Val Leu Lys
105                 110                 115                 120

act cca aaa tgt gca cta aaa atg gat gat ttt gag tgt gta act cct      1396
Thr Pro Lys Cys Ala Leu Lys Met Asp Asp Phe Glu Cys Val Thr Pro
                125                 130                 135

aaa tta gaa cac ttt ggt atc tct gaa tat act atg tgt tta aat gaa      1444
Lys Leu Glu His Phe Gly Ile Ser Glu Tyr Thr Met Cys Leu Asn Glu
            140                 145                 150

gat tac aca atg gga ctt aaa aat gcg agg aat aat aaa agt gag gag      1492
Asp Tyr Thr Met Gly Leu Lys Asn Ala Arg Asn Asn Lys Ser Glu Glu
        155                 160                 165

gcc ata gat aca gaa tcc agg ctc aat gat aat gtt ttt gcc act ccc      1540
Ala Ile Asp Thr Glu Ser Arg Leu Asn Asp Asn Val Phe Ala Thr Pro
    170                 175                 180

agc ccc atc atc cag cag ttg gaa aaa agt gat gcc gaa tat acc aac      1588
Ser Pro Ile Ile Gln Gln Leu Glu Lys Ser Asp Ala Glu Tyr Thr Asn
185                 190                 195                 200

tct cct ttg gta cct aca ttc tgt act cct ggt ttg aaa att cca tct      1636
Ser Pro Leu Val Pro Thr Phe Cys Thr Pro Gly Leu Lys Ile Pro Ser
                205                 210                 215

aca aag aac agc ata gct ttg gta tcc aca aat tac cca tta tca aaa      1684
Thr Lys Asn Ser Ile Ala Leu Val Ser Thr Asn Tyr Pro Leu Ser Lys
            220                 225                 230

aca aat agt tca tca aat gat ttg gaa gtt gaa gat cgt act tcg ttg      1732
Thr Asn Ser Ser Ser Asn Asp Leu Glu Val Glu Asp Arg Thr Ser Leu
        235                 240                 245

gtt tta aat tca gac aca tgc ttt gag aat tta aca gat ccc tct tca      1780
Val Leu Asn Ser Asp Thr Cys Phe Glu Asn Leu Thr Asp Pro Ser Ser
    250                 255                 260

cct acg att tct tct tat gag aat ctg ctc aga aca cct aca cct cca      1828
Pro Thr Ile Ser Ser Tyr Glu Asn Leu Leu Arg Thr Pro Thr Pro Pro
265                 270                 275                 280

gaa gta act aaa att cca gaa gat att ctc cag ctt tta tca aaa tac      1876
Glu Val Thr Lys Ile Pro Glu Asp Ile Leu Gln Leu Leu Ser Lys Tyr
                285                 290                 295

aac tca aac cta gct act cca ata gca att aaa gca gtg cca ccc agt      1924
Asn Ser Asn Leu Ala Thr Pro Ile Ala Ile Lys Ala Val Pro Pro Ser
            300                 305                 310

aaa agg ttc ctt aaa cat gga cag aac atc cga gat gtc agc aac aaa      1972
Lys Arg Phe Leu Lys His Gly Gln Asn Ile Arg Asp Val Ser Asn Lys
        315                 320                 325

gaa aac tga aattccagtg gatctatcca acacagaaac tgaacaaaat              2021
Glu Asn
    330

gagatgaaag ccgagctgga ccgattttaa cattcacatt gccctgcctc tgtcccccttt   2081

taaacgttga cccattttaa agacaaacat gaacattaac atcataatat gctttttatg    2141

aagtttcaat aaggtttaac cttagtcttg ttgacatgta gcccagtcat tcactcttta    2201

aggactatta gtgtttcatt gatactaaat tacccagctt aatcaacaga atggtttaag    2261

tagtaccagg aagtaggaca agtaatttca aaaatataaa ggtgtttgct actcagatga    2321

ggccgcccct gaccttctgg ccagagagac attgctgcca gccagctctg ccttcccatc    2381

atctcctttc aggaccgtcc cacacctttt acttgctcag tgctgtctga agatgcagtt    2441

gctgtttgca aacaacagga acaccagtta aactaattag gaaacagagg gagatttcca    2501

ggcctgggta actatatact gtgaccattg gcggttgaga ccggtcttca accagtggaa    2561
```

```
ccccgaactc tgctgtcagg gtgtggactt cggtgctctt ccaagttttc acctgggggg   2621

gggagctaac cccctatgtt cacgccttct attcccattg gcgctgaact cttaaggtca   2681

ctctggtcgc ttgtgacccc gtaaccctga tgtacccctc taaaaggtga ggggc        2736


<210> SEQ ID NO 19
<211> LENGTH: 330
<212> TYPE: PRT
<213> ORGANISM: Homo sapiens

<400> SEQUENCE: 19

Met Glu Lys Asn Ser Met Asp Ile Met Lys Ile Arg Glu Tyr Phe Gln
 1               5                  10                  15

Lys Tyr Gly Tyr Ser Pro Arg Val Lys Lys Asn Ser Val His Glu Gln
            20                  25                  30

Glu Ala Ile Asn Ser Asp Pro Glu Leu Ser Asn Cys Glu Asn Phe Gln
        35                  40                  45

Lys Thr Asp Val Lys Asp Asp Leu Ser Asp Pro Pro Val Ala Ser Ser
    50                  55                  60

Cys Ile Ser Glu Lys Ser Pro Arg Ser Pro Gln Leu Ser Asp Phe Gly
65                  70                  75                  80

Leu Glu Arg Tyr Ile Val Ser Gln Val Leu Pro Asn Pro Pro Gln Ala
                85                  90                  95

Val Asn Asn Tyr Lys Glu Glu Pro Val Ile Val Thr Pro Pro Thr Lys
            100                 105                 110

Gln Ser Leu Val Lys Val Leu Lys Thr Pro Lys Cys Ala Leu Lys Met
        115                 120                 125

Asp Asp Phe Glu Cys Val Thr Pro Lys Leu Glu His Phe Gly Ile Ser
    130                 135                 140

Glu Tyr Thr Met Cys Leu Asn Glu Asp Tyr Thr Met Gly Leu Lys Asn
145                 150                 155                 160

Ala Arg Asn Asn Lys Ser Glu Glu Ala Ile Asp Thr Glu Ser Arg Leu
                165                 170                 175

Asn Asp Asn Val Phe Ala Thr Pro Ser Pro Ile Ile Gln Gln Leu Glu
            180                 185                 190

Lys Ser Asp Ala Glu Tyr Thr Asn Ser Pro Leu Val Pro Thr Phe Cys
        195                 200                 205

Thr Pro Gly Leu Lys Ile Pro Ser Thr Lys Asn Ser Ile Ala Leu Val
    210                 215                 220

Ser Thr Asn Tyr Pro Leu Ser Lys Thr Asn Ser Ser Ser Asn Asp Leu
225                 230                 235                 240

Glu Val Glu Asp Arg Thr Ser Leu Val Leu Asn Ser Asp Thr Cys Phe
                245                 250                 255

Glu Asn Leu Thr Asp Pro Ser Ser Pro Thr Ile Ser Ser Tyr Glu Asn
            260                 265                 270

Leu Leu Arg Thr Pro Thr Pro Pro Glu Val Thr Lys Ile Pro Glu Asp
        275                 280                 285

Ile Leu Gln Leu Leu Ser Lys Tyr Asn Ser Asn Leu Ala Thr Pro Ile
    290                 295                 300

Ala Ile Lys Ala Val Pro Pro Ser Lys Arg Phe Leu Lys His Gly Gln
305                 310                 315                 320

Asn Ile Arg Asp Val Ser Asn Lys Glu Asn
                325                 330
```

```
<210> SEQ ID NO 20
<211> LENGTH: 2679
<212> TYPE: DNA
<213> ORGANISM: Homo sapiens
<220> FEATURE:
<221> NAME/KEY: CDS
<222> LOCATION: (805)...(1971)

<400> SEQUENCE: 20

tatcatctgt gactgaggaa atccctatct tcctatcaga ctaatgaaac cacaggacag     60

caattagact tttaagtatt ggggggttta gagctctaga tattcgatat gcagactact    120

catgtttgtt tgttttaata aagactggtc caaaggctca ttttcacaca agctacagtt    180

tttcagttcc aggaccaggt aaagatggtc agctccgtga tccataaaat ccaagggtga    240

cgactcagga ttaggaccat ttcttggtga cattgagatg gtcgagctgg tccgcaatga    300

atctatgcgg ggggaacttg gaagtggcgg ccgcctttat ggcctcgaag gcctccctcc    360

tgcgcaccgc ggcgtggccg cgctcctgct cccgggtcat gtagggcatg ctcagccagt    420

aatggttctc cgcctcgatc tccaggcggc ggatcatgtt ctgcttggcg cgcaacgaca    480

cgaaccgcgg ccgccggtgc ttcccgatcc actgacggcc gggaatgcgg ccgcgccaga    540

ggagcgcagt caggaacatg gtgcctgccg cgctgctcaa gactctgcgt ctccgcggcc    600

gccagcagac gccgtggcgt aagcgcaccc gtctcgcggg gtctccgggg gcctcggcga    660

gagacttcgg ctctcgcgag agaggactgc gcctgcgcag agccgaggac gcgtccggcg    720

ccgagattca aactagtggc gggaggctgt gagctgagcg gtggggtctg cgtacgcctg    780

gagtccttcc ccgctgtgct cagc atg gac cct atc cgg agc ttc tgc ggg       831
                           Met Asp Pro Ile Arg Ser Phe Cys Gly
                            1               5

aag ctg cgg tct ctg gcc agc acg ctg gac tgc gag acg gcc cgg ctg      879
Lys Leu Arg Ser Leu Ala Ser Thr Leu Asp Cys Glu Thr Ala Arg Leu
 10                  15                  20                  25

cag cga gcg ctg gac gga gag gaa agc gac ttt gaa gat tat cca atg      927
Gln Arg Ala Leu Asp Gly Glu Glu Ser Asp Phe Glu Asp Tyr Pro Met
                 30                  35                  40

aga att tta tat gac ctt cat tca gaa gtt cag act cta aag gat gat      975
Arg Ile Leu Tyr Asp Leu His Ser Glu Val Gln Thr Leu Lys Asp Asp
             45                  50                  55

gtt aat att ctt ctt gat aaa gca aga ttg gaa aat caa gaa ggc att     1023
Val Asn Ile Leu Leu Asp Lys Ala Arg Leu Glu Asn Gln Glu Gly Ile
         60                  65                  70

gat ttc ata aag gca aca aaa gta cta atg gaa aaa aat tca atg gat     1071
Asp Phe Ile Lys Ala Thr Lys Val Leu Met Glu Lys Asn Ser Met Asp
     75                  80                  85

att atg aaa ata aga gag tat ttc cag aag tat gga tat agt cca cgt     1119
Ile Met Lys Ile Arg Glu Tyr Phe Gln Lys Tyr Gly Tyr Ser Pro Arg
 90                  95                 100                 105

gtc aag aaa aat tca gta cac gag caa gaa gcc att aac tct gac cca     1167
Val Lys Lys Asn Ser Val His Glu Gln Glu Ala Ile Asn Ser Asp Pro
                110                 115                 120

gag ttg tct aat tgt gaa aat ttt cag aag act gat gtg aaa gat gat     1215
Glu Leu Ser Asn Cys Glu Asn Phe Gln Lys Thr Asp Val Lys Asp Asp
            125                 130                 135

ctg tct gat cct cct gtt gca agc agt tgt att tct gag aag tct cca     1263
Leu Ser Asp Pro Pro Val Ala Ser Ser Cys Ile Ser Glu Lys Ser Pro
        140                 145                 150

cgt agt cca caa ctt tca gat ttt gga ctt gag cgg tac atc gta tcc     1311
Arg Ser Pro Gln Leu Ser Asp Phe Gly Leu Glu Arg Tyr Ile Val Ser
    155                 160                 165
```

-continued

```
caa gtt cta cca aac cct cca cag gca gtg aac aac tat aag gaa gag     1359
Gln Val Leu Pro Asn Pro Pro Gln Ala Val Asn Asn Tyr Lys Glu Glu
170                 175                 180                 185

ccc gta att gta acc cca cct acc aaa caa tca cta gta aaa gta cta     1407
Pro Val Ile Val Thr Pro Pro Thr Lys Gln Ser Leu Val Lys Val Leu
                190                 195                 200

aaa act cca aaa tgt gca cta aaa atg gat gat ttt gag tgt gta act     1455
Lys Thr Pro Lys Cys Ala Leu Lys Met Asp Asp Phe Glu Cys Val Thr
            205                 210                 215

cct aaa tta gaa cac ttt ggt atc tct gaa tat act atg tgt tta aat     1503
Pro Lys Leu Glu His Phe Gly Ile Ser Glu Tyr Thr Met Cys Leu Asn
        220                 225                 230

gaa gat tac aca atg gga ctt aaa aat gcg agg aat aat aaa agt gag     1551
Glu Asp Tyr Thr Met Gly Leu Lys Asn Ala Arg Asn Asn Lys Ser Glu
    235                 240                 245

gag gcc ata gat aca gaa tcc agg ctc aat gat aat gtt ttt gcc act     1599
Glu Ala Ile Asp Thr Glu Ser Arg Leu Asn Asp Asn Val Phe Ala Thr
250                 255                 260                 265

ccc agc ccc atc atc cag cag ttg gaa aaa agt gat gcc gaa tat acc     1647
Pro Ser Pro Ile Ile Gln Gln Leu Glu Lys Ser Asp Ala Glu Tyr Thr
                270                 275                 280

aac tct cct ttg gta cct aca ttc tgt act cct ggt ttg aaa att cca     1695
Asn Ser Pro Leu Val Pro Thr Phe Cys Thr Pro Gly Leu Lys Ile Pro
            285                 290                 295

tct aca aag aac agc ata gct ttg gta tcc aca aat tac cca tta tca     1743
Ser Thr Lys Asn Ser Ile Ala Leu Val Ser Thr Asn Tyr Pro Leu Ser
        300                 305                 310

aaa aca aat agt tca tca aat gat ttg gaa gtt gaa gat cgt act tcg     1791
Lys Thr Asn Ser Ser Ser Asn Asp Leu Glu Val Glu Asp Arg Thr Ser
    315                 320                 325

ttg gtt tta aat tca gac aca tgc ttt gag aat tta aca gat ccc tct     1839
Leu Val Leu Asn Ser Asp Thr Cys Phe Glu Asn Leu Thr Asp Pro Ser
330                 335                 340                 345

tca cct acg att tct tct tat gag aat ctg ctc aga aca cct aca cct     1887
Ser Pro Thr Ile Ser Ser Tyr Glu Asn Leu Leu Arg Thr Pro Thr Pro
                350                 355                 360

cca gaa gta act aaa att cca gaa gat att ctc cag aaa ttc cag tgg     1935
Pro Glu Val Thr Lys Ile Pro Glu Asp Ile Leu Gln Lys Phe Gln Trp
            365                 370                 375

atc tat cca aca cag aaa ctg aac aaa atg aga tga aagccgagct          1981
Ile Tyr Pro Thr Gln Lys Leu Asn Lys Met Arg
        380                 385

ggaccgattt taacattcac attgccctgc ctctgtcccc ctttaaacgt tgacccattt   2041

taaagacaaa catgaacatt aacatcataa tatgcttttt atgaagtttc aataaggttt   2101

aaccttagtc ttgttgacat gtagcccagt cattcactct ttaaggacta ttagtgtttc   2161

attgatacta aattacccag cttaatcaac agaatggttt aagtagtacc aggaagtagg   2221

acaagtaatt tcaaaaatat aaaggtgttt gctactcaga tgaggccgcc cctgaccttc   2281

tggccagaga gacattgctg ccagccagct ctgccttccc atcatctcct ttcaggaccg   2341

tcccacacct tttacttgct cagtgctgtc tgaagatgca gttgctgttt gcaaacaaca   2401

ggaacaccag ttaaactaat taggaaacag agggagattt ccaggcctgg gtaactatat   2461

actgtgacca ttggcggttg agaccggtct tcaaccagtg gaaccccgaa ctctgctgtc   2521

agggtgtgga cttcggtgct cttccaagtt ttcacctggg ggggggagct aaccccctat   2581

gttcacgcct tctattccca ttggcgctga actcttaagg tcactctggt cgcttgtgac   2641
```

```
cccgtaaccc tgatgtaccc ctctaaaagg tgaggggc                   2679


<210> SEQ ID NO 21
<211> LENGTH: 388
<212> TYPE: PRT
<213> ORGANISM: Homo sapiens

<400> SEQUENCE: 21

Met Asp Pro Ile Arg Ser Phe Cys Gly Lys Leu Arg Ser Leu Ala Ser
 1               5                  10                  15

Thr Leu Asp Cys Glu Thr Ala Arg Leu Gln Arg Ala Leu Asp Gly Glu
            20                  25                  30

Glu Ser Asp Phe Glu Asp Tyr Pro Met Arg Ile Leu Tyr Asp Leu His
        35                  40                  45

Ser Glu Val Gln Thr Leu Lys Asp Asp Val Asn Ile Leu Leu Asp Lys
    50                  55                  60

Ala Arg Leu Glu Asn Gln Glu Gly Ile Asp Phe Ile Lys Ala Thr Lys
65                  70                  75                  80

Val Leu Met Glu Lys Asn Ser Met Asp Ile Met Lys Ile Arg Glu Tyr
                85                  90                  95

Phe Gln Lys Tyr Gly Tyr Ser Pro Arg Val Lys Lys Asn Ser Val His
            100                 105                 110

Glu Gln Glu Ala Ile Asn Ser Asp Pro Glu Leu Ser Asn Cys Glu Asn
        115                 120                 125

Phe Gln Lys Thr Asp Val Lys Asp Asp Leu Ser Asp Pro Pro Val Ala
    130                 135                 140

Ser Ser Cys Ile Ser Glu Lys Ser Pro Arg Ser Pro Gln Leu Ser Asp
145                 150                 155                 160

Phe Gly Leu Glu Arg Tyr Ile Val Ser Gln Val Leu Pro Asn Pro Pro
                165                 170                 175

Gln Ala Val Asn Asn Tyr Lys Glu Glu Pro Val Ile Val Thr Pro Pro
            180                 185                 190

Thr Lys Gln Ser Leu Val Lys Val Leu Lys Thr Pro Lys Cys Ala Leu
        195                 200                 205

Lys Met Asp Asp Phe Glu Cys Val Thr Pro Lys Leu Glu His Phe Gly
    210                 215                 220

Ile Ser Glu Tyr Thr Met Cys Leu Asn Glu Asp Tyr Thr Met Gly Leu
225                 230                 235                 240

Lys Asn Ala Arg Asn Asn Lys Ser Glu Glu Ala Ile Asp Thr Glu Ser
                245                 250                 255

Arg Leu Asn Asp Asn Val Phe Ala Thr Pro Ser Pro Ile Ile Gln Gln
            260                 265                 270

Leu Glu Lys Ser Asp Ala Glu Tyr Thr Asn Ser Pro Leu Val Pro Thr
        275                 280                 285

Phe Cys Thr Pro Gly Leu Lys Ile Pro Ser Thr Lys Asn Ser Ile Ala
    290                 295                 300

Leu Val Ser Thr Asn Tyr Pro Leu Ser Lys Thr Asn Ser Ser Ser Asn
305                 310                 315                 320

Asp Leu Glu Val Glu Asp Arg Thr Ser Leu Val Leu Asn Ser Asp Thr
                325                 330                 335

Cys Phe Glu Asn Leu Thr Asp Pro Ser Ser Pro Thr Ile Ser Ser Tyr
            340                 345                 350

Glu Asn Leu Leu Arg Thr Pro Thr Pro Pro Glu Val Thr Lys Ile Pro
        355                 360                 365
```

-continued

```
Glu Asp Ile Leu Gln Lys Phe Gln Trp Ile Tyr Pro Thr Gln Lys Leu
    370                 375                 380

Asn Lys Met Arg
385


<210> SEQ ID NO 22
<211> LENGTH: 2617
<212> TYPE: DNA
<213> ORGANISM: Homo sapiens
<220> FEATURE:
<221> NAME/KEY: CDS
<222> LOCATION: (989)...(1909)

<400> SEQUENCE: 22

tatcatctgt gactgaggaa atccctatct tcctatcaga ctaatgaaac cacaggacag      60

caattagact tttaagtatt ggggggttta gagctctaga tattcgatat gcagactact     120

catgtttgtt tgttttaata aagactggtc caaaggctca ttttcacaca agctacagtt     180

tttcagttcc aggaccaggt aaagatggtc agctccgtga tccataaaat ccaagggtga     240

cgactcagga ttaggaccat ttcttggtga cattgagatg gtcgagctgg tccgcaatga     300

atctatgcgg ggggaacttg gaagtggcgg ccgcctttat ggcctcgaag gcctccctcc     360

tgcgcaccgc ggcgtggccg cgctcctgct cccgggtcat gtagggcatg ctcagccagt     420

aatggttctc cgcctcgatc tccaggcggc ggatcatgtt ctgcttggcg cgcaacgaca     480

cgaaccgcgg ccgccggtgc ttcccgatcc actgacggcc gggaatgcgg ccgcgccaga     540

ggagcgcagt caggaacatg gtgcctgccg cgctgctcaa gactctgcgt ctccgcggcc     600

gccagcagac gccgtggcgt aagcgcaccc gtctcgcggg gtctccgggg gcctcggcga     660

gagacttcgg ctctcgcgag agaggactgc gcctgcgcag agccgaggac gcgtccggcg     720

ccgagattca aactagtggc gggaggctgt gagctgagcg gtggggtctg cgtacgcctg     780

gagtccttcc ccgctgtgct cagcatggac cctatccgga gcttctgcgg gaagctgcgg     840

tctctggcca gcacgctgga ctgcgagacg gcccggctgc agcgagcgct ggacggagag     900

gaaagcggat gatgttaata ttcttcttga taaagcaaga ttggaaaatc aagaaggcat     960

tgatttcata aaggcaacaa aagtacta atg gaa aaa aat tca atg gat att      1012
                               Met Glu Lys Asn Ser Met Asp Ile
                                1               5

atg aaa ata aga gag tat ttc cag aag tat gga tat agt cca cgt gtc     1060
Met Lys Ile Arg Glu Tyr Phe Gln Lys Tyr Gly Tyr Ser Pro Arg Val
     10                  15                  20

aag aaa aat tca gta cac gag caa gaa gcc att aac tct gac cca gag     1108
Lys Lys Asn Ser Val His Glu Gln Glu Ala Ile Asn Ser Asp Pro Glu
 25                  30                  35                  40

ttg tct aat tgt gaa aat ttt cag aag act gat gtg aaa gat gat ctg     1156
Leu Ser Asn Cys Glu Asn Phe Gln Lys Thr Asp Val Lys Asp Asp Leu
                 45                  50                  55

tct gat cct cct gtt gca agc agt tgt att tct ggg aag tct cca cgt     1204
Ser Asp Pro Pro Val Ala Ser Ser Cys Ile Ser Gly Lys Ser Pro Arg
             60                  65                  70

agt cca caa ctt tca gat ttt gga ctt gag cgg tac atc gta tcc caa     1252
Ser Pro Gln Leu Ser Asp Phe Gly Leu Glu Arg Tyr Ile Val Ser Gln
         75                  80                  85

gtt cta cca aac cct cca cag gca gtg aac aac tat aag gaa gag ccc     1300
Val Leu Pro Asn Pro Pro Gln Ala Val Asn Asn Tyr Lys Glu Glu Pro
     90                  95                 100

gta att gta acc cca cct acc aaa caa tca cta gta aaa gta cta aaa     1348
Val Ile Val Thr Pro Pro Thr Lys Gln Ser Leu Val Lys Val Leu Lys
```

-continued

```
105                 110                 115                 120

act cca aaa tgt gca cta aaa atg gat gat ttt gag tgt gta act cct     1396
Thr Pro Lys Cys Ala Leu Lys Met Asp Asp Phe Glu Cys Val Thr Pro
            125                 130                 135

aaa tta gaa cac ttt ggt atc tct gaa tat act atg tgt tta aat gaa     1444
Lys Leu Glu His Phe Gly Ile Ser Glu Tyr Thr Met Cys Leu Asn Glu
            140                 145                 150

gat tac aca atg gga ctt aaa aat gcg agg aat aat aaa agt gag gag     1492
Asp Tyr Thr Met Gly Leu Lys Asn Ala Arg Asn Asn Lys Ser Glu Glu
        155                 160                 165

gcc ata gat aca gaa tcc agg ctc aat gat aat gtt ttt gcc act ccc     1540
Ala Ile Asp Thr Glu Ser Arg Leu Asn Asp Asn Val Phe Ala Thr Pro
    170                 175                 180

agc ccc atc atc cag cag ttg gaa aaa agt gat gcc gaa tat acc aac     1588
Ser Pro Ile Ile Gln Gln Leu Glu Lys Ser Asp Ala Glu Tyr Thr Asn
185                 190                 195                 200

tct cct ttg gta cct aca ttc tgt act cct ggt ttg aaa att cca tct     1636
Ser Pro Leu Val Pro Thr Phe Cys Thr Pro Gly Leu Lys Ile Pro Ser
                205                 210                 215

aca aag aac agc ata gct ttg gta tcc aca aat tac cca tta tca aaa     1684
Thr Lys Asn Ser Ile Ala Leu Val Ser Thr Asn Tyr Pro Leu Ser Lys
            220                 225                 230

aca aat agt tca tca aat gat ttg gaa gtt gaa gat cgt act tcg ttg     1732
Thr Asn Ser Ser Ser Asn Asp Leu Glu Val Glu Asp Arg Thr Ser Leu
        235                 240                 245

gtt tta aat tca gac aca tgc ttt gag aat tta aca gat ccc tct tca     1780
Val Leu Asn Ser Asp Thr Cys Phe Glu Asn Leu Thr Asp Pro Ser Ser
    250                 255                 260

cct acg att tct tct tat gag aat ctg ctc aga aca cct aca cct cca     1828
Pro Thr Ile Ser Ser Tyr Glu Asn Leu Leu Arg Thr Pro Thr Pro Pro
265                 270                 275                 280

gaa gta act aaa att cca gaa gat att ctc cag aaa ttc cag tgg atc     1876
Glu Val Thr Lys Ile Pro Glu Asp Ile Leu Gln Lys Phe Gln Trp Ile
                285                 290                 295

tat cca aca cag aaa ctg aac aaa atg aga tga aagccgagct ggaccgattt   1929
Tyr Pro Thr Gln Lys Leu Asn Lys Met Arg
            300                 305

taacattcac attgccctgc ctctgtcccc ctttaaacgt tgacccattt taaagacaaa   1989

catgaacatt aacatcataa tatgcttttt atgaagtttc aataaggttt aaccttagtc   2049

ttgttgacat gtagcccagt cattcactct ttaaggacta ttagtgtttc attgatacta   2109

aattacccag cttaatcaac agaatggttt aagtagtacc aggaagtagg acaagtaatt   2169

tcaaaaatat aaaggtgttt gctactcaga tgaggccgcc cctgaccttc tggccagaga   2229

gacattgctg ccagccagct ctgccttccc atcatctcct ttcaggaccg tcccacacct   2289

tttacttgct cagtgctgtc tgaagatgca gttgctgttt gcaaacaaca ggaacaccag   2349

ttaaactaat taggaaacag agggagattt ccaggcctgg gtaactatat actgtgacca   2409

ttggcggttg agaccggtct tcaaccagtg gaaccccgaa ctctgctgtc agggtgtgga   2469

cttcggtgct cttccaagtt ttcacctggg ggggggagct aaccccctat gttcacgcct   2529

tctattccca ttggcgctga actcttaagg tcactctggt cgcttgtgac cccgtaaccc   2589

tgatgtaccc ctctaaaagg tgaggggc                                      2617

<210> SEQ ID NO 23
<211> LENGTH: 306
<212> TYPE: PRT
<213> ORGANISM: Homo sapiens
```

<400> SEQUENCE: 23

Met Glu Lys Asn Ser Met Asp Ile Met Lys Ile Arg Glu Tyr Phe Gln
1               5                   10                  15

Lys Tyr Gly Tyr Ser Pro Arg Val Lys Lys Asn Ser Val His Glu Gln
            20                  25                  30

Glu Ala Ile Asn Ser Asp Pro Glu Leu Ser Asn Cys Glu Asn Phe Gln
        35                  40                  45

Lys Thr Asp Val Lys Asp Asp Leu Ser Asp Pro Pro Val Ala Ser Ser
    50                  55                  60

Cys Ile Ser Gly Lys Ser Pro Arg Ser Pro Gln Leu Ser Asp Phe Gly
65                  70                  75                  80

Leu Glu Arg Tyr Ile Val Ser Gln Val Leu Pro Asn Pro Pro Gln Ala
                85                  90                  95

Val Asn Asn Tyr Lys Glu Glu Pro Val Ile Val Thr Pro Pro Thr Lys
            100                 105                 110

Gln Ser Leu Val Lys Val Leu Lys Thr Pro Lys Cys Ala Leu Lys Met
        115                 120                 125

Asp Asp Phe Glu Cys Val Thr Pro Lys Leu Glu His Phe Gly Ile Ser
    130                 135                 140

Glu Tyr Thr Met Cys Leu Asn Glu Asp Tyr Thr Met Gly Leu Lys Asn
145                 150                 155                 160

Ala Arg Asn Asn Lys Ser Glu Glu Ala Ile Asp Thr Glu Ser Arg Leu
                165                 170                 175

Asn Asp Asn Val Phe Ala Thr Pro Ser Pro Ile Ile Gln Gln Leu Glu
            180                 185                 190

Lys Ser Asp Ala Glu Tyr Thr Asn Ser Pro Leu Val Pro Thr Phe Cys
        195                 200                 205

Thr Pro Gly Leu Lys Ile Pro Ser Thr Lys Asn Ser Ile Ala Leu Val
    210                 215                 220

Ser Thr Asn Tyr Pro Leu Ser Lys Thr Asn Ser Ser Ser Asn Asp Leu
225                 230                 235                 240

Glu Val Glu Asp Arg Thr Ser Leu Val Leu Asn Ser Asp Thr Cys Phe
                245                 250                 255

Glu Asn Leu Thr Asp Pro Ser Ser Pro Thr Ile Ser Ser Tyr Glu Asn
            260                 265                 270

Leu Leu Arg Thr Pro Thr Pro Pro Glu Val Thr Lys Ile Pro Glu Asp
        275                 280                 285

Ile Leu Gln Lys Phe Gln Trp Ile Tyr Pro Thr Gln Lys Leu Asn Lys
    290                 295                 300

Met Arg
305

<210> SEQ ID NO 24
<211> LENGTH: 1781
<212> TYPE: DNA
<213> ORGANISM: Homo sapiens
<220> FEATURE:
<221> NAME/KEY: CDS
<222> LOCATION: (805)...(1026)

<400> SEQUENCE: 24
tatcatctgt gactgaggaa atccctatct tcctatcaga ctaatgaaac cacaggacag 60
caattagact tttaagtatt ggggggttta gagctctaga tattcgatat gcagactact 120
catgtttgtt tgttttaata aagactggtc caaaggctca ttttcacaca agctacagtt 180

```
tttcagttcc aggaccaggt aaagatggtc agctccgtga tccataaaat ccaagggtga    240

cgactcagga ttaggaccat ttcttggtga cattgagatg gtcgagctgg tccgcaatga    300

atctatgcgg ggggaacttg gaagtggcgg ccgcctttat ggcctcgaag gcctccctcc    360

tgcgcaccgc ggcgtggccg cgctcctgct cccgggtcat gtagggcatg ctcagccagt    420

aatggttctc cgcctcgatc tccaggcggc ggatcatgtt ctgcttggcg cgcaacgaca    480

cgaaccgcgg ccgccggtgc ttcccgatcc actgacggcc gggaatgcgg ccgcgccaga    540

ggagcgcagt caggaacatg gtgcctgccg cgctgctcaa gactctgcgt ctccgcggcc    600

gccagcagac gccgtggcgt aagcgcaccc gtctcgcggg gtctccgggg gcctcggcga    660

gagacttcgg ctctcgcgag agaggactgc gcctgcgcag agccgaggac gcgtccggcg    720

ccgagattca aactagtggc gggaggctgt gagctgagcg gtggggtctg cgtacgcctg    780

gagtccttcc ccgctgtgct cagc atg gac cct atc cgg agc ttc tgc ggg      831
                           Met Asp Pro Ile Arg Ser Phe Cys Gly
                            1               5

aag ctg cgg tct ctg gcc agc acg ctg gac tgc gag acg gcc cgg ctg      879
Lys Leu Arg Ser Leu Ala Ser Thr Leu Asp Cys Glu Thr Ala Arg Leu
 10                  15                  20                  25

cag cga gcg ctg gac gga gag gaa agc ctt tta tca aaa tac aac tca      927
Gln Arg Ala Leu Asp Gly Glu Glu Ser Leu Leu Ser Lys Tyr Asn Ser
                30                  35                  40

aac cta gct act cca ata gca att aaa gca gtg cca ccc agt aaa agg      975
Asn Leu Ala Thr Pro Ile Ala Ile Lys Ala Val Pro Pro Ser Lys Arg
            45                  50                  55

ttc ctt aaa cat gga cag aac atc cga gat gtc agc aac aaa gaa aac     1023
Phe Leu Lys His Gly Gln Asn Ile Arg Asp Val Ser Asn Lys Glu Asn
        60                  65                  70

tga aattccagtg gatctatcca acacagaaac tgaacaaaat gagatgaaag          1076

ccgagctgga ccgattttaa cattcacatt gccctgcctc tgtccccctt taaacgttga   1136

cccattttaa agacaaacat gaacattaac atcataatat gctttttatg aagtttcaat   1196

aaggtttaac cttagtcttg ttgacatgta gcccagtcat tcactcttta aggactatta   1256

gtgtttcatt gatactaaat tacccagctt aatcaacaga atggtttaag tagtaccagg   1316

aagtaggaca agtaatttca aaaatataaa ggtgtttgct actcagatga ggccgcccct   1376

gaccttctgg ccagagagac attgctgcca gccagctctg ccttcccatc atctcctttc   1436

aggaccgtcc cacacctttt acttgctcag tgctgtctga agatgcagtt gctgtttgca   1496

aacaacagga acaccagtta aactaattag gaaacagagg gagatttcca ggcctgggta   1556

actatatact gtgaccattg gcggttgaga ccggtcttca accagtggaa ccccgaactc   1616

tgctgtcagg gtgtggactt cggtgctctt ccaagttttc acctgggggg gggagctaac   1676

cccctatgtt cacgccttct attcccattg gcgctgaact cttaaggtca ctctggtcgc   1736

ttgtgacccc gtaaccctga tgtacccctc taaaaggtga ggggc                   1781


<210> SEQ ID NO 25
<211> LENGTH: 73
<212> TYPE: PRT
<213> ORGANISM: Homo sapiens

<400> SEQUENCE: 25

Met Asp Pro Ile Arg Ser Phe Cys Gly Lys Leu Arg Ser Leu Ala Ser
 1               5                  10                  15

Thr Leu Asp Cys Glu Thr Ala Arg Leu Gln Arg Ala Leu Asp Gly Glu
```

-continued

```
            20                  25                  30

Glu Ser Leu Leu Ser Lys Tyr Asn Ser Asn Leu Ala Thr Pro Ile Ala
        35                  40                  45

Ile Lys Ala Val Pro Pro Ser Lys Arg Phe Leu Lys His Gly Gln Asn
    50                  55                  60

Ile Arg Asp Val Ser Asn Lys Glu Asn
65                  70


<210> SEQ ID NO 26
<211> LENGTH: 2825
<212> TYPE: DNA
<213> ORGANISM: Homo sapiens
<220> FEATURE:
<221> NAME/KEY: CDS
<222> LOCATION: (952)...(2070)

<400> SEQUENCE: 26

tatcatctgt gactgaggaa atccctatct tcctatcaga ctaatgaaac cacaggacag      60

caattagact tttaagtatt ggggggttta gagctctaga tattcgatat gcagactact     120

catgtttgtt tgttttaata aagactggtc caaaggctca ttttcacaca agctacagtt     180

tttcagttcc aggaccaggt aaagatggtc agctccgtga tccataaaat ccaagggtga     240

cgactcagga ttaggaccat ttcttggtga cattgagatg gtcgagctgg tccgcaatga     300

atctatgcgg ggggaacttg gaagtggcgg ccgcctttat ggcctcgaag gcctccctcc     360

tgcgcaccgc ggcgtggccg cgctcctgct cccgggtcat gtagggcatg ctcagccagt     420

aatggttctc cgcctcgatc tccaggcggc ggatcatgtt ctgcttggcg cgcaacgaca     480

cgaaccgcgg ccgccggtgc ttcccgatcc actgacggcc gggaatgcgg ccgcgccaga     540

ggagcgcagt caggaacatg gtgcctgccg cgctgctcaa gactctgcgt ctccgcggcc     600

gccagcagac gccgtggcgt aagcgcaccc gtctcgcggg gtctccgggg gcctcggcga     660

gagacttcgg ctctcgcgag agaggactgc gcctgcgcag agccgaggac gcgtccggcg     720

ccgagattca aactagtggc gggaggctgt gagctgagcg gtggggtctg cgtacgcctg     780

gagtccttcc ccgctgtgct cagcatggac cctatccgga gcttctgcgg gaagctgcgg     840

tctctggcca gcacgctgga ctgcgagacg gcccggctgc agcgagcgct ggacggagag     900

gaaagcggtg cgtgaggcgg gcggccaggg cacgactttg aagattatcc a atg aga      957
                                                         Met Arg
                                                          1

att tta tat gac ctt cat tca gaa gtt cag act cta aag gat gat gtt     1005
Ile Leu Tyr Asp Leu His Ser Glu Val Gln Thr Leu Lys Asp Asp Val
         5                  10                  15

aat att ctt ctt gat aaa gca aga ttg gaa aat caa gaa ggc att gat     1053
Asn Ile Leu Leu Asp Lys Ala Arg Leu Glu Asn Gln Glu Gly Ile Asp
     20                  25                  30

ttc ata aag gca aca aaa gta cta atg gaa aaa aat tca atg gat att     1101
Phe Ile Lys Ala Thr Lys Val Leu Met Glu Lys Asn Ser Met Asp Ile
 35                  40                  45                  50

atg aaa ata aga gag tat ttc cag aag tat gga tat agt cca cgt gtc     1149
Met Lys Ile Arg Glu Tyr Phe Gln Lys Tyr Gly Tyr Ser Pro Arg Val
                 55                  60                  65

aag aaa aat tca gta cac gag caa gaa gcc att aac tct gac cca gag     1197
Lys Lys Asn Ser Val His Glu Gln Glu Ala Ile Asn Ser Asp Pro Glu
             70                  75                  80

ttg tct aat tgt gaa aat ttt cag aag act gat gtg aaa gat gat ctg     1245
Leu Ser Asn Cys Glu Asn Phe Gln Lys Thr Asp Val Lys Asp Asp Leu
         85                  90                  95
```

-continued

```
tct gat cct cct gtt gca agc agt tgt att tct ggg aag tct cca cgt     1293
Ser Asp Pro Pro Val Ala Ser Ser Cys Ile Ser Gly Lys Ser Pro Arg
    100                 105                 110

agt cca caa ctt tca gat ttt gga ctt gag cgg tac atc gta tcc caa     1341
Ser Pro Gln Leu Ser Asp Phe Gly Leu Glu Arg Tyr Ile Val Ser Gln
115                 120                 125                 130

gtt cta cca aac cct cca cag gca gtg aac aac tat aag gaa gag ccc     1389
Val Leu Pro Asn Pro Pro Gln Ala Val Asn Asn Tyr Lys Glu Glu Pro
                135                 140                 145

gta att gta acc cca cct acc aaa caa tca cta gta aaa gta cta aaa     1437
Val Ile Val Thr Pro Pro Thr Lys Gln Ser Leu Val Lys Val Leu Lys
            150                 155                 160

act cca aaa tgt gca cta aaa atg gat gat ttt gag tgt gta act cct     1485
Thr Pro Lys Cys Ala Leu Lys Met Asp Asp Phe Glu Cys Val Thr Pro
        165                 170                 175

aaa tta gaa cac ttt ggt atc tct gaa tat act atg tgt tta aat gaa     1533
Lys Leu Glu His Phe Gly Ile Ser Glu Tyr Thr Met Cys Leu Asn Glu
    180                 185                 190

gat tac aca atg gga ctt aaa aat gcg agg aat aat aaa agt gag gag     1581
Asp Tyr Thr Met Gly Leu Lys Asn Ala Arg Asn Asn Lys Ser Glu Glu
195                 200                 205                 210

gcc ata gat aca gaa tcc agg ctc aat gat aat gtt ttt gcc act ccc     1629
Ala Ile Asp Thr Glu Ser Arg Leu Asn Asp Asn Val Phe Ala Thr Pro
                215                 220                 225

agc ccc atc atc cag cag ttg gaa aaa agt gat gcc gaa tat acc aac     1677
Ser Pro Ile Ile Gln Gln Leu Glu Lys Ser Asp Ala Glu Tyr Thr Asn
            230                 235                 240

tct cct ttg gta cct aca ttc tgt act cct ggt ttg aaa att cca tct     1725
Ser Pro Leu Val Pro Thr Phe Cys Thr Pro Gly Leu Lys Ile Pro Ser
        245                 250                 255

aca aag aac agc ata gct ttg gta tcc aca aat tac cca tta tca aaa     1773
Thr Lys Asn Ser Ile Ala Leu Val Ser Thr Asn Tyr Pro Leu Ser Lys
    260                 265                 270

aca aat agt tca tca aat gat ttg gaa gtt gaa gat cgt act tcg ttg     1821
Thr Asn Ser Ser Ser Asn Asp Leu Glu Val Glu Asp Arg Thr Ser Leu
275                 280                 285                 290

gtt tta aat tca gac aca tgc ttt gag aat tta aca gat ccc tct tca     1869
Val Leu Asn Ser Asp Thr Cys Phe Glu Asn Leu Thr Asp Pro Ser Ser
                295                 300                 305

cct acg att tct tct tat gag aat ctg ctc aga aca cct aca cct cca     1917
Pro Thr Ile Ser Ser Tyr Glu Asn Leu Leu Arg Thr Pro Thr Pro Pro
            310                 315                 320

gaa gta act aaa att cca gaa gat att ctc cag ctt tta tca aaa tac     1965
Glu Val Thr Lys Ile Pro Glu Asp Ile Leu Gln Leu Leu Ser Lys Tyr
        325                 330                 335

aac tca aac cta gct act cca ata gca att aaa gca gtg cca ccc agt     2013
Asn Ser Asn Leu Ala Thr Pro Ile Ala Ile Lys Ala Val Pro Pro Ser
    340                 345                 350

aaa agg ttc ctt aaa cat gga cag aac atc cga gat gtc agc aac aaa     2061
Lys Arg Phe Leu Lys His Gly Gln Asn Ile Arg Asp Val Ser Asn Lys
355                 360                 365                 370

gaa aac tga aattccagtg gatctatcca acacagaaac tgaacaaaat             2110
Glu Asn

gagatgaaag ccgagctgga ccgattttaa cattcacatt gccctgcctc tgtccccctt   2170

taaacgttga cccattttaa agacaaacat gaacattaac atcataatat gctttttatg   2230

aagtttcaat aaggtttaac cttagtcttg ttgacatgta gcccagtcat tcactcttta   2290

aggactatta gtgtttcatt gatactaaat tacccagctt aatcaacaga atggtttaag   2350
```

-continued

```
tagtaccagg aagtaggaca agtaatttca aaaatataaa ggtgtttgct actcagatga   2410

ggccgcccct gaccttctgg ccagagagac attgctgcca gccagctctg ccttcccatc   2470

atctcctttc aggaccgtcc cacacctttt acttgctcag tgctgtctga agatgcagtt   2530

gctgtttgca aacaacagga acaccagtta aactaattag gaaacagagg gagatttcca   2590

ggcctgggta actatatact gtgaccattg gcggttgaga ccggtcttca accagtggaa   2650

ccccgaactc tgctgtcagg gtgtggactt cggtgctctt ccaagttttc acctgggggg   2710

gggagctaac cccctatgtt cacgccttct attcccattg gcgctgaact cttaaggtca   2770

ctctggtcgc ttgtgacccc gtaaccctga tgtacccctc taaaaggtga ggggc        2825
```

<210> SEQ ID NO 27
<211> LENGTH: 372
<212> TYPE: PRT
<213> ORGANISM: Homo sapiens

<400> SEQUENCE: 27

```
Met Arg Ile Leu Tyr Asp Leu His Ser Glu Val Gln Thr Leu Lys Asp
 1               5                  10                  15

Asp Val Asn Ile Leu Leu Asp Lys Ala Arg Leu Glu Asn Gln Glu Gly
            20                  25                  30

Ile Asp Phe Ile Lys Ala Thr Lys Val Leu Met Glu Lys Asn Ser Met
        35                  40                  45

Asp Ile Met Lys Ile Arg Glu Tyr Phe Gln Lys Tyr Gly Tyr Ser Pro
    50                  55                  60

Arg Val Lys Lys Asn Ser Val His Glu Gln Glu Ala Ile Asn Ser Asp
65                  70                  75                  80

Pro Glu Leu Ser Asn Cys Glu Asn Phe Gln Lys Thr Asp Val Lys Asp
                85                  90                  95

Asp Leu Ser Asp Pro Pro Val Ala Ser Ser Cys Ile Ser Gly Lys Ser
            100                 105                 110

Pro Arg Ser Pro Gln Leu Ser Asp Phe Gly Leu Glu Arg Tyr Ile Val
        115                 120                 125

Ser Gln Val Leu Pro Asn Pro Pro Gln Ala Val Asn Asn Tyr Lys Glu
    130                 135                 140

Glu Pro Val Ile Val Thr Pro Pro Thr Lys Gln Ser Leu Val Lys Val
145                 150                 155                 160

Leu Lys Thr Pro Lys Cys Ala Leu Lys Met Asp Asp Phe Glu Cys Val
                165                 170                 175

Thr Pro Lys Leu Glu His Phe Gly Ile Ser Glu Tyr Thr Met Cys Leu
            180                 185                 190

Asn Glu Asp Tyr Thr Met Gly Leu Lys Asn Ala Arg Asn Asn Lys Ser
        195                 200                 205

Glu Glu Ala Ile Asp Thr Glu Ser Arg Leu Asn Asp Asn Val Phe Ala
    210                 215                 220

Thr Pro Ser Pro Ile Ile Gln Gln Leu Glu Lys Ser Asp Ala Glu Tyr
225                 230                 235                 240

Thr Asn Ser Pro Leu Val Pro Thr Phe Cys Thr Pro Gly Leu Lys Ile
                245                 250                 255

Pro Ser Thr Lys Asn Ser Ile Ala Leu Val Ser Thr Asn Tyr Pro Leu
            260                 265                 270

Ser Lys Thr Asn Ser Ser Ser Asn Asp Leu Glu Val Glu Asp Arg Thr
        275                 280                 285
```

-continued

```
Ser Leu Val Leu Asn Ser Asp Thr Cys Phe Glu Asn Leu Thr Asp Pro
    290                 295                 300

Ser Ser Pro Thr Ile Ser Ser Tyr Glu Asn Leu Leu Arg Thr Pro Thr
305                 310                 315                 320

Pro Pro Glu Val Thr Lys Ile Pro Glu Asp Ile Leu Gln Leu Leu Ser
                325                 330                 335

Lys Tyr Asn Ser Asn Leu Ala Thr Pro Ile Ala Ile Lys Ala Val Pro
            340                 345                 350

Pro Ser Lys Arg Phe Leu Lys His Gly Gln Asn Ile Arg Asp Val Ser
        355                 360                 365

Asn Lys Glu Asn
    370


<210> SEQ ID NO 28
<211> LENGTH: 412
<212> TYPE: PRT
<213> ORGANISM: Homo sapiens

<400> SEQUENCE: 28

Met Asp Pro Ile Arg Ser Phe Cys Gly Lys Leu Arg Ser Leu Ala Ser
 1               5                  10                  15

Thr Leu Asp Cys Glu Thr Ala Arg Leu Gln Arg Ala Leu Asp Gly Glu
            20                  25                  30

Glu Ser Asp Phe Glu Asp Tyr Pro Met Arg Ile Leu Tyr Asp Leu His
        35                  40                  45

Ser Glu Val Gln Thr Leu Lys Asp Asp Val Asn Ile Leu Leu Asp Lys
    50                  55                  60

Ala Arg Leu Glu Asn Gln Glu Gly Ile Asp Phe Ile Lys Ala Thr Lys
65                  70                  75                  80

Val Leu Met Glu Lys Asn Ser Met Asp Ile Met Lys Ile Arg Glu Tyr
                85                  90                  95

Phe Gln Lys Tyr Gly Tyr Ser Pro Arg Val Lys Lys Asn Ser Val His
            100                 105                 110

Glu Gln Glu Ala Ile Asn Ser Asp Pro Glu Leu Ser Asn Cys Glu Asn
        115                 120                 125

Phe Gln Lys Thr Asp Val Lys Asp Asp Leu Ser Asp Pro Pro Val Ala
    130                 135                 140

Ser Ser Cys Ile Ser Gly Lys Ser Pro Arg Ser Pro Gln Leu Ser Asp
145                 150                 155                 160

Phe Gly Leu Glu Arg Tyr Ile Val Ser Gln Val Leu Pro Asn Pro Pro
                165                 170                 175

Gln Ala Val Asn Asn Tyr Lys Glu Glu Pro Val Ile Val Thr Pro Pro
            180                 185                 190

Thr Lys Gln Ser Leu Val Lys Val Leu Lys Thr Pro Lys Cys Ala Leu
        195                 200                 205

Lys Met Asp Asp Phe Glu Cys Val Thr Pro Lys Leu Glu His Phe Gly
    210                 215                 220

Ile Ser Glu Tyr Thr Met Cys Leu Asn Glu Asp Tyr Thr Met Gly Leu
225                 230                 235                 240

Lys Asn Ala Arg Asn Asn Lys Ser Glu Glu Ala Ile Asp Thr Glu Ser
                245                 250                 255

Arg Leu Asn Asp Asn Val Phe Ala Thr Pro Ser Pro Ile Ile Gln Gln
            260                 265                 270

Leu Glu Lys Ser Asp Ala Glu Tyr Thr Asn Ser Pro Leu Val Pro Thr
        275                 280                 285
```

```
Phe Cys Thr Pro Gly Leu Lys Ile Pro Ser Thr Lys Asn Ser Ile Ala
    290                 295                 300

Leu Val Ser Thr Asn Tyr Pro Leu Ser Lys Thr Asn Ser Ser Ser Asn
305                 310                 315                 320

Asp Leu Glu Val Glu Asp Arg Thr Ser Leu Val Leu Asn Ser Asp Thr
                325                 330                 335

Cys Phe Glu Asn Leu Thr Asp Pro Ser Ser Pro Thr Ile Ser Ser Tyr
            340                 345                 350

Glu Asn Leu Leu Arg Thr Pro Thr Pro Pro Glu Val Thr Lys Ile Pro
        355                 360                 365

Glu Asp Ile Leu Gln Leu Leu Ser Lys Tyr Asn Ser Asn Leu Ala Thr
    370                 375                 380

Pro Ile Ala Ile Lys Ala Val Pro Pro Ser Lys Arg Phe Leu Lys His
385                 390                 395                 400

Gly Gln Asn Ile Arg Asp Val Ser Asn Lys Glu Asn
                405                 410


<210> SEQ ID NO 29
<211> LENGTH: 412
<212> TYPE: PRT
<213> ORGANISM: Homo sapiens

<400> SEQUENCE: 29

Met Asp Pro Ile Arg Ser Phe Cys Gly Lys Leu Arg Ser Leu Ala Ser
 1               5                  10                  15

Thr Leu Asp Cys Glu Thr Ala Arg Leu Gln Arg Ala Leu Asp Gly Glu
            20                  25                  30

Glu Ser Asp Phe Glu Asp Tyr Pro Met Arg Ile Leu Tyr Asp Leu His
        35                  40                  45

Ser Glu Val Gln Thr Leu Lys Asp Asp Val Asn Ile Leu Leu Asp Lys
    50                  55                  60

Ala Arg Leu Glu Asn Gln Glu Gly Ile Asp Phe Ile Lys Ala Thr Lys
65                  70                  75                  80

Val Leu Met Glu Lys Asn Ser Met Asp Ile Met Lys Ile Arg Glu Tyr
                85                  90                  95

Phe Gln Lys Tyr Gly Tyr Ser Pro Arg Val Lys Lys Asn Ser Val His
            100                 105                 110

Glu Gln Glu Ala Ile Asn Ser Asp Pro Glu Leu Ser Asn Cys Glu Asn
        115                 120                 125

Phe Gln Lys Thr Asp Val Lys Asp Asp Leu Ser Asp Pro Pro Val Ala
    130                 135                 140

Ser Ser Cys Ile Ser Glu Lys Ser Pro Arg Ser Pro Gln Leu Ser Asp
145                 150                 155                 160

Phe Gly Leu Glu Arg Tyr Ile Val Ser Gln Val Leu Pro Asn Pro Pro
                165                 170                 175

Gln Ala Val Asn Asn Tyr Lys Glu Glu Pro Val Ile Val Thr Pro Pro
            180                 185                 190

Thr Lys Gln Ser Leu Val Lys Val Leu Lys Thr Pro Lys Cys Ala Leu
        195                 200                 205

Lys Met Asp Asp Phe Glu Cys Val Thr Pro Lys Leu Glu His Phe Gly
    210                 215                 220

Ile Ser Glu Tyr Thr Met Cys Leu Asn Glu Asp Tyr Thr Met Gly Leu
225                 230                 235                 240

Lys Asn Ala Arg Asn Asn Lys Ser Glu Glu Ala Ile Asp Thr Glu Ser
```

```
                245                 250                 255

Arg Leu Asn Asp Asn Val Phe Ala Thr Pro Ser Pro Ile Ile Gln Gln
            260                 265                 270

Leu Glu Lys Ser Asp Ala Glu Tyr Thr Asn Ser Pro Leu Val Pro Thr
        275                 280                 285

Phe Cys Thr Pro Gly Leu Lys Ile Pro Ser Thr Lys Asn Ser Ile Ala
    290                 295                 300

Leu Val Ser Thr Asn Tyr Pro Leu Ser Lys Thr Asn Ser Ser Ser Asn
305                 310                 315                 320

Asp Leu Glu Val Glu Asp Arg Thr Ser Leu Val Leu Asn Ser Asp Thr
                325                 330                 335

Cys Phe Glu Asn Leu Thr Asp Pro Ser Ser Pro Thr Ile Ser Ser Tyr
            340                 345                 350

Glu Asn Leu Leu Arg Thr Pro Thr Pro Pro Glu Val Thr Lys Ile Pro
        355                 360                 365

Glu Asp Ile Leu Gln Leu Leu Ser Lys Tyr Asn Ser Asn Leu Ala Thr
    370                 375                 380

Pro Ile Ala Ile Lys Ala Val Pro Pro Ser Lys Arg Phe Leu Lys His
385                 390                 395                 400

Gly Gln Asn Ile Arg Asp Val Ser Asn Lys Glu Asn
                405                 410


<210> SEQ ID NO 30
<211> LENGTH: 412
<212> TYPE: PRT
<213> ORGANISM: Homo sapiens

<400> SEQUENCE: 30

Met Asp Pro Ile Arg Ser Phe Cys Gly Lys Leu Arg Ser Leu Ala Ser
 1               5                  10                  15

Thr Leu Asp Cys Glu Thr Ala Arg Leu Gln Arg Ala Leu Asp Gly Glu
            20                  25                  30

Glu Ser Asp Phe Glu Asp Tyr Pro Met Arg Ile Leu Tyr Asp Leu His
        35                  40                  45

Ser Glu Val Gln Thr Leu Lys Asp Asp Val Asn Ile Leu Leu Asp Lys
    50                  55                  60

Ala Arg Leu Glu Asn Gln Glu Gly Ile Asp Phe Ile Lys Ala Thr Lys
65                  70                  75                  80

Val Leu Met Glu Lys Asn Ser Met Asp Ile Met Lys Ile Arg Glu Tyr
                85                  90                  95

Phe Gln Lys Tyr Gly Tyr Ser Pro Arg Val Lys Lys Asn Ser Val His
            100                 105                 110

Glu Gln Glu Ala Ile Asn Ser Asp Pro Glu Leu Ser Asn Cys Glu Asn
        115                 120                 125

Phe Gln Lys Thr Asp Val Lys Asp Asp Leu Ser Asp Pro Pro Val Ala
    130                 135                 140

Ser Ser Cys Ile Ser Gly Lys Ser Pro Arg Ser Pro Gln Leu Ser Asp
145                 150                 155                 160

Phe Gly Leu Glu Arg Tyr Ile Val Ser Gln Val Leu Pro Asn Pro Pro
                165                 170                 175

Gln Ala Val Asn Asn Tyr Lys Glu Glu Pro Val Ile Val Thr Pro Pro
            180                 185                 190

Thr Lys Gln Ser Leu Val Lys Val Leu Lys Thr Pro Lys Cys Ala Leu
        195                 200                 205
```

-continued

```
Lys Met Asp Asp Phe Glu Cys Val Thr Pro Lys Leu Glu His Phe Gly
    210                 215                 220

Ile Ser Glu Tyr Thr Met Cys Leu Asn Glu Asp Tyr Thr Met Gly Leu
225                 230                 235                 240

Lys Asn Ala Arg Asn Asn Lys Ser Glu Glu Ala Ile Asp Ala Glu Ser
                245                 250                 255

Arg Leu Asn Asp Asn Val Phe Ala Thr Pro Ser Pro Ile Ile Gln Gln
            260                 265                 270

Leu Glu Lys Ser Asp Ala Glu Tyr Thr Asn Ser Pro Leu Val Pro Thr
        275                 280                 285

Phe Cys Thr Pro Gly Leu Lys Ile Pro Ser Thr Lys Asn Ser Ile Ala
    290                 295                 300

Leu Val Ser Thr Asn Tyr Pro Leu Ser Lys Thr Asn Ser Ser Ser Asn
305                 310                 315                 320

Asp Leu Glu Val Glu Asp Arg Thr Ser Leu Val Leu Asn Ser Asp Thr
                325                 330                 335

Cys Phe Glu Asn Leu Thr Asp Pro Ser Ser Pro Thr Ile Ser Ser Tyr
            340                 345                 350

Glu Asn Leu Leu Arg Thr Pro Thr Pro Pro Glu Val Thr Lys Ile Pro
        355                 360                 365

Glu Asp Ile Leu Gln Leu Leu Ser Lys Tyr Asn Ser Asn Leu Ala Thr
    370                 375                 380

Pro Ile Ala Ile Lys Ala Val Pro Pro Ser Lys Arg Phe Leu Lys His
385                 390                 395                 400

Gly Gln Asn Ile Arg Asp Val Ser Asn Lys Glu Asn
                405                 410


<210> SEQ ID NO 31
<211> LENGTH: 330
<212> TYPE: PRT
<213> ORGANISM: Homo sapiens

<400> SEQUENCE: 31

Met Glu Lys Asn Ser Met Asp Ile Met Lys Ile Arg Glu Tyr Phe Gln
 1               5                  10                  15

Lys Tyr Gly Tyr Ser Pro Arg Val Lys Lys Asn Ser Val His Glu Gln
            20                  25                  30

Glu Ala Ile Asn Ser Asp Pro Glu Leu Ser Asn Cys Glu Asn Phe Gln
        35                  40                  45

Lys Thr Asp Val Lys Asp Asp Leu Ser Asp Pro Pro Val Ala Ser Ser
    50                  55                  60

Cys Ile Ser Glu Lys Ser Pro Arg Ser Pro Gln Leu Ser Asp Phe Gly
65                  70                  75                  80

Leu Glu Arg Tyr Ile Val Ser Gln Val Leu Pro Asn Pro Pro Gln Ala
                85                  90                  95

Val Asn Asn Tyr Lys Glu Glu Pro Val Ile Val Thr Pro Pro Thr Lys
            100                 105                 110

Gln Ser Leu Val Lys Val Leu Lys Thr Pro Lys Cys Ala Leu Lys Met
        115                 120                 125

Asp Asp Phe Glu Cys Val Thr Pro Lys Leu Glu His Phe Gly Ile Ser
    130                 135                 140

Glu Tyr Thr Met Cys Leu Asn Glu Asp Tyr Thr Met Gly Leu Lys Asn
145                 150                 155                 160

Ala Arg Asn Asn Lys Ser Glu Glu Ala Ile Asp Thr Glu Ser Arg Leu
                165                 170                 175
```

```
Asn Asp Asn Val Phe Ala Thr Pro Ser Pro Ile Ile Gln Gln Leu Glu
            180                 185                 190

Lys Ser Asp Ala Glu Tyr Thr Asn Ser Pro Leu Val Pro Thr Phe Cys
        195                 200                 205

Thr Pro Gly Leu Lys Ile Pro Ser Thr Lys Asn Ser Ile Ala Leu Val
    210                 215                 220

Ser Thr Asn Tyr Pro Leu Ser Lys Thr Asn Ser Ser Ser Asn Asp Leu
225                 230                 235                 240

Glu Val Glu Asp Arg Thr Ser Leu Val Leu Asn Ser Asp Thr Cys Phe
                245                 250                 255

Glu Asn Leu Thr Asp Pro Ser Ser Pro Thr Ile Ser Ser Tyr Glu Asn
            260                 265                 270

Leu Leu Arg Thr Pro Thr Pro Pro Glu Val Thr Lys Ile Pro Glu Asp
        275                 280                 285

Ile Leu Gln Leu Leu Ser Lys Tyr Asn Ser Asn Leu Ala Thr Pro Ile
    290                 295                 300

Ala Ile Lys Ala Val Pro Pro Ser Lys Arg Phe Leu Lys His Gly Gln
305                 310                 315                 320

Asn Ile Arg Asp Val Ser Asn Lys Glu Asn
                325                 330


<210> SEQ ID NO 32
<211> LENGTH: 388
<212> TYPE: PRT
<213> ORGANISM: Homo sapiens

<400> SEQUENCE: 32

Met Asp Pro Ile Arg Ser Phe Cys Gly Lys Leu Arg Ser Leu Ala Ser
 1               5                  10                  15

Thr Leu Asp Cys Glu Thr Ala Arg Leu Gln Arg Ala Leu Asp Gly Glu
            20                  25                  30

Glu Ser Asp Phe Glu Asp Tyr Pro Met Arg Ile Leu Tyr Asp Leu His
        35                  40                  45

Ser Glu Val Gln Thr Leu Lys Asp Asp Val Asn Ile Leu Leu Asp Lys
    50                  55                  60

Ala Arg Leu Glu Asn Gln Glu Gly Ile Asp Phe Ile Lys Ala Thr Lys
65                  70                  75                  80

Val Leu Met Glu Lys Asn Ser Met Asp Ile Met Lys Ile Arg Glu Tyr
                85                  90                  95

Phe Gln Lys Tyr Gly Tyr Ser Pro Arg Val Lys Lys Asn Ser Val His
            100                 105                 110

Glu Gln Glu Ala Ile Asn Ser Asp Pro Glu Leu Ser Asn Cys Glu Asn
        115                 120                 125

Phe Gln Lys Thr Asp Val Lys Asp Asp Leu Ser Asp Pro Pro Val Ala
    130                 135                 140

Ser Ser Cys Ile Ser Glu Lys Ser Pro Arg Ser Pro Gln Leu Ser Asp
145                 150                 155                 160

Phe Gly Leu Glu Arg Tyr Ile Val Ser Gln Val Leu Pro Asn Pro Pro
                165                 170                 175

Gln Ala Val Asn Asn Tyr Lys Glu Glu Pro Val Ile Val Thr Pro Pro
            180                 185                 190

Thr Lys Gln Ser Leu Val Lys Val Leu Lys Thr Pro Lys Cys Ala Leu
        195                 200                 205

Lys Met Asp Asp Phe Glu Cys Val Thr Pro Lys Leu Glu His Phe Gly
```

-continued

```
    210                 215                 220

Ile Ser Glu Tyr Thr Met Cys Leu Asn Glu Asp Tyr Thr Met Gly Leu
225                 230                 235                 240

Lys Asn Ala Arg Asn Asn Lys Ser Glu Glu Ala Ile Asp Thr Glu Ser
                245                 250                 255

Arg Leu Asn Asp Asn Val Phe Ala Thr Pro Ser Pro Ile Ile Gln Gln
            260                 265                 270

Leu Glu Lys Ser Asp Ala Glu Tyr Thr Asn Ser Pro Leu Val Pro Thr
        275                 280                 285

Phe Cys Thr Pro Gly Leu Lys Ile Pro Ser Thr Lys Asn Ser Ile Ala
    290                 295                 300

Leu Val Ser Thr Asn Tyr Pro Leu Ser Lys Thr Asn Ser Ser Ser Asn
305                 310                 315                 320

Asp Leu Glu Val Glu Asp Arg Thr Ser Leu Val Leu Asn Ser Asp Thr
                325                 330                 335

Cys Phe Glu Asn Leu Thr Asp Pro Ser Ser Pro Thr Ile Ser Ser Tyr
            340                 345                 350

Glu Asn Leu Leu Arg Thr Pro Thr Pro Pro Glu Val Thr Lys Ile Pro
        355                 360                 365

Glu Asp Ile Leu Gln Lys Phe Gln Trp Ile Tyr Pro Thr Gln Lys Leu
    370                 375                 380

Asn Lys Met Arg
385


<210> SEQ ID NO 33
<211> LENGTH: 306
<212> TYPE: PRT
<213> ORGANISM: Homo sapiens

<400> SEQUENCE: 33

Met Glu Lys Asn Ser Met Asp Ile Met Lys Ile Arg Glu Tyr Phe Gln
 1               5                  10                  15

Lys Tyr Gly Tyr Ser Pro Arg Val Lys Lys Asn Ser Val His Glu Gln
            20                  25                  30

Glu Ala Ile Asn Ser Asp Pro Glu Leu Ser Asn Cys Glu Asn Phe Gln
        35                  40                  45

Lys Thr Asp Val Lys Asp Asp Leu Ser Asp Pro Pro Val Ala Ser Ser
    50                  55                  60

Cys Ile Ser Gly Lys Ser Pro Arg Ser Pro Gln Leu Ser Asp Phe Gly
65                  70                  75                  80

Leu Glu Arg Tyr Ile Val Ser Gln Val Leu Pro Asn Pro Pro Gln Ala
                85                  90                  95

Val Asn Asn Tyr Lys Glu Glu Pro Val Ile Val Thr Pro Pro Thr Lys
            100                 105                 110

Gln Ser Leu Val Lys Val Leu Lys Thr Pro Lys Cys Ala Leu Lys Met
        115                 120                 125

Asp Asp Phe Glu Cys Val Thr Pro Lys Leu Glu His Phe Gly Ile Ser
    130                 135                 140

Glu Tyr Thr Met Cys Leu Asn Glu Asp Tyr Thr Met Gly Leu Lys Asn
145                 150                 155                 160

Ala Arg Asn Asn Lys Ser Glu Glu Ala Ile Asp Thr Glu Ser Arg Leu
                165                 170                 175

Asn Asp Asn Val Phe Ala Thr Pro Ser Pro Ile Ile Gln Gln Leu Glu
            180                 185                 190
```

-continued

```
Lys Ser Asp Ala Glu Tyr Thr Asn Ser Pro Leu Val Pro Thr Phe Cys
        195                 200                 205

Thr Pro Gly Leu Lys Ile Pro Ser Thr Lys Asn Ser Ile Ala Leu Val
    210                 215                 220

Ser Thr Asn Tyr Pro Leu Ser Lys Thr Asn Ser Ser Ser Asn Asp Leu
225                 230                 235                 240

Glu Val Glu Asp Arg Thr Ser Leu Val Leu Asn Ser Asp Thr Cys Phe
                245                 250                 255

Glu Asn Leu Thr Asp Pro Ser Ser Pro Thr Ile Ser Ser Tyr Glu Asn
            260                 265                 270

Leu Leu Arg Thr Pro Thr Pro Pro Glu Val Thr Lys Ile Pro Glu Asp
        275                 280                 285

Ile Leu Gln Lys Phe Gln Trp Ile Tyr Pro Thr Gln Lys Leu Asn Lys
    290                 295                 300

Met Arg
305


<210> SEQ ID NO 34
<211> LENGTH: 73
<212> TYPE: PRT
<213> ORGANISM: Homo sapiens

<400> SEQUENCE: 34

Met Asp Pro Ile Arg Ser Phe Cys Gly Lys Leu Arg Ser Leu Ala Ser
 1               5                  10                  15

Thr Leu Asp Cys Glu Thr Ala Arg Leu Gln Arg Ala Leu Asp Gly Glu
            20                  25                  30

Glu Ser Leu Leu Ser Lys Tyr Asn Ser Asn Leu Ala Thr Pro Ile Ala
        35                  40                  45

Ile Lys Ala Val Pro Pro Ser Lys Arg Phe Leu Lys His Gly Gln Asn
    50                  55                  60

Ile Arg Asp Val Ser Asn Lys Glu Asn
65                  70


<210> SEQ ID NO 35
<211> LENGTH: 372
<212> TYPE: PRT
<213> ORGANISM: Homo sapiens

<400> SEQUENCE: 35

Met Arg Ile Leu Tyr Asp Leu His Ser Glu Val Gln Thr Leu Lys Asp
 1               5                  10                  15

Asp Val Asn Ile Leu Leu Asp Lys Ala Arg Leu Glu Asn Gln Glu Gly
            20                  25                  30

Ile Asp Phe Ile Lys Ala Thr Lys Val Leu Met Glu Lys Asn Ser Met
        35                  40                  45

Asp Ile Met Lys Ile Arg Glu Tyr Phe Gln Lys Tyr Gly Tyr Ser Pro
    50                  55                  60

Arg Val Lys Lys Asn Ser Val His Glu Gln Glu Ala Ile Asn Ser Asp
65                  70                  75                  80

Pro Glu Leu Ser Asn Cys Glu Asn Phe Gln Lys Thr Asp Val Lys Asp
                85                  90                  95

Asp Leu Ser Asp Pro Pro Val Ala Ser Ser Cys Ile Ser Gly Lys Ser
            100                 105                 110

Pro Arg Ser Pro Gln Leu Ser Asp Phe Gly Leu Glu Arg Tyr Ile Val
        115                 120                 125
```

-continued

```
Ser Gln Val Leu Pro Asn Pro Pro Gln Ala Val Asn Asn Tyr Lys Glu
    130                 135                 140

Glu Pro Val Ile Val Thr Pro Pro Thr Lys Gln Ser Leu Val Lys Val
145                 150                 155                 160

Leu Lys Thr Pro Lys Cys Ala Leu Lys Met Asp Asp Phe Glu Cys Val
                165                 170                 175

Thr Pro Lys Leu Glu His Phe Gly Ile Ser Glu Tyr Thr Met Cys Leu
            180                 185                 190

Asn Glu Asp Tyr Thr Met Gly Leu Lys Asn Ala Arg Asn Asn Lys Ser
        195                 200                 205

Glu Glu Ala Ile Asp Thr Glu Ser Arg Leu Asn Asp Asn Val Phe Ala
    210                 215                 220

Thr Pro Ser Pro Ile Ile Gln Gln Leu Glu Lys Ser Asp Ala Glu Tyr
225                 230                 235                 240

Thr Asn Ser Pro Leu Val Pro Thr Phe Cys Thr Pro Gly Leu Lys Ile
                245                 250                 255

Pro Ser Thr Lys Asn Ser Ile Ala Leu Val Ser Thr Asn Tyr Pro Leu
            260                 265                 270

Ser Lys Thr Asn Ser Ser Ser Asn Asp Leu Glu Val Glu Asp Arg Thr
        275                 280                 285

Ser Leu Val Leu Asn Ser Asp Thr Cys Phe Glu Asn Leu Thr Asp Pro
    290                 295                 300

Ser Ser Pro Thr Ile Ser Ser Tyr Glu Asn Leu Leu Arg Thr Pro Thr
305                 310                 315                 320

Pro Pro Glu Val Thr Lys Ile Pro Glu Asp Ile Leu Gln Leu Leu Ser
                325                 330                 335

Lys Tyr Asn Ser Asn Leu Ala Thr Pro Ile Ala Ile Lys Ala Val Pro
            340                 345                 350

Pro Ser Lys Arg Phe Leu Lys His Gly Gln Asn Ile Arg Asp Val Ser
        355                 360                 365

Asn Lys Glu Asn
    370


<210> SEQ ID NO 36
<211> LENGTH: 373
<212> TYPE: PRT
<213> ORGANISM: Homo sapiens

<400> SEQUENCE: 36

Met Asp Pro Ile Arg Ser Phe Cys Gly Lys Leu Arg Ser Leu Ala Ser
 1               5                  10                  15

Thr Leu Asp Cys Glu Thr Ala Arg Leu Gln Arg Ala Leu Asp Gly Glu
            20                  25                  30

Glu Ser Asp Phe Glu Asp Tyr Pro Met Arg Ile Leu Tyr Asp Leu His
        35                  40                  45

Ser Glu Val Gln Thr Leu Lys Asp Asp Val Asn Ile Leu Leu Asp Lys
    50                  55                  60

Ala Arg Leu Glu Asn Gln Glu Gly Ile Asp Phe Ile Lys Ala Thr Lys
65                  70                  75                  80

Val Leu Met Glu Lys Asn Ser Met Asp Ile Met Lys Ile Arg Glu Tyr
                85                  90                  95

Phe Gln Lys Tyr Gly Tyr Ser Pro Arg Val Lys Lys Asn Ser Val His
            100                 105                 110

Glu Gln Glu Ala Ile Asn Ser Asp Pro Glu Leu Ser Asn Cys Glu Asn
        115                 120                 125
```

```
Phe Gln Lys Thr Asp Val Lys Asp Asp Leu Ser Asp Pro Pro Val Ala
    130                 135                 140

Ser Ser Cys Ile Ser Gly Lys Ser Pro Arg Ser Pro Gln Leu Ser Asp
145                 150                 155                 160

Phe Gly Leu Glu Arg Tyr Ile Val Ser Gln Val Leu Pro Asn Pro Pro
                165                 170                 175

Gln Ala Val Asn Asn Tyr Lys Glu Glu Pro Val Ile Val Thr Pro Pro
            180                 185                 190

Thr Lys Gln Ser Leu Val Lys Val Leu Lys Thr Pro Lys Cys Ala Leu
        195                 200                 205

Lys Met Asp Asp Phe Glu Cys Val Thr Pro Lys Leu Glu His Phe Gly
    210                 215                 220

Ile Ser Glu Tyr Thr Met Cys Leu Asn Glu Asp Tyr Thr Met Gly Leu
225                 230                 235                 240

Lys Asn Ala Arg Asn Asn Lys Ser Glu Glu Ala Ile Asp Thr Glu Ser
                245                 250                 255

Arg Leu Asn Asp Asn Val Phe Ala Thr Pro Ser Pro Ile Ile Gln Gln
            260                 265                 270

Leu Glu Lys Ser Asp Ala Glu Tyr Thr Asn Ser Pro Leu Val Pro Thr
        275                 280                 285

Phe Cys Thr Pro Gly Leu Lys Ile Pro Ser Thr Lys Asn Ser Ile Ala
    290                 295                 300

Leu Val Ser Thr Asn Tyr Pro Leu Ser Lys Thr Asn Ser Ser Ser Asn
305                 310                 315                 320

Asp Leu Glu Val Glu Asp Arg Thr Ser Leu Val Leu Asn Ser Asp Thr
                325                 330                 335

Cys Phe Glu Asn Leu Thr Asp Pro Ser Ser Pro Thr Ile Ser Ser Tyr
            340                 345                 350

Glu Asn Leu Leu Arg Thr Pro Thr Pro Pro Glu Val Thr Lys Ile Pro
        355                 360                 365

Glu Asp Ile Leu Gln
    370


<210> SEQ ID NO 37
<211> LENGTH: 373
<212> TYPE: PRT
<213> ORGANISM: Homo sapiens

<400> SEQUENCE: 37

Met Asp Pro Ile Arg Ser Phe Cys Gly Lys Leu Arg Ser Leu Ala Ser
 1               5                  10                  15

Thr Leu Asp Cys Glu Thr Ala Arg Leu Gln Arg Ala Leu Asp Gly Glu
            20                  25                  30

Glu Ser Asp Phe Glu Asp Tyr Pro Met Arg Ile Leu Tyr Asp Leu His
        35                  40                  45

Ser Glu Val Gln Thr Leu Lys Asp Asp Val Asn Ile Leu Leu Asp Lys
    50                  55                  60

Ala Arg Leu Glu Asn Gln Glu Gly Ile Asp Phe Ile Lys Ala Thr Lys
65                  70                  75                  80

Val Leu Met Glu Lys Asn Ser Met Asp Ile Met Lys Ile Arg Glu Tyr
                85                  90                  95

Phe Gln Lys Tyr Gly Tyr Ser Pro Arg Val Lys Lys Asn Ser Val His
            100                 105                 110

Glu Gln Glu Ala Ile Asn Ser Asp Pro Glu Leu Ser Asn Cys Glu Asn
```

```
        115                 120                 125

Phe Gln Lys Thr Asp Val Lys Asp Asp Leu Ser Asp Pro Pro Val Ala
    130                 135                 140

Ser Ser Cys Ile Ser Glu Lys Ser Pro Arg Ser Pro Gln Leu Ser Asp
145                 150                 155                 160

Phe Gly Leu Glu Arg Tyr Ile Val Ser Gln Val Leu Pro Asn Pro Pro
                165                 170                 175

Gln Ala Val Asn Asn Tyr Lys Glu Glu Pro Val Ile Val Thr Pro Pro
            180                 185                 190

Thr Lys Gln Ser Leu Val Lys Val Leu Lys Thr Pro Lys Cys Ala Leu
        195                 200                 205

Lys Met Asp Asp Phe Glu Cys Val Thr Pro Lys Leu Glu His Phe Gly
    210                 215                 220

Ile Ser Glu Tyr Thr Met Cys Leu Asn Glu Asp Tyr Thr Met Gly Leu
225                 230                 235                 240

Lys Asn Ala Arg Asn Asn Lys Ser Glu Glu Ala Ile Asp Thr Glu Ser
                245                 250                 255

Arg Leu Asn Asp Asn Val Phe Ala Thr Pro Ser Pro Ile Ile Gln Gln
            260                 265                 270

Leu Glu Lys Ser Asp Ala Glu Tyr Thr Asn Ser Pro Leu Val Pro Thr
        275                 280                 285

Phe Cys Thr Pro Gly Leu Lys Ile Pro Ser Thr Lys Asn Ser Ile Ala
    290                 295                 300

Leu Val Ser Thr Asn Tyr Pro Leu Ser Lys Thr Asn Ser Ser Ser Asn
305                 310                 315                 320

Asp Leu Glu Val Glu Asp Arg Thr Ser Leu Val Leu Asn Ser Asp Thr
                325                 330                 335

Cys Phe Glu Asn Leu Thr Asp Pro Ser Ser Pro Thr Ile Ser Ser Tyr
            340                 345                 350

Glu Asn Leu Leu Arg Thr Pro Thr Pro Pro Glu Val Thr Lys Ile Pro
        355                 360                 365

Glu Asp Ile Leu Gln
    370


<210> SEQ ID NO 38
<211> LENGTH: 373
<212> TYPE: PRT
<213> ORGANISM: Homo sapiens

<400> SEQUENCE: 38

Met Asp Pro Ile Arg Ser Phe Cys Gly Lys Leu Arg Ser Leu Ala Ser
 1               5                  10                  15

Thr Leu Asp Cys Glu Thr Ala Arg Leu Gln Arg Ala Leu Asp Gly Glu
            20                  25                  30

Glu Ser Asp Phe Glu Asp Tyr Pro Met Arg Ile Leu Tyr Asp Leu His
        35                  40                  45

Ser Glu Val Gln Thr Leu Lys Asp Asp Val Asn Ile Leu Leu Asp Lys
    50                  55                  60

Ala Arg Leu Glu Asn Gln Glu Gly Ile Asp Phe Ile Lys Ala Thr Lys
65                  70                  75                  80

Val Leu Met Glu Lys Asn Ser Met Asp Ile Met Lys Ile Arg Glu Tyr
                85                  90                  95

Phe Gln Lys Tyr Gly Tyr Ser Pro Arg Val Lys Lys Asn Ser Val His
            100                 105                 110
```

-continued

```
Glu Gln Glu Ala Ile Asn Ser Asp Pro Glu Leu Ser Asn Cys Glu Asn
        115                 120                 125

Phe Gln Lys Thr Asp Val Lys Asp Asp Leu Ser Asp Pro Pro Val Ala
    130                 135                 140

Ser Ser Cys Ile Ser Glu Lys Ser Pro Arg Ser Pro Gln Leu Ser Asp
145                 150                 155                 160

Phe Gly Leu Glu Arg Tyr Ile Val Ser Gln Val Leu Pro Asn Pro Pro
                165                 170                 175

Gln Ala Val Asn Asn Tyr Lys Glu Glu Pro Val Ile Val Thr Pro Pro
            180                 185                 190

Thr Lys Gln Ser Leu Val Lys Val Leu Lys Thr Pro Lys Cys Ala Leu
        195                 200                 205

Lys Met Asp Asp Phe Glu Cys Val Thr Pro Lys Leu Glu His Phe Gly
    210                 215                 220

Ile Ser Glu Tyr Thr Met Cys Leu Asn Glu Asp Tyr Thr Met Gly Leu
225                 230                 235                 240

Lys Asn Ala Arg Asn Asn Lys Ser Glu Glu Ala Ile Asp Thr Glu Ser
                245                 250                 255

Arg Leu Asn Asp Asn Val Phe Ala Thr Pro Ser Pro Ile Ile Gln Gln
            260                 265                 270

Leu Glu Lys Ser Asp Ala Glu Tyr Thr Asn Ser Pro Leu Val Pro Thr
        275                 280                 285

Phe Cys Thr Pro Gly Leu Lys Ile Pro Ser Thr Lys Asn Ser Ile Ala
    290                 295                 300

Leu Val Ser Thr Asn Tyr Pro Leu Ser Lys Thr Asn Ser Ser Ser Asn
305                 310                 315                 320

Asp Leu Glu Val Glu Asp Arg Thr Ser Leu Val Leu Asn Ser Asp Thr
                325                 330                 335

Cys Phe Glu Asn Leu Thr Asp Pro Ser Ser Pro Thr Ile Ser Ser Tyr
            340                 345                 350

Glu Asn Leu Leu Arg Thr Pro Thr Pro Pro Glu Val Thr Lys Ile Pro
        355                 360                 365

Glu Asp Ile Leu Gln
    370


<210> SEQ ID NO 39
<211> LENGTH: 373
<212> TYPE: PRT
<213> ORGANISM: Homo sapiens

<400> SEQUENCE: 39

Met Asp Pro Ile Arg Ser Phe Cys Gly Lys Leu Arg Ser Leu Ala Ser
 1               5                  10                  15

Thr Leu Asp Cys Glu Thr Ala Arg Leu Gln Arg Ala Leu Asp Gly Glu
            20                  25                  30

Glu Ser Asp Phe Glu Asp Tyr Pro Met Arg Ile Leu Tyr Asp Leu His
        35                  40                  45

Ser Glu Val Gln Thr Leu Lys Asp Asp Val Asn Ile Leu Leu Asp Lys
    50                  55                  60

Ala Arg Leu Glu Asn Gln Glu Gly Ile Asp Phe Ile Lys Ala Thr Lys
65                  70                  75                  80

Val Leu Met Glu Lys Asn Ser Met Asp Ile Met Lys Ile Arg Glu Tyr
                85                  90                  95

Phe Gln Lys Tyr Gly Tyr Ser Pro Arg Val Lys Lys Asn Ser Val His
            100                 105                 110
```

```
Glu Gln Glu Ala Ile Asn Ser Asp Pro Glu Leu Ser Asn Cys Glu Asn
        115                 120                 125

Phe Gln Lys Thr Asp Val Lys Asp Asp Leu Ser Asp Pro Pro Val Ala
    130                 135                 140

Ser Ser Cys Ile Ser Glu Lys Ser Pro Arg Ser Pro Gln Leu Ser Asp
145                 150                 155                 160

Phe Gly Leu Glu Arg Tyr Ile Val Ser Gln Val Leu Pro Asn Pro Pro
                165                 170                 175

Gln Ala Val Asn Asn Tyr Lys Glu Glu Pro Val Ile Val Thr Pro Pro
            180                 185                 190

Thr Lys Gln Ser Leu Val Lys Val Leu Lys Thr Pro Lys Cys Ala Leu
        195                 200                 205

Lys Met Asp Asp Phe Glu Cys Val Thr Pro Lys Leu Glu His Phe Gly
    210                 215                 220

Ile Ser Glu Tyr Thr Met Cys Leu Asn Glu Asp Tyr Thr Met Gly Leu
225                 230                 235                 240

Lys Asn Ala Arg Asn Asn Lys Ser Glu Glu Ala Ile Asp Thr Glu Ser
                245                 250                 255

Arg Leu Asn Asp Asn Val Phe Ala Thr Pro Ser Pro Ile Ile Gln Gln
            260                 265                 270

Leu Glu Lys Ser Asp Ala Glu Tyr Thr Asn Ser Pro Leu Val Pro Thr
        275                 280                 285

Phe Cys Thr Pro Gly Leu Lys Ile Pro Ser Thr Lys Asn Ser Ile Ala
    290                 295                 300

Leu Val Ser Thr Asn Tyr Pro Leu Ser Lys Thr Asn Ser Ser Ser Asn
305                 310                 315                 320

Asp Leu Glu Val Glu Asp Arg Thr Ser Leu Val Leu Asn Ser Asp Thr
                325                 330                 335

Cys Phe Glu Asn Leu Thr Asp Pro Ser Ser Pro Thr Ile Ser Ser Tyr
            340                 345                 350

Glu Asn Leu Leu Arg Thr Pro Thr Pro Pro Glu Val Thr Lys Ile Pro
        355                 360                 365

Glu Asp Ile Leu Gln
    370


<210> SEQ ID NO 40
<211> LENGTH: 388
<212> TYPE: PRT
<213> ORGANISM: Homo sapiens

<400> SEQUENCE: 40

Met Asp Pro Ile Arg Ser Phe Cys Gly Lys Leu Arg Ser Leu Ala Ser
 1               5                  10                  15

Thr Leu Asp Cys Glu Thr Ala Arg Leu Gln Arg Ala Leu Asp Gly Glu
            20                  25                  30

Glu Ser Asp Phe Glu Asp Tyr Pro Met Arg Ile Leu Tyr Asp Leu His
        35                  40                  45

Ser Glu Val Gln Thr Leu Lys Asp Asp Val Asn Ile Leu Leu Asp Lys
    50                  55                  60

Ala Arg Leu Glu Asn Gln Glu Gly Ile Asp Phe Ile Lys Ala Thr Lys
65                  70                  75                  80

Val Leu Met Glu Lys Asn Ser Met Asp Ile Met Lys Ile Arg Glu Tyr
                85                  90                  95

Phe Gln Lys Tyr Gly Tyr Ser Pro Arg Val Lys Lys Asn Ser Val His
```

```
            100                 105                 110

Glu Gln Glu Ala Ile Asn Ser Asp Pro Glu Leu Ser Asn Cys Glu Asn
        115                 120                 125

Phe Gln Lys Thr Asp Val Lys Asp Asp Leu Ser Asp Pro Pro Val Ala
    130                 135                 140

Ser Ser Cys Ile Ser Glu Lys Ser Pro Arg Ser Pro Gln Leu Ser Asp
145                 150                 155                 160

Phe Gly Leu Glu Arg Tyr Ile Val Ser Gln Val Leu Pro Asn Pro Pro
                165                 170                 175

Gln Ala Val Asn Asn Tyr Lys Glu Glu Pro Val Ile Val Thr Pro Pro
            180                 185                 190

Thr Lys Gln Ser Leu Val Lys Val Leu Lys Thr Pro Lys Cys Ala Leu
        195                 200                 205

Lys Met Asp Asp Phe Glu Cys Val Thr Pro Lys Leu Glu His Phe Gly
    210                 215                 220

Ile Ser Glu Tyr Thr Met Cys Leu Asn Glu Asp Tyr Thr Met Gly Leu
225                 230                 235                 240

Lys Asn Ala Arg Asn Asn Lys Ser Glu Glu Ala Ile Asp Thr Glu Ser
                245                 250                 255

Arg Leu Asn Asp Asn Val Phe Ala Thr Pro Ser Pro Ile Ile Gln Gln
            260                 265                 270

Leu Glu Lys Ser Asp Ala Glu Tyr Thr Asn Ser Pro Leu Val Pro Thr
        275                 280                 285

Phe Cys Thr Pro Gly Leu Lys Ile Pro Ser Thr Lys Asn Ser Ile Ala
    290                 295                 300

Leu Val Ser Thr Asn Tyr Pro Leu Ser Lys Thr Asn Ser Ser Ser Asn
305                 310                 315                 320

Asp Leu Glu Val Glu Asp Arg Thr Ser Leu Val Leu Asn Ser Asp Thr
                325                 330                 335

Cys Phe Glu Asn Leu Thr Asp Pro Ser Ser Pro Thr Ile Ser Ser Tyr
            340                 345                 350

Glu Asn Leu Leu Arg Thr Pro Thr Pro Pro Glu Val Thr Lys Ile Pro
        355                 360                 365

Glu Asp Ile Leu Gln Lys Phe Gln Trp Ile Tyr Pro Thr Gln Lys Leu
    370                 375                 380

Asn Lys Met Arg
385


<210> SEQ ID NO 41
<211> LENGTH: 388
<212> TYPE: PRT
<213> ORGANISM: Homo sapiens

<400> SEQUENCE: 41

Met Asp Pro Ile Arg Ser Phe Cys Gly Lys Leu Arg Ser Leu Ala Ser
 1               5                  10                  15

Thr Leu Asp Cys Glu Thr Ala Arg Leu Gln Arg Ala Leu Asp Gly Glu
            20                  25                  30

Glu Ser Asp Phe Glu Asp Tyr Pro Met Arg Ile Leu Tyr Asp Leu His
        35                  40                  45

Ser Glu Val Gln Thr Leu Lys Asp Asp Val Asn Ile Leu Leu Asp Lys
    50                  55                  60

Ala Arg Leu Glu Asn Gln Glu Gly Ile Asp Phe Ile Lys Ala Thr Lys
65                  70                  75                  80
```

-continued

```
Val Leu Met Glu Lys Asn Ser Met Asp Ile Met Lys Ile Arg Glu Tyr
                85                  90                  95

Phe Gln Lys Tyr Gly Tyr Ser Pro Arg Val Lys Lys Asn Ser Val His
            100                 105                 110

Glu Gln Glu Ala Ile Asn Ser Asp Pro Glu Leu Ser Asn Cys Glu Asn
        115                 120                 125

Phe Gln Lys Thr Asp Val Lys Asp Asp Leu Ser Asp Pro Pro Val Ala
    130                 135                 140

Ser Ser Cys Ile Ser Glu Lys Ser Pro Arg Ser Pro Gln Leu Ser Asp
145                 150                 155                 160

Phe Gly Leu Glu Arg Tyr Ile Val Ser Gln Val Leu Pro Asn Pro Pro
                165                 170                 175

Gln Ala Val Asn Asn Tyr Lys Glu Glu Pro Val Ile Val Thr Pro Pro
            180                 185                 190

Thr Lys Gln Ser Leu Val Lys Val Leu Lys Thr Pro Lys Cys Ala Leu
        195                 200                 205

Lys Met Asp Asp Phe Glu Cys Val Thr Pro Lys Leu Glu His Phe Gly
    210                 215                 220

Ile Ser Glu Tyr Thr Met Cys Leu Asn Glu Asp Tyr Thr Met Gly Leu
225                 230                 235                 240

Lys Asn Ala Arg Asn Asn Lys Ser Glu Glu Ala Ile Asp Thr Glu Ser
                245                 250                 255

Arg Leu Asn Asp Asn Val Phe Ala Thr Pro Ser Pro Ile Ile Gln Gln
            260                 265                 270

Leu Glu Lys Ser Asp Ala Glu Tyr Thr Asn Ser Pro Leu Val Pro Thr
        275                 280                 285

Phe Cys Thr Pro Gly Leu Lys Ile Pro Ser Thr Lys Asn Ser Ile Ala
    290                 295                 300

Leu Val Ser Thr Asn Tyr Pro Leu Ser Lys Thr Asn Ser Ser Ser Asn
305                 310                 315                 320

Asp Leu Glu Val Glu Asp Arg Thr Ser Leu Val Leu Asn Ser Asp Thr
                325                 330                 335

Cys Phe Glu Asn Leu Thr Asp Pro Ser Ser Pro Thr Ile Ser Ser Tyr
            340                 345                 350

Glu Asn Leu Leu Arg Thr Pro Thr Pro Pro Glu Val Thr Lys Ile Pro
        355                 360                 365

Glu Asp Ile Leu Gln Lys Phe Gln Trp Ile Tyr Pro Thr Gln Lys Leu
    370                 375                 380

Asn Lys Met Arg
385


<210> SEQ ID NO 42
<211> LENGTH: 39
<212> TYPE: PRT
<213> ORGANISM: Homo sapiens

<400> SEQUENCE: 42

Met Asp Pro Ile Arg Ser Phe Cys Gly Lys Leu Arg Ser Leu Ala Ser
 1               5                  10                  15

Thr Leu Asp Cys Glu Thr Ala Arg Leu Gln Arg Ala Leu Asp Gly Glu
            20                  25                  30

Glu Ser Leu Leu Ser Lys Tyr
        35


<210> SEQ ID NO 43
```

<211> LENGTH: 39
<212> TYPE: PRT
<213> ORGANISM: Homo sapiens

<400> SEQUENCE: 43

Met Asp Pro Ile Arg Ser Phe Cys Gly Lys Leu Arg Ser Leu Ala Ser
1 5 10 15

Thr Leu Asp Cys Glu Thr Ala Arg Leu Gln Arg Ala Leu Asp Gly Glu
20 25 30

Glu Ser Asp Phe Glu Asp Tyr
35

<210> SEQ ID NO 44
<211> LENGTH: 47
<212> TYPE: PRT
<213> ORGANISM: Homo sapiens

<400> SEQUENCE: 44

Val Asn Ile Leu Leu Asp Lys Ala Arg Leu Glu Asn Gln Glu Gly Ile
1 5 10 15

Asp Phe Ile Lys Ala Thr Lys Val Leu Met Glu Lys Asn Ser Met Asp
20 25 30

Ile Met Lys Ile Arg Glu Tyr Phe Gln Lys Tyr Gly Tyr Ser Pro
35 40 45

<210> SEQ ID NO 45
<211> LENGTH: 49
<212> TYPE: PRT
<213> ORGANISM: Homo sapiens

<400> SEQUENCE: 45

Ile Gly Val Leu Ile Asp Arg Ile Arg Ile His Asn Pro His Ile Leu
1 5 10 15

Gly Cys Ile Ala Gly Asp Asp Thr Ile Leu Ile Leu Ser Lys Asn Lys
20 25 30

Glu Asp Ala Leu Glu Val Asn Asn Tyr Phe Gln Gln Tyr Leu Tyr His
35 40 45

Pro

<210> SEQ ID NO 46
<211> LENGTH: 129
<212> TYPE: PRT
<213> ORGANISM: Homo sapiens

<400> SEQUENCE: 46

Leu Asp Cys Glu Thr Ala Arg Leu Gln Arg Ala Leu Asp Gly Glu Glu
1 5 10 15

Ser Asp Phe Glu Asp Tyr Pro Met Arg Ile Leu Tyr Asp Leu His Ser
20 25 30

Glu Val Gln Thr Leu Lys Asp Asp Val Asn Ile Leu Leu Asp Lys Ala
35 40 45

Arg Leu Glu Asn Gln Glu Gly Ile Asp Phe Ile Lys Ala Thr Lys Val
50 55 60

Leu Met Glu Lys Asn Ser Met Asp Ile Met Lys Ile Arg Glu Tyr Phe
65 70 75 80

Gln Lys Tyr Gly Tyr Ser Pro Arg Val Lys Lys Asn Ser Val His Glu
85 90 95

Gln Glu Ala Ile Asn Ser Asp Pro Glu Leu Ser Asn Cys Glu Asn Phe
100 105 110

```
Gln Lys Thr Asp Val Lys Asp Asp Leu Ser Asp Pro Pro Val Ala Ser
        115                 120                 125

Ser


<210> SEQ ID NO 47
<211> LENGTH: 127
<212> TYPE: PRT
<213> ORGANISM: Homo sapiens

<400> SEQUENCE: 47

Val Asp Cys Leu Ser Ser His Phe Gln Glu Leu Ser Ile Tyr Gln Asp
 1               5                  10                  15

Gln Glu Gln Arg Ile Leu Lys Phe Leu Glu Glu Leu Gly Glu Gly Lys
            20                  25                  30

Ala Thr Thr Ala His Asp Leu Ser Gly Lys Leu Gly Thr Pro Lys Lys
        35                  40                  45

Glu Ile Asn Arg Val Leu Tyr Ser Leu Ala Lys Lys Gly Lys Leu Gln
    50                  55                  60

Lys Glu Ala Gly Thr Pro Pro Leu Trp Lys Ile Ala Val Ser Thr Gln
65                  70                  75                  80

Ala Trp Asn Gln His Ser Gly Val Val Arg Pro Asp Gly His Ser Gln
                85                  90                  95

Gly Ala Pro Asn Ser Asp Pro Ser Leu Glu Pro Glu Asp Arg Asn Ser
            100                 105                 110

Thr Ser Val Ser Glu Asp Leu Leu Glu Pro Phe Ile Ala Val Ser
        115                 120                 125


<210> SEQ ID NO 48
<211> LENGTH: 14
<212> TYPE: PRT
<213> ORGANISM: Tetanus toxoid

<400> SEQUENCE: 48

Gln Tyr Ile Lys Ala Asn Ser Lys Phe Ile Gly Ile Thr Glu
 1               5                  10


<210> SEQ ID NO 49
<211> LENGTH: 21
<212> TYPE: PRT
<213> ORGANISM: Plasmodium falciparum

<400> SEQUENCE: 49

Asp Ile Glu Lys Lys Ile Ala Lys Met Glu Lys Ala Ser Ser Val Phe
 1               5                  10                  15

Asn Val Val Asn Ser
            20


<210> SEQ ID NO 50
<211> LENGTH: 16
<212> TYPE: PRT
<213> ORGANISM: Streptococcus aureus

<400> SEQUENCE: 50

Gly Ala Val Asp Ser Ile Leu Gly Gly Val Ala Thr Tyr Gly Ala Ala
 1               5                  10                  15


<210> SEQ ID NO 51
<211> LENGTH: 13
<212> TYPE: PRT
<213> ORGANISM: Artificial Sequence
```

```
<220> FEATURE:
<221> NAME/KEY: VARIANT
<222> LOCATION: 3
<223> OTHER INFORMATION: Xaa =  cyclohexylalanine, phenylalanine, or
      tyrosine
<220> FEATURE:
<221> NAME/KEY: VARIANT
<222> LOCATION: 1, 13
<223> OTHER INFORMATION: Xaa =  D-alanine or L-alanine
<220> FEATURE:
<223> OTHER INFORMATION: Pan DR-binding epitope

<400> SEQUENCE: 51

Xaa Lys Xaa Val Ala Ala Trp Thr Leu Lys Ala Ala Xaa
 1               5                  10


<210> SEQ ID NO 52
<211> LENGTH: 14
<212> TYPE: DNA
<213> ORGANISM: Artificial Sequence
<220> FEATURE:
<223> OTHER INFORMATION: Primer

<400> SEQUENCE: 52

ttttgatcaa gctt                                                      14


<210> SEQ ID NO 53
<211> LENGTH: 42
<212> TYPE: DNA
<213> ORGANISM: Artificial Sequence
<220> FEATURE:
<223> OTHER INFORMATION: Primer

<400> SEQUENCE: 53

ctaatacgac tcactatagg gctcgagcgg ccgcccgggc ag                       42


<210> SEQ ID NO 54
<211> LENGTH: 12
<212> TYPE: DNA
<213> ORGANISM: Artificial Sequence
<220> FEATURE:
<223> OTHER INFORMATION: Primer

<400> SEQUENCE: 54

gatcctgccc gg                                                        12


<210> SEQ ID NO 55
<211> LENGTH: 40
<212> TYPE: DNA
<213> ORGANISM: Artificial Sequence
<220> FEATURE:
<223> OTHER INFORMATION: Primer

<400> SEQUENCE: 55

gtaatacgac tcactatagg gcagcgtggt cgcggccgag                         40


<210> SEQ ID NO 56
<211> LENGTH: 10
<212> TYPE: DNA
<213> ORGANISM: Artificial Sequence
<220> FEATURE:
<223> OTHER INFORMATION: Primer

<400> SEQUENCE: 56

gatcctcggc                                                           10


<210> SEQ ID NO 57
```

<211> LENGTH: 22
<212> TYPE: DNA
<213> ORGANISM: Artificial Sequence
<220> FEATURE:
<223> OTHER INFORMATION: Primer

<400> SEQUENCE: 57
ctaatacgac tcactatagg gc 22

<210> SEQ ID NO 58
<211> LENGTH: 22
<212> TYPE: DNA
<213> ORGANISM: Artificial Sequence
<220> FEATURE:
<223> OTHER INFORMATION: Primer

<400> SEQUENCE: 58
tcgagcggcc gcccgggcag ga 22

<210> SEQ ID NO 59
<211> LENGTH: 20
<212> TYPE: DNA
<213> ORGANISM: Artificial Sequence
<220> FEATURE:
<223> OTHER INFORMATION: Primer

<400> SEQUENCE: 59
agcgtggtcg cggccgagga 20

<210> SEQ ID NO 60
<211> LENGTH: 25
<212> TYPE: DNA
<213> ORGANISM: Artificial Sequence
<220> FEATURE:
<223> OTHER INFORMATION: Primer

<400> SEQUENCE: 60
atatcgccgc gctcgtcgtc gacaa 25

<210> SEQ ID NO 61
<211> LENGTH: 26
<212> TYPE: DNA
<213> ORGANISM: Artificial Sequence
<220> FEATURE:
<223> OTHER INFORMATION: Primer

<400> SEQUENCE: 61
agccacacgc agctcattgt agaagg 26

<210> SEQ ID NO 62
<211> LENGTH: 24
<212> TYPE: DNA
<213> ORGANISM: Artificial Sequence
<220> FEATURE:
<223> OTHER INFORMATION: Flag Sequence - Epitope tag

<400> SEQUENCE: 62
gattacaagg atgacgacga taag 24

<210> SEQ ID NO 63
<211> LENGTH: 4
<212> TYPE: PRT
<213> ORGANISM: Homo sapiens

<400> SEQUENCE: 63

Asn Lys Ser Glu

1

<210> SEQ ID NO 64
<211> LENGTH: 4
<212> TYPE: PRT
<213> ORGANISM: Homo sapiens

<400> SEQUENCE: 64

Asn Ser Ser Ser
1

<210> SEQ ID NO 65
<211> LENGTH: 4
<212> TYPE: PRT
<213> ORGANISM: Homo sapiens

<400> SEQUENCE: 65

Asn Leu Thr Asp
1

<210> SEQ ID NO 66
<211> LENGTH: 4
<212> TYPE: PRT
<213> ORGANISM: Homo sapiens

<400> SEQUENCE: 66

Lys Lys Asn Ser
1

<210> SEQ ID NO 67
<211> LENGTH: 4
<212> TYPE: PRT
<213> ORGANISM: Homo sapiens

<400> SEQUENCE: 67

Ser Thr Leu Asp
1

<210> SEQ ID NO 68
<211> LENGTH: 4
<212> TYPE: PRT
<213> ORGANISM: Homo sapiens

<400> SEQUENCE: 68

Ser Asp Phe Glu
1

<210> SEQ ID NO 69
<211> LENGTH: 4
<212> TYPE: PRT
<213> ORGANISM: Homo sapiens

<400> SEQUENCE: 69

Thr Leu Lys Asp
1

<210> SEQ ID NO 70
<211> LENGTH: 4
<212> TYPE: PRT
<213> ORGANISM: Homo sapiens

<400> SEQUENCE: 70

Ser Val His Glu
1

-continued

<210> SEQ ID NO 71
<211> LENGTH: 4
<212> TYPE: PRT
<213> ORGANISM: Homo sapiens

<400> SEQUENCE: 71

Ser Asp Pro Glu
1

<210> SEQ ID NO 72
<211> LENGTH: 4
<212> TYPE: PRT
<213> ORGANISM: Homo sapiens

<400> SEQUENCE: 72

Ser Asn Cys Glu
1

<210> SEQ ID NO 73
<211> LENGTH: 4
<212> TYPE: PRT
<213> ORGANISM: Homo sapiens

<400> SEQUENCE: 73

Ser Asp Ala Glu
1

<210> SEQ ID NO 74
<211> LENGTH: 4
<212> TYPE: PRT
<213> ORGANISM: Homo sapiens

<400> SEQUENCE: 74

Ser Ser Asn Asp
1

<210> SEQ ID NO 75
<211> LENGTH: 4
<212> TYPE: PRT
<213> ORGANISM: Homo sapiens

<400> SEQUENCE: 75

Thr Cys Phe Glu
1

<210> SEQ ID NO 76
<211> LENGTH: 4
<212> TYPE: PRT
<213> ORGANISM: Homo sapiens

<400> SEQUENCE: 76

Ser Ser Tyr Glu
1

<210> SEQ ID NO 77
<211> LENGTH: 4
<212> TYPE: PRT
<213> ORGANISM: Homo sapiens

<400> SEQUENCE: 77

Thr Pro Pro Glu
1

<210> SEQ ID NO 78

-continued

<211> LENGTH: 4
<212> TYPE: PRT
<213> ORGANISM: Homo sapiens

<400> SEQUENCE: 78

Ser Asn Lys Glu
 1

<210> SEQ ID NO 79
<211> LENGTH: 6
<212> TYPE: PRT
<213> ORGANISM: Homo sapiens

<400> SEQUENCE: 79

Gly Leu Lys Asn Ala Arg
 1               5

<210> SEQ ID NO 80
<211> LENGTH: 412
<212> TYPE: PRT
<213> ORGANISM: Homo sapiens

<400> SEQUENCE: 80

```
Met Asp Pro Ile Arg Ser Phe Cys Gly Lys Leu Arg Ser Leu Ala Ser
 1               5                  10                  15

Thr Leu Asp Cys Glu Thr Ala Arg Leu Gln Arg Ala Leu Asp Gly Glu
            20                  25                  30

Glu Ser Asp Phe Glu Asp Tyr Pro Met Arg Ile Leu Tyr Asp Leu His
        35                  40                  45

Ser Glu Val Gln Thr Leu Lys Asp Asp Val Asn Ile Pro Glu Leu Ser
    50                  55                  60

Asn Cys Glu Asn Phe Gln Lys Thr Asp Val Lys Asp Asp Leu Ser Asp
65                  70                  75                  80

Pro Pro Val Ala Ser Ser Cys Ile Ser Gly Lys Ser Pro Arg Ser Pro
                85                  90                  95

Gln Leu Ser Asp Phe Gly Leu Glu Arg Tyr Ile Val Ser Gln Val Leu
            100                 105                 110

Pro Asn Pro Pro Gln Ala Val Asn Leu Leu Asp Lys Ala Arg Leu Glu
        115                 120                 125

Asn Gln Glu Gly Ile Asp Phe Ile Lys Ala Thr Lys Val Leu Met Glu
    130                 135                 140

Lys Asn Ser Met Asp Ile Met Lys Ile Arg Glu Tyr Phe Gln Lys Tyr
145                 150                 155                 160

Gly Tyr Ser Pro Arg Val Lys Lys Asn Ser Val His Glu Gln Glu Ala
                165                 170                 175

Ile Asn Ser Asp Asn Tyr Lys Glu Glu Pro Val Ile Val Thr Pro Pro
            180                 185                 190

Thr Lys Gln Ser Leu Val Lys Val Leu Lys Thr Pro Lys Cys Ala Leu
        195                 200                 205

Lys Met Asp Asp Phe Glu Cys Val Thr Pro Lys Leu Glu His Phe Gly
    210                 215                 220

Ile Ser Glu Tyr Thr Met Cys Leu Asn Glu Asp Tyr Thr Met Gly Leu
225                 230                 235                 240

Lys Asn Ala Arg Asn Asn Lys Ser Glu Glu Ala Ile Asp Thr Glu Ser
                245                 250                 255

Arg Leu Asn Asp Asn Val Phe Ala Thr Pro Ser Pro Ile Ile Gln Gln
            260                 265                 270
```

-continued

```
Leu Glu Lys Ser Asp Ala Glu Tyr Thr Asn Ser Pro Leu Val Pro Thr
        275                 280                 285

Phe Cys Thr Pro Gly Leu Lys Ile Pro Ser Thr Lys Asn Ser Ile Ala
    290                 295                 300

Leu Val Ser Thr Asn Tyr Pro Leu Ser Lys Thr Asn Ser Ser Ser Asn
305                 310                 315                 320

Asp Leu Glu Val Glu Asp Arg Thr Ser Leu Val Leu Asn Ser Asp Thr
                325                 330                 335

Cys Phe Glu Asn Leu Thr Asp Pro Ser Ser Pro Thr Ile Ser Ser Tyr
            340                 345                 350

Glu Asn Leu Leu Arg Thr Pro Thr Pro Pro Glu Val Thr Lys Ile Pro
        355                 360                 365

Glu Asp Ile Leu Gln Leu Leu Ser Lys Tyr Asn Ser Asn Leu Ala Thr
    370                 375                 380

Pro Ile Ala Ile Lys Ala Val Pro Pro Ser Lys Arg Phe Leu Lys His
385                 390                 395                 400

Gly Gln Asn Ile Arg Asp Val Ser Asn Lys Glu Asn
                405                 410


<210> SEQ ID NO 81
<211> LENGTH: 17
<212> TYPE: PRT
<213> ORGANISM: Homo sapiens

<400> SEQUENCE: 81

Pro Val Ala Ser Ser Cys Ile Ser Glu Lys Ser Pro Arg Ser Pro Gln
 1               5                  10                  15

Leu


<210> SEQ ID NO 82
<211> LENGTH: 19
<212> TYPE: PRT
<213> ORGANISM: Homo sapiens

<400> SEQUENCE: 82

Pro Pro Val Ala Ser Ser Cys Ile Ser Glu Lys Ser Pro Arg Ser Pro
 1               5                  10                  15

Gln Leu Ser


<210> SEQ ID NO 83
<211> LENGTH: 29
<212> TYPE: PRT
<213> ORGANISM: Homo sapiens

<400> SEQUENCE: 83

Asp Asp Leu Ser Asp Pro Pro Val Ala Ser Ser Cys Ile Ser Glu Lys
 1               5                  10                  15

Ser Pro Arg Ser Pro Gln Leu Ser Asp Phe Gly Leu Glu
            20                  25


<210> SEQ ID NO 84
<211> LENGTH: 17
<212> TYPE: PRT
<213> ORGANISM: Homo sapiens

<400> SEQUENCE: 84

Asn Lys Ser Glu Glu Ala Ile Asp Ala Glu Ser Arg Leu Asn Asp Asn
 1               5                  10                  15

Val
```

<210> SEQ ID NO 85
<211> LENGTH: 19
<212> TYPE: PRT
<213> ORGANISM: Homo sapiens

<400> SEQUENCE: 85

Asn Asn Lys Ser Glu Glu Ala Ile Asp Ala Glu Ser Arg Leu Asn Asp
1 5 10 15

Asn Val Phe

<210> SEQ ID NO 86
<211> LENGTH: 29
<212> TYPE: PRT
<213> ORGANISM: Homo sapiens

<400> SEQUENCE: 86

Leu Lys Asn Ala Arg Asn Asn Lys Ser Glu Glu Ala Ile Asp Ala Glu
1 5 10 15

Ser Arg Leu Asn Asp Asn Val Phe Ala Thr Pro Ser Pro
20 25

<210> SEQ ID NO 87
<211> LENGTH: 23
<212> TYPE: PRT
<213> ORGANISM: Homo sapiens

<400> SEQUENCE: 87

Lys Ile Pro Glu Asp Ile Leu Gln Lys Phe Gln Trp Ile Tyr Pro Thr
1 5 10 15

Gln Lys Leu Asn Lys Met Arg
20

<210> SEQ ID NO 88
<211> LENGTH: 24
<212> TYPE: PRT
<213> ORGANISM: Homo sapiens

<400> SEQUENCE: 88

Thr Lys Ile Pro Glu Asp Ile Leu Gln Lys Phe Gln Trp Ile Tyr Pro
1 5 10 15

Thr Gln Lys Leu Asn Lys Met Arg
20

<210> SEQ ID NO 89
<211> LENGTH: 29
<212> TYPE: PRT
<213> ORGANISM: Homo sapiens

<400> SEQUENCE: 89

Thr Pro Pro Glu Val Thr Lys Ile Pro Glu Asp Ile Leu Gln Lys Phe
1 5 10 15

Gln Trp Ile Tyr Pro Thr Gln Lys Leu Asn Lys Met Arg
20 25

<210> SEQ ID NO 90
<211> LENGTH: 16
<212> TYPE: PRT
<213> ORGANISM: Homo sapiens

<400> SEQUENCE: 90

Arg Ala Leu Asp Gly Glu Glu Ser Leu Leu Ser Lys Tyr Asn Ser Asn

-continued

```
 1               5                   10                  15


<210> SEQ ID NO 91
<211> LENGTH: 18
<212> TYPE: PRT
<213> ORGANISM: Homo sapiens

<400> SEQUENCE: 91

Gln Arg Ala Leu Asp Gly Glu Glu Ser Leu Leu Ser Lys Tyr Asn Ser
 1               5                   10                  15

Asn Leu


<210> SEQ ID NO 92
<211> LENGTH: 28
<212> TYPE: PRT
<213> ORGANISM: Homo sapiens

<400> SEQUENCE: 92

Glu Thr Ala Arg Leu Gln Arg Ala Leu Asp Gly Glu Glu Ser Leu Leu
 1               5                   10                  15

Ser Lys Tyr Asn Ser Asn Leu Ala Thr Pro Ile Ala
            20                  25


<210> SEQ ID NO 93
<211> LENGTH: 2736
<212> TYPE: DNA
<213> ORGANISM: Homo sapiens

<400> SEQUENCE: 93

tatcatctgt gactgaggaa atccctatct tcctatcaga ctaatgaaac cacaggacag     60

caattagact tttaagtatt ggggggttta gagctctaga tattcgatat gcagactact    120

catgtttgtt tgttttaata aagactggtc caaaggctca ttttcacaca agctacagtt    180

tttcagttcc aggaccaggt aaagatggtc agctccgtga tccataaaat ccaagggtga    240

cgactcagga ttaggaccat ttcttggtga cattgagatg gtcgagctgg tccgcaatga    300

atctatgcgg ggggaacttg gaagtggcgg ccgcctttat ggcctcgaag gcctccctcc    360

tgcgcaccgc ggcgtggccg cgctcctgct cccgggtcat gtagggcatg ctcagccagt    420

aatggttctc cgcctcgatc tccaggcggc ggatcatgtt ctgcttggcg cgcaacgaca    480

cgaaccgcgg ccgccggtgc ttcccgatcc actgacggcc gggaatgcgg ccgcgccaga    540

ggagcgcagt caggaacatg gtgcctgccg cgctgctcaa gactctgcgt ctccgcggcc    600

gccagcagac gccgtggcgt aagcgcaccc gtctcgcggg gtctccgggg gcctcggcga    660

gagacttcgg ctctcgcgag agaggactgc gcctgcgcag agccgaggac gcgtccggcg    720

ccgagattca aactagtggc gggaggctgt gagctgagcg gtggggtctg cgtacgcctg    780

gagtccttcc ccgctgtgct cagcatggac cctatccgga gcttctgcgg gaagctgcgg    840

tctctggcca gcacgctgga ctgcgagacg gcccggctgc agcgagcgct ggacggagag    900

gaaagcggat gatgttaata ttcttcttga taaagcaaga ttggaaaatc aagaaggcat    960

tgatttcata aaggcaacaa aagtactaat ggaaaaaaat tcaatggata ttatgaaaat   1020

aagagagtat ttccagaagt atggatatag tccacgtgtc aagaaaaatt cagtacacga   1080

gcaagaagcc attaactctg acccagagtt gtctaattgt gaaaattttc agaagactga   1140

tgtgaaagat gatctgtctg atcctcctgt tgcaagcagt tgtatttctg ggaagtctcc   1200

acgtagtcca caactttcag attttggact tgagcggtac atcgtatccc aagttctacc   1260
```

-continued

```
aaaccctcca caggcagtga acaactataa ggaagagccc gtaattgtaa ccccacctac   1320

caaacaatca ctagtaaaag tactaaaaac tccaaaatgt gcactaaaaa tggatgattt   1380

tgagtgtgta actcctaaat tagaacactt tggtatctct gaatatacta tgtgtttaaa   1440

tgaagattac acaatgggac ttaaaaatgc gaggaataat aaaagtgagg aggccataga   1500

tacagaatcc aggctcaatg ataatgtttt tgccactccc agccccatca tccagcagtt   1560

ggaaaaaagt gatgccgaat ataccaactc tcctttggta cctacattct gtactcctgg   1620

tttgaaaatt ccatctacaa agaacagcat agctttggta tccacaaatt acccattatc   1680

aaaaacaaat agttcatcaa atgatttgga agttgaagat cgtacttcgt tggttttaaa   1740

ttcagacaca tgctttgaga atttaacaga tccctcttca cctacgattt cttcttatga   1800

gaatctgctc agaacaccta cacctccaga agtaactaaa attccagaag atattctcca   1860

gcttttatca aaatacaact caaacctagc tactccaata gcaattaaag cagtgccacc   1920

cagtaaaagg ttccttaaac atggacagaa catccgagat gtcagcaaca aagaaaactg   1980

aaattccagt ggatctatcc aacacagaaa ctgaacaaaa tgagatgaaa gccgagctgg   2040

accgatttta acattcacat tgccctgcct ctgtccccct ttaaacgttg acccatttta   2100

aagacaaaca tgaacattaa catcataata tgctttttat gaagtttcaa taaggtttaa   2160

ccttagtctt gttgacatgt agcccagtca ttcactcttt aaggactatt agtgtttcat   2220

tgatactaaa ttacccagct taatcaacag aatggtttaa gtagtaccag gaagtaggac   2280

aagtaatttc aaaaatataa aggtgtttgc tactcagatg aggccgcccc tgaccttctg   2340

gccagagaga cattgctgcc agccagctct gccttcccat catctccttt caggaccgtc   2400

ccacaccttt tacttgctca gtgctgtctg aagatgcagt tgctgtttgc aaacaacagg   2460

aacaccagtt aaactaatta ggaaacagag ggagatttcc aggcctgggt aactatatac   2520

tgtgaccatt ggcggttgag accggtcttc aaccagtgga accccgaact ctgctgtcag   2580

ggtgtggact tcggtgctct tccaagtttt cacctggggg ggggagctaa ccccctatgt   2640

tcacgccttc tattcccatt ggcgctgaac tcttaaggtc actctggtcg cttgtgaccc   2700

cgtaaccctg atgtacccct ctaaaaggtg aggggc                             2736
```

<210> SEQ ID NO 94
<211> LENGTH: 2737
<212> TYPE: DNA
<213> ORGANISM: Homo sapiens

<400> SEQUENCE: 94

```
tatcatctgt gactgaggaa atccctatct tcctatcaga ctaatgaaac cacaggacag     60

caattagact tttaagtatt ggggggttta gagctctaga tattcgatat gcagactact    120

catgtttgtt tgttttaata aagactggtc caaaggctca ttttcacaca agctacagtt    180

tttcagttcc aggaccaggt aaagatggtc agctccgtga tccataaaat ccaagggtga    240

cgactcagga ttaggaccat ttcttggtga cattgagatg gtcgagctgg tccgcaatga    300

atctatgcgg ggggaacttg gaagtggcgg ccgcctttat ggcctcgaag gcctccctcc    360

tgcgcaccgc ggcgtggccg cgctcctgct cccgggtcat gtagggcatg ctcagccagt    420

aatggttctc cgcctcgatc tccaggcggc ggatcatgtt ctgcttggcg cgcaacgaca    480

cgaaccgcgg ccgccggtgc ttcccgatcc actgacggcc gggaatgcgg ccgcgccaga    540

ggagcgcagt caggaacatg gtgcctgccg cgctgctcaa gactctgcgt ctccgcggcc    600

gccagcagac gccgtggcgt aagcgcaccc gtctcgcggg gtctccgggg gcctcggcga    660
```

```
gagacttcgg ctctcgcgag agaggactgc gcctgcgcag agccgaggac gcgtccggcg    720
ccgagattca aactagtggc gggaggctgt gagctgagcg gtggggtctg cgtacgcctg    780
gagtccttcc ccgctgtgct cagcatggac cctatccgga gcttctgcgg gaagctgcgg    840
tctctggcca gcacgctgga ctgcgagacg gcccggctgc agcgagcgct ggacggagag    900
gaaagcggga tgatgttaat attcttcttg ataaagcaag attggaaaat caagaaggca    960
ttgatttcat aaaggcaaca aaagtactaa tggaaaaaaa ttcaatggat attatgaaaa   1020
taagagagta tttccagaag tatggatata gtccacgtgt caagaaaaat tcagtacacg   1080
agcaagaagc cattaactct gacccagagt tgtctaattg tgaaaatttt cagaagactg   1140
atgtgaaaga tgatctgtct gatcctcctg ttgcaagcag ttgtatttct gggaagtctc   1200
cacgtagtcc acaactttca gattttggac ttgagcggta catcgtatcc caagttctac   1260
caaaccctcc acaggcagtg aacaactata aggaagagcc cgtaattgta accccaccta   1320
ccaaacaatc actagtaaaa gtactaaaaa ctccaaaatg tgcactaaaa atggatgatt   1380
ttgagtgtgt aactcctaaa ttagaacact ttggtatctc tgaatatact atgtgtttaa   1440
atgaagatta cacaatggga cttaaaaatg cgaggaataa taaaagtgag gaggccatag   1500
atacagaatc caggctcaat gataatgttt ttgccactcc cagccccatc atccagcagt   1560
tggaaaaaag tgatgccgaa tataccaact ctcctttggt acctacattc tgtactcctg   1620
gtttgaaaat tccatctaca aagaacagca tagctttggt atccacaaat tacccattat   1680
caaaaacaaa tagttcatca aatgatttgg aagttgaaga tcgtacttcg ttggttttaa   1740
attcagacac atgctttgag aatttaacag atccctcttc acctacgatt tcttcttatg   1800
agaatctgct cagaacacct acacctccag aagtaactaa aattccagaa gatattctcc   1860
agcttttatc aaaatacaac tcaaacctag ctactccaat agcaattaaa gcagtgccac   1920
ccagtaaaag gttccttaaa catggacaga acatccgaga tgtcagcaac aaagaaaact   1980
gaaattccag tggatctatc caacacagaa actgaacaaa atgagatgaa agccgagctg   2040
gaccgatttt aacattcaca ttgccctgcc tctgtccccc tttaaacgtt gacccatttt   2100
aaagacaaac atgaacatta acatcataat atgcttttta tgaagtttca ataaggttta   2160
accttagtct tgttgacatg tagcccagtc attcactctt taaggactat tagtgtttca   2220
ttgatactaa attacccagc ttaatcaaca gaatggttta agtagtacca ggaagtagga   2280
caagtaattt caaaaatata aaggtgtttg ctactcagat gaggccgccc ctgaccttct   2340
ggccagagag acattgctgc cagccagctc tgccttccca tcatctcctt tcaggaccgt   2400
cccacacctt ttacttgctc agtgctgtct gaagatgcag ttgctgtttg caaacaacag   2460
gaacaccagt taaactaatt aggaaacaga gggagatttc caggcctggg taactatata   2520
ctgtgaccat tggcggttga gaccggtctt caaccagtgg aaccccgaac tctgctgtca   2580
gggtgtggac ttcggtgctc ttccaagttt tcacctgggg gggggagcta accccctatg   2640
ttcacgcctt ctattcccat tggcgctgaa ctcttaaggt cactctggtc gcttgtgacc   2700
ccgtaaccct gatgtacccc tctaaaaggt gaggggc                            2737
```

<210> SEQ ID NO 95
<211> LENGTH: 2737
<212> TYPE: DNA
<213> ORGANISM: Homo sapiens

<400> SEQUENCE: 95

-continued

```
tatcatctgt gactgaggaa atccctatct tcctatcaga ctaatgaaac cacaggacag     60
caattagact tttaagtatt ggggggttta gagctctaga tattcgatat gcagactact    120
catgtttgtt tgttttaata aagactggtc caaaggctca ttttcacaca agctacagtt    180
tttcagttcc aggaccaggt aaagatggtc agctccgtga tccataaaat ccaagggtga    240
cgactcagga ttaggaccat ttcttggtga cattgagatg gtcgagctgg tccgcaatga    300
atctatgcgg ggggaacttg gaagtggcgg ccgcctttat ggcctcgaag gcctccctcc    360
tgcgcaccgc ggcgtggccg cgctcctgct cccgggtcat gtagggcatg ctcagccagt    420
aatggttctc cgcctcgatc tccaggcggc ggatcatgtt ctgcttggcg cgcaacgaca    480
cgaaccgcgg ccgccggtgc ttcccgatcc actgacggcc gggaatgcgg ccgcgccaga    540
ggagcgcagt caggaacatg gtgcctgccg cgctgctcaa gactctgcgt ctccgcggcc    600
gccagcagac gccgtggcgt aagcgcaccc gtctcgcggg gtctccgggg gcctcggcga    660
gagacttcgg ctctcgcgag agaggactgc gcctgcgcag agccgaggac gcgtccggcg    720
ccgagattca aactagtggc gggaggctgt gagctgagcg gtggggtctg cgtacgcctg    780
gagtccttcc ccgctgtgct cagcatggac cctatccgga gcttctgcgg gaagctgcgg    840
tctctggcca gcacgctgga ctgcgagacg gcccggctgc agcgagcgct ggacggagag    900
gaaagcggga tgatgttaat attcttcttg ataaagcaag attggaaaat caagaaggca    960
ttgatttcat aaaggcaaca aaagtactaa tggaaaaaaa ttcaatggat attatgaaaa   1020
taagagagta tttccagaag tatggatata gtccacgtgt caagaaaaat tcagtacacg   1080
agcaagaagc cattaactct gacccagagt tgtctaattg tgaaaatttt cagaagactg   1140
atgtgaaaga tgatctgtct gatcctcctg ttgcaagcag ttgtatttct gggaagtctc   1200
cacgtagtcc acaactttca gattttggac ttgagcggta catcgtatcc caagttctac   1260
caaaccctcc acaggcagtg aacaactata aggaagagcc cgtaattgta accccaccta   1320
ccaaacaatc actagtaaaa gtactaaaaa ctccaaaatg tgcactaaaa atggatgatt   1380
ttgagtgtgt aactcctaaa ttagaacact ttggtatctc tgaatatact atgtgtttaa   1440
atgaagatta cacaatggga cttaaaaatg cgaggaataa taaaagtgag gaggccatag   1500
atacagaatc caggctcaat gataatgttt ttgccactcc cagccccatc atccagcagt   1560
tggaaaaaag tgatgccgaa tataccaact ctcctttggt acctacattc tgtactcctg   1620
gtttgaaaat tccatctaca aagaacagca tagctttggt atccacaaat tacccattat   1680
caaaaacaaa tagttcatca aatgatttgg aagttgaaga tcgtacttcg ttggttttaa   1740
attcagacac atgctttgag aatttaacag atccctcttc acctacgatt tcttcttatg   1800
agaatctgct cagaacacct acacctccag aagtaactaa aattccagaa gatattctcc   1860
agcttttatc aaaatacaac tcaaacctag ctactccaat agcaattaaa gcagtgccac   1920
ccagtaaaag gttccttaaa catggacaga acatccgaga tgtcagcaac aaagaaaact   1980
gaaattccag tggatctatc caacacagaa actgaacaaa atgagatgaa agccgagctg   2040
gaccgatttt aacattcaca ttgccctgcc tctgtccccc tttaaacgtt gacccatttt   2100
aaagacaaac atgaacatta acatcataat atgcttttta tgaagtttca ataaggttta   2160
accttagtct tgttgacatg tagcccagtc attcactctt taaggactat tagtgtttca   2220
ttgatactaa attacccagc ttaatcaaca gaatggttta agtagtacca ggaagtagga   2280
caagtaattt caaaaatata aaggtgtttg ctactcagat gaggccgccc ctgaccttct   2340
ggccagagag acattgctgc cagccagctc tgccttccca tcatctcctt tcaggaccgt   2400
```

cccacacctt ttacttgctc agtgctgtct gaagatgcag ttgctgtttg caaacaacag 2460
gaacaccagt taaactaatt aggaaacaga gggagatttc caggcctggg taactatata 2520
ctgtgaccat tggcggttga gaccggtctt caaccagtgg aaccccgaac tctgctgtca 2580
gggtgtggac ttcggtgctc ttccaagttt tcacctgggg gggggagcta accccctatg 2640
ttcacgcctt ctattcccat tggcgctgaa ctcttaaggt cactctggtc gcttgtgacc 2700
ccgtaaccct gatgtacccc tctaaaaggt gaggggc 2737

<210> SEQ ID NO 96
<211> LENGTH: 330
<212> TYPE: PRT
<213> ORGANISM: Homo sapiens

<400> SEQUENCE: 96

```
Met Glu Lys Asn Ser Met Asp Ile Met Lys Ile Arg Glu Tyr Phe Gln
 1               5                  10                  15

Lys Tyr Gly Tyr Ser Pro Arg Val Lys Lys Asn Ser Val His Glu Gln
            20                  25                  30

Glu Ala Ile Asn Ser Asp Pro Glu Leu Ser Asn Cys Glu Asn Phe Gln
        35                  40                  45

Lys Thr Asp Val Lys Asp Asp Leu Ser Asp Pro Pro Val Ala Ser Ser
    50                  55                  60

Cys Ile Ser Gly Lys Ser Pro Arg Ser Pro Gln Leu Ser Asp Phe Gly
65                  70                  75                  80

Leu Glu Arg Tyr Ile Val Ser Gln Val Leu Pro Asn Pro Pro Gln Ala
                85                  90                  95

Val Asn Asn Tyr Lys Glu Glu Pro Val Ile Val Thr Pro Pro Thr Lys
            100                 105                 110

Gln Ser Leu Val Lys Val Leu Lys Thr Pro Lys Cys Ala Leu Lys Met
        115                 120                 125

Asp Asp Phe Glu Cys Val Thr Pro Lys Leu Glu His Phe Gly Ile Ser
    130                 135                 140

Glu Tyr Thr Met Cys Leu Asn Glu Asp Tyr Thr Met Gly Leu Lys Asn
145                 150                 155                 160

Ala Arg Asn Asn Lys Ser Glu Glu Ala Ile Asp Thr Glu Ser Arg Leu
                165                 170                 175

Asn Asp Asn Val Phe Ala Thr Pro Ser Pro Ile Ile Gln Gln Leu Glu
            180                 185                 190

Lys Ser Asp Ala Glu Tyr Thr Asn Ser Pro Leu Val Pro Thr Phe Cys
        195                 200                 205

Thr Pro Gly Leu Lys Ile Pro Ser Thr Lys Asn Ser Ile Ala Leu Val
    210                 215                 220

Ser Thr Asn Tyr Pro Leu Ser Lys Thr Asn Ser Ser Ser Asn Asp Leu
225                 230                 235                 240

Glu Val Glu Asp Arg Thr Ser Leu Val Leu Asn Ser Asp Thr Cys Phe
                245                 250                 255

Glu Asn Leu Thr Asp Pro Ser Ser Pro Thr Ile Ser Ser Tyr Glu Asn
            260                 265                 270

Leu Leu Arg Thr Pro Thr Pro Pro Glu Val Thr Lys Ile Pro Glu Asp
        275                 280                 285

Ile Leu Gln Leu Leu Ser Lys Tyr Asn Ser Asn Leu Ala Thr Pro Ile
    290                 295                 300

Ala Ile Lys Ala Val Pro Pro Ser Lys Arg Phe Leu Lys His Gly Gln
```

-continued

```
305                 310                 315                 320

Asn Ile Arg Asp Val Ser Asn Lys Glu Asn
                325                 330
```

<210> SEQ ID NO 97
<211> LENGTH: 330
<212> TYPE: PRT
<213> ORGANISM: Homo sapiens

<400> SEQUENCE: 97

```
Met Glu Lys Asn Ser Met Asp Ile Met Lys Ile Arg Glu Tyr Phe Gln
 1               5                  10                  15

Lys Tyr Gly Tyr Ser Pro Arg Val Lys Lys Asn Ser Val His Glu Gln
            20                  25                  30

Glu Ala Ile Asn Ser Asp Pro Glu Leu Ser Asn Cys Glu Asn Phe Gln
        35                  40                  45

Lys Thr Asp Val Lys Asp Asp Leu Ser Asp Pro Pro Val Ala Ser Ser
    50                  55                  60

Cys Ile Ser Gly Lys Ser Pro Arg Ser Pro Gln Leu Ser Asp Phe Gly
65                  70                  75                  80

Leu Glu Arg Tyr Ile Val Ser Gln Val Leu Pro Asn Pro Pro Gln Ala
                85                  90                  95

Val Asn Asn Tyr Lys Glu Glu Pro Val Ile Val Thr Pro Pro Thr Lys
            100                 105                 110

Gln Ser Leu Val Lys Val Leu Lys Thr Pro Lys Cys Ala Leu Lys Met
        115                 120                 125

Asp Asp Phe Glu Cys Val Thr Pro Lys Leu Glu His Phe Gly Ile Ser
    130                 135                 140

Glu Tyr Thr Met Cys Leu Asn Glu Asp Tyr Thr Met Gly Leu Lys Asn
145                 150                 155                 160

Ala Arg Asn Asn Lys Ser Glu Glu Ala Ile Asp Thr Glu Ser Arg Leu
                165                 170                 175

Asn Asp Asn Val Phe Ala Thr Pro Ser Pro Ile Ile Gln Gln Leu Glu
            180                 185                 190

Lys Ser Asp Ala Glu Tyr Thr Asn Ser Pro Leu Val Pro Thr Phe Cys
        195                 200                 205

Thr Pro Gly Leu Lys Ile Pro Ser Thr Lys Asn Ser Ile Ala Leu Val
    210                 215                 220

Ser Thr Asn Tyr Pro Leu Ser Lys Thr Asn Ser Ser Ser Asn Asp Leu
225                 230                 235                 240

Glu Val Glu Asp Arg Thr Ser Leu Val Leu Asn Ser Asp Thr Cys Phe
                245                 250                 255

Glu Asn Leu Thr Asp Pro Ser Ser Pro Thr Ile Ser Ser Tyr Glu Asn
            260                 265                 270

Leu Leu Arg Thr Pro Thr Pro Pro Glu Val Thr Lys Ile Pro Glu Asp
        275                 280                 285

Ile Leu Gln Leu Leu Ser Lys Tyr Asn Ser Asn Leu Ala Thr Pro Ile
    290                 295                 300

Ala Ile Lys Ala Val Pro Pro Ser Lys Arg Phe Leu Lys His Gly Gln
305                 310                 315                 320

Asn Ile Arg Asp Val Ser Asn Lys Glu Asn
                325                 330
```

<210> SEQ ID NO 98
<211> LENGTH: 330

<212> TYPE: PRT
<213> ORGANISM: Homo sapiens

<400> SEQUENCE: 98

```
Met Glu Lys Asn Ser Met Asp Ile Met Lys Ile Arg Glu Tyr Phe Gln
 1               5                  10                  15

Lys Tyr Gly Tyr Ser Pro Arg Val Lys Lys Asn Ser Val His Glu Gln
            20                  25                  30

Glu Ala Ile Asn Ser Asp Pro Glu Leu Ser Asn Cys Glu Asn Phe Gln
        35                  40                  45

Lys Thr Asp Val Lys Asp Asp Leu Ser Asp Pro Pro Val Ala Ser Ser
    50                  55                  60

Cys Ile Ser Gly Lys Ser Pro Arg Ser Pro Gln Leu Ser Asp Phe Gly
65                  70                  75                  80

Leu Glu Arg Tyr Ile Val Ser Gln Val Leu Pro Asn Pro Pro Gln Ala
                85                  90                  95

Val Asn Asn Tyr Lys Glu Glu Pro Val Ile Val Thr Pro Pro Thr Lys
            100                 105                 110

Gln Ser Leu Val Lys Val Leu Lys Thr Pro Lys Cys Ala Leu Lys Met
        115                 120                 125

Asp Asp Phe Glu Cys Val Thr Pro Lys Leu Glu His Phe Gly Ile Ser
    130                 135                 140

Glu Tyr Thr Met Cys Leu Asn Glu Asp Tyr Thr Met Gly Leu Lys Asn
145                 150                 155                 160

Ala Arg Asn Asn Lys Ser Glu Glu Ala Ile Asp Thr Glu Ser Arg Leu
                165                 170                 175

Asn Asp Asn Val Phe Ala Thr Pro Ser Pro Ile Ile Gln Gln Leu Glu
            180                 185                 190

Lys Ser Asp Ala Glu Tyr Thr Asn Ser Pro Leu Val Pro Thr Phe Cys
        195                 200                 205

Thr Pro Gly Leu Lys Ile Pro Ser Thr Lys Asn Ser Ile Ala Leu Val
    210                 215                 220

Ser Thr Asn Tyr Pro Leu Ser Lys Thr Asn Ser Ser Ser Asn Asp Leu
225                 230                 235                 240

Glu Val Glu Asp Arg Thr Ser Leu Val Leu Asn Ser Asp Thr Cys Phe
                245                 250                 255

Glu Asn Leu Thr Asp Pro Ser Ser Pro Thr Ile Ser Ser Tyr Glu Asn
            260                 265                 270

Leu Leu Arg Thr Pro Thr Pro Pro Glu Val Thr Lys Ile Pro Glu Asp
        275                 280                 285

Ile Leu Gln Leu Leu Ser Lys Tyr Asn Ser Asn Leu Ala Thr Pro Ile
    290                 295                 300

Ala Ile Lys Ala Val Pro Pro Ser Lys Arg Phe Leu Lys His Gly Gln
305                 310                 315                 320

Asn Ile Arg Asp Val Ser Asn Lys Glu Asn
                325                 330
```

<210> SEQ ID NO 99
<211> LENGTH: 2679
<212> TYPE: DNA
<213> ORGANISM: Homo sapiens

<400> SEQUENCE: 99

```
tatcatctgt gactgaggaa atccctatct tcctatcaga ctaatgaaac cacaggacag      60

caattagact tttaagtatt ggggggttta gagctctaga tattcgatat gcagactact     120
```

-continued

```
catgtttgtt tgttttaata aagactggtc caaaggctca ttttcacaca agctacagtt    180
tttcagttcc aggaccaggt aaagatggtc agctccgtga tccataaaat ccaagggtga    240
cgactcagga ttaggaccat ttcttggtga cattgagatg gtcgagctgg tccgcaatga    300
atctatgcgg ggggaacttg gaagtggcgg ccgcctttat ggcctcgaag gcctccctcc    360
tgcgcaccgc ggcgtggccg cgctcctgct cccgggtcat gtagggcatg ctcagccagt    420
aatggttctc cgcctcgatc tccaggcggc ggatcatgtt ctgcttggcg cgcaacgaca    480
cgaaccgcgg ccgccggtgc ttcccgatcc actgacggcc gggaatgcgg ccgcgccaga    540
ggagcgcagt caggaacatg gtgcctgccg cgctgctcaa gactctgcgt ctccgcggcc    600
gccagcagac gccgtggcgt aagcgcaccc gtctcgcggg gtctccgggg gcctcggcga    660
gagacttcgg ctctcgcgag agaggactgc gcctgcgcag agccgaggac gcgtccggcg    720
ccgagattca aactagtggc gggaggctgt gagctgagcg gtggggtctg cgtacgcctg    780
gagtccttcc ccgctgtgct cagcatggac cctatccgga gcttctgcgg gaagctgcgg    840
tctctggcca gcacgctgga ctgcgagacg gcccggctgc agcgagcgct ggacggagag    900
gaaagcgact ttgaagatta tccaatgaga attttatatg accttcattc agaagttcag    960
actctaaagg atgatgttaa tattcttctt gataaagcaa gattggaaaa tcaagaaggc   1020
attgatttca taaaggcaac aaaagtacta atggaaaaaa attcaatgga tattatgaaa   1080
ataagagagt atttccagaa gtatggatat agtccacgtg tcaagaaaaa ttcagtacac   1140
gagcaagaag ccattaactc tgacccagag ttgtctaatt gtgaaaattt tcagaagact   1200
gatgtgaaag atgatctgtc tgatcctcct gttgcaagca gttgtatttc tgggaagtct   1260
ccacgtagtc cacaactttc agattttgga cttgagcggt acatcgtatc ccaagttcta   1320
ccaaaccctc cacaggcagt gaacaactat aaggaagagc ccgtaattgt aaccccacct   1380
accaaacaat cactagtaaa agtactaaaa actccaaaat gtgcactaaa aatggatgat   1440
tttgagtgtg taactcctaa attagaacac tttggtatct ctgaatatac tatgtgttta   1500
aatgaagatt acacaatggg acttaaaaat gcgaggaata ataaaagtga ggaggccata   1560
gatacagaat ccaggctcaa tgataatgtt tttgccactc ccagccccat catccagcag   1620
ttggaaaaaa gtgatgccga atataccaac tctcctttgg tacctacatt ctgtactcct   1680
ggtttgaaaa ttccatctac aaagaacagc atagctttgg tatccacaaa ttacccatta   1740
tcaaaaacaa atagttcatc aaatgatttg gaagttgaag atcgtacttc gttggtttta   1800
aattcagaca catgctttga gaatttaaca gatccctctt cacctacgat ttcttcttat   1860
gagaatctgc tcagaacacc tacacctcca gaagtaacta aaattccaga agatattctc   1920
cagaaattcc agtggatcta tccaacacag aaactgaaca aaatgagatg aaagccgagc   1980
tggaccgatt ttaacattca cattgccctg cctctgtccc cctttaaacg ttgacccatt   2040
ttaaagacaa acatgaacat taacatcata atatgctttt tatgaagttt caataaggtt   2100
taaccttagt cttgttgaca tgtagcccag tcattcactc tttaaggact attagtgttt   2160
cattgatact aaattaccca gcttaatcaa cagaatggtt taagtagtac caggaagtag   2220
gacaagtaat ttcaaaaata taaaggtgtt tgctactcag atgaggccgc ccctgacctt   2280
ctggccagag agacattgct gccagccagc tctgccttcc catcatctcc tttcaggacc   2340
gtcccacacc ttttacttgc tcagtgctgt ctgaagatgc agttgctgtt tgcaaacaac   2400
aggaacacca gttaaactaa ttaggaaaca gagggagatt tccaggcctg ggtaactata   2460
```

-continued

```
tactgtgacc attggcggtt gagaccggtc ttcaaccagt ggaaccccga actctgctgt   2520

cagggtgtgg acttcggtgc tcttccaagt tttcacctgg gggggggagc taacccccta   2580

tgttcacgcc ttctattccc attggcgctg aactcttaag gtcactctgg tcgcttgtga   2640

ccccgtaacc ctgatgtacc cctctaaaag gtgaggggc                          2679
```

<210> SEQ ID NO 100
<211> LENGTH: 2680
<212> TYPE: DNA
<213> ORGANISM: Homo sapiens

<400> SEQUENCE: 100

```
tatcatctgt gactgaggaa atccctatct tcctatcaga ctaatgaaac cacaggacag     60

caattagact tttaagtatt ggggggttta gagctctaga tattcgatat gcagactact    120

catgtttgtt tgttttaata aagactggtc caaaggctca ttttcacaca agctacagtt    180

tttcagttcc aggaccaggt aaagatggtc agctccgtga tccataaaat ccaagggtga    240

cgactcagga ttaggaccat ttcttggtga cattgagatg gtcgagctgg tccgcaatga    300

atctatgcgg ggggaacttg gaagtggcgg ccgcctttat ggcctcgaag gcctccctcc    360

tgcgcaccgc ggcgtggccg cgctcctgct cccgggtcat gtagggcatg ctcagccagt    420

aatggttctc cgcctcgatc tccaggcggc ggatcatgtt ctgcttggcg cgcaacgaca    480

cgaaccgcgg ccgccggtgc ttcccgatcc actgacggcc gggaatgcgg ccgcgccaga    540

ggagcgcagt caggaacatg gtgcctgccg cgctgctcaa gactctgcgt ctccgcggcc    600

gccagcagac gccgtggcgt aagcgcaccc gtctcgcggg gtctccgggg gcctcggcga    660

gagacttcgg ctctcgcgag agaggactgc gcctgcgcag agccgaggac gcgtccggcg    720

ccgagattca aactagtggc gggaggctgt gagctgagcg gtggggtctg cgtacgcctg    780

gagtccttcc ccgctgtgct cagcatggac cctatccgga gcttctgcgg gaagctgcgg    840

tctctggcca gcacgctgga ctgcgagacg gcccggctgc agcgagcgct ggacggagag    900

gaaagcgact ttgaagatta tccaatgaga attttatatg accttcattc agaagttcag    960

actctaaagg atgatgttaa tattcttctt gataaagcaa gattggaaaa tcaagaaggc   1020

attgatttca taaaggcaac aaaagtacta atggaaaaaa attcaatgga tattatgaaa   1080

ataagagagt atttccagaa gtatggatat agtccacgtg tcaagaaaaa ttcagtacac   1140

gagcaagaag ccattaactc tgacccagag ttgtctaatt gtgaaaattt tcagaagact   1200

gatgtgaaag atgatctgtc tgatcctcct gttgcaagca gttgtatttc tgggaagtct   1260

ccacgtagtc cacaactttc agattttgga cttgagcggt acatcgtatc ccaagttcta   1320

ccaaaccctc cacaggcagt gaacaactat aaggaagagc ccgtaattgt aaccccacct   1380

accaaacaat cactagtaaa agtactaaaa actccaaaat gtgcactaaa aatggatgat   1440

tttgagtgtg taactcctaa attagaacac tttggtatct ctgaatatac tatgtgttta   1500

aatgaagatt acacaatggg acttaaaaat gcgaggaata ataaaagtga ggaggccata   1560

gatacagaat ccaggctcaa tgataatgtt tttgccactc ccagccccat catccagcag   1620

ttggaaaaaa gtgatgccga atataccaac tctcctttgg tacctacatt ctgtactcct   1680

ggtttgaaaa ttccatctac aaagaacagc atagctttgg tatccacaaa ttacccatta   1740

tcaaaaacaa atagttcatc aaatgatttg gaagttgaag atcgtacttc gttggtttta   1800

aattcagaca catgctttga gaatttaaca gatccctctt cacctacgat ttcttcttat   1860

gagaatctgc tcagaacacc tacacctcca gaagtaacta aaattccaga agatattctc   1920
```

caggaaattc cagtggatct atccaacaca gaaactgaac aaaatgagat gaaagccgag 1980
ctggaccgat tttaacattc acattgccct gcctctgtcc ccctttaaac gttgacccat 2040
tttaaagaca aacatgaaca ttaacatcat aatatgcttt ttatgaagtt tcaataaggt 2100
ttaaccttag tcttgttgac atgtagccca gtcattcact ctttaaggac tattagtgtt 2160
tcattgatac taaattaccc agcttaatca acagaatggt ttaagtagta ccaggaagta 2220
ggacaagtaa tttcaaaaat ataaaggtgt ttgctactca gatgaggccg cccctgacct 2280
tctggccaga gagacattgc tgccagccag ctctgccttc ccatcatctc ctttcaggac 2340
cgtcccacac cttttacttg ctcagtgctg tctgaagatg cagttgctgt ttgcaaacaa 2400
caggaacacc agttaaacta attaggaaac agagggagat ttccaggcct gggtaactat 2460
atactgtgac cattggcggt tgagaccggt cttcaaccag tggaaccccg aactctgctg 2520
tcagggtgtg gacttcggtg ctcttccaag ttttcacctg gggggggag ctaacccct 2580 atgttcacgc cttctattcc cattggcgct gaactcttaa ggtcactctg gtcgcttgtg 2640
accccgtaac cctgatgtac ccctctaaaa ggtgaggggc 2680

<210> SEQ ID NO 101
<211> LENGTH: 2680
<212> TYPE: DNA
<213> ORGANISM: Homo sapiens

<400> SEQUENCE: 101
tatcatctgt gactgaggaa atccctatct tcctatcaga ctaatgaaac cacaggacag 60
caattagact tttaagtatt ggggggttta gagctctaga tattcgatat gcagactact 120
catgtttgtt tgttttaata aagactggtc caaaggctca ttttcacaca agctacagtt 180
tttcagttcc aggaccaggt aaagatggtc agctccgtga tccataaaat ccaagggtga 240
cgactcagga ttaggaccat ttcttggtga cattgagatg gtcgagctgg tccgcaatga 300
atctatgcgg ggggaacttg gaagtggcgg ccgcctttat ggcctcgaag gcctccctcc 360
tgcgcaccgc ggcgtggccg cgctcctgct cccgggtcat gtagggcatg ctcagccagt 420
aatggttctc cgcctcgatc tccaggcggc ggatcatgtt ctgcttggcg cgcaacgaca 480
cgaaccgcgg ccgccggtgc ttcccgatcc actgacggcc gggaatgcgg ccgcgccaga 540
ggagcgcagt caggaacatg gtgcctgccg cgctgctcaa gactctgcgt ctccgcggcc 600
gccagcagac gccgtggcgt aagcgcaccc gtctcgcggg gtctccgggg gcctcggcga 660
gagacttcgg ctctcgcgag agaggactgc gcctgcgcag agccgaggac gcgtccggcg 720
ccgagattca aactagtggc gggaggctgt gagctgagcg gtggggtctg cgtacgcctg 780
gagtccttcc ccgctgtgct cagcatggac cctatccgga gcttctgcgg gaagctgcgg 840
tctctggcca gcacgctgga ctgcgagacg gcccggctgc agcgagcgct ggacggagag 900
gaaagcgact ttgaagatta tccaatgaga attttatatg accttcattc agaagttcag 960
actctaaagg atgatgttaa tattcttctt gataaagcaa gattggaaaa tcaagaaggc 1020
attgatttca taaaggcaac aaaagtacta atggaaaaaa attcaatgga tattatgaaa 1080
ataagagagt atttccagaa gtatggatat agtccacgtg tcaagaaaaa ttcagtacac 1140
gagcaagaag ccattaactc tgacccagag ttgtctaatt gtgaaaattt tcagaagact 1200
gatgtgaaag atgatctgtc tgatcctcct gttgcaagca gttgtatttc tgggaagtct 1260
ccacgtagtc cacaactttc agattttgga cttgagcggt acatcgtatc ccaagttcta 1320

-continued

```
ccaaaccctc cacaggcagt gaacaactat aaggaagagc ccgtaattgt aaccccacct   1380

accaaacaat cactagtaaa agtactaaaa actccaaaat gtgcactaaa aatggatgat   1440

tttgagtgtg taactcctaa attagaacac tttggtatct ctgaatatac tatgtgttta   1500

aatgaagatt acacaatggg acttaaaaat gcgaggaata ataaaagtga ggaggccata   1560

gatacagaat ccaggctcaa tgataatgtt tttgccactc ccagccccat catccagcag   1620

ttggaaaaaa gtgatgccga atataccaac tctcctttgg tacctacatt ctgtactcct   1680

ggtttgaaaa ttccatctac aaagaacagc atagctttgg tatccacaaa ttacccatta   1740

tcaaaaacaa atagttcatc aaatgatttg gaagttgaag atcgtacttc gttggtttta   1800

aattcagaca catgctttga gaatttaaca gatccctctt cacctacgat ttcttcttat   1860

gagaatctgc tcagaacacc tacacctcca gaagtaacta aaattccaga agatattctc   1920

caggaaattc cagtggatct atccaacaca gaaactgaac aaaatgagat gaaagccgag   1980

ctggaccgat tttaacattc acattgccct gcctctgtcc ccctttaaac gttgacccat   2040

tttaaagaca aacatgaaca ttaacatcat aatatgcttt ttatgaagtt tcaataaggt   2100

ttaaccttag tcttgttgac atgtagccca gtcattcact ctttaaggac tattagtgtt   2160

tcattgatac taaattaccc agcttaatca acagaatggt ttaagtagta ccaggaagta   2220

ggacaagtaa tttcaaaaat ataaaggtgt ttgctactca gatgaggccg cccctgacct   2280

tctggccaga gagacattgc tgccagccag ctctgccttc ccatcatctc ctttcaggac   2340

cgtcccacac cttttacttg ctcagtgctg tctgaagatg cagttgctgt ttgcaaacaa   2400

caggaacacc agttaaacta attaggaaac agagggagat ttccaggcct gggtaactat   2460

atactgtgac cattggcggt tgagaccggt cttcaaccag tggaaccccg aactctgctg   2520

tcagggtgtg gacttcggtg ctcttccaag ttttcacctg gggggggag ctaacccct     2580

atgttcacgc cttctattcc cattggcgct gaactcttaa ggtcactctg gtcgcttgtg   2640

accccgtaac cctgatgtac ccctctaaaa ggtgaggggc                         2680
```

<210> SEQ ID NO 102
<211> LENGTH: 388
<212> TYPE: PRT
<213> ORGANISM: Homo sapiens

<400> SEQUENCE: 102

```
Met Asp Pro Ile Arg Ser Phe Cys Gly Lys Leu Arg Ser Leu Ala Ser
 1               5                  10                  15

Thr Leu Asp Cys Glu Thr Ala Arg Leu Gln Arg Ala Leu Asp Gly Glu
            20                  25                  30

Glu Ser Asp Phe Glu Asp Tyr Pro Met Arg Ile Leu Tyr Asp Leu His
        35                  40                  45

Ser Glu Val Gln Thr Leu Lys Asp Asp Val Asn Ile Leu Leu Asp Lys
    50                  55                  60

Ala Arg Leu Glu Asn Gln Glu Gly Ile Asp Phe Ile Lys Ala Thr Lys
65                  70                  75                  80

Val Leu Met Glu Lys Asn Ser Met Asp Ile Met Lys Ile Arg Glu Tyr
                85                  90                  95

Phe Gln Lys Tyr Gly Tyr Ser Pro Arg Val Lys Lys Asn Ser Val His
            100                 105                 110

Glu Gln Glu Ala Ile Asn Ser Asp Pro Glu Leu Ser Asn Cys Glu Asn
        115                 120                 125

Phe Gln Lys Thr Asp Val Lys Asp Asp Leu Ser Asp Pro Pro Val Ala
```

```
    130                 135                 140

Ser Ser Cys Ile Ser Gly Lys Ser Pro Arg Ser Pro Gln Leu Ser Asp
145                 150                 155                 160

Phe Gly Leu Glu Arg Tyr Ile Val Ser Gln Val Leu Pro Asn Pro Pro
                165                 170                 175

Gln Ala Val Asn Asn Tyr Lys Glu Glu Pro Val Ile Val Thr Pro Pro
            180                 185                 190

Thr Lys Gln Ser Leu Val Lys Val Leu Lys Thr Pro Lys Cys Ala Leu
        195                 200                 205

Lys Met Asp Asp Phe Glu Cys Val Thr Pro Lys Leu Glu His Phe Gly
    210                 215                 220

Ile Ser Glu Tyr Thr Met Cys Leu Asn Glu Asp Tyr Thr Met Gly Leu
225                 230                 235                 240

Lys Asn Ala Arg Asn Asn Lys Ser Glu Glu Ala Ile Asp Thr Glu Ser
                245                 250                 255

Arg Leu Asn Asp Asn Val Phe Ala Thr Pro Ser Pro Ile Ile Gln Gln
            260                 265                 270

Leu Glu Lys Ser Asp Ala Glu Tyr Thr Asn Ser Pro Leu Val Pro Thr
        275                 280                 285

Phe Cys Thr Pro Gly Leu Lys Ile Pro Ser Thr Lys Asn Ser Ile Ala
    290                 295                 300

Leu Val Ser Thr Asn Tyr Pro Leu Ser Lys Thr Asn Ser Ser Ser Asn
305                 310                 315                 320

Asp Leu Glu Val Glu Asp Arg Thr Ser Leu Val Leu Asn Ser Asp Thr
                325                 330                 335

Cys Phe Glu Asn Leu Thr Asp Pro Ser Ser Pro Thr Ile Ser Ser Tyr
            340                 345                 350

Glu Asn Leu Leu Arg Thr Pro Thr Pro Pro Glu Val Thr Lys Ile Pro
        355                 360                 365

Glu Asp Ile Leu Gln Lys Phe Gln Trp Ile Tyr Pro Thr Gln Lys Leu
    370                 375                 380

Asn Lys Met Arg
385
```

<210> SEQ ID NO 103
<211> LENGTH: 373
<212> TYPE: PRT
<213> ORGANISM: Homo sapiens

<400> SEQUENCE: 103

```
Met Asp Pro Ile Arg Ser Phe Cys Gly Lys Leu Arg Ser Leu Ala Ser
 1               5                  10                  15

Thr Leu Asp Cys Glu Thr Ala Arg Leu Gln Arg Ala Leu Asp Gly Glu
            20                  25                  30

Glu Ser Asp Phe Glu Asp Tyr Pro Met Arg Ile Leu Tyr Asp Leu His
        35                  40                  45

Ser Glu Val Gln Thr Leu Lys Asp Asp Val Asn Ile Leu Leu Asp Lys
    50                  55                  60

Ala Arg Leu Glu Asn Gln Glu Gly Ile Asp Phe Ile Lys Ala Thr Lys
65                  70                  75                  80

Val Leu Met Glu Lys Asn Ser Met Asp Ile Met Lys Ile Arg Glu Tyr
                85                  90                  95

Phe Gln Lys Tyr Gly Tyr Ser Pro Arg Val Lys Lys Asn Ser Val His
            100                 105                 110
```

-continued

```
Glu Gln Glu Ala Ile Asn Ser Asp Pro Glu Leu Ser Asn Cys Glu Asn
        115                 120                 125

Phe Gln Lys Thr Asp Val Lys Asp Asp Leu Ser Asp Pro Pro Val Ala
    130                 135                 140

Ser Ser Cys Ile Ser Gly Lys Ser Pro Arg Ser Pro Gln Leu Ser Asp
145                 150                 155                 160

Phe Gly Leu Glu Arg Tyr Ile Val Ser Gln Val Leu Pro Asn Pro Pro
                165                 170                 175

Gln Ala Val Asn Asn Tyr Lys Glu Glu Pro Val Ile Val Thr Pro Pro
            180                 185                 190

Thr Lys Gln Ser Leu Val Lys Val Leu Lys Thr Pro Lys Cys Ala Leu
        195                 200                 205

Lys Met Asp Asp Phe Glu Cys Val Thr Pro Lys Leu Glu His Phe Gly
    210                 215                 220

Ile Ser Glu Tyr Thr Met Cys Leu Asn Glu Asp Tyr Thr Met Gly Leu
225                 230                 235                 240

Lys Asn Ala Arg Asn Asn Lys Ser Glu Glu Ala Ile Asp Thr Glu Ser
                245                 250                 255

Arg Leu Asn Asp Asn Val Phe Ala Thr Pro Ser Pro Ile Ile Gln Gln
            260                 265                 270

Leu Glu Lys Ser Asp Ala Glu Tyr Thr Asn Ser Pro Leu Val Pro Thr
        275                 280                 285

Phe Cys Thr Pro Gly Leu Lys Ile Pro Ser Thr Lys Asn Ser Ile Ala
    290                 295                 300

Leu Val Ser Thr Asn Tyr Pro Leu Ser Lys Thr Asn Ser Ser Ser Asn
305                 310                 315                 320

Asp Leu Glu Val Glu Asp Arg Thr Ser Leu Val Leu Asn Ser Asp Thr
                325                 330                 335

Cys Phe Glu Asn Leu Thr Asp Pro Ser Ser Pro Thr Ile Ser Ser Tyr
            340                 345                 350

Glu Asn Leu Leu Arg Thr Pro Thr Pro Pro Glu Val Thr Lys Ile Pro
        355                 360                 365

Glu Asp Ile Leu Gln
    370


<210> SEQ ID NO 104
<211> LENGTH: 373
<212> TYPE: PRT
<213> ORGANISM: Homo sapiens

<400> SEQUENCE: 104

Met Asp Pro Ile Arg Ser Phe Cys Gly Lys Leu Arg Ser Leu Ala Ser
 1               5                  10                  15

Thr Leu Asp Cys Glu Thr Ala Arg Leu Gln Arg Ala Leu Asp Gly Glu
            20                  25                  30

Glu Ser Asp Phe Glu Asp Tyr Pro Met Arg Ile Leu Tyr Asp Leu His
        35                  40                  45

Ser Glu Val Gln Thr Leu Lys Asp Asp Val Asn Ile Leu Leu Asp Lys
    50                  55                  60

Ala Arg Leu Glu Asn Gln Glu Gly Ile Asp Phe Ile Lys Ala Thr Lys
65                  70                  75                  80

Val Leu Met Glu Lys Asn Ser Met Asp Ile Met Lys Ile Arg Glu Tyr
                85                  90                  95

Phe Gln Lys Tyr Gly Tyr Ser Pro Arg Val Lys Lys Asn Ser Val His
            100                 105                 110
```

```
Glu Gln Glu Ala Ile Asn Ser Asp Pro Glu Leu Ser Asn Cys Glu Asn
        115                 120                 125

Phe Gln Lys Thr Asp Val Lys Asp Asp Leu Ser Asp Pro Pro Val Ala
    130                 135                 140

Ser Ser Cys Ile Ser Gly Lys Ser Pro Arg Ser Pro Gln Leu Ser Asp
145                 150                 155                 160

Phe Gly Leu Glu Arg Tyr Ile Val Ser Gln Val Leu Pro Asn Pro Pro
                165                 170                 175

Gln Ala Val Asn Asn Tyr Lys Glu Glu Pro Val Ile Val Thr Pro Pro
            180                 185                 190

Thr Lys Gln Ser Leu Val Lys Val Leu Lys Thr Pro Lys Cys Ala Leu
        195                 200                 205

Lys Met Asp Asp Phe Glu Cys Val Thr Pro Lys Leu Glu His Phe Gly
    210                 215                 220

Ile Ser Glu Tyr Thr Met Cys Leu Asn Glu Asp Tyr Thr Met Gly Leu
225                 230                 235                 240

Lys Asn Ala Arg Asn Asn Lys Ser Glu Glu Ala Ile Asp Thr Glu Ser
                245                 250                 255

Arg Leu Asn Asp Asn Val Phe Ala Thr Pro Ser Pro Ile Ile Gln Gln
            260                 265                 270

Leu Glu Lys Ser Asp Ala Glu Tyr Thr Asn Ser Pro Leu Val Pro Thr
        275                 280                 285

Phe Cys Thr Pro Gly Leu Lys Ile Pro Ser Thr Lys Asn Ser Ile Ala
    290                 295                 300

Leu Val Ser Thr Asn Tyr Pro Leu Ser Lys Thr Asn Ser Ser Ser Asn
305                 310                 315                 320

Asp Leu Glu Val Glu Asp Arg Thr Ser Leu Val Leu Asn Ser Asp Thr
                325                 330                 335

Cys Phe Glu Asn Leu Thr Asp Pro Ser Ser Pro Thr Ile Ser Ser Tyr
            340                 345                 350

Glu Asn Leu Leu Arg Thr Pro Thr Pro Pro Glu Val Thr Lys Ile Pro
        355                 360                 365

Glu Asp Ile Leu Gln
    370


<210> SEQ ID NO 105
<211> LENGTH: 2617
<212> TYPE: DNA
<213> ORGANISM: Homo sapiens

<400> SEQUENCE: 105

tatcatctgt gactgaggaa atccctatct tcctatcaga ctaatgaaac cacaggacag      60

caattagact tttaagtatt ggggggttta gagctctaga tattcgatat gcagactact     120

catgtttgtt tgttttaata aagactggtc caaaggctca ttttcacaca agctacagtt     180

tttcagttcc aggaccaggt aaagatggtc agctccgtga tccataaaat ccaagggtga     240

cgactcagga ttaggaccat ttcttggtga cattgagatg gtcgagctgg tccgcaatga     300

atctatgcgg ggggaacttg gaagtggcgg ccgcctttat ggcctcgaag gcctccctcc     360

tgcgcaccgc ggcgtggccg cgctcctgct cccgggtcat gtagggcatg ctcagccagt     420

aatggttctc cgcctcgatc tccaggcggc ggatcatgtt ctgcttggcg cgcaacgaca     480

cgaaccgcgg ccgccggtgc ttcccgatcc actgacggcc gggaatgcgg ccgcgccaga     540

ggagcgcagt caggaacatg gtgcctgccg cgctgctcaa gactctgcgt ctccgcggcc     600
```

```
gccagcagac gccgtggcgt aagcgcaccc gtctcgcggg gtctccgggg gcctcggcga    660
gagacttcgg ctctcgcgag agaggactgc gcctgcgcag agccgaggac gcgtccggcg    720
ccgagattca aactagtggc gggaggctgt gagctgagcg gtggggtctg cgtacgcctg    780
gagtccttcc ccgctgtgct cagcatggac cctatccgga gcttctgcgg gaagctgcgg    840
tctctggcca gcacgctgga ctgcgagacg gcccggctgc agcgagcgct ggacggagag    900
gaaagcggat gatgttaata ttcttcttga taaagcaaga ttggaaaatc aagaaggcat    960
tgatttcata aaggcaacaa aagtactaat ggaaaaaaat tcaatggata ttatgaaaat   1020
aagagagtat ttccagaagt atggatatag tccacgtgtc aagaaaaatt cagtacacga   1080
gcaagaagcc attaactctg acccagagtt gtctaattgt gaaaattttc agaagactga   1140
tgtgaaagat gatctgtctg atcctcctgt tgcaagcagt tgtatttctg ggaagtctcc   1200
acgtagtcca caactttcag attttggact tgagcggtac atcgtatccc aagttctacc   1260
aaaccctcca caggcagtga acaactataa ggaagagccc gtaattgtaa ccccacctac   1320
caaacaatca ctagtaaaag tactaaaaac tccaaaatgt gcactaaaaa tggatgattt   1380
tgagtgtgta actcctaaat tagaacactt tggtatctct gaatatacta tgtgtttaaa   1440
tgaagattac acaatgggac ttaaaaatgc gaggaataat aaaagtgagg aggccataga   1500
tacagaatcc aggctcaatg ataatgtttt tgccactccc agccccatca tccagcagtt   1560
ggaaaaaagt gatgccgaat ataccaactc tcctttggta cctacattct gtactcctgg   1620
tttgaaaatt ccatctacaa agaacagcat agctttggta tccacaaatt acccattatc   1680
aaaaacaaat agttcatcaa atgatttgga agttgaagat cgtacttcgt tggttttaaa   1740
ttcagacaca tgctttgaga atttaacaga tccctcttca cctacgattt cttcttatga   1800
gaatctgctc agaacaccta cacctccaga agtaactaaa attccagaag atattctcca   1860
gaaattccag tggatctatc caacacagaa actgaacaaa atgagatgaa agccgagctg   1920
gaccgatttt aacattcaca ttgccctgcc tctgtccccc tttaaacgtt gacccatttt   1980
aaagacaaac atgaacatta acatcataat atgcttttta tgaagtttca ataaggttta   2040
accttagtct tgttgacatg tagcccagtc attcactctt taaggactat tagtgtttca   2100
ttgatactaa attacccagc ttaatcaaca gaatggttta agtagtacca ggaagtagga   2160
caagtaattt caaaaatata aaggtgtttg ctactcagat gaggccgccc ctgaccttct   2220
ggccagagag acattgctgc cagccagctc tgccttccca tcatctcctt tcaggaccgt   2280
cccacacctt ttacttgctc agtgctgtct gaagatgcag ttgctgtttg caaacaacag   2340
gaacaccagt taaactaatt aggaaacaga gggagatttc caggcctggg taactatata   2400
ctgtgaccat tggcggttga gaccggtctt caaccagtgg aaccccgaac tctgctgtca   2460
gggtgtggac ttcggtgctc ttccaagttt tcacctgggg gggggagcta acccccctatg  2520
ttcacgcctt ctattcccat tggcgctgaa ctcttaaggt cactctggtc gcttgtgacc   2580
ccgtaaccct gatgtacccc tctaaaaggt gaggggc                            2617
```

<210> SEQ ID NO 106
<211> LENGTH: 2619
<212> TYPE: DNA
<213> ORGANISM: Homo sapiens

<400> SEQUENCE: 106

```
tatcatctgt gactgaggaa atccctatct tcctatcaga ctaatgaaac cacaggacag     60
```

-continued

```
caattagact tttaagtatt ggggggttta gagctctaga tattcgatat gcagactact    120
catgtttgtt tgttttaata aagactggtc caaaggctca ttttcacaca agctacagtt    180
tttcagttcc aggaccaggt aaagatggtc agctccgtga tccataaaat ccaagggtga    240
cgactcagga ttaggaccat ttcttggtga cattgagatg gtcgagctgg tccgcaatga    300
atctatgcgg ggggaacttg gaagtggcgg ccgcctttat ggcctcgaag gcctccctcc    360
tgcgcaccgc ggcgtggccg cgctcctgct cccgggtcat gtagggcatg ctcagccagt    420
aatggttctc cgcctcgatc tccaggcggc ggatcatgtt ctgcttggcg cgcaacgaca    480
cgaaccgcgg ccgccggtgc ttcccgatcc actgacggcc gggaatgcgg ccgcgccaga    540
ggagcgcagt caggaacatg gtgcctgccg cgctgctcaa gactctgcgt ctccgcggcc    600
gccagcagac gccgtggcgt aagcgcaccc gtctcgcggg gtctccgggg gcctcggcga    660
gagacttcgg ctctcgcgag agaggactgc gcctgcgcag agccgaggac gcgtccggcg    720
ccgagattca aactagtggc gggaggctgt gagctgagcg gtggggtctg cgtacgcctg    780
gagtccttcc ccgctgtgct cagcatggac cctatccgga gcttctgcgg gaagctgcgg    840
tctctggcca gcacgctgga ctgcgagacg gcccggctgc agcgagcgct ggacggagag    900
gaaagcggga tgatgttaat attcttcttg ataaagcaag attggaaaat caagaaggca    960
ttgatttcat aaaggcaaca aaagtactaa tggaaaaaaa ttcaatggat attatgaaaa   1020
taagagagta tttccagaag tatggatata gtccacgtgt caagaaaaat tcagtacacg   1080
agcaagaagc cattaactct gacccagagt tgtctaattg tgaaaatttt cagaagactg   1140
atgtgaaaga tgatctgtct gatcctcctg ttgcaagcag ttgtatttct gggaagtctc   1200
cacgtagtcc acaactttca gattttggac ttgagcggta catcgtatcc caagttctac   1260
caaaccctcc acaggcagtg aacaactata aggaagagcc cgtaattgta accccaccta   1320
ccaaacaatc actagtaaaa gtactaaaaa ctccaaaatg tgcactaaaa atggatgatt   1380
ttgagtgtgt aactcctaaa ttagaacact ttggtatctc tgaatatact atgtgtttaa   1440
atgaagatta cacaatggga cttaaaaatg cgaggaataa taaaagtgag gaggccatag   1500
atacagaatc caggctcaat gataatgttt ttgccactcc cagccccatc atccagcagt   1560
tggaaaaaag tgatgccgaa tataccaact ctcctttggt acctacattc tgtactcctg   1620
gtttgaaaat tccatctaca aagaacagca tagctttggt atccacaaat tacccattat   1680
caaaaacaaa tagttcatca aatgatttgg aagttgaaga tcgtacttcg ttggttttaa   1740
attcagacac atgctttgag aatttaacag atccctcttc acctacgatt tcttcttatg   1800
agaatctgct cagaacacct acacctccag aagtaactaa aattccagaa gatattctcc   1860
aggaaattcc agtggatcta tccaacacag aaactgaaca aaatgagatg aaagccgagc   1920
tggaccgatt ttaacattca cattgccctg cctctgtccc cctttaaacg ttgacccatt   1980
ttaaagacaa acatgaacat taacatcata atatgctttt tatgaagttt caataaggtt   2040
taaccttagt cttgttgaca tgtagcccag tcattcactc tttaaggact attagtgttt   2100
cattgatact aaattaccca gcttaatcaa cagaatggtt taagtagtac caggaagtag   2160
gacaagtaat ttcaaaaata taaaggtgtt tgctactcag atgaggccgc ccctgacctt   2220
ctggccagag agacattgct gccagccagc tctgccttcc catcatctcc tttcaggacc   2280
gtcccacacc ttttacttgc tcagtgctgt ctgaagatgc agttgctgtt tgcaaacaac   2340
aggaacacca gttaaactaa ttaggaaaca gagggagatt tccaggcctg ggtaactata   2400
tactgtgacc attggcggtt gagaccggtc ttcaaccagt ggaaccccga actctgctgt   2460
```

```
cagggtgtgg acttcggtgc tcttccaagt tttcacctgg ggggggggagc taacccccta   2520

tgttcacgcc ttctattccc attggcgctg aactcttaag gtcactctgg tcgcttgtga   2580

ccccgtaacc ctgatgtacc cctctaaaag gtgaggggc                          2619
```

```
<210> SEQ ID NO 107
<211> LENGTH: 2619
<212> TYPE: DNA
<213> ORGANISM: Homo sapiens

<400> SEQUENCE: 107

tatcatctgt gactgaggaa atccctatct tcctatcaga ctaatgaaac cacaggacag     60

caattagact tttaagtatt ggggggttta gagctctaga tattcgatat gcagactact    120

catgtttgtt tgttttaata aagactggtc caaaggctca ttttcacaca agctacagtt    180

tttcagttcc aggaccaggt aaagatggtc agctccgtga tccataaaat ccaagggtga    240

cgactcagga ttaggaccat ttcttggtga cattgagatg gtcgagctgg tccgcaatga    300

atctatgcgg ggggaacttg gaagtggcgg ccgcctttat ggcctcgaag gcctccctcc    360

tgcgcaccgc ggcgtggccg cgctcctgct cccgggtcat gtagggcatg ctcagccagt    420

aatggttctc cgcctcgatc tccaggcggc ggatcatgtt ctgcttggcg cgcaacgaca    480

cgaaccgcgg ccgccggtgc ttcccgatcc actgacggcc gggaatgcgg ccgcgccaga    540

ggagcgcagt caggaacatg gtgcctgccg cgctgctcaa gactctgcgt ctccgcggcc    600

gccagcagac gccgtggcgt aagcgcaccc gtctcgcggg gtctccgggg gcctcggcga    660

gagacttcgg ctctcgcgag agaggactgc gcctgcgcag agccgaggac gcgtccggcg    720

ccgagattca aactagtggc gggaggctgt gagctgagcg gtggggtctg cgtacgcctg    780

gagtccttcc ccgctgtgct cagcatggac cctatccgga gcttctgcgg gaagctgcgg    840

tctctggcca gcacgctgga ctgcgagacg gcccggctgc agcgagcgct ggacggagag    900

gaaagcggga tgatgttaat attcttcttg ataaagcaag attggaaaat caagaaggca    960

ttgatttcat aaaggcaaca aaagtactaa tggaaaaaaa ttcaatggat attatgaaaa   1020

taagagagta tttccagaag tatggatata gtccacgtgt caagaaaaat tcagtacacg   1080

agcaagaagc cattaactct gacccagagt tgtctaattg tgaaaatttt cagaagactg   1140

atgtgaaaga tgatctgtct gatcctcctg ttgcaagcag ttgtatttct gggaagtctc   1200

cacgtagtcc acaactttca gattttggac ttgagcggta catcgtatcc caagttctac   1260

caaaccctcc acaggcagtg aacaactata aggaagagcc cgtaattgta accccaccta   1320

ccaaacaatc actagtaaaa gtactaaaaa ctccaaaatg tgcactaaaa atggatgatt   1380

ttgagtgtgt aactcctaaa ttagaacact ttggtatctc tgaatatact atgtgtttaa   1440

atgaagatta cacaatggga cttaaaaatg cgaggaataa taaaagtgag gaggccatag   1500

atacagaatc caggctcaat gataatgttt ttgccactcc cagccccatc atccagcagt   1560

tggaaaaaag tgatgccgaa tataccaact ctcctttggt acctacattc tgtactcctg   1620

gtttgaaaat tccatctaca aagaacagca tagctttggt atccacaaat tacccattat   1680

caaaaacaaa tagttcatca aatgatttgg aagttgaaga tcgtacttcg ttggttttaa   1740

attcagacac atgctttgag aatttaacag atccctcttc acctacgatt tcttcttatg   1800

agaatctgct cagaacacct acacctccag aagtaactaa aattccagaa gatattctcc   1860

aggaaattcc agtggatcta tccaacacag aaactgaaca aaatgagatg aaagccgagc   1920
```

-continued

```
tggaccgatt ttaacattca cattgccctg cctctgtccc cctttaaacg ttgacccatt   1980

ttaaagacaa acatgaacat taacatcata atatgctttt tatgaagttt caataaggtt   2040

taaccttagt cttgttgaca tgtagcccag tcattcactc tttaaggact attagtgttt   2100

cattgatact aaattaccca gcttaatcaa cagaatggtt taagtagtac caggaagtag   2160

gacaagtaat ttcaaaaata taaaggtgtt tgctactcag atgaggccgc ccctgacctt   2220

ctggccagag agacattgct gccagccagc tctgccttcc catcatctcc tttcaggacc   2280

gtcccacacc ttttacttgc tcagtgctgt ctgaagatgc agttgctgtt tgcaaacaac   2340

aggaacacca gttaaactaa ttaggaaaca gagggagatt tccaggcctg ggtaactata   2400

tactgtgacc attggcggtt gagaccggtc ttcaaccagt ggaaccccga actctgctgt   2460

cagggtgtgg acttcggtgc tcttccaagt tttcacctgg ggggggagc taacccccta   2520

tgttcacgcc ttctattccc attggcgctg aactcttaag gtcactctgg tcgcttgtga   2580

ccccgtaacc ctgatgtacc cctctaaaag gtgaggggc                          2619
```

<210> SEQ ID NO 108
<211> LENGTH: 306
<212> TYPE: PRT
<213> ORGANISM: Homo sapiens

<400> SEQUENCE: 108

```
Met Glu Lys Asn Ser Met Asp Ile Met Lys Ile Arg Glu Tyr Phe Gln
 1               5                  10                  15

Lys Tyr Gly Tyr Ser Pro Arg Val Lys Lys Asn Ser Val His Glu Gln
            20                  25                  30

Glu Ala Ile Asn Ser Asp Pro Glu Leu Ser Asn Cys Glu Asn Phe Gln
        35                  40                  45

Lys Thr Asp Val Lys Asp Asp Leu Ser Asp Pro Pro Val Ala Ser Ser
    50                  55                  60

Cys Ile Ser Gly Lys Ser Pro Arg Ser Pro Gln Leu Ser Asp Phe Gly
65                  70                  75                  80

Leu Glu Arg Tyr Ile Val Ser Gln Val Leu Pro Asn Pro Pro Gln Ala
                85                  90                  95

Val Asn Asn Tyr Lys Glu Glu Pro Val Ile Val Thr Pro Pro Thr Lys
            100                 105                 110

Gln Ser Leu Val Lys Val Leu Lys Thr Pro Lys Cys Ala Leu Lys Met
        115                 120                 125

Asp Asp Phe Glu Cys Val Thr Pro Lys Leu Glu His Phe Gly Ile Ser
    130                 135                 140

Glu Tyr Thr Met Cys Leu Asn Glu Asp Tyr Thr Met Gly Leu Lys Asn
145                 150                 155                 160

Ala Arg Asn Asn Lys Ser Glu Glu Ala Ile Asp Thr Glu Ser Arg Leu
                165                 170                 175

Asn Asp Asn Val Phe Ala Thr Pro Ser Pro Ile Ile Gln Gln Leu Glu
            180                 185                 190

Lys Ser Asp Ala Glu Tyr Thr Asn Ser Pro Leu Val Pro Thr Phe Cys
        195                 200                 205

Thr Pro Gly Leu Lys Ile Pro Ser Thr Lys Asn Ser Ile Ala Leu Val
    210                 215                 220

Ser Thr Asn Tyr Pro Leu Ser Lys Thr Asn Ser Ser Ser Asn Asp Leu
225                 230                 235                 240

Glu Val Glu Asp Arg Thr Ser Leu Val Leu Asn Ser Asp Thr Cys Phe
                245                 250                 255
```

```
Glu Asn Leu Thr Asp Pro Ser Ser Pro Thr Ile Ser Ser Tyr Glu Asn
            260                 265                 270

Leu Leu Arg Thr Pro Thr Pro Pro Glu Val Thr Lys Ile Pro Glu Asp
        275                 280                 285

Ile Leu Gln Lys Phe Gln Trp Ile Tyr Pro Thr Gln Lys Leu Asn Lys
    290                 295                 300

Met Arg
305


<210> SEQ ID NO 109
<211> LENGTH: 291
<212> TYPE: PRT
<213> ORGANISM: Homo sapiens

<400> SEQUENCE: 109

Met Glu Lys Asn Ser Met Asp Ile Met Lys Ile Arg Glu Tyr Phe Gln
 1               5                  10                  15

Lys Tyr Gly Tyr Ser Pro Arg Val Lys Lys Asn Ser Val His Glu Gln
            20                  25                  30

Glu Ala Ile Asn Ser Asp Pro Glu Leu Ser Asn Cys Glu Asn Phe Gln
        35                  40                  45

Lys Thr Asp Val Lys Asp Asp Leu Ser Asp Pro Pro Val Ala Ser Ser
    50                  55                  60

Cys Ile Ser Gly Lys Ser Pro Arg Ser Pro Gln Leu Ser Asp Phe Gly
65                  70                  75                  80

Leu Glu Arg Tyr Ile Val Ser Gln Val Leu Pro Asn Pro Pro Gln Ala
                85                  90                  95

Val Asn Asn Tyr Lys Glu Glu Pro Val Ile Val Thr Pro Pro Thr Lys
            100                 105                 110

Gln Ser Leu Val Lys Val Leu Lys Thr Pro Lys Cys Ala Leu Lys Met
        115                 120                 125

Asp Asp Phe Glu Cys Val Thr Pro Lys Leu Glu His Phe Gly Ile Ser
    130                 135                 140

Glu Tyr Thr Met Cys Leu Asn Glu Asp Tyr Thr Met Gly Leu Lys Asn
145                 150                 155                 160

Ala Arg Asn Asn Lys Ser Glu Glu Ala Ile Asp Thr Glu Ser Arg Leu
                165                 170                 175

Asn Asp Asn Val Phe Ala Thr Pro Ser Pro Ile Ile Gln Gln Leu Glu
            180                 185                 190

Lys Ser Asp Ala Glu Tyr Thr Asn Ser Pro Leu Val Pro Thr Phe Cys
        195                 200                 205

Thr Pro Gly Leu Lys Ile Pro Ser Thr Lys Asn Ser Ile Ala Leu Val
    210                 215                 220

Ser Thr Asn Tyr Pro Leu Ser Lys Thr Asn Ser Ser Ser Asn Asp Leu
225                 230                 235                 240

Glu Val Glu Asp Arg Thr Ser Leu Val Leu Asn Ser Asp Thr Cys Phe
                245                 250                 255

Glu Asn Leu Thr Asp Pro Ser Ser Pro Thr Ile Ser Ser Tyr Glu Asn
            260                 265                 270

Leu Leu Arg Thr Pro Thr Pro Pro Glu Val Thr Lys Ile Pro Glu Asp
        275                 280                 285

Ile Leu Gln
    290
```

```
<210> SEQ ID NO 110
<211> LENGTH: 291
<212> TYPE: PRT
<213> ORGANISM: Homo sapiens

<400> SEQUENCE: 110

Met Glu Lys Asn Ser Met Asp Ile Met Lys Ile Arg Glu Tyr Phe Gln
 1               5                  10                  15

Lys Tyr Gly Tyr Ser Pro Arg Val Lys Lys Asn Ser Val His Glu Gln
            20                  25                  30

Glu Ala Ile Asn Ser Asp Pro Glu Leu Ser Asn Cys Glu Asn Phe Gln
        35                  40                  45

Lys Thr Asp Val Lys Asp Asp Leu Ser Asp Pro Pro Val Ala Ser Ser
    50                  55                  60

Cys Ile Ser Gly Lys Ser Pro Arg Ser Pro Gln Leu Ser Asp Phe Gly
65                  70                  75                  80

Leu Glu Arg Tyr Ile Val Ser Gln Val Leu Pro Asn Pro Pro Gln Ala
                85                  90                  95

Val Asn Asn Tyr Lys Glu Glu Pro Val Ile Val Thr Pro Pro Thr Lys
            100                 105                 110

Gln Ser Leu Val Lys Val Leu Lys Thr Pro Lys Cys Ala Leu Lys Met
        115                 120                 125

Asp Asp Phe Glu Cys Val Thr Pro Lys Leu Glu His Phe Gly Ile Ser
    130                 135                 140

Glu Tyr Thr Met Cys Leu Asn Glu Asp Tyr Thr Met Gly Leu Lys Asn
145                 150                 155                 160

Ala Arg Asn Asn Lys Ser Glu Glu Ala Ile Asp Thr Glu Ser Arg Leu
                165                 170                 175

Asn Asp Asn Val Phe Ala Thr Pro Ser Pro Ile Ile Gln Gln Leu Glu
            180                 185                 190

Lys Ser Asp Ala Glu Tyr Thr Asn Ser Pro Leu Val Pro Thr Phe Cys
        195                 200                 205

Thr Pro Gly Leu Lys Ile Pro Ser Thr Lys Asn Ser Ile Ala Leu Val
    210                 215                 220

Ser Thr Asn Tyr Pro Leu Ser Lys Thr Asn Ser Ser Ser Asn Asp Leu
225                 230                 235                 240

Glu Val Glu Asp Arg Thr Ser Leu Val Leu Asn Ser Asp Thr Cys Phe
                245                 250                 255

Glu Asn Leu Thr Asp Pro Ser Ser Pro Thr Ile Ser Ser Tyr Glu Asn
            260                 265                 270

Leu Leu Arg Thr Pro Thr Pro Pro Glu Val Thr Lys Ile Pro Glu Asp
        275                 280                 285

Ile Leu Gln
    290


<210> SEQ ID NO 111
<211> LENGTH: 1781
<212> TYPE: DNA
<213> ORGANISM: Homo sapiens

<400> SEQUENCE: 111

tatcatctgt gactgaggaa atccctatct tcctatcaga ctaatgaaac cacaggacag      60

caattagact tttaagtatt ggggggttta gagctctaga tattcgatat gcagactact     120

catgtttgtt tgttttaata aagactggtc caaaggctca ttttcacaca agctacagtt     180

tttcagttcc aggaccaggt aaagatggtc agctccgtga tccataaaat ccaagggtga     240
```

-continued

```
cgactcagga ttaggaccat ttcttggtga cattgagatg gtcgagctgg tccgcaatga    300
atctatgcgg ggggaacttg gaagtggcgg ccgcctttat ggcctcgaag gcctccctcc    360
tgcgcaccgc ggcgtggccg cgctcctgct cccgggtcat gtagggcatg ctcagccagt    420
aatggttctc cgcctcgatc tccaggcggc ggatcatgtt ctgcttggcg cgcaacgaca    480
cgaaccgcgg ccgccggtgc ttcccgatcc actgacggcc gggaatgcgg ccgcgccaga    540
ggagcgcagt caggaacatg gtgcctgccg cgctgctcaa gactctgcgt ctccgcggcc    600
gccagcagac gccgtggcgt aagcgcaccc gtctcgcggg gtctccgggg gcctcggcga    660
gagacttcgg ctctcgcgag agaggactgc gcctgcgcag agccgaggac gcgtccggcg    720
ccgagattca aactagtggc gggaggctgt gagctgagcg gtggggtctg cgtacgcctg    780
gagtccttcc ccgctgtgct cagcatggac cctatccgga gcttctgcgg gaagctgcgg    840
tctctggcca gcacgctgga ctgcgagacg gcccggctgc agcgagcgct ggacggagag    900
gaaagccttt tatcaaaata caactcaaac ctagctactc caatagcaat taaagcagtg    960
ccacccagta aaaggttcct taaacatgga cagaacatcc gagatgtcag caacaaagaa   1020
aactgaaatt ccagtggatc tatccaacac agaaactgaa caaaatgaga tgaaagccga   1080
gctggaccga ttttaacatt cacattgccc tgcctctgtc cccctttaaa cgttgaccca   1140
ttttaaagac aaacatgaac attaacatca taatatgctt tttatgaagt ttcaataagg   1200
tttaacctta gtcttgttga catgtagccc agtcattcac tctttaagga ctattagtgt   1260
ttcattgata ctaaattacc cagcttaatc aacagaatgg tttaagtagt accaggaagt   1320
aggacaagta atttcaaaaa tataaaggtg tttgctactc agatgaggcc gcccctgacc   1380
ttctggccag agagacattg ctgccagcca gctctgcctt cccatcatct cctttcagga   1440
ccgtcccaca ccttttactt gctcagtgct gtctgaagat gcagttgctg tttgcaaaca   1500
acaggaacac cagttaaact aattaggaaa cagagggaga tttccaggcc tgggtaacta   1560
tatactgtga ccattggcgg ttgagaccgg tcttcaacca gtggaacccc gaactctgct   1620
gtcagggtgt ggacttcggt gctcttccaa gttttcacct ggggggggga gctaaccccc   1680
tatgttcacg ccttctattc ccattggcgc tgaactctta aggtcactct ggtcgcttgt   1740
gaccccgtaa ccctgatgta cccctctaaa aggtgagggg c                       1781
```

<210> SEQ ID NO 112
<211> LENGTH: 1781
<212> TYPE: DNA
<213> ORGANISM: Homo sapiens

<400> SEQUENCE: 112

```
tatcatctgt gactgaggaa atccctatct tcctatcaga ctaatgaaac cacaggacag     60
caattagact tttaagtatt ggggggttta gagctctaga tattcgatat gcagactact    120
catgtttgtt tgttttaata aagactggtc caaaggctca ttttcacaca agctacagtt    180
tttcagttcc aggaccaggt aaagatggtc agctccgtga tccataaaat ccaagggtga    240
cgactcagga ttaggaccat ttcttggtga cattgagatg gtcgagctgg tccgcaatga    300
atctatgcgg ggggaacttg gaagtggcgg ccgcctttat ggcctcgaag gcctccctcc    360
tgcgcaccgc ggcgtggccg cgctcctgct cccgggtcat gtagggcatg ctcagccagt    420
aatggttctc cgcctcgatc tccaggcggc ggatcatgtt ctgcttggcg cgcaacgaca    480
cgaaccgcgg ccgccggtgc ttcccgatcc actgacggcc gggaatgcgg ccgcgccaga    540
```

```
ggagcgcagt caggaacatg gtgcctgccg cgctgctcaa gactctgcgt ctccgcggcc    600

gccagcagac gccgtggcgt aagcgcaccc gtctcgcggg gtctccgggg gcctcggcga    660

gagacttcgg ctctcgcgag agaggactgc gcctgcgcag agccgaggac gcgtccggcg    720

ccgagattca aactagtggc gggaggctgt gagctgagcg gtggggtctg cgtacgcctg    780

gagtccttcc ccgctgtgct cagcatggac cctatccgga gcttctgcgg gaagctgcgg    840

tctctggcca gcacgctgga ctgcgagacg gcccggctgc agcgagcgct ggacggagag    900

gaaagccttt tatcaaaata caactcaaac ctagctactc caatagcaat taaagcagtg    960

ccacccagta aaaggttcct taaacatgga cagaacatcc gagatgtcag caacaaagaa   1020

aactgaaatt ccagtggatc tatccaacac agaaactgaa caaaatgaga tgaaagccga   1080

gctggaccga ttttaacatt cacattgccc tgcctctgtc ccccttttaaa cgttgaccca   1140

ttttaaagac aaacatgaac attaacatca taatatgctt tttatgaagt ttcaataagg   1200

tttaacctta gtcttgttga catgtagccc agtcattcac tctttaagga ctattagtgt   1260

ttcattgata ctaaattacc cagcttaatc aacagaatgg tttaagtagt accaggaagt   1320

aggacaagta atttcaaaaa tataaaggtg tttgctactc agatgaggcc gcccctgacc   1380

ttctggccag agagacattg ctgccagcca gctctgcctt cccatcatct cctttcagga   1440

ccgtcccaca ccttttactt gctcagtgct gtctgaagat gcagttgctg tttgcaaaca   1500

acaggaacac cagttaaact aattaggaaa cagagggaga tttccaggcc tgggtaacta   1560

tatactgtga ccattggcgg ttgagaccgg tcttcaacca gtggaacccc gaactctgct   1620

gtcagggtgt ggacttcggt gctcttccaa gttttcacct ggggggggga gctaaccccc   1680

tatgttcacg ccttctattc ccattggcgc tgaactctta aggtcactct ggtcgcttgt   1740

gaccccgtaa ccctgatgta cccctctaaa aggtgagggg c                       1781
```

<210> SEQ ID NO 113
<211> LENGTH: 1781
<212> TYPE: DNA
<213> ORGANISM: Homo sapiens

<400> SEQUENCE: 113

```
tatcatctgt gactgaggaa atccctatct tcctatcaga ctaatgaaac cacaggacag     60

caattagact tttaagtatt ggggggttta gagctctaga tattcgatat gcagactact    120

catgtttgtt tgttttaata aagactggtc caaaggctca ttttcacaca agctacagtt    180

tttcagttcc aggaccaggt aaagatggtc agctccgtga tccataaaat ccaagggtga    240

cgactcagga ttaggaccat ttcttggtga cattgagatg gtcgagctgg tccgcaatga    300

atctatgcgg ggggaacttg gaagtggcgg ccgcctttat ggcctcgaag gcctccctcc    360

tgcgcaccgc ggcgtggccg cgctcctgct cccgggtcat gtagggcatg ctcagccagt    420

aatggttctc cgcctcgatc tccaggcggc ggatcatgtt ctgcttggcg cgcaacgaca    480

cgaaccgcgg ccgccggtgc ttcccgatcc actgacggcc gggaatgcgg ccgcgccaga    540

ggagcgcagt caggaacatg gtgcctgccg cgctgctcaa gactctgcgt ctccgcggcc    600

gccagcagac gccgtggcgt aagcgcaccc gtctcgcggg gtctccgggg gcctcggcga    660

gagacttcgg ctctcgcgag agaggactgc gcctgcgcag agccgaggac gcgtccggcg    720

ccgagattca aactagtggc gggaggctgt gagctgagcg gtggggtctg cgtacgcctg    780

gagtccttcc ccgctgtgct cagcatggac cctatccgga gcttctgcgg gaagctgcgg    840

tctctggcca gcacgctgga ctgcgagacg gcccggctgc agcgagcgct ggacggagag    900
```

```
gaaagccttt tatcaaaata caactcaaac ctagctactc caatagcaat taaagcagtg    960
ccacccagta aaaggttcct taaacatgga cagaacatcc gagatgtcag caacaaagaa   1020
aactgaaatt ccagtggatc tatccaacac agaaactgaa caaaatgaga tgaaagccga   1080
gctggaccga ttttaacatt cacattgccc tgcctctgtc cccctttaaa cgttgaccca   1140
ttttaaagac aaacatgaac attaacatca taatatgctt tttatgaagt ttcaataagg   1200
tttaacctta gtcttgttga catgtagccc agtcattcac tctttaagga ctattagtgt   1260
ttcattgata ctaaattacc cagcttaatc aacagaatgg tttaagtagt accaggaagt   1320
aggacaagta atttcaaaaa tataaaggtg tttgctactc agatgaggcc gcccctgacc   1380
ttctggccag agagacattg ctgccagcca gctctgcctt cccatcatct cctttcagga   1440
ccgtcccaca ccttttactt gctcagtgct gtctgaagat gcagttgctg tttgcaaaca   1500
acaggaacac cagttaaact aattaggaaa cagagggaga tttccaggcc tgggtaacta   1560
tatactgtga ccattggcgg ttgagaccgg tcttcaacca gtggaacccc gaactctgct   1620
gtcagggtgt ggacttcggt gctcttccaa gttttcacct gggggggga gctaaccccc   1680
tatgttcacg ccttctattc ccattggcgc tgaactctta aggtcactct ggtcgcttgt   1740
gaccccgtaa ccctgatgta cccctctaaa aggtgagggg c                       1781
```

<210> SEQ ID NO 114
<211> LENGTH: 73
<212> TYPE: PRT
<213> ORGANISM: Homo sapiens

<400> SEQUENCE: 114

```
Met Asp Pro Ile Arg Ser Phe Cys Gly Lys Leu Arg Ser Leu Ala Ser
 1               5                  10                  15

Thr Leu Asp Cys Glu Thr Ala Arg Leu Gln Arg Ala Leu Asp Gly Glu
            20                  25                  30

Glu Ser Leu Leu Ser Lys Tyr Asn Ser Asn Leu Ala Thr Pro Ile Ala
        35                  40                  45

Ile Lys Ala Val Pro Pro Ser Lys Arg Phe Leu Lys His Gly Gln Asn
    50                  55                  60

Ile Arg Asp Val Ser Asn Lys Glu Asn
65                  70
```

<210> SEQ ID NO 115
<211> LENGTH: 77
<212> TYPE: PRT
<213> ORGANISM: Homo sapiens

<400> SEQUENCE: 115

```
Met Asp Pro Ile Arg Ser Phe Cys Gly Lys Leu Arg Ser Leu Ala Ser
 1               5                  10                  15

Thr Leu Asp Cys Glu Thr Ala Arg Leu Gln Arg Ala Leu Asp Gly Glu
            20                  25                  30

Glu Ser Asp Phe Glu Asp Tyr Leu Leu Ser Lys Tyr Asn Ser Asn Leu
        35                  40                  45

Ala Thr Pro Ile Ala Ile Lys Ala Val Pro Pro Ser Lys Arg Phe Leu
    50                  55                  60

Lys His Gly Gln Asn Ile Arg Asp Val Ser Asn Lys Glu
65                  70                  75
```

<210> SEQ ID NO 116

-continued

<211> LENGTH: 78
<212> TYPE: PRT
<213> ORGANISM: Homo sapiens

<400> SEQUENCE: 116

Met Asp Pro Ile Arg Ser Phe Cys Gly Lys Leu Arg Ser Leu Ala Ser
1 5 10 15

Thr Leu Asp Cys Glu Thr Ala Arg Leu Gln Arg Ala Leu Asp Gly Glu
20 25 30

Glu Ser Leu Leu Ser Lys Tyr Leu Leu Ser Lys Tyr Asn Ser Asn Leu
35 40 45

Ala Thr Pro Ile Ala Ile Lys Ala Val Pro Pro Ser Lys Arg Phe Leu
50 55 60

Lys His Gly Gln Asn Ile Arg Asp Val Ser Asn Lys Glu Asn
65 70 75

<210> SEQ ID NO 117
<211> LENGTH: 2825
<212> TYPE: DNA
<213> ORGANISM: Homo sapiens

<400> SEQUENCE: 117
tatcatctgt gactgaggaa atccctatct tcctatcaga ctaatgaaac cacaggacag 60
caattagact tttaagtatt ggggggttta gagctctaga tattcgatat gcagactact 120
catgtttgtt tgttttaata aagactggtc caaaggctca ttttcacaca agctacagtt 180
tttcagttcc aggaccaggt aaagatggtc agctccgtga tccataaaat ccaagggtga 240
cgactcagga ttaggaccat ttcttggtga cattgagatg gtcgagctgg tccgcaatga 300
atctatgcgg ggggaacttg gaagtggcgg ccgcctttat ggcctcgaag gcctccctcc 360
tgcgcaccgc ggcgtggccg cgctcctgct cccgggtcat gtagggcatg ctcagccagt 420
aatggttctc cgcctcgatc tccaggcggc ggatcatgtt ctgcttggcg cgcaacgaca 480
cgaaccgcgg ccgccggtgc ttcccgatcc actgacggcc gggaatgcgg ccgcgccaga 540
ggagcgcagt caggaacatg gtgcctgccg cgctgctcaa gactctgcgt ctccgcggcc 600
gccagcagac gccgtggcgt aagcgcaccc gtctcgcggg gtctccgggg gcctcggcga 660
gagacttcgg ctctcgcgag agaggactgc gcctgcgcag agccgaggac gcgtccggcg 720
ccgagattca aactagtggc gggaggctgt gagctgagcg gtggggtctg cgtacgcctg 780
gagtccttcc ccgctgtgct cagcatggac cctatccgga gcttctgcgg gaagctgcgg 840
tctctggcca gcacgctgga ctgcgagacg gcccggctgc agcgagcgct ggacggagag 900
gaaagcggtg cgtgaggcgg gcggccaggg cacgactttg aagattatcc aatgagaatt 960
ttatatgacc ttcattcaga agttcagact ctaaaggatg atgttaatat tcttcttgat 1020
aaagcaagat tggaaaatca agaaggcatt gatttcataa aggcaacaaa agtactaatg 1080
gaaaaaaatt caatggatat tatgaaaata agagagtatt tccagaagta tggatatagt 1140
ccacgtgtca agaaaaattc agtacacgag caagaagcca ttaactctga cccagagttg 1200
tctaattgtg aaaattttca gaagactgat gtgaaagatg atctgtctga tcctcctgtt 1260
gcaagcagtt gtatttctgg gaagtctcca cgtagtccac aactttcaga ttttggactt 1320
gagcggtaca tcgtatccca agttctacca aaccctccac aggcagtgaa caactataag 1380
gaagagcccg taattgtaac cccacctacc aaacaatcac tagtaaaagt actaaaaact 1440
ccaaaatgtg cactaaaaat ggatgatttt gagtgtgtaa ctcctaaatt agaacacttt 1500

-continued

```
ggtatctctg aatatactat gtgtttaaat gaagattaca caatgggact taaaaatgcg   1560

aggaataata aaagtgagga ggccatagat acagaatcca ggctcaatga taatgttttt   1620

gccactccca gccccatcat ccagcagttg gaaaaaagtg atgccgaata taccaactct   1680

cctttggtac ctacattctg tactcctggt ttgaaaattc catctacaaa gaacagcata   1740

gctttggtat ccacaaatta cccattatca aaaacaaata gttcatcaaa tgatttggaa   1800

gttgaagatc gtacttcgtt ggttttaaat tcagacacat gctttgagaa tttaacagat   1860

ccctcttcac ctacgatttc ttcttatgag aatctgctca gaacacctac acctccagaa   1920

gtaactaaaa ttccagaaga tattctccag cttttatcaa aatacaactc aaacctagct   1980

actccaatag caattaaagc agtgccaccc agtaaaaggt tccttaaaca tggacagaac   2040

atccgagatg tcagcaacaa agaaaactga aattccagtg gatctatcca acacagaaac   2100

tgaacaaaat gagatgaaag ccgagctgga ccgattttaa cattcacatt gccctgcctc   2160

tgtcccccttt taaacgttga cccattttaa agacaaacat gaacattaac atcataaatat   2220

gctttttatg aagtttcaat aaggtttaac cttagtcttg ttgacatgta gcccagtcat   2280

tcactcttta aggactatta gtgtttcatt gatactaaat tacccagctt aatcaacaga   2340

atggtttaag tagtaccagg aagtaggaca agtaatttca aaaatataaa ggtgtttgct   2400

actcagatga ggccgcccct gaccttctgg ccagagagac attgctgcca gccagctctg   2460

ccttcccatc atctcctttc aggaccgtcc cacacctttt acttgctcag tgctgtctga   2520

agatgcagtt gctgtttgca aacaacagga acaccagtta aactaattag gaaacagagg   2580

gagatttcca ggcctgggta actatatact gtgaccattg gcggttgaga ccggtcttca   2640

accagtggaa ccccgaactc tgctgtcagg gtgtggactt cggtgctctt ccaagttttc   2700

acctgggggg gggagctaac cccctatgtt cacgccttct attcccattg gcgctgaact   2760

cttaaggtca ctctggtcgc ttgtgacccc gtaaccctga tgtacccctc taaaaggtga   2820

ggggc                                                                2825
```

<210> SEQ ID NO 118
<211> LENGTH: 3707
<212> TYPE: DNA
<213> ORGANISM: Homo sapiens

<400> SEQUENCE: 118

```
tatcatctgt gactgaggaa atccctatct tcctatcaga ctaatgaaac cacaggacag     60

caattagact tttaagtatt ggggggttta gagctctaga tattcgatat gcagactact    120

catgtttgtt tgttttaata aagactggtc caaaggctca ttttcacaca agctacagtt    180

tttcagttcc aggaccaggt aaagatggtc agctccgtga tccataaaat ccaagggtga    240

cgactcagga ttaggaccat ttcttggtga cattgagatg gtcgagctgg tccgcaatga    300

atctatgcgg ggggaacttg gaagtggcgg ccgcctttat ggcctcgaag gcctccctcc    360

tgcgcaccgc ggcgtggccg cgctcctgct cccgggtcat gtagggcatg ctcagccagt    420

aatggttctc cgcctcgatc tccaggcggc ggatcatgtt ctgcttggcg cgcaacgaca    480

cgaaccgcgg ccgccggtgc ttcccgatcc actgacggcc gggaatgcgg ccgcgccaga    540

ggagcgcagt caggaacatg gtgcctgccg cgctgctcaa gactctgcgt ctccgcggcc    600

gccagcagac gccgtggcgt aagcgcaccc gtctcgcggg gtctccgggg gcctcggcga    660

gagacttcgg ctctcgcgag agaggactgc gcctgcgcag agccgaggac gcgtccggcg    720

ccgagattca aactagtggc gggaggctgt gagctgagcg gtggggtctg cgtacgcctg    780
```

-continued

```
gagtccttcc ccgctgtgct cagcatggac cctatccgga gcttctgcgg gaagctgcgg    840
tctctggcca gcacgctgga ctgcgagacg gcccggctgc agcgagcgct ggacggagag    900
gaaagcgcga ctttgaagat tatccaatga gaattttata tgaccttcat tcagaagttc    960
agactctaaa ggatgatgtt aatattcttc ttgataaagc aagattggaa aatcaagaag   1020
gcattgattt cataaaggca acaaaagtac taatggaaaa aaattcaatg gatattatga   1080
aaataagaga gtatttccag aagtatggat atagtccacg tgtcaagaaa aattcagtac   1140
acgagcaaga agccattaac tctgacccag agttgtctaa ttgtgaaaat tttcagaaga   1200
ctgatgtgaa agatgatctg tctgatcctc ctgttgcaag cagttgtatt tctgggaagt   1260
ctccacgtag tccacaactt tcagattttg gacttgagcg gtacatcgta tcccaagttc   1320
taccaaaccc tccacaggca gtgaacaact ataaggaaga gcccgtaatt gtaaccccac   1380
ctaccaaaca atcactagta aaagtactaa aaactccaaa atgtgcacta aaaatggatg   1440
attttgagtg tgtaactcct aaattagaac actttggtat ctctgaatat actatgtgtt   1500
taaatgaaga ttacacaatg ggacttaaaa atgcgaggaa taataaaagt gaggaggcca   1560
tagatacaga atccaggctc aatgataatg tttttgccac tcccagcccc atcatccagc   1620
agttggaaaa aagtgatgcc gaatatacca actctccttt ggtacctaca ttctgtactc   1680
ctggtttgaa aattccatct acaaagaaca gcatagcttt ggtatccaca aattacccat   1740
tatcaaaaac aaatagttca tcaaatgatt tggaagttga agatcgtact tcgttggttt   1800
taaattcaga cacatgcttt gagaatttaa cagatccctc ttcacctacg atttcttctt   1860
atgagaatct gctcagaaca cctacacctc cagaagtaac taaaattcca gaagatattc   1920
tccagctttt atcaaaatac aactcaaacc tagctactcc aatagcaatt aaagcagtgc   1980
cacccagtaa aaggttcctt aaacatggac agaacatccg agatgtcagc aacaaagaaa   2040
actgaaattc cagtggatct atccaacaca gaaactgaac aaaatgagat gaaagccgag   2100
ctggaccgat tttaacattc acattgccct gcctctgtcc ccctttaaac gttgacccat   2160
tttaaagaca aacatgaaca ttaacatcat aatatgcttt ttatgaagtt tcaataaggt   2220
ttaaccttag tcttgttgac atgtagccca gtcattcact ctttaaggac tattagtgtt   2280
tcattgatac taaattaccc agcttaatca acagaatggt ttaagtagta ccaggaagta   2340
ggacaagtaa tttcaaaaat ataaaggtgt ttgctactca gatgaggccg cccctgacct   2400
tctggccaga gagacattgc tgccagccag ctctgccttc ccatcatctc ctttcaggac   2460
cgtcccacac cttttacttg ctcagtgctg tctgaagatg cagttgctgt ttgcaaacaa   2520
caggaacacc agttaaacta attaggaaac agagggagat ttccaggcct gggtaactat   2580
atactgtgac cattggcggt tgagaccggt cttcaaccag tggaaccccg aactctgctg   2640
tcagggtgtg gacttcggtg ctcttccaag ttttcacctg gggggggggag ctaacccccct   2700
atgttcacgc cttctattcc cattggcgct gaactcttaa ggtcactctg gtcgcttgtg   2760
accccgtaac cctgatgtac ccctctaaaa ggtgaggggc tatcatctgt gactgaggaa   2820
atccctatct tcctatcaga ctaatgaaac cacaggacag caattagact tttaagtatt   2880
ggggggttta gagctctaga tattcgatat gcagactact catgtttgtt tgttttaata   2940
aagactggtc caaaggctca ttttcacaca agctacagtt tttcagttcc aggaccaggt   3000
aaagatggtc agctccgtga tccataaaat ccaagggtga cgactcagga ttaggaccat   3060
ttcttggtga cattgagatg gtcgagctgg tccgcaatga atctatgcgg ggggaacttg   3120
```

```
gaagtggcgg ccgcctttat ggcctcgaag gcctccctcc tgcgcaccgc ggcgtggccg   3180

cgctcctgct cccgggtcat gtagggcatg ctcagccagt aatggttctc cgcctcgatc   3240

tccaggcggc ggatcatgtt ctgcttggcg cgcaacgaca cgaaccgcgg ccgccggtgc   3300

ttcccgatcc actgacggcc gggaatgcgg ccgcgccaga ggagcgcagt caggaacatg   3360

gtgcctgccg cgctgctcaa gactctgcgt ctccgcggcc gccagcagac gccgtggcgt   3420

aagcgcaccc gtctcgcggg gtctccgggg gcctcggcga gagacttcgg ctctcgcgag   3480

agaggactgc gcctgcgcag agccgaggac gcgtccggcg ccgagattca aactagtggc   3540

gggaggctgt gagctgagcg gtggggtctg cgtacgcctg gagtccttcc ccgctgtgct   3600

cagcatggac cctatccgga gcttctgcgg gaagctgcgg tctctggcca gcacgctgga   3660

ctgcgagacg gcccggctgc agcgagcgct ggacggagag gaaagcg                 3707
```

<210> SEQ ID NO 119
<211> LENGTH: 3707
<212> TYPE: DNA
<213> ORGANISM: Homo sapiens

<400> SEQUENCE: 119

```
tatcatctgt gactgaggaa atccctatct tcctatcaga ctaatgaaac cacaggacag     60

caattagact tttaagtatt ggggggttta gagctctaga tattcgatat gcagactact    120

catgtttgtt tgttttaata aagactggtc caaaggctca ttttcacaca agctacagtt    180

tttcagttcc aggaccaggt aaagatggtc agctccgtga tccataaaat ccaagggtga    240

cgactcagga ttaggaccat ttcttggtga cattgagatg gtcgagctgg tccgcaatga    300

atctatgcgg ggggaacttg gaagtggcgg ccgcctttat ggcctcgaag gcctccctcc    360

tgcgcaccgc ggcgtggccg cgctcctgct cccgggtcat gtagggcatg ctcagccagt    420

aatggttctc cgcctcgatc tccaggcggc ggatcatgtt ctgcttggcg cgcaacgaca    480

cgaaccgcgg ccgccggtgc ttcccgatcc actgacggcc gggaatgcgg ccgcgccaga    540

ggagcgcagt caggaacatg gtgcctgccg cgctgctcaa gactctgcgt ctccgcggcc    600

gccagcagac gccgtggcgt aagcgcaccc gtctcgcggg gtctccgggg gcctcggcga    660

gagacttcgg ctctcgcgag agaggactgc gcctgcgcag agccgaggac gcgtccggcg    720

ccgagattca aactagtggc gggaggctgt gagctgagcg gtggggtctg cgtacgcctg    780

gagtccttcc ccgctgtgct cagcatggac cctatccgga gcttctgcgg gaagctgcgg    840

tctctggcca gcacgctgga ctgcgagacg gcccggctgc agcgagcgct ggacggagag    900

gaaagcgcga ctttgaagat tatccaatga gaattttata tgaccttcat tcagaagttc    960

agactctaaa ggatgatgtt aatattcttc ttgataaagc aagattggaa aatcaagaag   1020

gcattgattt cataaaggca acaaaagtac taatggaaaa aaattcaatg gatattatga   1080

aaataagaga gtatttccag aagtatggat atagtccacg tgtcaagaaa aattcagtac   1140

acgagcaaga agccattaac tctgacccag agttgtctaa ttgtgaaaat tttcagaaga   1200

ctgatgtgaa agatgatctg tctgatcctc ctgttgcaag cagttgtatt tctgggaagt   1260

ctccacgtag tccacaactt tcagattttg gacttgagcg gtacatcgta tcccaagttc   1320

taccaaaccc tccacaggca gtgaacaact ataaggaaga gcccgtaatt gtaaccccac   1380

ctaccaaaca atcactagta aaagtactaa aaactccaaa atgtgcacta aaaatggatg   1440

attttgagtg tgtaactcct aaattagaac actttggtat ctctgaatat actatgtgtt   1500

taaatgaaga ttacacaatg ggacttaaaa atgcgaggaa taataaaagt gaggaggcca   1560
```

-continued

```
tagatacaga atccaggctc aatgataatg tttttgccac tcccagcccc atcatccagc   1620
agttggaaaa aagtgatgcc gaatatacca actctccttt ggtacctaca ttctgtactc   1680
ctggtttgaa aattccatct acaaagaaca gcatagcttt ggtatccaca aattacccat   1740
tatcaaaaac aaatagttca tcaaatgatt tggaagttga agatcgtact tcgttggttt   1800
taaattcaga cacatgcttt gagaatttaa cagatccctc ttcacctacg atttcttctt   1860
atgagaatct gctcagaaca cctacacctc cagaagtaac taaaattcca gaagatattc   1920
tccagctttt atcaaaatac aactcaaacc tagctactcc aatagcaatt aaagcagtgc   1980
cacccagtaa aaggttcctt aaacatggac agaacatccg agatgtcagc aacaaagaaa   2040
actgaaattc cagtggatct atccaacaca gaaactgaac aaaatgagat gaaagccgag   2100
ctggaccgat tttaacattc acattgccct gcctctgtcc cccttttaaac gttgacccat   2160
tttaaagaca aacatgaaca ttaacatcat aatatgcttt ttatgaagtt tcaataaggt   2220
ttaaccttag tcttgttgac atgtagccca gtcattcact ctttaaggac tattagtgtt   2280
tcattgatac taaattaccc agcttaatca acagaatggt ttaagtagta ccaggaagta   2340
ggacaagtaa tttcaaaaat ataaaggtgt ttgctactca gatgaggccg cccctgacct   2400
tctggccaga gagacattgc tgccagccag ctctgccttc ccatcatctc ctttcaggac   2460
cgtcccacac cttttacttg ctcagtgctg tctgaagatg cagttgctgt ttgcaaacaa   2520
caggaacacc agttaaacta attaggaaac agagggagat ttccaggcct gggtaactat   2580
atactgtgac cattggcggt tgagaccggt cttcaaccag tggaaccccg aactctgctg   2640
tcagggtgtg gacttcggtg ctcttccaag ttttcacctg ggggggggag ctaacccccct   2700
atgttcacgc cttctattcc cattggcgct gaactcttaa ggtcactctg gtcgcttgtg   2760
accccgtaac cctgatgtac ccctctaaaa ggtgaggggc tatcatctgt gactgaggaa   2820
atccctatct tcctatcaga ctaatgaaac cacaggacag caattagact tttaagtatt   2880
gggggggttta gagctctaga tattcgatat gcagactact catgtttgtt tgttttaata   2940
aagactggtc caaaggctca ttttcacaca agctacagtt tttcagttcc aggaccaggt   3000
aaagatggtc agctccgtga tccataaaat ccaagggtga cgactcagga ttaggaccat   3060
ttcttggtga cattgagatg gtcgagctgg tccgcaatga atctatgcgg ggggaacttg   3120
gaagtggcgg ccgcctttat ggcctcgaag gcctccctcc tgcgcaccgc ggcgtggccg   3180
cgctcctgct cccgggtcat gtagggcatg ctcagccagt aatggttctc cgcctcgatc   3240
tccaggcggc ggatcatgtt ctgcttggcg cgcaacgaca cgaaccgcgg ccgccggtgc   3300
ttcccgatcc actgacggcc gggaatgcgg ccgcgccaga ggagcgcagt caggaacatg   3360
gtgcctgccg cgctgctcaa gactctgcgt ctccgcggcc gccagcagac gccgtggcgt   3420
aagcgcaccc gtctcgcggg gtctccgggg gcctcggcga gagacttcgg ctctcgcgag   3480
agaggactgc gcctgcgcag agccgaggac gcgtccggcg ccgagattca aactagtggc   3540
gggaggctgt gagctgagcg gtggggtctg cgtacgcctg gagtccttcc ccgctgtgct   3600
cagcatggac cctatccgga gcttctgcgg gaagctgcgg tctctggcca gcacgctgga   3660
ctgcgagacg gcccggctgc agcgagcgct ggacggagag gaaagcg                 3707
```

<210> SEQ ID NO 120
<211> LENGTH: 372
<212> TYPE: PRT
<213> ORGANISM: Homo sapiens

<400> SEQUENCE: 120

```
Met Arg Ile Leu Tyr Asp Leu His Ser Glu Val Gln Thr Leu Lys Asp
 1              5                   10                  15

Asp Val Asn Ile Leu Leu Asp Lys Ala Arg Leu Glu Asn Gln Glu Gly
            20                  25                  30

Ile Asp Phe Ile Lys Ala Thr Lys Val Leu Met Glu Lys Asn Ser Met
        35                  40                  45

Asp Ile Met Lys Ile Arg Glu Tyr Phe Gln Lys Tyr Gly Tyr Ser Pro
    50                  55                  60

Arg Val Lys Lys Asn Ser Val His Glu Gln Glu Ala Ile Asn Ser Asp
65                  70                  75                  80

Pro Glu Leu Ser Asn Cys Glu Asn Phe Gln Lys Thr Asp Val Lys Asp
                85                  90                  95

Asp Leu Ser Asp Pro Pro Val Ala Ser Ser Cys Ile Ser Gly Lys Ser
            100                 105                 110

Pro Arg Ser Pro Gln Leu Ser Asp Phe Gly Leu Glu Arg Tyr Ile Val
        115                 120                 125

Ser Gln Val Leu Pro Asn Pro Pro Gln Ala Val Asn Asn Tyr Lys Glu
    130                 135                 140

Glu Pro Val Ile Val Thr Pro Pro Thr Lys Gln Ser Leu Val Lys Val
145                 150                 155                 160

Leu Lys Thr Pro Lys Cys Ala Leu Lys Met Asp Asp Phe Glu Cys Val
                165                 170                 175

Thr Pro Lys Leu Glu His Phe Gly Ile Ser Glu Tyr Thr Met Cys Leu
            180                 185                 190

Asn Glu Asp Tyr Thr Met Gly Leu Lys Asn Ala Arg Asn Asn Lys Ser
        195                 200                 205

Glu Glu Ala Ile Asp Thr Glu Ser Arg Leu Asn Asp Asn Val Phe Ala
    210                 215                 220

Thr Pro Ser Pro Ile Ile Gln Gln Leu Glu Lys Ser Asp Ala Glu Tyr
225                 230                 235                 240

Thr Asn Ser Pro Leu Val Pro Thr Phe Cys Thr Pro Gly Leu Lys Ile
                245                 250                 255

Pro Ser Thr Lys Asn Ser Ile Ala Leu Val Ser Thr Asn Tyr Pro Leu
            260                 265                 270

Ser Lys Thr Asn Ser Ser Ser Asn Asp Leu Glu Val Glu Asp Arg Thr
        275                 280                 285

Ser Leu Val Leu Asn Ser Asp Thr Cys Phe Glu Asn Leu Thr Asp Pro
    290                 295                 300

Ser Ser Pro Thr Ile Ser Ser Tyr Glu Asn Leu Leu Arg Thr Pro Thr
305                 310                 315                 320

Pro Pro Glu Val Thr Lys Ile Pro Glu Asp Ile Leu Gln Leu Leu Ser
                325                 330                 335

Lys Tyr Asn Ser Asn Leu Ala Thr Pro Ile Ala Ile Lys Ala Val Pro
            340                 345                 350

Pro Ser Lys Arg Phe Leu Lys His Gly Gln Asn Ile Arg Asp Val Ser
        355                 360                 365

Asn Lys Glu Asn
    370
```

<210> SEQ ID NO 121
<211> LENGTH: 372
<212> TYPE: PRT
<213> ORGANISM: Homo sapiens

<400> SEQUENCE: 121

```
Met Arg Ile Leu Tyr Asp Leu His Ser Glu Val Gln Thr Leu Lys Asp
 1               5                   10                  15

Asp Val Asn Ile Leu Leu Asp Lys Ala Arg Leu Glu Asn Gln Glu Gly
            20                  25                  30

Ile Asp Phe Ile Lys Ala Thr Lys Val Leu Met Glu Lys Asn Ser Met
        35                  40                  45

Asp Ile Met Lys Ile Arg Glu Tyr Phe Gln Lys Tyr Gly Tyr Ser Pro
    50                  55                  60

Arg Val Lys Lys Asn Ser Val His Glu Gln Glu Ala Ile Asn Ser Asp
65                  70                  75                  80

Pro Glu Leu Ser Asn Cys Glu Asn Phe Gln Lys Thr Asp Val Lys Asp
                85                  90                  95

Asp Leu Ser Asp Pro Pro Val Ala Ser Ser Cys Ile Ser Gly Lys Ser
            100                 105                 110

Pro Arg Ser Pro Gln Leu Ser Asp Phe Gly Leu Glu Arg Tyr Ile Val
        115                 120                 125

Ser Gln Val Leu Pro Asn Pro Pro Gln Ala Val Asn Asn Tyr Lys Glu
    130                 135                 140

Glu Pro Val Ile Val Thr Pro Pro Thr Lys Gln Ser Leu Val Lys Val
145                 150                 155                 160

Leu Lys Thr Pro Lys Cys Ala Leu Lys Met Asp Asp Phe Glu Cys Val
                165                 170                 175

Thr Pro Lys Leu Glu His Phe Gly Ile Ser Glu Tyr Thr Met Cys Leu
            180                 185                 190

Asn Glu Asp Tyr Thr Met Gly Leu Lys Asn Ala Arg Asn Asn Lys Ser
        195                 200                 205

Glu Glu Ala Ile Asp Thr Glu Ser Arg Leu Asn Asp Asn Val Phe Ala
    210                 215                 220

Thr Pro Ser Pro Ile Ile Gln Gln Leu Glu Lys Ser Asp Ala Glu Tyr
225                 230                 235                 240

Thr Asn Ser Pro Leu Val Pro Thr Phe Cys Thr Pro Gly Leu Lys Ile
                245                 250                 255

Pro Ser Thr Lys Asn Ser Ile Ala Leu Val Ser Thr Asn Tyr Pro Leu
            260                 265                 270

Ser Lys Thr Asn Ser Ser Ser Asn Asp Leu Glu Val Glu Asp Arg Thr
        275                 280                 285

Ser Leu Val Leu Asn Ser Asp Thr Cys Phe Glu Asn Leu Thr Asp Pro
    290                 295                 300

Ser Ser Pro Thr Ile Ser Ser Tyr Glu Asn Leu Leu Arg Thr Pro Thr
305                 310                 315                 320

Pro Pro Glu Val Thr Lys Ile Pro Glu Asp Ile Leu Gln Leu Leu Ser
                325                 330                 335

Lys Tyr Asn Ser Asn Leu Ala Thr Pro Ile Ala Ile Lys Ala Val Pro
            340                 345                 350

Pro Ser Lys Arg Phe Leu Lys His Gly Gln Asn Ile Arg Asp Val Ser
        355                 360                 365

Asn Lys Glu Asn
    370
```

<210> SEQ ID NO 122
<211> LENGTH: 372
<212> TYPE: PRT

<213> ORGANISM: Homo sapiens

<400> SEQUENCE: 122

Met Arg Ile Leu Tyr Asp Leu His Ser Glu Val Gln Thr Leu Lys Asp
1 5 10 15

Asp Val Asn Ile Leu Leu Asp Lys Ala Arg Leu Glu Asn Gln Glu Gly
20 25 30

Ile Asp Phe Ile Lys Ala Thr Lys Val Leu Met Glu Lys Asn Ser Met
35 40 45

Asp Ile Met Lys Ile Arg Glu Tyr Phe Gln Lys Tyr Gly Tyr Ser Pro
50 55 60

Arg Val Lys Lys Asn Ser Val His Glu Gln Glu Ala Ile Asn Ser Asp
65 70 75 80

Pro Glu Leu Ser Asn Cys Glu Asn Phe Gln Lys Thr Asp Val Lys Asp
85 90 95

Asp Leu Ser Asp Pro Pro Val Ala Ser Ser Cys Ile Ser Gly Lys Ser
100 105 110

Pro Arg Ser Pro Gln Leu Ser Asp Phe Gly Leu Glu Arg Tyr Ile Val
115 120 125

Ser Gln Val Leu Pro Asn Pro Pro Gln Ala Val Asn Asn Tyr Lys Glu
130 135 140

Glu Pro Val Ile Val Thr Pro Pro Thr Lys Gln Ser Leu Val Lys Val
145 150 155 160

Leu Lys Thr Pro Lys Cys Ala Leu Lys Met Asp Asp Phe Glu Cys Val
165 170 175

Thr Pro Lys Leu Glu His Phe Gly Ile Ser Glu Tyr Thr Met Cys Leu
180 185 190

Asn Glu Asp Tyr Thr Met Gly Leu Lys Asn Ala Arg Asn Asn Lys Ser
195 200 205

Glu Glu Ala Ile Asp Thr Glu Ser Arg Leu Asn Asp Asn Val Phe Ala
210 215 220

Thr Pro Ser Pro Ile Ile Gln Gln Leu Glu Lys Ser Asp Ala Glu Tyr
225 230 235 240

Thr Asn Ser Pro Leu Val Pro Thr Phe Cys Thr Pro Gly Leu Lys Ile
245 250 255

Pro Ser Thr Lys Asn Ser Ile Ala Leu Val Ser Thr Asn Tyr Pro Leu
260 265 270

Ser Lys Thr Asn Ser Ser Ser Asn Asp Leu Glu Val Glu Asp Arg Thr
275 280 285

Ser Leu Val Leu Asn Ser Asp Thr Cys Phe Glu Asn Leu Thr Asp Pro
290 295 300

Ser Ser Pro Thr Ile Ser Ser Tyr Glu Asn Leu Leu Arg Thr Pro Thr
305 310 315 320

Pro Pro Glu Val Thr Lys Ile Pro Glu Asp Ile Leu Gln Leu Leu Ser
325 330 335

Lys Tyr Asn Ser Asn Leu Ala Thr Pro Ile Ala Ile Lys Ala Val Pro
340 345 350

Pro Ser Lys Arg Phe Leu Lys His Gly Gln Asn Ile Arg Asp Val Ser
355 360 365

Asn Lys Glu Asn
370

<210> SEQ ID NO 123
<211> LENGTH: 412

<212> TYPE: PRT
<213> ORGANISM: Homo sapiens

<400> SEQUENCE: 123

```
Met Asp Pro Ile Arg Ser Phe Cys Gly Lys Leu Arg Ser Leu Ala Ser
 1               5                  10                  15

Thr Leu Asp Cys Glu Thr Ala Arg Leu Gln Arg Ala Leu Asp Gly Glu
            20                  25                  30

Glu Ser Asp Phe Glu Asp Tyr Pro Met Arg Ile Leu Tyr Asp Leu His
        35                  40                  45

Ser Glu Val Gln Thr Leu Lys Asp Asp Val Asn Ile Leu Leu Asp Lys
    50                  55                  60

Ala Arg Leu Glu Asn Gln Glu Gly Ile Asp Phe Ile Lys Ala Thr Lys
65                  70                  75                  80

Val Leu Met Glu Lys Asn Ser Met Asp Ile Met Lys Ile Arg Glu Tyr
                85                  90                  95

Phe Gln Lys Tyr Gly Tyr Ser Pro Arg Val Lys Lys Asn Ser Val His
            100                 105                 110

Glu Gln Glu Ala Ile Asn Ser Asp Pro Glu Leu Ser Asn Cys Glu Asn
        115                 120                 125

Phe Gln Lys Thr Asp Val Lys Asp Asp Leu Ser Asp Pro Pro Val Ala
    130                 135                 140

Ser Ser Cys Ile Ser Glu Lys Ser Pro Arg Ser Pro Gln Leu Ser Asp
145                 150                 155                 160

Phe Gly Leu Glu Arg Tyr Ile Val Ser Gln Val Leu Pro Asn Pro Pro
                165                 170                 175

Gln Ala Val Asn Asn Tyr Lys Glu Glu Pro Val Ile Val Thr Pro Pro
            180                 185                 190

Thr Lys Gln Ser Leu Val Lys Val Leu Lys Thr Pro Lys Cys Ala Leu
        195                 200                 205

Lys Met Asp Asp Phe Glu Cys Val Thr Pro Lys Leu Glu His Phe Gly
    210                 215                 220

Ile Ser Glu Tyr Thr Met Cys Leu Asn Glu Asp Tyr Thr Met Gly Leu
225                 230                 235                 240

Lys Asn Ala Arg Asn Asn Lys Ser Glu Glu Ala Ile Asp Thr Glu Ser
                245                 250                 255

Arg Leu Asn Asp Asn Val Phe Ala Thr Pro Ser Pro Ile Ile Gln Gln
            260                 265                 270

Leu Glu Lys Ser Asp Ala Glu Tyr Thr Asn Ser Pro Leu Val Pro Thr
        275                 280                 285

Phe Cys Thr Pro Gly Leu Lys Ile Pro Ser Thr Lys Asn Ser Ile Ala
    290                 295                 300

Leu Val Ser Thr Asn Tyr Pro Leu Ser Lys Thr Asn Ser Ser Ser Asn
305                 310                 315                 320

Asp Leu Glu Val Glu Asp Arg Thr Ser Leu Val Leu Asn Ser Asp Thr
                325                 330                 335

Cys Phe Glu Asn Leu Thr Asp Pro Ser Ser Pro Thr Ile Ser Ser Tyr
            340                 345                 350

Glu Asn Leu Leu Arg Thr Pro Thr Pro Pro Glu Val Thr Lys Ile Pro
        355                 360                 365

Glu Asp Ile Leu Gln Leu Leu Ser Lys Tyr Asn Ser Asn Leu Ala Thr
    370                 375                 380

Pro Ile Ala Ile Lys Ala Val Pro Pro Ser Lys Arg Phe Leu Lys His
385                 390                 395                 400
```

```
Gly Gln Asn Ile Arg Asp Val Ser Asn Lys Glu Asn
                405                 410


<210> SEQ ID NO 124
<211> LENGTH: 6
<212> TYPE: PRT
<213> ORGANISM: Artificial Sequence
<220> FEATURE:
<223> OTHER INFORMATION: Peptide motif

<400> SEQUENCE: 124

Thr Ile Leu Val Met Ser
 1               5


<210> SEQ ID NO 125
<211> LENGTH: 7
<212> TYPE: PRT
<213> ORGANISM: Artificial Sequence
<220> FEATURE:
<223> OTHER INFORMATION: Peptide motif

<400> SEQUENCE: 125

Leu Ile Val Met Ala Thr Gln
 1               5


<210> SEQ ID NO 126
<211> LENGTH: 6
<212> TYPE: PRT
<213> ORGANISM: Artificial Sequence
<220> FEATURE:
<223> OTHER INFORMATION: Peptide motif

<400> SEQUENCE: 126

Ile Val Met Ala Thr Leu
 1               5


<210> SEQ ID NO 127
<211> LENGTH: 7
<212> TYPE: PRT
<213> ORGANISM: Artificial Sequence
<220> FEATURE:
<223> OTHER INFORMATION: Peptide motif

<400> SEQUENCE: 127

Val Ser Met Ala Thr Leu Ile
 1               5


<210> SEQ ID NO 128
<211> LENGTH: 8
<212> TYPE: PRT
<213> ORGANISM: Artificial Sequence
<220> FEATURE:
<223> OTHER INFORMATION: Peptide motif

<400> SEQUENCE: 128

Tyr Phe Trp Ile Val Leu Met Thr
 1               5


<210> SEQ ID NO 129
<211> LENGTH: 6
<212> TYPE: PRT
<213> ORGANISM: Artificial Sequence
<220> FEATURE:
<223> OTHER INFORMATION: Peptide motif

<400> SEQUENCE: 129
```

-continued

```
Phe Ile Tyr Trp Leu Met
 1               5


<210> SEQ ID NO 130
<211> LENGTH: 8
<212> TYPE: PRT
<213> ORGANISM: Artificial Sequence
<220> FEATURE:
<223> OTHER INFORMATION: Peptide motif

<400> SEQUENCE: 130

Val Ile Leu Phe Met Trp Tyr Ala
 1               5


<210> SEQ ID NO 131
<211> LENGTH: 8
<212> TYPE: PRT
<213> ORGANISM: Artificial Sequence
<220> FEATURE:
<223> OTHER INFORMATION: Peptide motif

<400> SEQUENCE: 131

Phe Tyr Leu Trp Met Ile Val Ala
 1               5


<210> SEQ ID NO 132
<211> LENGTH: 8
<212> TYPE: PRT
<213> ORGANISM: Artificial Sequence
<220> FEATURE:
<223> OTHER INFORMATION: Peptide motif

<400> SEQUENCE: 132

Phe Trp Tyr Leu Ile Met Val Ala
 1               5


<210> SEQ ID NO 133
<211> LENGTH: 8
<212> TYPE: PRT
<213> ORGANISM: Artificial Sequence
<220> FEATURE:
<223> OTHER INFORMATION: Peptide motif

<400> SEQUENCE: 133

Phe Trp Tyr Leu Ile Val Met Ala
 1               5


<210> SEQ ID NO 134
<211> LENGTH: 6
<212> TYPE: PRT
<213> ORGANISM: Artificial Sequence
<220> FEATURE:
<223> OTHER INFORMATION: Peptide motif

<400> SEQUENCE: 134

Gln Leu Ile Val Met Pro
 1               5


<210> SEQ ID NO 135
<211> LENGTH: 8
<212> TYPE: PRT
<213> ORGANISM: Artificial Sequence
<220> FEATURE:
<223> OTHER INFORMATION: Peptide motif

<400> SEQUENCE: 135

Phe Trp Tyr Met Ile Val Leu Ala
```

1 5

<210> SEQ ID NO 136
<211> LENGTH: 7
<212> TYPE: PRT
<213> ORGANISM: Artificial Sequence
<220> FEATURE:
<223> OTHER INFORMATION: Peptide motif

<400> SEQUENCE: 136

Leu Met Val Gln Ile Ala Thr
1 5

<210> SEQ ID NO 137
<211> LENGTH: 6
<212> TYPE: PRT
<213> ORGANISM: Artificial Sequence
<220> FEATURE:
<223> OTHER INFORMATION: Peptide motif

<400> SEQUENCE: 137

Val Leu Ile Met Ala Thr
1 5

<210> SEQ ID NO 138
<211> LENGTH: 11
<212> TYPE: PRT
<213> ORGANISM: Artificial Sequence
<220> FEATURE:
<223> OTHER INFORMATION: Peptide motif

<400> SEQUENCE: 138

Leu Met Val Ile Ser Ala Thr Phe Cys Gly Asp
1 5 10

<210> SEQ ID NO 139
<211> LENGTH: 6
<212> TYPE: PRT
<213> ORGANISM: Artificial Sequence
<220> FEATURE:
<223> OTHER INFORMATION: Peptide motif

<400> SEQUENCE: 139

Lys Tyr Arg His Phe Ala
1 5

<210> SEQ ID NO 140
<211> LENGTH: 12
<212> TYPE: PRT
<213> ORGANISM: Artificial Sequence
<220> FEATURE:
<223> OTHER INFORMATION: Peptide motif

<400> SEQUENCE: 140

Val Thr Met Leu Ile Ser Ala Gly Asn Cys Asp Phe
1 5 10

<210> SEQ ID NO 141
<211> LENGTH: 4
<212> TYPE: PRT
<213> ORGANISM: Artificial Sequence
<220> FEATURE:
<223> OTHER INFORMATION: Peptide motif

<400> SEQUENCE: 141

Lys Arg Tyr His
1

<210> SEQ ID NO 142
<211> LENGTH: 4
<212> TYPE: PRT
<213> ORGANISM: Artificial Sequence
<220> FEATURE:
<223> OTHER INFORMATION: Peptide motif

<400> SEQUENCE: 142

Tyr Phe Trp Met
 1

<210> SEQ ID NO 143
<211> LENGTH: 4
<212> TYPE: PRT
<213> ORGANISM: Artificial Sequence
<220> FEATURE:
<223> OTHER INFORMATION: Peptide motif

<400> SEQUENCE: 143

Phe Leu Ile Trp
 1

<210> SEQ ID NO 144
<211> LENGTH: 7
<212> TYPE: PRT
<213> ORGANISM: Artificial Sequence
<220> FEATURE:
<223> OTHER INFORMATION: Peptide motif

<400> SEQUENCE: 144

Met Val Thr Ala Leu Ile Ser
 1               5

<210> SEQ ID NO 145
<211> LENGTH: 8
<212> TYPE: PRT
<213> ORGANISM: Artificial Sequence
<220> FEATURE:
<223> OTHER INFORMATION: Peptide motif

<400> SEQUENCE: 145

Met Val Ala Leu Phe Ile Ser Thr
 1               5

<210> SEQ ID NO 146
<211> LENGTH: 7
<212> TYPE: PRT
<213> ORGANISM: Artificial Sequence
<220> FEATURE:
<223> OTHER INFORMATION: Peptide motif

<400> SEQUENCE: 146

Ala Val Thr Met Ser Leu Ile
 1               5

<210> SEQ ID NO 147
<211> LENGTH: 8
<212> TYPE: PRT
<213> ORGANISM: Artificial Sequence
<220> FEATURE:
<223> OTHER INFORMATION: Peptide motif

<400> SEQUENCE: 147

Leu Met Phe Trp Tyr Ala Ile Val
 1               5

<210> SEQ ID NO 148
<211> LENGTH: 8
<212> TYPE: PRT
<213> ORGANISM: Artificial Sequence
<220> FEATURE:
<223> OTHER INFORMATION: Peptide motif

<400> SEQUENCE: 148

Leu Met Phe Trp Tyr Ile Val Ala
1 5

<210> SEQ ID NO 149
<211> LENGTH: 8
<212> TYPE: PRT
<213> ORGANISM: Artificial Sequence
<220> FEATURE:
<223> OTHER INFORMATION: Peptide motif

<400> SEQUENCE: 149

Leu Ile Val Phe Trp Tyr Ala Met
1 5

<210> SEQ ID NO 150
<211> LENGTH: 8
<212> TYPE: PRT
<213> ORGANISM: Artificial Sequence
<220> FEATURE:
<223> OTHER INFORMATION: Peptide motif

<400> SEQUENCE: 150

Ile Met Phe Trp Tyr Ala Leu Val
1 5

<210> SEQ ID NO 151
<211> LENGTH: 9
<212> TYPE: PRT
<213> ORGANISM: Artificial Sequence
<220> FEATURE:
<223> OTHER INFORMATION: Peptide motif

<400> SEQUENCE: 151

Ala Thr Ile Val Leu Met Phe Trp Tyr
1 5

<210> SEQ ID NO 152
<211> LENGTH: 7
<212> TYPE: PRT
<213> ORGANISM: Artificial Sequence
<220> FEATURE:
<223> OTHER INFORMATION: Peptide motif

<400> SEQUENCE: 152

Phe Met Tyr Leu Ile Val Trp
1 5

<210> SEQ ID NO 153
<211> LENGTH: 9
<212> TYPE: PRT
<213> ORGANISM: Artificial Sequence
<220> FEATURE:
<223> OTHER INFORMATION: Peptide motif

<400> SEQUENCE: 153

Val Ser Thr Cys Pro Ala Leu Ile Met
1 5

<210> SEQ ID NO 154
<211> LENGTH: 7
<212> TYPE: PRT
<213> ORGANISM: Artificial Sequence
<220> FEATURE:
<223> OTHER INFORMATION: Peptide motif

<400> SEQUENCE: 154

Met Phe Leu Ile Val Trp Tyr
 1               5

<210> SEQ ID NO 155
<211> LENGTH: 4
<212> TYPE: PRT
<213> ORGANISM: Artificial Sequence
<220> FEATURE:
<223> OTHER INFORMATION: Peptide motif

<400> SEQUENCE: 155

Pro Ala Met Gln
 1

<210> SEQ ID NO 156
<211> LENGTH: 9
<212> TYPE: PRT
<213> ORGANISM: Artificial Sequence
<220> FEATURE:
<223> OTHER INFORMATION: Peptide motif

<400> SEQUENCE: 156

Val Met Ala Thr Ser Pro Leu Ile Cys
 1               5

<210> SEQ ID NO 157
<211> LENGTH: 7
<212> TYPE: PRT
<213> ORGANISM: Artificial Sequence
<220> FEATURE:
<223> OTHER INFORMATION: Peptide motif

<400> SEQUENCE: 157

Met Phe Leu Ile Val Trp Tyr
 1               5

<210> SEQ ID NO 158
<211> LENGTH: 9
<212> TYPE: PRT
<213> ORGANISM: Artificial Sequence
<220> FEATURE:
<223> OTHER INFORMATION: Peptide motif

<400> SEQUENCE: 158

Ile Val Met Ser Ala Cys Thr Pro Leu
 1               5

<210> SEQ ID NO 159
<211> LENGTH: 6
<212> TYPE: PRT
<213> ORGANISM: Artificial Sequence
<220> FEATURE:
<223> OTHER INFORMATION: Peptide motif

<400> SEQUENCE: 159

Leu Ile Val Met Phe Tyr
 1               5

<210> SEQ ID NO 160

<211> LENGTH: 7
<212> TYPE: PRT
<213> ORGANISM: Artificial Sequence
<220> FEATURE:
<223> OTHER INFORMATION: Peptide motif

<400> SEQUENCE: 160

Leu Ile Val Met Phe Ala Tyr
1 5

<210> SEQ ID NO 161
<211> LENGTH: 6
<212> TYPE: PRT
<213> ORGANISM: Artificial Sequence
<220> FEATURE:
<223> OTHER INFORMATION: Peptide motif

<400> SEQUENCE: 161

Asp Asn Gln Glu Ser Thr
1 5

<210> SEQ ID NO 162
<211> LENGTH: 7
<212> TYPE: PRT
<213> ORGANISM: Artificial Sequence
<220> FEATURE:
<223> OTHER INFORMATION: Peptide motif

<400> SEQUENCE: 162

Met Phe Leu Ile Val Trp Tyr
1 5

<210> SEQ ID NO 163
<211> LENGTH: 9
<212> TYPE: PRT
<213> ORGANISM: Artificial Sequence
<220> FEATURE:
<223> OTHER INFORMATION: Peptide motif

<400> SEQUENCE: 163

Val Met Ser Thr Ala Cys Pro Leu Ile
1 5

<210> SEQ ID NO 164
<211> LENGTH: 6
<212> TYPE: PRT
<213> ORGANISM: Artificial Sequence
<220> FEATURE:
<223> OTHER INFORMATION: Peptide motif

<400> SEQUENCE: 164

Thr Ile Leu Val Met Ser
1 5

<210> SEQ ID NO 165
<211> LENGTH: 7
<212> TYPE: PRT
<213> ORGANISM: Artificial Sequence
<220> FEATURE:
<223> OTHER INFORMATION: Peptide motif

<400> SEQUENCE: 165

Leu Ile Val Met Ala Thr Gln
1 5

<210> SEQ ID NO 166
<211> LENGTH: 6

<212> TYPE: PRT
<213> ORGANISM: Artificial Sequence
<220> FEATURE:
<223> OTHER INFORMATION: Peptide motif

<400> SEQUENCE: 166

Leu Ile Val Met Ala Thr
 1               5

<210> SEQ ID NO 167
<211> LENGTH: 7
<212> TYPE: PRT
<213> ORGANISM: Artificial Sequence
<220> FEATURE:
<223> OTHER INFORMATION: Peptide motif

<400> SEQUENCE: 167

Val Ser Met Ala Thr Leu Ile
 1               5

<210> SEQ ID NO 168
<211> LENGTH: 8
<212> TYPE: PRT
<213> ORGANISM: Artificial Sequence
<220> FEATURE:
<223> OTHER INFORMATION: Peptide motif

<400> SEQUENCE: 168

Tyr Phe Trp Ile Val Leu Met Thr
 1               5

<210> SEQ ID NO 169
<211> LENGTH: 6
<212> TYPE: PRT
<213> ORGANISM: Artificial Sequence
<220> FEATURE:
<223> OTHER INFORMATION: Peptide motif

<400> SEQUENCE: 169

Phe Ile Tyr Trp Leu Met
 1               5

<210> SEQ ID NO 170
<211> LENGTH: 4
<212> TYPE: PRT
<213> ORGANISM: Artificial Sequence
<220> FEATURE:
<223> OTHER INFORMATION: Peptide motif

<400> SEQUENCE: 170

Leu Ile Val Met
 1

<210> SEQ ID NO 171
<211> LENGTH: 8
<212> TYPE: PRT
<213> ORGANISM: Artificial Sequence
<220> FEATURE:
<223> OTHER INFORMATION: Peptide motif

<400> SEQUENCE: 171

Val Ile Leu Phe Met Trp Tyr Ala
 1               5

<210> SEQ ID NO 172
<211> LENGTH: 8
<212> TYPE: PRT

<213> ORGANISM: Artificial Sequence
<220> FEATURE:
<223> OTHER INFORMATION: Peptide motif

<400> SEQUENCE: 172

Phe Tyr Leu Trp Met Ile Val Ala
 1               5

<210> SEQ ID NO 173
<211> LENGTH: 8
<212> TYPE: PRT
<213> ORGANISM: Artificial Sequence
<220> FEATURE:
<223> OTHER INFORMATION: Peptide motif

<400> SEQUENCE: 173

Phe Trp Tyr Leu Ile Met Val Ala
 1               5

<210> SEQ ID NO 174
<211> LENGTH: 8
<212> TYPE: PRT
<213> ORGANISM: Artificial Sequence
<220> FEATURE:
<223> OTHER INFORMATION: Peptide motif

<400> SEQUENCE: 174

Phe Trp Tyr Leu Ile Val Met Ala
 1               5

<210> SEQ ID NO 175
<211> LENGTH: 6
<212> TYPE: PRT
<213> ORGANISM: Artificial Sequence
<220> FEATURE:
<223> OTHER INFORMATION: Peptide motif

<400> SEQUENCE: 175

Gln Leu Ile Val Met Pro
 1               5

<210> SEQ ID NO 176
<211> LENGTH: 8
<212> TYPE: PRT
<213> ORGANISM: Artificial Sequence
<220> FEATURE:
<223> OTHER INFORMATION: Peptide motif

<400> SEQUENCE: 176

Phe Trp Tyr Met Ile Val Leu Ala
 1               5

<210> SEQ ID NO 177
<211> LENGTH: 4
<212> TYPE: PRT
<213> ORGANISM: Artificial Sequence
<220> FEATURE:
<223> OTHER INFORMATION: Peptide motif

<400> SEQUENCE: 177

Gly Phe Tyr Trp
 1

<210> SEQ ID NO 178
<211> LENGTH: 4
<212> TYPE: PRT
<213> ORGANISM: Artificial Sequence
<220> FEATURE:
<223> OTHER INFORMATION: Peptide motif

<400> SEQUENCE: 178

Asp Glu Gln Asn
1

<210> SEQ ID NO 179
<211> LENGTH: 8
<212> TYPE: PRT
<213> ORGANISM: Artificial Sequence
<220> FEATURE:
<223> OTHER INFORMATION: Peptide motif

<400> SEQUENCE: 179

Arg His Lys Leu Ile Val Met Pro
1 5

<210> SEQ ID NO 180
<211> LENGTH: 4
<212> TYPE: PRT
<213> ORGANISM: Artificial Sequence
<220> FEATURE:
<223> OTHER INFORMATION: Peptide motif

<400> SEQUENCE: 180

Gly Arg His Lys
1

<210> SEQ ID NO 181
<211> LENGTH: 8
<212> TYPE: PRT
<213> ORGANISM: Artificial Sequence
<220> FEATURE:
<223> OTHER INFORMATION: Peptide motif

<400> SEQUENCE: 181

Ala Ser Thr Cys Leu Ile Val Met
1 5

<210> SEQ ID NO 182
<211> LENGTH: 4
<212> TYPE: PRT
<213> ORGANISM: Artificial Sequence
<220> FEATURE:
<223> OTHER INFORMATION: Peptide motif

<400> SEQUENCE: 182

Asp Glu Ala Ser
1

<210> SEQ ID NO 183
<211> LENGTH: 4
<212> TYPE: PRT
<213> ORGANISM: Artificial Sequence
<220> FEATURE:
<223> OTHER INFORMATION: Peptide motif

<400> SEQUENCE: 183

Gly Ser Thr Cys
1

<210> SEQ ID NO 184
<211> LENGTH: 4
<212> TYPE: PRT
<213> ORGANISM: Artificial Sequence
<220> FEATURE:

<223> OTHER INFORMATION: Peptide motif

<400> SEQUENCE: 184

Ala Ser Thr Cys
1

<210> SEQ ID NO 185
<211> LENGTH: 4
<212> TYPE: PRT
<213> ORGANISM: Artificial Sequence
<220> FEATURE:
<223> OTHER INFORMATION: Peptide motif

<400> SEQUENCE: 185

Leu Ile Val Met
1

<210> SEQ ID NO 186
<211> LENGTH: 9
<212> TYPE: PRT
<213> ORGANISM: Artificial Sequence
<220> FEATURE:
<223> OTHER INFORMATION: Peptide motif

<400> SEQUENCE: 186

Arg His Lys Asp Glu Pro Tyr Phe Trp
1 5

<210> SEQ ID NO 187
<211> LENGTH: 5
<212> TYPE: PRT
<213> ORGANISM: Artificial Sequence
<220> FEATURE:
<223> OTHER INFORMATION: Peptide motif

<400> SEQUENCE: 187

Asp Glu Ala Gln Asn
1 5

<210> SEQ ID NO 188
<211> LENGTH: 5
<212> TYPE: PRT
<213> ORGANISM: Artificial Sequence
<220> FEATURE:
<223> OTHER INFORMATION: Peptide motif

<400> SEQUENCE: 188

Tyr Phe Trp Gln Asn
1 5

<210> SEQ ID NO 189
<211> LENGTH: 5
<212> TYPE: PRT
<213> ORGANISM: Artificial Sequence
<220> FEATURE:
<223> OTHER INFORMATION: Peptide motif

<400> SEQUENCE: 189

Pro Ala Ser Thr Cys
1 5

<210> SEQ ID NO 190
<211> LENGTH: 8
<212> TYPE: PRT
<213> ORGANISM: Artificial Sequence
<220> FEATURE:
<223> OTHER INFORMATION: Peptide motif

<400> SEQUENCE: 190

Arg His Lys Gly Leu Ile Val Met
 1               5

<210> SEQ ID NO 191
<211> LENGTH: 6
<212> TYPE: PRT
<213> ORGANISM: Artificial Sequence
<220> FEATURE:
<223> OTHER INFORMATION: Peptide motif

<400> SEQUENCE: 191

Arg His Lys Tyr Phe Trp
 1               5

<210> SEQ ID NO 192
<211> LENGTH: 7
<212> TYPE: PRT
<213> ORGANISM: Artificial Sequence
<220> FEATURE:
<223> OTHER INFORMATION: Peptide motif

<400> SEQUENCE: 192

Ser Thr Cys Leu Ile Val Met
 1               5

<210> SEQ ID NO 193
<211> LENGTH: 4
<212> TYPE: PRT
<213> ORGANISM: Artificial Sequence
<220> FEATURE:
<223> OTHER INFORMATION: Peptide motif

<400> SEQUENCE: 193

Asp Glu Ala Ser
 1

<210> SEQ ID NO 194
<211> LENGTH: 9
<212> TYPE: PRT
<213> ORGANISM: Artificial Sequence
<220> FEATURE:
<223> OTHER INFORMATION: Peptide motif

<400> SEQUENCE: 194

Arg His Lys Asp Glu Pro Tyr Phe Trp
 1               5

<210> SEQ ID NO 195
<211> LENGTH: 4
<212> TYPE: PRT
<213> ORGANISM: Artificial Sequence
<220> FEATURE:
<223> OTHER INFORMATION: Peptide motif

<400> SEQUENCE: 195

Pro Arg His Lys
 1

<210> SEQ ID NO 196
<211> LENGTH: 7
<212> TYPE: PRT
<213> ORGANISM: Artificial Sequence
<220> FEATURE:
<223> OTHER INFORMATION: Peptide motif

<400> SEQUENCE: 196

Leu Met Ile Val Gln Ala Thr
 1               5

<210> SEQ ID NO 197
<211> LENGTH: 6
<212> TYPE: PRT
<213> ORGANISM: Artificial Sequence
<220> FEATURE:
<223> OTHER INFORMATION: Peptide motif

<400> SEQUENCE: 197

Val Leu Ile Met Ala Thr
 1               5

<210> SEQ ID NO 198
<211> LENGTH: 5
<212> TYPE: PRT
<213> ORGANISM: Artificial Sequence
<220> FEATURE:
<223> OTHER INFORMATION: Peptide motif

<400> SEQUENCE: 198

Asp Glu Arg Lys His
 1               5

<210> SEQ ID NO 199
<211> LENGTH: 5
<212> TYPE: PRT
<213> ORGANISM: Artificial Sequence
<220> FEATURE:
<223> OTHER INFORMATION: Peptide motif

<400> SEQUENCE: 199

Asp Glu Arg Lys His
 1               5

<210> SEQ ID NO 200
<211> LENGTH: 7
<212> TYPE: PRT
<213> ORGANISM: Artificial Sequence
<220> FEATURE:
<223> OTHER INFORMATION: Peptide motif

<400> SEQUENCE: 200

Leu Met Ile Val Gln Ala Thr
 1               5

<210> SEQ ID NO 201
<211> LENGTH: 4
<212> TYPE: PRT
<213> ORGANISM: Artificial Sequence
<220> FEATURE:
<223> OTHER INFORMATION: Peptide motif

<400> SEQUENCE: 201

Leu Val Ile Met
 1

<210> SEQ ID NO 202
<211> LENGTH: 7
<212> TYPE: PRT
<213> ORGANISM: Artificial Sequence
<220> FEATURE:
<223> OTHER INFORMATION: Peptide motif

<400> SEQUENCE: 202

-continued

Phe Tyr Trp Leu Val Ile Met
1 5

<210> SEQ ID NO 203
<211> LENGTH: 6
<212> TYPE: PRT
<213> ORGANISM: Artificial Sequence
<220> FEATURE:
<223> OTHER INFORMATION: Peptide motif

<400> SEQUENCE: 203

Val Leu Ile Met Ala Thr
1 5

<210> SEQ ID NO 204
<211> LENGTH: 4
<212> TYPE: PRT
<213> ORGANISM: Artificial Sequence
<220> FEATURE:
<223> OTHER INFORMATION: Peptide motif

<400> SEQUENCE: 204

Arg Lys His Ala
1

<210> SEQ ID NO 205
<211> LENGTH: 5
<212> TYPE: PRT
<213> ORGANISM: Artificial Sequence
<220> FEATURE:
<223> OTHER INFORMATION: Peptide motif

<400> SEQUENCE: 205

Asp Glu Arg Lys His
1 5

<210> SEQ ID NO 206
<211> LENGTH: 11
<212> TYPE: PRT
<213> ORGANISM: Artificial Sequence
<220> FEATURE:
<223> OTHER INFORMATION: Peptide motif

<400> SEQUENCE: 206

Leu Met Val Ile Ser Ala Thr Phe Cys Gly Asp
1 5 10

<210> SEQ ID NO 207
<211> LENGTH: 7
<212> TYPE: PRT
<213> ORGANISM: Artificial Sequence
<220> FEATURE:
<223> OTHER INFORMATION: Peptide motif

<400> SEQUENCE: 207

Pro Arg His Lys Tyr Phe Trp
1 5

<210> SEQ ID NO 208
<211> LENGTH: 6
<212> TYPE: PRT
<213> ORGANISM: Artificial Sequence
<220> FEATURE:
<223> OTHER INFORMATION: Peptide motif

<400> SEQUENCE: 208

-continued

```
Lys Tyr Arg His Phe Ala
 1               5


<210> SEQ ID NO 209
<211> LENGTH: 12
<212> TYPE: PRT
<213> ORGANISM: Artificial Sequence
<220> FEATURE:
<223> OTHER INFORMATION: Peptide motif

<400> SEQUENCE: 209

Val Thr Leu Met Ile Ser Ala Gly Asn Cys Asp Phe
 1               5                  10


<210> SEQ ID NO 210
<211> LENGTH: 4
<212> TYPE: PRT
<213> ORGANISM: Artificial Sequence
<220> FEATURE:
<223> OTHER INFORMATION: Peptide motif

<400> SEQUENCE: 210

Lys Arg Tyr His
 1


<210> SEQ ID NO 211
<211> LENGTH: 6
<212> TYPE: PRT
<213> ORGANISM: Artificial Sequence
<220> FEATURE:
<223> OTHER INFORMATION: Peptide motif

<400> SEQUENCE: 211

Tyr Phe Trp Arg His Lys
 1               5


<210> SEQ ID NO 212
<211> LENGTH: 4
<212> TYPE: PRT
<213> ORGANISM: Artificial Sequence
<220> FEATURE:
<223> OTHER INFORMATION: Peptide motif

<400> SEQUENCE: 212

Tyr Phe Trp Met
 1


<210> SEQ ID NO 213
<211> LENGTH: 4
<212> TYPE: PRT
<213> ORGANISM: Artificial Sequence
<220> FEATURE:
<223> OTHER INFORMATION: Peptide motif

<400> SEQUENCE: 213

Phe Leu Ile Trp
 1


<210> SEQ ID NO 214
<211> LENGTH: 5
<212> TYPE: PRT
<213> ORGANISM: Artificial Sequence
<220> FEATURE:
<223> OTHER INFORMATION: Peptide motif

<400> SEQUENCE: 214

Asp Glu Arg His Lys
```

1 5

<210> SEQ ID NO 215
<211> LENGTH: 4
<212> TYPE: PRT
<213> ORGANISM: Artificial Sequence
<220> FEATURE:
<223> OTHER INFORMATION: Peptide motif

<400> SEQUENCE: 215

Tyr Phe Trp Met
1

<210> SEQ ID NO 216
<211> LENGTH: 4
<212> TYPE: PRT
<213> ORGANISM: Artificial Sequence
<220> FEATURE:
<223> OTHER INFORMATION: Peptide motif

<400> SEQUENCE: 216

Tyr Phe Trp Pro
1

<210> SEQ ID NO 217
<211> LENGTH: 4
<212> TYPE: PRT
<213> ORGANISM: Artificial Sequence
<220> FEATURE:
<223> OTHER INFORMATION: Peptide motif

<400> SEQUENCE: 217

Phe Leu Ile Trp
1

<210> SEQ ID NO 218
<211> LENGTH: 7
<212> TYPE: PRT
<213> ORGANISM: Artificial Sequence
<220> FEATURE:
<223> OTHER INFORMATION: Peptide motif

<400> SEQUENCE: 218

Met Val Thr Ala Leu Ile Ser
1 5

<210> SEQ ID NO 219
<211> LENGTH: 8
<212> TYPE: PRT
<213> ORGANISM: Artificial Sequence
<220> FEATURE:
<223> OTHER INFORMATION: Peptide motif

<400> SEQUENCE: 219

Met Val Ala Leu Phe Ile Ser Thr
1 5

<210> SEQ ID NO 220
<211> LENGTH: 4
<212> TYPE: PRT
<213> ORGANISM: Artificial Sequence
<220> FEATURE:
<223> OTHER INFORMATION: Peptide motif

<400> SEQUENCE: 220

Ala Tyr Phe Trp
1

<210> SEQ ID NO 221
<211> LENGTH: 6
<212> TYPE: PRT
<213> ORGANISM: Artificial Sequence
<220> FEATURE:
<223> OTHER INFORMATION: Peptide motif

<400> SEQUENCE: 221

Tyr Phe Trp Ser Thr Cys
1 5

<210> SEQ ID NO 222
<211> LENGTH: 7
<212> TYPE: PRT
<213> ORGANISM: Artificial Sequence
<220> FEATURE:
<223> OTHER INFORMATION: Peptide motif

<400> SEQUENCE: 222

Ala Val Thr Met Ser Leu Ile
1 5

<210> SEQ ID NO 223
<211> LENGTH: 7
<212> TYPE: PRT
<213> ORGANISM: Artificial Sequence
<220> FEATURE:
<223> OTHER INFORMATION: Peptide motif

<400> SEQUENCE: 223

Tyr Phe Trp Leu Ile Val Met
1 5

<210> SEQ ID NO 224
<211> LENGTH: 6
<212> TYPE: PRT
<213> ORGANISM: Artificial Sequence
<220> FEATURE:
<223> OTHER INFORMATION: Peptide motif

<400> SEQUENCE: 224

Arg His Lys Phe Trp Tyr
1 5

<210> SEQ ID NO 225
<211> LENGTH: 8
<212> TYPE: PRT
<213> ORGANISM: Artificial Sequence
<220> FEATURE:
<223> OTHER INFORMATION: Peptide motif

<400> SEQUENCE: 225

Leu Met Phe Trp Tyr Ala Ile Val
1 5

<210> SEQ ID NO 226
<211> LENGTH: 5
<212> TYPE: PRT
<213> ORGANISM: Artificial Sequence
<220> FEATURE:
<223> OTHER INFORMATION: Peptide motif

<400> SEQUENCE: 226

Asp Glu Gln Asn Pro
1 5

```
<210> SEQ ID NO 227
<211> LENGTH: 7
<212> TYPE: PRT
<213> ORGANISM: Artificial Sequence
<220> FEATURE:
<223> OTHER INFORMATION: Peptide motif

<400> SEQUENCE: 227

Phe Trp Tyr Leu Ile Val Met
 1               5


<210> SEQ ID NO 228
<211> LENGTH: 8
<212> TYPE: PRT
<213> ORGANISM: Artificial Sequence
<220> FEATURE:
<223> OTHER INFORMATION: Peptide motif

<400> SEQUENCE: 228

Leu Met Phe Trp Tyr Ile Val Ala
 1               5


<210> SEQ ID NO 229
<211> LENGTH: 7
<212> TYPE: PRT
<213> ORGANISM: Artificial Sequence
<220> FEATURE:
<223> OTHER INFORMATION: Peptide motif

<400> SEQUENCE: 229

Leu Ile Val Met Phe Trp Tyr
 1               5


<210> SEQ ID NO 230
<211> LENGTH: 8
<212> TYPE: PRT
<213> ORGANISM: Artificial Sequence
<220> FEATURE:
<223> OTHER INFORMATION: Peptide motif

<400> SEQUENCE: 230

Leu Ile Val Phe Trp Tyr Ala Met
 1               5


<210> SEQ ID NO 231
<211> LENGTH: 11
<212> TYPE: PRT
<213> ORGANISM: Artificial Sequence
<220> FEATURE:
<223> OTHER INFORMATION: Peptide motif

<400> SEQUENCE: 231

Ala Gly Pro Asp Glu Arg His Lys Ser Thr Cys
 1               5                   10


<210> SEQ ID NO 232
<211> LENGTH: 4
<212> TYPE: PRT
<213> ORGANISM: Artificial Sequence
<220> FEATURE:
<223> OTHER INFORMATION: Peptide motif

<400> SEQUENCE: 232

Asp Glu Gln Asn
 1
```

```
<210> SEQ ID NO 233
<211> LENGTH: 7
<212> TYPE: PRT
<213> ORGANISM: Artificial Sequence
<220> FEATURE:
<223> OTHER INFORMATION: Peptide motif

<400> SEQUENCE: 233

Leu Ile Val Met Phe Trp Tyr
 1               5


<210> SEQ ID NO 234
<211> LENGTH: 7
<212> TYPE: PRT
<213> ORGANISM: Artificial Sequence
<220> FEATURE:
<223> OTHER INFORMATION: Peptide motif

<400> SEQUENCE: 234

Leu Ile Val Met Phe Trp Tyr
 1               5


<210> SEQ ID NO 235
<211> LENGTH: 8
<212> TYPE: PRT
<213> ORGANISM: Artificial Sequence
<220> FEATURE:
<223> OTHER INFORMATION: Peptide motif

<400> SEQUENCE: 235

Ile Met Phe Trp Tyr Ala Leu Val
 1               5


<210> SEQ ID NO 236
<211> LENGTH: 5
<212> TYPE: PRT
<213> ORGANISM: Artificial Sequence
<220> FEATURE:
<223> OTHER INFORMATION: Peptide motif

<400> SEQUENCE: 236

Ala Gly Pro Gln Asn
 1               5


<210> SEQ ID NO 237
<211> LENGTH: 5
<212> TYPE: PRT
<213> ORGANISM: Artificial Sequence
<220> FEATURE:
<223> OTHER INFORMATION: Peptide motif

<400> SEQUENCE: 237

Arg His Lys Gln Asn
 1               5


<210> SEQ ID NO 238
<211> LENGTH: 7
<212> TYPE: PRT
<213> ORGANISM: Artificial Sequence
<220> FEATURE:
<223> OTHER INFORMATION: Peptide motif

<400> SEQUENCE: 238

Phe Trp Tyr Leu Ile Val Met
 1               5


<210> SEQ ID NO 239
```

```
<211> LENGTH: 4
<212> TYPE: PRT
<213> ORGANISM: Artificial Sequence
<220> FEATURE:
<223> OTHER INFORMATION: Peptide motif

<400> SEQUENCE: 239

Leu Ile Val Met
 1


<210> SEQ ID NO 240
<211> LENGTH: 5
<212> TYPE: PRT
<213> ORGANISM: Artificial Sequence
<220> FEATURE:
<223> OTHER INFORMATION: Peptide motif

<400> SEQUENCE: 240

Ala Leu Ile Val Met
 1               5


<210> SEQ ID NO 241
<211> LENGTH: 5
<212> TYPE: PRT
<213> ORGANISM: Artificial Sequence
<220> FEATURE:
<223> OTHER INFORMATION: Peptide motif

<400> SEQUENCE: 241

Phe Trp Tyr Ala Pro
 1               5


<210> SEQ ID NO 242
<211> LENGTH: 9
<212> TYPE: PRT
<213> ORGANISM: Artificial Sequence
<220> FEATURE:
<223> OTHER INFORMATION: Peptide motif

<400> SEQUENCE: 242

Ala Thr Ile Val Leu Met Phe Trp Tyr
 1               5


<210> SEQ ID NO 243
<211> LENGTH: 6
<212> TYPE: PRT
<213> ORGANISM: Artificial Sequence
<220> FEATURE:
<223> OTHER INFORMATION: Peptide motif

<400> SEQUENCE: 243

Gly Pro Gln Asn Asp Glu
 1               5


<210> SEQ ID NO 244
<211> LENGTH: 6
<212> TYPE: PRT
<213> ORGANISM: Artificial Sequence
<220> FEATURE:
<223> OTHER INFORMATION: Peptide motif

<400> SEQUENCE: 244

Gly Asp Glu Ser Thr Cys
 1               5


<210> SEQ ID NO 245
<211> LENGTH: 5
```

<212> TYPE: PRT
<213> ORGANISM: Artificial Sequence
<220> FEATURE:
<223> OTHER INFORMATION: Peptide motif

<400> SEQUENCE: 245

Arg His Lys Asp Glu
1 5

<210> SEQ ID NO 246
<211> LENGTH: 5
<212> TYPE: PRT
<213> ORGANISM: Artificial Sequence
<220> FEATURE:
<223> OTHER INFORMATION: Peptide motif

<400> SEQUENCE: 246

Gln Asn Asp Gly Glu
1 5

<210> SEQ ID NO 247
<211> LENGTH: 4
<212> TYPE: PRT
<213> ORGANISM: Artificial Sequence
<220> FEATURE:
<223> OTHER INFORMATION: Peptide motif

<400> SEQUENCE: 247

Asp Glu Ala Ser
1

<210> SEQ ID NO 248
<211> LENGTH: 8
<212> TYPE: PRT
<213> ORGANISM: Artificial Sequence
<220> FEATURE:
<223> OTHER INFORMATION: Peptide motif

<400> SEQUENCE: 248

Ala Ile Leu Met Val Phe Trp Tyr
1 5

<210> SEQ ID NO 249
<211> LENGTH: 7
<212> TYPE: PRT
<213> ORGANISM: Artificial Sequence
<220> FEATURE:
<223> OTHER INFORMATION: Peptide motif

<400> SEQUENCE: 249

Ala Ile Leu Met Val Ser Thr
1 5

<210> SEQ ID NO 250
<211> LENGTH: 6
<212> TYPE: PRT
<213> ORGANISM: Artificial Sequence
<220> FEATURE:
<223> OTHER INFORMATION: Peptide motif

<400> SEQUENCE: 250

Ala Ile Leu Met Val Thr
1 5

<210> SEQ ID NO 251
<211> LENGTH: 6
<212> TYPE: PRT

<213> ORGANISM: Artificial Sequence
<220> FEATURE:
<223> OTHER INFORMATION: Peptide motif

<400> SEQUENCE: 251

Ala Ile Leu Met Val Thr
1 5

<210> SEQ ID NO 252
<211> LENGTH: 8
<212> TYPE: PRT
<213> ORGANISM: Artificial Sequence
<220> FEATURE:
<223> OTHER INFORMATION: Peptide motif

<400> SEQUENCE: 252

Tyr Phe Trp Ile Val Leu Met Thr
1 5

<210> SEQ ID NO 253
<211> LENGTH: 6
<212> TYPE: PRT
<213> ORGANISM: Artificial Sequence
<220> FEATURE:
<223> OTHER INFORMATION: Peptide motif

<400> SEQUENCE: 253

Phe Ile Tyr Trp Leu Met
1 5

<210> SEQ ID NO 254
<211> LENGTH: 8
<212> TYPE: PRT
<213> ORGANISM: Artificial Sequence
<220> FEATURE:
<223> OTHER INFORMATION: Peptide motif

<400> SEQUENCE: 254

Phe Trp Tyr Leu Ile Met Val Ala
1 5

<210> SEQ ID NO 255
<211> LENGTH: 6
<212> TYPE: PRT
<213> ORGANISM: Artificial Sequence
<220> FEATURE:
<223> OTHER INFORMATION: Peptide motif

<400> SEQUENCE: 255

Thr Ile Leu Val Met Ser
1 5

<210> SEQ ID NO 256
<211> LENGTH: 6
<212> TYPE: PRT
<213> ORGANISM: Artificial Sequence
<220> FEATURE:
<223> OTHER INFORMATION: Peptide motif

<400> SEQUENCE: 256

Phe Tyr Leu Trp Met Ile
1 5

<210> SEQ ID NO 257
<211> LENGTH: 6
<212> TYPE: PRT
<213> ORGANISM: Artificial Sequence -continued

```
<220> FEATURE:
<223> OTHER INFORMATION: Peptide motif

<400> SEQUENCE: 257

Gln Leu Ile Val Met Pro
 1               5


<210> SEQ ID NO 258
<211> LENGTH: 6
<212> TYPE: PRT
<213> ORGANISM: Artificial Sequence
<220> FEATURE:
<223> OTHER INFORMATION: Peptide motif

<400> SEQUENCE: 258

Phe Trp Tyr Met Ile Val
 1               5


<210> SEQ ID NO 259
<211> LENGTH: 6
<212> TYPE: PRT
<213> ORGANISM: Artificial Sequence
<220> FEATURE:
<223> OTHER INFORMATION: Peptide motif

<400> SEQUENCE: 259

Phe Trp Tyr Leu Ile Val
 1               5
```

NUCLEIC ACID AND CORRESPONDING PROTEIN ENTITLED 193P1E1B USEFUL IN TREATMENT AND DETECTION OF CANCER

CROSS-REFERENCE TO RELATED APPLICATIONS

This application claims priority from pending U.S. patent application Ser. No. 10/013,312, filed 7 Dec. 2001. The contents of the application listed in this paragraph is fully incorporated by reference herein.

STATEMENT OF RIGHTS TO INVENTIONS MADE UNDER FEDERALLY SPONSORED RESEARCH

Not applicable.

FIELD OF THE INVENTION

The invention described herein relates to a gene and its encoded protein, termed 193P1E1B, expressed in certain cancers, and to diagnostic and therapeutic methods and compositions useful in the management of cancers that express 193P1E1B.

BACKGROUND OF THE INVENTION

Cancer is the second leading cause of human death next to coronary disease. Worldwide, millions of people die from cancer every year. In the United States alone, as reported by the American Cancer Society, cancer causes the death of well over a half-million people annually, with over 1.2 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Furthermore, many cancer patients experience a recurrence.

Worldwide, prostate cancer is the fourth most prevalent cancer in men. In North America and Northern Europe, it is by far the most common cancer in males and is the second leading cause of cancer death in men. In the United States alone, well over 30,000 men die annually of this disease—second only to lung cancer. Despite the magnitude of these figures, there is still no effective treatment for metastatic prostate cancer. Surgical prostatectomy, radiation therapy, hormone ablation therapy, surgical castration and chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the diagnosis and management of this disease. Although the serum prostate specific antigen (PSA) assay has been a very useful tool, however its specificity and general utility is widely regarded as lacking in several important respects.

Progress in identifying additional specific markers for prostate cancer has been improved by the generation of prostate cancer xenografts that can recapitulate different stages of the disease in mice. The LAPC (Los Angeles Prostate Cancer) xenografts are prostate cancer xenografts that have survived passage in severe combined immune deficient (SCID) mice and have exhibited the capacity to mimic the transition from androgen dependence to androgen independence (Klein et al., 1997, Nat. Med. 3:402). More recently identified prostate cancer markers include PCTA-1 (Su et al., 1996, Proc. Natl. Acad. Sci. USA 93: 7252), prostate-specific membrane (PSM) antigen (Pinto et al., Clin Cancer Res Sep. 2, 1996 (9): 1445-51), STEAP (Hubert, et al., Proc Natl Acad Sci USA. 1999 Dec 7; 96(25): 14523-8) and prostate stem cell antigen (PSCA) (Reiter et al., 1998, Proc. Natl. Acad. Sci. USA 95: 1735).

While previously identified markers such as PSA, PSM, PCTA and PSCA have facilitated efforts to diagnose and treat prostate cancer, there is need for the identification of additional markers and therapeutic targets for prostate and related cancers in order to further improve diagnosis and therapy.

Renal cell carcinoma (RCC) accounts for approximately 3 percent of adult malignancies. Once adenomas reach a diameter of 2 to 3 cm, malignant potential exists. In the adult, the two principal malignant renal tumors are renal cell adenocarcinoma and transitional cell carcinoma of the renal pelvis or ureter. The incidence of renal cell adenocarcinoma is estimated at more than 29,000 cases in the United States, and more than 11,600 patients died of this disease in 1998. Transitional cell carcinoma is less frequent, with an incidence of approximately 500 cases per year in the United States.

Surgery has been the primary therapy for renal cell adenocarcinoma for many decades. Until recently, metastatic disease has been refractory to any systemic therapy. With recent developments in systemic therapies, particularly immunotherapies, metastatic renal cell carcinoma may be approached aggressively in appropriate patients with a possibility of durable responses. Nevertheless, there is a remaining need for effective therapies for these patients.

Of all new cases of cancer in the United States, bladder cancer represents approximately 5 percent in men (fifth most common neoplasm) and 3 percent in women (eighth most common neoplasm). The incidence is increasing slowly, concurrent with an increasing older population. In 1998, there was an estimated 54,500 cases, including 39,500 in men and 15,000 in women. The age-adjusted incidence in the United States is 32 per 100,000 for men and eight per 100,000 in women. The historic male/female ratio of 3:1 may be decreasing related to smoking patterns in women. There were an estimated 11,000 deaths from bladder cancer in 1998 (7,800 in men and 3,900 in women). Bladder cancer incidence and mortality strongly increase with age and will be an increasing problem as the population becomes more elderly.

Most bladder cancers recur in the bladder. Bladder cancer is managed with a combination of transurethral resection of the bladder (TUR) and intravesical chemotherapy or immunotherapy. The multifocal and recurrent nature of bladder cancer points out the limitations of TUR. Most muscle-invasive cancers are not cured by TUR alone. Radical cystectomy and urinary diversion is the most effective means to eliminate the cancer but carry an undeniable impact on urinary and sexual function. There continues to be a significant need for treatment modalities that are beneficial for bladder cancer patients.

An estimated 130,200 cases of colorectal cancer occurred in 2000 in the United States, including 93,800 cases of colon cancer and 36,400 of rectal cancer. Colorectal cancers are the third most common cancers in men and women. Incidence rates declined significantly during 1992-1996 (−2.1% per year). Research suggests that these declines have been due to increased screening and polyp removal, preventing progression of polyps to invasive cancers. There were an estimated 56,300 deaths (47,700 from colon cancer, 8,600 from rectal cancer) in 2000, accounting for about 11% of all U.S. cancer deaths.

At present, surgery is the most common form of therapy for colorectal cancer, and for cancers that have not spread, it is frequently curative. Chemotherapy, or chemotherapy plus radiation, is given before or after surgery to most patients whose cancer has deeply perforated the bowel wall or has spread to the lymph nodes. A permanent colostomy (creation of an abdominal opening for elimination of body wastes) is occasionally needed for colon cancer and is infrequently required for rectal cancer. There continues to be a need for effective diagnostic and treatment modalities for colorectal cancer.

There were an estimated 164,100 new cases of lung and bronchial cancer in 2000, accounting for 14% of all U.S. cancer diagnoses. The incidence rate of lung and bronchial cancer is declining significantly in men, from a high of 86.5 per 100,000 in 1984 to 70.0 in 1996. In the 1990s, the rate of increase among women began to slow. In 1996, the incidence rate in women was 42.3 per 100,000.

Lung and bronchial cancer caused an estimated 156,900 deaths in 2000, accounting for 28% of all cancer deaths. During 1992-1996, mortality from lung cancer declined significantly among men (−1.7% per year) while rates for women were still significantly increasing (0.9% per year). Since 1987, more women have died each year of lung cancer than breast cancer, which, for over 40 years, was the major cause of cancer death in women. Decreasing lung cancer incidence and mortality rates most likely resulted from decreased smoking rates over the previous 30 years; however, decreasing smoking patterns among women lag behind those of men. Of concern, although the declines in adult tobacco use have slowed, tobacco use in youth is increasing again.

Treatment options for lung and bronchial cancer are determined by the type and stage of the cancer and include surgery, radiation therapy, and chemotherapy. For many localized cancers, surgery is usually the treatment of choice. Because the disease has usually spread by the time it is discovered, radiation therapy and chemotherapy are often needed in combination with surgery. Chemotherapy alone or combined with radiation is the treatment of choice for small cell lung cancer; on this regimen, a large percentage of patients experience remission, which in some cases is long lasting. There is however, an ongoing need for effective treatment and diagnostic approaches for lung and bronchial cancers.

An estimated 182,800 new invasive cases of breast cancer were expected to occur among women in the United States during 2000. Additionally, about 1,400 new cases of breast cancer were expected to be diagnosed in men in 2000. After increasing about 4% per year in the 1980s, breast cancer incidence rates in women have leveled off in the 1990s to about 110.6 cases per 100,000.

In the U.S. alone, there were an estimated 41,200 deaths (40,800 women, 400 men) in 2000 due to breast cancer. Breast cancer ranks second among cancer deaths in women. According to the most recent data, mortality rates declined significantly during 1992-1996 with the largest decreases in younger women, both white and black. These decreases were probably the result of earlier detection and improved treatment.

Taking into account the medical circumstances and the patient's preferences, treatment of breast cancer may involve lumpectomy (local removal of the tumor) and removal of the lymph nodes under the arm; mastectomy (surgical removal of the breast) and removal of the lymph nodes under the arm; radiation therapy; chemotherapy; or hormone therapy. Often, two or more methods are used in combination. Numerous studies have shown that, for early stage disease, long-term survival rates after lumpectomy plus radiotherapy are similar to survival rates after modified radical mastectomy. Significant advances in reconstruction techniques provide several options for breast reconstruction after mastectomy. Recently, such reconstruction has been done at the same time as the mastectomy.

Local excision of ductal carcinoma in situ (DCIS) with adequate amounts of surrounding normal breast tissue may prevent the local recurrence of the DCIS. Radiation to the breast and/or tamoxifen may reduce the chance of DCIS occurring in the remaining breast tissue. This is important because DCIS, if left untreated, may develop into invasive breast cancer. Nevertheless, there are serious side effects or sequelae to these treatments. There is, therefore, a need for efficacious breast cancer treatments.

There were an estimated 23,100 new cases of ovarian cancer in the United States in 2000. It accounts for 4% of all cancers among women and ranks second among gynecologic cancers. During 1992-1996, ovarian cancer incidence rates were significantly declining. Consequent to ovarian cancer, there were an estimated 14,000 deaths in 2000. Ovarian cancer causes more deaths than any other cancer of the female reproductive system.

Surgery, radiation therapy, and chemotherapy are treatment options for ovarian cancer. Surgery usually includes the removal of one or both ovaries, the fallopian tubes (salpingo-oophorectomy), and the uterus (hysterectomy). In some very early tumors, only the involved ovary will be removed, especially in young women who wish to have children. In advanced disease, an attempt is made to remove all intra-abdominal disease to enhance the effect of chemotherapy. There continues to be an important need for effective treatment options for ovarian cancer.

There were an estimated 28,300 new cases of pancreatic cancer in the United States in 2000. Over the past 20 years, rates of pancreatic cancer have declined in men. Rates among women have remained approximately constant but may be beginning to decline. Pancreatic cancer caused an estimated 28,200 deaths in 2000 in the United States. Over the past 20 years, there has been a slight but significant decrease in mortality rates among men (about −0.9% per year) while rates have increased slightly among women.

Surgery, radiation therapy, and chemotherapy are treatment options for pancreatic cancer. These treatment options can extend survival and/or relieve symptoms in many patients but are not likely to produce a cure for most. There is a significant need for additional therapeutic and diagnostic options for pancreatic cancer.

SUMMARY OF THE INVENTION

The present invention relates to a gene, designated 193P1 E1 B, that has now been found to be over-expressed in the cancer(s) listed in Table I. Northern blot expression analysis of 193P1E1B gene expression in normal tissues shows a restricted expression pattern in adult tissues. The nucleotide (FIG. 2) and amino acid (FIG. 2, and FIG. 3) sequences of 193P1E1B are provided. The tissue-related profile of 193P1 E1B in normal adult tissues, combined with the over-expression observed in the tissues listed in Table I, shows that 193P1 E1B is aberrantly over-expressed in at least some cancers, and thus serves as a useful diagnostic, prophylactic, prognostic, and/or therapeutic target for cancers of the tissue(s) such as those listed in Table I.

The invention provides polynucleotides corresponding or complementary to all or part of the 193P1E1B genes, mRNAs, and/or coding sequences, preferably in isolated form, including polynucleotides encoding 193P1E1B-related proteins and fragments of 4, 5, 6, 7, 8, 9, 10, 11, 12, 13, 14, 15, 16, 17, 18, 19, 20, 21, 22, 23, 24, 25, or more than 25 contiguous amino acids; at least 30, 35, 40, 45, 50, 55, 60, 65, 70, 80, 85, 90, 95, 100 or more than 100 contiguous amino acids of a 193P1E1B-related protein, as well as the peptides/proteins themselves; DNA, RNA, DNA/RNA hybrids, and related molecules, polynucleotides or oligonucleotides complementary or having at least a 90% homology to the 193P1E1B genes or mRNA sequences or parts thereof, and polynucleotides or oligonucleotides that hybridize to the 193P1E1B genes, mRNAs, or to 193P1E1B-encoding polynucleotides. Also provided are means for isolating cDNAs and the genes encoding 193P1E1B. Recombinant DNA molecules containing 193P1E1B polynucleotides, cells transformed or transduced with such molecules, and host-vector systems for the expression of 193P1E1B gene products are also provided. The invention further provides antibodies that bind to 193P1E1B proteins and polypeptide fragments thereof, including polyclonal and monoclonal antibodies, murine and other mammalian antibodies, chimeric antibodies, humanized and fully human antibodies, and antibodies labeled with a detectable marker or therapeutic agent. In certain embodiments, there is a proviso that the entire nucleic acid sequence of FIG. 2 is not encoded and/or the entire amino acid sequence of FIG. 2 is not prepared. In certain embodiments, the entire nucleic acid sequence of FIG. 2 is encoded and/or the entire amino acid sequence of FIG. 2 is prepared, either of which are in respective human unit dose forms.

The invention further provides methods for detecting the presence and status of 193P1E1B polynucleotides and proteins in various biological samples, as well as methods for identifying cells that express 193P1E1B. A typical embodiment of this invention provides methods for monitoring 193P1E1B gene products in a issue or hematology sample having or suspected of having some form of growth dysregulation such as cancer.

The invention further provides various immunogenic or therapeutic compositions and strategies for treating cancers that express 193P1E1B such as cancers of tissues listed in Table I, including therapies aimed at inhibiting the transcription, translation, processing or function of 193P1E1B as well as cancer vaccines. In one aspect, the invention provides compositions, and methods comprising them, for treating a cancer that expresses 193P1E1B in a human subject wherein the composition comprises a carrier suitable for human use and a human unit dose of one or more than one agent that inhibits the production or function of 193P1E1B. Preferably, the carrier is a uniquely human carrier. In another aspect of the invention, the agent is a moiety that is immunoreactive with 193P1E1B protein. Non-limiting examples of such moieties include, but are not limited to, antibodies (such as single chain, monoclonal, polyclonal, humanized, chimeric, or human antibodies), functional equivalents thereof (whether naturally occurring or synthetic), and combinations thereof. The antibodies can be conjugated to a diagnostic or therapeutic moiety. In another aspect, the agent is a small molecule as defined herein.

In another aspect, the agent comprises one or more than one peptide which comprises a cytotoxic T lymphocyte (CTL) epitope that binds an HLA class I molecule in a human to elicit a CTL response to 193P1E1B and/or one or more than one peptide which comprises a helper T lymphocyte (HTL) epitope which binds an HLA class II molecule in a human to elicit an HTL response. The peptides of the invention may be on the same or on one or more separate polypeptide molecules. In a further aspect of the invention, the agent comprises one or more than one nucleic acid molecule that expresses one or more than one of the CTL or HTL response stimulating peptides as described above. In yet another aspect of the invention, the one or more than one nucleic acid molecule may express a moiety that is immunologically reactive with 193P1E1B as described above. The one or more than one nucleic acid molecule may also be, or encodes, a molecule that inhibits production of 193P1E1B. Non-limiting examples of such molecules include, but are not limited to, those complementary to a nucleotide sequence essential for production of 193P1E1B (e.g. antisense sequences or molecules that form a triple helix with a nucleotide double helix essential for 193P1E1B production) or a ribozyme effective to lyse 193P1E1B mRNA.

Note that to determine the starting position of any peptide set forth in Tables VIII-XXI and XXII to XLIX (collectively HLA Peptide Tables) respective to its parental protein, e.g., variant 1, variant 2, etc., reference is made to three factors: the particular variant, the length of the peptide in an HLA Peptide Table, and the Search Peptides in Table VII. Generally, a unique Search Peptide is used to obtain HLA peptides of a particular for a particular variant. The position of each Search Peptide relative to its respective parent molecule is listed in Table VII. Accordingly, if a Search Peptide begins at position "X", one must add the value "X−1" to each position in Tables VIII-XXI and XXII to XLIX to obtain the actual position of the HLA peptides in their parental molecule. For example, if a particular Search Peptide begins at position 150 of its parental molecule, one must add 150−1, i.e., 149 to each HLA peptide amino acid position to calculate the position of that amino acid in the parent molecule.

One embodiment of the invention comprises an HLA peptide, that occurs at least twice in Tables VIII-XXI and XXII to XLIX collectively, or an oligonucleotide that encodes the HLA peptide. Another embodiment of the invention comprises an HLA peptide that occurs at least once in Tables VIII-XXI and at least once in tables XXII to XLIX, or an oligonucleotide that encodes the HLA peptide.

Another embodiment of the invention is antibody epitopes, which comprise a peptide regions, or an oligonucleotide encoding the peptide region, that has one two, three, four, or five of the following characteristics:

i) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Hydrophilicity profile of FIG. 5;

ii) a peptide region of at least 5 amino acids of a particular peptide of FIG. 3, in any whole number increment up to the full length of that protein in FIG. 3, that includes an amino acid position having a value equal to or less than 0.5, 0.4, 0.3, 0.2, 0.1, or having a value equal to 0.0, in the Hydropathicity profile of FIG. 6;

iii) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Percent Accessible Residues profile of FIG. 7;

iv) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Average Flexibility profile of FIG. 8; or v) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Beta-turn profile of FIG. 9.

BRIEF DESCRIPTION OF THE FIGURES

FIG. 1. The 193P1E1B SSH sequence of 227 nucleotides.

FIG. 2. A) The cDNA and amino acid sequence of 193P1E1B variant 1 (also called "193P1E1B v.1" or "193P1E1B variant 1") is shown in FIG. 2A. The start methionine is underlined. The open reading frame extends from nucleic acid 805-2043 including the stop codon.

Figure 10:
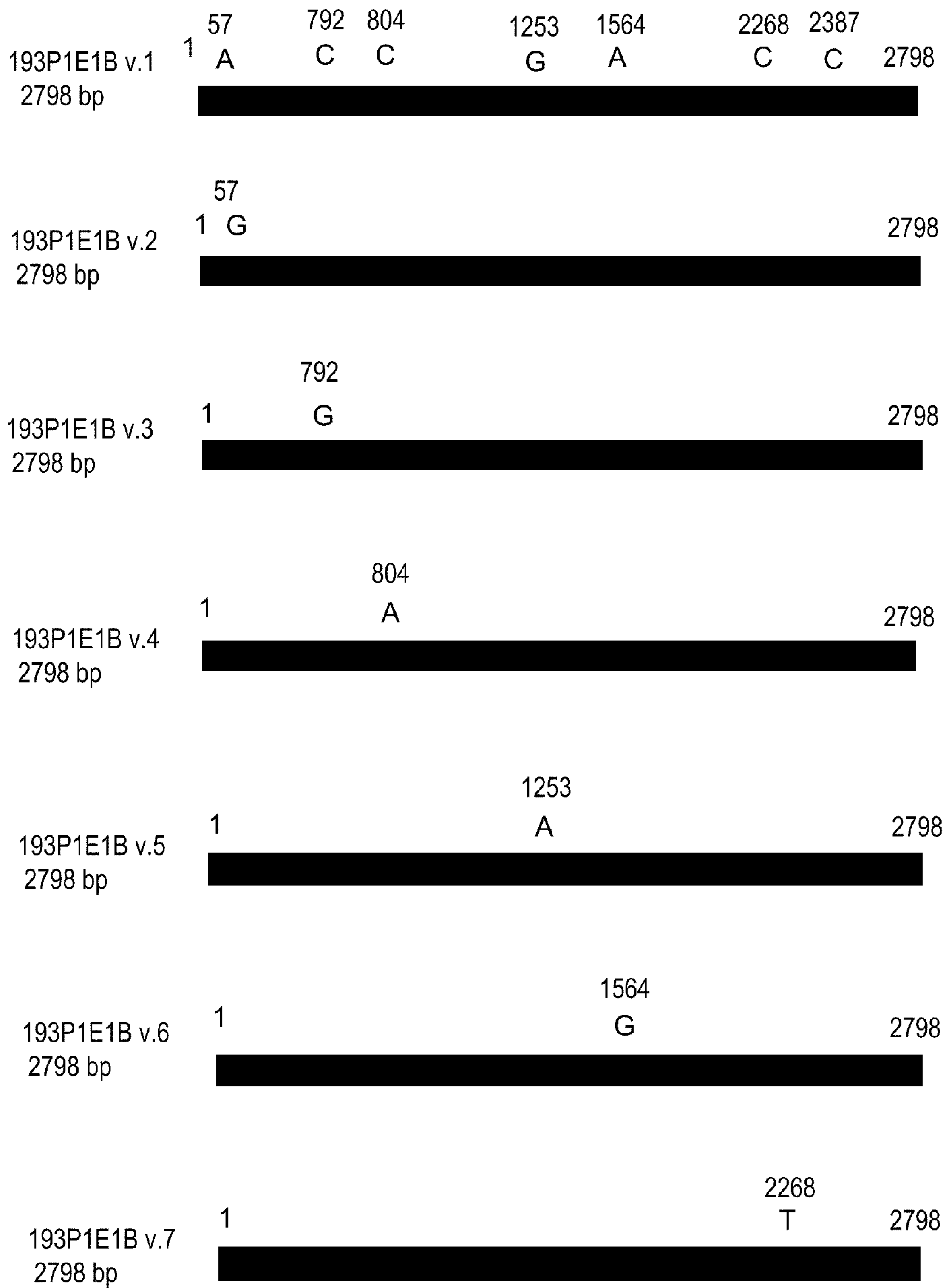

B) The cDNA and amino acid sequence of 193P1E1B variant 2 (also called "193P1E1B v.2") is shown in FIG. 2B. The codon for the start methionine is underlined. The open reading frame extends from nucleic acid 805-2043 including the stop codon.

C) The cDNA and amino acid sequence of 193P1E1B variant 3 (also called "193P1E1B v.3") is shown in FIG. 2C. The codon for the start methionine is underlined. The open reading frame extends from nucleic acid 805-2043 including the stop codon.

D) The cDNA and amino acid sequence of 193P1E1B variant 4 (also called "193P1E1B v.4") is shown in FIG. 2D. The codon for the start methionine is underlined. The open reading frame extends from nucleic acid 805-2043 including the stop codon.

E) The cDNA and amino acid sequence of 193P1E1B variant 5 (also called "193P1E1B v.5") is shown in FIG. 2E. The codon for the start methionine is underlined. The open reading frame extends from nucleic acid 805-2043 including the stop codon.

F) The cDNA and amino acid sequence of 193P1E1B variant 6 (also called "193P1E1B v.6") is shown in FIG. 2F. The codon for the start methionine is underlined. The open reading frame extends from nucleic acid 805-2043 including the stop codon.

G) The cDNA and amino acid sequence of 193P1E1B variant 7 (also called "193P1E1B v.7") is shown in FIG. 2G. The codon for the start methionine is underlined. The open reading frame extends from nucleic acid 805-2043 including the stop codon.

H) The cDNA and amino acid sequence of 193P1E1B variant 8 (also called "193P1E1B v.8") is shown in FIG. 2H. The codon for the start methionine is underlined. The open reading frame extends from nucleic acid 805-2043 including the stop codon.

I) The cDNA and amino acid sequence of 193P1E1B variant 9 (also called "193P1E1B v.9") is shown in FIG. 21. The codon for the start methionine is underlined. The open reading frame extends from nucleic acid 989-1981 including the stop codon.

J) The cDNA and amino acid sequence of 193P1E1B variant 10 (also called "193P1E1B v.10") is shown in FIG. 2J. The codon for the start methionine is underlined. The open reading frame extends from nucleic acid 805-1971 including the stop codon.

K) The cDNA and amino acid sequence of 193P1E1B variant 11 (also called "193P1E1B v.11") is shown in FIG. 2K. The codon for the start methionine is underlined. The open reading frame extends from nucleic acid 989-1909 including the stop codon.

L) The cDNA and amino acid sequence of 193P1E1B variant 12 (also called "193P1E1B v.12") is shown in FIG. 2L. The codon for the start methionine is underlined. The open reading frame extends from nucleic acid 805-1026 including the stop codon.

M) The cDNA and amino acid sequence of 193P1E1B variant 13 (also called "193P1E1B v.13") is shown in FIG. 2M. The codon for the start methionine is underlined. The open reading frame extends from nucleic acid 952-2070 including the stop codon.

FIG. 3.

A) Amino acid sequence of 193P1E1B v.1 is shown in FIG. 3A; it has 412 amino acids.

B) The amino acid sequence of 193P1E1B v.5 is shown in FIG. 3B; it has 412 amino acids.

C) The amino acid sequence of 193P1E1B v.6 is shown in FIG. 3C; it has 412 amino acids.

D) The amino acid sequence of 193P1E1B v.9 is shown in FIG. 3D; it has 330 amino acids.

E) The amino acid sequence of 193P1E1B v.10 is shown in FIG. 3E; it has 388 amino acids.

F) The amino acid sequence of 193P1E1B v.11 is shown in FIG. 3F; it has 308 amino acids.

G) The amino acid sequence of 193P1E1B v.12 is shown in FIG. 3G; it has 73 amino acids.

H) The amino acid sequence of 193P1E1B v.13 is shown in FIG. 3H; it has 372 amino acids. As used herein, a reference to 193P1E1B includes all variants thereof, including those shown in FIGS. 2, 3, 10, and 11, unless the context clearly indicates otherwise.

FIG. 4. FIG. 4A shows the alignment of 193P1E1B v.1 with gi 2178775. FIG. 4B shows the alignment of 193P1E1B v.5 with gi 2178775. FIG. 4C shows the alignment of 193P1E1B v.11 with gi 2178775. FIG. 4D shows the alignment of 193P1E1B v.12 with gi 2178775. FIG. 4E shows the alignment of 193P1E1B v.1 with *E. coli* arginine repressor. FIG. 4F shows the Alignment of 193P1E1B v.1 with human adenosine deaminase. FIG. 4G shows the Clustal alignment of 193P1E1B protein variants.

FIG. 5. Hydrophilicity amino acid profile of 193P1E1B determined by computer algorithm sequence analysis using the method of Hopp and Woods (Hopp T. P., Woods K. R., 1981. Proc. Natl. Acad. Sci. U.S.A. 78:3824-3828) accessed on the Protscale website located on the World Wide Web through the ExPasy molecular biology server.

FIG. 6. Hydropathicity amino acid profile of 193P1E1B determined by computer algorithm sequence analysis using the method of Kyte and Doolittle (Kyte J., Doolittle R. F., 1982. J. Mol. Biol. 157:105-132) accessed on the ProtScale website located on the World Wide Web through the ExPasy molecular biology server.

FIG. 7. Percent accessible residues amino acid profile of 193P1E1B determined by computer algorithm sequence analysis using the method of Janin (Janin J., 1979 Nature 277:491-492) accessed on the ProtScale website located on the World Wide Web through the ExPasy molecular biology server.

FIG. 8. Average flexibility amino acid profile of 193P1E1B determined by computer algorithm sequence analysis using the method of Bhaskaran and Ponnuswamy (Bhaskaran R., and Ponnuswamy P. K., 1988. Int. J. Pept. Protein Res. 32:242-255) accessed on the ProtScale website located on the World Wide Web through the ExPasy molecular biology server.

FIG. 9. Beta-turn amino acid profile of 193P1E1B determined by computer algorithm sequence analysis using the method of Deleage and Roux (Deleage, G., Roux B. 1987 Protein Engineering 1:289-294) accessed on the ProtScale website located on the World Wide Web through the ExPasy molecular biology server.

FIG. 10. Schematic alignment of SNP variants of 193P1E1B. Variants 193P1E1B v.2 through v.8 are variants with single nucleotide differences. Though these SNP variants are shown separately, they could also occur in any combinations and in any transcript variants that contains the base pairs. Numbers correspond to those of 193P1E1B v.1. Black box shows the same sequence as 193P1E1B v. 1. SNPs are indicated above the box.

Figure 11:
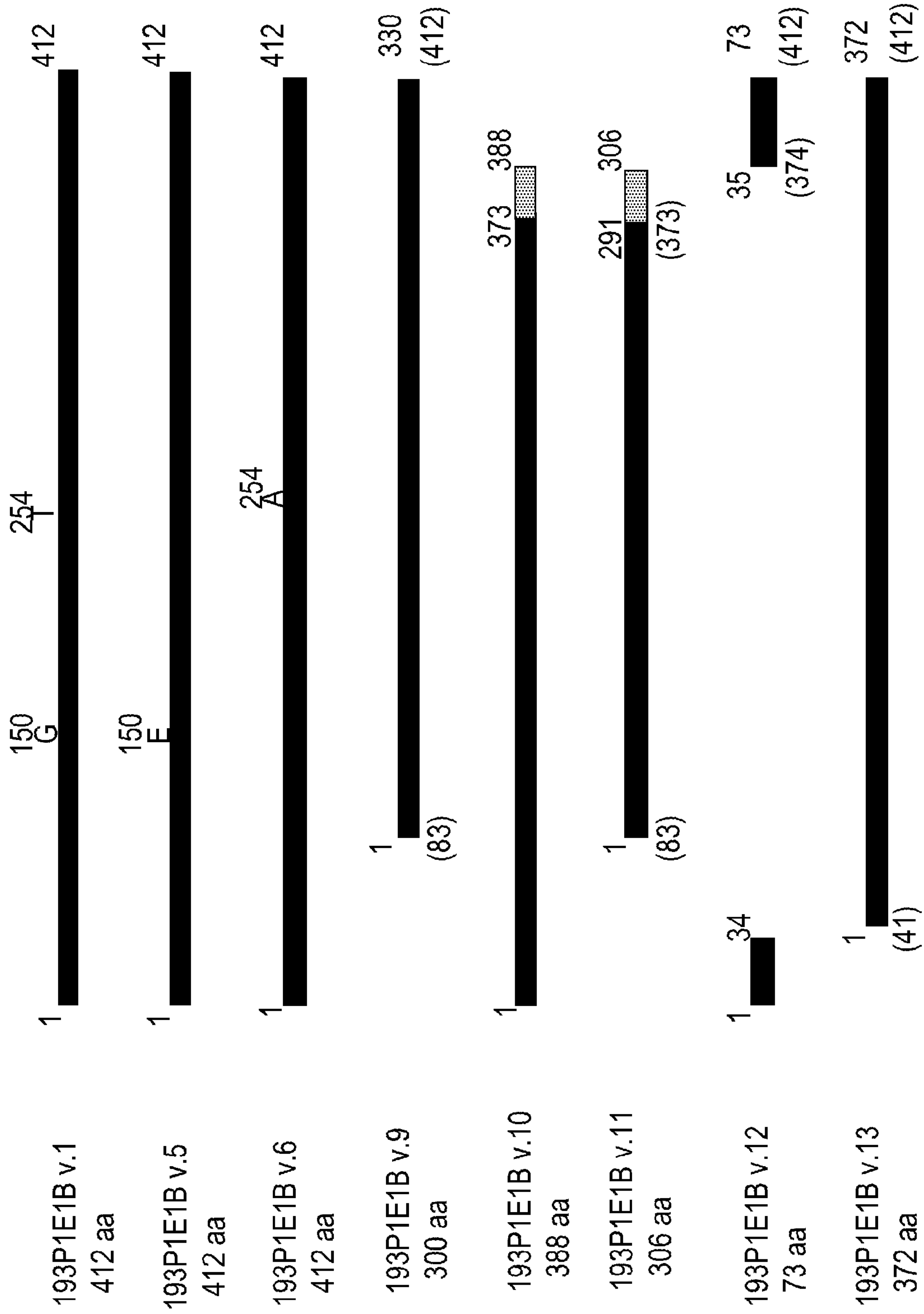

FIG. 11. Schematic alignment of protein variants of 193P1E1B. Protein variants correspond to nucleotide variants. Nucleotide variants 193P1E1B v.2, v.3, v.4, v.7, and v.8 in FIG. 10 code for the same protein as 193P1E1B v.1. Nucleotide variants 193P1E1B v.9 through v.13 are splice variants of v.1. Single amino acid differences were indicated above the boxes. Black boxes represent the same sequence as 193P1E1B v.1. Numbers underneath the box correspond to amino acid positions in 193P1E1B v.1.

FIG. 12. Intentionally Omitted.

FIG. 13. Secondary structure prediction for 193P1E1B (SEQ ID NO: 123). The secondary structure of 193P1E1B protein was predicted using the HNN-Hierarchical Neural Network method , accessed from the ExPasy molecular biology server. This method predicts the presence and location of alpha helices, extended strands, and random coils from the primary protein sequence. The percent of the protein in a given secondary structure is as follows: h: Alpha helix 29.13%; c: Random coil 60.92%; e: Extended strand 9.95%.

FIG. 14. Expression of 193P1E1B by RT-PCR. (A) The schematic diagram depicts the location of PCR primers Set A and set B on the sequences of the 3 variants of 193P1E1B. (B and C) First strand cDNA was prepared from vital pool 1 (VP1: liver, lung and kidney), vital pool 2 (VP2, pancreas, colon and stomach), prostate xenograft pool (LAPC-4AD, LAPC-4AI, LAPC-9AD, LAPC-9AI), normal thymus, prostate cancer pool, bladder cancer pool, kidney cancer pool, colon cancer pool, lung cancer pool, ovary cancer pool, breast cancer pool, metastasis cancer pool, pancreas cancer pool, and from prostate cancer metastasis to lymph node from 2 different patients. Normalization was performed by PCR using primers to actin and GAPDH. Semi-quantitative PCR, using primer Set A (B) or primer Set B (C) to 193P1E1B, was performed at 30 cycles of amplification. Strong expression of 193P1E1B was observed in prostate cancer xenograft pool, bladder cancer pool, kidney cancer pool, colon cancer pool, lung cancer pool, ovary cancer pool, breast cancer pool, metastasis pool, pancreas cancer pool, and in the 2 different prostate cancer metastasis to lymph node. Low expression was observed in prostate cancer pool, but no expression was detected in VP1 and VP2. FIG. 14C shows that the transcipt encoding encoding 193P1E1B v. 1 through v.8, is expressed ate higher levels that the transcript encoding 193P1E1B v.9. But both transcripts are expressed at similar proportion in all tissues tested.

FIG. 15. Expression of 193P1E1B in normal human tissues. Two multiple tissue northern blots, with 2 μg of mRNA/lane were probed with 193P1E1B sequence. Size standards in kilobases (kb) are indicated on the side. The results show expression of two 193P1E1B transcripts, approximately 3.5 kb and 2 kb, in testis and thymus.

FIG. 16. Expression of 193P1E1B in prostate cancer xenografts. RNA was extracted from normal prostate, and from prostate cancer xenografts, LAPC-4AD, LAPC4AI, LAPC-9AD, and LAPC-9AI. Northern blot with 10 μg of total RNA/lane was probed with 193P1E1B sequence. Size standards in kilobases (kb) are indicated on the side. The results show expression of 193P1E1B in all 4 xenografts but not in normal prostate.

FIG. 17. Expression of 193P1E1B in patient cancer specimens. RNA was extracted from a pool of three patients for each of the following, bladder cancer, colon cancer, ovary cancer and metastasis cancer, as well as from normal prostate (NP), normal bladder (NB), normal kidney (NK), normal colon (NC). Northern blots with 10 μg of total RNA/lane were probed with 193P1E1B sequence. Size standards in kilobases (kb) are indicated on the side. The results show expression of 193P1E1B in bladder cancer pool, colon cancer pool, ovary cancer pool and metastasis cancer pool, but not in any of the normal tissues tested.

FIG. 18. Expression of 193P1E1B in bladder cancer patient specimens. RNA was extracted from bladder cancer cell lines (CL), normal bladder (N), bladder tumors (T) and matched normal adjacent tissue (NAT) isolated from bladder cancer patients. Northern blots with 10 μg of total RNA/lane were probed with 193P1E1B sequence. Size standards in kilobases (kb) are indicated on the side. The results show expression of 193P1E1B in the two bladder cancer cell lines, and in 3 patient bladder tumors tested but not in normal bladder tissues.

FIG. 19. Expression of 193P1E1B in cancer metastasis patient specimens. RNA was extracted from the following cancer metastasis tissues, colon metastasis to lung, lung metastasis to lymph node, lung metastasis to skin, and breast metastasis to lymph node, as well as from normal bladder (NB), normal lung (NL), normal breast (NBr), and normal ovary (NO). Northern blots with 10 μg of total RNA/lane were probed with 193P1E1B sequence. Size standards in kilobases (kb) are indicated on the side. The results show expression of 193P1E1B in all four different cancer metastasis samples but not in normal tissues.

FIG. 20. Expression of 193P1E1B in pancreas, ovary and testis cancer patient specimens. RNA was extracted from pancreatic cancer (P1), ovarian cancer (P2, P3), and testicular cancer (P4, P5) isolated from cancer patients, as well as from normal pancreas (NPa). Northern blots with 10 μg of total RNA/lane were probed with 193P1E1B sequence. Size standards in kilobases (kb) are indicated on the side. The results show expression of 193P1E1B in pancreatic, ovarian and testicular cancer specimens but not in normal pancreas.

FIG. 21. Expression of 193P1E1B in Normal versus Patient Cancer Specimens. First strand cDNA was prepared from a panel of normal tissues (stomach, brain, heart, liver, spleen, skeletal muscle, tests prostate, bladder, kidney, colon, lung and pancreas) and from a panel of patient cancer pools (prostate cancer pool, bladder cancer pool, kidney cancer pool, colon cancer pool, lung cancer pool, pancreas cancer pool, ovary cancer pool, breast cancer pool, metastasis cancer pool, LAPC prostate xenograft pool (XP), and from prostate cancer metastasis to lymph node from 2 different patients (PMLN2). Normalization was performed by PCR using primers to actin. Semi-quantitative PCR, using primer Set A as described in FIG. 14, was performed was performed at 26 and 30 cycles of amplification. Samples were run on an agarose gel, and PCR products were quantitated using the Alphalmager software. Relative expression was calculated by normalizing to signal obtained using actin primers. Results show restricted 193P1E1B expression in normal testis amongst all normal tissues tested. 193P1E1B expression was strongly upregulated in cancers of the bladder, colon, lung, pancreas, ovary, breast, and to a lesser extent in prostate and kidney cancers.

FIG. 22. Expression of 193P1E1B in Normal versus Patient Cancer Specimens. First strand cDNA was prepared from a panel of normal tissues (stomach, brain, heart, liver, spleen, skeletal muscle, testis prostate, bladder, kidney, colon, lung and pancreas) and from a panel of patient cancer pools (prostate cancer pool, bladder cancer pool, kidney cancer pool, colon cancer pool, lung cancer pool, pancreas cancer pool, ovary cancer pool, breast cancer pool, metastasis cancer pool, LAPC prostate xenograft pool (XP), and from prostate cancer metastasis to lymph node from 2 different patients (PMLN2). Normalization was performed by PCR using primers to actin. Semi-quantitative PCR, using primer Set A as described in FIG. 14, was performed was performed at 26 and 30 cycles of amplification. Samples were run on an agarose gel, and PCR products were quantitated using the Alphalmager software. Relative expression was calculated by normalizing to signal obtained using actin primers. Results show restricted 193P1E1B expression in normal testis amongst all normal tissues tested. 193P1E1B expression was strongly upregulated in cancers of the bladder, colon, lung, pancreas, ovary, breast, and to a lesser extent in prostate and kidney cancers.

DETAILED DESCRIPTION OF THE INVENTION

Outline of Sections

I.) Definitions
II.) 193P1E1B Polynucleotides
II.A.) Uses of 193P1E1B Polynucleotides
II.A.1.) Monitoring of Genetic Abnormalities
II.A.2.) Antisense Embodiments
II.A.3.) Primers and Primer Pairs
II.A.4.) Isolation of 193P1E1B-Encoding Nucleic Acid Molecules
II.A.5.) Recombinant Nucleic Acid Molecules and Host-Vector Systems
III.) 193P1E1B-related Proteins
III.A.) Motif-bearing Protein Embodiments
III.B.) Expression of 193P1E1B-related Proteins
III.C.) Modifications of 193P1E1B-related Proteins
III.D.) Uses of 193P1E1B-related Proteins
IV.) 193P1E1B Antibodies
V.) 193P1E1B Cellular Immune Responses
VI.) 193P1E1B Transgenic Animals
VII.) Methods for the Detection of 193P1E1B
VIII.) Methods for Monitoring the Status of 193P1E1B-related Genes and Their Products
IX.) Identification of Molecules That Interact With 193P1E1B
X.) Therapeutic Methods and Compositions
X.A.) Anti-Cancer Vaccines
X.B.) 193P1E1B as a Target for Antibody-Based Therapy
X.C.) 193P1E1B as a Target for Cellular Immune Responses
X.C.1. Minigene Vaccines
X.C.2. Combinations of CTL Peptides with Helper Peptides
X.C.3. Combinations of CTL Peptides with T Cell Priming Agents
X.C.4. Vaccine Compositions Comprising DC Pulsed with CTL and/or HTL Peptides
X.D.) Adoptive Immunotherapy
X.E.) Administration of Vaccines for Therapeutic or Prophylactic Purposes
XI.) Diagnostic and Prognostic Embodiments of 193P1E1B.
XII.) Inhibition of 193P1E1B Protein Function
XII.A.) Inhibition of 193P1E1B With Intracellular Antibodies
XII.B.) Inhibition of 193P1E1B with Recombinant Proteins
XII.C.) Inhibition of 193P1E1B Transcription or Translation
XII.D.) General Considerations for Therapeutic Strategies
XIII.) Identification, Characterization and Use of Modulators of 193P1E1B
XIV.) KITS/Articles of Manufacture

I.) Definitions:

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

The terms "advanced prostate cancer", "locally advanced prostate cancer", "advanced disease" and "locally advanced disease" mean prostate cancers that have extended through the prostate capsule, and are meant to include stage C disease under the American Urological Association (AUA) system, stage C1-C2 disease under the Whitmore-Jewell system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

"Altering the native glycosylation pattern" is intended for purposes herein to mean deleting one or more carbohydrate moieties found in native sequence 193P1E1B (either by removing the underlying glycosylation site or by deleting the glycosylation by chemical and/or enzymatic means), and/or adding one or more glycosylation sites that are not present in the native sequence 193P1E1B. In addition, the phrase includes qualitative changes in the glycosylation of the native proteins, involving a change in the nature and proportions of the various carbohydrate moieties present.

The term "analog" refers to a molecule which is structurally similar or shares similar or corresponding attributes with another molecule (e.g. a 193P1E1B-related protein). For example, an analog of a 193P1E1B protein can be specifically bound by an antibody or T cell that specifically binds to 193P1E1B.

The term "antibody" is used in the broadest sense. Therefore, an "antibody" can be naturally occurring or man-made such as monoclonal antibodies produced by conventional hybridoma technology. Anti-193P1E1B antibodies comprise monoclonal and polyclonal antibodies as well as fragments containing the antigen-binding domain and/or one or more complementarity determining regions of these antibodies.

An "antibody fragment" is defined as at least a portion of the variable region of the immunoglobulin molecule that binds to its target, i.e., the antigen-binding region. In one embodiment it specifically covers single anti-193P1E1B antibodies and clones thereof (including agonist, antagonist and neutralizing antibodies) and anti-193P1E1B antibody compositions with polyepitopic specificity.

The term "codon optimized sequences" refers to nucleotide sequences that have been optimized for a particular host species by replacing any codons having a usage frequency of less than about 20%. Nucleotide sequences that have been optimized for expression in a given host species by elimination of spurious polyadenylation sequences, elimination of exon/intron splicing signals, elimination of transposon-like repeats and/or optimization of GC content in addition to codon optimization are referred to herein as an "expression enhanced sequences."

A "combinatorial library" is a collection of diverse chemical compounds generated by either chemical synthesis or biological synthesis by combining a number of chemical "building blocks" such as reagents. For example, a linear combinatorial chemical library, such as a polypeptide (e.g., mutein) library, is formed by combining a set of chemical building blocks called amino acids in every possible way for a given compound length (i.e., the number of amino acids in a polypeptide compound). Numerous chemical compounds are synthesized through such combinatorial mixing of chemical building blocks (Gallop et al., J. Med. Chem. 37(9): 1233-1251 (1994)).

Preparation and screening of combinatorial libraries is well known to those of skill in the art. Such combinatorial chemical libraries include, but are not limited to, peptide libraries (see, e.g., U.S. Pat. No. 5,010,175, Furka, Pept. Prot. Res. 37:487-493 (1991), Houghton et al., Nature, 354:84-88 (1991)), peptoids (PCT Publication No WO 91/19735), encoded peptides (PCT Publication WO 93/20242), random bio-oligomers (PCT Publication WO 92/00091), benzodiazepines (U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with a Beta-D-Glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbarnates (Cho, et al., Science 261: 1303 (1993)), and/or peptidyl phosphonates (Campbell et al., J. Org. Chem. 59:658 (1994)). See, generally, Gordon et al., J. Med. Chem. 37:1385 (1994), nucleic acid libraries (see, e.g., Stratagene, Corp.), peptide nucleic acid libraries (see, e.g., U.S. Pat. No. 5,539,083), antibody libraries (see, e.g., Vaughn et al., Nature Biotechnology 14(3): 309-314 (1996), and PCT/US96110287), carbohydrate libraries (see, e.g., Liang et al., Science 274:1520-1522 (1996), and U.S. Pat. No. 5,593,853), and small organic molecule libraries (see, e.g., benzodiazepines, Baum, C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514; and the like).

Devices for the preparation of combinatorial libraries are commercially available (see, e.g., 357 NIPS, 390 NIPS, Advanced Chem Tech, Louisville Ky.; Symphony, Rainin, Woburn, Mass.; 433A, Applied Biosystems, Foster City, Calif.; 9050, Plus, Millipore, Bedford, Mass.). A number of well-known robotic systems have also been developed for solution phase chemistries. These systems include automated workstations such as the automated synthesis apparatus developed by Takeda Chemical Industries, LTD. (Osaka, Japan) and many robotic systems utilizing robotic arms (Zymate H, Zymark Corporation, Hopkinton, Mass.; Orca, Hewlett-Packard, Palo Alto, Calif.), which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J.; Asinex, Moscow, RU; Tripos, Inc., St. Louis, Mo.; ChemStar, Ltd, Moscow, RU; 3D Pharmaceuticals, Exton, Pa.; Martek Biosciences, Columbia, Md.; etc.).

The term "cytotoxic agent" refers to a substance that inhibits or prevents the expression activity of cells, function of cells and/or causes destruction of cells. The term is intended to include radioactive isotopes chemotherapeutic agents, and toxins such as small molecule toxins or enzymatically active toxins of bacterial, fungal, plant or animal origin, including fragments and/or variants thereof. Examples of cytotoxic agents include, but are not limited to auristatins, auromycins, maytansinoids, yttrium, bismuth, ricin, ricin A-chain, combrestatin, duocarmycins, dolostatins, doxorubicin, daunorubicin, taxol, cisplatin, cc1065, ethidium bromide, mitomycin, etoposide, tenoposide, vincristine, vinblastine, colchicine, dihydroxy anthracin dione, actinomycin, diphtheria toxin, Pseudomonas exotoxin (PE) A, PE40, abrin, abrin A chain, modeccin A chain, alpha-sarcin, gelonin, mitogellin, retstrictocin, phenomycin, enomycin, curicin, crotin, calicheamicin, *Sapaonana officinalis* inhibitor, and glucocorticoid and other chemotherapeutic agents, as well as radioisotopes such as $At^{211}$, $I^{131}$, $I^{125}$, $Y^{90}$, $Re^{186}$, $Re^{188}$, $Sm^{153}$, $Bi^{212 \text{ or } 213}$, $P^{32}$ and radioactive isotopes of Lu including $Lu^{177}$. Antibodies may also be conjugated to an anti-cancer pro-drug activating enzyme capable of converting the pro-drug to its active form.

The "gene product" is sometimes referred to herein as a protein or mRNA. For example, a "gene product of the invention" is sometimes referred to herein as a "cancer amino acid sequence", "cancer protein", "protein of a cancer listed in Table I", a "cancer mRNA", "mRNA of a cancer listed in Table I", etc. In one embodiment, the cancer protein is encoded by a nucleic acid of FIG. 2. The cancer protein can be a fragment, or alternatively, be the full-length protein to the fragment encoded by the nucleic acids of FIG. 2. In one embodiment, a cancer amino acid sequence is used to determine sequence identity or similarity. In another embodiment, the sequences are naturally occurring allelic variants of a protein encoded by a nucleic acid of FIG. 2. In another embodiment, the sequences are sequence variants as further described herein.

"High throughput screening" assays for the presence, absence, quantification, or other properties of particular nucleic acids or protein products are well known to those of skill in the art. Similarly, binding assays and reporter gene assays are similarly well known. Thus, e.g., U.S. Pat. No. 5,559,410 discloses high throughput screening methods for proteins; U.S. Pat. No. 5,585,639 discloses high throughput screening methods for nucleic acid binding (i.e., in arrays); while U.S. Pat. Nos. 5,576,220 and 5,541,061 disclose high throughput methods of screening for ligand/antibody binding.

In addition, high throughput screening systems are commercially available (see, e.g., Amersham Biosciences, Piscataway, N.J.; Zymark Corp., Hopkinton, Mass.; Air Technical Industries, Mentor, Ohio; Beckman Instruments, Inc. Fullerton, Calif.; Precision Systems, Inc., Natick, Mass.; etc.). These systems typically automate entire procedures, including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, e.g., Zymark Corp. provides technical bulletins describing screening systems for detecting the modulation of gene transcription, ligand binding, and the like.

The term "homolog" refers to a molecule which exhibits homology to another molecule, by for example, having sequences of chemical residues that are the same or similar at corresponding positions.

"Human Leukocyte Antigen" or "HLA" is a human class I or class II Major Histocompatibility Complex (MHC) protein (see, e.g., Stites, et al., IMMUNOLOGY, $8^{TH}$ ED., Lange Publishing, Los Altos, Calif. (1994).

The terms "hybridize", "hybridizing", "hybridizes" and the like, used in the context of polynucleotides, are meant to refer to conventional hybridization conditions, preferably such as hybridization in 50% formamide/6×SSC/0.1% SDS/100 μg/ml ssDNA, in which temperatures for hybridization are above 37 degrees C. and temperatures for washing in 0.1×SSC/0.1% SDS are above 55 degrees C.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment. For example, a polynucleotide is said to be "isolated" when it is substantially separated from contaminant polynucleotides that correspond or are complementary to genes other than the 193P1E1B genes or that encode polypeptides other than 193P1E1B gene product or fragments thereof. A skilled artisan can readily employ nucleic acid isolation procedures to obtain an isolated 193P1E1B polynucleotide. A protein is said to be "isolated," for example, when physical, mechanical or chemical methods are employed to remove the 193P1E1B proteins from cellular constituents that are normally associated with the protein. A skilled artisan can readily employ standard purification methods to obtain an isolated 193P1E1B protein. Alternatively, an isolated protein can be prepared by chemical means.

The term "mammal" refers to any organism classified as a mammal, including mice, rats, rabbits, dogs, cats, cows, horses and humans. In one embodiment of the invention, the mammal is a mouse. In another embodiment of the invention, the mammal is a human.

The terms "metastatic prostate cancer" and "metastatic disease" mean prostate cancers that have spread to regional lymph nodes or to distant sites, and are meant to include stage D disease under the AUA system and stage TxNxM+ under the TNM system. As is the case with locally advanced prostate cancer, surgery is generally not indicated for patients with metastatic disease, and hormonal (androgen ablation) therapy is a preferred treatment modality. Patients with metastatic prostate cancer eventually develop an androgen-refractory state within 12 to 18 months of treatment initiation. Approximately half of these androgen-refractory patients die within 6 months after developing that status. The most common site for prostate cancer metastasis is bone. Prostate cancer bone metastases are often osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

The term "modulator" or "test compound" or "drug candidate" or grammatical equivalents as used herein describe any molecule, e.g., protein, oligopeptide, small organic molecule, polysaccharide, polynucleotide, etc., to be tested for the capacity to directly or indirectly alter the cancer phenotype or the expression of a cancer sequence, e.g., a nucleic acid or protein sequences, or effects of cancer sequences (e.g., signaling, gene expression, protein interaction, etc.) In one aspect, a modulator will neutralize the effect of a cancer protein of the invention. By "neutralize" is meant that an activity of a protein is inhibited or blocked, along with the consequent effect on the cell. In another aspect, a modulator will neutralize the effect of a gene, and its corresponding protein, of the invention by normalizing levels of said protein. In preferred embodiments, modulators alter expression profiles, or expression profile nucleic acids or proteins provided herein, or downstream effector pathways. In one embodiment, the modulator suppresses a cancer phenotype, e.g. to a normal tissue fingerprint. In another embodiment, a modulator induced a cancer phenotype. Generally, a plurality of assay mixtures is run in parallel with different agent concentrations to obtain a differential response to the various concentrations. Typically, one of these concentrations serves as a negative control, i.e., at zero concentration or below the level of detection.

Modulators, drug candidates or test compounds encompass numerous chemical classes, though typically they are organic molecules, preferably small organic compounds having a molecular weight of more than 100 and less than about 2,500 Daltons. Preferred small molecules are less than 2000, or less than 1500 or less than 1000 or less than 500 D. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Modulators also comprise biomolecules such as peptides, saccharides, fatty acids, steroids, purines, pyrimidines, derivatives, structural analogs or combinations thereof. Particularly preferred are peptides. One class of modulators are peptides, for example of from about five to about 35 amino acids, with from about five to about 20 amino acids being preferred, and from about 7 to about 15 being particularly preferred. Preferably, the cancer modulatory protein is soluble, includes a non-transmembrane region, and/or, has an N-terminal Cys to aid in solubility. In one embodiment, the C-terminus of the fragment is kept as a free acid and the N-terminus is a free amine to aid in coupling, i.e., to cysteine. In one embodiment, a cancer protein of the invention is conjugated to an immunogenic agent as discussed herein. In one embodiment, the cancer protein is conjugated to BSA. The peptides of the invention, e.g., of preferred lengths, can be linked to each other or to other amino acids to create a longer peptide/protein. The modulatory peptides can be digests of naturally occurring proteins as is outlined above, random peptides, or "biased" random peptides. In a preferred embodiment, peptide/protein-based modulators are antibodies, and fragments thereof, as defined herein.

Modulators of cancer can also be nucleic acids. Nucleic acid modulating agents can be naturally occurring nucleic acids, random nucleic acids, or "biased" random nucleic acids. For example, digests of prokaryotic or eukaryotic genomes can be used in an approach analogous to that outlined above for proteins.

The term "monoclonal antibody" refers to an antibody obtained from a population of substantially homogeneous antibodies, i.e., the antibodies comprising the population are identical except for possible naturally occurring mutations that are present in minor amounts.

A"motif", as in biological motif of a 193P1E1B-related protein, refers to any pattern of amino acids forming part of the primary sequence of a protein, that is associated with a particular function (e.g. protein-protein interaction, protein-DNA interaction, etc) or modification (e.g. that is phosphorylated, glycosylated or amidated), or localization (e.g. secretory sequence, nuclear localization sequence, etc.) or a sequence that is correlated with being immunogenic, either humorally or cellularly. A motif can be either contiguous or capable of being aligned to certain positions that are generally correlated with a certain function or property. In the context of HLA motifs, "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs for HLA binding are typically different for each protein encoded by each human HLA allele and differ in the patter of the primary and secondary anchor residues.

A "pharmaceutical excipient" comprises a material such as an adjuvant, a carrier, pH-adjusting and buffering agents, tonicity adjusting agents, wetting agents, preservative, and the like.

"Pharmaceutically acceptable" refers to a non-toxic, inert, and/or composition that is physiologically compatible with humans or other mammals.

The term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term if often used interchangeably with "oligonucleotide". A polynucleotide can comprise a nucleotide sequence disclosed herein wherein thymidine (T), as shown for example in FIG. 2, can also be uracil (U); this definition pertains to the differences between the chemical structures of DNA and RNA, in particular the observation that one of the four major bases in RNA is uracil (U) instead of thymidine (T).

The term "polypeptide" means a polymer of at least about 4, 5, 6, 7, or 8 amino acids. Throughout the specification, standard three letter or single letter designations for amino acids are used. In the art, this term is often used interchangeably with "peptide" or "protein".

An HLA "primary anchor residue" is an amino acid at a specific position along a peptide sequence which is understood to provide a contact point between the immunogenic peptide and the HLA molecule. One to three, usually two, primary anchor residues within a peptide of defined length generally defines a "motif" for an immunogenic peptide. These residues are understood to fit in close contact with peptide binding groove of an HLA molecule, with their side chains buried in specific pockets of the binding groove. In one embodiment, for example, the primary anchor residues for an HLA class I molecule are located at position 2 (from the amino terminal position) and at the carboxyl terminal position of a 8, 9, 10, 11, or 12 residue peptide epitope in accordance with the invention. Alternatively, in another embodiment, the primary anchor residues of a peptide binds an HLA class II molecule are spaced relative to each other, rather than to the termini of a peptide, where the peptide is generally of at least 9 amino acids in length. The primary anchor positions for each motif and supermotif are set forth in Table IV. For example, analog peptides can be created by altering the presence or absence of particular residues in the primary and/or secondary anchor positions shown in Table IV. Such analogs are used to modulate the binding affinity and/or population coverage of a peptide comprising a particular HLA motif or supermotif.

"Radioisotopes" include, but are not limited to the following (non-limiting exemplary uses are also set forth):

Examples of Medical Isotopes:

Isotope

Description of use

Actinium-225

(AC-225)

See Thorium-229 (Th-229)

Actinium-227

(AC-227)

Parent of Radium-223 (Ra-223) which is an alpha emitter used to treat metastases in the skeleton resulting from cancer (i.e., breast and prostate cancers), and cancer radioimmunotherapy Bismuth-212

(Bi-212)

See Thorium-228 (Th-228)

Bismuth-213

(Bi-213)

See Thorium-229 (Th-229)

Cadmium-109

(Cd-109)

Cancer detection

Cobalt-60

(Co-60)

Radiation source for radiotherapy of cancer, for food irradiators, and for sterilization of medical supplies Copper-64
(Cu-64)
A positron emitter used for cancer therapy and SPECT imaging Copper-67
(Cu-67)
Beta/gamma emitter used in cancer radioimmunotherapy and diagnostic studies (i.e., breast and colon cancers, and lymphoma)

Dysprosium-166
(Dy-166)
Cancer radioimmunotherapy

Erbium-169
(Er-169)
Rheumatoid arthritis treatment, particularly for the small joints associated with fingers and toes Europium-152
(Eu-152)
Radiation source for food irradiation and for sterilization of medical supplies Europium-154
(Eu-154)
Radiation source for food irradiation and for sterilization of medical supplies Gadolinium-153
(Gd-153)
Osteoporosis detection and nuclear medical quality assurance devices Gold-198
(Au-198)
Implant and intracavity therapy of ovarian, prostate, and brain cancers Holmium-166
(Ho-166)
Multiple myeloma treatment in targeted skeletal therapy, cancer radioimmunotherapy, bone marrow ablation, and rheumatoid arthritis treatment Iodine-125
(I-125)
Osteoporosis detection, diagnostic imaging, tracer drugs, brain cancer treatment, radiolabeling, tumor imaging, mapping of receptors in the brain, interstitial radiation therapy, brachytherapy for treatment of prostate cancer, determination of glomerular filtration rate (GFR), determination of plasma volume, detection of deep vein thrombosis of the legs Iodine-131
(I-131)
Thyroid function evaluation, thyroid disease detection, treatment of thyroid cancer as well as other non-malignant thyroid diseases (i.e., Graves disease, goiters, and hyperthyroidism), treatment of leukemia, lymphoma, and other forms of cancer (e.g., breast cancer) using radioimmunotherapy Iridium-192
(Ir-192)
Brachytherapy, brain and spinal cord tumor treatment, treatment of blocked arteries (i.e., arteriosclerosis and restenosis), and implants for breast and prostate tumors Lutetium-177
(Lu-177)
Cancer radioimmunotherapy and treatment of blocked arteries (i.e., arteriosclerosis and restenosis)

Molybdenum-99
(Mo-99)
Parent of Technetium-99m (Tc-99m) which is used for imaging the brain, liver, lungs, heart, and other organs. Currently, Tc-99m is the most widely used radioisotope used for diagnostic imaging of various cancers and diseases involving the brain, heart, liver, lungs; also used in detection of deep vein thrombosis of the legs Osmium-194
(Os-194)
Cancer radioimmunotherapy Palladium-103
(Pd-103)
Prostate cancer treatment Platinum-195m
(Pt-195m)
Studies on biodistribution and metabolism of cisplatin, a chemotherapeutic drug Phosphorus-32
(P-32)
Polycythemia rubra vera (blood cell disease) and leukemia treatment, bone cancer diagnosis/treatment; colon, pancreatic, and liver cancer treatment; radiolabeling nucleic acids for in vitro research, diagnosis of superficial tumors, treatment of blocked arteries (i.e., arteriosclerosis and restenosis), and intracavity therapy Phosphorus-33
(P-33)
Leukemia treatment, bone disease diagnosis/treatment, radiolabeling, and treatment of blocked arteries (i.e., arteriosclerosis and restenosis)

Radium-223
(Ra-223)
See Actinium-227 (Ac-227)

Rhenium-186
(Re-186)
Bone cancer pain relief, rheumatoid arthritis treatment, and diagnosis and treatment of lymphoma and bone, breast, colon, and liver cancers using radioimmunotherapy Rhenium-188
(Re-188)
Cancer diagnosis and treatment using radioimmunotherapy, bone cancer pain relief, treatment of rheumatoid arthritis, and treatment of prostate cancer Rhodium-105
(Rh-105)
Cancer radioimmunotherapy Samarium-145
(Sm-145)
Ocular cancer treatment Samarium-153
(Sm-153)
Cancer radioimmunotherapy and bone cancer pain relief Scandium-47
(Sc-47)
Cancer radioimmunotherapy and bone cancer pain relief Selenium-75
(Se-75)
Radiotracer used in brain studies, imaging of adrenal cortex by gamma-scintigraphy, lateral locations of steroid secreting tumors, pancreatic scanning, detection of hyperactive parathyroid glands, measure rate of bile acid loss from the endogenous pool Strontium-85
(Sr-85)
Bone cancer detection and brain scans Strontium-89
(Sr-89)
Bone cancer pain relief, multiple myeloma treatment, and osteoblastic therapy Technetium-99m
(Tc-99m)
See Molybdenum-99 (Mo-99)

Thorium-228
(Th-228)
Parent of Bismuth-212 (Bi-212) which is an alpha emitter used in cancer radioimmunotherapy Thorium-229
(Th-229)
Parent of Actinium-225 (Ac-225) and grandparent of Bismuth-213 (Bi-213) which are alpha emitters used in cancer radioimmunotherapy Thulium-170
(Tm-170)
Gamma source for blood irradiators, energy source for implanted medical devices Tin-117m
(Sn-117m)
Cancer immunotherapy and bone cancer pain relief Tungsten-188
(W-188)
Parent for Rhenium-188 (Re-188) which is used for cancer diagnostics/treatment, bone cancer pain relief, rheumatoid arthritis treatment, and treatment of blocked arteries (i.e., arteriosclerosis and restenosis)

Xenon-127
(Xe-127)
Neuroimaging of brain disorders, high resolution SPECT studies, pulmonary function tests, and cerebral blood flow studies Ytterbium-175
(Yb-175)
Cancer radioimmunotherapy Yttrium-90
(Y-90)
Microseeds obtained from irradiating Yttrium-89 (Y-89) for liver cancer treatment Yttrium-91
(Y-91)
A gamma-emitting label for Yttrium-90 (Y-90) which is used for cancer radioimmunotherapy (i.e., lymphoma, breast, colon, kidney, lung, ovarian, prostate, pancreatic, and inoperable liver cancers)

By "randomized" or grammatical equivalents as herein applied to nucleic acids and proteins is meant that each nucleic acid and peptide consists of essentially random nucleotides and amino acids, respectively. These random peptides (or nucleic acids, discussed herein) can incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, a library is "fully randomized," with no sequence preferences or constants at any position. In another embodiment, the library is a "biased random" library. That is, some positions within the sequence either are held constant, or are selected from a limited number of possibilities. For example, the nucleotides or amino acid residues are randomized within a defined class, e.g., of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc., or to purines, etc.

A "recombinant" DNA or RNA molecule is a DNA or RNA molecule that-has been subjected to molecular manipulation in vitro.

Non-limiting examples of small molecules include compounds that bind or interact with 193P1E1B, ligands including hormones, neuropeptides, chemokines, odorants, phospholipids, and functional equivalents thereof that bind and preferably inhibit 193P1E1B protein function. Such non-limiting small molecules preferably have a molecular weight of less than about 10 kDa, more preferably below about 9, about 8, about 7, about 6, about 5 or about 4 kDa. In certain embodiments, small molecules physically associate with, or bind, 193P1E1B protein; are not found in naturally occurring metabolic pathways; and/or are more soluble in aqueous than non-aqueous solutions "Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, are identified by, but not limited to, those that: (1) employ low ionic strength and high temperature for washing, for example 0.015 M sodium chloride/0.0015 M sodium citrate/0.1% sodium dodecyl sulfate at 5° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5 x SSC (0.75 M NaCl, 0.075 M sodium citrate), 50 mM sodium phosphate (pH 6.8), 0.1% sodium pyrophosphate, 5 x Denhardt's solution, sonicated salmon sperm DNA (50 μg/ml), 0.1% SDS, and 10% dextran sulfate at 42° C., with washes at 42° C. in 0.2 x SSC (sodium chloride/sodium. citrate) and 50% formamide at 55° C., followed by a high-stringency wash consisting of 0.1 x SSC containing EDTA at 55° C. "Moderately stringent conditions" are described by, but not limited to, those in Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5 x SSC (150 mM NaCl, 15 mM trisodium citrate), 50 mM sodium phosphate (pH 7.6), 5 x Denhardt's solution, 10% dextran sulfate, and 20 mg/mL denatured sheared salmon sperm DNA, followed by washing the filters in 1 x SSC at about 37-50° C. The skilled artisan will recognize how to adjust the temperature, ionic strength, etc. as necessary to accommodate factors such as probe length and the like.

An HLA "supermotif" is a peptide binding specificity shared by HLA molecules encoded by two or more HLA alleles. Overall phenotypic frequencies of HLA-supertypes in different ethnic populations are set forth in Table IV (F). The non-limiting constituents of various supetypes are as follows:

A2: A*0201, A*0202, A*0203, A*0204, A*0205, A*0206, A*6802, A*6901, A*0207

A3: A3, A11, A31, A*3301, A*6801, A*0301, A*1101, A*3101

B7: B7, B*3501-03, B*51, B*5301, B*5401, B*5501, B*5502, B*5601, B*6701, B*7801, B*0702, B*5101, B*5602

B44: B*3701, B*4402, B*4403, B*60 (B*4001), B61 (B*4006)

A1: A*0102, A*2604, A*3601, A*4301, A*8001

A24: A*24, A*30, A*2403, A*2404, A*3002, A*3003

B27: B*1401-02, B*1503, B*1509, B*1510, B*1518, B*3801-02, B*3901, B*3902, B*3903-04, B*4801-02, B*7301, B*2701-08

B58: B*1516, B*1517, B*5701, B*5702, B58

B62: B*4601, 652, B*1501 (B62), B*1502 (B75), B*1513 (B77)

Calculated population coverage afforded by different HLA-supertype combinations are set forth in Table IV (G).

As used herein "to treat" or "therapeutic" and grammatically related terms, refer to any improvement of any consequence of disease, such as prolonged survival, less morbidity, and/or a lessening of side effects which are the byproducts of an alternative therapeutic modality; full eradication of disease is not required.

A "transgenic animal" (e.g., a mouse or rat) is an animal having cells that contain a transgene, which transgene was introduced into the animal or an ancestor of the animal at a prenatal, e.g., an embryonic stage. A "transgene" is a DNA that is integrated into the genome of a cell from which a transgenic animal develops.

As used herein, an HLA or cellular immune response "vaccine" is a composition that contains or encodes one or more peptides of the invention. There are numerous embodiments of such vaccines, such as a cocktail of one or more individual peptides; one or more peptides of the invention comprised by a polyepitopic peptide; or nucleic acids that encode such individual peptides or polypeptides, e.g., a minigene that encodes a polyepitopic peptide. The "one or more peptides" can include any whole unit integer from 1-150 or more, e.g., at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, or 150 or more peptides of the invention. The peptides or polypeptides can optionally be modified, such as by lipidation, addition of targeting or other sequences. HLA class I peptides of the invention can be admixed with, or linked to, HLA class II peptides, to facilitate activation of both cytotoxic T lymphocytes and helper T lymphocytes. HLA vaccines can also comprise peptide-pulsed antigen presenting cells, e.g., dendritic cells.

The term "variant" refers to a molecule that exhibits a variation from a described type or norm, such as a protein that has one or more different amino acid residues in the corresponding position(s) of a specifically described protein (e.g. the 193P1E1B protein shown in FIG. 2 or FIG. 3. An analog is an example of a variant protein. Splice isoforms and single nucleotides polymorphisms (SNPs) are further examples of variants.

The "193P1E1B-related proteins" of the invention include those specifically identified herein, as well as allelic variants, conservative substitution variants, analogs and homologs that can be isolated/generated and characterized without undue experimentation following the methods outlined herein or readily available in the art. Fusion proteins that combine parts of different 193P1E1B proteins or fragments thereof, as well as fusion proteins of a 193P1E1B protein and a heterologous polypeptide are also included. Such 193P1E1B proteins are collectively referred to as the 193P1E1B-related proteins, the proteins of the invention, or 193P1E1B. The term "193P1E1B-related protein" refers to a polypeptide fragment or a 193P1E1B protein sequence of 4, 5, 6, 7, 8, 9, 10, 11, 12, 13, 14, 15, 16, 17, 18, 19, 20, 21, 22, 23, 24, 25, or more than 25amino acids; or, at least 30, 35, 40, 45, 50, 55, 60, 65, 70, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500, 525, 550, 575, 600, 625, 650, or 664 or more amino acids.

II.) 193P1E1B Polynucleotides

One aspect of the invention provides polynucleotides corresponding or complementary to all or part of a 193P1E1B gene, mRNA, and/or coding sequence, preferably in isolated form, including polynucleotides encoding a 193P1E1B-related protein and fragments thereof, DNA, RNA, DNA/RNA hybrid, and related molecules, polynucleotides or oligonucleotides complementary to a 193P1E1B gene or mRNA sequence or a part thereof, and polynucleotides or oligonucleotides that hybridize to a 193P1E1B gene, mRNA, or to a 193P1E1B encoding polynucleotide (collectively, "193P1E1B polynucleotides"). In all instances when referred to in this section, T can also be U in FIG. 2.

Embodiments of a 193P1E1B polynucleotide include: a 193P1E1B polynucleotide having the sequence shown in FIG. 2, the nucleotide sequence of 193P1E1B as shown in FIG. 2 wherein T is U; at least 10 contiguous nucleotides of a polynucleotide having the sequence as shown in FIG. 2; or, at least 10 contiguous nucleotides of a polynucleotide having the sequence as shown in FIG. 2 where T is U. For example, embodiments of 193P1E1B nucleotides comprise, without limitation:

(I) a polynucleotide comprising, consisting essentially of, or consisting of a sequence as shown in FIG. 2, wherein T can also be U;

(II) a polynucleotide comprising, consisting essentially of, or consisting of the sequence as shown in FIG. 2A, from nucleotide residue number 805 through nucleotide residue number 2043, including the stop codon, wherein T can also be U;

(III) a polynucleotide comprising, consisting essentially of, or consisting of the sequence as shown in FIG. 2B, from nucleotide residue number 805 through nucleotide residue number 2043, including the stop codon, wherein T can also be U;

(IV) a polynucleotide comprising, consisting essentially of, or consisting of the sequence as shown in FIG. 2C, from nucleotide residue number 805 through nucleotide residue number 2043, including the a stop codon, wherein T can also be U;

(V) a polynucleotide comprising, consisting essentially of, or consisting of the sequence as shown in FIG. 2D, from nucleotide residue number 805 through nucleotide residue number 2043, including the stop codon, wherein T can also be U;

(VI) a polynucleotide comprising, consisting essentially of, or consisting of the sequence as shown in FIG. 2E, from nucleotide residue number 805 through nucleotide residue number 2043, including the stop codon, wherein T can also be U;

(VII) a polynucleotide comprising, consisting essentially of, or consisting of the sequence as shown in FIG. 2F, from nucleotide residue number 805 through nucleotide residue number 2043, including the stop codon, wherein T can also be U;

(VIII) a polynucleotide comprising, consisting essentially of, or consisting of the sequence as shown in FIG. 2G, from nucleotide residue number 805 through nucleotide residue number 2043, including the stop codon, wherein T can also be U;

(IX) a polynucleotide comprising, consisting essentially of, or consisting of the sequence as shown in FIG. 2H, from nucleotide residue number 805 through nucleotide residue number 2043, including the stop codon, wherein T can also be U;

(X) a polynucleotide comprising, consisting essentially of, or consisting of the sequence as shown in FIG. 21, from nucleotide residue number 989 through nucleotide residue number 1981, including the stop codon, wherein T can also be U;

(XI) a polynucleotide comprising, consisting essentially of, or consisting of the sequence as shown in FIG. 2J, from nucleotide residue number 805 through nucleotide residue number 1971, including the stop codon, wherein T can also be U;

(XII) a polynucleotide comprising, consisting essentially of, or consisting of the sequence as shown in FIG. 2K, from nucleotide residue number 989 through nucleotide residue number 1909, including the stop codon, wherein T can also be U;

(XIII) a polynucleotide comprising, consisting essentially of, or consisting of the sequence as shown in FIG. 2L, from nucleotide residue number 805 through nucleotide residue number 1026, including the stop codon, wherein T can also be U;

(XIV) a polynucleotide comprising, consisting essentially of, or consisting of the sequence as shown in FIG. 2M, from nucleotide residue number 952 through nucleotide residue number 2070, including the stop codon, wherein T can also be U;

(XV) a polynucleotide that encodes a 193P1E1B-related protein that is at least 90, 91, 92, 93, 94, 95, 96, 97, 98, 99 or 100% homologous to an entire amino acid sequence shown in FIGS. 2A-M;

(XVI) a polynucleotide that encodes a 193P1E1B-related protein that is at least 90, 91, 92, 93, 94, 95, 96, 97, 98, 99 or 100% identical to an entire amino acid sequence shown in FIGS. 2A-M;

(XVII) a polynucleotide that encodes at least one peptide set forth in Tables VIII-XXI and XXII-XLIX;

(XVIII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIGS. 3A-C in any whole number increment up to 412 that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(XIX) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIGS. 3A-C in any whole number increment up to 412 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydropathicity profile of FIG. 6;

(XX) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIGS. 3A-C in any whole number increment up to 412 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XXI) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIGS. 3A-C in any whole number increment up to 412 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Average Flexibility profile of FIG. 8;

(XXII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIGS. 3A-C in any whole number increment up to 412 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9;

(XXIII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3D in any whole number increment up to 330 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(XXIV) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3D in any whole number increment up to 330 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydropathicity profile of FIG. 6;

(XXV) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3D in any whole number increment up to 330 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XXVI) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3D in any whole number increment up to 330 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Average Flexibility profile of FIG. 8;

(XXVII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3D in any whole number increment up to 330 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9

(XXVIII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3E in any whole number increment up to 388 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(XXIX) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3E in any whole number increment up to 388 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydropathicity profile of FIG. 6;

(XXX) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3E in any whole number increment up to 388 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XXXI) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3E in any whole number increment up to 388 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Average Flexibility profile of FIG. 8;

(XXXII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3E in any whole number increment up to 388 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9

(XXXIII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3F in any whole number increment up to 308 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(XXXIV) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3F in any whole number increment up to 308 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydropathicity profile of FIG. 6;

(XXXV) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3F in any whole number increment up to 308 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XXXVI) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3F in any whole number increment up to 308 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33,,34, 35 amino acid position(s) having a value greater than 0.5 in the Average Flexibility profile of FIG. 8;

(XXXVII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3F in any whole number increment up to 308 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9

(XXXVIII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3G in any whole number increment up to 73 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(XXXIX) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3G in any whole number increment up to 73 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydropathicity profile of FIG. 6;

(XL) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3G in any whole number increment up to 73 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XLI) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3G in any whole number increment up to 73 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Average Flexibility profile of FIG. 8;

(XLII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3G in any whole number increment up to 73 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9

(XLIII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3H in any whole number increment up to 372 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(XLIV) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3H in any whole number increment up to 372 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydropathicity profile of FIG. 6;

(XLV) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3H in any whole number increment up to 372 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XLVI) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3H in any whole number increment up to 372 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Average Flexibility profile of FIG. 8;

(XLVII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3H in any whole number increment up to 372 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9

(XLVIII) a polynucleotide that is fully complementary to a polynucleotide of any one of (I)-(XLVII). (XLIX) a peptide that is encoded by any of (I) to (XLVIII); and (L) a composition comprising a polynucleotide of any of (I)-(XLVIII) or peptide of (XLIX) together with a pharmaceutical excipient and/or in a human unit dose form.

(LI) a method of using a polynucleotide of any (I)-(XLVIII) or peptide of (XLIX) or a composition of (L) in a method to modulate a cell expressing 193P1E1B, (LII) a method of using a polynucleotide of any (I)-(XLVIII) or peptide of (XLIX) or a composition of (L) in a method to diagnose, prophylax, prognose, or treat an individual who bears a cell expressing 193P1E1B (LIII) a method of using a polynucleotide of any (I)-(XLVIII) or peptide of (XLIX) or a composition of (L) in a method to diagnose, prophylax, prognose, or treat an individual who bears a cell expressing 193P1E1B, said cell from a cancer of a tissue listed in Table I;

(LIV) a method of using a polynucleotide of any (I)-(XLVIII) or peptide of (XLIX) or a composition of (L) in a method to diagnose, prophylax, prognose, or treat a a cancer;

(LV) a method of using a polynucleotide of any (I)-(XLVIII) or peptide of (XLIX) or a composition of (L) in a method to diagnose, prophylax, prognose, or treat a a cancer of a tissue listed in Table I; and, (LVI) a method of using a polynucleotide of any (I)-(XLVIII) or peptide of (XLIX) or a composition of (L) in a method to identify or characterize a modulator of a cell expressing 193P1E1B.

As used herein, a range is understood to disclose specifically all whole unit positions thereof.

Typical embodiments of the invention disclosed herein include 193P1E1B polynucleotides that encode specific portions of 193P1E1B mRNA sequences (and those which are complementary to such sequences) such as those that encode the proteins and/or fragments thereof, for example:

(a) 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 410, 412 or more contiguous amino acids of 193P1E1B variant 1; the maximal lengths relevant for other variants are: variant 5, 412 amino acids; variant 6, 412 amino acids, variant 9, 330 amino acids, variant 10, 388 amino acids, variant 11, 308 amino acids, variant 12, 73 amino acids, and variant 13, 372 amino acids.

For example, representative embodiments of the invention disclosed herein include: polynucleotides and their encoded peptides themselves encoding about amino acid 1 to about amino acid 10 of the 193P1E1B protein shown in FIG. 2 or FIG. 3, polynucleotides encoding about amino acid 10 to about amino acid 20 of the 193P1E1B protein shown in FIG. 2 or FIG. 3, polynucleotides encoding about amino acid 20 to about amino acid 30 of the 193P1E1B protein shown in FIG. 2 or FIG. 3, polynucleotides encoding about amino acid 30 to about amino acid 40 of the 193P1E1B protein shown in FIG. 2 or FIG. 3, polynucleotides encoding about amino acid 40 to about amino acid 50 of the 193P1E1B protein shown in FIG. 2 or FIG. 3, polynucleotides encoding about amino acid 50 to about amino acid 60 of the 193P1E1B protein shown in FIG. 2 or FIG. 3, polynucleotides encoding about amino acid 60 to about amino acid 70 of the 193P1E1B protein shown in FIG. 2 or FIG. 3, polynucleotides encoding about amino acid 70 to about amino acid 80 of the 193P1E1B protein shown in FIG. 2 or FIG. 3, polynucleotides encoding about amino acid 80 to about amino acid 90 of the 193P1E1B protein shown in FIG. 2 or FIG. 3, polynucleotides encoding about amino acid 90 to about amino acid 100 of the 193P1E1B protein shown in FIG. 2 or FIG. 3, in increments of about 10 amino acids, ending at the carboxyl terminal amino acid set forth in FIG. 2 or FIG. 3. Accordingly, polynucleotides encoding portions of the amino acid sequence (of about 10 amino acids), of amino acids, 100 through the carboxyl terminal amino acid of the 193P1E1B protein are embodiments of the invention. Wherein it is understood that each particular amino acid position discloses that position plus or minus five amino acid residues.

Polynucleotides encoding relatively long portions of a 193P1E1B protein are also within the scope of the invention. For example, polynucleotides encoding from about amino acid 1 (or 20 or 30 or 40 etc.) to about amino acid 20, (or 30, or 40 or 50 etc.) of the 193P1E1B protein "or variant" shown in FIG. 2 or FIG. 3 can be generated by a variety of techniques well known in the art. These polynucleotide fragments can include any portion of the 193P1E1B sequence as shown in FIG. 2.

Additional illustrative embodiments of the invention disclosed herein include 193P1E1B polynucleotide fragments encoding one or more of the biological motifs contained within a 193P1E1B protein "or variant" sequence, including one or more of the motif-bearing subsequences of a 193P1E1B protein "or variant" set forth in Tables VIII-XXI and XXII-XLIX. In another embodiment, typical polynucleotide fragments of the invention encode one or more of the regions of 193P1E1B protein or variant that exhibit homology to a known molecule. In another embodiment of the invention, typical polynucleotide fragments can encode one or more of the 193P1E1B protein or variant N-glycosylation sites, cAMP and cGMP-dependent protein kinase phosphorylation sites, casein kinase II phosphorylation sites or N-myristoylation site and amidation sites.

Note that to determine the starting position of any peptide set forth in Tables VIII-XXI and Tables XXII to XLIX (collectively HLA Peptide Tables) respective to its parental protein, e.g., variant 1, variant 2, etc., reference is made to three factors: the particular variant, the length of the peptide in an HLA Peptide Table, and the Search Peptides listed in Table LVII. Generally, a unique Search Peptide is used to obtain HLA peptides for a particular variant. The position of each Search Peptide relative to its respective parent molecule is listed in Table VII. Accordingly, if a Search Peptide begins at position "X", one must add the value "X minus 1" to each position in Tables VIII-XXI and Tables XXII-IL to obtain the actual position of the HLA peptides in their parental molecule. For example if a particular Search Peptide begins at position 150 of its parental molecule, one must add 150 -1, i.e., 149 to each HLA peptide amino acid position to calculate the position of that amino acid in the parent molecule.

II.A.) Uses of 193P1E1B Polynucleotides

II.A.1.) Monitoring of Genetic Abnormalities

The polynucleotides of the preceding paragraphs have a number of different specific uses. The human 193P1E1B gene maps to the chromosomal location set forth in the Example entitled "Chromosomal Mapping of 193P1E1B." For example, because the 193P1E1B gene maps to this chromosome, polynucleotides that encode different regions of the 193P1E1B proteins are used to characterize cytogenetic abnormalities of this chromosomal locale, such as abnormalities that are identified as being associated with various cancers. In certain genes, a variety of chromosomal abnormalities including rearrangements have been identified as frequent cytogenetic abnormalities in a number of different cancers (see e.g. Krajinovic et al., Mutat. Res. 382(3-4): 81-83 (1998); Johansson et al., Blood 86(10): 3905-3914 (1995) and Finger et al., P.N.A.S. 85(23): 9158-9162 (1988)). Thus, polynucleotides encoding specific regions of the 193P1E1B proteins provide new tools that can be used to delineate, with greater precision than previously possible, cytogenetic abnormalities in the chromosomal region that encodes 193P1E1B that may contribute to the malignant phenotype. In this context, these polynucleotides satisfy a need in the art for expanding the sensitivity of chromosomal screening in order to identify more subtle and less common chromosomal abnormalities (see e.g. Evans et al., Am. J. Obstet. Gynecol 171(4): 1055-1057 (1994)).

Furthermore, as 193P1E1B was shown to be highly expressed in bladder and other cancers, 193P1E1B polynucleotides are used in methods assessing the status of 193P1E1B gene products in normal versus cancerous tissues. Typically, polynucleotides that encode specific regions of the 193P1E1B proteins are used to assess the presence of perturbations (such as deletions, insertions, point mutations, or alterations resulting in a loss of an antigen etc.) in specific regions of the 193P1E1B gene, such as regions containing one or more motifs. Exemplary assays include both RT-PCR assays as well as single-strand conformation polymorphism (SSCP) analysis (see, e.g., Marrogi et al., J. Cutan. Pathol. 26(8): 369-378 (1999), both of which utilize polynucleotides encoding specific regions of a protein to examine these regions within the protein.

II.A.2.) Antisense Embodiments

Other specifically contemplated nucleic acid related embodiments of the invention disclosed herein are genomic DNA, cDNAs, ribozymes, and antisense molecules, as well as nucleic acid molecules based on an alternative backbone, or including alternative bases, whether derived from natural sources or synthesized, and include molecules capable of inhibiting the RNA or protein expression of 193P1E1B. For example, antisense molecules can be RNAs or other molecules, including peptide nucleic acids (PNAs) or non-nucleic acid molecules such as phosphorothioate derivatives that specifically bind DNA or RNA in a base pair-dependent manner. A skilled artisan can readily obtain these classes of nucleic acid molecules using the 193P1E1B polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., 193P1E1B. See for example, Jack Cohen, Oligodeoxynucleotides, Antisense Inhibitors of Gene Expression, CRC Press, 1989; and Synthesis 1:1-5 (1988). The 193P1E1B antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention can be prepared by treatment of the corresponding O-oligos with 3H-1,2-benzodithiol-3-one-1,1-dioxide, which is a sulfur transfer reagent. See, e.g., Iyer, R. P. et al., J. Org. Chem. 55:4693-4698 (1990); and Iyer, R. P. et al., J. Am. Chem. Soc. 112:1253-1254(1990). Additional 193P1E1B antisense oligonucleotides of the present invention include morpholino antisense oligonucleotides known in the art (see, e.g., Partridge et al., 1996, Antisense & Nucleic Acid Drug Development 6: 169-175).

The 193P1E1B antisense oligonucleotides of the present invention typically can be RNA or DNA that is complementary to and stably hybridizes with the first 100 5' codons or last 100 3' codons of a 193P1E1B genomic sequence or the corresponding mRNA. Absolute complementarity is not required, although high degrees of complementarity are preferred. Use of an oligonucleotide complementary to this region allows for the selective hybridization to 193P1E1B mRNA and not to mRNA specifying other regulatory subunits of protein kinase. In one embodiment, 193P1E1B antisense oligonucleotides of the present invention are 15 to 30-mer fragments of the antisense DNA molecule that have a sequence that hybridizes to 193P1E1B mRNA. Optionally, 193P1E1B antisense oligonucleotide is a 30-mer oligonucleotide that is complementary to a region in the first 10 5' codons or last 10 3' codons of 193P1E1B. Alternatively, the antisense molecules are modified to employ ribozymes in the inhibition of 193P1E1B expression, see, e.g., L. A. Couture & D. T. Stinchcomb; Trends Genet 12: 510-515 (1996).

II.A.3.) Primers and Primer Pairs

Further specific embodiments of these nucleotides of the invention include primers and primer pairs, which allow the specific amplification of polynucleotides of the invention or of any specific parts thereof, and probes that selectively or specifically hybridize to nucleic acid molecules of the invention or to any part thereof. Probes can be labeled with a detectable marker, such as, for example, a radioisotope, fluorescent compound, bioluminescent compound, a chemiluminescent compound, metal chelator or enzyme. Such probes and primers are used to detect the presence of a 193P1E1B polynucleotide in a sample and as a means for detecting a cell expressing a 193P1E1B protein.

Examples of such probes include polypeptides comprising all or part of the human 193P1E1B cDNA sequence shown in FIG. 2. Examples of primer pairs capable of specifically amplifying 193P1E1B mRNAs are also described in the Examples. As will be understood by the skilled artisan, a great many different primers and probes can be prepared based on the sequences provided herein and used effectively to amplify and/or detect a 193P1E1B mRNA.

The 193P1E1B polynucleotides of the invention are useful for a variety of purposes, including but not limited to their use as probes and primers for the amplification and/or detection of the 193P1E1B gene(s), mRNA(s), or fragments thereof; as reagents for the diagnosis and/or prognosis of prostate cancer and other cancers; as coding sequences capable of directing the expression of 193P1E1B polypeptides; as tools for modulating or inhibiting the expression of the 193P1E1B gene(s) and/or translation of the 193P1E1B transcript(s); and as therapeutic agents.

The present invention includes the use of any probe as described herein to identify and isolate a 193P1E1B or 193P1E1B related nucleic acid sequence from a naturally occurring source, such as humans or other mammals, as well as the isolated nucleic acid sequence per se, which would comprise all or most of the sequences found in the probe used.

II.A.4.) Isolation of 193P1E1B-Encoding Nucleic Acid Molecules

The 193P1E1B cDNA sequences described herein enable the isolation of other polynucleotides encoding 193P1E1B gene product(s), as well as the isolation of polynucleotides encoding 193P1E1B gene product homologs, alternatively spliced isoforms, allelic variants, and mutant forms of a 193P1E1B gene product as well as polynucleotides that encode analogs of 193P1E1B-related proteins. Various molecular cloning methods that can be employed to isolate full length cDNAs encoding a 193P1E1B gene are well known (see, for example, Sambrook, J. et al., Molecular Cloning: A Laboratory Manual, 2d edition, Cold Spring Harbor Press, New York, 1989; Current Protocols in Molecular Biology. Ausubel et al., Eds., Wiley and Sons, 1995). For example, lambda phage cloning methodologies can be conveniently employed, using commercially available cloning systems (e.g., Lambda ZAP Express, Stratagene). Phage clones containing 193P1E1B gene cDNAs can be identified by probing with a labeled 193P1E1B cDNA or a fragment thereof. For example, in one embodiment, a 193P1E1B cDNA (e.g., FIG. 2) or a portion thereof can be synthesized and used as a probe to retrieve overlapping and full-length cDNAs corresponding to a 193P1E1B gene. A 193P1E1B gene itself can be isolated by screening genomic DNA libraries, bacterial artificial chromosome libraries (BACs), yeast artificial chromosome libraries (YACs), and the like, with 193P1E1B DNA probes or primers.

II.A.5.) Recombinant Nucleic Acid Molecules and Host-Vector Systems

The invention also provides recombinant DNA or RNA molecules containing a 193P1E1B polynucleotide, a fragment, analog or homologue thereof, including but not limited to phages, plasmids, phagemids, cosmids, YACs, BACs, as well as various viral and non-viral vectors well known in the art and cells transformed or transfected with such recombinant DNA or RNA molecules. Methods for generating such molecules are well known (see, for example, Sambrook et al., 1989, supra).

The invention further provides a host-vector system comprising a recombinant DNA molecule containing a 193P1E1B polynucleotide, fragment, analog or homologue thereof within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 or HighFive cell). Examples of suitable mammalian cells include various prostate cancer cell lines such as DU145 and TsuPrl, other transfectable or transducible prostate cancer cell lines, primary cells (PrEC), as well as a number of mammalian cells routinely used for the expression of recombinant proteins (e.g., COS, CHO, 293, 293T cells). More particularly, a polynucleotide comprising the coding sequence of 193P1E1B or a fragment, analog or homolog thereof can be used to generate 193P1E1B proteins or fragments thereof using any number of host-vector systems routinely used and widely known in the art.

A wide range of host-vector systems suitable for the expression of 193P1E1B proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαtkneo (Muller et al., 1991, MCB 11:1785). Using these expression vectors, 193P1E1B can be expressed in several prostate cancer and non-prostate cell lines, including for example 293, 293T, rat-1, NIH 3T3 and TsuPrl. The host-vector systems of the invention are useful for the production of a 193P1E1B protein or fragment thereof. Such host-vector systems can be employed to study the functional properties of 193P1E1B and 193P1E1B mutations or analogs.

Recombinant human 193P1E1B protein or an analog or homolog or fragment thereof can be produced by mammalian cells transfected with a construct encoding a 193P1E1B- related nucleotide. For example, 293T cells can be transfected with an expression plasmid encoding 193P1E1B or fragment, analog or homolog thereof, a 193P1E1B-related protein is expressed in the 293T cells, and the recombinant 193P1E1B protein is isolated using standard purification methods (e.g., affinity purification using anti-193P1E1B antibodies). In another embodiment, a 193P1E1B coding sequence is subcloned into the retroviral vector pSRαMSVtkneo and used to infect various mammalian cell lines, such as NIH 3T3, TsuPr1,293 and rat-1 in order to establish 193P1E1B expressing cell lines. Various other expression systems well known in the art can also be employed. Expression constructs encoding a leader peptide joined in frame to a 193P1E1B coding sequence can be used for the generation of a secreted form of recombinant 193P1E1B protein.

As discussed herein, redundancy in the genetic code permits variation in 193P1E1B gene sequences. In particular, it is known in the art that specific host species often have specific codon preferences, and thus one can adapt the disclosed sequence as preferred for a desired host. For example, preferred analog codon sequences typically have rare codons (i.e., codons having a usage frequency of less than about 20% in known sequences of the desired host) replaced with higher frequency codons. Codon preferences for a specific species are calculated, for example, by utilizing codon usage tables available on the INTERNET.

Additional sequence modifications are known to enhance protein expression in a cellular host. These include elimination of sequences encoding spurious polyadenylation signals, exon/intron splice site signals, transposon-like repeats, and/or other such well-characterized sequences that are deleterious to gene expression. The GC content of the sequence is adjusted to levels average for a given cellular host, as calculated by reference to known genes expressed in the host cell. Where possible, the sequence is modified to avoid predicted hairpin secondary mRNA structures. Other useful modifications include the addition of a translational initiation consensus sequence at the start of the open reading frame, as described in Kozak, *Mol. Cell Biol.,* 9:5073-5080 (1989). Skilled artisans understand that the general rule that eukaryotic ribosomes initiate translation exclusively at the 5' proximal AUG codon is abrogated only under rare conditions (see, e.g., Kozak PNAS 92(7): 2662-2666, (1995) and Kozak NAR 15(20): 8125-8148 (1987)).

III.) 193P1E1B-Related Proteins

Another aspect of the present invention provides 193P1E1B-related proteins. Specific embodiments of 193P1E1B proteins comprise a polypeptide having all or part of the amino acid sequence of human 193P1E1B as shown in FIG. 2 or FIG. 3. Alternatively, embodiments of 193P1E1B proteins comprise variant, homolog or analog polypeptides that have alterations in the amino acid sequence of 193P1E1B shown in FIG. 2 or FIG. 3.

Embodiments of a 193P1E1B polypeptide include: a 193P1E1B polypeptide having a sequence shown in FIG. 2, a peptide sequence of a 193P1E1B as shown in FIG. 2 wherein T is U; at least 10 contiguous nucleotides of a polypeptide having the sequence as shown in FIG. 2; or, at least 10 contiguous peptides of a polypeptide having the sequence as shown in FIG. 2 where T is U. For example, embodiments of 193P1E1B peptides comprise, without limitation:

(I) a protein comprising, consisting essentially of, or consisting of an amino acid sequence as shown in FIGS. 2A-M or FIGS. 3A-H;

(II) a 193P1E1B-related protein that is at least 90, 91, 92, 93, 94, 95, 96, 97, 98, 99 or 100% homologous to an entire amino acid sequence shown in FIGS. 2A-M;

(III) a 193P1E1B-related protein that is at least 90, 91, 92, 93, 94, 95, 96, 97, 98, 99 or 100% identical to an entire amino acid sequence shown in FIGS. 2A-M or 3A-H;

(IV) a protein that comprises at least one peptide set forth in Tables VIII to XLIX, optionally with a proviso that it is not an entire protein of FIG. 2;

(V) a protein that comprises at least one peptide set forth in Tables VIII-XXI, collectively, which peptide is also set forth in Tables XXII to XLIX, collectively, optionally with a proviso that it is not an entire protein of FIG. 2;

(VI) a protein that comprises at least two peptides selected from the peptides set forth in Tables VIII-XLIX, optionally with a proviso that it is not an entire protein of FIG. 2;

(VII) a protein that comprises at least two peptides selected from the peptides set forth in Tables VIII to XLIX collectively, with a proviso that the protein is not a contiguous sequence from an amino acid sequence of FIG. 2;

(VIII) a protein that comprises at least one peptide selected from the peptides set forth in Tables VIII-XXI; and at least one peptide selected from the peptides set forth in Tables XXII to XLIX, with a proviso that the protein is not a contiguous sequence from an amino acid sequence of FIG. 2;

(IX) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIGS. 3A, 3B, 3C, 3D, 3E, 3F, 3G, or 3H in any whole number increment up to 412, 412, 412, 330, 388, 308, 73, or 372 respectively that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(X) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIGS. 3A, 3B, 3C, 3D, 3E, 3F, 3G, or 3H in any whole number increment up to 412, 412, 412, 330, 388, 308, 73, or 372 respectively, that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydropathicity profile of FIG. 6;

(XI) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIGS. 3A, 3B, 3C, 3D, 3E, 3F, 3G, or 3H in any whole number increment up to 412, 412, 412, 330, 388, 308, 73, or 372 respectively, that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XII) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIGS. 3A, 3B, 3C, 3D, 3E, 3F, 3G, or 3H in any whole number increment up to 412, 412, 412, 330, 388, 308, 73, or 372 respectively, that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Average Flexibility profile of FIG. 8;

(XIII) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIGS. 3A, 3B, 3C, 3D, 3E, 3F, 3G, or 3H in any whole number increment up to 412, 412, 412, 330, 388, 308, 73, or 372 respectively, that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9;

(XIV) a peptide that occurs at least twice in Tables VIII-XXI and XXII to XLIX, collectively;

(XV) a peptide that occurs at least three times in Tables VIII-XXI and XXII to XLIX, collectively;

(XVI) a peptide that occurs at least four times in Tables VIII-XXI and XXII to XLIX, collectively;

(XVII) a peptide that occurs at least five times in Tables VIII-XXI and XXII to XLIX, collectively;

(XVIII) a peptide that occurs at least once in Tables VIII-XXI, and at least once in tables XXII to XLIX;

(XIX) a peptide that occurs at least once in Tables VIII-XXI, and at least twice in tables XXII to XLIX;

(XX) a peptide that occurs at least twice in Tables VIII-XXI, and at least once in tables XXII to XLIX;

(XXI) a peptide that occurs at least twice in Tables VIII-XXI, and at least twice in tables XXII to XLIX;

(XXII) a peptide which comprises one two, three, four, or five of the following characteristics, or an oligonucleotide encoding such peptide:

i) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Hydrophilicity profile of FIG. 5;

ii) a region of at least 5 amino acids of a particular peptide of FIG. 3, in any whole number increment up to the full length of that protein in FIG. 3, that includes an amino acid position having a value equal to or less than 0.5, 0.4, 0.3, 0.2, 0.1, or having a value equal to 0.0, in the Hydropathicity profile of FIG. 6;

iii) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Percent Accessible Residues profile of FIG. 7;

iv) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Average Flexibility profile of FIG. 8; or, v) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Beta-turn profile of FIG. 9;

(XXIII) a composition comprising a peptide of (I)-(XXII) or an antibody or binding region thereof together with a pharmaceutical excipient and/or in a human unit dose form.

(XXIV) a method of using a peptide of (I)-(XXII), or an antibody or binding region thereof or a composition of (XXIII) in a method to modulate a cell expressing 193P1E1B, (XXV) a method of using a peptide of (I)-(XXII) or an antibody or binding region thereof or a composition of (XXIII) in a method to diagnose, prophylax, prognose, or treat an individual who bears a cell expressing 193P1E1B (XXVI) a method of using a peptide of (I)-(XXII) or an antibody or binding region thereof or a composition (XXIII) in a method to diagnose, prophylax, prognose, or treat an individual who bears a cell expressing 193P1E1B, said cell from a cancer of a tissue listed in Table I;

(XXVII) a method of using a peptide of (I)-(XXII) or an antibody or binding region thereof or a composition of (XXIII) in a method to diagnose, prophylax, prognose, or treat a a cancer;

(XXVIII) a method of using a peptide of (I)-(XXII) or an antibody or binding region thereof or a composition of (XXIII) in a method to diagnose, prophylax, prognose, or treat a a cancer of a tissue listed in Table I; and, (XXIX) a method of using a a peptide of (I)-(XXII) or an antibody or binding region thereof or a composition (XXIII) in a method to identify or characterize a modulator of a cell expressing 193P1E1B.

As used herein, a range is understood to specifically disclose all whole unit positions thereof.

Typical embodiments of the invention disclosed herein include 193P1E1B polynucleotides that encode specific portions of 193P1E1B mRNA sequences (and those which are complementary to such sequences) such as those that encode the proteins and/or fragments thereof, for example:

(a) 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 410, 412 or more contiguous amino acids of 193P1E1B variant 1; the maximal lengths relevant for other variants are: variant 5, 412 amino acids; variant 6, 412 amino acids, variant 9, 330, variant 10, 388 amino acids, variant 11, 308 amino acids, variant 12, 73, and variant 13, 372 amino acids.

In general, naturally occurring allelic variants of human 193P1E1B share a high degree of structural identity and homology (e.g., 90% or more homology). Typically, allelic variants of a 193P1E1B protein contain conservative amino acid substitutions within the 193P1E1B sequences described herein or contain a substitution of an amino acid from a corresponding position in a homologue of 193P1E1B. One class of 193P1E1B allelic variants are proteins that share a high degree of homology with at least a small region of a particular 193P1E1B amino acid sequence, but further contain a radical departure from the sequence, such as a non-conservative substitution, truncation, insertion or frame shift. In comparisons of protein sequences, the terms, similarity, identity, and homology each have a distinct meaning as appreciated in the field of genetics. Moreover, orthology and paralogy can be important concepts describing the relationship of members of a given protein family in one organism to the members of the same family in other organisms.

Amino acid abbreviations are provided in Table II. Conservative amino acid substitutions can frequently be made in a protein without altering either the conformation or the function of the protein. Proteins of the invention can comprise 1, 2, 3, 4, 5, 6, 7, 8, 9, 10, 11, 12, 13, 14, 15 conservative substitutions. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g. Table III herein; pages 13-15 "Biochemistry" 2nd ED. Lubert Stryer ed (Stanford University); Henikoff et al., PNAS 1992 Vol 89 10915-10919; Lei et al., J Biol Chem May 19, 1995; 270(20):11882-6).

Embodiments of the invention disclosed herein include a wide variety of art-accepted variants or analogs of 193P1E1B proteins such as polypeptides having amino acid insertions, deletions and substitutions. 193P1E1B variants can be made using methods known in the art such as site-directed mutagenesis, alanine scanning, and PCR mutagenesis. Site-directed mutagenesis (Carter et al., *Nucl. Acids Res.,* 13:4331 (1986); Zoller et al., *Nucl. Acids Res.,* 10:6487 (1987)), cassette mutagenesis (Wells et al., Gene, 34:315 (1985)), restriction selection mutagenesis (Wells et al., *Philos. Trans. R. Soc. London SerA,* 317:415 (1986)) or other known techniques can be performed on the cloned DNA to produce the 193P1E1B variant DNA.

Scanning amino acid analysis can also be employed to identify one or more amino acids along a contiguous sequence that is involved in a specific biological activity such as a protein-protein interaction. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, *The Proteins,* (W. H. Freeman & Co., N.Y.); Chothia, J. Mol. Biol., 150:1 (1976)). If alanine substitution does not yield adequate amounts of variant, an isosteric amino acid can be used.

As defined herein, 193P1E1B variants, analogs or homologs, have the distinguishing attribute of having at least one epitope that is "cross reactive" with a 193P1E1B protein having an amino acid sequence of FIG. 3. As used in this sentence, "cross reactive" means that an antibody or T cell that specifically binds to a 193P1E1B variant also specifically binds to a 193P1E1B protein having an amino acid sequence set forth in FIG. 3. A polypeptide ceases to be a variant of a protein shown in FIG. 3, when it no longer contains any epitope capable of being recognized by an antibody or T cell that specifically binds to the starting 193P1E1B protein. Those skilled in the art understand that antibodies that recognize proteins bind to epitopes of varying size, and a grouping of the order of about four or five amino acids, contiguous or not, is regarded as a typical number of amino acids in a minimal epitope. See, e.g., Nair et al., J. Immunol 2000 165 (12): 6949-6955; Hebbes et al., Mol Immunol (1989) 26(9): 865-73; Schwartz et al., J Immunol (1985) 135(4):2598-608.

Other classes of 193P1E1B-related protein variants share 70%, 75%, 80%, 85% or 90% or more similarity with an amino acid sequence of FIG. 3, or a fragment thereof. Another specific class of 193P1E1B protein variants or analogs comprises one or more of the 193P1E1B biological motifs described herein or presently known in the art. Thus, encompassed by the present invention are analogs of 193P1E1B fragments (nucleic or amino acid) that have altered functional (e.g. immunogenic) properties relative to the starting fragment. It is to be appreciated that motifs now or which become part of the art are to be applied to the nucleic or amino acid sequences of FIG. 2 or FIG. 3.

As discussed herein, embodiments of the claimed invention include polypeptides containing less than the full amino acid sequence of a 193P1E1B protein shown in FIG. 2 or FIG. 3. For example, representative embodiments of the invention comprise peptides/proteins having any 4, 5, 6, 7, 8, 9, 10, 11, 12, 13, 14, 15 or more contiguous amino acids of a 193P1E1B protein shown in FIG. 2 or FIG. 3.

Moreover, representative embodiments of the invention disclosed herein include polypeptides consisting of about amino acid 1 to about amino acid 10 of a 193P1E1B protein shown in FIG. 2 or FIG. 3, polypeptides consisting of about amino acid 10 to about amino acid 20 of a 193P1E1B protein shown in FIG. 2 or FIG. 3, polypeptides consisting of about amino acid 20 to about amino acid 30 of a 193P1E1B protein shown in FIG. 2 or FIG. 3, polypeptides consisting of about amino acid 30 to about amino acid 40 of a 193P1E1B protein shown in FIG. 2 or FIG. 3, polypeptides consisting of about amino acid 40 to about amino acid 50 of a 193P1E1B protein shown in FIG. 2 or FIG. 3, polypeptides consisting of about amino acid 50 to about amino acid 60 of a 193P1E1B protein shown in FIG. 2 or FIG. 3, polypeptides consisting of about amino acid 60 to about amino acid 70 of a 193P1E1B protein shown in FIG. 2 or FIG. 3, polypeptides consisting of about amino acid 70 to about amino acid 80 of a 193P1E1B protein shown in FIG. 2 or FIG. 3, polypeptides consisting of about amino acid 80 to about amino acid 90 of a 193P1E1B protein shown in FIG. 2 or FIG. 3, polypeptides consisting of about amino acid 90 to about amino acid 100 of a 193P1E1B protein shown in FIG. 2 or FIG. 3, etc. throughout the entirety of a 193P1E1B amino acid sequence. Moreover, polypeptides consisting of about amino acid 1 (or 20or 30 or 40 etc.) to about amino acid 20, (or 130, or 140 or 150 etc.) of a 193P1E1B protein shown in FIG. 2 or FIG. 3 are embodiments of the invention. It is to be appreciated that the starting and stopping positions in this paragraph refer to the specified position as well as that position plus or minus 5 residues.

193P1E1B-related proteins are generated using standard peptide synthesis technology or using chemical cleavage methods well known in the art. Alternatively, recombinant methods can be used to generate nucleic acid molecules that encode a 193P1E1B-related protein. In one embodiment, nucleic acid molecules provide a means to generate defined fragments of a 193P1E1B protein (or variants, homologs or analogs thereof).

III.A.) Motif-Bearing Protein Embodiments

Additional illustrative embodiments of the invention disclosed herein include 193P1E1B polypeptides comprising the amino acid residues of one or more of the biological motifs contained within a 193P1E1B polypeptide sequence set forth in FIG. 2 or FIG. 3. Various motifs are known in the art, and a protein can be evaluated for the presence of such motifs by a number of publicly available Internet sites.

Motif bearing subsequences of all 193P1E1B variant proteins are set forth and identified in Tables VIII-XXI and XXII-XLIX.

Table V sets forth several frequently occurring motifs based on pfam searches. The columns of Table V list (1) motif name abbreviation, (2) percent identity found amongst the different member of the motif family, (3) motif name or description and (4) most common function; location information is included if the motif is relevant for location.

Polypeptides comprising one or more of the 193P1E1B motifs discussed above are useful in elucidating the specific characteristics of a malignant phenotype in view of the observation that the 193P1E1B motifs discussed above are associated with growth dysregulation and because 193P1E1B is overexpressed in certain cancers (See, e.g., Table I). Casein kinase 11, cAMP and camp-dependent protein kinase, and Protein Kinase C, for example, are enzymes known to be associated with the development of the malignant phenotype (see e.g. Chen et al., Lab Invest., 78(2): 165-174 (1998); Gaiddon et al., Endocrinology 136(10): 4331-4338 (1995); Hall et al., Nucleic Acids Research 24(6): 1119-1126 (1996); Peterziel et al., Oncogene 18(46): 6322-6329 (1999) and O'Brian, Oncol. Rep. 5(2): 305-309 (1998)). Moreover, both glycosylation and myristoylation are protein modifications also associated with cancer and cancer progression (see e.g. Dennis et al., Biochem. Biophys. Acta 1473(1):21-34 (1999); Raju et al., Exp. Cell Res. 235(1): 145-154 (1997)). Amidation is another protein modification also associated with cancer and cancer progression (see e.g. Treston et al., J. Natl. Cancer Inst. Monogr. (13): 169-175 (1992)).

In another embodiment, proteins of the invention comprise one or more of the immunoreactive epitopes identified in accordance with art-accepted methods, such as the peptides set forth in Tables VIII-XXI and XXII-XLIX. CTL epitopes can be determined using specific algorithms to identify peptides within a 193P1E1B protein that are capable of optimally binding to specified HLA alleles. Moreover, processes for identifying peptides that have sufficient binding affinity for HLA molecules and which are correlated with being immunogenic epitopes, are well known in the art, and are carried out without undue experimentation. In addition, processes for identifying peptides that are immunogenic epitopes, are well known in the art, and are carried out without undue experimentation either in vitro or in vivo.

Also known in the art are principles for creating analogs of such epitopes in order to modulate immunogenicity. For example, one begins with an epitope that bears a CTL or HTL motif (see, e.g., the HLA Class I and HLA Class II motifs/supermotifs of Table IV). The epitope is analoged by substituting out an amino acid at one of the specified positions, and replacing it with another amino acid specified for that position. For example, on the basis of residues defined in Table IV, one can substitute out a deleterious residue in favor of any other residue, such as a preferred residue; substitute a less-preferred residue with a preferred residue; or substitute an originally-occurring preferred residue with another preferred residue. Substitutions can occur at primary anchor positions or at other positions in a peptide; see, e.g., Table IV.

A variety of references reflect the art regarding the identification and generation of epitopes in a protein of interest as well as analogs thereof. See, for example, WO 97/33602 to Chesnut et al.; Sette, Immunogenetics 1999 50(34): 201-212; Sette et al., J. Immunol. 2001 166(2): 1389-1397; Sidney et al., Hum. Immunol. 1997 58(1): 12-20; Kondo et al., Immunogenetics 1997 45(4): 249-258; Sidney et al., J. Immunol. 1996 157(8): 3480-90; and Falk et al., Nature 351: 290-6 (1991); Hunt et al., Science 255:1261-3 (1992); Parker et al., J. Immunol. 149:3580-7 (1992); Parker et al., J. Immunol. 152:163-75 (1994)); Kast et al., 1994 152(8): 3904-12; Borras-Cuesta et al., Hum. Immunol. 2000 61(3): 266-278; Alexander et al., J. Immunol. 2000 164(3); 164(3): 1625-1633; Alexander et al., PMID: 7895164, UI: 95202582; O'Sullivan et al., J. Immunol. 1991 147(8): 2663-2669; Alexander et al., Immunity 1994 1(9): 751-761 and Alexander et al., Immunol. Res. 1998 18(2): 79-92.

Related embodiments of the invention include polypeptides comprising combinations of the different motifs set forth in Table VI, and/or, one or more of the predicted CTL epitopes of Tables VIII-XXI and XXII-XLIX, and/or, one or more of the predicted HTL epitopes of Tables XLVI-XLIX, and/or, one or more of the T cell binding motifs known in the art. Preferred embodiments contain no insertions, deletions or substitutions either within the motifs or within the intervening sequences of the polypeptides. In addition, embodiments which include a number of either N-terminal and/or C-terminal amino acid residues on either side of these motifs may be desirable (to, for example, include a greater portion of the polypeptide architecture in which the motif is located). Typically, the number of N-terminal and/or C-terminal amino acid residues on either side of a motif is between about 1 to about 100 amino acid residues, preferably 5 to about 50 amino acid residues.

193P1E1B-related proteins are embodied in many forms, preferably in isolated form. A purified 193P1E1B protein molecule will be substantially free of other proteins or molecules that impair the binding of 193P1E1B to antibody, T cell or other ligand. The nature and degree of isolation and purification will depend on the intended use. Embodiments of a 193P1E1B-related proteins include purified 193P1E1B-related proteins and functional, soluble 193P1E1B-related proteins. In one embodiment, a functional, soluble 193P1E1B protein or fragment thereof retains the ability to be bound by antibody, T cell or other ligand.

The invention also provides 193P1E1B proteins comprising biologically active fragments of a 193P1E1B amino acid sequence shown in FIG. 2 or FIG. 3. Such proteins exhibit properties of the starting 193P1E1B protein, such as the ability to elicit the generation of antibodies that specifically bind an epitope associated with the starting 193P1E1B protein; to be bound by such antibodies; to elicit the activation of HTL or CTL; and/or, to be recognized by HTL or CTL that also specifically bind to the starting protein.

193P1E1B-related polypeptides that contain particularly interesting structures can be predicted and/or identified using various analytical techniques well known in the art, including, for example, the methods of Chou-Fasman, Gamier-Robson, Kyte-Doolittle, Eisenberg, Karplus-Schultz or Jameson-Wolf analysis, or based on immunogenicity. Fragments that contain such structures are particularly useful in generating subunit-specific anti-193P1E1B antibodies or T cells or in identifying cellular factors that bind to 193P1E1B. For example, hydrophilicity profiles can be generated, and immunogenic peptide fragments identified, using the method of Hopp, T. P. and Woods, K. R., 1981, Proc. Natl. Acad. Sci. U.S.A. 78:3824-3828. Hydropathicity profiles can be generated, and immunogenic peptide fragments identified, using the method of Kyte, J. and Doolittle, R. F., 1982, J. Mol. Biol. 157:105-132. Percent (%) Accessible Residues profiles can be generated, and immunogenic peptide fragments identified, using the method of Janin J., 1979, Nature 277:491492. Average Flexibility profiles can be generated, and immunogenic peptide fragments identified, using the method of Bhaskaran R., Ponnuswamy P. K., 1988, Int. J. Pept. Protein Res. 32:242-255. Beta-turn profiles can be generated, and immunogenic peptide fragments identified, using the method of Deleage, G., Roux B., 1987, Protein Engineering 1:289-294.

CTL epitopes can be determined using specific algorithms to identify peptides within a 193P1E1B protein that are capable of optimally binding to specified HLA alleles (e.g., by using the SYFPEITHI site at World Wide Web; Epimatrix™ and Epimer™, Brown University, URL and BIMAS. Illustrating this, peptide epitopes from 193P1E1B that are presented in the context of human MHC Class I molecules, e.g., HLA-A1, A2, A3, A11, A24, B7 and B35 were predicted (see, e.g., Tables VIII-XXI, XXII-XLIX). Specifically, the complete amino acid sequence of the 193P1E1B protein and relevant portions of other variants, i.e., for HLA Class I predictions 9 flanking residues on either side of a point mutation or exon junction, and for HLA Class II predictions 14 flanking residues on either side of a point mutation or exon junction corresponding to that variant, were entered into the HLA Peptide Motif Search algorithm found in the Bioinformatics and Molecular Analysis Section (BIMAS) web site listed above; in addition to the site SYFPEITHI.

The HLA peptide motif search algorithm was developed by Dr. Ken Parker based on binding of specific peptide sequences in the groove of HLA Class I molecules, in particular HLA-A2 (see, e.g., Falk et al., Nature 351: 290-6 (1991); Hunt et al., Science 255:1261-3 (1992); Parker et al, J. Immunol. 149:3580-7 (1992); Parker et at, J. Immunol. 152:163-75 (1994)). This algorithm allows location and ranking of 8-mer, 9-mer, and 10-mer peptides from a complete protein sequence for predicted binding to HLA-A2 as well as numerous other HLA Class I molecules. Many HLA class I binding peptides are 8-, 9-, 10 or 11-mers. For example, for Class I HLA-A2, the epitopes preferably contain a leucine (L) or methionine (M) at position 2 and a valine (V) or leucine (L) at the C-terminus (see, e.g., Parker et al., J. Immunol. 149: 3580-7 (1992)). Selected results of 193P1E1B predicted binding peptides are shown in Tables VIII-XXI and XXII-XLIX herein. In Tables VIII-XXI and XXII-XLVII, selected candidates, 9-mers and 10-mers, for each family member are shown along with their location, the amino acid sequence of each specific peptide, and an estimated binding score. In Tables XLVI-XLIX, selected candidates, 15-mers, for each family member are shown along with their location, the amino acid sequence of each specific peptide, and an estimated binding score. The binding score corresponds to the estimated half time of dissociation of complexes containing the peptide at 37° C. at pH 6.5. Peptides with the highest binding score are predicted to be the most tightly bound to HLA Class I on the cell surface for the greatest period of time and thus represent the best immunogenic targets for T-cell recognition.

Actual binding of peptides to an HLA allele can be evaluated by stabilization of HLA expression on the antigen-processing defective cell line T2 (see, e.g., Xue et al., Prostate 30:73-8 (1997) and Peshwa et al., Prostate 36:129-38 (1998)). Immunogenicity of specific peptides can be evaluated in vitro by stimulation of CD8+ cytotoxic T lymphocytes (CTL) in the presence of antigen presenting cells such as dendritic cells.

It is to be appreciated that every epitope predicted by the BIMAS site, Epimer™ and Epimatrix™ sites, or specified by the HLA class I or class II motifs available in the art or which become part of the art such as set forth in Table IV (or determined using SYFPETHI or BIMAS, are to be "applied" to a 193P1E1B protein in accordance with the invention. As used in this context "applied" means that a 193P1E1B protein is evaluated, e.g., visually or by computer-based patterns finding methods, as appreciated by those of skill in the relevant art. Every subsequence of a 193P1E1B protein of 8, 9, 10, or 11 amino acid residues that bears an HLA Class I motif, or a subsequence of 9 or more amino acid residues that bear an HLA Class II motif are within the scope of the invention.

III.B.) Expression of 193P1E1B-related Proteins

In an embodiment described in the examples that follow, 193P1E1B can be conveniently expressed in cells (such as 293T cells) transfected with a commercially available expression vector such as a CMV-driven expression vector encoding 193P1E1B with a C-terminal 6×His and MYC tag (pcDNA3.1/mycHIS, Invitrogen or Tag5, GenHunter Corporation, Nashville Tenn.). The Tag5 vector provides an IgGK secretion signal that can be used to facilitate the production of a secreted 193P1E1B protein in transfected cells. The secreted HIS-tagged 193P1E1B in the culture media can be purified, e.g., using a nickel column using standard techniques.

III.C.) Modifications of 193P1E1B-Related Proteins

Modifications of 193P1E1B-related proteins such as covalent modifications are included within the scope of this invention. One type of covalent modification includes reacting targeted amino acid residues of a 193P1E1B polypeptide with an organic derivatizing agent that is capable of reacting with selected side chains or the N- or C-terminal residues of a 193P1E1B protein. Another type of covalent modification of a 193P1E1B polypeptide included within the scope of this invention comprises altering the native glycosylation pattern of a protein of the invention. Another type of covalent modification of 193P1E1B comprises linking a 193P1E1B polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The 193P1E1B-related proteins of the present invention can also be modified to form a chimeric molecule comprising 193P1E1B fused to another, heterologous polypeptide or amino acid sequence. Such a chimeric molecule can be synthesized chemically or recombinantly. A chimeric molecule can have a protein of the invention fused to another tumor-associated antigen or fragment thereof. Alternatively, a protein in accordance with the invention can comprise a fusion of fragments of a 193P1E1B sequence (amino or nucleic acid) such that a molecule is created that is not, through its length, directly homologous to the amino or nucleic acid sequences shown in FIG. 2 or FIG. 3. Such a chimeric molecule can comprise multiples of the same subsequence of 193P1E1B. A chimeric molecule can comprise a fusion of a 193P1E1B-related protein with a polyhistidine epitope tag, which provides an epitope to which immobilized nickel can selectively bind, with cytokines or with growth factors. The epitope tag is generally placed at the amino- or carboxyl-terminus of a 193P1E1B protein. In an alternative embodiment, the chimeric molecule can comprise a fusion of a 193P1E1B-related protein with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a 193P1E1B polypeptide in place of at least one variable region within an Ig molecule. In a preferred embodiment, the immunoglobulin fusion includes the hinge, CH2 and CH3, or the hinge, CH1, CH2 and CH3 regions of an IgGI molecule. For the production of immunoglobulin fusions see, e.g., U.S. Pat. No. 5,428,130 issued Jun. 27, 1995.

III.D.) Uses of 193P1E1B-Related Proteins

The proteins of the invention have a number of different specific uses. As 193P1E1B is highly expressed in prostate and other cancers, 193P1E1B-related proteins are used in methods that assess the status of 193P1E1B gene products in normal versus cancerous tissues, thereby elucidating the malignant phenotype. Typically, polypeptides from specific regions of a 193P1E1B protein are used to assess the presence of perturbations (such as deletions, insertions, point mutations etc.) in those regions (such as regions containing one or more motifs). Exemplary assays utilize antibodies or T cells targeting 193P1E1B-related proteins comprising the amino acid residues of one or more of the biological motifs contained within a 193P1E1B polypeptide sequence in order to evaluate the characteristics of this region in normal versus cancerous tissues or to elicit an immune response to the epitope. Alternatively, 193P1E1B-related proteins that contain the amino acid residues of one or more of the biological motifs in a 193P1E1B protein are used to screen for factors that interact with that region of 193P1E1B.

193P1E1B protein fragments/subsequences are particularly useful in generating and characterizing domain-specific antibodies (e.g., antibodies recognizing an extracellular or intracellular epitope of a 193P1E1B protein), for identifying agents or cellular factors that bind to 193P1E1B or a particular structural domain thereof, and in various therapeutic and diagnostic contexts, including but not limited to diagnostic assays, cancer vaccines and methods of preparing such vaccines.

Proteins encoded by the 193P1E1B genes, or by analogs, homologs or fragments thereof, have a variety of uses, including but not limited to generating antibodies and in methods for identifying ligands and other agents and cellular constituents that bind to a 193P1E1B gene product. Antibodies raised against a 193P1E1B protein or fragment thereof are useful in diagnostic and prognostic assays, and imaging methodologies in the management of human cancers characterized by expression of 193P1E1B protein, such as those listed in Table I. Such antibodies can be expressed intracellularly and used in methods of treating patients with such cancers. 193P1E1B-related nucleic acids or proteins are also used in generating HTL or CTL responses.

Various immunological assays useful for the detection of 193P1E1B proteins are used, including but not limited to various types of radioimmunoassays, enzyme-linked immunosorbent assays (ELISA), enzyme-linked immunofluorescent assays (ELIFA), immunocytochemical methods, and the like. Antibodies can be labeled and used as immunological imaging reagents capable of detecting 193P1E1B-expressing cells (e.g., in radioscintigraphic imaging methods). 193P1E1B proteins are also particularly useful in generating cancer vaccines, as further described herein.

IV.) 193P1E1B Antibodies

Another aspect of the invention provides antibodies that bind to 193P1E1B-related proteins. Preferred antibodies specifically bind to a 193P1E1B-related protein and do not bind (or bind weakly) to peptides or proteins that are not 193P1E1B-related proteins under physiological conditions. In this context, examples of physiological conditions include: 1) phosphate buffered saline; 2) Tris-buffered saline containing 25mM Tris and 150 mM NaCl; or saline (0.9% NaCl); 4) animal serum such as human serum; or 5) a combination of any of 1) through 4); these reactions preferably taking place at pH 7.5, alternatively in a range of pH 7.0 to 8.0, or alternatively in a range of pH 6.5 to 8.5; also, these reactions taking place at a temperature between 4° C. to 37° C. For example, antibodies that bind 193P1E1B can bind 193P1E1B-related proteins such as the homologs or analogs thereof.

193P1E1B antibodies of the invention are particularly useful in cancer (see, e.g., Table I) diagnostic and prognostic assays, and imaging methodologies. Similarly, such antibodies are useful in the treatment, diagnosis, and/or prognosis of other cancers, to the extent 193P1E1B is also expressed or overexpressed in these other cancers. Moreover, intracellularly expressed antibodies (e.g., single chain antibodies) are therapeutically useful in treating cancers in which the expression of 193P1E1B is involved, such as advanced or metastatic prostate cancers.

The invention also provides various immunological assays useful for the detection and quantification of 193P1E1B and mutant 193P1E1B-related proteins. Such assays can comprise one or more 193P1E1B antibodies capable of recognizing and binding a 193P1E1B-related protein, as appropriate. These assays are performed within various immunological assay formats well known in the art, including but not limited to various types of radioimmunoassays, enzyme-linked immunosorbent assays (ELISA), enzyme-linked immunofluorescent assays (ELIFA), and the like.

Immunological non-antibody assays of the invention also comprise T cell immunogenicity assays (inhibitory or stimulatory) as well as major histocompatibility complex (MHC) binding assays.

In addition, immunological imaging methods capable of detecting prostate cancer and other cancers expressing 193P1E1B are also provided by the invention, including but not limited to radioscintigraphic imaging methods using labeled 193P1E1B antibodies. Such assays are clinically useful in the detection, monitoring, and prognosis of 193P1E1B expressing cancers such as prostate cancer.

193P1E1B antibodies are also used in methods for purifying a 193P1E1B-related protein and for isolating 193P1E1B homologues and related molecules. For example, a method of purifying a 193P1E1B-related protein comprises incubating a 193P1E1B antibody, which has been coupled to a solid matrix, with a lysate or other solution containing a 193P1E1B-related protein under conditions that permit the 193P1E1B antibody to bind to the 193P1E1B-related protein; washing the solid matrix to eliminate impurities; and eluting the 193P1E1B-related protein from the coupled antibody. Other uses of 193P1E1B antibodies in accordance with the invention include generating ant-idiotypic antibodies that mimic a 193P1E1B protein.

Various methods for the preparation of antibodies are well known in the art. For example, antibodies can be prepared by immunizing a suitable mammalian host using a 193P1E1B-related protein, peptide, or fragment, in isolated or immunoconjugated form (Antibodies: A Laboratory Manual, CSH Press, Eds., Harlow, and Lane (1988); Harlow, Antibodies, Cold Spring Harbor Press, N.Y. (1989)). In addition, fusion proteins of 193P1E1B can also be used, such as a 193P1E1B GST-fusion protein. In a particular embodiment, a GST fusion protein comprising all or most of the amino add sequence of FIG. 2 or FIG. 3 is produced, then used as an immunogen to generate appropriate antibodies. In another embodiment, a 193P1E1B-related protein is synthesized and used as an immunogen.

In addition, naked DNA immunization techniques known in the art are used (with or without purified 193P1E1B-related protein or 193P1E1B expressing cells) to generate an immune response to the encoded immunogen (for review, see Donnelly et al., 1997, Ann. Rev. Immunol. 15: 617-648).

The amino acid sequence of a 193P1E1B protein as shown in FIG. 2 or FIG. 3 can be analyzed to select specific regions of the 193P1E1B protein for generating antibodies. For example, hydrophobicity and hydrophilicity analyses of a 193P1E1B amino acid sequence are used to identify hydrophilic regions in the 193P1E1B structure. Regions of a 193P1E1B protein that show immunogenic structure, as well as other regions and domains, can readily be identified using various other methods known in the art, such as Chou-Fasman, Gamier-Robson, Kyte-Doolittle, Eisenberg, Karplus-Schultz or Jameson-Wolf analysis. Hydrophilicity profiles can be generated using the method of Hopp, T. P. and Woods, K. R., 1981, Proc. Natl. Acad. Sci. U.S.A. 78:3824-3828. Hydropathicity profiles can be generated using the method of Kyte, J. and Doolittle, R. F., 1982, J. Mol. Biol. 157:105-132. Percent (%) Accessible Residues profiles can be generated using the method of Janin J., 1979, Nature 277:491-492. Average Flexibility profiles can be generated-using the method of Bhaskaran R., Ponnuswamy P. K., 1988, Int. J. Pept. Protein Res. 32:242-255. Beta-turn profiles can be generated using the method of Deleage, G., Roux B., 1987, Protein Engineering 1:289-294. Thus, each region identified by any of these programs or methods is within the scope of the present invention. Methods for the generation of 193P1E1B antibodies are further illustrated by way of the examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodiimide reagents are used; in other instances linking reagents such as those supplied by Pierce Chemical Co., Rockford, Ill., are effective. Administration of a 193P1E1B immunogen is often conducted by injection over a suitable time period and with use of a suitable adjuvant, as is understood in the art During the immunization schedule, titers of antibodies can be taken to determine adequacy of antibody formation.

193P1E1B monoclonal antibodies can be produced by various means well known in the art For example, immortalized cell lines that secrete a desired monoclonal antibody are prepared using the standard hybridoma technology of Kohler and Milstein or modifications that immortalize antibody-producing B cells, as is generally known. Immortalized cell lines that secrete the desired antibodies are screened by immunoassay in which the antigen is a 193P1E1B-related protein. When the appropriate immortalized cell culture is identified, the cells can be expanded and antibodies produced either from in vitro cultures or from ascites fluid.

The antibodies or fragments of the invention can also be produced, by recombinant means. Regions that bind specifically to the desired regions of a 193P1E1B protein can also be produced in the context of chimeric or complementarity-determining region (CDR) grafted antibodies of multiple species origin. Humanized or human 193P1E1B antibodies can also be produced, and are preferred for use in therapeutic contexts. Methods for humanizing murine and other non-human antibodies, by substituting one or more of the non-human antibody CDRs for corresponding human antibody sequences, are well known (see for example, Jones et al., 1986, Nature 321: 522-525; Riechmann et al., 1988, Nature 332: 323-327; Verhoeyen et al., 1988, Science 239: 1534-1536). See also, Carter et al., 1993, Proc. Natl. Acad. Sci. USA 89: 4285 and Sims et al., 1993, J. Immunol. 151: 2296.

Methods for producing fully human monoclonal antibodies include phage display and transgenic methods (for review, see Vaughan et al., 1998, Nature Biotechnology 16: 535-539). Fully human 193P1E1B monoclonal antibodies can be generated using cloning technologies employing large human Ig gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man, Clark, M. (Ed.), Nottingham Academic, pp 45-64 (1993); Burton and Barbas, Human Antibodies from combinatorial libraries. Id., pp 65-82). Fully human 193P1E1B monoclonal antibodies can also be produced using transgenic mice engineered to contain human immunoglobulin gene loci as described in PCT Patent Application WO98/24893, Kuchelapati and Jakobovits et at, published Dec. 3, 1997 (see also, Jakobovits, 1998, Exp. Opin. Invest. Drugs 7(4): 607-614; U.S. Pat. Nos. 6,162,963 issued Dec. 19, 2000; 6,150,584 issued Nov. 12, 2000; and, 6,114,598 issued Sep. 5, 2000). This method avoids the in vitro manipulation required with phage display technology and efficiently produces high affinity authentic human antibodies.

Reactivity of 193P1E1B antibodies with a 193P1E1B-related protein can be established by a number of well known means, including Western blot, immunoprecipitation, ELISA, and FACS analyses using, as appropriate, 193P1E1B-related proteins, 193P1E1B-expressing cells or extracts thereof. A 193P1E1B antibody or fragment thereof can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more 193P1E1B epitopes are generated using methods generally known in the art. Homodimeric antibodies can also be generated by cross-linking techniques known in the art (e.g., Wolff et al., Cancer Res. 53: 2560-2565).

V.) 193Pi E1B Cellular Immune Responses

The mechanism by which T cells recognize antigens has been delineated. Efficacious peptide epitope vaccine compositions of the invention induce a therapeutic or prophylactic immune responses in very broad segments of the world-wide population. For an understanding of the value and efficacy of compositions of the invention that induce cellular immune responses, a brief review of immunology-related technology is provided.

A complex of an HLA molecule and a peptidic antigen acts as the ligand recognized by HLA-restricted T cells (Buus, S. et al., *Cell* 47:1071, 1986; Babbitt, B. P. et al., *Nature* 317: 359, 1985; Townsend, A. and Bodmer, H., *Annu. Rev. Immunol* 7:601, 1989; Germain, R. N., *Annu. Rev. Immunol.* 11:403, 1993). Through the study of single amino acid substituted antigen analogs and the sequencing of endogenously bound, naturally processed peptides, critical residues that correspond to motifs required for specific binding to HLA antigen molecules have been identified and are set forth in Table IV (see also, e.g., Southwood, et al., *J. Immunol* 160: 3363, 1998; Rammensee, et al., *Immunogenetics* 41:178, 1995; Rammensee et al., SYFPEITHI, access via World Wide Web; Sette, A. and Sidney, J. *Curr. Opin. Immunol* 10:478, 1998; Engelhard, V. H., *Curr. Opin. Immunol.* 6:13, 1994; Sette, A. and Grey, H. M., *Curr. Opin. Immunol.* 4:79, 1992; Sinigaglia, F. and Hammer, *J. Curr. Biol.* 6:52, 1994; Ruppert et al., *Cell* 74:929-937, 1993; Kondo et al., *J. Immunol.* 155: 4307-4312, 1995; Sidney et al., *J. Immunol* 157:3480-3490, 1996; Sidney et al., *Human Immunol.* 45:79-93, 1996; Selle, A. and Sidney, *J. Immunogenetics* 1999 Nov; 50(3-4):201-12, Review).

Furthermore, x-ray crystallographic analyses of HLA-peptide complexes have revealed pockets within the peptide binding cleft/groove of HLA molecules which accommodate, in an allele-specific mode, residues borne by peptide ligands; these residues in turn determine the HLA binding capacity of the peptides in which they are present. (See, e.g., Madden, D. R. *Annu. Rev. Immunol.* 13:587, 1995; Smith, et al., *Immunity* 4:203, 1996; Fremont et at, *Immunity* 8:305, 1998; Stern et al., *Structure* 2:245, 1994; Jones, E. Y. *Curr. Opin. Immunol*

9:75, 1997; Brown, J. H. et al., *Nature* 364:33, 1993; Guo, H. C. et al., *Proc. Natl. Acad. Sci. USA* 90:8053, 1993; Guo, H. C. et al., *Nature* 360:364, 1992; Silver, M. L. et al., *Nature* 360:367, 1992; Matsumura, M. et al., *Science* 257:927, 1992; Madden et al., *Cell* 70:1035, 1992; Fremont, D. H. et al., *Science* 257:919, 1992; Saper, M. A., Bjorkman, P. J. and Wiley, D. C., *J. Mol Biol.* 219:277, 1991.)

Accordingly, the definition of class I and class II allele-specific HLA binding motifs, or class I or class II supermotifs allows identification of regions within a protein that are correlated with binding to particular HLA antigen(s).

Thus, by a process of HLA motif identification, candidates for epitope-based vaccines have been identified; such candidates can be further evaluated by HLA-peptide binding assays to determine binding affinity and/or the time period of association of the epitope and its corresponding HLA molecule. Additional confirmatory work can be performed to select, amongst these vaccine candidates, epitopes with preferred characteristics in terms of population coverage, and/or immunogenicity.

Various strategies can be utilized to evaluate cellular immunogenicity, including:

1) Evaluation of primary T cell cultures from normal individuals (see, e.g., Wentworth, P. A. et al., *Mol. Immunol.* 32:603, 1995; Celis, E. et al., *Proc. Natl. Acad. Sci. USA* 91:2105, 1994; Tsai, V. et al., *J. Immunol.* 158:1796, 1997; Kawashima, I. et al., *Human Immunol.* 59:1, 1998). This procedure involves the stimulation of peripheral blood lymphocytes (PBL) from normal subjects with a test peptide in the presence of antigen presenting cells in vitro over a period of several weeks. T cells specific for the peptide become activated during this time and are detected using, e.g., a lymphokine- or $^{51}$Cr-release assay involving peptide sensitized target cells.

2) Immunization of HLA transgenic mice (see, e.g., Wentworth, P. A. et al., *J. Immunol.* 26:97, 1996; Wentworth, P. A. et al., *Int. Immunol* 8:651, 1996; Alexander, J. et al., *J. Immunol.* 159:4753, 1997). For example, in such methods peptides in incomplete Freund's adjuvant are administered subcutaneously to HLA transgenic mice. Several weeks following immunization, splenocytes are removed and cultured in vitro in the presence of test peptide for approximately one week. Peptide-specific T cells are detected using, e.g., a $^{51}$ Cr-release assay involving peptide sensitized target cells and target cells expressing endogenously generated antigen.

3) Demonstration of recall T cell responses from immune individuals who have been either effectively vaccinated and/or from chronically ill patients (see, e.g., Rehermann, B. et al., *J. Exp. Med.* 181:1047, 1995; Doolan, D. L. et al., *Immunity* 7:97, 1997; Bertoni, R. et al., *J. Clin. Invest.* 100:503, 1997; Threlkeld, S. C. et al., *J. Immunol.* 159:1648, 1997; Diepolder, H. M. et al., *J. Virol.* 71:6011, 1997). Accordingly, recall responses are detected by culturing PBL from subjects that have been exposed to the antigen due to disease and thus have generated an immune response "naturally", or from patients who were vaccinated against the antigen. PBL from subjects are cultured in vitro for 1-2 weeks in the presence of test peptide plus antigen presenting cells (APC) to allow activation of "memory" T cells, as compared to "naive" T cells. At the end of the culture period, T cell activity is detected using assays including $^{51}$ Cr release involving peptide-sensitized targets, T cell proliferation, or lymphokine release.

VI.) 193P1E1B Transgenic Animals

Nucleic acids that encode a 193P1E1B-related protein can also be used to generate either transgenic animals or "knock out" animals that, in turn, are useful in the development and screening of therapeutically useful reagents. In accordance with established techniques, cDNA encoding 193P1E1B can be used to clone genomic DNA that encodes 193P1E1B. The cloned genomic sequences can then be used to generate transgenic animals containing cells that express DNA that encode 193P1E1B. Methods for generating transgenic animals, particularly animals such as mice or rats, have become conventional in the art and are described, for example, in U.S. Pat. Nos. 4,736,866 issued Apr. 12, 1988, and 4,870,009 issued Sep. 26, 1989. Typically, particular cells would be targeted for 193P1E1B transgene incorporation with tissue-specific enhancers.

Transgenic animals that include a copy of a transgene encoding 193P1E1B can be used to examine the effect of increased expression of DNA that encodes 193P1E1B. Such animals can be used as tester animals for reagents thought to confer protection from, for example, pathological conditions associated with its overexpression. In accordance with this aspect of the invention, an animal is treated with a reagent and a reduced incidence of a pathological condition, compared to untreated animals that bear the transgene, would indicate a potential therapeutic intervention for the pathological condition.

Alternatively, non-human homologues of 193P1E1B can be used to construct a 193P1E1B "knockout" animal that has a defective or altered gene encoding 193P1E1B as a result of homologous recombination between the endogenous gene encoding 193P1E1B and altered genomic DNA encoding 193P1E1B introduced into an embryonic cell of the animal. For example, cDNA that encodes 193P1E1B can be used to clone genomic DNA encoding 193P1E1B in accordance with established techniques. A portion of the genomic DNA encoding 193P1E1B can be deleted or replaced with another gene, such as a gene encoding a selectable marker that can be used to monitor integration. Typically, several kilobases of unaltered flanking DNA (both at the 5' and 3' ends) are included in the vector (see, e.g., Thomas and Capecchi, *Cell,* 51:503 (1987) for a description of homologous recombination vectors). The vector is introduced into an embryonic stem cell line (e.g., by electroporation) and cells in which the introduced DNA has homologously recombined with the endogenous DNA are selected (see, e.g., Li et al., *Cell,* 69:915 (1992)). The selected cells are then injected into a blastocyst of an animal (e.g., a mouse or rat) to form aggregation chimeras (see, e.g., Bradley, in *Teratocarcinomas and Embryonic Stem Cells: A Practical Approach,* E. J. Robertson, ed. (IRL, Oxford, 1987), pp. 113-152). A chimeric embryo can then be implanted into a suitable pseudopregnant female foster animal, and the embryo brought to term to create a "knock out" animal. Progeny harboring the homologously recombined DNA in their germ cells can be identified by standard techniques and used to breed animals in which all cells of the animal contain the homologously recombined DNA. Knock out animals can be characterized, for example, for their ability to defend against certain pathological conditions or for their development of pathological conditions due to absence of a 193P1E1B polypeptide.

VIII.) Methods for the Detection of 193P1E1B

Another aspect of the present invention relates to methods for detecting 193P1E1B polynucleotides and 193P1E1B-related proteins, as well as methods for identifying a cell that expresses 193P1E1B. The expression profile of 193P1E1B makes it a diagnostic marker for metastasized disease. Accordingly, the status of 193P1E1B gene products provides information useful for predicting a variety of factors including susceptibility to advanced stage disease, rate of progression, and/or tumor aggressiveness. As discussed in detail herein, the status of 193P1E1B gene products in patient samples can be analyzed by a variety protocols that are well known in the art including immunohistochemical analysis, the variety of Northern blotting techniques including in situ hybridization, RT-PCR analysis (for example on laser capture micro-dissected samples), Western blot analysis and tissue array analysis.

More particularly, the invention provides assays for the detection of 193P1E1B polynucleotides in a biological sample, such as serum, bone, prostate, and other tissues, urine, semen, cell preparations, and the like. Detectable 193P1E1B polynucleotides include, for example, a 193P1E1B gene or fragment thereof, 193P1E1B mRNA, alternative splice variant 193P1E1B mRNAs, and recombinant DNA or RNA molecules that contain a 193P1E1B polynucleotide. A number of methods for amplifying and/or detecting the presence of 193P1E1B polynucleotides are well known in the art and can be employed in the practice of this aspect of the invention.

In one embodiment, a method for detecting a 193P1E1B mRNA in a biological sample comprises producing cDNA from the sample by reverse transcription using at least one primer; amplifying the cDNA so produced using a 193P1E1B polynucleotides as sense and antisense primers to amplify 193P1E1B cDNAs therein; and detecting the presence of the amplified 193P1E1B cDNA. Optionally, the sequence of the amplified 193P1E1B cDNA can be determined.

In another embodiment, a method of detecting a 193P1E1B gene in a biological sample comprises first isolating genomic DNA from the sample; amplifying the isolated genomic DNA using 193P1E1B polynucleotides as sense and antisense primers; and detecting the presence of the amplified 193P1E1B gene. Any number of appropriate sense and antisense probe combinations can be designed from a 193P1E1B nucleotide sequence (see, e.g., FIG. 2) and used for this purpose.

The invention also provides assays for detecting the presence of a 193P1E1B protein in a tissue or other biological sample such as serum, semen, bone, prostate, urine, cell preparations, and the like. Methods for detecting a 193P1E1B-related protein are also well known and include, for example, immunoprecipitation, immunohistochemical analysis, Western blot analysis, molecular binding assays, ELISA, ELIFA and the like. For example, a method of detecting the presence of a 193P1E1B-related protein in a biological sample comprises first contacting the sample with a 193P1E1B antibody, a 193P1E1B-reactive fragment thereof, or a recombinant protein containing an antigen-binding region of a 193P1E1B antibody; and then detecting the binding of 193P1E1B-related protein in the sample.

Methods for identifying a cell that expresses 193P1E1B are also within the scope of the invention. In one embodiment, an assay for identifying a cell that expresses a 193P1E1B gene comprises detecting the presence of 193P1E1B mRNA in the cell. Methods for the detection of particular mRNAs in cells are well known and include, for example, hybridization assays using complementary DNA probes (such as in situ hybridization using labeled 193P1E1B riboprobes, Northern blot and related techniques) and various nucleic acid amplification assays (such as RT-PCR using complementary primers specific for 193P1E1B, and other amplification type detection methods, such as, for example, branched DNA, SISBA, TMA and the like). Alternatively, an assay for identifying a cell that expresses a 193P1E1B gene comprises detecting the presence of 193P1E1B-related protein in the cell or secreted by the cell. Various methods for the detection of proteins are well known in the art and are employed for the detection of 193P1E1B-related proteins and cells that express 193P1E1B-related proteins.

193P1E1B expression analysis is also useful as a tool for identifying and evaluating agents that modulate 193P1E1B gene expression. For example, 193P1E1B expression is significantly upregulated in prostate cancer, and is expressed in cancers of the tissues listed in Table I. Identification of a molecule or biological agent that inhibits 193P1E1B expression or over-expression in cancer cells is of therapeutic value. For example, such an agent can be identified by using a screen that quantifies 193P1E1B expression by RT-PCR, nucleic acid hybridization or antibody binding.

VIII.) Methods for Monitoring the Status of 193P1E1B-Related Genes and Their Products Oncogenesis is known to be a multistep process where cellular growth becomes progressively dysregulated and cells progress from a normal physiological state to precancerous and then cancerous states (see, e.g., Alers et al., Lab Invest. 77(5): 437-438 (1997) and Isaacs et al., Cancer Surv. 23: 19-32 (1995)). In this context, examining a biological sample for evidence of dysregulated cell growth (such as aberrant 193P1E1B expression in cancers) allows for early detection of such aberrant physiology, before a pathologic state such as cancer has progressed to a stage that therapeutic options are more limited and or the prognosis is worse. In such examinations, the status of 193P1E1B in a biological sample of interest can be compared, for example, to the status of 193P1E1B in a corresponding normal sample (e.g. a sample from that individual or alternatively another individual that is not affected by a pathology). An alteration in the status of 193P1E1B in the biological sample (as compared to the normal sample) provides evidence of dysregulated cellular growth. In addition to using a biological sample that is not affected by a pathology as a normal sample, one can also use a predetermined normative value such as a predetermined normal level of mRNA expression (see, e.g., Grever et al., J. Comp. Neurol. Dec. 9, 1996; 376(2): 306-14 and U.S. Pat. No. 5,837,501) to compare 193P1E1B status in a sample.

The term "status" in this context is used according to its art accepted meaning and refers to the condition or state of a gene and its products. Typically, skilled artisans use a number of parameters to evaluate the condition or state of a gene and its products. These include, but are not limited to the location of expressed gene products (including the location of 193P1E1B expressing cells) as well as the level, and biological activity of expressed gene products (such as 193P1E1B mRNA, polynucleotides and polypeptides). Typically, an alteration in the status of 193P1E1B comprises a change in the location of 193P1E1B and/or 193P1E1B expressing cells and/or an increase in 193P1E1B mRNA and/or protein expression.

193P1E1B status in a sample can be analyzed by a number of means well known in the art, including without limitation, immunohistochemical analysis, in situ hybridization, RT-PCR analysis on laser capture micro-dissected samples, Western blot analysis, and tissue array analysis. Typical protocols for evaluating the status of a 193P1E1B gene and gene products are found, for example in Ausubel et al. eds., 1995, Current Protocols In Molecular Biology, Units 2 (Northern Blotting), 4 (Southern Blotting), 15 (Immunoblotting) and 18 (PCR Analysis). Thus, the status of 193P1E1B in a biological sample is evaluated by various methods utilized by skilled artisans including, but not limited to genomic Southern analysis (to examine, for example perturbations in a 193P1E1B gene), Northern analysis and/or PCR analysis of 193P1E1B mRNA (to examine, for example alterations in the polynucleotide sequences or expression levels of 193P1E1B mRNAs), and, Western and/or immunohistochemical analysis (to examine, for example alterations in polypeptide sequences, alterations in polypeptide localization within a sample, alterations in expression levels of 193P1E1B proteins and/or associations of 193P1E1B proteins with polypeptide binding partners). Detectable 193P1E1B polynucleotides include, for example, a 193P1E1B gene or fragment thereof, 193P1E1B mRNA, alternative splice variants, 193P1E1B mRNAs, and recombinant DNA or RNA molecules containing a 193P1E1B polynucleotide.

The expression profile of 193P1E1B makes it a diagnostic marker for local and/or metastasized disease, and provides information on the growth or oncogenic potential of a biological sample. In particular, the status of 193P1E1B provides information useful for predicting susceptibility to particular disease stages, progression, and/or tumor aggressiveness. The invention provides methods and assays for determining 193P1E1B status and diagnosing cancers that express 193P1E1B, such as cancers of the tissues listed in Table I. For example, because 193P1E1B mRNA is so highly expressed in prostate and other cancers relative to normal prostate tissue, assays that evaluate the levels of 193P1E1B mRNA transcripts or proteins in a biological sample can be used to diagnose a disease associated with 193P1E1B dysregulation, and can provide prognostic information useful in defining appropriate therapeutic options.

The expression status of 193P1E1B provides information including the presence, stage and location of dysplastic, precancerous and cancerous cells, predicting susceptibility to various stages of disease, and/or for gauging tumor aggressiveness. Moreover, the expression profile makes it useful as an imaging reagent for metastasized disease. Consequently, an aspect of the invention is directed to the various molecular prognostic and diagnostic methods for examining the status of 193P1E1B in biological samples such as those from individuals suffering from, or suspected of suffering from a pathology characterized by dysregulated cellular growth, such as cancer.

As described above, the status of 193P1E1B in a biological sample can be examined by a number of well-known procedures in the art. For example, the status of 193P1E1B in a biological sample taken from a specific location in the body can be examined by evaluating the sample for the presence or absence of 193P1E1B expressing cells (e.g. those that express 193P1E1B mRNAs or proteins). This examination can provide evidence of dysregulated cellular growth, for example, when 193P1E1B-expressing cells are found in a biological sample that does not normally contain such cells (such as a lymph node), because such alterations in the status of 193P1E1B in a biological sample are often associated with dysregulated cellular growth. Specifically, one indicator of dysregulated cellular growth is the metastases of cancer cells from an organ of origin (such as the prostate) to a different area of the body (such as a lymph node). In this context, evidence of dysregulated cellular growth is important for example because occult lymph node metastases can be detected in a substantial proportion of patients with prostate cancer, and such metastases are associated with known predictors of disease progression (see, e.g., Murphy et al., Prostate 42(4): 315-317 (2000);Su et al., Semin. Surg. Oncol. 18(1): 17-28 (2000) and Freeman et al., J Urol August 1995 154(2 Pt 1):474-8).

In one aspect, the invention provides methods for monitoring 193P1E1B gene products by determining the status of 193P1E1B gene products expressed by cells from an individual suspected of having a disease associated with dysregulated cell growth (such as hyperplasia or cancer) and then comparing the status so determined to the status of 193P1E1B gene products in a corresponding normal sample. The presence of aberrant 193P1E1B gene products in the test sample relative to the normal sample provides an indication of the presence of dysregulated cell growth within the cells of the individual.

In another aspect, the invention provides assays useful in determining the presence of cancer in an individual, comprising detecting a significant increase in 193P1E1B mRNA or protein expression in a test cell or tissue sample relative to expression levels in the corresponding normal cell or tissue. The presence of 193P1E1B mRNA can, for example, be evaluated in tissues including but not limited to those listed in Table I. The presence of significant 193P1E1B expression in any of these tissues is useful to indicate the emergence, presence and/or severity of a cancer, since the corresponding normal tissues do not express 193P1E1B mRNA or express it at lower levels.

In a related embodiment, 193P1E1B status is determined at the protein level rather than at the nucleic acid level. For example, such a method comprises determining the level of 193P1E1B protein expressed by cells in a test tissue sample and comparing the level so determined to the level of 193P1E1B expressed in a corresponding normal sample. In one embodiment, the presence of 193P1E1B protein is evaluated, for example, using immunohistochemical methods. 193P1E1B antibodies or binding partners capable of detecting 193P1E1B protein expression are used in a variety of assay formats well known in the art for this purpose.

In a further embodiment, one can evaluate the status of 193P1E1B nucleotide and amino add sequences in a biological sample in order to identify perturbations in the structure of these molecules. These perturbations can include insertions, deletions, substitutions and the like. Such evaluations are useful because perturbations in the nucleotide and amino acid sequences are observed in a large number of proteins associated with a growth dysregulated phenotype (see, e.g., Marrogi et al., 1999, J. Cutan. Pathol. 26(8):369-378). For example, a mutation in the sequence of 193P1E1B may be indicative of the presence or promotion of a tumor. Such assays therefore have diagnostic and predictive value where a mutation in 193P1E1B indicates a potential loss of function or increase in tumor growth.

A wide variety of assays for observing perturbations in nucleotide and amino acid sequences are well known in the art. For example, the size and structure of nucleic acid or amino acid sequences of 193P1E1B gene products are observed by the Northern, Southern, Western, PCR and DNA sequencing protocols discussed herein. In addition, other methods for observing perturbations in nucleotide and amino acid sequences such as single strand conformation polymorphism analysis are well known in the art (see, e.g., U.S. Pat. Nos. 5,382,510 issued Sep. 7, 1999, and 5,952,170 issued Jan. 17, 1995).

Additionally, one can examine the methylation status of a 193P1E1B gene in a biological sample. Aberrant demethylation and/or hypermethylation of CpG islands in gene 5' regulatory regions frequency occurs in immortalized and transformed cells, and can result in altered expression of various genes. For example, promoter hypermethylation of the pi-class glutathione S-transferase (a protein expressed in normal prostate but not expressed in >90% of prostate carcinomas) appears to permanently silence transcription of this gene and is the most frequently detected genomic alteration in prostate carcinomas (De Marzo et al., Am. J. Pathol. 155(6): 1985-1992 (1999)). In addition, this alteration is present in at least 70% of cases of high-grade prostatic intraepithelial neoplasia (PIN) (Brooks et al., Cancer Epidemiol. Biomarkers Prev., 1998, 7:531-536). In another example, expression of the LAGE-I tumor specific gene (which is not expressed in normal prostate but is expressed in 25-50% of prostate cancers) is induced by deoxy-azacytidine in lymphoblastoid cells, suggesting that tumoral expression is due to demethylation (Lethe et al., Int. J. Cancer 76(6): 903-908 (1998)). A variety of assays for examining methylation status of a gene are well known in the art. For example, one can utilize, in Southern hybridization approaches, methylation-sensitive restriction enzymes that cannot cleave sequences that contain methylated CpG sites to assess the methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in Current Protocols In Molecular Biology, Unit 12, Frederick M. Ausubel et at. eds., 1995.

Gene amplification is an additional method for assessing the status of 193P1E1B. Gene amplification is measured in a sample directly, for example, by conventional Southern blotting or Northern blotting to quantitate the transcription of mRNA (Thomas, 1980, Proc. Natl. Acad. Sci. USA, 77:5201-5205), dot blotting (DNA analysis), or in situ hybridization, using an appropriately labeled probe, based on the sequences provided herein. Alternatively, antibodies are employed that recognize specific duplexes, including DNA duplexes, RNA duplexes, and DNA-RNA hybrid duplexes or DNA-protein duplexes. The antibodies in turn are labeled and the assay carried out where the duplex is bound to a surface, so that upon the formation of duplex on the surface, the presence of antibody bound to the duplex can be detected.

Biopsied tissue or peripheral blood can be conveniently assayed for the presence of cancer cells using for example, Northern, dot blot or RT-PCR analysis to detect 193P1E1B expression. The presence of RT-PCR amplifiable 193P1E1B mRNA provides an indication of the presence of cancer. RT-PCR assays are well known in the art. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25:373-384; Ghossein et al., 1995, J. Clin. Oncol. 13:1195-2000; Heston et al., 1995, Clin. Chem. 41:1687-1688).

A further aspect of the invention is an assessment of the susceptibility that an individual has for developing cancer. In one embodiment, a method for predicting susceptibility to cancer comprises detecting 193P1E1B mRNA or 193P1E1B protein in a tissue sample, its presence indicating susceptibility to cancer, wherein the degree of 193P1E1B mRNA expression correlates to the degree of susceptibility. In a specific embodiment, the presence of 193P1E1B in prostate or other tissue is examined, with the presence of 193P1E1B in the sample providing an indication of prostate cancer susceptibility (or the emergence or existence of a prostate tumor). Similarly, one can evaluate the integrity 193P1E1B nucleotide and amino acid sequences in a biological sample, in order to identify perturbations in the structure of these molecules such as insertions, deletions, substitutions and the like. The presence of one or more perturbations in 193P1E1B gene products in the sample is an indication of cancer susceptibility (or the emergence or existence of a tumor).

The invention also comprises methods for gauging tumor aggressiveness. In one embodiment, a method for gauging aggressiveness of a tumor comprises determining the level of 193P1E1B mRNA or 193P1E1B protein expressed by tumor cells, comparing the level so determined to the level of 193P1E1B mRNA or 193P1E1B protein expressed in a corresponding normal tissue taken from the same individual or a normal tissue reference sample, wherein the degree of 193P1E1B mRNA or 193P1E1B protein expression in the tumor sample relative to the normal sample indicates the degree of aggressiveness. In a specific embodiment, aggressiveness of a tumor is evaluated by determining the extent to which 193P1E1B is expressed in the tumor cells, with higher expression levels indicating more aggressive tumors. Another embodiment is the evaluation of the integrity of 193P1E1B nucleotide and amino acid sequences in a biological sample, in order to identify perturbations in the structure of these molecules such as insertions, deletions, substitutions and the like. The presence of one or more perturbations indicates more aggressive tumors.

Another embodiment of the invention is directed to methods for observing the progression of a malignancy in an individual over time. In one embodiment, methods for observing the progression of a malignancy in an individual over time comprise determining the level of 193P1E1B mRNA or 193P1E1B protein expressed by cells in a sample of the tumor, comparing the level so determined to the level of 193P1E1B mRNA or 193P1E1B protein expressed in an equivalent tissue sample taken from the same individual at a different time, wherein the degree of 193P1E1B mRNA or 193P1E1B protein expression in the tumor sample over time provides information on the progression of the cancer. In a specific embodiment, the progression of a cancer is evaluated by determining 193P1E1B expression in the tumor cells over time, where increased expression over time indicates a progression of the cancer. Also, one can evaluate the integrity 193P1E1B nucleotide and amino acid sequences in a biological sample in order to identify perturbations in the structure of these molecules such as insertions, deletions, substitutions and the like, where the presence of one or more perturbations indicates a progression of the cancer.

The above diagnostic approaches can be combined with any one of a wide variety of prognostic and diagnostic protocols known in the art. For example, another embodiment of the invention is directed to methods for observing a coincidence between the expression of 193P1E1B gene and 193P1E1B gene products (or perturbations in 193P1E1B gene and 193P1E1B gene products) and a factor that is associated with malignancy, as a means for diagnosing and prognosticating the status of a tissue sample. A wide variety of factors associated with malignancy can be utilized, such as the expression of genes associated with malignancy (e.g. PSA, PSCA and PSM expression for prostate cancer etc.) as well as gross cytological observations (see, e.g., Bocking et al., 1984, Anal. Quant. Cytol. 6(2):74-88; Epstein, 1995, Hum. Pathol. 26(2):223-9; Thorson et al., 1998, Mod. Pathol. 11(6):543-51; Baisden et al., 1999, Am. J. Surg. Pathol. 23(8):918-24). Methods for observing a coincidence between the expression of 193P1E1B gene and 193P1E1B gene products (or perturbations in 193P1E1B gene and 193P1E1B gene products) and another factor that is associated with malignancy are useful, for example, because the presence of a set of specific factors that coincide with disease provides information crucial for diagnosing and prognosticating the status of a tissue sample.

In one embodiment, methods for observing a coincidence between the expression of 193P1E1B gene and 193P1E1B gene products (or perturbations in 193P1E1B gene and 193P1E1B gene products) and another factor associated with malignancy entails detecting the overexpression of 193P1E1B mRNA or protein in a tissue sample, detecting the overexpression of PSA mRNA or protein in a tissue sample (or PSCA or PSM expression), and observing a coincidence of 193P1E1B mRNA or protein and PSA mRNA or protein overexpression (or PSCA or PSM expression). In a specific embodiment, the expression of 193P1E1B and PSA mRNA in prostate tissue is examined, where the coincidence of 193P1E1B and PSA mRNA overexpression in the sample indicates the existence of prostate cancer, prostate cancer susceptibility or the emergence or status of a prostate tumor.

Methods for detecting and quantifying the expression of 193P1E1B mRNA or protein are described herein, and standard nucleic acid and protein detection and quantification technologies are well known in the art. Standard methods for the detection and quantification of 193P1E1B mRNA include in situ hybridization using labeled 193P1E1B riboprobes, Northern blot and related techniques using 193P1E1B polynucleotide probes, RT-PCR analysis using primers specific for 193P1E1B, and other amplification type detection methods, such as, for example, branched DNA, SISBA, TMA and the like. In a specific embodiment, semi-quantitative RT-PCR is used to detect and quantify 193P1E1B mRNA expression. Any number of primers capable of amplifying 193P1E1B can be used for this purpose, including but not limited to the various primer sets specifically described herein. In a specific embodiment, polyclonal or monoclonal antibodies specifically reactive with the wild-type 193P1E1B protein can be used in an immunohistochemical assay of biopsied tissue.

IX.) Identification of Molecules That Interact With 193P1E1B

The 193P1E1B protein and nucleic acid sequences disclosed herein allow a skilled artisan to identify proteins, small molecules and other agents that interact with 193P1E1B, as well as pathways activated by 193P1E1B via anyone of a variety of art accepted protocols. For example, one can utilize one of the so-called interaction trap systems (also referred to as the "two-hybrid assay"). In such systems, molecules interact and reconstitute a transcription factor which directs expression of a reporter gene, whereupon the expression of the reporter gene is assayed. Other systems identify protein-protein interactions in vivo through reconstitution of a eukaryotic transcriptional activator, see, e.g., U.S. Pat. Nos. 5,955,280 issued Sep. 21, 1999, 5,925,523 issued Jul. 20, 1999, 5,846,722 issued Dec. 8, 1998 and 6,004,746 issued Dec. 21, 1999. Algorithms are also available in the art for genome-based predictions of protein function (see, e.g., Marcotte, et al., Nature 402: Nov. 4, 1999, 83-86).

Alternatively one can screen peptide libraries to identify molecules that interact with 193P1E1B protein sequences. In such methods, peptides that bind to 193P1E1B are identified by screening libraries that encode a random or controlled collection of amino acids. Peptides encoded by the libraries are expressed as fusion proteins of bacteriophage coat proteins, the bacteriophage particles are then screened against the 193P1E1B protein(s).

Accordingly, peptides having a wide variety of uses, such as therapeutic, prognostic or diagnostic reagents, are thus identified without any prior information on the structure of the expected ligand or receptor molecule. Typical peptide libraries and screening methods that can be used to identify molecules that interact with 193P1E1B protein sequences are disclosed for example in U.S. Pat. Nos. 5,723,286 issued Mar. 3, 1998 and 5,733,731 issued Mar. 31, 1998.

Alternatively, cell lines that express 193P1E1B are used to identify protein-protein interactions mediated by 193P1E1B. Such interactions can be examined using immunoprecipitation techniques (see, e.g., Hamilton B. J., et al. Biochem. Biophys. Res. Commun. 1999, 261:646-51). 193P1E1B protein can be immunoprecipitated from 193P1E1B-expressing cell lines using anti-193P1E1B antibodies. Alternatively, antibodies against His-tag can be used in a cell line engineered to express fusions of 193P1E1B and a His-tag (vectors mentioned above). The immunoprecipitated complex can be examined for protein association by procedures such as Western blotting, $^{35}$S-methionine labeling of proteins, protein microsequencing, silver staining and two-dimensional gel electrophoresis.

Small molecules and ligands that interact with 193P1E1B can be identified through related embodiments of such screening assays. For example, small molecules can be identified that interfere with protein function, including molecules that interfere with 193P1E1B's ability to mediate phosphorylation and de-phosphorylation, interaction with DNA or RNA molecules as an indication of regulation of cell cycles, second messenger signaling or tumorigenesis. Similarly, small molecules that modulate 193P1E1B-related ion channel, protein pump, or cell communication functions are identified and used to treat patients that have a cancer that expresses 193P1E1B (see, e.g., Hille, B., Ionic Channels of Excitable Membranes 2$^{nd}$ Ed., Sinauer Assoc., Sunderland, Mass., 1992). Moreover, ligands that regulate 193P1E1B function can be identified based on their ability to bind 193P1E1B and activate a reporter construct. Typical methods are discussed for example in U.S. Pat. No. 5,928,868 issued Jul. 27, 1999, and include methods for forming hybrid ligands in which at least one ligand is a small molecule. In an illustrative embodiment, cells engineered to express a fusion protein of 193P1E1B and a DNA-binding protein are used to co-express a fusion protein of a hybrid ligand/small molecule and a cDNA library transcriptional activator protein. The cells further contain a reporter gene, the expression of which is conditioned on the proximity of the first and second fusion proteins to each other, an event that occurs only if the hybrid ligand binds to target sites on both hybrid proteins. Those cells that express the reporter gene are selected and the unknown small molecule or the unknown ligand is identified. This method provides a means of identifying modulators, which activate or inhibit 193P1E1B.

An embodiment of this invention comprises a method of screening for a molecule that interacts with a 193P1E1B amino acid sequence shown in FIG. 2 or FIG. 3, comprising the steps of contacting a population of molecules with a 193P1E1B amino acid sequence, allowing the population of molecules and the 193P1E1B amino acid sequence to interact under conditions that facilitate an interaction, determining the presence of a molecule that interacts with the 193P1E1B amino acid sequence, and then separating molecules that do not interact with the 193P1E1B amino acid sequence from molecules that do. In a specific embodiment, the method further comprises purifying, characterizing and identifying a molecule that interacts with the 193P1E1B amino acid sequence. The identified molecule can be used to modulate a function performed by 193P1E1B. In a preferred embodiment, the 193P1E1B amino acid sequence is contacted with a library of peptides.

X.) Therapeutic Methods and Compositions

The identification of 193P1E1B as a protein that is normally expressed in a restricted set of tissues, but which is also expressed in prostate and other cancers, opens a number of therapeutic approaches to the treatment of such cancers. As contemplated herein, 193P1E1B functions as a transcription factor involved in activating tumor-promoting genes or repressing genes that block tumorigenesis.

Accordingly, therapeutic approaches that inhibit the activity of a 193P1E1B protein are useful for patients suffering from a cancer that expresses 193P1E1B. These therapeutic approaches generally fall into two classes. One class comprises various methods for inhibiting the binding or association of a 193P1E1B protein with its binding partner or with other proteins. Another class comprises a variety of methods for inhibiting the transcription of a 193P1E1B gene or translation of 193P1E1B mRNA.

X.A.) Anti-Cancer Vaccines

The invention provides cancer vaccines comprising a 193P1E1B-related protein or 193P1E1B related nucleic acid. In view of the expression of 193P1E1B, cancer vaccines prevent and/or treat 193P1E1B-expressing cancers with minimal or no effects on non-target tissues. The use of a tumor antigen in a vaccine that generates humoral and/or cell-mediated immune responses as anti-cancer therapy is well known in the art and has been employed in prostate cancer using human PSMA and rodent PAP immunogens (Hodge et al., 1995, Int J. Cancer 63:231-237; Fong et al., 1997, J. Immunol. 159:3113-3117).

Such methods can be readily practiced by employing a 193P1E1B-related protein, or a 193P1E1B-encoding nucleic acid molecule and recombinant vectors capable of expressing and presenting the 193P1E1B immunogen (which typically comprises a number of antibody or T cell epitopes). Skilled artisans understand that a wide variety of vaccine systems for delivery of immunoreactive epitopes are known in the art (see, e.g., Heryln et al., Ann Med 1999 Feb 31(1):66-78; Maruyama et al., Cancer Immunol Immunother June 2000 49(3):123-32) Briefly, such methods of generating an immune response (e.g. humoral and/or cell-mediated) in a mammal, comprise the steps of: exposing the mammal's immune system to an immunoreactive epitope (e.g. an epitope present in a 193P1E1B protein shown in FIG. 3 or analog or homolog thereof) so that the mammal generates an immune response that is specific for that epitope (e.g. generates antibodies that specifically recognize that epitope). In a preferred method, a 193P1E1B immunogen contains a biological motif, see e.g., Tables VIII-XXI and XXII-XLIX, or a peptide of a size range from 193P1E1B indicated in FIG. 5, FIG. 6, FIG. 7, FIG. 8, and FIG. 9.

The entire 193P1E1B protein, immunogenic regions or epitopes thereof can be combined and delivered by various means. Such vaccine compositions can include, for example, lipopeptides (e.g., Vitiello, A. et al., *J. Clin. Invest.* 95:341, 1995), peptide compositions encapsulated in poly(DL-lactide-co-glycolide) ("PLG") microspheres (see, e.g., Eldridge, et al., *Molec. Immunol.* 28:287-294, 1991: Alonso et al., Vaccine 12:299-306, 1994; Jones et al., *Vaccine* 13:675-681, 1995), peptide compositions contained in immune stimulating complexes (ISCOMS) (see, e.g., Takahashi et al., *Nature* 344:873-875, 1990; Hu et al., *Clin Exp Immunol.* 113:235-243, 1998), multiple antigen peptide systems (MAPs) (see e.g., Tam, J. P., *Proc. Natl. Acad. Sci. U.S.A.* 85:5409-5413, 1988; Tam, J. P., *J. Immunol. Methods* 196:17-32, 1996), peptides formulated as multivalent peptides; peptides for use in ballistic delivery systems, typically crystallized peptides, viral delivery vectors (Perkus, M. E. et al., In: Concepts in vaccine development, Kaufmann, S. H. E., ed., p. 379, 1996; Chakrabarti, S. et al., *Nature* 320:535, 1986; Hu, S. L. et al., *Nature* 320:537, 1986; Kieny, M.-P. et al., *AIDS Bio/Technology* 4:790, 1986; Top, F. H. et al., *J. Infect. Dis.* 124:148, 1971; Chanda, P. K. et al., *Virology* 175:535, 1990), particles of viral or synthetic origin (e.g., Kofler, N. et al., *J. Immunol. Methods.* 192:25, 1996; Eldridge, J. H. et al., *Sem. Hematol.* 30:16, 1993; Falo, L. D., Jr. et al., *Nature Med.* 7:649, 1995), adjuvants (Warren, H. S., Vogel, F. R., and Chedid, L. A. *Annu. Rev. Immunol.* 4:369, 1986; Gupta, R. K. et al., *Vaccine* 11:293, 1993), liposomes (Reddy, R. et al., *J. Immunol.* 148:1585, 1992; Rock, K. L., *Immunol. Today* 17:131, 1996), or, naked or particle absorbed cDNA (Ulmer, J. B. et al., *Science* 259:1745, 1993; Robinson, H. L., Hunt, L. A., and Webster, R. G., *Vaccine* 11:957, 1993; Shiver, J. W. et al., In: *Concepts in vaccine development,* Kaufmann, S. H. E., ed., p. 423, 1996; Cease, K. B., and Berzofsky, J. A., *Annu. Rev. Immunol.* 12:923, 1994 and Eldridge, J. H. et al., *Sem. Hematol.* 30:16, 1993). Toxin-targeted delivery technologies, also known as receptor mediated targeting, such as those of Avant Immunotherapeutics, Inc. (Needham, Mass.) may also be used.

In patients with 193P1E1B-associated cancer, the vaccine compositions of the invention can also be used in conjunction with other treatments used for cancer, e.g., surgery, chemotherapy, drug therapies, radiation therapies, etc. including use in combination with immune adjuvants such as IL-2, IL-12, GM-CSF, and the like.

Cellular Vaccines:

CTL epitopes can be determined using specific algorithms to identify peptides within 193P1E1B protein that bind corresponding HLA alleles (see e.g., Table IV; Epimer™ and Epimatrix™, Brown University; and, BIMAS, and SYFPEITHI. In a preferred embodiment, a 193P1E1B immunogen contains one or more amino acid sequences identified using techniques well known in the art, such as the sequences shown in Tables VIII-XXI and XXII-XLIX or a peptide of 8, 9, 10 or 11 amino acids specified by an HLA Class I motif/supermotif (e.g., Table IV (A), Table IV (D), or Table IV (E)) and/or a peptide of at least 9 amino acids that comprises an HLA Class II motif/supermotif (e.g., Table IV (B) or Table IV (C)). As is appreciated in the art, the HLA Class I binding groove is essentially closed ended so that peptides of only a particular size range can fit into the groove and be bound, generally HLA Class I epitopes are 8, 9, 10, or 11 amino acids long. In contrast, the HLA Class II binding groove is essentially open ended; therefore a peptide of about 9 or more amino acids can be bound by an HLA Class 11 molecule. Due to the binding groove differences between HLA Class I and 11, HLA Class I motifs are length specific, i.e., position two of a Class I motif is the second amino acid in an amino to carboxyl direction of the peptide. The amino acid positions in a Class II motif are relative only to each other, not the overall peptide, i.e., additional amino acids can be attached to the amino and/or carboxyl termini of a motif-bearing sequence. HLA Class II epitopes are often 9, 10, 11, 12, 13, 14, 15, 16, 17, 18, 19, 20, 21, 22, 23, 24, or 25 amino acids long, or longer than 25 amino acids.

Antibody-Based Vaccines

A wide variety of methods for generating an immune response in a mammal are known in the art (for example as the first step in the generation of hybridomas). Methods of generating an immune response in a mammal comprise exposing the mammal's immune system to an immunogenic epitope on a protein (e.g. a 193P1E1B protein) so that an immune response is generated. A typical embodiment consists of a method for generating an immune response to 193P1E1B in a host, by contacting the host with a sufficient amount of at least one 193P1E1B B cell or cytotoxic T-cell epitope or analog thereof; and at least one periodic interval thereafter re-contacting the host with the 193P1E1B B cell or cytotoxic T-cell epitope or analog thereof. A specific embodiment consists of a method of generating an immune response against a 193P1E1B-related protein or a man-made multiepitopic peptide comprising: administering 193P1E1B immunogen (e.g. a 193P1E1B protein or a peptide fragment thereof, a 193P1E1B fusion protein or analog etc.) in a vaccine preparation to a human or another mammal. Typically, such vaccine preparations further contain a suitable adjuvant (see, e.g., U.S. Pat. No. 6,146,635) or a universal helper epitope such as a PADRE™ peptide (Epimmune Inc., San Diego, Calif.; see, e.g., Alexander et al., J. Immunol. 2000 164(3); 164(3): 1625-1633; Alexander et al., Immunity 1994 1(9): 751-761 and Alexander et al., Immunol. Res. 1998 18(2): 79-92). An alternative method comprises generating an immune response in an individual against a 193P1E1B immunogen by: administering in vivo to muscle or skin of the individual's body a DNA molecule that comprises a DNA sequence that encodes a 193P1E1B immunogen, the DNA sequence operatively linked to regulatory sequences which control the expression of the DNA sequence; wherein the DNA molecule is taken up by cells, the DNA sequence is expressed in the cells and an immune response is generated against the immunogen (see, e.g., U.S. Pat. No. 5,962,428). Optionally a genetic vaccine facilitator such as anionic lipids; saponins; lectins; estrogenic compounds; hydroxylated lower alkyls; dimethyl sulfoxide; and urea is also administered. In addition, an antiidiotypic antibody can be administered that mimics 193P1E1B, in order to generate a response to the target antigen.

Nucleic Acid Vaccines:

Vaccine compositions of the invention include nucleic acid-mediated modalities. DNA or RNA that encode protein(s) of the invention can be administered to a patient. Genetic immunization methods can be employed to generate prophylactic or therapeutic humoral and cellular immune responses directed against cancer cells expressing 193P1E1B. Constructs comprising DNA encoding a 193P1E1B-related protein/immunogen and appropriate regulatory sequences can be injected directly into muscle or skin of an individual, such that the cells of the muscle or skin take-up the construct and express the encoded 193P1E1B protein/immunogen. Alternatively, a vaccine comprises a 193P1E1B-related protein. Expression of the 193P1E1B-related protein immunogen results in the generation of prophylactic or therapeutic humoral and cellular immunity against cells that bear a 193P1E1B protein. Various prophylactic and therapeutic genetic immunization techniques known in the art can be used (for review, see information and references published at Internet address genweb.com). Nucleic acid-based delivery is described, for instance, in Wolff et. al., Science 247:1465 (1990) as well as U.S. Pat. Nos. 5,580,859; 5,589,466; 5,804,566; 5,739,118; 5,736,524; 5,679,647; WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

For therapeutic or prophylactic immunization purposes, proteins of the invention can be expressed via viral or bacterial vectors. Various viral gene delivery systems that can be used in the practice of the invention include, but are not limited to, vaccinia, fowlpox, canarypox, adenovirus, influenza, poliovirus, adeno-associated virus, lentivirus, and sindbis virus (see, e.g., Restifo, 1996, Curr. Opin. Immunol. 8:658-663; Tsang et al. *J. Natl. Cancer Inst.* 87:982-990 (1995)). Non-viral delivery systems can also be employed by introducing naked DNA encoding a 193P1E1B-related protein into the patent (e.g., intramuscularly or intradermally) to induce an anti-tumor response.

Vaccinia virus is used, for example, as a vector to express nucleotide sequences that encode the peptides of the invention. Upon introduction into a host, the recombinant vaccinia virus expresses the protein immunogenic peptide, and thereby elicits a host immune response. Vaccinia vectors and methods useful in immunization protocols are described in, e.g., U.S. Pat. No. 4,722,848. Another vector is BCG (Bacille Calmelte Guerin). BCG vectors are described in Stover et al., *Nature* 351:456-460 (1991). A wide variety of other vectors useful for therapeutic administration or immunization of the peptides of the invention, e.g. adeno and adeno-associated virus vectors, retroviral vectors, *Salmonella typhi* vectors, detoxified anthrax toxin vectors, and the like, will be apparent to those skilled in the art from the description herein.

Thus, gene delivery systems are used to deliver a 193P1E1B-related nucleic add molecule. In one embodiment, the full-length human 193P1E1B cDNA is employed. In another embodiment, 193P1E1B nucleic acid molecules encoding specific cytotoxic T lymphocyte (CTL) and/or antibody epitopes are employed.

Ex Vivo Vaccines

Various ex vivo strategies can also be employed to generate an immune response. One approach involves the use of antigen presenting cells (APCS) such as dendritic cells (DC) to present 193P1E1B antigen to a patient's immune system. Dendritic cells express MHC class I and II molecules, B7 co-stimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28:65-69; Murphy et al., 1996, Prostate 29:371-380). Thus, dendritic cells can be used to present 193P1E1B peptides to T cells in the context of MHC class I or II molecules. In one embodiment, autologous dendritic cells are pulsed with 193P1E1B peptides capable of binding to MHC class I and/or class II molecules. In another embodiment, dendritic cells are pulsed with the complete 193P1E1B protein. Yet another embodiment involves engineering the overexpression of a 193P1E1B gene in dendritic cells using various implementing vectors known in the art, such as adenovirus (Arthur et al., 1997, Cancer Gene Ther. 4:17-25), retrovirus (Henderson et al., 1996, Cancer Res. 56:3763-3770), lentivirus, adeno-associated virus, DNA transfection (Ribas et al., 1997, Cancer Res. 57:2865-2869), or tumor-derived RNA transfection (Ashley et al., 1997, J. Exp. Med. 186: 1177-1182). Cells that express 193P1E1B can also be engineered to express immune modulators, such as GM-CSF, and used as immunizing agents.

X.B.) 193P1E1B as a Target for Antibody-Based Therapy

193P1E1B is an attractive target for antibody-based therapeutic strategies. A number of antibody strategies are known in the art for targeting both extracellular and intracellular molecules (see, e.g., complement and ADCC mediated killing as well as the use of intrabodies). Because 193P1E1B is expressed by cancer cells of various lineages relative to corresponding normal cells, systemic administration of 193P1E1B-immunoreactive compositions are prepared that exhibit excellent sensitivity without toxic, non-specific and/or non-target effects caused by binding of the immunoreactive composition to non-target organs and tissues. Antibodies specifically reactive with domains of 193P1E1B are useful to treat 193P1E1B-expressing cancers systemically, either as conjugates with a toxin or therapeutic agent, or as naked antibodies capable of inhibiting cell proliferation or function.

193P1E1B antibodies can be introduced into a patient such that the antibody binds to 193P1E1B and modulates a function, such as an interaction with a binding partner, and consequently mediates destruction of the tumor cells and/or inhibits the growth of the tumor cells. Mechanisms by which such antibodies exert a therapeutic effect can include complement-mediated cytolysis, antibody-dependent cellular cytotoxicity, modulation of the physiological function of 193P1E1B, inhibition of ligand binding or signal transduction pathways, modulation of tumor cell differentiation, alteration of tumor angiogenesis factor profiles, and/or apoptosis.

Those skilled in the art understand that antibodies can be used to specifically target and bind immunogenic molecules such as an immunogenic region of a 193P1E1B sequence shown in FIG. 2 or FIG. 3. In addition, skilled artisans understand that it is routine to conjugate antibodies to cytotoxic agents (see, e.g., Slevers et al. *Blood* 93:11 3678-3684 (Jun. 1, 1999)). When cytotoxic and/or therapeutic agents are delivered directly to cells, such as by conjugating them to antibodies specific for a molecule expressed by that cell (e.g. 193P1E1B), the cytotoxic agent will exert its known biological effect (i.e. cytotoxicity) on those cells.

A wide variety of compositions and methods for using antibody-cytotoxic agent conjugates to kill cells are known in the art. In the context of cancers, typical methods entail administering to an animal having a tumor a biologically effective amount of a conjugate comprising a selected cytotoxic and/or therapeutic agent linked to a targeting agent (e.g. an anti-193P1E1B antibody) that binds to a marker (e.g. 193P1E1B) expressed, accessible to binding or localized on the cell surfaces. A typical embodiment is a method of delivering a cytotoxic and/or therapeutic agent to a cell expressing 193P1E1B, comprising conjugating the cytotoxic agent to an antibody that immunospecifically binds to a 193P1E1B epitope, and, exposing the cell to the antibody-agent conjugate. Another illustrative embodiment is a method of treating an individual suspected of suffering from metastasized cancer, comprising a step of administering parenterally to said individual a pharmaceutical composition comprising a therapeutically effective amount of an antibody conjugated to a cytotoxic and/or therapeutic agent.

Cancer immunotherapy using anti-193P1E1B antibodies can be done in accordance with various approaches that have been successfully employed in the treatment of other types of cancer, including but not limited to colon cancer (Arlen et al., 1998, Crit. Rev. Immunol. 18:133-138), multiple myeloma (Ozaki et al., 1997, Blood 90:3179-3186, Tsunenari et al., 1997, Blood 90:2437-2444), gastric cancer (Kasprzyk et al., 1992, Cancer Res. 52:2771-2776), B-cell lymphoma (Funakoshi et al., 1996, J. Immunother. Emphasis Tumor Immunol. 19:93-101), leukemia (Zhong et al., 1996, Leuk. Res. 20:581-589), colorectal cancer (Moun et al., 1994, Cancer Res. 54:6160-6166; Velders et al., 1995, Cancer Res. 55:4398-4403), and breast cancer (Shepard et al., 1991, J. Clin. Immunol. 11:117-127). Some therapeutic approaches involve conjugation of naked antibody to a toxin or radioisotope, such as the conjugation of $Y^{91}$ or $I^{131}$ to anti-CD20 antibodies (e.g., Zevalin™, IDEC Pharmaceuticals Corp. or Bexxar™, Coulter Pharmaceuticals), while others involve co-administration of antibodies and other therapeutic agents, such as Herceptin™ (trastuzumab) with paclitaxel (Genentech, Inc.). The antibodies can be conjugated to a therapeutic agent. To treat prostate cancer, for example, 193P1E1B antibodies can be administered in conjunction with radiation, chemotherapy or hormone ablation. Also, antibodies can be conjugated to a toxin such as calicheamicin (e.g., Mylotarg™, Wyeth-Ayerst, Madison, N.J., a recombinant humanized IgG4 kappa antibody conjugated to antitumor antibiotic calicheamicin) or a maytansinoid (e.g., taxane-based Tumor-Activated Prodrug, TAP, platform, ImmunoGen, Cambridge, Mass., also see e.g., U.S. Pat. No. 5,416,064).

Although 193P1E1B antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well. Fan et al. (Cancer Res. 53:4637-4642, 1993), Prewett et al. (International J. of Onco. 9:217-224, 1996), and Hancock et al. (Cancer Res. 51:4575-4580, 1991) describe the use of various antibodies together with chemotherapeutic agents.

Although 193P1E1B antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well.

Cancer patients can be evaluated for the presence and level of 193P1E1B expression, preferably using immunohistochemical assessments of tumor tissue, quantitative 193P1E1B imaging, or other techniques that reliably indicate the presence and degree of 193P1E1B expression. Immunohistochemical analysis of tumor biopsies or surgical specimens is preferred for this purpose. Methods for immunohistochemical analysis of tumor tissues are well known in the art.

Anti-193P1E1B monoclonal antibodies that treat prostate and other cancers include those that initiate a potent immune response against the tumor or those that are directly cytotoxic. In this regard, anti-193P1E1B monoclonal antibodies (mAbs) can elicit tumor cell lysis by either complement-mediated or antibody-dependent cell cytotoxicity (ADCC) mechanisms, both of which require an intact Fc portion of the immunoglobulin molecule for interaction with effector cell Fc receptor sites on complement proteins. In addition, anti-193P1E1B mAbs that exert a direct biological effect on tumor growth are useful to treat cancers that express 193P1E1B. Mechanisms by which directly cytotoxic mAbs act include: inhibition of cell growth, modulation of cellular differentiation, modulation of tumor angiogenesis factor profiles, and the induction of apoptosis. The mechanism(s) by which a particular anti-193P1E1B mAb exerts an anti-tumor effect is evaluated using any number of in vitro assays that evaluate cell death such as ADCC, ADMMC, complement-mediated cell lysis, and so forth, as is generally known in the art.

In some patients, the use of murine or other non-human monoclonal antibodies, or human/mouse chimeric mAbs can induce moderate to strong immune responses against the non-human antibody. This can result in clearance of the antibody from circulation and reduced efficacy. In the most severe cases, such an immune response can lead to the extensive formation of immune complexes which, potentially, can cause renal failure. Accordingly, preferred monoclonal antibodies used in the therapeutic methods of the invention are those that are either fully human or humanized and that bind specifically to the target 193P1E1B antigen with high affinity but exhibit low or no antigenicity in the patient.

Therapeutic methods of the invention contemplate the administration of single anti-193P1E1B mAbs as well as combinations, or cocktails, of different mAbs. Such mAb cocktails can have certain advantages inasmuch as they contain mAbs that target different epitopes, exploit different effector mechanisms or combine directly cytotoxic mAbs with mAbs that rely on immune effector functionality. Such mAbs in combination can exhibit synergistic therapeutic effects. In addition, anti-193P1E1B mAbs can be administered concomitantly with other therapeutic modalities, including but not limited to various chemotherapeutic agents, androgen-blockers, immune modulators (e.g., IL-2, GM-CSF), surgery or radiation. The anti-193P1E1B mAbs are administered in their "naked" or unconjugated form, or can have a therapeutic agent(s) conjugated to them.

Anti-193P1E1B antibody formulations are administered via any route capable of delivering the antibodies to a tumor cell. Routes of administration include, but are not limited to, intravenous, intraperitoneal, intramuscular, intratumor, intradermal, and the like. Treatment generally involves repeated administration of the anti-193P1E1B antibody preparation, via an acceptable route of administration such as intravenous injection (IV), typically at a dose in the range of about 0.1, 0.2, 0.3, 0.4, 0.5, 0.6, 0.7, 0.8, 0.9., 1, 2, 3, 4, 5, 6, 7, 8, 9, 10, 15, 20, or 25 mg/kg body weight. In general, doses in the range of 10-1000 mg mAb per week are effective and well tolerated.

Based on clinical experience with the Herceptin™ mAb in the treatment of metastatic breast cancer, an initial loading dose of approximately 4 mg/kg patient body weight IV, followed by weekly doses of about 2 mg/kg IV of the anti-193P1E1B mAb preparation represents an acceptable dosing regimen. Preferably, the initial loading dose is administered as a 90-minute or longer infusion. The periodic maintenance dose is administered as a 30 minute or longer infusion, provided the initial dose was well tolerated. As appreciated by those of skill in the art, various factors can influence the ideal dose regimen in a particular case. Such factors include, for example, the binding affinity and half life of the Ab or mAbs used, the degree of 193P1E1B expression in the patient, the extent of circulating shed 193P1E1B antigen, the desired steady-state antibody concentration level, frequency of treatment, and the influence of chemotherapeutic or other agents used in combination with the treatment method of the invention, as well as the health status of a particular patient.

Optionally, patients should be evaluated for the levels of 193P1E1B in a given sample (e.g. the levels of circulating 193P1E1B antigen and/or 193P1E1B expressing cells) in order to assist in the determination of the most effective dosing regimen, etc. Such evaluations are also used for monitoring purposes throughout therapy, and are useful to gauge therapeutic success in combination with the evaluation of other parameters (for example, urine cytology and/or ImmunoCyt levels in bladder cancer therapy, or by analogy, serum PSA levels in prostate cancer therapy).

Anti-idiotypic anti-193P1E1B antibodies can also be used in anti-cancer therapy as a vaccine for inducing an immune response to cells expressing a 193P1E1B-related protein. In particular, the generation of anti-idiotypic antibodies is well known in the art; this methodology can readily be adapted to generate anti-idiotypic anti-193P1E1B antibodies that mimic an epitope on a 193P1E1B-related protein (see, for example, Wagner et al., 1997, Hybridoma 16: 33-40; Foon et al., 1995, J. Clin. Invest. 96:334-342; Herlyn et al., 1996, Cancer Immunol. Immunother. 43:65-76). Such an anti-idiotypic antibody can be used in cancer vaccine strategies.

X.C.) 193P1E1B as a Target for Cellular Immune Responses

Vaccines and methods of preparing vaccines that contain an immunogenically effective amount of one or more HLA-binding peptides as described herein are further embodiments of the invention. Furthermore, vaccines in accordance with the invention encompass compositions of one or more of the claimed peptides. A peptide can be present in a vaccine individually. Alternatively, the peptide can exist as a homopolymer comprising multiple copies of the same peptide, or as a heteropolymer of various peptides. Polymers have the advantage of increased immunological reaction and, where different peptide epitopes are used to make up the polymer, the additional ability to induce antibodies and/or CTLs that react with different antigenic determinants of the pathogenic organism or tumor-related peptide targeted for an immune response. The composition can be a naturally occurring region of an antigen or can be prepared, e.g., recombinantly or by chemical synthesis.

Carriers that can be used with vaccines of the invention are well known in the art, and include, e.g., thyroglobulin, albumins such as human serum albumin, tetanus toxoid, polyamino acids such as poly L-lysine, poly L-glutamic acid, influenza, hepatitis B virus core protein, and the like. The vaccines can contain a physiologically tolerable (i.e., acceptable) diluent such as water, or saline, preferably phosphate buffered saline. The vaccines also typically include an adjuvant. Adjuvants such as incomplete Freund's adjuvant, aluminum phosphate, aluminum hydroxide, or alum are examples of materials well known in the art. Additionally, as disclosed herein, CTL responses can be primed by conjugating peptides of the invention to lipids, such as tripalmitoyl-S-glycerylcysteinlyseryl-serine ($P_3CSS$). Moreover, an adjuvant such as a synthetic cytosine-phosphorothiolated-guanine-containing (CpG) oligonucleotides has been found to increase CTL responses 10- to 100-fold. (see, e.g. Davila and Celis, J. Immunol. 165:539-547 (2000))

Upon immunization with a peptide composition in accordance with the invention, via injection, aerosol, oral, transdermal, transmucosal, intrapleural, intrathecal, or other suitable routes, the immune system of the host responds to the vaccine by producing large amounts of CTLs and/or HTLs specific for the desired antigen. Consequently, the host becomes at least partially immune to later development of cells that express or overexpress 193P1E1B antigen, or derives at least some therapeutic benefit when the antigen was tumor-associated.

In some embodiments, it may be desirable to combine the class I peptide components with components that induce or facilitate neutralizing antibody and or helper T cell responses directed to the target antigen. A preferred embodiment of such a composition comprises class I and class II epitopes in accordance with the invention. An alternative embodiment of such a composition comprises a class I and/or class II epitope in accordance with the invention, along with a cross reactive HTL epitope such as PADRE™ (Epimmune, San Diego, Calif.) molecule (described e.g., in U.S. Pat. No. 5,736,142).

A vaccine of the invention can also include antigen-presenting cells (APC), such as dendritic cells (DC), as a vehicle to present peptides of the invention. Vaccine compositions can be created in vitro, following dendritic cell mobilization and harvesting, whereby loading of dendritic cells occurs in vitro. For example, dendritic cells are transfected, e.g., with a minigene in accordance with the invention, or are pulsed with peptides. The dendritic cell can then be administered to a patient to elicit immune responses in vivo. Vaccine compositions, either DNA- or peptide-based, can also be administered in vivo in combination with dendritic cell mobilization whereby loading of dendritic cells occurs in vivo.

Preferably, the following principles are utilized when selecting an array of epitopes for inclusion in a polyepitopic composition for use in a vaccine, or for selecting discrete epitopes to be included in a vaccine and/or to be encoded by nucleic acids such as a minigene. It is preferred that each of the following principles be balanced in order to make the selection. The multiple epitopes to be incorporated in a given vaccine composition may be, but need not be, contiguous in sequence in the native antigen from which the epitopes are derived.

1.) Epitopes are selected which, upon administration, mimic immune responses that have been observed to be correlated with tumor clearance. For HLA Class I this includes 3-4 epitopes that come from at least one tumor associated antigen (TM). For HLA Class II a similar rationale is employed; again 34 epitopes are selected from at least one TAA (see, e.g., Rosenberg et al., *Science* 278:1447-1450). Epitopes from one TAA may be used in combination with epitopes from one or more additional TAAs to produce a vaccine that targets tumors with varying expression patterns of frequently-expressed TAAs.

2.) Epitopes are selected that have the requisite binding affinity established to be correlated with immunogenicity: for HLA Class I an $IC_{50}$ of 500 nM or less, often 200 nM or less; and for Class II an $IC_{50}$ of 1000 nM or less.

3.) Sufficient supermotif bearing-peptides, or a sufficient array of allele-specific motif-bearing peptides, are selected to give broad population coverage. For example, it is preferable to have at least 80% population coverage. A Monte Carlo analysis, a statistical evaluation known in the art, can be employed to assess the breadth, or redundancy of, population coverage.

4.) When selecting epitopes from cancer-related antigens it is often useful to select analogs because the patient may have developed tolerance to the native epitope.

5.) Of particular relevance are epitopes referred to as "nested epitopes." Nested epitopes occur where at least two epitopes overlap in a given peptide sequence. A nested peptide sequence can comprise B cell, HLA class I and/or HLA class II epitopes. When providing nested epitopes, a general objective is to provide the greatest number of epitopes per sequence. Thus, an aspect is to avoid providing a peptide that is any longer than the amino terminus of the amino terminal epitope and the carboxyl terminus of the carboxyl terminal epitope in the peptide. When providing a multi-epitopic sequence, such as a sequence comprising nested epitopes, it is generally important to screen the sequence in order to insure that it does not have pathological or other deleterious biological properties.

6.) If a polyepitopic protein is created, or when creating a minigene, an objective is to generate the smallest peptide that encompasses the epitopes of interest. This principle is similar, if not the same as that employed when selecting a peptide comprising nested epitopes. However, with an artificial polyepitopic peptide, the size minimization objective is balanced against the need to integrate any spacer sequences between epitopes in the polyepitopic protein. Spacer amino acid residues can, for example, be introduced to avoid junctional epitopes (an epitope recognized by the immune system, not present in the target antigen, and only created by the man-made juxtaposition of epitopes), or to facilitate cleavage between epitopes and thereby enhance epitope presentation. Junctional epitopes are generally to be avoided because the recipient may generate an immune response to that non-native epitope. Of particular concern is a junctional epitope that is a "dominant epitope." A dominant epitope may lead to such a zealous response that immune responses to other epitopes are diminished or suppressed.

7.) Where the sequences of multiple variants of the same target protein are present, potential peptide epitopes can also be selected on the basis of their conservancy. For example, a criterion for conservancy may define that the entire sequence of an HLA class I binding peptide or the entire 9-mer core of a class II binding peptide be conserved in a designated percentage of the sequences evaluated for a specific protein antigen.

X.C.1. Minigene Vaccines

A number of different approaches are available which allow simultaneous delivery of multiple epitopes. Nucleic acids encoding the peptides of the invention are a particularly useful embodiment of the invention. Epitopes for inclusion in a minigene are preferably selected according to the guidelines set forth in the previous section. A preferred means of administering nucleic acids encoding the peptides of the invention uses minigene constructs encoding a peptide comprising one or multiple epitopes of the invention.

The use of multi-epitope minigenes is described below and in, Ishioka et al., *J. Immunol.* 162:3915-3925, 1999; An, L. and Whitton, J. L., *J. Virol.* 71:2292, 1997; Thomson, S. A. et al., *J. Immunol.* 157:822, 1996; Whitton, J. L. et al., *J. Virol.* 67:348, 1993; Hanke, R. et al., *Vaccine* 16:426, 1998. For example, a multi-epitope DNA plasmid encoding supermotif- and/or motif-bearing epitopes derived 193P1E1B, the PADRE® universal helper T cell epitope or multiple HTL epitopes from 193P1E1B (see e.g., Tables VIII-XXI and XXII to XLIX), and an endoplasmic reticulum-translocating signal sequence can be engineered. A vaccine may also comprise epitopes that are derived from other TAAs.

The immunogenicity of a multi-epitopic minigene can be confirmed in transgenic mice to evaluate the magnitude of CTL induction responses against the epitopes tested. Further, the immunogenicity of DNA-encoded epitopes in vivo can be correlated with the in vitro responses of specific CTL lines against target cells transfected with the DNA plasmid. Thus, these experiments can show that the minigene serves to both: 1.) generate a CTL response and 2.) that the induced CTLs recognized cells expressing the encoded epitopes.

For example, to create a DNA sequence encoding the selected epitopes (minigene) for expression in human cells, the amino acid sequences of the epitopes may be reverse translated. A human codon usage table can be used to guide the codon choice for each amino acid. These epitope-encoding DNA sequences may be directly adjoined, so that when translated, a continuous polypeptide sequence is created. To optimize expression and/or immunogenicity, additional elements can be incorporated into the minigene design. Examples of amino acid sequences that can be reverse translated and included in the minigene sequence include: HLA class I epitopes, HLA class II epitopes, antibody epitopes, a ubiquitination signal sequence, and/or an endoplasmic reticulum targeting signal. In addition, HLA presentation of CTL and HTL epitopes may be improved by including synthetic (e.g. poly-alanine) or naturally-occurring flanking sequences adjacent to the CTL or HTL epitopes; these larger peptides comprising the epitope(s) are within the scope of the invention.

The minigene sequence may be converted to DNA by assembling oligonucleotides that encode the plus and minus strands of the minigene. Overlapping oligonucleotides (30-100 bases long) may be synthesized, phosphorylated, purified and annealed under appropriate conditions using well known techniques. The ends of the oligonucleotides can be joined, for example, using T4 DNA ligase. This synthetic minigene, encoding the epitope polypeptide, can then be cloned into a desired expression vector.

Standard regulatory sequences well known to those of skill in the art are preferably included in the vector to ensure expression in the target cells. Several vector elements are desirable: a promoter with a down-stream cloning site for minigene insertion; a polyadenylation signal for efficient transcription termination; an *E. coli* origin of replication; and an *E. coli* selectable marker (e.g. ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences and sequences for replication in mammalian cells may also be considered for increasing minigene expression.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

In addition, immunostimulatory sequences (ISSs or CpGs) appear to play a role in the immunogenicity of DNA vaccines. These sequences may be included in the vector, outside the minigene coding sequence, if desired to enhance immunogenicity.

In some embodiments, a bi-cistronic expression vector which allows production of both the minigene-encoded epitopes and a second protein (included to enhance or decrease immunogenicity) can be used. Examples of proteins or polypeptides that could beneficially enhance the immune response if co-expressed include cytokines (e.g., IL-2, IL-12, GM-CSF), cytokine-inducing molecules (e.g., LeIF), costimulatory molecules, or for HTL responses, pan-DR binding proteins (PADRE™, Epimmune, San Diego, Calif.). Helper (HTL) epitopes can be joined to intracellular targeting signals and expressed separately from expressed CTL epitopes; this allows direction of the HTL epitopes to a cell compartment different than that of the CTL epitopes. If required, this could facilitate more efficient entry of HTL epitopes into the HLA class II pathway, thereby improving HTL induction. In contrast to HTL or CTL induction, specifically decreasing the immune response by co-expression of immunosuppressive molecules (e.g. TGF-β) may be beneficial in certain diseases.

Therapeutic quantities of plasmid DNA can be produced for example, by fermentation in *E. coli*, followed by purification. Aliquots from the working cell bank are used to inoculate growth medium, and grown to saturation in shaker flasks or a bioreactor according to well-known techniques. Plasmid DNA can be purified using standard bioseparation technologies such as solid phase anion-exchange resins supplied by QIAGEN, Inc. (Valencia, Calif.). If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). This approach, known as "naked DNA," is currently being used for intramuscular (IM) administration in clinical trials. To maximize the immunotherapeutic effects of minigene DNA vaccines, an alternative method for formulating purified plasmid DNA may be desirable. A variety of methods have been described, and new techniques may become available. Cationic lipids, glycolipids, and fusogenic liposomes can also be used in the formulation (see, e.g., as described by WO 93/24640; Mannino & Gould-Fogerite, *BioTechniques* 6(7): 682 (1988); U.S. Pat No. 5,279,833; WO 91/06309; and Feigner, et al., *Proc. Nat'l. Acad. Sci. USA* 84:7413 (1987). In addition, peptides and compounds referred to collectively as protective, interactive, non-condensing compounds (PINC) could also be complexed to purified plasmid DNA to influence variables such as stability, intramuscular dispersion, or trafficking to specific organs or cell types.

Target cell sensitization can be used as a functional assay for expression and HLA class I presentation of minigene-encoded CTL epitopes. For example, the plasmid DNA is introduced into a mammalian cell line that is suitable as a target for standard CTL chromium release assays. The transfection method used will be dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 ($^{51}$Cr) labeled and used as target cells for epitope-specific CTL lines; cytolysis, detected by $^{51}$Cr release, indicates both production of, and HLA presentation of, minigene-encoded CTL epitopes. Expression of HTL epitopes may be evaluated in an analogous manner using assays to assess HTL activity.

In vivo immunogenicity is a second approach for functional testing of minigene DNA formulations. Transgenic mice expressing appropriate human HLA proteins are immunized with the DNA product. The dose and route of administration are formulation dependent (e.g., IM for DNA in PBS, intraperitoneal (i.p.) for lipid-complexed DNA). Twenty-one days after immunization, splenocytes are harvested and restimulated for one week in the presence of peptides encoding each epitope being tested. Thereafter, for CTL effector cells, assays are conducted for cytolysis of peptide-loaded, $^{51}$Cr-labeled target cells using standard techniques. Lysis of target cells that were sensitized by HLA loaded with peptide epitopes, corresponding to minigene-encoded epitopes, demonstrates DNA vaccine function for in vivo induction of CTLs. Immunogenicity of HTL epitopes is confirmed in transgenic mice in an analogous manner.

Alternatively, the nucleic acids can be administered using ballistic delivery as described, for instance, in U.S. Pat. No. 5,204,253. Using this technique, particles comprised solely of DNA are administered. In a further alternative embodiment, DNA can be adhered to particles, such as gold particles.

Minigenes can also be delivered using other bacterial or viral delivery systems well known in the art, e.g., an expression construct encoding epitopes of the invention can be incorporated into a viral vector such as vaccinia.

XC.2. Combinations of CTL Peptides with Helper Peptides

Vaccine compositions comprising CTL peptides of the invention can be modified, e.g., analoged, to provide desired attributes, such as improved serum half life, broadened population coverage or enhanced immunogenicity.

For instance, the ability of a peptide to induce CTL activity can be enhanced by linking the peptide to a sequence which contains at least one epitope that is capable of inducing a T helper cell response. Although a CTL peptide can be directly linked to a T helper peptide, often CTL epitope/HTL epitope conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues and sometimes 10 or more residues. The CTL peptide epitope can be linked to the T helper peptide epitope either directly or via a spacer either at the amino or carboxy terminus of the CTL peptide. The amino terminus of either the immunogenic peptide or the T helper peptide may be acylated.

In certain embodiments, the T helper peptide is one that is recognized by T helper cells present in a majority of a genetically diverse population. This can be accomplished by selecting peptides that bind to many, most, or all of the HLA class II molecules. Examples of such amino acid bind many HLA Class II molecules include sequences from antigens such as tetanus toxoid at positions 830-843 (QYIKANSKFIGITE; SEQ ID NO: 48), *Plasmodium falciparum* circumsporozoite (CS) protein at positions 378-398 (DIEKKIAKMEKASSVFNVVNS; SEQ ID NO: 49), and Streptococcus 18 kD protein at positions 116-131 (GAVDSILGGVATYGAA; SEQ ID NO: 50). Other examples include peptides bearing a DR 14-7 supermotif, or either of the DR3 motifs.

Alternatively, it is possible to prepare synthetic peptides capable of stimulating T helper lymphocytes, in a loosely HLA-restricted fashion, using amino acid sequences not found in nature (see, e.g., PCT publication WO 95/07707). These synthetic compounds called Pan-DR-binding epitopes (e.g., PADRE™, Epimmune, Inc., San Diego, Calif.) are designed, most preferably, to bind most HLA-DR (human HLA class II) molecules. For instance, a pan-DR-binding epitope peptide having the formula: AKXVAAWTLKAAA (SEQ ID NO: 51), where a is either cyclohexylalanine, phenylalanine, or tyrosine, and a is either D-alanine or L-alanine, has been found to bind to most HLA-DR alleles, and to stimulate the response of T helper lymphocytes from most individuals, regardless of their HLA type. An alternative of a pan-DR binding epitope comprises all "L" natural amino acids and can be provided in the form of nucleic acids that encode the epitope.

HTL peptide epitopes can also be modified to alter their biological properties. For example, they can be modified to include D-amino acids to increase their resistance to proteases and thus extend their serum half life, or they can be conjugated to other molecules such as lipids, proteins, carbohydrates, and the like to increase their biological activity. For example, a T helper peptide can be conjugated to one or more palmitic acid chains at either the amino or carboxyl termini.

X.C.3. Combinations of CTL Peptides with T Cell Priming Agents

In some embodiments it may be desirable to include in the pharmaceutical compositions of the invention at least one component which primes B lymphocytes or T lymphocytes. Lipids have been identified as agents capable of priming CTL in vivo. For example, palmitic acid residues can be attached to the $\epsilon$- and $\alpha$-amino groups of a lysine residue and then linked, e.g., via one or more linking residues such as Gly, Gly-Gly-, Ser, Ser-Ser, or the like, to an immunogenic peptide. The lipidated peptide can then be administered either directly in a micelle or particle, incorporated into a liposome, or emulsified in an adjuvant, e.g., incomplete Freund's adjuvant. In a preferred embodiment, a particularly effective immunogenic composition comprises palmitic acid attached to $\epsilon$- and $\alpha$-amino groups of Lys, which is attached via linkage, e.g., Ser-Ser, to the amino terminus of the immunogenic peptide.

As another example of lipid priming of CTL responses, *E. coli* lipoproteins, such as tripalmitoyl-S-glycerylcysteinlyseryl-serine ($P_3CSS$) can be used to prime virus specific CTL when covalently attached to an appropriate peptide (see, e.g., Deres, et al., *Nature* 342:561, 1989). Peptides of the invention can be coupled to $P_3CSS$, for example, and the lipopeptide administered to an individual to prime specifically an immune response to the target antigen. Moreover, because the induction of neutralizing antibodies can also be primed with P3CSS-conjugated epitopes, two such compositions can be combined to more effectively elicit both humoral and cell-mediated responses.

X.C.4. Vaccine Compositions Comprising DC Pulsed with CTL and/or HTL Peptides

An embodiment of a vaccine composition in accordance with the invention comprises ex vivo administration of a cocktail of epitope-bearing peptides to PBMC, or isolated DC therefrom, from the patient's blood. A pharmaceutical to facilitate harvesting of DC can be used, such as Progenipoietin™ (Pharmacia-Monsanto, St. Louis, Mo.) or GM-CSF/IL-4. After pulsing the DC with peptides and prior to reinfusion into patients, the DC are washed to remove unbound peptides. In this embodiment, a vaccine comprises peptide-pulsed DCs which present the pulsed peptide epitopes complexed with HLA molecules on their surfaces.

The DC can be pulsed ex vivo with a cocktail of peptides, some of which stimulate CTL responses to 193P1E1B. Optionally, a helper T cell (HTL) peptide, such as a natural or artificial loosely restricted HLA Class II peptide, can be included to facilitate the CTL response. Thus, a vaccine in accordance with the invention is used to treat a cancer which expresses or overexpresses 193P1E1B.

X.D. Adoptive Immunotherapy

Antigenic 193P1E1B-related peptides are used to elicit a CTL and/or HTL response ex vivo, as well. The resulting CTL or HTL cells, can be used to treat tumors in patients that do not respond to other conventional forms of therapy, or will not respond to a therapeutic vaccine peptide or nucleic acid in accordance with the invention. Ex vivo CTL or HTL responses to a particular antigen are induced by incubating in tissue culture the patient's, or genetically compatible, CTL or HTL precursor cells together with a source of antigen-presenting cells (APC), such as dendritic cells, and the appropriate immunogenic peptide. After an appropriate incubation time (typically about 7-28 days), in which the precursor cells are activated and expanded into effector cells, the cells are infused back into the patient, where they will destroy (CTL) or facilitate destruction (HTL) of their specific target cell (e.g., a tumor cell). Transfected dendritic cells may also be used as antigen presenting cells.

X.E. Administration of Vaccines for Therapeutic or Prophylactic Purposes

Pharmaceutical and vaccine compositions of the invention are typically used to treat and/or prevent a cancer that expresses or overexpresses 193P1E1B. In therapeutic applications, peptide and/or nucleic acid compositions are administered to a patient in an amount sufficient to elicit an effective B cell, CTL and/or HTL response to the antigen and to cure or at least partially arrest or slow symptoms and/or complications. An amount adequate to accomplish this is defined as "therapeutically effective dose." Amounts effective for this use will depend on, e.g., the particular composition administered, the manner of administration, the stage and severity of the disease being treated, the weight and general state of health of the patient, and the judgment of the prescribing physician.

For pharmaceutical compositions, the immunogenic peptides of the invention, or DNA encoding them, are generally administered to an individual already bearing a tumor that expresses 193P1E1B. The peptides or DNA encoding them can be administered individually or as fusions of one or more peptide sequences. Patients can be treated with the immunogenic peptides separately or in conjunction with other treatments, such as surgery, as appropriate.

For therapeutic use, administration should generally begin at the first diagnosis of 193P1E1B-associated cancer. This is followed by boosting doses until at least symptoms are substantially abated and for a period thereafter. The embodiment of the vaccine composition (i.e., including, but not limited to embodiments such as peptide cocktails, polyepitopic polypeptides, minigenes, or TAA-specific CTLs or pulsed dendritic cells) delivered to the patient may vary according to the stage of the disease or the patient's health status. For example, in a patient with a tumor that expresses 193P1E1B, a vaccine comprising 193P1E1B-specific CTL may be more efficacious in killing tumor cells in patient with advanced disease than alternative embodiments.

It is generally important to provide an amount of the peptide epitope delivered by a mode of administration sufficient to stimulate effectively a cytotoxic T cell response; compositions which stimulate helper T cell responses can also be given in accordance with this embodiment of the invention.

The dosage for an initial therapeutic immunization generally occurs in a unit dosage range where the lower value is about 1, 5, 50, 500, or 1,000 μg and the higher value is about 10,000; 20,000; 30,000; or 50,000 μg. Dosage values for a human typically range from about 500 μg to about 50,000 μg per 70 kilogram patient. Boosting dosages of between about 1.0 μg to about 50,000 μg of peptide pursuant to a boosting regimen over weeks to months may be administered depending upon the patient's response and condition as determined by measuring the specific activity of CTL and HTL obtained from the patient's blood. Administration should continue until at least clinical symptoms or laboratory tests indicate that the neoplasia, has been eliminated or reduced and for a period thereafter. The dosages, routes of administration, and dose schedules are adjusted in accordance with methodologies known in the art.

In certain embodiments, the peptides and compositions of the present invention are employed in serious disease states, that is, life-threatening or potentially life threatening situations. In such cases, as a result of the minimal amounts of extraneous substances and the relative nontoxic nature of the peptides in preferred compositions of the invention, it is possible and may be felt desirable by the treating physician to administer substantial excesses of these peptide compositions relative to these stated dosage amounts.

The vaccine compositions of the invention can also be used purely as prophylactic agents. Generally the dosage for an initial prophylactic immunization generally occurs in a unit dosage range where the lower value is about 1, 5, 50, 500, or 1000 μg and the higher value is about 10,000; 20,000; 30,000; or 50,000 μg. Dosage values for a human typically range from about 500 μg to about 50,000 μg per 70 kilogram patient. This is followed by boosting dosages of between about 1.0 μg to about 50,000 μg of peptide administered at defined intervals from about four weeks to six months after the initial administration of vaccine. The immunogenicity of the vaccine can be assessed by measuring the specific activity of CTL and HTL obtained from a sample of the patient's blood.

The pharmaceutical compositions for therapeutic treatment are intended for parenteral, topical, oral, nasal, intrathecal, or local (e.g. as a cream or topical ointment) administration. Preferably, the pharmaceutical compositions are administered parentally, e.g., intravenously, subcutaneously, intradermally, or intramuscularly. Thus, the invention provides compositions for parenteral administration which comprise a solution of the immunogenic peptides dissolved or suspended in an acceptable carrier, preferably an aqueous carrier.

A variety of aqueous carriers may be used, e.g., water, buffered water, 0.8% saline, 0.3% glycine, hyaluronic acid and the like. These compositions may be sterilized by conventional, well-known sterilization techniques, or may be sterile filtered. The resulting aqueous solutions may be packaged for use as is, or lyophilized, the lyophilized preparation being combined with a sterile solution prior to administration.

The compositions may contain pharmaceutically acceptable auxiliary substances as required to approximate physiological conditions, such as pH-adjusting and buffering agents, tonicity adjusting agents, wetting agents, preservatives, and the like, for example, sodium acetate, sodium lactate, sodium chloride, potassium chloride, calcium chloride, sorbitan monolaurate, triethanolamine oleate, etc.

The concentration of peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

A human unit dose form of a composition is typically included in a pharmaceutical composition that comprises a human unit dose of an acceptable carrier, in one embodiment an aqueous carrier, and is administered in a volume/quantity that is known by those of skill in the art to be used for administration of such compositions to humans (see, e.g., Remington's Pharmaceutical Sciences, 17$^{th}$ Edition, A. Gennaro, Editor, Mack Publishing Co., Easton, Pa., 1985). For example a peptide dose for initial immunization can be from about 1 to about 50,000 μ, generally 100-5,000 μg, for a 70 kg patient. For example, for nucleic acids an initial immunization may be performed using an expression vector in the form of naked nucleic acid administered IM (or SC or ID) in the amounts of 0.5-5 mg at multiple sites. The nucleic acid (0.1 to 1000 μg) can also be administered using a gene gun. Following an incubation period of 3-4 weeks, a booster dose is then administered. The booster can be recombinant fowlpox virus administered at a dose of 5-$10^7$ to $5\times10^9$ pfu.

For antibodies, a treatment generally involves repeated administration of the anti-193P1E1B antibody preparation, via an acceptable route of administration such as intravenous injection (IV), typically at a dose in the range of about 0.1 to about 10 mg/kg body weight. In general, doses in the range of 10-500 mg mAb per week are effective and well tolerated. Moreover, an initial loading dose of approximately 4 mg/kg patient body weight IV, followed by weekly doses of about 2 mg/kg IV of the anti-193P1E1B mAb preparation represents an acceptable dosing regimen. As appreciated by those of skill in the art, various factors can influence the ideal dose in a particular case. Such factors include, for example, half life of a composition, the binding affinity of an Ab, the immunogenicity of a substance, the degree of 193P1E1B expression in the patient, the extent of circulating shed 193P1E1B antigen, the desired steady-state concentration level, frequency of treatment, and the influence of chemotherapeutic or other agents used in combination with the treatment method of the invention, as well as the health status of a particular patient. Non-limiting preferred human unit doses are, for example, 500 μg -1 mg, 1 mg-50 mg, 50 mg-100 mg, 100 mg-200 mg, 200 mg-300 mg, 400 mg-500 mg, 500 mg-600 mg, 600 mg -700 mg, 700 mg-800 mg, 800 mg-900 mg, 900 mg-1 g, or 1 mg-700 mg. In certain embodiments, the dose is in a range of 2-5 mg/kg body weight, e.g., with follow on weekly doses of 1-3 mg/kg; 0.5 mg, 1, 2, 3, 4, 5, 6, 7, 8, 9, 10 mg/kg body weight followed, e.g., in two, three or four weeks by weekly doses; 0.5 -10 mg/kg body weight, e.g., followed in two, three or four weeks by weekly doses; 225, 250, 275, 300, 325, 350, 375, 400 mg $m^2$ of body area weekly; 1-600 mg $m^2$ of body area weekly; 225-400 mg $m^2$ of body area weekly; these does can be followed by weekly doses for 2, 3, 4, 5, 6, 7, 8, 9, 19, 11, 12 or more weeks.

In one embodiment, human unit dose forms of polynucleotides comprise a suitable dosage range or effective amount that provides any therapeutic effect. As appreciated by one of ordinary skill in the art a therapeutic effect depends on a number of factors, including the sequence of the polynucleotide, molecular weight of the polynucleotide and route of administration. Dosages are generally selected by the physician or other health care professional in accordance with a variety of parameters known in the art, such as severity of symptoms, history of the patient and the like. Generally, for a polynucleotide of about 20 bases, a dosage range may be selected from, for example, an independently selected lower limit such as about 0.1, 0.25, 0.5, 1, 2, 5, 10, 20, 30, 40, 50, 60, 70, 80, 90, 100, 200, 300, 400 or 500 mg/kg up to an independently selected upper limit, greater than the lower limit, of about 60, 80, 100, 200, 300, 400, 500, 750, 1000, 1500, 2000, 3000, 4000, 5000, 6000, 7000, 8000, 9000 or 10,000 mg/kg. For example, a dose may be about any of the following: 0.1 to 100 mg/kg, 0.1 to 50 mg/kg, 0.1 to 25 mg/kg, 0.1 to 10 mg/kg, 1 to 500 mg/kg, 100 to 400 mg/kg, 200 to 300 mg/kg, 1 to 100 mg/kg, 100 to 200 mg/kg, 300 to 400 mg/kg, 400 to 500 mg/kg, 500 to 1000 mg/kg, 500 to 5000 mg/kg, or 500 to 10,000 mg/kg. Generally, parenteral routes of administration may require higher doses of polynucleotide compared to more direct application to the nucleotide to diseased tissue, as do polynucleotides of increasing length.

In one embodiment, human unit dose forms of T-cells comprise a suitable dosage range or effective amount that provides any therapeutic effect. As appreciated by one of ordinary skill in the art, a therapeutic effect depends on a number of factors. Dosages are generally selected by the physician or other health care professional in accordance with a variety of parameters known in the art, such as severity of symptoms, history of the patient and the like. A dose may be about $10^4$ cells to about $10^6$ cells, about $10^6$ cells to about $10^8$ cells, about $10^8$ to about $10^{11}$ cells, or about $10^8$ to about $5\times10^{10}$ cells. A dose may also about $10^6$ cells/$m^2$ to about $10^{10}$ cells/$m^2$, or about $10^6$ cells/$m^2$ to about $10^8$ cells/$m^2$.

Proteins(s) of the invention, and/or nucleic acids encoding the protein(s), can also be administered via liposomes, which may also serve to: 1) target the proteins(s) to a particular tissue, such as lymphoid tissue; 2) to target selectively to diseases cells; or, 3) to increase the half-life of the peptide composition. Liposomes include emulsions, foams, micelles, insoluble monolayers, liquid crystals, phospholipid dispersions, lamellar layers and the like. In these preparations, the peptide to be delivered is incorporated as part of a liposome, alone or in conjunction with a molecule which binds to a receptor prevalent among lymphoid cells, such as monoclonal antibodies which bind to the CD45 antigen, or with other therapeutic or immunogenic compositions. Thus, liposomes either filled or decorated with a desired peptide of the invention can be directed to the site of lymphoid cells, where the liposomes then deliver the peptide compositions. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., *Ann. Rev. Biophys. Bioeng.* 9:467 (1980), and U.S. Pat. Nos. 4,235,871, 4,501,728, 4,837,028, and 5,019,369.

For targeting cells of the immune system, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, immunogenic peptides are preferably supplied in finely divided form along with a surfactant and propellant. Typical percentages of peptides are about 0.01 %-20% by weight, preferably about 1%-10%. The surfactant must, of course, be nontoxic, and preferably soluble in the propellant. Representative of such agents are the esters or partial esters of fatty acids containing from about 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute about 0.1%-20% by weight of the composition, preferably about 0.25-5%. The balance of the composition is ordinarily propellant. A carrier can also be included, as desired, as with, e.g., lecithin for intranasal delivery.

XI.) Diagnostic and Prognostic Embodiments of 193P1E1B.

As disclosed herein, 193P1E1B polynucleotides, polypeptides, reactive cytotoxic T cells (CTL), reactive helper T cells (HTL) and anti-polypeptide antibodies are used in well known diagnostic, prognostic and therapeutic assays that examine conditions associated with dysregulated cell growth such as cancer, in particular the cancers listed in Table I (see, e.g., both its specific pattern of tissue expression as well as its overexpression in certain cancers as described for example in the Example entitled "Expression analysis of 193P1E1B in normal tissues, and patient specimens").

193P1E1B can be analogized to a prostate associated antigen PSA, the archetypal marker that has been used by medical practitioners for years to identify and monitor the presence of prostate cancer (see, e.g., Merrill et al., J. Urol. 163(2): 503-

5120 (2000); Polascik et al., J. Urol. Aug; 162(2):293-306 (1999) and Fortier et al., J. Nat. Cancer Inst. 91(19): 1635-1640(1999)). A variety of other diagnostic markers are also used in similar contexts including p53 and K-ras (see, e.g., Tulchinsky et al., Int J Mol Med Jul. 4, 1999 (1):99-102 and Minimoto et al., Cancer Detect Prev 2000;24(1):1-12). Therefore, this disclosure of 193P1E1B polynucleotides and polypeptides (as well as 193P1E1B polynucleotide probes and anti-193P1E1B antibodies used to identify the presence of these molecules) and their properties allows skilled artisans to utilize these molecules in methods that are analogous to those used, for example, in a variety of diagnostic assays directed to examining conditions associated with cancer.

Typical embodiments of diagnostic methods which utilize the 193P1E1B polynucleotides, polypeptides, reactive T cells and antibodies are analogous to those methods from well-established diagnostic assays, which employ, e.g., PSA polynucleotides, polypeptides, reactive T cells and antibodies. For example, just as PSA polynucleotides are used as probes (for example in Northern analysis, see, e.g., Sharief et al., Biochem. Mol. Biol. Int. 33(3):567-74(1994)) and primers (for example in PCR analysis, see, e.g., Okegawa et al., J. Urol. 163(4): 1189-1190 (2000)) to observe the presence and/or the level of PSA mRNAs in methods of monitoring PSA overexpression or the metastasis of prostate cancers, the 193P1E1B polynucleotides described herein can be utilized in the same way to detect 193P1E1B overexpression or the metastasis of prostate and other cancers expressing this gene. Alternatively, just as PSA polypeptides are used to generate antibodies specific for PSA which can then be used to observe the presence and/or the level of PSA proteins in methods to monitor PSA protein overexpression (see, e.g., Stephan et al., Urology 55(4):560-3 (2000)) or the metastasis of prostate cells (see, e.g., Alanen et al., Pathol. Res. Pract. 192(3):233-7 (1996)), the 193P1E1B polypeptides described herein can be utilized to generate antibodies for use in detecting 193P1E1B overexpression or the metastasis of prostate cells and cells of other cancers expressing this gene.

Specifically, because metastases involves the movement of cancer cells from an organ of origin (such as the lung or prostate gland etc.) to a different area of the body (such as a lymph node), assays which examine a biological sample for the presence of cells expressing 193P1E1B polynucleotides and/or polypeptides can be used to provide evidence of metastasis. For example, when a biological sample from tissue that does not normally contain 193P1E1B-expressing cells (lymph node) is found to contain 193P1E1B-expressing cells such as the 193P1E1B expression seen in LAPC4 and LAPC9, xenografts isolated from lymph node and bone metastasis, respectively, this finding is indicative of metastasis.

Alternatively 193P1E1B polynucleotides and/or polypeptides can be used to provide evidence of cancer, for example, when cells in a biological sample that do not normally express 193P1E1B or express 193P1E1B at a different level are found to express 193P1E1B or have an increased expression of 193P1E1B (see, e.g., the 193P1E1B expression in the cancers listed in Table I and in patient samples etc. shown in the accompanying Figures). In such assays, artisans may further wish to generate supplementary evidence of metastasis by testing the biological sample for the presence of a second tissue restricted marker (in addition to 193P1E1B) such as PSA, PSCA etc. (see, e.g., Alanen et al., Pathol. Res. Pract. 192(3): 233-237 (1996)).

Just as PSA polynucleotide fragments and polynucleotide variants are employed by skilled artisans for use in methods of monitoring PSA, 193P1E1B polynucleotide fragments and polynucleotide variants are used in an analogous manner. In particular, typical PSA polynucleotides used in methods of monitoring PSA are probes or primers which consist of fragments of the PSA cDNA sequence. Illustrating this, primers used to PCR amplify a PSA polynucleotide must include less than the whole PSA sequence to function in the polymerase chain reaction. In the context of such PCR reactions, skilled artisans generally create a variety of different polynucleotide fragments that can be used as primers in order to amplify different portions of a polynucleotide of interest or to optimize amplification reactions (see, e.g., Caetano-Anolles, G. Biotechniques 25(3): 472-476, 478-480 (1998); Robertson et al., Methods Mol. Biol. 98:121-154 (1998)). An additional illustration of the use of such fragments is provided in the Example entitled "Expression analysis of 193P1E1B in normal tissues, and patient specimens," where a 193P1E1B polynucleotide fragment is used as a probe to show the expression of 193P1E1B RNAs in cancer cells. In addition, variant polynucleotide sequences are typically used as primers and probes for the corresponding mRNAs in PCR and Northern analyses (see, e.g., Sawai et al., Fetal Diagn. Ther. November-December 1996 11 (6):407-13 and Current Protocols In Molecular Biology, Volume 2, Unit 2, Frederick M. Ausubel et al. eds., 1995)). Polynucleotide fragments and variants are useful in this context where they are capable of binding to a target polynucleotide sequence (e.g., a 193P1E1B polynucleotide shown in FIG. 2 or variant thereof) under conditions of high stringency.

Furthermore, PSA polypeptides which contain an epitope that can be recognized by an antibody or T cell that specifically binds to that epitope are used in methods of monitoring PSA. 193P1E1B polypeptide fragments and polypeptide analogs or variants can also be used in an analogous manner. This practice of using polypeptide fragments or polypeptide variants to generate antibodies (such as anti-PSA antibodies or T cells) is typical in the art with a wide variety of systems such as fusion proteins being used by practitioners (see, e.g., Current Protocols In Molecular Biology, Volume 2, Unit 16, Frederick M. Ausubel et al. eds., 1995). In this context, each epitope(s) functions to provide the architecture with which an antibody or T cell is reactive. Typically, skilled artisans create a variety of different polypeptide fragments that can be used in order to generate immune responses specific for different portions of a polypeptide of interest (see, e.g., U.S. Pat. No. 5,840,501 and U.S. Pat. No. 5,939,533). For example it may be preferable to utilize a polypeptide comprising one of the 193P1E1B biological motifs discussed herein or a motif-bearing subsequence which is readily identified by one of skill in the art based on motifs available in the art. Polypeptide fragments, variants or analogs are typically useful in this context as long as they comprise an epitope capable of generating an antibody or T cell specific for a target polypeptide sequence (e.g. a 193P1E1B polypeptide shown in FIG. 3).

As shown herein, the 193P1E1B polynucleotides and polypeptides (as well as the 193P1E1B polynucleotide probes and anti-193P1E1B antibodies or T cells used to identify the presence of these molecules) exhibit specific properties that make them useful in diagnosing cancers such as those listed in Table I. Diagnostic assays that measure the presence of 193P1E1B gene products, in order to evaluate the presence or onset of a disease condition described herein, such as prostate cancer, are used to identify patients for preventive measures or further monitoring, as has been done so successfully with PSA. Moreover, these materials satisfy a need in the art for molecules having similar or complementary characteristics to PSA in situations where, for example, a definite diagnosis of metastasis of prostatic origin cannot be made on the basis of a test for PSA alone (see, e.g., Alanen et al., Pathol. Res. Pract. 192(3): 233-237 (1996)), and consequently, materials such as 193P1E1B polynucleotides and polypeptides (as well as the 193P1E1B polynucleotide probes and anti-193P1E1B antibodies used to identify the presence of these molecules) need to be employed to confirm a metastases of prostatic origin.

Finally, in addition to their use in diagnostic assays, the 193P1E1B polynucleotides disclosed herein have a number of other utilities such as their use in the identification of oncogenetic associated chromosomal abnormalities in the chromosomal region to which the 193P1E1B gene maps (see the Example entitled "Chromosomal Mapping of 193P1E1B" below). Moreover, in addition to their use in diagnostic assays, the 193P1E1B-related proteins and polynucleotides disclosed herein have other utilities such as their use in the forensic analysis of tissues of unknown origin (see, e.g., Takahama K Forensic Sci Int Jun. 28, 1996;80(1-2): 63-9).

Additionally, 193P1E1B-related proteins or polynucleotides of the invention can be used to treat a pathologic condition characterized by the over-expression of 193P1E1B. For example, the amino acid or nucleic acid sequence of FIG. 2 or FIG. 3, or fragments of either, can be used to generate an immune response to a 193P1E1B antigen. Antibodies or other molecules that react with 193P1E1B can be used to modulate the function of this molecule, and thereby provide a therapeutic benefit.

XII.) Inhibition of 193P1E1B Protein Function

The invention includes various methods and compositions for inhibiting the binding of 193P1E1B to its binding partner or its association with other protein(s) as well as methods for inhibiting 193P1E1B function.

XII.A.) Inhibition of 193P1E1B With Intracellular Antibodies

In one approach, a recombinant vector that encodes single chain antibodies that specifically bind to 193P1E1B are introduced into 193P1E1B expressing cells via gene transfer technologies. Accordingly, the encoded single chain anti-193P1E1B antibody is expressed intracellularly, binds to 193P1E1B protein, and thereby inhibits its function. Methods for engineering such intracellular single chain antibodies are well known. Such intracellular antibodies, also known as "intrabodies", are specifically targeted to a particular compartment within the cell, providing control over where the inhibitory activity of the treatment is focused. This technology has been successfully applied in the art (for review, see Richardson and Marasco, 1995, TIBTECH vol. 13). Intrabodies have been shown to virtually eliminate the expression of otherwise abundant cell surface receptors (see, e.g., Richardson et al., 1995, Proc. Natl. Acad. Sci. USA 92: 3137-3141; Beerli et al., 1994, J. Biol. Chem. 289: 23931-23936; Deshane et al., 1994, Gene Ther. 1: 332-337).

Single chain antibodies comprise the variable domains of the heavy and light chain joined by a flexible linker polypeptide, and are expressed as a single polypeptide. Optionally, single chain antibodies are expressed as a single chain variable region fragment joined to the light chain constant region. Well-known intracellular trafficking signals are engineered into recombinant polynucleotide vectors encoding such single chain antibodies in order to target precisely the intrabody to the desired intracellular compartment. For example, intrabodies targeted to the endoplasmic reticulum (ER) are engineered to incorporate a leader peptide and, optionally, a C-terminal ER retention signal, such as the KDEL amino acid motif. Intrabodies intended to exert activity in the nucleus are engineered to include a nuclear localization signal. Lipid moieties are joined to intrabodies in order to tether the intrabody to the cytosolic side of the plasma membrane. Intrabodies can also be targeted to exert function in the cytosol. For example, cytosolic intrabodies are used to sequester factors within the cytosol, thereby preventing them from being transported to their natural cellular destination.

In one embodiment, intrabodies are used to capture 193P1E1B in the nucleus, thereby preventing its activity within the nucleus. Nuclear targeting signals are engineered into such 193P1E1B intrabodies in order to achieve the desired targeting. Such 193P1E1B intrabodies are designed to bind specifically to a particular 193P1E1B domain. In another embodiment, cytosolic intrabodies that specifically bind to a 193P1E1B protein are used to prevent 193P1E1B from gaining access to the nucleus, thereby preventing it from exerting any biological activity within the nucleus (e.g., preventing 193P1E1B from forming transcription complexes with other factors).

In order to specifically direct the expression of such intrabodies to particular cells, the transcription of the intrabody is placed under the regulatory control of an appropriate tumor-specific promoter and/or enhancer. In order to target intrabody expression specifically to prostate, for example, the PSA promoter and/or promoter/enhancer can be utilized (See, for example, U.S. Pat. No. 5,919,652 issued Jul. 6, 1999).

XII.B.) Inhibition of 193P1E1B with Recombinant Proteins

In another approach, recombinant molecules bind to 193P1E1B and thereby inhibit 193P1E1B function. For example, these recombinant molecules prevent or inhibit 193P1E1B from accessing/binding to its binding partner(s) or associating with other protein(s). Such recombinant molecules can, for example, contain the reactive part(s) of a 193P1E1B specific antibody molecule. In a particular embodiment, the 193P1E1B binding domain of a 193P1E1B binding partner is engineered into a dimeric fusion protein, whereby the fusion protein comprises two 193P1E1B ligand binding domains linked to the Fc portion of a human IgG, such as human IgG1. Such IgG portion can contain, for example, the $C_H2$ and $C_H3$ domains and the hinge region, but not the $C_H1$ domain. Such dimeric fusion proteins are administered in soluble form to patients suffering from a cancer associated with the expression of 193P1E1B, whereby the dimeric fusion protein specifically binds to 193P1E1B and blocks 193P1E1B interaction with a binding partner. Such dimeric fusion proteins are further combined into multimeric proteins using known antibody linking technologies.

XII.C.) Inhibition of 193P1E1B Transcription or Translation

The present invention also comprises various methods and compositions for inhibiting the transcription of the 193P1E1B gene. Similarly, the invention also provides methods and compositions for inhibiting the translation of 193P1E1B mRNA into protein.

In one approach, a method of inhibiting the transcription of the 193P1E1B gene comprises contacting the 193P1E1B gene with a 193P1E1B antisense polynucleotide. In another approach, a method of inhibiting 193P1E1B mRNA translation comprises contacting a 193P1E1B mRNA with an antisense polynucleotide. In another approach, a 193P1E1B specific ribozyme is used to cleave a 193P1E1B message, thereby inhibiting translation. Such antisense and ribozyme based methods can also be directed to the regulatory regions of the 193P1E1B gene, such as 193P1E1B promoter and/or enhancer elements. Similarly, proteins capable of inhibiting a 193P1E1B gene transcription factor are used to inhibit 193P1E1B mRNA transcription. The various polynucleotides and compositions useful in the aforementioned methods have been described above. The use of antisense and ribozyme molecules to inhibit transcription and translation is well known in the art.

Other factors that inhibit the transcription of 193P1E1B by interfering with 193P1E1B transcriptional activation are also useful to treat cancers expressing 193P1E1B. Similarly, factors that interfere with 193P1E1B processing are useful to treat cancers that express 193P1E1B. Cancer treatment methods utilizing such factors are also within the scope of the invention.

XII.D.) General Considerations for Therapeutic Strategies

Gene transfer and gene therapy technologies can be used to deliver therapeutic polynucleotide molecules to tumor cells synthesizing 193P1E1B (i.e., antisense, ribozyme, polynucleotides encoding intrabodies and other 193P1E1B inhibitory molecules). A number of gene therapy approaches are known in the art. Recombinant vectors encoding 193P1E1B antisense polynucleotides, ribozymes, factors capable of interfering with 193P1E1B transcription, and so forth, can be delivered to target tumor cells using such gene therapy approaches.

The above therapeutic approaches can be combined with any one of a wide variety of surgical, chemotherapy or radiation therapy regimens. The therapeutic approaches of the invention can enable the use of reduced dosages of chemotherapy (or other therapies) and/or less frequent administration, an advantage for all patients and particularly for those that do not tolerate the toxicity of the chemotherapeutic agent well.

The anti-tumor activity of a particular composition (e.g., antisense, ribozyme, intrabody), or a combination of such compositions, can be evaluated using various in vitro and in vivo assay systems. In vitro assays that evaluate therapeutic activity include cell growth assays, soft agar assays and other assays indicative of tumor promoting activity, binding assays capable of determining the extent to which a therapeutic composition will inhibit the binding of 193P1E1B to a binding partner, etc.

In vivo, the effect of a 193P1E1B therapeutic composition can be evaluated in a suitable animal model. For example, xenogenic prostate cancer models can be used, wherein human prostate cancer explants or passaged xenograft tissues are introduced into immune compromised animals, such as nude or SCID mice (Klein et al., 1997, Nature Medicine 3: 402-408). For example, PCT Patent Application WO98/16628 and U.S. Pat. No. 6,107,540 describe various xenograft models of human prostate cancer capable of recapitulating the development of primary tumors, micrometastasis, and the formation of osteoblastic metastases characteristic of late stage disease. Efficacy can be predicted using assays that measure inhibition of tumor formation, tumor regression or metastasis, and the like.

In vivo assays that evaluate the promotion of apoptosis are useful in evaluating therapeutic compositions. In one embodiment, xenografts from tumor bearing mice treated with the therapeutic composition can be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences $16^{th}$ Edition, A. Osal., Ed., 1980).

Therapeutic formulations can be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations can be lyophilized and stored as sterile powders, preferably under vacuum, and then reconstituted in bacteriostatic water (containing for example, benzyl alcohol preservative) or in sterile water prior to injection.

Dosages and administration protocols for the treatment of cancers using the foregoing methods will vary with the method and the target cancer, and will generally depend on a number of other factors appreciated in the art.

XIII.) Identification, Characterization and Use of Modulators of 193P1E1B

Methods to Identify and Use Modulators

In one embodiment, screening is performed to identify modulators that induce or suppress a particular expression profile, suppress or induce specific pathways, preferably generating the associated phenotype thereby. In another embodiment, having identified differentially expressed genes important in a particular state; screens are performed to identify modulators that alter expression of individual genes, either increase or decrease. In another embodiment, screening is performed to identify modulators that alter a biological function of the expression product of a differentially expressed gene. Again, having identified the importance of a gene in a particular state, screens are performed to identify agents that bind and/or modulate the biological activity of the gene product.

In addition, screens are done for genes that are induced in response to a candidate agent. After identifying a modulator (one that suppresses a cancer expression pattern leading to a normal expression pattern, or a modulator of a cancer gene that leads to expression of the gene as in normal tissue) a screen is performed to identify genes that are specifically modulated in response to the agent. Comparing expression profiles between normal tissue and agent-treated cancer tissue reveals genes that are not expressed in normal tissue or cancer tissue, but are expressed in agent treated tissue, and vice versa. These agent-specific sequences are identified and used by methods described herein for cancer genes or proteins. In particular these sequences and the proteins they encode are used in marking or identifying agent-treated cells. In addition, antibodies are raised against the agent-induced proteins and used to target novel therapeutics to the treated cancer tissue sample.

Modulator-Related Identification and Screening Assays:

Gene Expression-Related Assays

Proteins, nucleic acids, and antibodies of the invention are used in screening assays. The cancer-associated proteins, antibodies, nucleic acids, modified proteins and cells containing these sequences are used in screening assays, such as evaluating the effect of drug candidates on a "gene expression profile," expression profile of polypeptides or alteration of biological function. In one embodiment, the expression profiles are used, preferably in conjunction with high throughput screening techniques to allow monitoring for expression profile genes after treatment with a candidate agent (e.g., Davis, G F, et al., J Biol Screen 7:69 (2002); Zlokarnik, et al., Science 279:84-8 (1998); Heid, Genome Res 6:986-94, 1996).

The cancer proteins, antibodies, nucleic acids, modified proteins and cells containing the native or modified cancer proteins or genes are used in screening assays. That is, the present invention comprises methods for screening for compositions which modulate the cancer phenotype or a physiological function of a cancer protein of the invention. This is done on a gene itself or by evaluating the effect of drug candidates on a "gene expression profile" or biological function. In one embodiment, expression profiles are used, preferably in conjunction with high throughput screening techniques to allow monitoring after treatment with a candidate agent, see Zlokamik, supra.

A variety of assays are executed directed to the genes and proteins of the invention. Assays are run on an individual nucleic acid or protein level. That is, having identified a particular gene as up regulated in cancer, test compounds are screened for the ability to modulate gene expression or for binding to the cancer protein of the invention. "Modulation" in this context includes an increase or a decrease in gene expression. The preferred amount of modulation will depend on the original change of the gene expression in normal versus tissue undergoing cancer, with changes of at least 10%, preferably 50%, more preferably 100-300%, and in some embodiments 300-1000% or greater. Thus, if a gene exhibits a 4-fold increase in cancer tissue compared to normal tissue, a decrease of about four-fold is often desired; similarly, a 10-fold decrease in cancer tissue compared to normal tissue a target value of a 10-fold increase in expression by the test compound is often desired. Modulators that exacerbate the type of gene expression seen in cancer are also useful, e.g., as an upregulated target in further analyses.

The amount of gene expression is monitored using nucleic acid probes and the quantification of gene expression levels, or, alternatively, a gene product itself is monitored, e.g., through the use of antibodies to the cancer protein and standard immunoassays. Proteomics and separation techniques also allow for quantification of expression.

Expression Monitoring to Identify Compounds that Modify Gene Expression

In one embodiment, gene expression monitoring, i.e., an expression profile, is monitored simultaneously for a number of entities. Such profiles will typically involve one or more of the genes of FIG. 2. In this embodiment, e.g., cancer nucleic acid probes are attached to biochips to detect and quantify cancer sequences in a particular cell. Alternatively, PCR can be used. Thus, a series, e.g., wells of a microtiter plate, can be used with dispensed primers in desired wells. A PCR reaction can then be performed and analyzed for each well.

Expression monitoring is performed to identify compounds that modify the expression of one or more cancer-associated sequences, e.g., a polynucleotide sequence set out in FIG. 2. Generally, a test modulator is added to the cells prior to analysis. Moreover, screens are also provided to identify agents that modulate cancer, modulate cancer proteins of the invention, bind to a cancer protein of the invention, or interfere with the binding of a cancer protein of the invention and an antibody or other binding partner.

In one embodiment, high throughput screening methods involve providing a library containing a large number of potential therapeutic compounds (candidate compounds). Such "combinatorial chemical libraries" are then screened in one or more assays to identify those library members (particular chemical species or subclasses) that display a desired characteristic activity. The compounds thus identified can serve as conventional "lead compounds," as compounds for screening, or as therapeutics.

In certain embodiments, combinatorial libraries of potential modulators are screened for an ability to bind to a cancer polypeptide or to modulate activity. Conventionally, new chemical entities with useful properties are generated by identifying a chemical compound (called a "lead compound") with some desirable property or activity, e.g., inhibiting activity, creating variants of the lead compound, and evaluating the property and activity of those variant compounds. Often, high throughput screening (HTS) methods are employed for such an analysis.

As noted above, gene expression monitoring is conveniently used to test candidate modulators (e.g., protein, nucleic acid or small molecule). After the candidate agent has been added and the cells allowed to incubate for a period, the sample containing a target sequence to be analyzed is, e.g., added to a biochip.

If required, the target sequence is prepared using known techniques. For example, a sample is treated to lyse the cells, using known lysis buffers, electroporation, etc., with purification and/or amplification such as PCR performed as appropriate. For example, an in vitro transcription with labels covalently attached to the nucleotides is performed. Generally, the nucleic acids are labeled with biotin-FITC or PE, or with cy3 or cy5.

The target sequence can be labeled with, e.g., a fluorescent, a chemiluminescent, a chemical, or a radioactive signal, to provide a means of detecting the target sequence's specific binding to a probe. The label also can be an enzyme, such as alkaline phosphatase or horseradish peroxidase, which when provided with an appropriate substrate produces a product that is detected. Alternatively, the label is a labeled compound or small molecule, such as an enzyme inhibitor, that binds but is not catalyzed or altered by the enzyme. The label also can be a moiety or compound, such as, an epitope tag or biotin which specifically binds to streptavidin. For the example of biotin, the streptavidin is labeled as described above, thereby, providing a detectable signal for the bound target sequence. Unbound labeled streptavidin is typically removed prior to analysis.

As will be appreciated by those in the art, these assays can be direct hybridization assays or can comprise "sandwich assays", which include the use of multiple probes, as is generally outlined in U.S. Pat. Nos. 5,681,702; 5,597,909; 5,545,730; 5,594,117; 5,591,584; 5,571,670; 5,580,731; 5,571,670; 5,591,584; 5,624,802; 5,635,352; 5,594,118; 5,359,100; 5,124,246; and 5,681,697. In this embodiment, in general, the target nucleic acid is prepared as outlined above, and then added to the biochip comprising a plurality of nucleic acid probes, under conditions that allow the formation of a hybridization complex.

A variety of hybridization conditions are used in the present invention, including high, moderate and low stringency conditions as outlined above. The assays are generally run under stringency conditions which allow formation of the label probe hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc. These parameters may also be used to control non-specific binding, as is generally outlined in U.S.

Pat. No. 5,681,697. Thus, it can be desirable to perform certain steps at higher stringency conditions to reduce nonspecific binding.

The reactions outlined herein can be accomplished in a variety of ways. Components of the reaction can be added simultaneously, or sequentially, in different orders, with preferred embodiments outlined below. In addition, the reaction may include a variety of other reagents. These include salts, buffers, neutral proteins, e.g. albumin, detergents, etc. which can be used to facilitate optimal hybridization and detection, and/or reduce nonspecific or background interactions. Reagents that otherwise improve the efficiency of the assay, such as protease inhibitors, nuclease inhibitors, anti-microbial agents, etc., may also be used as appropriate, depending on the sample preparation methods and purity of the target. The assay data are analyzed to determine the expression levels of individual genes, and changes in expression levels as between states, forming a gene expression profile.

Biological Activity-Related Assays

The invention provides methods identify or screen for a compound that modulates the activity of a cancer-related gene or protein of the invention. The methods comprise adding a test compound, as defined above, to a cell comprising a cancer protein of the invention. The cells contain a recombinant nucleic acid that encodes a cancer protein of the invention. In another embodiment, a library of candidate agents is tested on a plurality of cells.

In one aspect, the assays are evaluated in the presence or absence or previous or subsequent exposure of physiological signals, e.g. hormones, antibodies, peptides, antigens, cytokines, growth factors, action potentials, pharmacological agents including chemotherapeutics, radiation, carcinogenics, or other cells (i.e., cell-cell contacts). In another example, the determinations are made at different stages of the cell cycle process. In this way, compounds that modulate genes or proteins of the invention are identified. Compounds with pharmacological activity are able to enhance or interfere with the activity of the cancer protein of the invention. Once identified, similar structures are evaluated to identify critical structural features of the compound.

In one embodiment, a method of modulating (e.g., inhibiting) cancer cell division is provided; the method comprises administration of a cancer modulator. In another embodiment, a method of modulating (e.g., inhibiting) cancer is provided; the method comprises administration of a cancer modulator. In a further embodiment, methods of treating cells or individuals with cancer are provided; the method comprises administration of a cancer modulator.

In one embodiment, a method for modulating the status of a cell that expresses a gene of the invention is provided. As used herein status comprises such art-accepted parameters such as growth, proliferation, survival, function, apoptosis, senescence, location, enzymatic activity, signal transduction, etc. of a cell. In one embodiment, a cancer inhibitor is an antibody as discussed above. In another embodiment, the cancer inhibitor is an antisense molecule. A variety of cell growth, proliferation, and metastasis assays are known to those of skill in the art, as described herein.

High Throughput Screening to Identify Modulators

The assays to identify suitable modulators are amenable to high throughput screening. Preferred assays thus detect enhancement or inhibition of cancer gene transcription, inhibition or enhancement of polypeptide expression, and inhibition or enhancement of polypeptide activity.

In one embodiment, modulators evaluated in high throughput screening methods are proteins, often naturally occurring proteins or fragments of naturally occurring proteins. Thus, e.g., cellular extracts containing proteins, or random or directed digests of proteinaceous cellular extracts, are used. In this way, libraries of proteins are made for screening in the methods of the invention. Particularly preferred in this embodiment are libraries of bacterial, fungal, viral, and mammalian proteins, with the latter being preferred, and human proteins being especially preferred. Particularly useful test compound will be directed to the class of proteins to which the target belongs, e.g., substrates for enzymes, or ligands and receptors.

Use of Soft Agar Growth and Colony Formation to Identify and Characterize Modulators Normal cells require a solid substrate to attach and grow. When cells are transformed, they lose this phenotype and grow detached from the substrate. For example, transformed cells can grow in stirred suspension culture or suspended in semi-solid media, such as semi-solid or soft agar. The transformed cells, when transfected with tumor suppressor genes, can regenerate normal phenotype and once again require a solid substrate to attach to and grow. Soft agar growth or colony formation in assays are used to identify modulators of cancer sequences, which when expressed in host cells, inhibit abnormal cellular proliferation and transformation. A modulator reduces or eliminates the host cells' ability to grow suspended in solid or semisolid media, such as agar.

Techniques for soft agar growth or colony formation in suspension assays are described in Freshney, Culture of Animal Cells a Manual of Basic Technique (3rd ed., 1994). See also, the methods section of Garkavtsev et al. (1996), supra.

Evaluation of Contact Inhibition and Growth Density Limitation to Identify and Characterize Modulators Normal cells typically grow in a flat and organized pattern in cell culture until they touch other cells. When the cells touch one another, they are contact inhibited and stop growing. Transformed cells, however, are not contact inhibited and continue to grow to high densities in disorganized foci. Thus, transformed cells grow to a higher saturation density than corresponding normal cells. This is detected morphologically by the formation of a disoriented monolayer of cells or cells in foci. Alternatively, labeling index with ($^3$H)-thymidine at saturation density is used to measure density limitation of growth, similarly an MTT or Alamar blue assay will reveal proliferation capacity of cells and the the ability of modulators to affect same. See Freshney (1994), supra. Transformed cells, when transfected with tumor suppressor genes, can regenerate a normal phenotype and become contact inhibited and would grow to a lower density.

In this assay, labeling index with $^3$H)-thymidine at saturation density is a preferred method of measuring density limitation of growth. Transformed host cells are transfected with a cancer-associated sequence and are grown for 24 hours at saturation density in non-limiting medium conditions. The percentage of cells labeling with ($^3$H)-thymidine is determined by incorporated cpm.

Contact independent growth is used to identify modulators of cancer sequences, which had led to abnormal cellular proliferation and transformation. A modulator reduces or eliminates contact independent growth, and returns the cells to a normal phenotype.

Evaluation of Growth Factor or Serum Dependence to Identify and Characterize Modulators Transformed cells have lower serum dependence than their normal counterparts (see, e.g., Temin, J. Natl. Cancer Inst. 37:167-175 (1966); Eagle et al., J. Exp. Med 131:836-879 (1970)); Freshney, supra. This is in part due to release of various growth factors by the transformed cells. The degree of growth factor or serum dependence of transformed host cells can be compared with that of control. For example, growth factor or serum dependence of a cell is monitored in methods to identify and characterize compounds that modulate cancer-associated sequences of the invention.

Use of Tumor-specific Marker Levels to Identify and Characterize Modulators

Tumor cells release an increased amount of certain factors (hereinafter "tumor specific markers") than their normal counterparts. For example, plasminogen activator (PA) is released from human glioma at a higher level than from normal brain cells (see, e.g., Gullino, Angiogenesis, Tumor Vascularization, and Potential Interference with Tumor Growth, in Biological Responses in Cancer, pp. 178-184 (Mihich (ed.) 1985)). Similarly, Tumor Angiogenesis Factor (TAF) is released at a higher level in tumor cells than their normal counterparts. See, e.g., Folkman, Angiogenesis and Cancer, Sem Cancer Biol. (1992)), while bFGF is released from endothelial tumors (Ensoli, B et al).

Various techniques which measure the release of these factors are described in Freshney (1994), supra. Also, see, Unkless et al., J. Biol. Chem. 249:4295-4305 (1974); Strickland & Beers, J. Biol. Chem. 251:5694-5702 (1976); Whur et al., Br. J. Cancer 42:305 312 (1980); Gullino, Angiogenesis, Tumor Vascularization, and Potential Interference with Tumor Growth, in Biological Responses in Cancer, pp. 178-184 (Mihich (ed.) 1985); Freshney, Anticancer Res. 5:111-130 (1985). For example, tumor specific marker levels are monitored in methods to identify and characterize compounds that modulate cancer-associated sequences of the invention.

Invasiveness into Matrigel to Identify and Characterize Modulators

The degree of invasiveness into Matrigel or an extracellular matrix constituent can be used as an assay to identify and characterize compounds that modulate cancer associated sequences. Tumor cells exhibit a positive correlation between malignancy and invasiveness of cells into Matrigel or some other extracellular matrix constituent. In this assay, tumorigenic cells are typically used as host cells. Expression of a tumor suppressor gene in these host cells would decrease invasiveness of the host cells. Techniques described in Cancer Res. 1999; 59:6010; Freshney (1994), supra, can be used. Briefly, the level of invasion of host cells is measured by using filters coated with Matrigel or some other extracellular matrix constituent. Penetration into the gel, or through to the distal side of the filter, is rated as invasiveness, and rated histologically by number of cells and distance moved, or by prelabeling the cells with $^{125}1$ and counting the radioactivity on the distal side of the filter or bottom of the dish. See, e.g., Freshney (1984), supra.

Evaluation of Tumor Growth In Vivo to Identify and Characterize Modulators

Effects of cancer-associated sequences on cell growth are tested in transgenic or immune-suppressed organisms. Transgenic organisms are prepared in a variety of art-accepted ways. For example, knock-out transgenic organisms, e.g., mammals such as mice, are made, in which a cancer gene is disrupted or in which a cancer gene is inserted. Knock-out transgenic mice are made by insertion of a marker gene or other heterologous gene into the endogenous cancer gene site in the mouse genome via homologous recombination. Such mice can also be made by substituting the endogenous cancer gene with a mutated version of the cancer gene, or by mutating the endogenous cancer gene, e.g., by exposure to carcinogens.

To prepare transgenic chimeric animals, e.g., mice, a DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells some of which are derived from the mutant cell line. Therefore, by breeding the chimeric mice it is possible to obtain a new line of mice containing the introduced genetic lesion (see, e.g., Capecchi et al., Science 244:1288 (1989)). Chimeric mice can be derived according to U.S. Pat. No. 6,365,797, issued Apr. 2, 2002; U.S. Pat. No. 6,107,540 issued Aug. 22, 2000; Hogan et al., Manipulating the Mouse Embryo: A laboratory Manual, Cold Spring Harbor Laboratory (1988) and Teratocarcinomas and Embryonic Stem Cells: A Practical Approach, Robertson, ed., IRL Press, Washington, D.C., (1987).

Alternatively, various immune-suppressed or immune-deficient host animals can be used. For example, a genetically athymic "nude" mouse (see, e.g., Giovanella et al., J. Natl. Cancer Inst. 52:921 (1974)), a SCID mouse, a thymectomized mouse, or an irradiated mouse (see, e.g., Bradley et al., Br. J. Cancer 38:263 (1978); Selby et al., Br. J. Cancer 41:52 (1980)) can be used as a host. Transplantable tumor cells (typically about $10^6$ cells) injected into isogenic hosts produce invasive tumors in a high proportion of cases, while normal cells of similar origin will not. In hosts which developed invasive tumors, cells expressing cancer-associated sequences are injected subcutaneously or orthotopically. Mice are then separated into groups, including control groups and treated experimental groups) e.g. treated with a modulator). After a suitable length of time, preferably 4-8 weeks, tumor growth is measured (e.g., by volume or by its two largest dimensions, or weight) and compared to the control. Tumors that have statistically significant reduction (using, e.g., Student's T test) are said to have inhibited growth.

In Vitro Assays to Identify and Characterize Modulators

Assays to identify compounds with modulating activity can be performed in vitro. For example, a cancer polypeptide is first contacted with a potential modulator and incubated for a suitable amount of time, e.g., from 0.5 to 48 hours. In one embodiment, the cancer polypeptide levels are determined in vitro by measuring the level of protein or mRNA. The level of protein is measured using immunoassays such as Western blotting, ELISA and the like with an antibody that selectively binds to the cancer polypeptide or a fragment thereof. For measurement of mRNA, amplification, e.g., using PCR, LCR, or hybridization assays, e. g., Northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, a reporter gene system can be devised using a cancer protein promoter operably linked to a reporter gene such as luciferase, green fluorescent protein, CAT, or P-gal. The reporter construct is typically transfected into a cell. After treatment with a potential modulator, the amount of reporter gene transcription, translation, or activity is measured according to standard techniques known to those of skill in the art (Davis G F, supra; Gonzalez, J. & Negulescu, P. Curr. Opin. Biotechnol. 1998: 9:624).

As outlined above, in vitro screens are done on individual genes and gene products. That is, having identified a particular differentially expressed gene as important in a particular state, screening of modulators of the expression of the gene or the gene product itself is performed.

In one embodiment, screening for modulators of expression of specific gene(s) is performed. Typically, the expression of only one or a few genes is evaluated. In another embodiment, screens are designed to first find compounds that bind to differentially expressed proteins. These compounds are then evaluated for the ability to modulate differentially expressed activity. Moreover, once initial candidate compounds are identified, variants can be further screened to better evaluate structure activity relationships.

Binding Assays to Identify and Characterize Modulators

In binding assays in accordance with the invention, a purified or isolated gene product of the invention is generally used. For example, antibodies are generated to a protein of the invention, and immunoassays are run to determine the amount and/or location of protein. Alternatively, cells comprising the cancer proteins are used in the assays.

Thus, the methods comprise combining a cancer protein of the invention and a candidate compound such as a ligand, and determining the binding of the compound to the cancer protein of the invention. Preferred embodiments utilize the human cancer protein; animal models of human disease of can also be developed and used. Also, other analogous mammalian proteins also can be used as appreciated by those of skill in the art. Moreover, in some embodiments variant or derivative cancer proteins are used.

Generally, the cancer protein of the invention, or the ligand, is non-diffusibly bound to an insoluble support. The support can, e.g., be one having isolated sample receiving areas (a microtiter plate, an array, etc.). The insoluble supports can be made of any composition to which the compositions can be bound, is readily separated from soluble material, and is otherwise compatible with the overall method of screening. The surface of such supports can be solid or porous and of any convenient shape.

Examples of suitable insoluble supports include microtiter plates, arrays, membranes and beads. These are typically made of glass, plastic (e.g., polystyrene), polysaccharide, nylon, nitrocellulose, or Teflon™, etc. Microtiter plates and arrays are especially convenient because a large number of assays can be carried out simultaneously, using small amounts of reagents and samples. The particular manner of binding of the composition to the support is not crucial so long as it is compatible with the reagents and overall methods of the invention, maintains the activity of the composition and is nondiffusable. Preferred methods of binding include the use of antibodies which do not sterically block either the ligand binding site or activation sequence when attaching the protein to the support, direct binding to "sticky" or ionic supports, chemical crosslinking, the synthesis of the protein or agent on the surface, etc. Following binding of the protein or ligand/binding agent to the support, excess unbound material is removed by washing. The sample receiving areas may then be blocked through incubation with bovine serum albumin (BSA), casein or other innocuous protein or other moiety.

Once a cancer protein of the invention is bound to the support, and a test compound is added to the assay. Alternatively, the candidate binding agent is bound to the support and the cancer protein of the invention is then added. Binding agents include specific antibodies, non-natural binding agents identified in screens of chemical libraries, peptide analogs, etc.

Of particular interest are assays to identify agents that have a low toxicity for human cells. A wide variety of assays can be used for this purpose, including proliferation assays, cAMP assays, labeled in vitro protein-protein binding assays, electrophoretic mobility shift assays, immunoassays for protein binding, functional assays (phosphorylation assays, etc.) and the like.

A determination of binding of the test compound (ligand, binding agent, modulator, etc.) to a cancer protein of the invention can be done in a number of ways. The test compound can be labeled, and binding determined directly, e.g., by attaching all or a portion of the cancer protein of the invention to a solid support, adding a labeled candidate compound (e.g., a fluorescent label), washing off excess reagent, and determining whether the label is present on the solid support. Various blocking and washing steps can be utilized as appropriate.

In certain embodiments, only one of the components is labeled, e.g., a protein of the invention or ligands labeled. Alternatively, more than one component is labeled with different labels, e.g., $I^{125}$, for the proteins and a fluorophor for the compound. Proximity reagents, e.g., quenching or energy transfer reagents are also useful.

Competitive Binding to Identify and Characterize Modulators

In one embodiment, the binding of the "test compound" is determined by competitive binding assay with a "competitor." The competitor is a binding moiety that binds to the target molecule (e.g., a cancer protein of the invention). Competitors include compounds such as antibodies, peptides, binding partners, ligands, etc. Under certain circumstances, the competitive binding between the test compound and the competitor displaces the test compound. In one embodiment, the test compound is labeled. Either the test compound, the competitor, or both, is added to the protein for a time sufficient to allow binding. Incubations are performed at a temperature that facilitates optimal activity, typically between four and 40° C. Incubation periods are typically optimized, e.g., to facilitate rapid high throughput screening; typically between zero and one hour will be sufficient. Excess reagent is generally removed or washed away. The second component is then added, and the presence or absence of the labeled component is followed, to indicate binding.

In one embodiment, the competitor is added first, followed by the test compound. Displacement of the competitor is an indication that the test compound is binding to the cancer protein and thus is capable of binding to, and potentially modulating, the activity of the cancer protein. In this embodiment, either component can be labeled. Thus, e.g., if the competitor is labeled, the presence of label in the post-test compound wash solution indicates displacement by the test compound. Alternatively, if the test compound is labeled, the presence of the label on the support indicates displacement.

In an alternative embodiment, the test compound is added first, with incubation and washing, followed by the competitor. The absence of binding by the competitor indicates that the test compound binds to the cancer protein with higher affinity than the competitor. Thus, if the test compound is labeled, the presence of the label on the support, coupled with a lack of competitor binding, indicates that the test compound binds to and thus potentially modulates the cancer protein of the invention.

Accordingly, the competitive binding methods comprise differential screening to identity agents that are capable of modulating the activity of the cancer proteins of the invention. In this embodiment, the methods comprise combining a cancer protein and a competitor in a first sample. A second sample comprises a test compound, the cancer protein, and a competitor. The binding of the competitor is determined for both samples, and a change, or difference in binding between the two samples indicates the presence of an agent capable of binding to the cancer protein and potentially modulating its activity. That is, if the binding of the competitor is different in the second sample relative to the first sample, the agent is capable of binding to the cancer protein.

Alternatively, differential screening is used to identify drug candidates that bind to the native cancer protein, but cannot bind to modified cancer proteins. For example the structure of the cancer protein is modeled and used in rational drug design to synthesize agents that interact with that site, agents which generally do not bind to site-modified proteins. Moreover, such drug candidates that affect the activity of a native cancer protein are also identified by screening drugs for the ability to either enhance or reduce the activity of such proteins.

Positive controls and negative controls can be used in the assays. Preferably control and test samples are performed in at least triplicate to obtain statistically significant results. Incubation of all samples occurs for a time sufficient to allow for the binding of the agent to the protein. Following incubation, samples are washed free of non-specifically bound material and the amount of bound, generally labeled agent determined. For example, where a radiolabel is employed, the samples can be counted in a scintillation counter to determine the amount of bound compound.

A variety of other reagents can be included in the screening assays. These include reagents like salts, neutral proteins, e.g. albumin, detergents, etc. which are used to facilitate optimal protein-protein binding and/or reduce non-specific or background interactions. Also reagents that otherwise improve the efficiency of the assay, such as protease inhibitors, nuclease inhibitors, anti-microbial agents, etc., can be used. The mixture of components is added in an order that provides for the requisite binding.

Use of Polynucleotides to Down-Regulate or Inhibit a Protein of the Invention.

Polynucleotide modulators of cancer can be introduced into a cell containing the target nucleotide sequence by formation of a conjugate with a ligand-binding molecule, as described in WO 91/04753. Suitable ligand-binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell. Alternatively, a polynucleotide modulator of cancer can be introduced into a cell containing the target nucleic acid sequence, e.g., by formation of a polynucleotide-lipid complex, as described in WO 90/10448. It is understood that the use of antisense molecules or knock out and knock in models may also be used in screening assays as discussed above, in addition to methods of treatment.

Inhibitory and Antisense Nucleotides

In certain embodiments, the activity of a cancer-associated protein is down-regulated, or entirely inhibited, by the use of antisense polynucleotide or inhibitory small nuclear RNA (snRNA), i.e., a nucleic acid complementary to, and which can preferably hybridize specifically to, a coding mRNA nucleic acid sequence, e.g., a cancer protein of the invention, mRNA, or a subsequence thereof. Binding of the antisense polynucleotide to the mRNA reduces the translation and/or stability of the mRNA.

In the context of this invention, antisense polynucleotides can comprise naturally occurring nucleotides, or synthetic species formed from naturally occurring subunits or their close homologs. Antisense polynucleotides may also have altered sugar moieties or inter-sugar linkages. Exemplary among these are the phosphorothioate and other sulfur containing species which are known for use in the art. Analogs are comprised by this invention so long as they function effectively to hybridize with nucleotides of the invention. See, e.g., Isis Pharmaceuticals, Carlsbad, Calif.; Sequitor, Inc., Natick, Mass.

Such antisense polynucleotides can readily be synthesized using recombinant means, or can be synthesized in vitro. Equipment for such synthesis is sold by several vendors, including Applied Biosystems. The preparation of other oligonucleotides such as phosphorothioates and alkylated derivatives is also well known to those of skill in the art.

Antisense molecules as used herein include antisense or sense oligonudeotides. Sense oligonucleotides can, e.g., be employed to block transcription by binding to the anti-sense strand. The antisense and sense oligonucleotide comprise a single stranded nucleic acid sequence (either RNA or DNA) capable of binding to target mRNA (sense) or DNA (antisense) sequences for cancer molecules. Antisense or sense oligonucleotides, according to the present invention, comprise a fragment generally at least about 12 nucleotides, preferably from about 12 to 30 nucleotides. The ability to derive an antisense or a sense oligonucleotide, based upon a cDNA sequence encoding a given protein is described in, e.g., Stein & Cohen (Cancer Res. 48:2659 (1988 and van der Krol et al. (BioTechniques 6:958 (1988)).

Ribozymes

In addition to antisense polynucleotides, ribozymes can be used to target and inhibit transcription of cancer-associated nucleotide sequences. A ribozyme is an RNA molecule that catalytically cleaves other RNA molecules. Different kinds of ribozymes have been described, including group I ribozymes, hammerhead ribozymes, hairpin ribozymes, RNase P, and axhead ribozymes (see, e.g., Castanotto et al., Adv. in Pharmacology 25: 289-317 (1994) for a general review of the properties of different ribozymes).

The general features of hairpin ribozymes are described, e.g., in Hampel et al., Nucl. Acids Res. 18:299-304 (1990); European Patent Publication No. 0360257; U.S. Pat. No. 5,254,678. Methods of preparing are well known to those of skill in the art (see, e.g., WO 94/26877; Ojwang et al., Proc. Natl. Acad. Sci. USA 90:6340-6344 (1993); Yamada et al., Human Gene Therapy 1:39-45 (1994); Leavitt et al., Proc. Natl. Acad Sci. USA 92:699-703 (1995); Leavitt et al., Human Gene Therapy 5: 1151-120 (1994); and Yamada et al., Virology 205: 121-126 (1994)).

Use of Modulators in Phenotypic Screening

In one embodiment, a test compound is administered to a population of cancer cells, which have an associated cancer expression profile. By "administration" or "contacting" herein is meant that the modulator is added to the cells in such a manner as to allow the modulator to act upon the cell, whether by uptake and intracellular action, or by action at the cell surface. In some embodiments, a nucleic acid encoding a proteinaceous agent (i.e., a peptide) is put into a viral construct such as an adenoviral or retroviral construct, and added to the cell, such that expression of the peptide agent is accomplished, e.g., PCT US97/01019. Regulatable gene therapy systems can also be used. Once the modulator has been administered to the cells, the cells are washed if desired and are allowed to incubate under preferably physiological conditions for some period. The cells are then harvested and a new gene expression profile is generated. Thus, e.g., cancer tissue is screened for agents that modulate, e.g., induce or suppress, the cancer phenotype. A change in at least one gene, preferably many, of the expression profile indicates that the agent has an effect on cancer activity. Similarly, altering a biological function or a signaling pathway is indicative of modulator activity. By defining such a signature for the cancer phenotype, screens for new drugs that alter the phenotype are devised. With this approach, the drug target need not be known and need not be represented in the original gene/protein expression screening platform, nor does the level of transcript for the target protein need to change. The modulator inhibiting function will serve as a surrogate marker As outlined above, screens are done to assess genes or gene products. That is, having identified a particular differentially expressed gene as important in a particular state, screening of modulators of either the expression of the gene or the gene product itself is performed.

Use of Modulators to Affect Peptides of the Invention

Measurements of cancer polypeptide activity, or of the cancer phenotype are performed using a variety of assays. For example, the effects of modulators upon the function of a cancer polypeptide(s) are measured by examining parameters described above. A physiological change that affects activity is used to assess the influence of a test compound on the polypeptides of this invention. When the functional outcomes are determined using intact cells or animals, a variety of effects can be assesses such as, in the case of a cancer associated with solid tumors, tumor growth, tumor metastasis, neovascularization, hormone release, transcriptional changes to both known and uncharacterized genetic markers (e.g., by Northern blots), changes in cell metabolism such as cell growth or pH changes, and changes in intracellular second messengers such as cGNIP.

Methods of Identifying Characterizing Cancer-associated Sequences

Expression of various gene sequences is correlated with cancer. Accordingly, disorders based on mutant or variant cancer genes are determined. In one embodiment, the invention provides methods for identifying cells containing variant cancer genes, e.g., determining the presence of, all or part, the sequence of at least one endogenous cancer gene in a cell. This is accomplished using any number of sequencing techniques. The invention comprises methods of identifying the cancer genotype of an individual, e.g., determining all or part of the sequence of at least one gene of the invention in the individual. This is generally done in at least one tissue of the individual, e.g., a tissue set forth in Table I, and may include the evaluation of a number of tissues or different samples of the same tissue. The method may include comparing the sequence of the sequenced gene to a known cancer gene, i.e., a wild-type gene to determine the presence of family members, homologies, mutations or variants. The sequence of all or part of the gene can then be compared to the sequence of a known cancer gene to determine if any differences exist. This is done using any number of known homology programs, such as BLAST, Besffit, etc. The presence of a difference in the sequence between the cancer gene of the patient and the known cancer gene correlates with a disease state or a propensity for a disease state, as outlined herein.

In a preferred embodiment, the cancer genes are used as probes to determine the number of copies of the cancer gene in the genome. The cancer genes are used as probes to determine the chromosomal localization of the cancer genes. Information such as chromosomal localization finds use in providing a diagnosis or prognosis in particular when chromosomal abnormalities such as translocations, and the like are identified in the cancer gene locus.

XIV.) Kits/Articles of Manufacture

For use in the diagnostic and therapeutic applications described herein, kits are also within the scope of the invention. Such kits can comprise a carrier, package or container that is compartmentalized to receive one or more containers such as vials, tubes, and the like, each of the container(s) comprising one of the separate elements to be used in the method. For example, the container(s) can comprise a probe that is or can be detectably labeled. Such probe can be an antibody or polynucleotide specific for a FIG. 2-*related* protein or a FIG. 2 gene or message, respectively. Where the method utilizes nucleic acid hybridization to detect the target nucleic acid, the kit can also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label. The kit can include all or part of the amino acid sequences in FIG. 2 or FIG. 3 or analogs thereof, or a nucleic acid molecules that encodes such amino acid sequences.

The kit of the invention will typically comprise the container described above and one or more other containers comprising materials desirable from a commercial and user standpoint, including buffers, diluents, filters, needles, syringes; carrier, package, container, vial and/or tube labels listing contents and/or instructions for use, and package inserts with instructions for use.

A label can be present on the container to indicate that the composition is used for a specific therapy or non-therapeutic application, such as a diagnostic or laboratory application, and can also indicate directions for either in vivo or in viro use, such as those described herein. Directions and or other information can also be included on an insert(s) or label(s) which is included with or on the kit The terms "kit" and "article of manufacture" can be used as synonyms.

In another embodiment of the invention, an article(s) of manufacture containing compositions, such as amino acid sequence(s), small molecule(s), nucleic acid sequence(s), and/or antibody(s), e.g., materials useful for the diagnosis, prognosis, prophylaxis and/or treatment of neoplasias of tissues such as those set forth in Table I is provided. The article of manufacture typically comprises at least one container and at least one label. Suitable containers include, for example, bottles, vials, syringes, and test tubes. The containers can be formed from a variety of materials such as glass or plastic. The container can hold amino acid sequence(s), small molecule(s), nucleic acid sequence(s), and/or antibody(s), in one embodiment the container holds a polynucleotide for use in examining the mRNA expression profile of a cell, together with reagents used for this purpose.

The container can alternatively hold a composition which is effective for treating, diagnosis, prognosing or prophylaxing a condition and can have a sterile access port (for example the container can be an intravenous solution bag or a vial having a stopper pierceable by a hypodermic injection needle). The active agents in the composition can be an antibody capable of specifically binding 193P1E1B and modulating the function of 193P1E1B.

The label can be on or associated with the container. A label a can be on a container when letters, numbers or other characters forming the label are molded or etched into the container itself; a label can be associated with a container when it is present within a receptacle or carrier that also holds the container, e.g., as a package insert. The label can indicate that the composition is used for diagnosing, treating, prophylaxing or prognosing a condition, such as a neoplasia of a issue set forth in Table I. The article of manufacture can further comprise a second container comprising a pharmaceutically-acceptable buffer, such as phosphate-buffered saline, Ringer's solution and/ordextrose solution. It can further include other materials desirable from a commercial and user standpoint, including other buffers, diluents, filters, stirrers, needles, syringes, and/or package inserts with indications and/or instructions for use.

EXAMPLES

Various aspects of the invention are further described and illustrated by way of the several examples that follow, none of which are intended to limit the scope of the invention.

Example 1

SSH-Generated Isolation of cDNA Fragment of the 193P1E1B Gene

To isolate genes that are over-expressed in prostate cancer we used the Suppression Subtractive Hybridization (SSH) procedure using cDNA derived from prostate cancer xenograft tissues. LAPC-9AD xenograft was obtained from Dr. Charles Sawyers (UCLA) and was generated as described (Klein et al., 1997, Nature Med. 3:402-408; Craft et al., 1999, Cancer Res. 59:5030-5036). LAPC-9AD$^2$ was generated from LAPC-9AD xenograft by growing LAPC-9AD xenograft tissues within a piece of human bone implanted in SCID mice. Tumors were then harvested and subsequently passaged subcutaneously into other SCID animals to generate LAPC-9AD$^2$.

The 193P1E1B SSH cDNA sequence was derived from a subtraction consisting of a prostate cancer xenograft LAPC-9AD$^2$ minus prostate cancer xenograft LAPC-9AD. By RT-PCR, the 193P1E1B cDNA was identified as highly expressed in the prostate cancer xenograft pool (LAPC4-AD, LAPC4-AI, LAPC9-AD, LAPC9-AI), bladder cancer pool, kidney cancer pool, colon cancer pool, lung cancer pool, ovary cancer pool, breast cancer pool, metastasis cancer pool, pancreas cancer pool, with low expression observed in the prostate cancer pool, and no expression observed in vital pool 1 (kidney, liver, lung), and in vital pool 2 (stomach, colon, pancreas) (FIG. 14).

The 193P1E1B SSH cDNA of 227 bp is listed in FIG. 1. The full length 193P1E1B cDNAs and ORFs are described in FIG. 2 with the protein sequences listed in FIG. 3. 193P1E1B v.1, v.2, v.3, v.4, v.5, v.6, v.7, v.8, v.11, v.12 and v.13 are novel proteins and have not been previously described. 193P1E1B v.9 shows 99% identity to a hypothetical protein, MGC4832. 193P1E1B v.10 shows 100% identity to a novel unnamed protein BAC03484.1.

Materials and Methods

RNA Isolation:

Tumor tissues were homogenized in Trizol reagent (Life Technologies, Gibco BRL) using 10 ml/g tissue or 10 ml/$10^8$ cells to isolate total RNA. Poly A RNA was purified from total RNA using Qiagen's Oligotex mRNA Mini and Midi kits. Total and mRNA were quantified by spectrophotometric analysis (O.D. 260/280 nm) and analyzed by gel electrophoresis.

Oligonucleotides:

The following HPLC purified oligonucleotides were used.

DPNCDN (cDNA synthesis primer):
5'TTTTGATCAAGCTT$_{30}$3' (SEQ ID NO: 52)

Adaptor 1:
5'CTAATACGACTCACTATAGGGCTCGAGCGGCCGCCCGGGCAG3' (SEQ ID NO: 53)
3'GGCCCGTCCTAG5' (SEQ ID NO: 54)

Adaptor 2:
5'GTAATACGACTCACTATAGGGCAGCGTGGTCGCGGCCGAG3' (SEQ ID NO: 55)
3'CGGCTCCTAG5' (SEQ ID NO: 56)

PCR primer 1:
5'CTAATACGACTCACTATAGGGC3' (SEQ ID NO: 57)

Nested primer (NP)1:
5'TCGAGCGGCCGCCCGGGCAGGA3' (SEQ ID NO: 58)

Nested primer (NP)2:
5'AGCGTGGTCGCGGCCGAGGA3' (SEQ ID NO: 59)

Suppression Subtractive Hybridization (SSH) was used to identify cDNAs corresponding to genes that may be differentially expressed in prostate cancer. The SSH reaction utilized cDNA from prostate cancer xenograft LAPC-9AD$^2$. The gene 193P1E1B was derived from a prostate cancer xenograft LAPC-9AD$^2$ minus prostate cancer xenograft LAPC-9AD tissues. The SSH DNA sequence (FIG. 1) was identified.

The cDNA derived from prostate cancer xenograft LAPC-9AD tissue was used as the source of the "driver" cDNA, while the cDNA from prostate cancer xenograft LAPC-9AD$^2$ was used as the source of the tester cDNA. Double stranded cDNAs corresponding to tester and driver cDNAs were synthesized from 2 μg of poly(A)$^+$ RNA isolated from the relevant tissue, as described above, using CLONTECH's PCR-Select cDNA Subtraction Kit and 1 ng of oligonucleotide DPNCDN as primer. First- and second-strand synthesis were carried out as described in the Kit's user manual protocol (CLONTECH Protocol No. PT1117-1, Catalog No. K1804-1). The resulting cDNA was digested with Dpn II for 3 hrs at 37° C. Digested cDNA was extracted with phenol/chloroform (1:1) and ethanol precipitated.

Tester cDNA was generated by diluting 1 p of Dpn II digested cDNA from the relevant tissue source (see above) (400 ng) in 5 μl of water. The diluted cDNA (2 μl, 160 ng) was then ligated to 2 μl of Adaptor 1 and Adaptor 2 (10 μM), in separate ligation reactions, in a total volume of 10 μl at 16° C. overnight, using 400 u of T4 DNA ligase (CLONTECH). Ligation was terminated with 1 μl of 0.2 M EDTA and heating at 72° C. for 5 min.

The first hybridization was performed by adding 1.5 μl (600 ng) of driver cDNA to each of two tubes containing 1.5 μl (20 ng) Adaptor 1- and Adaptor 2-ligated tester cDNA. In a final volume of 4 μl, the samples were overlaid with mineral oil, denatured in an MJ Research thermal cycler at 98° C. for 1.5 minutes, and then were allowed to hybridize for 8 hrs at 68° C. The two hybridizations were then mixed together with an additional 1 μl of fresh denatured driver cDNA and were allowed to hybridize overnight at 68° C. The second hybridization was then diluted in 200 μl of 20 mM Hepes, pH 8.3, 50 mM NaCl, 0.2 mM EDTA, heated at 70° C. for 7 min. and stored at −20° C.

PCR Amplification, Cloning and Sequencing of Gene Fragments Generated from SSH:

To amplify gene fragments resulting from SSH reactions, two PCR amplifications were performed. In the primary PCR reaction 1 μl of the diluted final hybridization mix was added to 1 μl of PCR primer 1 (10 μM), 0.5 μl dNTP mix (10 μM), 2.5 μl 10 x reaction buffer (CLONTECH) and 0.5 μl 50 x Advantage cDNA polymerase Mix (CLONTECH) in a final volume of 25 μl..PCR 1 was conducted using the following conditions: 75° C. for 5 min., 94° C. for 25 sec., then 27 cycles of 94° C. for 10 sec, 66° C. for 30 sec, 72° C. for 1.5 min. Five separate primary PCR reactions were performed for each experiment. The products were pooled and diluted 1:10 with water. For the secondary PCR reaction, 1 μl from the pooled and diluted primary PCR reaction was added to the same reaction mix as used for PCR 1, except that primers NP1 and NP2 (10 μM) were used instead of PCR primer 1. PCR 2 was performed using 10-12 cycles of 94° C. for 10 sec, 68° C. for 30 sec, and 72° C. for 1.5 minutes. The PCR products were analyzed using 2% agarose gel electrophoresis.

The PCR products were inserted into pCR2.1 using the T/A vector cloning kit (Invitrogen). Transformed *E. coli* were subjected to blue/white and ampicillin selection. White colonies were picked and arrayed into 96 well plates and were grown in liquid culture overnight. To identify inserts, PCR amplification was performed on 1 ml of bacterial culture using the conditions of PCR1 and NP1 and NP2 as primers. PCR products were analyzed using 2% agarose gel electrophoresis.

Bacterial clones were stored in 20% glycerol in a 96 well format. Plasmid DNA was prepared, sequenced, and subjected to nucleic acid homology searches of the GenBank, dBest, and NCI-CGAP databases.

RT-PCR Expression Analysis:

First strand cDNAs can be generated from 1 μg of mRNA with oligo (dT)12-18 priming using the Gibco-BRL Superscript Preamplification system. The manufacturer's protocol was used which included an incubation for 50 min at 42° C. with reverse transcriptase followed by RNAse H treatment at 37° C. for 20 min. After completing the reaction, the volume can be increased to 200 μl with water prior to normalization. First strand cDNAs from 16 different normal human tissues can be obtained from Clontech.

Normalization of the first strand cDNAs from multiple tissues was performed by using the primers 5'atatcgccgcgctcgtcgtcgacaa3' (SEQ ID NO: 60) and 5'agccacacgcagctcattgtagaagg 3' (SEQ ID NO: 61) to amplify β-acon. First strand cDNA (5 μl) were amplified in a total volume of 50 μl containing 0.4 μM primers, 0.2 μM each dNTPs, 1×PCR buffer (Clontech, 10 mM Tris-HCL, 1.5 mM $MgCl_2$, 50 mM KCl, pH8.3) and 1× Klentaq DNA polymerase (Clontech). Five μl of the PCR reaction can be removed at 18, 20, and 22 cycles and used for agarose gel electrophoresis. PCR was performed using an MJ Research thermal cycler under the following conditions: Initial denaturation can be at 94° C. for 15 sec, followed by a 18, 20, and 22 cycles of 94° C. for 15, 65° C. for 2 min, 72° C. for 5 sec. A final extension at 72° C. was carried out for 2 min. After agarose gel electrophoresis, the band intensities of the 283 bp β-actin bands from multiple tissues were compared by visual inspection. Dilution factors for the first strand cDNAs were calculated to result in equal β-actin band intensities in all tissues after 22 cycles of PCR. Three rounds of normalization can be required to achieve equal band intensities in all tissues after 22 cycles of PCR.

To determine expression levels of the 193P1E1B gene, 5 μl of normalized first strand cDNA were analyzed by PCR using 26, and 30 cycles of amplification. Semi-quantitative expression analysis can be achieved by comparing the PCR products at cycle numbers that give light band intensities.

A typical RT-PCR expression analysis is shown in FIG. 14. RT-PCR expression analysis was performed on first strand cDNA generated using pools of tissues from multiple samples. The cDNA samples were shown to be normalized using beta-actin PCR. Strong expression of 193P1E1B was observed in prostate cancer xenograft pool, bladder cancer pool, kidney cancer pool, colon cancer pool, lung cancer pool, ovary cancer pool, breast cancer pool, and metastasis pool. Low expression was observed in prostate cancer pool, but no expression was detected in VP1 and VP2.

Example 2

Isolation of Full Length 193P1E1B Encoding cDNA

To isolate genes that are involved in prostate cancer, an experiment was conducted using the prostate cancer xenograft LAPC-9AD[2]. The gene 193P1E1B was derived from a subtraction consisting of a prostate cancer xenograft LAPC-9AD[2] minus prostate cancer xenograft LAPC-9AD. The SSH DNA sequence (FIG. 1) was designated 193P1E1B. Thirteen variants of 193P1E11 were identified (FIGS. 2 and 3). cDNA clone 193P1E1B v.1 and 193P1E1B v.5 were cloned from bladder cancer pool cDNA. 193P1E1B v.9 was cloned from LAPC-4AD cDNA library. All other variants were identified by bioinformatic analysis.

193P1E1B v.1 through v.8 differ from each other by one nucleic acid substitution. 193P1E1B v.1, v.2, v.4 v.7 and v.8 code for the same protein, whereas 193P1E1B v.5 and v.6 contain one amino acid substitution as shown in FIG. 12.

Absence of a 62-nucleotide sequence was identified in 193P1E1B v.9, nucleic acid positions 907-969 of 193P1E1B v.1. This resulted in an 82-amino acid truncation at the amino terminus of 193P1E1B v.9. Other splice variants were identified and referred to as 193P1E1B v.10, v.11, v.12 and v.13. 193P1E1B v.1, v.2, v.3, v.4, v.5, v.6, v.7, v.8, v.11, v.12 and v.13 are novel proteins and have not been previously described. 193P1E1B v.9 shows 99% identity to a hypothetical protein, MGC4832. 193P1E1B v.10 shows 100% identity to a novel unnamed protein BAC03484.1.

Example 3

Chromosomal Mapping of 193P1E1B

Chromosomal localization can implicate genes in disease pathogenesis. Several chromosome mapping approaches are available including fluorescent in situ hybridization (FISH), human/hamster radiation hybrid (RH) panels (Walter et al., 1994; Nature Genetics 7:22; Research Genetics, Huntsville Ala.), human-rodent somatic cell hybrid panels such as is available from the Coriell Institute (Camden, N.J.), and genomic viewers utilizing BLAST homologies to sequenced and mapped genomic clones (NCBI, Bethesda, Md.).

193P1E1B maps to chromosome 13q11, using 193P1E1B sequence and the NCBI BLAST tool. This 13q11 region has been previously implicated in bladder cancer (Wada T, Louhelainen J, Hemminki K, Adolfsson J, Wijkstrom H, Norming U, Borgstrom E, Hansson J, Sandstedt B, Steineck G. Bladder cancer: allelic deletions at and around the retinoblastoma tumor suppressor gene in relation to stage and grade. Clin Cancer Res. 2000 Feb;6(2):610-5.).

Example 4

Expression Analysis of 193P1E1B

Expression of 193P1E1B was analyzed using 2 sets of primers as illustrated in FIG. 14A. First strand cDNA was prepared from vital pool 1 (VP1: liver, lung and kidney), vital pool 2 (VP2, pancreas, colon and stomach), prostate xenograft pool (LAPC-4AD, LAPC-4AI, LAPC-9AD, LAPC-9AI), normal thymus, prostate cancer pool, bladder cancer pool, kidney cancer pool, colon cancer pool, lung cancer pool, ovary cancer pool, breast cancer pool, metastasis cancer pool, pancreas cancer pool, and from prostate cancer metastasis to lymph node from 2 different patients. Normalization was performed by PCR using primers to actin and GAPDH. Semi-quantitative PCR, using Primer Set A (B) or Primer Set B (C) to 193P1E1B, was performed at 30 cycles of amplification. A schematic diagram depicting the location of the 2 primer sets A and B is shown in FIG. 14A. Primer Set A detected a PCR product of 190 bp which is identical in all variants of 193P1E1B (FIG. 14B). Expression of 193P1E1B was observed in prostate cancer xenograft pool, prostate cancer pool, bladder cancer pool, kidney cancer pool, colon cancer pool, lung cancer pool, ovary cancer pool, breast cancer pool, metastasis cancer pool, pancreas cancer pool, as well as the 2 prostate metastasis to lymph node, but not in VP1 and VP2 (FIG. 14B). In order to test abundance of expression of 193P1E1B v.1 through v.8 compared to 193P1E1B v.9, an experiment was conducted in which RT-PCR was performed using Primer Set B (FIG. 14C). Primer Set B detected a PCR product of 239 bp from 193P1E1B v.1 through v.8, and of 177 bp from 193P1E1B v.9 (FIG. 14C). FIG. 14C shows that the transcipt encoding encoding 193P1E1B v.1 through v.8, is expressed ate higher levels that the transcript encoding 193P1E1B v.9. But both transcripts are expressed at similar proportion in all tissues tested.

Extensive northern blot analysis of 193P1E1B in 16 human normal tissues confirms the expression observed by RT-PCR (FIG. 15). Two transcripts of approximately 3.5 kb and 2 kb are only detected in testis and thymus, but not in any other normal tissue tested.

FIG. 16 shows expression of 193P1E1B in prostate cancer xenografts. RNA was extracted from normal prostate, and from prostate cancer xenografts, LAPC-4AD, LAPC-4AI, LAPC-9AD, and LAPC-9AI. Northern blot with 10 ug of total RNA/lane was probed with 193P1E1B SSH sequence. Northern blot analysis shows expression of 193P1E1B in all 4 tissues, LAPC4AD, LAPC-4AI, LAPC-9AD, LAPC-9AI, with the lowest expression detected in the LAPC-9AD tissue, but not in normal prostate.

To test expression of 193P1E1B in patient cancer specimens, RNA was extracted from a pool of three patients for each of the following, bladder cancer, colon cancer, ovary cancer and metastasis cancer, as well as from normal prostate (NP), normal bladder (NB), normal kidney (NK), normal colon (NC). Northern blots with 10 ug of total RNA/lane were probed with 193P1E1B SSH sequence (FIG. 17). Results show expression of 193P1E1B in bladder cancer pool, colon cancer pool, ovary cancer pool and metastasis cancer pool, but not in any of the normal tissues tested.

Analysis of individual bladder cancer tissues by northern blot shows expression of 193P1E1B in the 2 bladder cancer cell lines and in the 3 bladder cancer patient specimens tested, but not in normal bladder tissues (FIG. 18).

FIG. 19 shows expression of 193P1E1Bin cancer metastasis patient specimens. RNA was extracted from the following cancer metastasis tissues, colon metastasis to lung, lung metastasis to lymph node, lung metastasis to skin, and breast metastasis to lymph node, as well as from normal bladder (NB), normal lung (NL), normal breast (NBr), and normal ovary (NO). Northern blots with 10 ug of total RNA/lane were probed with 193P1E1B sequence. Size standards in kilobases (kb) are indicated on the side. The results show expression of 193P1E1B in all four different cancer metastasis samples but not in the normal tissues tested.

FIG. 20 shows expression of 193P1E1B in pancreatic, ovarian and testicular cancer patient specimens. RNA was extracted from pancreatic cancer (P1), ovarian cancer (P2, P3), and testicular cancer (P4, P5) isolated from cancer patients, as well as from normal pancreas(NPa). Northern blots with 10 ug of total RNA/lane were probed with 193P1E1B sequence. Size standards in kilobases (kb) are indicated on the side. The results show expression of 193P1E1B in pancreatic, ovarian and testicular cancer specimens but not in normal pancreas.

FIG. 21 shows expression of 193P1E1B in normal compared to patient cancer specimens. First strand cDNA was prepared from a panel of normal tissues (stomach, brain, heart, liver, spleen, skeletal muscle, testis prostate, bladder, kidney, colon, lung and pancreas) and from a panel of patient cancer pools (prostate cancer pool, bladder cancer pool, kidney cancer pool, colon cancer pool, lung cancer pool, pancreas cancer pool, ovary cancer pool, breast cancer pool, metastasis cancer pool, LAPC prostate xenograft pool (XP), and from prostate cancer metastasis to lymph node from 2 different patients (PMLN2). Normalization was performed by PCR using primers to actin. Semi-quantitative PCR, using primer Set A as described in FIG. 14, was performed was performed at 26 and 30 cycles of amplification. Samples were run on an agarose gel, and PCR products were quantitated using the AlphaImager software. Relative expression was calculated by normalizing to signal obtained using actin primers. Results show restricted 193P1E1B expression in normal testis amongst all normal tissues tested. 193P1E1B expression was strongly upregulated in cancers of the bladder, colon, lung, pancreas, ovary, breast, and to a lesser extent in prostate and kidney cancers.

193P1E1B was also shown to be expressed in uterus, melanoma and bone cancer patient specimens. First strand cDNA was prepared from a panel of uterus patient cancer specimens (A), melanoma and bone cancer specimens (B). Semi-quantitative PCR, using primers to 193P1E1B, was performed at 26 and 30 cycles of amplification. Samples were run on an agarose gel, and PCR products were quantitated using the Alphalmager software. Expression was recorded as absent, low, or strong. Results show expression of 193P1E1B in the majority of uterus patient cancer specimens tested, as well as in the 2 melanoma specimens and in the bone tumor tested.

193P1E1B expression is reminiscent of a cancer-testis gene. Its restricted normal tissue expression to normal testis, and the upregulation detected in prostate cancer, bladder cancer, kidney cancer, colon cancer, lung cancer, ovary cancer, breast cancer and pancreatic cancer suggest that 193P1E1B is a potential therapeutic target and a diagnostic marker for human cancers.

Example 5

Transcript Variants of 193P1E1B

Transcript variants are variants of mature mRNA from the same gene which arise by alternative transcription or alternative splicing. Alternative transcripts are transcripts from the same gene but start transcription at different points. Splice variants are mRNA variants spliced differently from the same transcript. In eukaryotes, when a multi-exon gene is transcribed from genomic DNA, the initial RNA is spliced to produce functional mRNA, which has only exons and is used for translation into an amino acid sequence. Accordingly, a given gene can have zero to many alternative transcripts and each transcript can have zero to many splice variants. Each transcript variant has a unique exon makeup, and can have different coding and/or non-coding (5' or 3' end) portions, from the original transcript. Transcript variants can code for similar or different proteins with the same or a similar function or can encode proteins with different functions, and can be expressed in the same tissue at the same time, or in different tissues at the same time, or in the same tissue at different times, or in different tissues at different times. Proteins encoded by transcript variants can have similar or different cellular or extracellular localizations, e.g., secreted versus intracellular.

Transcript variants are identified by a variety of art-accepted methods. For example, alternative transcripts and splice variants are identified by full-length cloning experiment, or by use of full-length transcript and EST sequences. First, all human ESTs were grouped into clusters which show direct or indirect identity with each other. Second, ESTs in the same cluster were further grouped into sub-clusters and assembled into a consensus sequence. The original gene sequence is compared to the consensus sequence(s) or other full-length sequences. Each consensus sequence is a potential splice variant for that gene. Even when a variant is identified that is not a full-length clone, that portion of the variant is very useful for antigen generation and for further cloning of the full-length splice variant, using techniques known in the art.

Moreover, computer programs are available in the art that identify transcript variants based on genomic sequences. Genomic-based transcript variant identification programs include FgenesH (A. Salamov and V. Solovyev, "Ab initio gene finding in Drosophila genomic DNA," Genome Research. April 2000; 10(4):516-22); Grail and GenScan. For a general discussion of splice variant identification protocols see., e.g., Southan, C., A genomic perspective on human proteases, FEBS Lett. Jun. 8, 2001; 498(2-3):214-8; de Souza, S. J., et al., Identification of human chromosome 22 transcribed sequences with ORF expressed sequence tags, Proc. Natl. Acad. Sci USA. Nov. 7, 2000; 97(23):12690-3.

To further confirm the parameters of a transcript variant, a variety of techniques are available in the art, such as full-length cloning, proteomic validation, PCR-based validation, and 5' RACE validation, etc. (see e.g., Proteomic Validation: Brennan, S. O., et al., Albumin banks peninsula: a new termination variant characterized by electrospray mass spectrometry, Biochem Biophys Acta. Aug. 17, 1999;1433(1-2): 321-6; Ferranti P, et al., Differential splicing of pre-messenger RNA produces multiple forms of mature caprine alpha(s1)-casein, Eur J Biochem. Oct. 1, 1997;249(1):1-7. For PCR-based Validation: Wellmann S, et al., Specific reverse transcription-PCR quantification of vascular endothelial growth factor (VEGF) splice variants by LightCycler technology, Clin Chem. April 2001;47(4):654-60; Jia, H. P., et al., Discovery of new human beta-defensins using a genomics-based approach, Gene. Jan. 24, 2001; 263(1-2): 211-8. For PCR-based and 5' RACE Validation: Brigle, K. E., et al., Organization of the murine reduced folate carrier gene and identification of variant splice forms, Biochem Biophys Acta. Aug. 7, 1997; 1353(2): 191-8).

It is known in the art that genomic regions are modulated in cancers. When the genomic region to which a gene maps is modulated in a particular cancer, the alternative transcripts or splice variants of the gene are modulated as well. Disclosed herein is that 193P1E1B has a particular expression profile related to cancer. Alternative transcripts and splice variants of 193P1E1B may also be involved in cancers in the same or different tissues, thus serving as tumor-associated markers/antigens.

Using the full-length gene and EST sequences, three transcript variants were identified, designated as 193P1E1B v.7, v.8 and v.9. Compared with 193P1E1B v.1, transcript variant 193P1E1B v.7 has spliced out exons 10 and 11 from variant 193P1E1B v.1, as shown in FIG. 12. Variant 193P1E1B v.8 inserted 36 bp in between 1931 and 1932 of variant 193P1E1B v.1 and variant 193P1E1B v.9 replaced with 36 bp the segment 1136-1163 of variant 193P1E1B v.1. Theoretically, each different combination of exons in spatial order, e.g. exons 2 and 3, is a potential splice variant. Tables LI through LXX are set forth on a variant-by-variant bases. Tables LI, LV, LIX, LXIII, and LXVII show the nucleotide sequence of the transcript variant. Tables LII, LVI, LX, LXIV, and LXVIII show the alignment of the transcript variant with nucleic acid sequence of 193P1E1B v.1. Tables LIII, LVII, LXI, LXV, and LXIX show the amino acid translation of the transcript variant for the identified reading frame orientation. Tables LIV, LVIII, LXII, LXVI, and LXX display alignments of the amino acid sequence encoded by the splice variant with that of 193P1E1Bv.1.

Example 6

Single Nucleotide Polymorphisms of 193P1E1B

A Single Nucleotide Polymorphism (SNP) is a single base pair variation in a nucleotide sequence at a specific location. At any given point of the genome, there are four possible nucleotide base pairs: A/T, CIG, G/C and T/A. Genotype refers to the specific base pair sequence of one or more locations in the genome of an individual. Haplotype refers to the base pair sequence of more than one location on the same DNA molecule (or the same chromosome in higher organisms), often in the context of one gene or in the context of several tightly linked genes. SNPs that occur on a cDNA are called cSNPs. These cSNPs may change amino acids of the protein encoded by the gene and thus change the functions of the protein. Some SNPs cause inherited diseases; others contribute to quantitative variations in phenotype and reactions to environmental factors including diet and drugs among individuals. Therefore, SNPs and/or combinations of alleles (called haplotypes) have many applications, including diagnosis of inherited diseases, determination of drug reactions and dosage, identification of genes responsible for diseases, and analysis of the genetic relationship between individuals (P. Nowotny, J. M. Kwon and A. M. Goate, "SNP analysis to dissect human traits," Curr. Opin. Neurobiol. October 2001; 11(5):637-641; M. Pirmohamed and B. K. Park, "Genetic susceptibility to adverse drug reactions," Trends Pharmacol. Sci. June 2001; 22(6):298-305; J. H. Riley, C. J. Allan, E. Lai and A. Roses, "The use of single nucleotide polymorphisms in the isolation of common disease genes," Pharmacogenomics. February 2000; 1(1):3947; R. Judson, J. C. Stephens and A. Windemuth, "The predictive power of haplotypes in clinical response," Pharmacogenomics. 2000 feb; 1(1):15-26).

SNPs are identified by a variety of art-accepted methods (P. Bean, "The promising voyage of SNP target discovery," Am. Clin. Lab. October-November 2001; 20(9):18-20; K. M. Weiss, "In search of human variation," Genome Res. July 1998; 8(7):691-697; M. M. She, "Enabling large-scale pharmacogenetic studies by high-throughput mutation detection and genotyping technologies," Clin. Chem. 2001 Feb; 47(2): 164-172). For example, SNPs are identified by sequencing DNA fragments that show polymorphism by gel-based methods such as restriction fragment length polymorphism (RFLP) and denaturing gradient gel electrophoresis (DGGE). They can also be discovered by direct sequencing of DNA samples pooled from different individuals or by comparing sequences from different DNA samples. With the rapid accumulation of sequence data in public and private databases, one can discover SNPs by comparing sequences using computer programs (Z. Gu, L. Hillier and P. Y. Kwok, "Single nucleotide polymorphism hunting in cyberspace," Hum. Mutat. 1998; 12(4):221-225). SNPs can be verified and genotype or haplotype of an individual can be determined by a variety of methods including direct sequencing and high throughput microarrays (P. Y. Kwok, "Methods for genotyping single nucleotide polymorphisms," Annu. Rev. Genomics Hum. Genet. 2001; 2:235-258; M. Kokoris, K. Dix, K. Moynihan, J. Mathis, B. Erwin, P. Grass, B. Hines and A. Duesterhoeft, "High-throughput SNP genotyping with the Masscode system," Mol. Diagn. December 2000; 5(4):329-340). Using the methods described above, seven SNPs were identified in the original transcript, 193P1E1B v.1, at positions 57 (A/G), 792 (C/G), 804 (C/A), 1253 (G/A), 1564 (A/G), 2268 (C/T) and 2387 (C/T). The transcripts or proteins with alternative alleles were designated as variants 193P1E1B v.2, v.3, v.4, v.5 and v.6, respectively. FIG. 10 shows the schematic alignment of the SNP variants. FIG. 11 shows the schematic alignment of protein variants, corresponding to nucleotide variants. Nucleotide variants that code for the same amino acid sequence as variant 1 are not shown in FIG. 11. These alleles of the SNPs, though shown separately here, can occur in different combinations (haplotypes) and in any one of the transcript variants (such as 193P1E1B v.9) that contains the sequence context of the SNPs.

Example 7

Production of Recombinant 193P1E1B in Prokaryotic Systems

To express recombinant 193P1E1B in prokaryotic cells, the full or partial length 193P1E1B cDNA sequences can be cloned into any one of a variety of expression vectors known in the art. One or more of the following regions of 193P1E1B are expressed in these constructs, amino acids 1 to 412 of variant 5 or variant 2; or amino acids 1 to 388 of variant 10, or any 8, 9, 10, 11, 12, 13, 14, 15, 16, 17, 18, 19, 20, 21, 22, 23, 24, 25, 26, 27, 28, 29, 30 or more contiguous amino acids from 193P1E1B, variants, or analogs thereof. In certain embodiments a region of 193P1E1B is expressed that encodes an amino acid not shared amongst at least variants.

A. In vitro transcription and translation constructs:

pCRII: To generate 193P1E1B sense and anti-sense RNA probes for RNA in situ investigations, pCRII constructs (Invitrogen, Carlsbad Calif.) are generated encoding either all or fragments of a 193P1E1B cDNA. The pCRII vector has Sp6 and T7 promoters flanking the insert to drive the transcription of 193P1E1B RNA for use as probes in RNA in situ hybridization experiments. These probes are used to analyze the cell and tissue expression of 193P1E1B at the RNA level. Transcribed 193P1E1B RNA representing the cDNA amino acid coding region of the 193P1E1B gene is used in in vitro translation systems such as the TnT™ Coupled Reticulolysate System (Promega, Corp., Madison, Wis.) to synthesize 193P1E1B protein.

B. Bacterial Constructs:

PGEX Constructs: To generate recombinant 193P1E1B proteins in bacteria that are fused to the Glutathione S-transferase (GST) protein, all or parts of a 193P1E1B cDNA protein coding sequence are fused to the GST gene by cloning into pGEX-6P-1 or any other GST-fusion vector of the pGEX family (Amersham Pharmacia Biotech, Piscataway, N.J.). These constructs allow controlled expression of recombinant 193P1E1B protein sequences with GST fused at the amino-terminus and a six histidine epitope (6×His) at the carboxyl-terminus. The GST and 6×His tags permit purification of the recombinant fusion protein from induced bacteria with the appropriate affinity matrix and allow recognition of the fusion protein with anti-GST and anti-His antibodies. The 6×His tag is generated by adding 6 histidine codons to the cloning primer at the 3' end, e.g., of the open reading frame (ORF). A proteolytic cleavage site, such as the PreScission™ recognition site in pGEX-6P-1, may be employed such that it permits cleavage of the GST tag from 193P1E1B-related protein. The ampicillin resistance gene and pBR322 origin permits selection and maintenance of the pGEX plasmids in *E. coli.* pMAL Constructs: To generate, in bacteria, recombinant 193P1E1B proteins that are fused to maltose-binding protein (MBP), all or parts of a 193P1E1B cDNA protein coding sequence are fused to the MBP gene by cloning into the pMAL-c2X and pMAL-p2X vectors (New England Biolabs, Beverly, Mass.). These constructs allow controlled expression of recombinant 193P1E1B protein sequences with MBP fused at the amino-terminus and a 6×His epitope tag at the carboxyl-terminus. The MBP and 6×His tags permit purification of the recombinant protein from induced bacteria with the appropriate affinity matrix and allow recognition of the fusion protein with anti-MBP and anti-His antibodies. The 6×His epitope tag is generated by adding 6 histidine codons to the 3' cloning primer. A Factor Xa recognition site permits cleavage of the pMAL tag from 193P1E1B. The pMAL-c2X and pMAL-p2X vectors are optimized to express the recombinant protein in the cytoplasm or periplasm respectively. Periplasm expression enhances folding of proteins with disulfide bonds.

pET Constructs: To express 193P1E1B in bacterial cells, all or parts of a 193P1E1B cDNA protein coding sequence are cloned into the pET family of vectors (Novagen, Madison, Wis.). These vectors allow tightly controlled expression of recombinant 193P1E1B protein in bacteria with and without fusion to proteins that enhance solubility, such as NusA and thioredoxin (Trx), and epitope tags, such as 6×His and S-Tag Tm that aid purification and detection of the recombinant protein. For example, constructs are made utilizing pET NusA fusion system 43.1 such that regions of a 193P1E1B protein are expressed as amino-terminal fusions to NusA.

C. Yeast Constructs:

pESC Constructs: To express 193P1E1B in the yeast species Saccharomyces cerevisiae for generation of recombinant protein and functional studies, all or parts of a 193P1E1B cDNA protein coding sequence are cloned into the pESC family of vectors each of which contain 1 of 4 selectable markers, HIS3, TRP1, LEU2, and URA3 (Stratagene, La Jolla, Calif.). These vectors allow controlled expression from the same plasmid of up to 2 different genes or cloned sequences containing either Flag™ or Myc epitope tags in the same yeast cell. This system is useful to confirm protein-protein interactions of 193P1E1B. In addition, expression in yeast yields similar post-translational modifications, such as glycosylations and phosphorylations, that are found when expressed in eukaryotic cells.

pESP Constructs: To express 193P1E1B in the yeast species *Saccharomyces pombe,* all or parts of a 193P1E1B cDNA protein coding sequence are cloned into the pESP family of vectors. These vectors allow controlled high level of expression of a 193P1E1B protein sequence that is fused at either the amino terminus or at the carboxyl terminus to GST which aids purification of the recombinant protein. A Flag™ epitope tag allows detection of the recombinant protein with anti-Flag™ antibody.

Example 8

Production of Recombinant 193P1E1B in Higher Eukaryotic Systems

A. Mammalian Constructs:

To express recombinant 193P1E1B in eukaryotic cells, the full or partial length 193P1E1B cDNA sequences can be cloned into any one of a variety of expression vectors known in the art. One or more of the following regions of 193P1E1B are expressed in these constructs, amino acids 1 to 412; or any 8, 9, 10, 11, 12, 13, 14, 15, 16, 17, 18, 19, 20, 21, 22, 23, 24, 25, 26, 27, 28, 29, 30 or more contiguous amino acids from 193P1E1B, variants, or analogs thereof.

The constructs can be transfected into any one of a wide variety of mammalian cells such as 293T cells. Transfected 293T cell lysates can be probed with the anti-193P1E1B polyclonal serum, described herein.

pcDNA4/HisMax Constructs: To express 193P1E1B in mammalian cells, the 193P1E1B ORF, or portions thereof, of 193P1E1B are cloned into pcDNA4/HisMax Version A (Invitrogen, Carlsbad, Calif.). Protein expression is driven from the cytomegalovirus (CMV) promoter and the SP16 translational enhancer. The recombinant protein has Xpress™ and six histidine (6×His) epitopes fused to the amino-terminus. The pcDNA4/HisMax vector also contains the bovine growth hormone (BGH) polyadenylation signal and transcription termination sequence to enhance mRNA stability along with the SV40 origin for episomal replication and simple vector rescue in cell lines expressing the large T antigen. The Zeocin resistance gene allows for selection of mammalian cells expressing the protein and the ampicillin resistance gene and ColE1 origin permits selection and maintenance of the plasmid in *E. coli.* pcDNA3.11MycHis Constructs: To express 193P1E1B in mammalian cells, the 193P1E1B ORF, or portions thereof, of 193P1E1B with a consensus Kozak translation initiation site are cloned into pcDNA3.1/MycHis Version A (Invitrogen, Carlsbad, Calif.). Protein expression is driven from the cytomegalovirus (CMV) promoter. The recombinant proteins have the myc epitope and 6×His epitope fused to the carboxyl-terminus. The pcDNA3.1/MycHis vector also contains the bovine growth hormone (BGH) polyadenylation signal and transcription termination sequence to enhance mRNA stability, along with the SV40 origin for episomal replication and simple vector rescue in cell lines expressing the large T antigen. The Neomycin resistance gene can be used, as it allows for selection of mammalian cells expressing the protein and the ampicillin resistance gene and ColE1 origin permits selection and maintenance of the plasmid in *E. coli.* pcDNA3.1/CT-GFP-TOPO Construct: To express 193P1E1B in mammalian cells and to allow detection of the recombinant proteins using fluorescence, the 193P1E1B ORF, or portions thereof, of 193P1E1B with a consensus Kozak translation initiation site are cloned into pcDNA3.1/CT-GFP-TOPO (Invitrogen, Calif.). Protein expression is driven from the cytomegalovirus (CMV) promoter. The recombinant proteins have the Green Fluorescent Protein (GFP) fused to the carboxyl-terminus facilitating non-invasive, in vivo detection and cell biology studies. The pcDNA3.1 CT-GFP-TOPO vector also contains the bovine growth hormone (BGH) polyadenylation signal and transcription termination sequence to enhance mRNA stability along with the SV40 origin for episomal replication and simple vector rescue in cell lines expressing the large T antigen. The Neomycin resistance gene allows for selection of mammalian cells that express the protein, and the ampicillin resistance gene and ColE1 origin permits selection and maintenance of the plasmid in *E. coli*. Additional constructs with an amino-terminal GFP fusion are made in pcDNA3.1/NT-GFP-TOPO spanning the entire length of the 193P1E1B proteins.

PAPtag: The 193P1E1B ORF, or portions thereof, of 193P1E1B are cloned into pAPtag-5 (GenHunter Corp. Nashville, Tenn.). This construct generates an alkaline phosphatase fusion at the carboxyl-terminus of the 193P1E1B proteins while fusing the IgGκ signal sequence to the amino-terminus. Constructs are also generated in which alkaline phosphatase with an amino-terminal IgGκ signal sequence is fused to the amino-terminus of 193P1E1B proteins. The resulting recombinant 193P1E1B proteins are optimized for secretion into the media of transfected mammalian cells and can be used to identify proteins such as ligands or receptors that interact with the 193P1E1B proteins. Protein expression is driven from the CMV promoter and the recombinant proteins also contain myc and 6×His epitopes fused at the carboxyl-terminus that facilitates detection and purification. The Zeocin resistance gene present in the vector allows for selection of mammalian cells expressing the recombinant protein and the ampicillin resistance gene permits selection of the plasmid in *E. coli.* ptag5: The 193P1E1B ORF, or portions thereof, of 193P1E1B are cloned into pTag-5. This vector is similar to pAPtag but without the alkaline phosphatase fusion. This construct generates 193P1E1B protein with an amino-terminal IgGκ signal sequence and myc and 6×His epitope tags at the carboxyl-terminus that facilitate detection and affinity purification. The resulting recombinant 193P1E1B protein is optimized for secretion into the media of transfected mammalian cells, and is used as immunogen or ligand to identify proteins such as ligands or receptors that interact with the 193P1E1B proteins. Protein expression is driven from the CMV promoter. The Zeocin resistance gene present in the vector allows for selection of mammalian cells expressing the protein, and the ampicillin resistance gene permits selection of the plasmid in *E. coli*.

PsecFc: The 193P1E1B ORF, or portions thereof, of 193P1E1B are also cloned into psecFc. The psecFc vector was assembled by cloning the human immunoglobulin G1 (IgG) Fc (hinge, CH2, CH3 regions) into pSecTag2 (Invitrogen, California). This construct generates an IgG1 Fc fusion at the carboxyl-terminus of the 193P1E1B proteins, while fusing the IgGK signal sequence to N-terminus. 193P1E1B fusions utilizing the murine IgG1 Fc region are also used. The resulting recombinant 193P1E1B proteins are optimized for secretion into the media of transfected mammalian cells, and can be used as immunogens or to identify proteins such as ligands or receptors that interact with the 193P1E1B protein. Protein expression is driven from the CMV promoter. The hygromycin resistance gene present in the vector allows for selection of mammalian cells that express the recombinant protein, and the ampicillin resistance gene permits selection of the plasmid in *E. coli*.

pSRα Constructs: To generate mammalian cell lines that express 193P1E1B constitutively, 193P1E1B ORF, or portions thereof, of 193P1E1B are cloned into pSRα constructs. Amphotropic and ecotropic retroviruses are generated by transfection of pSRα constructs into the 293T-10A1 packaging line or co-transfection of pSRα and a helper plasmid (containing deleted packaging sequences) into the 293 cells, respectively. The retrovirus is used to infect a variety of mammalian cell lines, resulting in the integration of the cloned gene, 193P1E1B, into the host cell-lines. Protein expression is driven from a long terminal repeat (LTR). The Neomycin resistance gene present in the vector allows for selection of mammalian cells that express the protein, and the ampicillin resistance gene and ColE1 origin permit selection and maintenance of the plasmid in *E. coli*. The retroviral vectors can thereafter be used for infection and generation of various cell lines using, for example, PC3, NIH 3T3, TsuPr1, 293 or rat-1 cells.

Additional pSRα constructs are made that fuse an epitope tag such as the FLAG™ tag to the carboxyl-terminus of 193P1E1B sequences to allow detection using anti-Flag antibodies. For example, the FLAG™ sequence 5' gat tac aag gat gac gac gat aag 3' (SEQ ID NO: 62) is added to cloning primer at the 3' end of the ORF. Additional pSRα constructs are made to produce both amino-terminal and carboxyl-terminal GFP and myc/6×His fusion proteins of the full-length 193P1E1B proteins.

Additional Viral Vectors: Additional constructs are made for viral-mediated delivery and expression of 193P1E1B. High virus titer leading to high level expression of 193P1E1B is achieved in viral delivery systems such as adenoviral vectors and herpes amplicon vectors. The 193P1E1B coding sequences or fragments thereof are amplified by PCR and subcloned into the AdEasy shuffle vector (Stratagene). Recombination and virus packaging are performed according to the manufacturer's instructions to generate adenoviral vectors. Alternatively, 193P1E1B coding sequences or fragments thereof are cloned into the HSV-1 vector (Imgenex) to generate herpes viral vectors. The viral vectors are thereafter used for infection of various cell lines such as PC3, NIH 3T3, 293 or rat-1 cells.

Regulated Expression Systems: To control expression of 193P1E1B in mammalian cells, coding sequences of 193P1E1B, or portions thereof, are cloned into regulated mammalian expression systems such as the T-Rex System (Invitrogen), the GeneSwitch System (Invitrogen) and the tightly-regulated Ecdysone System (Sratagene). These systems allow the study of the temporal and concentration dependent effects of recombinant 193P1E1B. These vectors are thereafter used to control expression of 193P1E1B in various cell lines such as PC3, NIH 3T3, 293 or rat-1 cells.

B. Baculovirus Expression Systems

To generate recombinant 193P1E1B proteins in a baculovirus expression system, 193P1E1B ORF, or portions thereof, are cloned into the baculovirus transfer vector pBlueBac 4.5 (Invitrogen), which provides a His-tag at the N-terminus. Specifically, pBlueBac-193P1E1B is co-transfected with helper plasmid pBac-N-Blue (Invitrogen) into SF9 (*Spodoptera frugiperda*) insect cells to generate recombinant baculovirus (see Invitrogen instruction manual for details). Baculovirus is then collected from cell supernatant and purified by plaque assay.

Recombinant 193P1E1B protein is then generated by infection of HighFive insect cells (Invitrogen) with purified baculovirus. Recombinant 193P1E1B protein can be detected using anti-193P1E1B or anti-His-tag antibody. 193P1E1B protein can be purified and used in various cell-based assays or as immunogen to generate polyclonal and monoclonal antibodies specific for 193P1E1B.

Example 9

Antigenicity Profiles and Secondary Structure

FIG. 5, FIG. 6, FIG. 7, FIG. 8, and FIG. 9 depict graphically five amino acid profiles of the 193P1E1B amino acid sequence (variant 1), each assessment is available by accessing the ProtScale website on the ExPasy molecular biology server.

These profiles: FIG. 5, Hydrophilicity, (Hopp T. P., Woods K. R., 1981. Proc. Natl. Acad. Sci. U.S.A. 78:3824-3828); FIG. 6, Hydropathicity, (Kyte J., Doolittle R. F., 1982. J. Mol. Biol. 157:105-132); FIG. 7, Percentage Accessible Residues (Janin J., 1979 Nature 277:491-492); FIG. 8, Average Flexibility, (Bhaskaran R., and Ponnuswamy P. K., 1988. Int. J. Pept. Protein Res. 32:242-255); FIG. 9, Beta-turn (Deleage, G., Roux B. 1987 Protein Engineering 1:289-294); and optionally others available in the art, such as on the ProtScale website, were used to identify antigenic regions of 193P1E1B protein. Each of the above amino acid profiles of 193P1E1B were generated using the following ProtScale parameters for analysis: 1) A window size of 9; 2) 100% weight of the window edges compared to the window center; and, 3) amino acid profile values normalized to lie between 0 and 1.

Hydrophilicity (FIG. 5), Hydropathicity (FIG. 6) and Percentage Accessible Residues (FIG. 7) profiles were used to determine stretches of hydrophilic amino acids (i.e., values greater than 0.5 on the Hydrophilicity and Percentage Accessible Residues profiles, and values less than 0.5 on the Hydropathicity profile). Such regions are likely to be exposed to the aqueous environment, be present on the surface of the protein, and thus available for immune recognition, such as by antibodies.

Average Flexibility (FIG. 8) and Beta-turn (FIG. 9) profiles determine stretches of amino acids (i.e., values greater than 0.5 on the Beta-turn profile and the Average Flexibility profile) that are not constrained in secondary structures such as beta sheets and alpha helices. Such regions are also more likely to be exposed on the protein and thus accessible to immune recognition, such as by antibodies.

Antigenic sequences of the full length 193P1E1B protein (variant 1) indicated, e.g., by the profiles set forth in FIG. 5, FIG. 6, FIG. 7, FIG. 8, and/or FIG. 9 are used to prepare immunogens, either peptides or nucleic acids that encode them, to generate therapeutic and diagnostic anti-193P1E1B antibodies. The immunogen can be any 5, 6, 7, 8, 9, 10, 11, 12, 13, 14, 15, 16, 17, 18, 19, 20, 21, 22, 23, 24, 25, 30, 35, 40, 45, 50 or more than 50 contiguous amino acids, or the corresponding nucleic acids that encode them, from 193P1E1B protein. In particular, peptide immunogens of the invention can comprise, a peptide region of at least 5 amino acids of FIG. 2 in any whole number increment up to 412 that includes an amino acid position having a value greater than 0.5 in the Hydrophilicity profile of FIG. 5; a peptide region of at least 5 amino acids of FIG. 2 in any whole number increment up to 412 that includes an amino acid position having a value less than 0.5 in the Hydropathicity profile of FIG. 6; a peptide region of at least 5 amino acids of FIG. 2 in any whole number increment up to 412 that includes an amino acid position having a value greater than 0.5 in the Percent Accessible Residues profile of FIG. 7; a peptide region of at least 5 amino acids of FIG. 2 in any whole number increment up to 412 that includes an amino acid position having a value greater than 0.5 in the Average Flexibility profile on FIG. 8; and, a peptide region of at least 5 amino acids of FIG. 2 in any whole number increment up to 412 that includes an amino acid position having a value greater than 0.5 in the Beta-turn profile of FIG. 9. Peptide immunogens of the invention can also comprise nucleic acids that encode any of the forgoing.

All immunogens of the invention, peptide or nucleic acid, can be embodied in human unit dose form, or comprised by a composition that includes a pharmaceutical excipient compatible with human physiology.

The secondary structure of 193P1E1B, namely the predicted presence and location of alpha helices, extended strands, and random coils, is predicted from the primary amino acid sequence of 193P1E1B variant 1 using the HNN-Hierarchical Neural Network method, accessed from the ExPasy molecular biology server. The analysis indicates that 193P1E1B is composed 29.13% alpha helix, 9.95% extended strand, and 60.92% random coil (FIG. 13).

Analysis of 193P1E1B using a variety of transmembrane prediction algorithms accessed from the ExPasy molecular biology server did not predict the presence of such domains, confirming that 193P1E1B is a soluble protein.

Example 10

Generation of 193P1E1B Polyclonal Antibodies

Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. In addition to immunizing with the full length 193P1E1B protein, computer algorithms are employed in design of immunogens that, based on amino acid sequence analysis contain characteristics of being antigenic and available for recognition by the immune system of the immunized host (see Example 9 entitled "Antigenicity Profiles and Secondary Structure"). Such regions would be predicted to be hydrophilic, flexible, in beta-turn conformations, and be exposed on the surface of the protein (see, e.g., FIG. 5, FIG. 6, FIG. 7, FIG. 8, or FIG. 9 for amino acid profiles that indicate such regions of 193P1E1B).

For example, 193P1E1B recombinant bacterial fusion proteins or peptides containing hydrophilic, flexible, beta-turn regions of 193P1E1B are used as antigens to generate polyclonal antibodies in New Zealand White rabbits. For example, such regions include, but are not limited to, amino acids 20-43, amino acids 100-164, amino acids 241-261, or amino acids 310-331. It is useful to conjugate the immunizing agent to a protein known to be immunogenic in the mammal being immunized. Examples of such immunogenic proteins include, but are not limited to, keyhole limpet hemocyanin (KLH), serum albumin, bovine thyroglobulin, and soybean trypsin inhibitor. In one embodiment, a peptide encoding amino acids 241-261 of 193P1E1B is conjugated to KLH and used to immunize the rabbit. Alternatively the immunizing agent may include all or portions of a 193P1E1B protein, analogs or fusion proteins thereof. For example, a 193P1E1B amino acid sequence can be fused using recombinant DNA techniques to any one of a variety of fusion protein partners that are well known in the art, such as glutathione-S-transferase (GST) and HIS tagged fusion proteins. Such fusion proteins are purified from induced bacteria using the appropriate affinity matrix.

In one embodiment, a GST-fusion protein containing an entire 193P1E1B coding sequence is produced and purified and used as immunogen. Other recombinant bacterial fusion proteins that can be employed include maltose binding protein, LacZ, thioredoxin, NusA, or an immunoglobulin constant region (see the section entitled "Production of 193P1E1B in Prokaryotic Systems" and Current Protocols In Molecular Biology, Volume 2, Unit 16, Frederick M. Ausubul et al. eds., 1995; Linsley, P. S., Brady, W., Urnes, M., Grosmaire, L., Damle, N., and Ledbetter, L.(1991) J.Exp. Med. 174, 561-566).

In addition to bacterial-derived fusion proteins, mammalian-expressed protein antigens are also used. These antigens are expressed from mammalian expression vectors such as the Tag5 and Fc-fusion vectors (see Example 8 entitled "Production of Recombinant 193P1E1B in Eukaryotic Systems"), and retain post-translational modifications such as glycosylations found in native protein. In one embodiment, an entire 193P1E1B coding sequence is cloned into the Tag5 mammalian secretion vector. The recombinant protein is purified by metal chelate chromatography from tissue culture supernatants of 293T cells stably expressing the recombinant vector. The purified Tag5 193P1E1B protein is then used as immunogen.

During the immunization protocol, it is useful to mix or emulsify the antigen in adjuvants that enhance the immune response of the host animal. Examples of adjuvants include, but are not limited to, complete Freund's adjuvant (CFA) and MPL-TDM adjuvant (monophosphoryl Lipid A, synthetic trehalose dicorynomycolate).

In a typical protocol, rabbits are initially immunized subcutaneously with up to 200 μg, typically 100-200 μg, of fusion protein or peptide conjugated to KLH mixed in complete Freund's adjuvant (CFA). Rabbits are then injected subcutaneously every two weeks with up to 200 μg, typically 100-200 μg, of the immunogen in incomplete Freund's adjuvant (IFA).

Test bleeds are taken approximately 7-10 days following each immunization and used to monitor the titer of the antiserum by ELISA.

To test reactivity and specificity of immune serum, such as the rabbit serum derived from immunization with Tag5 193P1E1B protein or KLH-coupled peptide encoding amino acids 241-261, the full-length 193P1E1B cDNA is cloned into pCDNA 3.1 myc-his expression vector (invitrogen, see the Example entitled "Production of Recombinant 193P1E1B in Eukaryotic Systems"). After transfection of the constructs into 293T cells, cell lysates are probed with the anti-193P1E1B serum and with anti-His antibody (Santa Cruz Biotechnologies, Santa Cruz, Calif.) to determine specific reactivity to denatured 193P1E1B protein using the Western blot technique. Immunoprecipitation and flow cytometric analyses of 293T and other recombinant 193P1E1B-expressing cells determine recognition of native protein by the antiserum. In addition, Western blot, immunoprecipitation, fluorescent microscopy, and flow cytometric techniques using cells that endogenously express 193P1E1B are carded out to test specificity.

The anti-serum from the Tag5 193P1E1B immunized rabbit is affinity purified by passage over a column composed of the Tag5 antigen covalently coupled to Affigel matrix (Bio-Rad, Hercules, Calif.). The serum is then further purified by protein G affinity chromatography to isolate the IgG fraction. Serum from rabbits immunized with fusion proteins, such as GST and MBP fusion proteins, are purified by depletion of antibodies reactive to the fusion partner sequence by passage over an affinity column containing the fusion partner either alone or in the context of an irrelevant fusion protein. Sera from other His-tagged antigens and peptide immunized rabbits as well as fusion partner depleted sera are affinity purified by passage over a column matrix composed of the original protein immunogen or free peptide.

Example 11

Generation of 193P1E1B Monoclonal Antibodies (mAbs)

In one embodiment, therapeutic mAbs to 193P1E1B comprise those that react with epitopes of the protein that would disrupt or modulate the biological function of 193P1E1B, for example those that would disrupt its interaction with ligands, proteins, or substrates that mediate its biological activity. Immunogens for generation of such mAbs include those designed to encode or contain an entire 193P1E1B protein or its variants or regions of a193P1E1B protein predicted to be antigenic from computer analysis of the amino acid sequence (see, e.g., FIG. 5, FIG. 6, FIG. 7, FIG. 8, or FIG. 9, and Example 9 entitled "Antigenicity Profiles and Secondary Structure"). Immunogens include peptides, recombinant bacterial proteins, and mammalian expressed Tag 5 proteins and human and murine IgG FC fusion proteins. In addition, cells expressing high levels of 193P1E1B, such as 293T-193P1E1B or 300.19-193P1E1B murine Pre-B cells, are used to immunize mice.

To generate mAbs to 193P1E1B, mice are first immunized intraperitoneally (IP) with, typically, 10-50 μg of protein immunogen or $10^7$ 193P1E1B-expressing cells mixed in complete Freund's adjuvant. Mice are then subsequently immunized IP every 2-4 weeks with, typically, 10-50 μg of protein immunogen or $10^7$ cells mixed in incomplete Freund's adjuvant. Alternatively, MPL-TDM adjuvant is used in immunizations. In addition to the above protein and cell-based immunization strategies, a DNA-based immunization protocol is employed in which a mammalian expression vector encoding 193P1E1B sequence is used to immunize mice by direct injection of the plasmid DNA. For example, an entire coding sequence of 193P1E1B, e.g., amino acids 1-412 of 193P1E1B variant 1, is cloned into the Tag5 mammalian secretion vector and the recombinant vector is used as immunogen. In another example the amino acids are cloned into an Fc-fusion secretion vector in which a 193P1E1B sequence is fused at the amino-terminus to an IgK leader sequence and at the carboxyl-terminus to the coding sequence of the human or murine IgG Fc region. This recombinant vector is then used as immunogen. The plasmid immunization protocols are used in combination with purified proteins expressed from the same vector and with cells expressing 193P1E1B.

During the immunization protocol, test bleeds are taken 7-10 days following an injection to monitor titer and specificity of the immune response. Once appropriate reactivity and specificity is obtained as determined by ELISA, Western blotting, immunoprecipitation, fluorescence microscopy, and flow cytometric analyses, fusion and hybridoma generation is then carried out with established procedures well known in the art (see, e.g., Harlow and Lane, 1988).

In one embodiment, monoclonal antibodies are derived that distinguish between, e.g., the various 193P1E1B variants, e.g., the amino terminal truncated splice variant 3, encoding amino acids 83-412 and the full length protein encoding amino acids 1-412. In one method, two different Fc-fusion proteins are derived, one encoding amino acids 1-82, and the other encoding amino acids 83-412. These are expressed and purified from stably transfected 293T cells. Balb C mice are initially immunized intraperitoneally with 25 μg of the Tag5-193P1E1B protein mixed in complete Freund's adjuvant. Mice are subsequently immunized every two weeks with 25 μg of the antigen mixed in incomplete Freund's adjuvant for a total of three immunizations. ELISA using the Tag5 antigen determines the titer of serum from immunized mice. Reactivity and specificity of serum to the full length 193P1E1B protein and to amino terminal truncated variant 3 is monitored by Western blotting, immunoprecipitation and flow cytometry using 293T cells transfected with an expression vector encoding each of the respective 193P1E1B cDNAs (see e.g., the Example entitled "Production of Recombinant 193P1E1B in Eukaryotic Systems"). Other recombinant 193P1E1B-expressing cells or cells endogenously expressing 193P1E1B are also used. Mice showing the strongest reactivity are rested and given a final injection of Tag5 antigen in PBS and then sacrificed four days later. The spleens of the sacrificed mice are harvested and fused to SPO/2 myeloma cells using standard procedures (see, e.g., Harlow and Lane, 1988). Supernatants from HAT selected growth wells are screened by ELISA, Western blot, immunoprecipitation, fluorescent microscopy, and flow cytometry to identify 193P1E1B specific antibody-producing clones.

The binding affinity of a 193P1E1B monoclonal antibody is determined using standard technologies. Affinity measurements quantify the strength of antibody to epitope binding and are used to help define which 193P1E1B monoclonal antibodies preferred, e.g., for diagnostic or therapeutic use, as appreciated by one of skill in the art. The BIAcore system (Uppsala, Sweden) is a preferred method for determining binding affinity. The BIAcore system uses surface plasmon resonance (SPR, Welford K. 1991, Opt. Quant. Elect. 23:1; Morton and Myszka, 1998, Methods in Enzymology 295: 268) to monitor biomolecular interactions in real time. BIAcore analysis conveniently generates association rate constants, dissociation rate constants, equilibrium dissociation constants, and affinity constants.

Example 12

HLA Class I and Class II Binding Assays

HLA class I and class II binding assays using purified HLA molecules are performed in accordance with disclosed protocols (e.g., PCT publications WO 94/20127 and WO 94/03205; Sidney et al., *Current Protocols in Immunology* 18.3.1 (1998); Sidney, et al., *J. Immunol.* 154:247 (1995); Sette, et al., *Mol. Immunol.* 31:813 (1994)). Briefly, purified MHC molecules (5 to 500 nM) are incubated with various unlabeled peptide inhibitors and 1-10 nM $^{125}$I-radiolabeled probe peptides as described. Following incubation, MHC-peptide complexes are separated from free peptide by gel filtration and the fraction of peptide bound is determined. Typically, in preliminary experiments, each MHC preparation is titered in the presence of fixed amounts of radiolabeled peptides to determine the concentration of HLA molecules necessary to bind 10-20% of the total radioactivity. All subsequent inhibition and direct binding assays are performed using these HLA concentrations.

Since under these conditions [label]<[HLA] and $IC_{50} \geqq$ [HLA], the measured $IC_{50}$ values are reasonable approximations of the true KD values. Peptide inhibitors are typically tested at concentrations ranging from 120 μg/ml to 1.2 ng/ml, and are tested in two to four completely independent experiments. To allow comparison of the data obtained in different experiments, a relative binding figure is calculated for each peptide by dividing the $IC_{50}$ of a positive control for inhibition by the $IC_{50}$ for each tested peptide (typically unlabeled versions of the radiolabeled probe peptide). For database purposes, and inter-experiment comparisons, relative binding values are compiled. These values can subsequently be converted back into $IC_{50}$ nM values by dividing the $IC_{50}$ nM of the positive controls for inhibition by the relative binding of the peptide of interest. This method of data compilation is accurate and consistent for comparing peptides that have been tested on different days, or with different lots of purified MHC.

Binding assays as outlined above may be used to analyze HLA supermotif and/or HLA motif-bearing peptides (see Table IV).

Example 13

Identification of HLA Supermotif-and Motif-Bearing CTL Candidate Epitopes

HLA vaccine compositions of the invention can include multiple epitopes. The multiple epitopes can comprise multiple HLA supermotifs or motifs to achieve broad population coverage. This example illustrates the identification and confirmation of supermotif- and motif-bearing epitopes for the inclusion in such a vaccine composition. Calculation of population coverage is performed using the strategy described below.

Computer Searches and Algorithms for Identification of Supermotif and/or Motif-Bearing Epitopes The searches performed to identify the motif-bearing peptide sequences in the Example entitled "Antigenicity Profiles" and Tables VIII-XXI and XXII-XLIX employ the protein sequence data from the gene product of 193P1E1B. set forth in FIGS. 2 and 3, the specific search peptides used to generate the tables are listed in Table VII.

Computer searches for epitopes bearing HLA Class I or Class II supermotifs or motifs are performed as follows. All translated 193P1E1B protein sequences are analyzed using a text string search software program to identify potential peptide sequences containing appropriate HLA binding motifs; such programs are readily produced in accordance with information in the art in view of known motif/supermotif disclosures. Furthermore, such calculations can be made mentally.

Identified A2-, A3-, and DR-supermotif sequences are scored using polynomial algorithms to predict their capacity to bind to specific HLA-Class I or Class II molecules. These polynomial algorithms account for the impact of different amino acids at different positions, and are essentially based on the premise that the overall affinity (or AG) of peptide-HLA molecule interactions can be approximated as a linear polynomial function of the type:

$$\text{“}\Delta G\text{”} = a_{1i} \times a_{2i} \times a_{3i} \ldots \times a_{ni}$$

where $a_{ji}$ is a coefficient which represents the effect of the presence of a given amino acid (j) at a given position (i) along the sequence of a peptide of n amino acids. The crucial assumption of this method is that the effects at each position are essentially independent of each other (i.e., independent binding of individual side-chains). When residue j occurs at position i in the peptide, it is assumed to contribute a constant amount j, to the free energy of binding of the peptide irrespective of the sequence of the rest of the peptide.

The method of derivation of specific algorithm coefficients has been described in Gulukota et al., *J. Mol. Biol.* 267:1258-126, 1997; (see also Sidney et al., *Human Immunol.* 45:79-93, 1996; and Southwood et al., *J. Immunol.* 160:3363-3373, 1998). Briefly, for all i positions, anchor and non-anchor alike, the geometric mean of the average relative binding (ARB) of all peptides carrying j is calculated relative to the remainder of the group, and used as the estimate of $j_i$. For Class II peptides, if multiple alignments are possible, only the highest scoring alignment is utilized, following an iterative procedure. To calculate an algorithm score of a given peptide in a test set, the ARB values corresponding to the sequence of the peptide are multiplied. If this product exceeds a chosen threshold, the peptide is predicted to bind. Appropriate thresholds are chosen as a function of the degree of stringency of prediction desired.

Selection of HLA-A2 Supertype Cross-Reactive Peptides

Protein sequences from 193P1E1B are scanned utilizing motif identification software, to identify 8-, 9-10- and 11-mer sequences containing the HLA-A2-supermotif main anchor specificity. Typically, these sequences are then scored using the protocol described above and the peptides corresponding to the positive-scoring sequences are synthesized and tested for their capacity to bind purified HLA-A*0201 molecules in vitro (HLA-A*0201 is considered a prototype A2 supertype molecule).

These peptides are then tested for the capacity to bind to additional A2-supertype molecules (A*0202, A*0203, A*0206, and A*6802). Peptides that bind to at least three of the five A2-supertype alleles tested are typically deemed A2-supertype cross-reactive binders. Preferred peptides bind at an affinity equal to or less than 500 nM to three or more HLA-A2 supertype molecules.

Selection of HLA-A3 Supermotif-Bearing Epitopes

The 193P1E1B protein sequence(s) scanned above is also examined for the presence of peptides with the HLA-A3-supermotif primary anchors. Peptides corresponding to the HLA A3 supermotif-bearing sequences are then synthesized and tested for binding to HLA-A*0301 and HLA-A*1101 molecules, the molecules encoded by the two most prevalent A3-supertype alleles. The peptides that bind at least one of the two alleles with binding affinities of ≦500 nM, often ≦200 nM, are then tested for binding cross-reactivity to the other common A3-supertype alleles (e.g., A*3101, A*3301, and A*6801) to identify those that can bind at least three of the five HLA-A3-supertype molecules tested.

Selection of HLA-B7 supermotif bearing epitopes

The 193P1E1B protein(s) scanned above is also analyzed for the presence of 8-, 9- 10-, or 11-mer peptides with the HLA-B7-supermotif. Corresponding peptides are synthesized and tested for binding to HLA-B*0702, the molecule encoded by the most common B7-supertype allele (i.e., the prototype B7 supertype allele). Peptides binding B*0702 with $IC_{50}$ of ≦500 nM are identified using standard methods. These peptides are then tested for binding to other common B7-supertype molecules (e.g., B*3501, B*5101, B*5301, and B*5401). Peptides capable of binding to three or more of the five B7-supertype alleles tested are thereby identified.

Selection of A1 and A24 Motif-Bearing Epitopes

To further increase population coverage, HLA-A1 and -A24 epitopes can also be incorporated into vaccine compositions. An analysis of the 193P1E1B protein can also be performed to identify HLA-A1- and A24-motif-containing sequences.

High affinity and/or cross-reactive binding epitopes that bear other motif and/or supermotifs are identified using analogous methodology.

Example 14

Confirmation of Immunogenicity

Cross-reactive candidate CTL A2-supermotif-bearing peptides that are identified as described herein are selected to confirm in vitro immunogenicity. Confirmation is performed using the following methodology:

Target Cell Lines for Cellular Screening:

The .221A2.1 cell line, produced by transferring the HLA-A2.1 gene into the HLA-A, -B, -C null mutant human B-lymphoblastoid cell line 721.221, is used as the peptide-loaded target to measure activity of HLA-A2.1-restricted CTL. This cell line is grown in RPMI-1640 medium supplemented with antibiotics, sodium pyruvate, nonessential amino acids and 10% (v/v) heat inactivated FCS. Cells that express an antigen of interest, or transfectants comprising the gene encoding the antigen of interest, can be used as target cells to confirm the ability of peptide-specific CTLs to recognize endogenous antigen.

Primary CTL Induction Cultures:

Generation of Dendritic Cells (DC): PBMCs are thawed in RPMI with 30 μg/ml DNAse, washed twice and resuspended in complete medium (RPMI-1640 plus 5% AB human serum, non-essential amino acids, sodium pyruvate, L-glutamine and penicillin/streptomycin). The monocytes are purified by plating $10\times10^6$ PBMC/well in a 6-well plate. After 2 hours at 37° C., the non-adherent cells are removed by gently shaking the plates and aspirating the supernatants. The wells are washed a total of three times with 3 ml RPMI to remove most of the non-adherent and loosely adherent cells. Three ml of complete medium containing 50 ng/ml of GM-CSF and 1,000 U/ml of IL-4 are then added to each well. TNFα is added to the DCs on day 6 at 75 ng/ml and the cells are used for CTL induction cultures on day 7.

Induction of CTL with DC and Peptide: CD8+ T-cells are isolated by positive selection with Dynal immunomagnetic beads (Dynabeads® M450) and the detacha-bead® reagent. Typically about 200-250$\times10^6$ PBMC are processed to obtain $24\times10^6$ CD8, T-cells (enough for a 48-well plate culture). Briefly, the PBMCs are thawed in RPMI with 30 μg/ml DNAse, washed once with PBS containing 1% human AB serum and resuspended in PBS/1% AB serum at a concentration of $20\times10^6$cells/ml. The magnetic beads are washed 3 times with PBS/AB serum, added to the cells (140 μl beads/$20\times10^6$ cells) and incubated for 1 hour at 4° C. with continuous mixing. The beads and cells are washed 4× with PBS/AB serum to remove the nonadherent cells and resuspended at $100\times10^6$ cells/ml (based on the original cell number) in PBS/AB serum containing 100 μl/ml detacha-bead® reagent and 30 μg/ml DNAse. The mixture is incubated for 1 hour at room temperature with continuous mixing. The beads are washed again with PBS/AB/DNAse to collect the CD8+ T-cells. The DC are collected and centrifuged at 1300 rpm for 5-7 minutes, washed once with PBS with 1% BSA, counted and pulsed with 40 μg/ml of peptide at a cell concentration of 1-2$\times10^6$/ml in the presence of 3 μg/ml 92-microglobulin for 4 hours at 20° C. The DC are then irradiated (4,200 rads), washed 1 time with medium and counted again.

Setting up induction cultures: 0.25 ml cytokine-generated DC (at $1\times10^5$ cells/ml) are co-cultured with 0.25 ml of CD8+ T-cells (at $2\times10^6$ cell/ml) in each well of a 48-well plate in the presence of 10 μg/ml of IL-7. Recombinant human IL-10 is added the next day at a final concentration of 10 μg/ml and rhuman IL-2 is added 48 hours later at 10 IU/ml.

Restimulation of the induction cultures with peptide-pulsed adherent cells: Seven and fourteen days after the primary induction, the cells are restimulated with peptide-pulsed adherent cells. The PBMCs are thawed and washed twice with RPMI and DNAse. The cells are resuspended at $5\times10^6$ cells/ml and irradiated at −4200 rads. The PBMCs are plated at $2\times10^6$ in 0.5 ml complete medium per well and incubated for 2 hours at 37° C. The plates are washed twice with RPMI by tapping the plate gently to remove the nonadherent cells and the adherent cells pulsed with 10 μg/ml of peptide in the presence of 3 μg/ml 92 microglobulin in 0.25 ml RPMI/5% AB per well for 2 hours at 37° C. Peptide solution from each well is aspirated and the wells are washed once with RPMI. Most of the media is aspirated from the induction cultures (CD8+ cells) and brought to 0.5 ml with fresh media. The cells are then transferred to the wells containing the peptide-pulsed adherent cells. Twenty four hours later recombinant human IL-10 is added at a final concentration of 10 μg/ml and recombinant human IL2 is added the next day and again 2-3 days later at 50 UI/ml (Tsai et al., *Critical Reviews in Immunology* 18(1-2):65-75, 1998). Seven days later, the cultures are assayed for CTL activity in a $^{51}$Cr release assay. In some experiments the cultures are assayed for peptide-specific recognition in the in situ IFNγ ELISA at the time of the second restimulation followed by assay of endogenous recognition 7 days later. After expansion, activity is measured in both assays for a side-by-side comparison.

Measurement of CTL Lytic Activity by $^{51}$Cr Release.

Seven days after the second restimulation, cytotoxicity is determined in a standard (5 hr) $^{51}$Cr release assay by assaying individual wells at a single E:T. Peptide-pulsed targets are prepared by incubating the cells with 10 μg/ml peptide overnight at 37° C.

Adherent target cells are removed from culture flasks with trypsin-EDTA. Target cells are labeled with 200 μCi of $^{51}$Cr sodium chromate (Dupont, Wilmington, Del.) for 1 hour at 37° C. Labeled target cells are resuspended at $10^6$ per ml and diluted 1:10 with K562 cells at a concentration of $3.3\times10^6$/ml (an NK-sensitive erythroblastoma cell line used to reduce non-specific lysis). Target cells (100 μl) and effectors (100 μl) are plated in 96 well round-bottom plates and incubated for 5 hours at 37° C. At that time, 100 μl of supernatant are collected from each well and percent lysis is determined according to the formula:

[(cpm of the test sample-cpm of the spontaneous $^{51}$Cr release sample)/(cpm of the maximal $^{51}$Cr release sample-cpm of the spontaneous $^{51}$Cr release sample)]×100.

Maximum and spontaneous release are determined by incubating the labeled targets with 1% Triton X-100 and media alone, respectively. A positive culture is defined as one in which the specific lysis (sample-background) is 10% or higher in the case of individual wells and is 15% or more at the two highest E:T ratios when expanded cultures are assayed.

In Situ Measurement of Human IFNγ Production as an Indicator of Peptide-Specific and Endogenous Recognition Immulon 2 plates are coated with mouse anti-human IFNγ monoclonal antibody (4 μg/ml 0.1M $NaHCO_3$, pH8.2) overnight at 4° C. The plates are washed with $Ca^{2+}$, $Mg^{2+}$ free PBS/0.05% Tween 20 and blocked with PBS/10% FCS for two hours, after which the CTLs (100 μl/well) and targets (100 μl/well) are added to each well, leaving empty wells for the standards and blanks (which received media only). The target cells, either peptide-pulsed or endogenous targets, are used at a concentration of $1\times10^6$ cells/mi. The plates are incubated for 48 hours at 37° C. with 5% $CO_2$.

Recombinant human IFN-gamma is added to the standard wells starting at 400 pg or 1200 pg/100 microliter/well and the plate incubated for two hours at 37° C. The plates are washed and 100 μl of biotinylated mouse anti-human IFN-gamma monoclonal antibody (2 microgram/ml in PBS/3% FCS/0.05% Tween 20) are added and incubated for 2 hours at room temperature. After washing again, 100 microliter HRP-streptavidin (1:4000) are added and the plates incubated for one hour at room temperature. The plates are then washed 6× with wash buffer, 100 microliter/well developing solution (TMB 1:1) are added, and the plates allowed to develop for 5-15 minutes. The reaction is stopped with 50 microliter/well 1M $H_3PO_4$ and read at OD450. A culture is considered positive if it measured at least 50 pg of IFN-gamma/well above background and is twice the background level of expression.

CTL Expansion.

Those cultures that demonstrate specific lytic activity against peptide-pulsed targets and/or tumor targets are expanded over a two week period with anti-CD3. Briefly, $5\times10^4$ CD8+ cells are added to a T25 flask containing the following: $1\times10^6$ irradiated (4, 200 rad) PBMC (autologous or allogeneic) per ml, $2\times10^5$ irradiated (8,000 rad) EBV-transformed cells per ml, and OKT3 (anti-CD3) at 30 ng per ml in RPMI-1640 containing 10% (v/v) human AB serum, non-essential amino acids, sodium pyruvate, 25μM 2-mercaptoethanol, L-glutamine and penicillin/streptomycin. Recombinant human IL2 is added 24 hours later at a final concentration of 200 IU/ml and every three days thereafter with fresh media at 50 IU/ml. The cells are split if the cell concentration exceeds $1\times10^6$/ml and the cultures are assayed between days 13 and 15 at E:T ratios of 30, 10, 3 and 1:1 in the $^{51}$Cr release assay or at $1\times10^6$/ml in the in situ IFNγ assay using the same targets as before the expansion.

Cultures are expanded in the absence of anti-CD3, as follows. Those cultures that demonstrate specific lytic activity against peptide and endogenous targets are selected and $5\times10^4$ CD8+ cells are added to a T25 flask containing the following: $1\times10^6$ autologous PBMC per ml which have been peptide-pulsed with 10 μg/ml peptide for two hours at 37° C. and irradiated (4,200 rad); $2\times10^5$ irradiated (8,000 rad) EBV-transformed cells per ml RPMI-1640 containing 10% (v/v) human AB serum, non-essential AA, sodium pyruvate, 25 mM 2-ME, L-glutamine and gentamicin.

Immunogenicity of A2 Supermotif-Bearing Peptides

A2-supermotif cross-reactive binding peptides are tested in the cellular assay for the ability to induce peptide-specific CTL in normal individuals. In this analysis, a peptide is typically considered to be an epitope if it induces peptide-specific CTLs in at least individuals, and preferably, also recognizes the endogenously expressed peptide.

Immunogenicity can also be confirmed using PBMCs isolated from patients bearing a tumor that expresses 193P1E1B. Briefly, PBMCs are isolated from patients, re-stimulated with peptide-pulsed monocytes and assayed for the ability to recognize peptide-pulsed target cells as well as transfected cells endogenously expressing the antigen.

Evaluation of A*03/A11 Immunogenicity

HLA-A3 supermotif-bearing cross-reactive binding peptides are also evaluated for immunogenicity using methodology analogous for that used to evaluate the immunogenicity of the HLA-A2 supermotif peptides.

Evaluation of B7 Immunogenicity

Immunogenicity screening of the B7-supertype cross-reactive binding peptides identified as set forth herein are confirmed in a manner analogous to the confirmation of A2-and A3-supermotif-bearing peptides.

Peptides bearing other supermotifs/motifs, e.g., HLA-A1, HLA-A24 etc. are also confirmed using similar methodology

Example 15

Implementation of the Extended Supermotif to Improve the Binding Capacity of Native Epitopes by Creating Analogs HLA motifs and supermotifs (comprising primary and/or secondary residues) are useful in the identification and preparation of highly cross-reactive native peptides, as demonstrated herein. Moreover, the definition of HLA motifs and supermotifs also allows one to engineer highly cross-reactive epitopes by identifying residues within a native peptide sequence which can be analoged to confer upon the peptide certain characteristics, e.g. greater cross-reactivity within the group of HLA molecules that comprise a supertype, and/or greater binding affinity for some or all of those HLA molecules. Examples of analoging peptides to exhibit modulated binding affinity are set forth in this example.

Analoging at Primary Anchor Residues

Peptide engineering strategies are implemented to further increase the cross-reactivity of the epitopes. For example, the main anchors of A2-supermotif-bearing peptides are altered, for example, to introduce a preferred L, I, V, or M at position 2, and I or V at the C-terminus.

To analyze the cross-reactivity of the analog peptides, each engineered analog is initially tested for binding to the prototype A2 supertype allele A*0201, then, if A*0201 binding capacity is maintained, for A2-supertype cross-reactivity.

Alternatively, a peptide is confirmed as binding one or all supertype members and then analoged to modulate binding affinity to any one (or more) of the supertype members to add population coverage.

The selection of analogs for immunogenicity in a cellular screening analysis is typically further restricted by the capacity of the parent wild type (WT) peptide to bind at least weakly, i.e., bind at an $IC_{50}$ of 5000 nM or less, to three of more A2 supertype alleles. The rationale for this requirement is that the WT peptides must be present endogenously in sufficient quantity to be biologically relevant. Analoged peptides have been shown to have increased immunogenicity and cross-reactivity by T cells specific for the parent epitope (see, e.g., Parkhurst et al., *J. Immunol.* 157:2539, 1996; and Pogue et al., *Proc. Natl. Acad. Sci. USA* 92:8166, 1995).

In the cellular screening of these peptide analogs, it is important to confirm that analog-specific CTLs are also able to recognize the wild-type peptide and, when possible, target cells that endogenously express the epitope.

Analoging of HLA-A3 and B7-Supermotif-Bearing Peptides

Analogs of HLA-A3 supermotif-bearing epitopes are generated using strategies similar to those employed in analoging HLA-A2 supermotif-bearing peptides. For example, peptides binding to 3/5 of the A3-supertype molecules are engineered at primary anchor residues to possess a preferred residue (V, S, M, or A) at position 2.

The analog peptides are then tested for the ability to bind A*03 and A*11 (prototype A3 supertype alleles). Those peptides that demonstrate ≦500 nM binding capacity are then confirmed as having A3-supertype cross-reactivity.

Similarly to the A2- and A3-motif bearing peptides, peptides binding 3 or more B7-supertype alleles can be improved, where possible, to achieve increased cross-reactive binding or greater binding affinity or binding half life. B7 supermotif-bearing peptides are, for example, engineered to possess a preferred residue (V, I, L, or F) at the C-terminal primary anchor position, as demonstrated by Sidney et al. (*J. Immunol.* 157:3480-3490, 1996).

Analoging at primary anchor residues of other motif and/or supermotif-bearing epitopes is performed in a like manner.

The analog peptides are then be confirmed for immunogenicity, typically in a cellular screening assay. Again, it is generally important to demonstrate that analog-specific CTLs are also able to recognize the wild-type peptide and, when possible, targets that endogenously express the epitope.

Analoging at Secondary Anchor Residues

Moreover, HLA supermotifs are of value in engineering highly cross-reactive peptides and/or peptides that bind HLA molecules with increased affinity by identifying particular residues at secondary anchor positions that are associated with such properties. For example, the binding capacity of a B7 supermotif-bearing peptide with an F residue at position 1 is analyzed. The peptide is then analoged to, for example, substitute L for F at position 1. The analoged peptide is evaluated for increased binding affinity, binding half life and/or increased cross-reactivity. Such a procedure identifies analoged peptides with enhanced properties.

Engineered analogs with sufficiently improved binding capacity or cross-reactivity can also be tested for immunogenicity in HLA-B7-transgenic mice, following for example, IFA immunization or lipopeptide immunization. Analoged peptides are additionally tested for the ability to stimulate a recall response using PBMC from patients with 193P1E1B-expressing tumors.

Other Analoging Strategies

Another form of peptide analoging, unrelated to anchor positions, involves the substitution of a cysteine with α-amino butyric acid. Due to its chemical nature, cysteine has the propensity to form disulfide bridges and sufficiently alter the peptide structurally so as to reduce binding capacity. Substitution of α-amino butyric acid for cysteine not only alleviates this problem, but has been shown to improve binding and crossbinding capabilities in some instances (see, e.g., the review by Sette et al., In: Persistent Viral Infections, Eds. R. Ahmed and 1. Chen, John Wiley & Sons, England, 1999).

Thus, by the use of single amino acid substitutions, the binding properties and/or cross-reactivity of peptide ligands for HLA supertype molecules can be modulated.

Example 16

Identification and Confirmation of 193P1E1B-Derived Sequences with HLA-DR Binding Motifs Peptide epitopes bearing an HLA class II supermotif or motif are identified and confirmed as outlined below using methodology similar to that described for HLA Class I peptides.

Selection of HLA-DR-Supermotif-Bearing Epitopes.

To identify 193P1E1B-derived, HLA class II HTL epitopes, a 193P1E1B antigen is analyzed for the presence of sequences bearing an HLA-DR-motif or supermotif. Specifically, 15-mer sequences are selected comprising a DR-supermotif, comprising a 9-mer core, add three-residue N- and C-terminal flanking regions (15 amino acids total).

Protocols for predicting peptide binding to DR molecules have been developed (Southwood et al., *J. Immunol.* 160:3363-3373, 1998). These protocols, specific for individual DR molecules, allow the scoring, and ranking, of 9-mer core regions. Each protocol not only scores peptide sequences for the presence of DR-supermotif primary anchors (i.e., at position 1 and position 6) within a 9-mer core, but additionally evaluates sequences for the presence of secondary anchors. Using allele-specific selection tables (see, e.g., Southwood et al., ibid.), it has been found that these protocols efficiently select peptide sequences with a high probability of binding a particular DR molecule. Additionally, it has been found that performing these protocols in tandem, specifically those for DR1, DR4w4, and DR7, can efficiently select DR cross-reactive peptides.

The 193P1E1B-derived peptides identified above are tested for their binding capacity for various common HLA-DR molecules. All peptides are initially tested for binding to the DR molecules in the primary panel: DR1, DR4w4, and DR7. Peptides binding at least two of these three DR molecules are then tested for binding to DR2w2 β1, DR2w2 β2, DR6w19, and DR9 molecules in secondary assays. Finally, peptides binding at least two of the four secondary panel DR molecules, and thus cumulatively at least four of seven different DR molecules, are screened for binding to DR4w15, DR5w11, and DR8w2 molecules in tertiary assays. Peptides binding at least seven of the ten DR molecules comprising the primary, secondary, and tertiary screening assays are considered cross-reactive DR binders. 193P1E1B-derived peptides found to bind common HLA-DR alleles are of particular interest.

Selection of DR3 Motif Peptides

Because HLA-DR3 is an allele that is prevalent in Caucasian, Black, and Hispanic populations, DR3 binding capacity is a relevant criterion in the selection of HTL epitopes. Thus, peptides shown to be candidates may also be assayed for their DR3 binding capacity. However, in view of the binding specificity of the DR3 motif, peptides binding only to DR3 can also be considered as candidates for inclusion in a vaccine formulation.

To efficiently identify peptides that bind DR3, target 193P1E1B antigens are analyzed for sequences carrying one of the two DR3-specific binding motifs reported by Geluk et al. (*J. Immunol.* 152:5742-5748, 1994). The corresponding peptides are then synthesized and confirmed as having the ability to bind DR3 with an affinity of 1 μM or better, i.e., less than 1 μM. Peptides are found that meet this binding criterion and qualify as HLA class II high affinity binders.

DR3 binding epitopes identified in this manner are included in vaccine compositions with DR supermotif-bearing peptide epitopes.

Similarly to the case of HLA class I motif-bearing peptides, the class II motif-bearing peptides are analoged to improve affinity or cross-reactivity. For example, aspartic acid at position 4 of the 9-mer core sequence is an optimal residue for DR3 binding, and substitution for that residue often improves DR 3 binding.

Example 17

Immunogenicity of 193P1E1B-Derived HTL Epitopes

This example determines immunogenic DR supermotif- and DR3 motif-bearing epitopes among those identified using the methodology set forth herein.

Immunogenicity of HTL epitopes are confirmed in a manner analogous to the determination of immunogenicity of CTL epitopes, by assessing the ability to stimulate HTL responses and/or by using appropriate transgenic mouse models. Immunogenicity is determined by screening for: 1.) in vitro primary induction using normal PBMC or 2.) recall responses from patients who have 193P1E1B-expressing tumors.

Example 18

Calculation of Phenotypic Frequencies of HLA-Supertypes in Various Ethnic Backgrounds to Determine Breadth of Population Coverage This example illustrates the assessment of the breadth of population coverage of a vaccine composition comprised of multiple epitopes comprising multiple supermotifs and/or motifs.

In order to analyze population coverage, gene frequencies of HLA alleles are determined. Gene frequencies for each HLA allele are calculated from antigen or allele frequencies utilizing the binomial distribution formulae gf=1-(SQRT(1-af)) (see, e.g., Sidney et al., *Human Immunol.* 45:79-93, 1996). To obtain overall phenotypic frequencies, cumulative gene frequencies are calculated, and the cumulative antigen frequencies derived by the use of the inverse formula [af=1-(1-Cgf)$^2$].

Where frequency data is not available at the level of DNA typing, correspondence to the serologically defined antigen frequencies is assumed. To obtain total potential supertype population coverage no linkage disequilibrium is assumed, and only alleles confirmed to belong to each of the supertypes are included (minimal estimates). Estimates of total potential coverage achieved by inter-loci combinations are made by adding to the A coverage the proportion of the non-A covered population that could be expected to be covered by the B alleles considered (e.g., total=A+B*(1-A)). Confirmed members of the A3-like supertype are A3, A11, A31, A*3301, and A*6801. Although the A3-like supertype may also include A34, A66, and A*7401, these alleles were not included in overall frequency calculations. Likewise, confirmed members of the A2-like supertype family are A*0201, A*0202, A*0203, A*0204, A*0205, A*0206, A*0207, A*6802, and A*6901. Finally, the B7-like supertype-confirmed alleles are: B7, B*3501-03, B51, B*5301, B*5401, B*5501-2, B*5601, B*6701, and B*7801 (potentially also B*1401, B*3504-06, B*4201, and B*5602).

Population coverage achieved by combining the A2-, A3- and B7-supertypes is approximately 86% in five major ethnic groups. Coverage may be extended by including peptides bearing the A1 and A24 motifs. On average, A1 is present in 12% and A24 in 29% of the population across five different major ethnic groups (Caucasian, North American Black, Chinese, Japanese, and Hispanic). Together, these alleles are represented with an average frequency of 39% in these same ethnic populations. The total coverage across the major ethnicities when A1 and A24 are combined with the coverage of the A2-, A3- and B7-supertype alleles is >95%, see, e.g., Table IV (G). An analogous approach can be used to estimate population coverage achieved with combinations of class II motif-bearing epitopes.

Immunogenicity studies in humans (e.g., Bertoni et al., *J. Clin. Invest.* 100:503, 1997; Doolan et al., *Immunity* 7:97, 1997; and Threlkeld et al., *J. Immunol.* 159:1648, 1997) have shown that highly cross-reactive binding peptides are almost always recognized as epitopes. The use of highly cross-reactive binding peptides is an important selection criterion in identifying candidate epitopes for inclusion in a vaccine that is immunogenic in a diverse population.

With a sufficient number of epitopes (as disclosed herein and from the art), an average population coverage is predicted to be greater than 95% in each of five major ethnic populations. The game theory Monte Carlo simulation analysis, which is known in the art (see e.g., Osborne, M. J. and Rubinstein, A. "A course in game theory" MIT Press, 1994), can be used to estimate what percentage of the individuals in a population comprised of the Caucasian, North American Black, Japanese, Chinese, and Hispanic ethnic groups would recognize the vaccine epitopes described herein. A preferred percentage is 90%. A more preferred percentage is 95%.

Example 19

CTL Recognition Of Endogenously Processed Antigens After Priming

This example confirms that CTL induced by native or analoged peptide epitopes identified and selected as described herein recognize endogenously synthesized, i.e., native antigens.

Effector cells isolated from transgenic mice that are immunized with peptide epitopes, for example HLA-A2 supermotif-bearing epitopes, are re-stimulated in vitro using peptide-coated stimulator cells. Six days later, effector cells are assayed for cytotoxicity and the cell lines that contain peptide-specific cytotoxic activity are further re-stimulated. An additional six days later, these cell lines are tested for cytotoxic activity on $^{51}$Cr labeled Jurkat-A2.1/K$^b$ target cells in the absence or presence of peptide, and also tested on $^{51}$Cr labeled target cells bearing the endogenously synthesized antigen, i.e. cells that are stably transfected with 193P1E1B expression vectors.

The results demonstrate that CTL lines obtained from animals primed with peptide epitope recognize endogenously synthesized 193P1E1B antigen. The choice of transgenic mouse model to be used for such an analysis depends upon the epitope(s) that are being evaluated. In addition to HLA-A*0201/K$^b$ transgenic mice, several other transgenic mouse models including mice with human A11, which may also be used to evaluate A3 epitopes, and B7 alleles have been characterized and others (e.g., transgenic mice for HLA-A1 and A24) are being developed. HLA-DR1 and HLA-DR3 mouse models have also been developed, which may be used to evaluate HTL epitopes.

Example 20

Activity Of CTL-HTL Conjugated Epitopes In Transgenic Mice

This example illustrates the induction of CTLs and HTLs in transgenic mice, by use of a 193P1E1B-derived CTL and HTL peptide vaccine compositions. The vaccine composition used herein comprise peptides to be administered to a patient with a 193P1E1B-expressing tumor. The peptide composition can comprise multiple CTL and/or HTL epitopes. The epitopes are identified using methodology as described herein. This example also illustrates that enhanced immunogenicity can be achieved by inclusion of one or more HTL epitopes in a CTL vaccine composition; such a peptide composition can comprise an HTL epitope conjugated to a CTL epitope. The CTL epitope can be one that binds to multiple HLA family members at an affinity of 500 nM or less, or analogs of that epitope. The peptides may be lipidated, if desired.

Immunization procedures: Immunization of transgenic mice is performed as described (Alexander et al., *J. Immunol.* 159:4753-4761, 1997). For example, A2/$K^b$ mice, which are transgenic for the human HLA A2.1 allele and are used to confirm the immunogenicity of HLA-A*0201 motif- or HLA-A2 supermotif-bearing epitopes, and are primed subcutaneously (base of the tail) with a 0.1 ml of peptide in Incomplete Freund's Adjuvant, or if the peptide composition is a lipidated CTL/HTL conjugate, in DMSO/saline, or if the peptide composition is a polypeptide, in PBS or Incomplete Freund's Adjuvant. Seven days after priming, splenocytes obtained from these animals are restimulated with syngenic irradiated LPS-activated lymphoblasts coated with peptide.

Cell lines: Target cells for peptide-specific cytotoxicity assays are Jurkat cells transfected with the HLA-A2.1/$K^b$ chimeric gene (e.g., Vitiello et at, *J. Exp. Med.* 173:1007, 1991)

In vitro CTL activation: One week after priming, spleen cells ($30\times10^6$ cells/flask) are co-cultured at 37° C. with syngeneic, irradiated (3000 rads), peptide coated lymphoblasts ($10\times10^6$ cells/flask) in 10 ml of culture medium/T25 flask. After six days, effector cells are harvested and assayed for cytotoxic activity.

Assay for cytotoxic activity: Target cells (1.0 to $1.5\times10^6$) are incubated at 37° C. in the presence of 200 μl of $^{51}$Cr. After 60 minutes, cells are washed three times and resuspended in R10 medium. Peptide is added where required at a concentration of 1 μg/ml. For the assay, $10^4$ $^{51}$Cr-labeled target cells are added to different concentrations of effector cells (final volume of 200 μl) in U-bottom 96-well plates. After a six hour incubation period at 37° C., a 0.1 ml aliquot of supernatant is removed from each well and radioactivity is determined in a Micromedic automatic gamma counter. The percent specific lysis is determined by the formula: percent specific release=100×(experimental release−spontaneous release)/(maximum release−spontaneous release). To facilitate comparison between separate CTL assays run under the same conditions, % $^{51}$Cr release data is expressed as lytic units/$10^6$ cells. One lytic unit is arbitrarily defined as the number of effector cells required to achieve 30% lysis of 10,000 target cells in a six hour $^{51}$Cr release assay. To obtain specific lytic units/$10^6$, the lytic units/$10^6$ obtained in the absence of peptide is subtracted from the lytic units/$10^6$ obtained in the presence of peptide. For example, if 30% $^{51}$Cr release is obtained at the effector (E): target (T) ratio of 50:1 (i.e., $5\times10^5$ effector cells for 10,000 targets) in the absence of peptide and 5:1 (i.e., $5\times10^4$ effector cells for 10,000 targets) in the presence of peptide, the specific lytic units would be: $[(1/50,000)-(1/500,000)]\times10^6=18$ LU.

The results are analyzed to assess the magnitude of the CTL responses of animals injected with the immunogenic CTL/HTL conjugate vaccine preparation and are compared to the magnitude of the CTL response achieved using, for example, CTL epitopes as outlined above in the Example entitled "Confirmation of Immunogenicity." Analyses similar to this may be performed to confirm the immunogenicity of peptide conjugates containing multiple CTL epitopes and/or multiple HTL epitopes. In accordance with these procedures, it is found that a CTL response is induced, and concomitantly that an HTL response is induced upon administration of such compositions.

Example 21

Selection of CTL and HTL Epitopes for Inclusion in a 193P1E1B-Specific Vaccine.

This example illustrates a procedure for selecting peptide epitopes for vaccine compositions of the invention. The peptides in the composition can be in the form of a nucleic acid sequence, either single or one or more sequences (i.e., minigene) that encodes peptide(s), or can be single and/or polyepitopic peptides.

The following principles are utilized when selecting a plurality of epitopes for inclusion in a vaccine composition. Each of the following principles is balanced in order to make the selection.

Epitopes are selected which, upon administration, mimic immune responses that are correlated with 193P1E1B clearance. The number of epitopes used depends on observations of patients who spontaneously clear 193P1E1B. For example, if it has been observed that patients who spontaneously clear 193P1E1B-expressing cells generate an immune response to at least three (3) epitopes from 193P1E1B antigen, then at least three epitopes should be included for HLA class I. A similar rationale is used to determine HLA class II epitopes.

Epitopes are often selected that have a binding affinity of an $IC_{50}$ of 500 nM or less for an HLA class I molecule, or for class II, an $IC_{50}$ of 1000 nM or less; or HLA Class I peptides with high binding scores from the BIMAS web site.

In order to achieve broad coverage of the vaccine through out a diverse population, sufficient supermotif bearing peptides, or a sufficient array of allele-specific motif bearing peptides, are selected to give broad population coverage. In one embodiment, epitopes are selected to provide at least 80% population coverage. A Monte Carlo analysis, a statistical evaluation known in the art, can be employed to assess breadth, or redundancy, of population coverage.

When creating polyepitopic compositions, or a minigene that encodes same, it is typically desirable to generate the smallest peptide possible that encompasses the epitopes of interest. The principles employed are similar, if not the same, as those employed when selecting a peptide comprising nested epitopes. For example, a protein sequence for the vaccine composition is selected because it has maximal number of epitopes contained within the sequence, i.e., it has a high concentration of epitopes. Epitopes may be nested or overlapping (i.e., frame shifted relative to one another). For example, with overlapping epitopes, two 9-mer epitopes and one 10-mer epitope can be present in a 10 amino acid peptide. Each epitope can be exposed and bound by an HLA molecule upon administration of such a peptide. A multi-epitopic, peptide can be generated synthetically, recombinantly, or via cleavage from the native source. Alternatively, an analog can be made of this native sequence, whereby one or more of the epitopes comprise substitutions that alter the cross-reactivity and/or binding affinity properties of the polyepitopic peptide. Such a vaccine composition is administered for therapeutic or prophylactic purposes. This embodiment provides for the possibility that an as yet undiscovered aspect of immune system processing will apply to the native nested sequence and thereby facilitate the production of therapeutic or prophylactic immune response-inducing vaccine compositions. Additionally such an embodiment provides for the possibility of motif-bearing epitopes for an HLA makeup that is presently unknown. Furthermore, this embodiment (absent the creating of any analogs) directs the immune response to multiple peptide sequences that are actually present in 193P1E1B, thus avoiding the need to evaluate any junctional epitopes. Lastly, the embodiment provides an economy of scale when producing nucleic acid vaccine compositions. Related to this embodiment, computer programs can be derived in accordance with principles in the art, which identify in a target sequence, the greatest number of epitopes per sequence length.

A vaccine composition comprised of selected, peptides, when administered, is safe, efficacious, and elicits an immune response similar in magnitude to an immune response that controls or clears cells that bear or overexpress 193P1E1B.

Example 22

Construction of "Minigene" Multi-Epitope DNA Plasmids

This example discusses the construction of a minigene expression plasmid. Minigene plasmids may, of course, contain various configurations of B cell, CTL and/or HTL epitopes or epitope analogs as described herein.

A minigene expression plasmid typically includes multiple CTL and HTL peptide epitopes. In the present example, HLA-A2, -A3, -B7 supermotif-bearing peptide epitopes and HLA-A1 and -A24 motif-bearing peptide epitopes are used in conjunction with DR supenmotif-bearing epitopes and/or DR3 epitopes. HLA class I supermotif or motif-bearing peptide epitopes derived 193P1E1B, are selected such that multiple supermotifs/motifs are represented to ensure broad population coverage. Similarly, HLA class II epitopes are selected from 193P1E1B to provide broad population coverage, i.e. both HLA DR-1-4-7 supermotif-bearing epitopes and HLA DR-3 motif-bearing epitopes are selected for inclusion in the minigene construct. The selected CTL and HTL epitopes are then incorporated into a minigene for expression in an expression vector.

Such a construct may additionally include sequences that direct the HTL epitopes to the endoplasmic reticulum. For example, the li protein may be fused to one or more HTL epitopes as described in the art, wherein the CLIP sequence of the li protein is removed and replaced with an HLA class II epitope sequence so that HLA class II epitope is directed to the endoplasmic reticulum, where the epitope binds to an HLA class II molecules.

This example illustrates the methods to be used for construction of a minigene-bearing expression plasmid. Other expression vectors that may be used for minigene compositions are available and known to those of skill in the art.

The minigene DNA plasmid of this example contains a consensus Kozak sequence and a consensus murine kappa Ig-light chain signal sequence followed by CTL and/or HTL epitopes selected in accordance with principles disclosed herein. The sequence encodes an open reading frame fused to the Myc and His antibody epitope tag coded for by the pcDNA 3.1 Myc-His vector.

Overlapping oligonucleotides that can, for example, average about 70 nucleotides in length with 15 nucleotide overlaps, are synthesized and HPLC-purified. The oligonucleotides encode the selected peptide epitopes as well as appropriate linker nucleotides, Kozak sequence, and signal sequence. The final multiepitope minigene is assembled by extending the overlapping oligonucleotides in three sets of reactions using PCR. A Perkin/Elmer 9600 PCR machine is used and a total of 30 cycles are performed using the following conditions: 95° C. for 15 sec, annealing temperature (5° below the lowest calculated Tm of each primer pair) for 30 sec, and 72° C. for 1 min.

For example, a minigene is prepared as follows. For a first PCR reaction, 5 μg of each of two oligonucleotides are annealed and extended: In an example using eight oligonucleotides, i.e., four pairs of primers, oligonucleotides 1+2, 3+4, 5+6, and 7+8 are combined in 100 μl reactions containing Pfu polymerase buffer (1×=10 mM KCL, 10 mM $(NH4)_2SO_4$, 20 mM Tris-chloride, pH 8.75, 2 mM $MgSO_4$, 0.1% Triton X-100, 100 μg/ml BSA), 0.25 mM each dNTP, and 2.5 U of Pfu polymerase. The full-length dimer products are gel-purified, and two reactions containing the product of 1+2 and 3+4, and the product of 5+6 and 7+8 are mixed, annealed, and extended for 10 cycles. Half of the two reactions are then mixed, and 5 cycles of annealing and extension carried out before flanking primers are added to amplify the full length product. The full-length product is gel-purified and cloned into pCR-blunt (Invitrogen) and individual clones are screened by sequencing.

Example 23

The Plasmid Construct and the Degree to Which It Induces Immunogenicity.

The degree to which a plasmid construct, for example a plasmid constructed in accordance with the previous Example, is able to induce immunogenicity is confirmed in vitro by determining epitope presentation by APC following transduction or transfection of the APC with an epitope-expressing nucleic acid construct. Such a study determines "antigenicity" and allows the use of human APC. The assay determines the ability of the epitope to be presented by the APC in a context that is recognized by a T cell by quantifying the density of epitope-HLA class I complexes on the cell surface. Quantitation can be performed by directly measuring the amount of peptide eluted from the APC (see, e.g., Sijts et al., *J. Immunol.* 156:683-692, 1996; Demotz et al., *Nature* 342:682-684, 1989); or the number of peptide-HLA class I complexes can be estimated by measuring the amount of lysis or lymphokine release induced by diseased or transfected target cells, and then determining the concentration of peptide necessary to obtain equivalent levels of lysis or lymphokine release (see, e.g., Kageyama et al., *J. Immunol.* 154:567-576, 1995).

Alternatively, immunogenicity is confirmed through in vivo injections into mice and subsequent in vitro assessment of CTL and HTL activity, which are analyzed using cytotoxicity and proliferation assays, respectively, as detailed e.g., in Alexander et al., *Immunity* 1:751-761, 1994.

For example, to confirm the capacity of a DNA minigene construct containing at least one HLA-A2 supermotif peptide to induce CTLs in vivo, HLA-A2.1/$K^b$ transgenic mice, for example, are immunized intramuscularly with 100 μg of naked cDNA. As a means of comparing the level of CTLs induced by cDNA immunization, a control group of animals is also immunized with an actual peptide composition that comprises multiple epitopes synthesized as a single polypeptide as they would be encoded by the minigene.

Splenocytes from immunized animals are stimulated twice with each of the respective compositions (peptide epitopes encoded in the minigene or the polyepitopic peptide), then assayed for peptide-specific cytotoxic activity in a $^{51}Cr$ release assay. The results indicate the magnitude of the CTL response directed against the A2-restricted epitope, thus indicating the in vivo immunogenicity of the minigene vaccine and polyepitopic vaccine.

It is, therefore, found that the minigene elicits immune responses directed toward the HLA-A2 supermotif peptide epitopes as does the polyepitopic peptide vaccine. A similar analysis is also performed using other HLA-A3 and HLA-B7 transgenic mouse models to assess CTL induction by HLA-A3 and HLA-B7 motif or supermotif epitopes, whereby it is also found that the minigene elicits appropriate immune responses directed toward the provided epitopes.

To confirm the capacity of a class II epitope-encoding minigene to induce HTLs in vivo, DR transgenic mice, or for those epitopes that cross react with the appropriate mouse MHC molecule, I-$A^b$-restricted mice, for example, are immunized intramuscularly with 100 μg of plasmid DNA. As a means of comparing the level of HTLs induced by DNA immunization, a group of control animals is also immunized with an actual peptide composition emulsified in complete Freund's adjuvant. CD4+ T cells, i.e. HTLs, are purified from splenocytes of immunized animals and stimulated with each of the respective compositions (peptides encoded in the minigene). The HTL response is measured using a $^{3}H$-thymidine incorporation proliferation assay, (see, e.g., Alexander et al. Immunity 1:751-761, 1994). The results indicate the magnitude of the HTL response, thus demonstrating the in vivo immunogenicity of the minigene.

DNA minigenes, constructed as described in the previous Example, can also be confirmed as a vaccine in combination with a boosting agent using a prime boost protocol. The boosting agent can consist of recombinant protein (e.g., Bamelt et al., *Aids Res. and Human Retrovinises* 14, Supplement 3:S299-S309, 1998) or recombinant vaccinia, for example, expressing a minigene or DNA encoding the complete protein of interest (see, e.g., Hanke et al., *Vaccine* 16:439-445, 1998; Sedegah et al., *Proc. Natl. Acad. Sci USA* 95:7648-53, 1998; Hanke and McMichael, *Immunol. Letters* 66:177-181, 1999; and Robinson et al., *Nature Med.* 5:526-34, 1999).

For example, the efficacy of the DNA minigene used in a prime boost protocol is initially evaluated in transgenic mice. In this example, A2.1/$K^b$ transgenic mice are immunized IM with 100 μg of a DNA minigene encoding the immunogenic peptides including at least one HLA-A2 supermotif-bearing peptide. After an incubation period (ranging from 3-9 weeks), the mice are boosted IP with $10^7$pfu/mouse of a recombinant vaccinia virus expressing the same sequence encoded by the DNA minigene. Control mice are immunized with 100 μg of DNA or recombinant vaccinia without the minigene sequence, or with DNA encoding the minigene, but without the vaccinia boost. After an additional incubation period of two weeks, splenocytes from the mice are immediately assayed for peptide-specific activity in an ELISPOT assay. Additionally, splenocytes are stimulated in vitro with the A2-restricted peptide epitopes encoded in the minigene and recombinant vaccinia, then assayed for peptide-specific activity in an alpha, beta and/or gamma IFN ELISA.

It is found that the minigene utilized in a prime-boost protocol elicits greater immune responses toward the HLA-A2 supermotif peptides than with DNA alone. Such an analysis can also be performed using HLA-A11 or HLA-B7 transgenic mouse models to assess CTL induction by HLA-A3 or HLA-B7 motif or supermotif epitopes. The use of prime boost protocols in humans is described below in the Example entitled "Induction of CTL Responses Using a Prime Boost Protocol."

Example 24

Peptide Compositions for Prophylactic Uses

Vaccine compositions of the present invention can be used to prevent 193P1E1B expression in persons who are at risk for tumors that bear this antigen. For example, a polyepitopic peptide epitope composition (or a nucleic acid comprising the same) containing multiple CTL and HTL epitopes such as those selected in the above Examples, which are also selected to target greater than 80% of the population, is administered to individuals at risk for a 193P1E1B-associated tumor.

For example, a peptide-based composition is provided as a single polypeptide that encompasses multiple epitopes. The vaccine is typically administered in a physiological solution that comprises an adjuvant, such as Incomplete Freunds Adjuvant. The dose of peptide for the initial immunization is from about 1 to about 50,000 μg, generally 100-5,000 μg, for a 70 kg patient. The initial administration of vaccine is followed by booster dosages at 4 weeks followed by evaluation of the magnitude of the immune response in the patient, by techniques that determine the presence of epitope-specific CTL populations in a PBMC sample. Additional booster doses are administered as required. The composition is found to be both safe and efficacious as a prophylaxis against 193P1E1B-associated disease.

Alternatively, a composition typically comprising transfecting agents is used for the administration of a nucleic acid-based vaccine in accordance with methodologies known in the art and disclosed herein.

Example 25

Polyepitopic Vaccine Compositions Derived from Native 193P1E1B Sequences

A native 193P1E1B polyprotein sequence is analyzed, preferably using computer algorithms defined for each class I and/or class II supermotif or motif, to identify "relatively short" regions of the polyprotein that comprise multiple epitopes. The "relatively short" regions are preferably less in length than an entire native antigen. This relatively short sequence that contains multiple distinct or overlapping, "nested" epitopes can be used to generate a minigene construct. The construct is engineered to express the peptide, which corresponds to the native protein sequence. The "relatively short" peptide is generally less than 250 amino acids in length, often less than 100 amino acids in length, preferably less than 75 amino acids in length, and more preferably less than 50 amino acids in length. The protein sequence of the vaccine composition is selected because it has maximal number of epitopes contained within the sequence, i.e., it has a high concentration of epitopes. As noted herein, epitope motifs may be nested or overlapping (i.e., frame shifted relative to one another). For example, with overlapping epitopes, two 9-mer epitopes and one 10-mer epitope can be present in a 10 amino acid peptide. Such a vaccine composition is administered for therapeutic or prophylactic purposes.

The vaccine composition will include, for example, multiple CTL epitopes from 193P1E1B antigen and at least one HTL epitope. This polyepitopic native sequence is administered either as a peptide or as a nucleic acid sequence which encodes the peptide. Alternatively, an analog can be made of this native sequence, whereby one or more of the epitopes comprise substitutions that alter the cross-reactivity and/or binding affinity properties of the polyepitopic peptide.

The embodiment of this example provides for the possibility that an as yet undiscovered aspect of immune system processing will apply to the native nested sequence and thereby facilitate the production of therapeutic or prophylactic immune response-inducing vaccine compositions. Additionally, such an embodiment provides for the possibility of motif-bearing epitopes for an HLA makeup(s) that is presently unknown. Furthermore, this embodiment (excluding an analoged embodiment) directs the immune response to multiple peptide sequences that are actually present in native 193P1E1B, thus avoiding the need to evaluate any junctional epitopes. Lastly, the embodiment provides an economy of scale when producing peptide or nucleic acid vaccine compositions.

Related to this embodiment, computer programs are available in the art which can be used to identify in a target sequence, the greatest number of epitopes per sequence length.

Example 26

Polyepitopic Vaccine Compositions from Multiple Antigens

The 193P1E1B peptide epitopes of the present invention are used in conjunction with epitopes from other target tumor-associated antigens, to create a vaccine composition that is useful for the prevention or treatment of cancer that expresses 193P1E1B and such other antigens. For example, a vaccine composition can be provided as a single polypeptide that incorporates multiple epitopes from 193P1E1B as well as tumor-associated antigens that are often expressed with a target cancer associated with 193P1E1B expression, or can be administered as a composition comprising a cocktail of one or more discrete epitopes. Alternatively, the vaccine can be administered as a minigene construct or as dendritic cells which have been loaded with the peptide epitopes in vitro.

Example 27

Use of Peptides to Evaluate an Immune Response

Peptides of the invention may be used to analyze an immune response for the presence of specific antibodies, CTL or HTL directed to 193P1E1B. Such an analysis can be performed in a manner described by Ogg et al., *Science* 279: 2103-2106, 1998. In this Example, peptides in accordance with the invention are used as a reagent for diagnostic or prognostic purposes, not as an immunogen.

In this example highly sensitive human leukocyte antigen tetrameric complexes ("tetramers") are used for a cross-sectional analysis of, for example, 193P1E1B HLA-A*0201 -specific CTL frequencies from HLA A*0201 -positive individuals at different stages of disease or following immunization comprising a 193P1E1B peptide containing an A*0201 motif. Tetrameric complexes are synthesized as described (Musey et al., *N. Engl. J. Med.* 337:1267, 1997). Briefly, purified HLA heavy chain (A*0201 in this example) and P2-microglobulin are synthesized by means of a prokaryotic expression system. The heavy chain is modified by deletion of the transmembrane-cytosolic tail and COOH-terminal addition of a sequence containing a BirA enzymatic biotinylation site. The heavy chain, β2-microglobulin, and peptide are refolded by dilution. The 45-kD refolded product is isolated by fast protein liquid chromatography and then biotinylated by BirA in the presence of biotin (Sigma, St. Louis, Mo.), adenosine 5' triphosphate and magnesium. Streptavidin-phycoerythrin conjugate is added in a 1:4 molar ratio, and the tetrameric product is concentrated to 1 mg/ml. The resulting product is referred to as tetramer-phycoerythrin.

For the analysis of patient blood samples, approximately one million PBMCs are centrifuged at 300 g for 5 minutes and resuspended in 50 μl of cold phosphate-buffered saline. Tricolor analysis is performed with the tetramer-phycoerythrin, along with anti-CD8-Tricolor, and anti-CD38. The PBMCs are incubated with tetramer and antibodies on ice for 30 to 60 min and then washed twice before formaldehyde fixation. Gates are applied to contain >99.98% of control samples. Controls for the tetramers include both A*0201-negative individuals and A*0201-positive non-diseased donors. The percentage of cells stained with the tetramer is then determined by flow cytometry. The results indicate the number of cells in the PBMC sample that contain epitope-restricted CTLs, thereby readily indicating the extent of immune response to the 193P1E1B epitope, and thus the status of exposure to 193P1E1B, or exposure to a vaccine that elicits a protective or therapeutic response.

Example 28

Use of Peptide Epitopes to Evaluate Recall Responses

The peptide epitopes of the invention are used as reagents to evaluate T cell responses, such as acute or recall responses, in patients. Such an analysis may be performed on patients who have recovered from 193P1E1B-associated disease or who have been vaccinated with a 193P1E1B vaccine.

For example, the class I restricted CTL response of persons who have been vaccinated may be analyzed. The vaccine may be any 193P1E1B vaccine. PBMC are collected from vaccinated individuals and HLA typed. Appropriate peptide epitopes of the invention that, optimally, bear supermotifs to provide cross-reactivity with multiple HLA supertype family members, are then used for analysis of samples derived from individuals who bear that HLA type.

PBMC from vaccinated individuals are separated on Ficoll-Histopaque density gradients (Sigma Chemical Co., St. Louis, Mo.), washed three times in HBSS (GIBCO Laboratories), resuspended in RPMI-1640 (GIBCO Laboratories) supplemented with L-glutamine (2mM), penicillin (50U/ml), streptomycin (50 μg/ml), and Hepes (10 mM) containing 10% heat-inactivated human AB serum (complete RPMI) and plated using microculture formats. A synthetic peptide comprising an epitope of the invention is added at 10 μg/ml to each well and HBV core 128-140 epitope is added at 1 μg/ml to each well as a source of T cell help during the first week of stimulation.

In the microculture format, $4\times10^5$ PBMC are stimulated with peptide in 8 replicate cultures in 96-well round bottom plate in 100 Il/well of complete RPMI. On days 3 and 10, 100 μl of complete RPMI and 20 U/ml final concentration of rIL-2 are added to each well. On day 7 the cultures are transferred into a 96-well flat-bottom plate and restimulated with peptide, rIL-2 and $10^5$ irradiated (3,000 rad) autologous feeder cells. The cultures are tested for cytotoxic activity on day 14. A positive CTL response requires two or more of the eight replicate cultures to display greater than 10% specific $^{51}$Cr release, based on comparison with non-diseased control subjects as previously described (Rehermann, et al., *Nature Med.* 2:1104, 1108, 1996; Rehermann et al., J. Clin. Invest. 97:1655-1665, 1996; and Rehermann et al. *J. Clin. Invest.* 98:1432-1440, 1996).

Target cell lines are autologous and allogeneic EBV-transformed B-LCL that are either purchased from the American Society for Histocompatibility and Immunogenetics (ASHI, Boston, Mass.) or established from the pool of patients as described (Guilhot, et al. *J. Virol.* 66:2670-2678, 1992).

Cytotoxicity assays are performed in the following manner. Target cells consist of either allogeneic HLA-matched or autologous EBV-transformed B lymphoblastoid cell line that are incubated overnight with the synthetic peptide epitope of the invention at 10 μM, and labeled with 100 μCi of $^{51}$Cr (Amersham Corp., Arlington Heights, Ill.) for 1 hour after which they are washed four times with HBSS.

Cytolytic activity is determined in a standard 4-h, split well $^{51}$Cr release assay using U-bottomed 96 well plates containing 3,000 targets/well. Stimulated PBMC are tested at effector/target (E/T) ratios of 20-50:1 on day 14. Percent cytotoxicity is determined from the formula: 100×[(experimental release-spontaneous release)/maximum release-spontaneous release)]. Maximum release is determined by lysis of targets by detergent (2% Triton X-100; Sigma Chemical Co., St. Louis, Mo.). Spontaneous release is <25% of maximum release for all experiments.

The results of such an analysis indicate the extent to which HLA-restricted CTL populations have been stimulated by previous exposure to 193P1E1B or a 193P1E1B vaccine.

Similarly, Class II restricted HTL responses may also be analyzed. Purified PBMC are cultured in a 96-well flat bottom plate at a density of $1.5\times10^5$ cells/well and are stimulated with 10 μg/ml synthetic peptide of the invention, whole 193P1E1B antigen, or PHA. Cells are routinely plated in replicates of 4-6 wells for each condition. After seven days of culture, the medium is removed and replaced with fresh medium containing 10 U/ml IL-2. Two days later, 1 μCi $^3$H-thymidine is added to each well and incubation is continued for an additional 18 hours. Cellular DNA is then harvested on glass fiber mats and analyzed for $^3$H-thymidine incorporation. Antigen-specific T cell proliferation is calculated as the ratio of $^3$H-thymidine incorporation in the presence of antigen divided by the $^3$H-thymidine incorporation in the absence of antigen.

Example 29

Induction Of Specific CTL Response In Humans

A human clinical trial for an immunogenic composition comprising CTL and HTL epitopes of the invention is set up as an IND Phase I, dose escalation study and carried out as a randomized, double-blind, placebo-controlled trial. Such a trial is designed, for example, as follows:

A total of about 27 individuals are enrolled and divided into 3 groups:

Group I: 3 subjects are injected with placebo and 6 subjects are injected with 5 μg of peptide composition;

Group II: 3 subjects are injected with placebo and 6 subjects are injected with 50 μg peptide composition;

Group III: 3 subjects are injected with placebo and 6 subjects are injected with 500 μg of peptide composition.

After 4 weeks following the first injection, all subjects receive a booster inoculation at the same dosage.

The endpoints measured in this study relate to the safety and tolerability of the peptide composition as well as its immunogenicity. Cellular immune responses to the peptide composition are an index of the intrinsic activity of this the peptide composition, and can therefore be viewed as a measure of biological efficacy. The following summarize the clinical and laboratory data that relate to safety and efficacy endpoints.

Safety: The incidence of adverse events is monitored in the placebo and drug treatment group and assessed in terms of degree and reversibility.

Evaluation of Vaccine Efficacy: For evaluation of vaccine efficacy, subjects are bled before and after injection. Peripheral blood mononuclear cells are isolated from fresh heparinized blood by Ficoll-Hypaque density gradient centrifugation, aliquoted in freezing media and stored frozen. Samples are assayed for CTL and HTL activity.

The vaccine is found to be both safe and efficacious.

Example 30

Phase II Trials In Patients Expressing 193P1E1B

Phase II trials are performed to study the effect of administering the CTL-HTL peptide compositions to patients having cancer that expresses 193P1E1B. The main objectives of the trial are to determine an effective dose and regimen for inducing CTLs in cancer patients that express 193P1E1B, to establish the safety of inducing a CTL and HTL response in these patients, and to see to what extent activation of CTLs improves the clinical picture of these patients, as manifested, e.g., by the reduction and/or shrinking of lesions. Such a study is designed, for example, as follows:

The studies are performed in multiple centers. The trial design is an open-label, uncontrolled, dose escalation protocol wherein the peptide composition is administered as a single dose followed six weeks later by a single booster shot of the same dose. The dosages are 50, 500 and 5,000 micrograms per injection. Drug-associated adverse effects (severity and reversibility) are recorded.

There are three patient groupings. The first group is injected with 50 micrograms of the peptide composition and the second and third groups with 500 and 5,000 micrograms of peptide composition, respectively. The patients within each group range in age from 21-65 and represent diverse ethnic backgrounds. All of them have a tumor that expresses 193P1E1B.

Clinical manifestations or antigen-specific T-cell responses are monitored to assess the effects of administering the peptide compositions. The vaccine composition is found to be both safe and efficacious in the treatment of 193P1E1B-associated disease.

Example 31

Induction of CTL Responses Using a Prime Boost Protocol

A prime boost protocol similar in its underlying principle to that used to confirm the efficacy of a DNA vaccine in transgenic mice, such as described above in the Example entitled "The Plasmid Construct and the Degree to Which It Induces Immunogenicity," can also be used for the administration of the vaccine to humans. Such a vaccine regimen can include an initial administration of, for example, naked DNA followed by a boost using recombinant virus encoding the vaccine, or recombinant protein/polypeptide or a peptide mixture administered in an adjuvant.

For example, the initial immunization may be performed using an expression vector, such as that constructed in the Example entitled "Construction of "Minigene" Multi-Epitope DNA Plasmids" in the form of naked nucleic acid administered IM (or SC or ID) in the amounts of 0.5-5 mg at multiple sites. The nucleic acid (0.1 to 1000 μg) can also be administered using a gene gun. Following an incubation period of 3-4 weeks, a booster dose is then administered. The booster can be recombinant fowlpox virus administered at a dose of $5\text{-}10^7$ to $5\times10^9$ pfu. An alternative recombinant virus, such as an MVA, canarypox, adenovirus, or adeno-associated virus, can also be used for the booster, or the polyepitopic protein or a mixture of the peptides can be administered. For evaluation of vaccine efficacy, patient blood samples are obtained before immunization as well as at intervals following administration of the initial vaccine and booster doses of the vaccine. Peripheral blood mononuclear cells are isolated from fresh heparinized blood by Ficoll-Hypaque density gradient centrifugation, aliquoted in freezing media and stored frozen. Samples are assayed for CTL and HTL activity.

Analysis of the results indicates that a magnitude of response sufficient to achieve a therapeutic or protective immunity against 193P1E1B is generated.

Example 32

Administration of Vaccine Compositions Using Dendritic Cells (DC)

Vaccines comprising peptide epitopes of the invention can be administered using APCs, or "professional" APCs such as DC. In this example, peptide-pulsed DC are administered to a patient to stimulate a CTL response in vivo. In this method, dendritic cells are isolated, expanded, and pulsed with a vaccine comprising peptide CTL and HTL epitopes of the invention. The dendritic cells are infused back into the patient to elicit CTL and HTL responses in vivo. The induced CTL and HTL then destroy or facilitate destruction, respectively, of the target cells that bear the 193P1E1B protein from which the epitopes in the vaccine are derived.

For example, a cocktail of epitope-comprising peptides is administered ex vivo to PBMC, or isolated DC therefrom. A pharmaceutical to facilitate harvesting of DC can be used, such as Progenipoietin™ (Monsanto, St. Louis, Mo.) or GM-CSF/IL-4. After pulsing the DC with peptides, and prior to reinfusion into patients, the DC are washed to remove unbound peptides.

As appreciated clinically, and readily determined by one of skill based on clinical outcomes, the number of DC reinfused into the patient can vary (see, e.g., *Nature Med.* 4:328, 1998; *Nature Med.* 2:52, 1996 and *Prostate* 32:272, 1997). Although $2\text{-}50\times10^6$ DC per patient are typically administered, larger number of DC, such as $10^7$ or $10^8$ can also be provided. Such cell populations typically contain between 50-90% DC.

In some embodiments, peptide-loaded PBMC are injected into patients without purification of the DC. For example, PBMC generated after treatment with an agent such as Progenipoietin™ are injected into patients without purification of the DC. The total number of PBMC that are administered often ranges from $10^8$ to $10^{10}$. Generally, the cell doses injected into patients is based on the percentage of DC in the blood of each patient, as determined, for example, by immunofluorescence analysis with specific anti-DC antibodies. Thus, for example, if Progenipoietin™ mobilizes 2% DC in the peripheral blood of a given patient, and that patient is to receive $5\times10^6$ DC, then the patient will be injected with a total of $2.5\times10^8$ peptide-loaded PBMC. The percent DC mobilized by an agent such as Progenipoietin™ is typically estimated to be between 2-10%, but can vary as appreciated by one of skill in the art.

Ex Vivo Activation of CTL/HTL Responses

Alternatively, ex vivo CTL or HTL responses to 193P1E1B antigens can be induced by incubating, in tissue culture, the patient's, or genetically compatible, CTL or HTL precursor cells together with a source of APC, such as DC, and immunogenic peptides. After an appropriate incubation time (typically about 7-28 days), in which the precursor cells are activated and expanded into effector cells, the cells are infused into the patient, where they will destroy (CTL) or facilitate destruction (HTL) of their specific target cells, i.e., tumor cells.

Example 33

An Alternative Method of Identifying and Confirming Motif-Bearing Peptides

Another method of identifying and confirming motif-bearing peptides is to elute them from cells bearing defined MHC molecules. For example, EBV transformed B cell lines used for tissue typing have been extensively characterized to determine which HLA molecules they express. In certain cases these cells express only a single type of HLA molecule. These cells can be transfected with nucleic acids that express the antigen of interest, e.g. 193P1E1B. Peptides produced by endogenous antigen processing of peptides produced as a result of transfection will then bind to HLA molecules within the cell and be transported and displayed on the cell's surface. Peptides are then eluted from the HLA molecules by exposure to mild acid conditions and their amino acid sequence determined, e.g., by mass spectral analysis (e.g., Kubo et at., *J. Immunol.* 152:3913, 1994). Because the majority of peptides that bind a particular HLA molecule are motif-bearing, this is an alternative modality for obtaining the motif-bearing peptides correlated with the particular HLA molecule expressed on the cell.

Alternatively, cell lines that do not express endogenous HLA molecules can be transfected with an expression construct encoding a single HLA allele. These cells can then be used as described, i.e., they can then be transfected with nucleic acids that encode 193P1E1B to isolate peptides corresponding to 193P1E1B that have been presented on the cell surface. Peptides obtained from such an analysis will bear motif(s) that correspond to binding to the single HLA allele that is expressed in the cell.

As appreciated by one in the art, one can perform a similar analysis on a cell bearing more than one HLA allele and subsequently determine peptides specific for each HLA allele expressed. Moreover, one of skill would also recognize that means other than transfection, such as loading with a protein antigen, can be used to provide a source of antigen to the cell.

Example 34

Complementary Polynucleotides

Sequences complementary to the 193P1E1B-encoding sequences, or any parts thereof, are used to detect, decrease, or inhibit expression of naturally occurring 193P1E1B. Although use of oligonucleotides comprising from about 15 to 30 base pairs is described, essentially the same procedure is used with smaller or with larger sequence fragments. Appropriate oligonucleotides are designed using, e.g., OLIGO 4.06 software (National Biosciences) and the coding sequence of 193P1E1B. To inhibit transcription, a complementary oligonucleotide is designed from the most unique 5' sequence and used to prevent promoter binding to the coding sequence. To inhibit translation, a complementary oligonucleotide is designed to prevent ribosomal binding to a 193P1E1B-encoding transcript.

Example 35

Purification of Naturally-Occurring or Recombinant 193P1E1B Using 193P1E1B-Specific Antibodies Naturally occurring or recombinant 193P1E1B is substantially purified by immunoaffinity chromatography using antibodies specific for 193P1E1B. An immunoaffinity column is constructed by covalently coupling anti-193P1E1B antibody to an activated chromatographic resin, such as CNBr-activated SEPHAROSE (Amersham Pharmacia Biotech). After the coupling, the resin is blocked and washed according to the manufacturer's instructions.

Media containing 193P1E1B are passed over the immunoaffinity column, and the column is washed under conditions that allow the preferential absorbance of 193P1E1B (e.g., high ionic strength buffers in the presence of detergent). The column is eluted under conditions that disrupt antibody/193P1E1B binding (e.g., a buffer of pH 2 to pH 3, or a high concentration of a chaotrope, such as urea or thiocyanate ion), and GCR.P is collected.

Example 36

Identification of Molecules Which Interact with 193P1E1B

193P1E1B, or biologically active fragments thereof, are labeled with 121 1 Bolton-Hunter reagent. (See, e.g., Bolton et al. (1973) Biochem. J. 133:529.) Candidate molecules previously arrayed in the wells of a multi-well plate are incubated with the labeled 193P1E1B, washed, and any wells with labeled 193P1E1B complex are assayed. Data obtained using different concentrations of 193P1E1B are used to calculate values for the number, affinity, and association of 193P1E1B with the candidate molecules.

Example 37

In Vivo Assay for 193P1E1B Tumor Growth Promotion

The effect of a 193P1E1B protein on tumor cell growth can be confirmed in vivo by gene overexpression in a variety of cancer cells such as those in Table I. For example, SCID mice can be injected SQ on each flank with $1\times10^6$ prostate, kidney, colon or bladder cancer cells (such as PC3, LNCaP, SCaBER, UM-UC-3, HT1376, SK-CO, Caco, RT4, T24, Caki, A-498 and SW839 cells) containing tkNeo empty vector or 193P1E1B.

At least two strategies can be used:

(1) Constitutive 193P1E1B expression under regulation of a promoter such as a constitutive promoter obtained from the genomes of viruses such as polyoma virus, fowlpox virus (UK 2, 211, 504 published Jul. 5, 1989), adenovirus (such as Adenovirus 2), bovine papilloma virus, avian sarcoma virus, cytomegalovirus, a retrovirus, hepatitis-B virus and Simian Virus 40 (SV40), or from heterologous mammalian promoters, e.g., the actin promoter or an immunoglobulin promoter, provided such promoters are compatible with the host cell systems.

(2) Regulated expression under control of an inducible vector system, such as ecdysone, tet, etc., can be used provided such promoters are compatible with the host cell systems. Tumor volume is then monitored at the appearance of palpable tumors or by following serum markers such as PSA. Tumor development is followed over time to validate that 193P1E1B-expressing cells grow at a faster rate and/or that tumors produced by 193P1E1B-expressing cells demonstrate characteristics of altered aggressiveness (e.g., enhanced metastasis, vascularization, reduced responsiveness to chemotherapeutic drugs). Tumor volume is evaluated by caliper measurements. Additionally, mice can be implanted with the same cells orthotopically in the prostate, bladder, colon or kidney to determine if 193P1E1B has an effect on local growth, e.g., in the prostate, bladder, colon or kidney or on the ability of the cells to metastasize, specifically to lungs or lymph nodes (Saffran et al., Proc Natl Acad Sci USA. 2001, 98: 2658; Fu, X., et al., Int. J. Cancer, 1991. 49: 938-939; Chang, S., et al., Anticancer Res., 1997, 17: 3239-3242; Peralta, E. A., et al., J. Urol., 1999. 162:1806-1811). For instance, the orthotopic growth of PC3 and PC3-193P1E1B can be compared in the prostate of SCID mice. Such experiments reveal the effect of 193P1E1B on orthotopic tumor growth, metastasis and/or angiogenic potential.

Furthermore, this assay is useful to confirm the inhibitory effect of candidate therapeutic compositions, such as 193P1E1B antibodies or intrabodies, and 193P1E1B antisense molecules or ribozymes, or 193P1E1B directed small molecules, on cells that express a 193P1E1B protein.

Example 38

193P1E1B Monoclonal Antibody-mediated Inhibition of Prostate Tumors In Vivo.

The significant expression of 193P1E1B, in cancer tissues, together with its restricted expression in normal tissues makes 193P1E1B an excellent target for antibody therapy. Similarly, 193P1E1B is a target for T cell-based immunotherapy. Thus, the therapeutic efficacy of anti-193P1E1B mAbs is evaluated, e.g., in human prostate cancer xenograft mouse models using androgen-independent LAPC-4 and LAPC-9 xenografts (Craft, N., et al. Cancer Res, 1999. 59(19): p. 5030-5036), kidney cancer xenografts (AGS-K3, AGS-K6), kidney cancer metastases to lymph node (AGS-K6 met) xenografts, and kidney cancer cell lines transfected with 193P1E1B, such as 769P-193P E1B, A498-193P1E1B.

Antibody efficacy on tumor growth and metastasis formation is studied, e.g., in mouse orthotopic prostate cancer xenograft models and mouse kidney xenograft models. The antibodies can be unconjugated, as discussed in this example, or can be conjugated to a therapeutic modality, as appreciated in the art. Anti-193P1E1B mAbs inhibit formation of both the androgen-dependent LAPC-9 and androgen-independent PC3-193P1E1B tumor xenografts. Anti-193P1E1B mAbs also retard the growth of established orthotopic tumors and prolonged survival of tumor-bearing mice. These results indicate the utility of anti-193P1E1B mAbs in the treatment of local and advanced stages of, e.g., prostate cancer. (See, e.g., Saffran, D., et al., PNAS 10:1073-1078. Similarly, anti-193P1E1B mAbs inhibit formation of AGS-K3 and AGS-K6 tumors in SCID mice, and prevent or retard the growth A498-

193P1E1B tumor xenografts. These results indicate the use of anti-193P1E1B mAbs in the treatment of prostate and/or kidney cancer.

Administration of the anti-193P1E1B mAbs leads to retardation of established orthotopic tumor growth and inhibition of metastasis to distant sites, resulting in a significant prolongation in the survival of tumor-bearing mice. These studies indicate that 193P1E1B is an attractive target for immunotherapy and demonstrate the therapeutic use of anti-193P1E1B mAbs for the treatment of local and metastatic cancer. This example demonstrates that unconjugated 193P1E1B monoclonal antibodies are effective to inhibit the growth of human prostate tumor xenografts and human kidney xenografts grown in SCID mice.

Tumor Inhibition Using Multiple Unconjugated 193P1E1B mAbs

Materials and Methods

193P1E1B Monoclonal Antibodies:

Monoclonal antibodies are obtained against 193P1E1B, as described in Example 11 entitled: Generation of 193P1E1B Monoclonal Antibodies (mAbs), or may be obtained commercially. The antibodies are characterized by ELISA, Western blot, FACS, and immunoprecipitation for their capacity to bind 193P1E1B. Epitope mapping data for the anti-193P1E1B mAbs, as determined by ELISA and Western analysis, recognize epitopeson a 193P1E1B protein. Immunohistochemical analysis of cancer tissues and cells is performed with these antibodies.

The monoclonal antibodies are purified from ascites or hybridoma tissue culture supernatants by Protein-G Sepharose chromatography, dialyzed against PBS, filter sterilized, and stored at −20° C. Protein determinations are performed by a Bradford assay (Bio-Rad, Hercules, Calif.). A therapeutic monoclonal antibody or a cocktail comprising a mixture of individual monoclonal antibodies is prepared and used for the treatment of mice receiving subcutaneous or orthotopic injections of, e.g., LAPC-9 prostate tumor xenografts.

Cancer Xenografts and Cell Lines

The LAPC-9 xenograft, which expresses a wild-type androgen receptor and produces prostate-specific antigen (PSA), is passaged in 6- to 8-week-old male ICR-severe combined immunodeficient (SCID) mice (Taconic Farms) by subcutaneous (s.c.) trocar implant (Craft, N., et al., 1999, Cancer Res. 59:5030-5036). The AGS-K3 and AGS-K6 kidney xenografts are also passaged by subcutaneous implants in 6- to 8-week old SCID mice. Single-cell suspensions of tumor cells are prepared as described in Craft, et al. The prostate carcinoma cell line PC3 (American Type Culture Collection) is maintained in RPMI supplemented with L-glutamine and 10% FBS, and the kidney carcinoma line A498 (American Type Culture Collection) is maintained in DMEM supplemented with L-glutamine and 10% FBS.

PC3-193P1E1B and A498-193P1E1B cell populations are generated by retroviral gene transfer as described in Hubert, R. S., et al., STEAP: A Prostate-specific Cell-surface Antigen Highly Expressed in Human Prostate Tumors, Proc Nat. Acad. Sci. USA, 1999. 96(25): p. 14523-14528. Anti-193P1E1B staining is detected by using, e.g., an FITC-conjugated goat anti-mouse antibody (Southern Biotechnology Associates) followed by analysis on a Coulter Epics-XL flow cytometer.

Xenograft Mouse Models.

Subcutaneous (s.c.) tumors are generated by injection of $1\times10^6$ LAPC-9, AGS-K3, AGS-K6, PC3, PC3-193P1E1B, A498 or A498-193P1E1B cells mixed at a 1:1 dilution with Matrigel (Collaborative Research) in the right flank of male SCID mice. To test antibody efficacy on tumor formation, i.p. antibody injections are started on the same day as tumor-cell injections. As a control, mice are injected with either purified mouse IgG (ICN) or PBS; or a purified monoclonal antibody that recognizes an irrelevant antigen not expressed in human cells. In preliminary studies, no difference is found between mouse IgG or PBS on tumor growth. Tumor sizes are determined by vemier caliper measurements, and the tumor volume is calculated as length×width×height. Mice with s.c. tumors greater than 1.5 cm in diameter are sacrificed. PSA levels are determined by using a PSA ELISA kit (Anogen, Mississauga, Ontario). Circulating levels of anti-193P1E1B mAbs are determined by a capture ELISA kit (Bethyl Laboratories, Montgomery, Tex.). (See, e.g., (Saffran, D., et al., PNAS 10:1073-1078 .

Orthotopic prostate injections are performed under anesthesia by using ketamine/xylazine. For prostate orthotopic studies, an incision is made through the abdominal muscles to expose the bladder and seminal vesicles, which then are delivered through the incision to expose the dorsal prostate. LAPC-9 cells ($5\times10^5$) mixed with Matrigel are injected into each dorsal lobe in a 10 μl volume. To monitor tumor growth, mice are bled on a weekly basis for determination of PSA levels. For kidney orthotopic models, an incision is made through the abdominal muscles to expose the kidney. AGS-K3 or AGS-K6 cells mixed with Matrigel are injected under the kidney capsule. The mice are segregated into groups for appropriate treatments, with anti-193P1E1B or control mAbs being injected i.p.

Anti-193P1E1B mAbs Inhibit Growth of 193P1E1B-Expressing Xenograft-Cancer Tumors The effect of anti-193P1E1B mAbs on tumor formation is tested by using, e.g., LAPC-9 and/or AGS-K3 orthotopic models. As compared with the s.c. tumor model, the orthotopic model, which requires injection of tumor cells directly in the mouse prostate or kidney, respectively, results in a local tumor growth, development of metastasis in distal sites, deterioration of mouse health, and subsequent death (Saffran, D., et al., PNAS supra; Fu, X., et al., Int J Cancer, 1992. 52(6): p. 987-90; Kubota, T., J Cell Biochem, 1994. 56(1): p. 4-8). The features make the orthotopic model more representative of human disease progression and allow for tracking of the therapeutic effect of mAbs on clinically relevant end points.

Accordingly, tumor cells are injected into the mouse prostate or kidney, and the mice are segregated into two groups and treated with either: a) 200-500 μg of anti-193P1E1B Ab, or b) PBS for two to five weeks.

As noted, a major advantage of the orthotopic prostate-cancer model is the ability to study the development of metastases. Formation of metastasis in mice bearing established orthotopic tumors is studied by IHC analysis on lung sections using an antibody against a prostate-specific cell-surface protein STEAP expressed at high levels in LAPC-9 xenografts (Hubert, R. S., et al., Proc Natl. Acad. Sci. USA, 1999. 96(25): p. 14523-14528) or anti-G250 antibody for kidney cancer models. G250 is a clinically relevant marker for renal clear cell carcinoma, which is selectively expressed on tumor but not normal kidney cells (Grabmaier K et al., Int J Cancer. 2000, 85: 865).

Mice bearing established orthotopic LAPC-9 tumors are administered 500-1000 μg injections of either anti-193P1E1B mAb or PBS over a 4-week period. Mice in both groups are allowed to establish a high tumor burden (PSA levels greater than 300 μg/ml), to ensure a high frequency of metastasis formation in mouse lungs. Mice then are killed and their prostate/kidney and lungs are analyzed for the presence of tumor cells by IHC analysis. These studies demonstrate a broad anti-tumor efficacy of anti-193P1E1B antibodies on initiation and/or progression of prostate and kidney cancer in xenograft mouse models. Anti-193P1E1B antibodies inhibit tumor formation of both androgen-dependent and androgen-independent prostate tumors as well as retarding the growth of already established tumors and prolong the survival of treated mice. Moreover, anti-193P1E1B mAbs demonstrate a dramatic inhibitory effect on the spread of local prostate tumor to distal sites, even in the presence of a large tumor burden. Similar therapeutic effects are seen in the kidney cancer model. Thus, anti-193P1E1B mAbs are efficacious on major clinically relevant end points (tumor growth), prolongation of survival, and health.

Example 39

Therapeutic and Diagnostic Use of Anti-193P1E1B Antibodies in Humans.

Anti-193P1E1B monoclonal antibodies are safely and effectively used for diagnostic, prophylactic, prognostic and/or therapeutic purposes in humans. Western blot and immunohistochemical analysis of cancer tissues and cancer xenografts with anti-193P1E1B mAb show strong extensive staining in carcinoma but significantly lower or undetectable levels in normal tissues. Detection of 193P1E1B in carcinoma and in metastatic disease demonstrates the usefulness of the mAb as a diagnostic and/or prognostic indicator. Anti-193P1E1B antibodies are therefore used in diagnostic applications such as immunohistochemistry of kidney biopsy specimens to detect cancer from suspect patients.

As determined by flow cytometry, anti-193P1E1B mAb specifically binds to carcinoma cells. Thus, anti-193P1E1B antibodies are used in diagnostic whole body imaging applications, such as radioimmunoscintigraphy and radioimmunotherapy, (see, e.g., Potamianos S., et. al. Anticancer Res 20(2A):925-948 (2000)) for the detection of localized and metastatic cancers that exhibit expression of 193P1E1B. Shedding or release of an extracellular domain of 193P1E1B into the extracellular milieu, such as that seen for alkaline phosphodiesterase B10 (Meerson, N. R., Hepatology 27:563-568 (1998)), allows diagnostic detection of 193P1E1B by anti-193P1E1B antibodies in serum and/or urine samples from suspect patients.

Anti-193P1E1B antibodies that specifically bind 193P1E1B are used in therapeutic applications for the treatment of cancers that express 193P1E1B. Anti-193P1E1B antibodies are used as an unconjugated modality and as conjugated form in which the antibodies are attached to one of various therapeutic or imaging modalities well known in the art, such as a prodrugs, enzymes or radioisotopes. In preclinical studies, unconjugated and conjugated anti-193P1E1B antibodies are tested for efficacy of tumor prevention and growth inhibition in the SCID mouse cancer xenograft models, e.g., kidney cancer models AGS-K3 and AGS-K6, (see, e.g., the Example entitled "193P1E1B Monoclonal Antibody-mediated Inhibition of Bladder and Lung Tumors In Vivo"). Either conjugated and unconjugated anti-193P1E1B antibodies are used as a therapeutic modality in human clinical trials either alone or in combination with other treatments as described in following Examples.

Example 40

Human Clinical Trials for the Treatment and Diagnosis of Human Carcinomas Through use of Human Anti-193P1E1B Antibodies In Vivo Antibodies are used in accordance with the present invention which recognize an epitope on 193P1E1B, and are used in the treatment of certain tumors such as those listed in Table I. Based upon a number of factors, including 193P1E1B expression levels, tumors such as those listed in Table I are presently preferred indications. In connection with each of these indications, three clinical approaches are successfully pursued.

I.) Adjunctive therapy: In adjunctive therapy, patients are treated with anti-193P1E1B antibodies in combination with a chemotherapeutic or antineoplastic agent and/or radiation therapy. Primary cancer targets, such as those listed in Table I, are treated under standard protocols by the addition anti-193P1E1B antibodies to standard first and second line therapy. Protocol designs address effectiveness as assessed by reduction in tumor mass as well as the ability to reduce usual doses of standard chemotherapy. These dosage reductions allow additional and/or prolonged therapy by reducing dose-related toxicity of the chemotherapeutic agent. Anti-193P1E1B antibodies are utilized in several adjunctive clinical trials in combination with the chemotherapeutic or antineoplastic agents adriamycin (advanced prostrate carcinoma), cisplatin (advanced head and neck and lung carcinomas), taxol (breast cancer), and doxorubicin (preclinical).

II.) Monotherapy: In connection with the use of the anti-193P1E1B antibodies in monotherapy of tumors, the antibodies are administered to patients without a chemotherapeutic or antineoplastic agent. In one embodiment, monotherapy is conducted clinically in end stage cancer patients with extensive metastatic disease. Patients show some disease stabilization. Trials demonstrate an effect in refractory patients with cancerous tumors.

III.) Imaging Agent: Through binding a radionuclide (e.g., iodine or yttrium ($I^{131}$, $Y^{90}$) to anti-193P1E1B antibodies, the radiolabeled antibodies are utilized as a diagnostic and/or imaging agent. In such a role, the labeled antibodies localize to both solid tumors, as well as, metastatic lesions of cells expressing 193P1E1B. In connection with the use of the anti-193P1E1B antibodies as imaging agents, the antibodies are used as an adjunct to surgical treatment of solid tumors, as both a pre-surgical screen as well as a post-operative follow-up to determine what tumor remains and/or returns. In one embodiment, a ($^{111}In$)-193P1E1B antibody is used as an imaging agent in a Phase I human clinical trial in patients having a carcinoma that expresses 193P1E1B (by analogy see, e.g., Divgi et al. *J. Natl. Cancer Inst.* 83:97-104 (1991)). Patients are followed with standard anterior and posterior gamma camera. The results indicate that primary lesions and metastatic lesions are identified Dose and Route of Administration As appreciated by those of ordinary skill in the art, dosing considerations can be determined through comparison with the analogous products that are in the clinic. Thus, anti-193P1E1B antibodies can be administered with doses in the range of 5 to 400 $mg/m^2$, with the lower doses used, e.g., in connection with safety studies. The affinity of anti-193P1E1B antibodies relative to the affinity of a known antibody for its target is one parameter used by those of skill in the art for determining analogous dose regimens. Further, anti-193P1E1B antibodies that are fully human antibodies, as compared to the chimeric antibody, have slower clearance; accordingly, dosing in patients with such fully human anti-193P1E1B antibodies can be lower, perhaps in the range of 50 to 300 mg/m$^2$ and still remain efficacious. Dosing in mg/m$^2$, as opposed to the conventional measurement of dose in mg/kg, is a measurement based on surface area and is a convenient dosing measurement that is designed to include patients of all sizes from infants to adults.

Three distinct delivery approaches are useful for delivery of anti-193P1E1B antibodies. Conventional intravenous delivery is one standard delivery technique for many tumors. However, in connection with tumors in the peritoneal cavity, such as tumors of the ovaries, biliary duct, other ducts, and the like, intraperitoneal administration may prove favorable for obtaining high dose of antibody at the tumor and to also minimize antibody clearance. In a similar manner, certain solid tumors possess vasculature that is appropriate for regional perfusion. Regional perfusion allows for a high dose of antibody at the site of a tumor and minimizes short term clearance of the antibody.

Clinical Development Plan (CDP)

Overview: The CDP follows and develops treatments of anti-193P1E1B antibodies in connection with adjunctive therapy, monotherapy, and as an imaging agent. Trials initially demonstrate safety and thereafter confirm efficacy in repeat doses. Trails are open label comparing standard chemotherapy with standard therapy plus anti-193P1E1B antibodies. As will be appreciated, one criteria that can be utilized in connection with enrollment of patients is 193P1E1B expression levels in their tumors as determined by biopsy.

As with any protein or antibody infusion-based therapeutic, safety concerns are related primarily to (i) cytokine release syndrome, i.e., hypotension, fever, shaking, chills; (ii) the development of an immunogenic response to the material (i.e., development of human antibodies by the patient to the antibody therapeutic, or HAHA response); and, (iii) toxicity to normal cells that express 193P1E1B. Standard tests and follow-up are utilized to monitor each of these safety concerns. Anti-193P1E1B antibodies are found to be safe upon human administration.

Example 41

Human Clinical Trial Adjunctive Therapy with Human Anti-193P1E1B Antibody and Chemotherapeutic Agent A phase I human clinical trial is initiated to assess the safety of six intravenous doses of a human anti-193P1E1B antibody in connection with the treatment of a solid tumor, e.g., a cancer of a tissue listed in Table I. In the study, the safety of single doses of anti-193P1E1B antibodies when utilized as an adjunctive therapy to an antineoplastic or chemotherapeutic agent as defined herein, such as, without limitation: cisplatin, topotecan, doxorubicin, adriamycin, taxol, or the like, is assessed. The trial design includes delivery of six single doses of an anti-193P1E1B antibody with dosage of antibody escalating from approximately about 25 mg/m$^2$to about 275 mg/m$^2$over the course of the treatment in accordance with the following schedule:

| | Day 0 | Day 7 | Day 14 | Day 21 | Day 28 | Day 35 |
|---|---|---|---|---|---|---|
| mAb Dose | 25 mg/m$^2$ | 75 mg/m$^2$ | 125 mg/m$^2$ | 175 mg/m$^2$ | 225 mg/m$^2$ | 275 mg/m$^2$ |
| Chemotherapy (standard dose) | + | + | + | + | + | + |

Patients are closely followed for one-week following each administration of antibody and chemotherapy. In particular, patients are assessed for the safety concerns mentioned above: (i).cytokine release syndrome, i.e., hypotension, fever, shaking, chills; (ii) the development of an immunogenic response to the material (i.e., development of human antibodies by the patient to the human antibody therapeutic, or HAHA response); and, (iii) toxicity to normal cells that express 193P1E1B. Standard tests and follow-up are utilized to monitor each of these safety concerns. Patients are also assessed for clinical outcome, and particularly reduction in tumor mass as evidenced by MRI or other imaging.

The anti-193P1E1B antibodies are demonstrated to be safe and efficacious, Phase II trials confirm the efficacy and refine optimum dosing.

Example 42

Human Clinical Trial: Monotherapy with Human Anti-193P1E1B Antibody

Anti-193P1E1B antibodies are safe in connection with the above-discussed adjunctive trial, a Phase II human clinical trial confirms the efficacy and optimum dosing for monotherapy. Such trial is accomplished, and entails the same safety and outcome analyses, to the above-described adjunctive trial with the exception being that patients do not receive chemotherapy concurrently with the receipt of doses of anti-193P1E1B antibodies.

Example 43

Human Clinical Trial: Diagnostic Imaging with Anti-193P1E1B Antibody

Once again, as the adjunctive therapy discussed above is safe within the safety criteria discussed above, a human clinical trial is conducted concerning the use of anti-193P1E1B antibodies as a diagnostic imaging agent. The protocol is designed in a substantially similar manner to those described in the art, such as in Divgi et al. *J. Natl. Cancer Inst.* 83:97-104 (1991). The antibodies are found to be both safe and efficacious when used as a diagnostic modality.

Example 44

Homology Comparison of 193P1E1B to Known Sequences

The 193P1E1B protein has several forms, including 3 SNPs and 5 splice variants (FIG. 4G). Three variants, namely 193P1E1B v. 1, v.5 and v.6, consist of 412 amino acids each, with calculated molecular weight of 46.25 kDa, and pl of 5.18, and differ from each other by one amino acid. 193P1E1B v.10, v.9 and v.12 are progressively smaller proteins, with 388, 330, and 73 amino acids respectively. These variants differ with regards to their molecular weights and isoelectic points, as shown in Table L. All variants of 193P1E1B are predicted to be nuclear proteins, with possible localization to the mitochondria (193P1E3B v.1, v.5, v.6, v.9, v.10, v.11 and v.13) or cytoplasm (193P1E3B v.12). Motif analysis revealed no known motifs.

All protein variants of 193P1E1B show best homology to a human un-named protein (gi 21748775) of unknown function, with 193P1E1B v.5 showing 100% identity with gi 21748775 over the entire length of the protein, and 193P1E1B sharing 99% identity with the same protein. Similarly, the other variants show highest homology to the human un-named protein (gi 21748775). The variant with the lowest homology to gi 21748775 is 193P1E1B v.12, with 89% identity and 89% homology over the first 39 amino acids of the protein (FIGS. 4A-D).

The 193P1E1B protein shows homology to a protein of known function, namely the arginine repressor (gi14349114) of *E. coli*, also known as carbamate kinase. Variant 193P1E1B v.1 shows 30% identity and 57% homology with that protein (FIG. 4E). This homology indicates that 193P1E1B may regulate ATP synthesis and metabolism (Marina A et al., Eur J Biochem 1998, 253:280; Alcantara C et al., FEBS Left. 2000, 484:261), a key factor in cell growth and biological function.

In addition, 193P1E1B also exhibit some homology to human double-stranded RNA-specific adenosine deaminase (ADAR-c isoform) (gi 7669475). 193P1E1Bv.1 shares 26% identity and 40% homology with ADAR-c (FIG. 4F). Similar results were obtained with 193P1E1Bv.5, v.6, v.9, v.10 and v.13. This suggests that 193P1E1B has the ability to bind specifically to double stranded RNA or DNA (Schwartz T., et al., Nature Struc. Biol. 2001, 8:761). Adenosine deaminases acting on RNA have been shown to be involved in RNA editing (Raitskin, O., et al., Proc. Natl. Acad. Sci 2001, 98:6571). Recent studies have associated adenosine deaminase with cancer and cellular proliferation (Eroglu A, et al., Med Oncol. 2000, 17:319-24; Barry C. P., and, Lind, S. E., Cancer Res. 2000, 60:1887-94). In addition, adenosine deaminase is highly expressed in tumor tissue relative to normal tissues in such cancers as colon, leukemia and other lymphoid cancers (Blatt, J., et al., N Engl J Med. 1980; 303:918; Eroglu, A., et al., Med Oncol. 2000, 17:319). Adenosine deaminase has been considered a potential marker for lymphoid malignancies (Blatt J et al., N Engl J Med. 1980;303: 918). In addition, inhibition of adenosine deaminase was found to result in cell death of epithelial cells (Barry, C. P., and, Lind, S. E., Cancer Res. 2000, 60:1887).

This information indicates that 193P1E1B plays a role in the transformation of mammalian cells, supports cell survival and proliferation, and regulates gene transcription by regulating events in the nucleus. Accordingly, when 193P1E1B functions as a regulator of cell transformation, tumor formation, or as a modulator of transcription involved in activating genes associated with inflammation, tumorigenesis or proliferation, 193P1E1B is used for therapeutic, diagnostic, prognostic and/or preventative purposes.

Example 45

Identification and Confirmation of Potential Signal Transduction Pathways

Many mammalian proteins have been reported to interact with signaling molecules and to participate in regulating signaling pathways. (J Neurochem. 2001; 76:217-223). In particular, adenosine deaminase has been found to associate with G-proteins, thereby regulating several signaling pathways (Ciruela F et al., FEBS Lett. 1996, 380:219). Using immunoprecipitation and Western blotting techniques, proteins are identified that associate with 193P1E1B and mediate signaling events. Several pathways known to play a role in cancer biology can be regulated by 193P1E1B, including phospholipid pathways such as P13K, AKT, etc, adhesion and migration pathways, including FAK, Rho, Rac-1, etc, as well as mitogenic/survival cascades such as ERK, p38, etc .(Cell Growth Differ. 2000, 11:279; J Biol Chem. 1999, 274:801; Oncogene. 2000, 19:3003, J. Cell Biol. 1997, 138:913).

To confirm that 193P1E1B directly or indirectly activates known signal transduction pathways in cells, luciferase (luc) based transcriptional reporter assays are carried out in cells expressing individual genes. These transcriptional reporters contain consensus-binding sites for known transcription factors that lie downstream of well-characterized signal transduction pathways. The reporters and examples of these associated transcription factors, signal transduction pathways, and activation stimuli are listed below.

1. NFkB-luc, NFkB/Rel; Ik-kinase/SAPK; growth/apoptosis/stress
2. SRE-luc, SRF/TCF/ELK1; MAPK/SAPK; growth/differentiation
3. AP-1-luc, FOS/JUN; MAPK/SAPK/PKC; growth/apoptosis/stress
4. ARE-luc, androgen receptor; steroids/MAPK; growth/differentiation/apoptosis
5. p53-luc, p53; SAPK; growth/differentiation/apoptosis
6. CRE-luc, CREB/ATF2; PKA/p38; growth/apoptosis/stress Gene-mediated effects can be assayed in cells showing mRNA expression. Luciferase reporter plasmids can be introduced by lipid-mediated transfection (TFX-50, Promega). Luciferase activity, an indicator of relative transcriptional activity, is measured by incubation of cell extracts with luciferin substrate and luminescence of the reaction is monitored in a luminometer.

Signaling pathways activated by 193P1E1B are mapped and used for the identification and validation of therapeutic targets. When 193P1E1B is involved in cell signaling, it is used as target for diagnostic, prognostic, preventative and/or therapeutic purposes.

Example 46

Regulation of Transcription

The nuclear localization of 193P1E1B and its ability to regulate adenosine deaminase indicate that it is effectively used as a modulator of the transcriptional regulation of eukaryotic genes. Regulation of gene expression is confirmed, e.g., by studying gene expression in cells expressing or lacking 193P1E1B. For this purpose, two types of experiments are performed.

In the first set of experiments, RNA from parental and 193P1E1B-expressing cells are extracted and hybridized to commercially available gene arrays (Clontech) (Smid-Koopman E et al. Br J Cancer. 2000. 83:246). Resting cells as well as cells treated with FBS, pheromones, or growth factors are compared. Differentally expressed genes are identified in accordance with procedures known in the art. The differentially expressed genes are then mapped to biological pathways (Chen K et al. Thyroid. 2001. 11:41.).

In the second set of experiments, specific transcriptional pathway activation is evaluated using commercially available (Stratagene) luciferase reporter constructs including: NFkB-luc, SRE-luc, ELK1-luc, ARE-luc, p53-luc, and CRE-luc. These transcriptional reporters contain consensus binding sites for known transcription factors that lie downstream of well-characterized signal transduction pathways, and represent a good tool to ascertain pathway activation and screen for positive and negative modulators of pathway activation. Thus, 193P1E1B plays a role in gene regulation, and it is used as a target for diagnostic, prognostic, preventative and/or therapeutic purposes.

Example 47

Involvement in Tumor Progression

The 193P1E1B gene can contribute to the growth of cancer cells. The role of 193P1E1B in tumor growth is confirmed in a variety of primary and transfected cell lines including prostate, colon, bladder and kidney cell lines, as well as NIH 3T3 cells engineered to stably express 193P1E1B. Parental cells lacking 193P1E1B and cells expressing 193P1E1B are evaluated for cell growth using a well-documented proliferation assay (Fraser S P, et al., Prostate 2000;44:61, Johnson DE, Ochieng J, Evans SL. Anticancer Drugs. 1996, 7:288). The effect of 193P1E1B can also be observed on cell cycle progression. Control and 193P1E1B-expressing cells are grown in low serum overnight, and treated with 10% FBS for 48 and 72 hrs. Cells are analyzed for BrdU and propidium iodide incorporation by FACS analysis.

To confirm the role of 193P1E1B in the transformation process, its effect in colony forming assays is investigated. Parental NIH-3T3 cells lacking 193P1E1B are compared to NIH-3T3 cells expressing 193P1E1B, using a soft agar assay under stringent and more permissive conditions (Song Z. et al. Cancer Res. 2000;60:6730).

To confirm the role of 193P1E1B in invasion and metastasis of cancer cells, a well-established assay is used. A non-limiting example is the use of an assay which provides a basement membrane or an analog thereof used to detect whether cells are invasive (e.g., a Transwell Insert System assay (Becton Dickinson) (Cancer Res. 1999; 59:6010)). Control cells, including prostate, and bladder cell lines lacking 193P1E1B are compared to cells expressing 193P1E1B. Cells are loaded with the fluorescent dye, calcein, and plated in the top well of a support structure coated with a basement membrane analog (e.g. the Transwell insert) and used in the assay. Invasion is determined by fluorescence of cells in the lower chamber relative to the fluorescence of the entire cell population.

193P1E1B can also play a role in cell cycle and apoptosis. Parental cells and cells expressing 193P1E1B are compared for differences in cell cycle regulation using a well-established BrdU assay (Abdel-Malek ZA. J Cell Physiol. 1988, 136:247). In short, cells are grown under both optimal (full serum) and limiting (low serum) conditions are labeled with BrdU and stained with anti-BrdU Ab and propidium iodide. Cells are analyzed for entry into the G1, S, and G2M phases of the cell cycle. Alternatively, the effect of stress on apoptosis is evaluated in control parental cells and cells expressing 193P1E1B, including normal and tumor prostate, and kidney cells. Engineered and parental cells are treated with various chemotherapeutic agents, such as etoposide, flutamide, etc, and protein synthesis inhibitors, such as cycloheximide. Cells are stained with annexin V-FITC and cell death is measured by FACS analysis. The modulation of cell death by 193P1E1B can play a critical role in regulating tumor progression and tumor load.

When 193P1E1B plays a role in cell growth, transformation, invasion or apoptosis, it is used as a target for diagnostic, prognostic, preventative and/or therapeutic purposes.

Example 48

Involvement in Angiogenesis

Angiogenesis or new capillary blood vessel formation is necessary for tumor growth (Hanahan D, Folkman J. Cell. 1996, 86:353; Folkman J. Endocrinology. 1998 139:441). Based on the effect of phsophodieseterase inhibitors on endothelial cells, 193P1E1B plays a role in angiogenesis (DeFouw L et al., Microvasc Res 2001, 62:263). Several assays have been developed to measure angiogenesis in vitro and in vivo, such as the tissue culture assays endothelial cell tube formation and endothelial cell proliferation. Using these assays as well as in vitro neo-vascularization, the role of 193P1E1B in angiogenesis, enhancement or inhibition, is confirmed. For example, endothelial cells engineered to express 193P1E1B are evaluated using tube formation and proliferation assays. The effect of 193P1E1B is also confirmed in animal models in vivo. For example, cells either expressing or lacking 193P1E1B are implanted subcutaneously in immunocompromised mice. Endothelial cell migration and angiogenesis are evaluated 5-15 days later using immunohistochemistry techniques. 193P1E1B affects angiogenesis, and it is used as a target for diagnostic, prognostic, preventative and/or therapeutic purposes.

Example 49

Involvement in Cell Adhesion

Cell adhesion plays a critical role in tissue colonization and metastasis. 193P1E1B can participate in cellular organization, and as a consequence cell adhesion and motility. To confirm that 193P1E1B regulates cell adhesion, control cells lacking 193P1E1B are compared to cells expressing 193P1E1B, using techniques previously described (see, e.g., Haier et al., Br. J. Cancer. 1999, 80:1867; Lehr and Pienta, J. Natl. Cancer Inst. 1998, 90:118). Briefly, in one embodiment, cells labeled with a fluorescent indicator, such as calcein, are incubated on tissue culture wells coated with media alone or with matrix proteins. Adherent cells are detected by fluorimetric analysis and percent adhesion is calculated. In another embodiment, cells lacking or expressing 193P1E1B are analyzed for their ability to mediate cell-cell adhesion using similar experimental techniques as described above. Both of these experimental systems are used to identify proteins, antibodies and/or small molecules that modulate cell adhesion to extracellular matrix and cell-cell interaction. Cell adhesion plays a critical role in tumor growth, progression, and, colonization, and 193P1E1B is involved in these processes. Thus, it serves as a diagnostic, prognostic, preventative and/or therapeutic modality.

Example 50

Protein-Protein Association

Several adenosine deaminasess have been shown to interact with other proteins, thereby regulating gene transcription, protein function, as well as cell growth (Raitskin et al above; Morimoto C, and Schlossman SF, Immunol Rev. 1998, 161: 55.). Using immunoprecipitation techniques as well as two yeast hybrid systems, proteins are identified that associate with 193P1E1B. Immunoprecipitates from cells expressing 193P1E1B and cells lacking 193P1E1B are compared for specific protein-protein associations.

Studies are performed to confirm the extent of association of 193P1E1B with effector molecules, such as nuclear proteins, transcription factors, kinases, phosphates, etc. Studies comparing 193P1E1B positive and 193P1E1B negative cells as well as studies comparing unstimulated/resting cells and cells treated with epithelial cell activators, such as cytokines, growth factors, androgen and anti-integrin Ab reveal unique interactions.

In addition, protein-protein interactions are confirmed using two yeast hybrid methodology (Curr. Opin. Chem. Biol. 1999, 3:64). A vector carrying a library of proteins fused to the activation domain of a transcription factor is introduced into yeast expressing a 193P1E1B-DNA-binding domain fusion protein and a reporter construct. Protein-protein interaction is detected by colorimetric reporter activity. Specific association with effector molecules and transcription factors directs one of skill to the mode of action of 193P1E1B, and thus identifies therapeutic, prognostic, preventative and/or diagnostic targets for cancer. This and similar assays are also used to identify and screen for small molecules that interact with 193P1E1B. Thus it is found that 193P1E1B associates with proteins and small molecules. Accordingly, 193P1E1Band these proteins and small molecules are used for diagnostic, prognostic, preventative and/or therapeutic purposes.

Throughout this application, various website data content, publications, patent applications and patents are referenced. (Websites are referenced by their Uniform Resource Locator, or URL, addresses on the World Wide Web.) The disclosures of each of these references are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

Tables:

TABLE I

| Tissues that Express 193P1E1B: |
|---|
| a. Malignant Tissues |
| Prostate |
| Bladder |
| Kidney |
| Colon |
| Lung |
| Ovary |
| Breast |
| Pancreas |
| Testis |
| Uterus |
| Skin |
| Bone |

TABLE II

Amino Acid Abbreviations

| SINGLE LETTER | THREE LETTER | FULL NAME |
|---|---|---|
| F | Phe | phenylalanine |
| L | Leu | leucine |
| S | Ser | serine |
| Y | Tyr | tyrosine |
| C | Cys | cysteine |
| W | Trp | tryptophan |
| P | Pro | proline |
| H | His | histidine |
| Q | Gln | glutamine |
| R | Arg | arginine |
| I | Ile | isoleucine |
| M | Met | methionine |
| T | Thr | threonine |
| N | Asn | asparagine |
| K | Lys | lysine |
| V | Val | valine |
| A | Ala | alanine |
| D | Asp | aspartic acid |
| E | Glu | glutamic acid |
| G | Gly | glycine |

Adapted from the GCG Software 9.0 BLOSUM62 amino acid substitution matrix (block substitution matrix). The higher the value, the more likely a substitution is found in related, natural proteins.

| A | C | D | E | F | G | H | I | K | L | M | N | P | Q | R | S | T | V | W | Y | . |
|---|---|---|---|---|---|---|---|---|---|---|---|---|---|---|---|---|---|---|---|---|
| 4 | 0 | −2 | −1 | −2 | 0 | −2 | −1 | −1 | −1 | −1 | −2 | −1 | −1 | −1 | 1 | 0 | 0 | −3 | −2 | A |
| | 9 | −3 | −4 | −2 | −3 | −3 | −1 | −3 | −1 | −1 | −3 | −3 | −3 | −3 | −1 | −1 | −1 | −2 | −2 | C |
| | | 6 | 2 | −3 | −1 | −1 | −3 | −1 | −4 | −3 | 1 | −1 | 0 | −2 | 0 | −1 | −3 | −4 | −3 | D |
| | | | 5 | −3 | −2 | 0 | −3 | 1 | −3 | −2 | 0 | −1 | 2 | 0 | 0 | −1 | −2 | −3 | −2 | E |
| | | | | 6 | −3 | −1 | 0 | −3 | 0 | 0 | −3 | −4 | −3 | −3 | −2 | −2 | −1 | 1 | 3 | F |
| | | | | | 6 | −2 | −4 | −2 | −4 | −3 | 0 | −2 | −2 | −2 | 0 | −2 | −3 | −2 | −3 | G |
| | | | | | | 8 | −3 | −1 | −3 | −2 | 1 | −2 | 0 | 0 | −1 | −2 | −3 | −2 | 2 | H |
| | | | | | | | 4 | −3 | 2 | 1 | −3 | −3 | −3 | −3 | −2 | −1 | 3 | −3 | −1 | I |
| | | | | | | | | 5 | −2 | −1 | 0 | −1 | 1 | 2 | 0 | −1 | −2 | −3 | −2 | K |
| | | | | | | | | | 4 | 2 | −3 | −3 | −2 | −2 | −2 | −1 | 1 | −2 | −1 | L |
| | | | | | | | | | | 5 | −2 | −2 | 0 | −1 | −1 | −1 | 1 | −1 | −1 | M |
| | | | | | | | | | | | 6 | −2 | 0 | 0 | 1 | 0 | −3 | −4 | −2 | N |
| | | | | | | | | | | | | 7 | −1 | −2 | −1 | −1 | −2 | −4 | −3 | P |
| | | | | | | | | | | | | | 5 | 1 | 0 | −1 | −2 | −2 | −1 | Q |
| | | | | | | | | | | | | | | 5 | −1 | −1 | −3 | −3 | −2 | R |
| | | | | | | | | | | | | | | | 4 | 1 | −2 | −3 | −2 | S |
| | | | | | | | | | | | | | | | | 5 | 0 | −2 | −2 | T |
| | | | | | | | | | | | | | | | | | 4 | −3 | −1 | V |
| | | | | | | | | | | | | | | | | | | 11 | 2 | W |
| | | | | | | | | | | | | | | | | | | | 7 | Y |

TABLE IV (A): HLA Class I Supermotifs/Motifs

| | POSITION 2 (Primary Anchor) | POSITION 3 (Primary Anchor) | POSITION C Terminus (Primary Anchor) |
|---|---|---|---|
| SUPERMOTIF | | | |
| A1 | **TI***LVMS* (SEQ ID NO:124) | | **FWY** |
| A2 | **LIVM***ATQ* (SEQ ID NO:125) | | **IV***MATL* (SEQ ID NO:126) |
| A3 | **VSMA***TLI* (SEQ ID NO:127) | | **RK** |
| A24 | **YF***WIVLMT* (SEQ ID NO:128) | | **FI***YWLM* (SEQ ID NO:129) |
| B7 | **P** | | **VILF***MWYA* (SEQ ID NO:130) |
| B27 | **RHK** | | **FYL***WMIVA* (SEQ ID NO:131) |
| B44 | **E***D* | | **FWYLIMVA** (SEQ ID NO:132) |
| B58 | **ATS** | | **FWY***LIVMA* (SEQ ID NO:133) |
| B62 | **QL***IVMP* (SEQ ID NO:134) | | **FWY***MIVLA* (SEQ ID NO:135) |
| MOTIFS | | | |
| A1 | **TSM** | | **Y** |
| A1 | | **DE***AS* (SEQ ID NO:247) | **Y** |
| A2.1 | **LM***VQIAT* (SEQ ID NO:136) | | **V***LIMAT* (SEQ ID NO:137) |
| A3 | **LMVISATF***CGD* (SEQ ID NO:138) | | **KYR***HFA* (SEQ ID NO:139) |
| A11 | **VTMLISAGN***CDF* (SEQ ID NO:140) | | **K***RYH* (SEQ ID NO:141) |
| A24 | **YFW***M* (SEQ ID NO:142) | | **FLIW** (SEQ ID NO:143) |
| A*3101 | **MVT***ALIS* (SEQ ID NO:144) | | **R***K* |
| A*3301 | **MVALF***IST* (SEQ ID NO:145) | | **RK** |
| A*6801 | **AVT***MSLI* (SEQ ID NO:146) | | **RK** |
| B*0702 | **P** | | **LMF***WYAIV* (SEQ ID NO:147) |
| B*3501 | **P** | | **LMFWY***IVA* (SEQ ID NO:148) |
| B51 | **P** | | **LIVF***WYAM* (SEQ ID NO:149) |
| B*5301 | **P** | | **IMFWY***ALV* (SEQ ID NO:150) |
| B*5401 | **P** | | **ATIVL***MFWY* (SEQ ID NO:151) |

Bolded residues are preferred, italicized residues are less preferred: A peptide is considered motif-bearing if it has primary anchors at each primary anchor position for a motif or supermotif as specified in the above table.

TABLE IV (B): HLA Class II Supermotif

| 1 | 6 | 9 |
|---|---|---|
| W, F, Y, V, I, L | A, V, I, L, P, C, S, T | A, V, I, L, C, S, T, M, Y |

TABLE IV (C): HLA Class II Motifs

| MOTIFS | | 1° anchor 1 | 2 | 3 | 4 | 5 | 1° anchor 6 | 7 | 8 | 9 |
|---|---|---|---|---|---|---|---|---|---|---|
| DR4 | preferred | FMY*LIVW* | M | T | | I | VST*CPALIM* | MH | | MH |
| | deleterious | (SEQ ID NO:152) | | | W | | (SEQ ID NO:153) | R | | WDE |
| DR1 | preferred | MF*LIVWY* | | | PAMQ | | VMAT*SPLIC* | M | | AVM |
| | deleterious | (SEQ ID NO:154) | | C | (SEQ ID NO:155) | CWD | (SEQ ID NO:156) | GDE | D | |
| | | | | CH | FD | | | | | |
| DR7 | preferred | MF*LIVWY* | M | W | A | | IVMSA*CTPL* | M | | IV |
| | deleterious | (SEQ ID NO:157) | C | | G | | (SEQ ID NO:158) | GRD | N | G |
| DR3 | MOTIFS | 1° anchor 1 | 2 | 3 | 1° anchor 4 | 5 | 1° anchor 6 | | | |
| Motif a preferred | | LIVMFY (SEQ ID NO:159) | | | D | | | | | |
| Motif b preferred | | LIVMFAY (SEQ ID NO:160) | | | DNQEST (SEQ ID NO:161) | | KRH | | | |
| DR Supermotif | | MF*LIVWY* | | | | | VMSTA*CPLI* | | | |
| | (SEQ ID NO:162) | | | | | (SEQ ID NO:163) | | | | |

Italicized residues indicate less preferred or "tolerated" residues

TABLE IV (D): HLA Class I Supermotifs

| SUPERMOTIFS | POSITION | 1 | 2 | 3 | 4 | 5 | 6 | 7 | 8 | C-terminus |
|---|---|---|---|---|---|---|---|---|---|---|
| A1 | | | 1° Anchor TI*LVMS* (SEQ ID NO:164) | | | | | | | 1° Anchor FWY |

TABLE IV-continued (D): HLA Class I Supermotifs

| SUPER-MOTIFS | POSITION | 1 | 2 | 3 | 4 | 5 | 6 | 7 | 8 | C-terminus |
|---|---|---|---|---|---|---|---|---|---|---|
| A2 | | | 1° Anchor LIVM*ATQ* (SEQ ID NO:165) | | | | | | | 1° Anchor LIVMAT (SEQ ID NO:166) |
| A3 | Preferred | | 1° Anchor VSMA*TLI* (SEQ ID NO:167) | YFW (4/5) | | | YFW (3/5) | YFW (4/5) | P (4/5) | 1° Anchor RK |
| | deleterious | DE (3/5); P (5/5) | | DE (4/5) | | | | | | |
| A24 | | | 1° Anchor YF*WIVLMT* (SEQ ID NO:168) | | | | | | | 1° Anchor FIY*WLM* (SEQ ID NO:169) |
| B7 | Preferred | FWY (5/5) LIVM (3/5) (SEQ ID NO:170) | 1° Anchor P | FWY (4/5) | | | | | FWY (3/5) | 1° Anchor VILF*MWYA* (SEQ ID NO:171) |
| | deleterious | DE (3/5); P(5/5); G(4/5); A(3/5); QN(3/5) | | | | DE (3/5) | G (4/5) | QN (4/5) | DE (4/5) | |
| B27 | | | 1° Anchor RHK | | | | | | | 1° Anchor FYL*WMIVA* (SEQ ID NO:172) |
| B44 | | | 1° Anchor E*D* | | | | | | | 1° Anchor FWYLIMVA (SEQ ID NO:173) |
| B58 | | | 1° Anchor ATS | | | | | | | 1° Anchor FWY*LIVMA* (SEQ ID NO:174) |
| B62 | | | 1° Anchor QL*IVMP* (SEQ ID NO:175) | | | | | | | 1° Anchor FWY*MIVLA* (SEQ ID NO:176) |

Italicized residues indicate less preferred or "tolerated" residues

TABLE IV (E): HLA Class I Motifs

| | POSITION | 1 | 2 | 3 | 4 | 5 | 6 | 7 | 8 | 9 or C-terminus | C-terminus |
|---|---|---|---|---|---|---|---|---|---|---|---|
| A1 9-mer | preferred | GFYW (SEQ ID NO:177) | 1° Anchor STM | DEA | YFW | | P | DEQN (SEQ ID NO:178) | YFW | 1° Anchor Y | |
| | deleterious | DE | | RHKLIVMP (SEQ ID NO:179) | A | G | A | | | | |
| A1 9-mer | preferred | GRHK (SEQ ID NO:180) | ASTCLIVM * (SEQ ID NO:181) | 1° Anchor DEAS (SEQ ID NO:182) | GSTC (SEQ ID NO:183) | | ASTC (SEQ ID NO:184) | LIVM (SEQ ID NO:185) | DE | 1° Anchor Y | |
| | deleterious | A | RHKDEPYFW (SEQ ID NO:186) | | DE | PQN | RHK | PG | GP | | |
| A1 10-mer | preferred | YFW | 1° Anchor STM | DEAQN (SEQ ID NO:187) | A | YFWQN (SEQ ID NO:188) | | PASTC (SEQ ID NO:189) | GDE | P | 1° Anchor Y |
| | deleterious | GP | | RHKGLIVM (SEQ ID NO:190) | DE | RHK | QNA * | RHKYFW (SEQ ID NO:191) | RHK | A | |
| A1 10-mer | preferred | YFW | STCLIVM (SEQ ID NO:192) | 1° Anchor DEAS (SEQ ID NO:193) | A | YFW | | PG | G | YFW | 1° Anchor Y |
| | deleterious | RHK | RHKDEPYFW (SEQ ID NO:194) | | | P | G | | PRHK (SEQ ID NO:195) | QN | |
| A2.1 9-mer | preferred | YFW | 1° Anchor LMIVQAT (SEQ ID NO:196) | YFW | STC | YFW | | A | P | 1° Anchor VLIMAT (SEQ ID NO:197) | |
| | del- | DEP | | DERKH | | | RKH | DERKH | | | |

TABLE IV-continued

| (E): HLA Class I Motifs | | | | | | | | | | | |
|---|---|---|---|---|---|---|---|---|---|---|---|
| | deleterious | | | (SEQ ID NO:198) | | | | (SEQ ID NO:199) | | | |
| | POSITION: | 1 | 2 | 3 | 4 | 5 | 6 | 7 | 8 | 9 | C-Terminus |
| A2.1 10-mer | preferred | AYFW | 1° Anchor LMIVQAT (SEQ ID NO:200) | LVIM (SEQ ID NO:201) | G | | G | | FYWLVIM (SEQ ID NO:202) | | 1° Anchor VLIMAT (SEQ ID NO:203) |
| | deleterious | DEP | | DE | RKHA (SEQ ID NO:204) | P | | RKH | DERKH (SEQ ID NO:205) | RKH | |
| A3 | preferred | RHK | 1° Anchor LMVISATFCGD (SEQ ID NO:206) | YFW | PRHKYFW (SEQ ID NO:207) | A | YFW | | P | 1° Anchor KYRHFA (SEQ ID NO:208) | |
| | deleterious | DEP | | DE | | | | | | | |
| A11 | preferred | A | 1° Anchor VTLMISAGNCDF (SEQ ID NO:209) | YFW | YFW | A | YFW | YFW | P | 1° Anchor KRYH (SEQ ID NO:210) | |
| | deleterious | DEP | | | | | | A | G | | |
| A24 9-mer | preferred | YFWRHK (SEQ ID NO:211) | 1° Anchor YFWM (SEQ ID NO:212) | | STC | | | YFW | YFW | 1° Anchor FLIW (SEQ ID NO:213) | |
| | deleterious | DEG | | DE | G | QNP | DERHK (SEQ ID NO:214) | G | AQN | | |
| A24 10-mer | Preferred | | 1° Anchor YFWM (SEQ ID NO:215) | | P | YFWP (SEQ ID NO:216) | | P | | | 1° Anchor FLIW (SEQ ID NO:217) |
| | Deleterious | | | GDE | QN | RHK | DE | A | QN | DEA | |
| A31-01 | Preferred | RHK | 1° Anchor MVTALIS (SEQ ID NO:218) | YFW | P | | YFW | YFW | AP | 1° Anchor RK | |
| | Deleterious | DEP | | DE | | ADE | DE | DE | DE | | |
| A33-01 | Preferred | | 1° Anchor MVALFIST (SEQ ID NO:219) | YFW | | | | AYFW (SEQ ID NO:220) | | 1° Anchor RK | |
| | Deleterious | GP | | DE | | | | | | | |
| A68-01 | Preferred | YFWSTC (SEQ ID NO:221) | 1° Anchor AVTMSLI (SEQ ID NO:222) | | | YFWLIVM (SEQ ID NO:223) | | YFW | P | 1° Anchor RK | |
| | deleterious | GP | | DEG | | RHK | | | A | | |
| B07-02 | Preferred | RHKFWY (SEQ ID NO:224) | 1° Anchor P | RHK | | RHK | RHK | RHK | PA | 1° Anchor LMFWYAIV (SEQ ID NO:225) | |
| | deleterious | DEQNP (SEQ ID NO:226) | | DEP | DE | DE | GDE | QN | DE | | |

TABLE IV-continued

| (E): HLA Class I Motifs | | | | | | | | | | |
|---|---|---|---|---|---|---|---|---|---|---|
| B35-01 | Preferred | FWYLIVM (SEQ ID NO:227) | 1° Anchor P | FWY | | | | FWY | | 1° Anchor LMFWYIVA (SEQ ID NO:228) |
| | deleterious | AGP | | | | G | G | | | |
| B51 | Preferred | LIVMFWY (SEQ ID NO:229) | 1° Anchor P | FWY | STC | FWY | | G | FWY | 1° Anchor LIVFWYAM (SEQ ID NO:230) |
| | deleterious | AGPDERHKSTC (SEQ ID NO:231) | | | | DE | G | DEQN (SEQ ID NO:232) | GDE | |
| B53-01 | preferred | LIVMFWY (SEQ ID NO:233) | 1° Anchor P | FWY | STC | FWY | | LIVMFWY (SEQ ID NO:234) | FWY | 1° Anchor IMFWYALV (SEQ ID NO:235) |
| | deleterious | AGPQN (SEQ ID NO:236) | | | | | G | RHKQN (SEQ ID NO:237) | DE | |
| B54-01 | preferred | FWY | 1° Anchor P | FWYLIVM (SEQ ID NO:238) | | LIVM (SEQ ID NO:239) | | ALIVM (SEQ ID NO:240) | EWYAP (SEQ ID NO:241) | 1° Anchor ATIVLMFWY (SEQ ID NO:242) |
| | deleterious | GPQNDE (SEQ ID NO:243) | | GDESTC (SEQ ID NO:244) | | RHKDE (SEQ ID NO:245) | DE | QNDGE (SEQ ID NO:246) | DE | |

TABLE IV (F):
Summary of HLA-supertypes
Overall phenotypic frequencies of HLA-supertypes in different ethnic populations

| Specificity | | | | | Phenotypic frequency | | | | | |
|---|---|---|---|---|---|---|---|---|---|---|
| Supertype | Position 2 | | C-Terminus | | Caucasian | N.A. Black | Japanese | Chinese | Hispanic | Average |
| B7 | P | | AILMVFWY | (SEQ ID NO:248) | 43.2 | 55.1 | 57.1 | 43.0 | 49.3 | 49.5 |
| A3 | AILMVST | (SEQ ID NO:249) | RK | | 37.5 | 42.1 | 45.8 | 52.7 | 43.1 | 44.2 |
| A2 | AILMVT | (SEQ ID NO:250) | AILMVT | (SEQ ID NO:251) | 45.8 | 39.0 | 42.4 | 45.9 | 43.0 | 42.2 |
| A24 | YF (WIVLMT) | (SEQ ID NO:252) | FI (YWLM) | (SEQ ID NO:253) | 23.9 | 38.9 | 58.6 | 40.1 | 38.3 | 40.0 |
| B44 | E (D) | | FWYLIMVA | (SEQ ID NO:254) | 43.0 | 21.2 | 42.9 | 39.1 | 39.0 | 37.0 |
| A1 | TI (LVMS) | (SEQ ID NO:255) | FWY | | 47.1 | 16.1 | 21.8 | 14.7 | 26.3 | 25.2 |
| B27 | RHK | | FYL (WMI) | (SEQ ID NO:256) | 28.4 | 26.1 | 13.3 | 13.9 | 35.3 | 23.4 |
| B62 | QL (IVMP) | (SEQ ID NO:257) | FWY (MIV) | (SEQ ID NO:258) | 12.6 | 4.8 | 36.5 | 25.4 | 11.1 | 18.1 |
| B58 | ATS | | FWY (LIV) | (SEQ ID NO:259) | 10.0 | 25.1 | 1.6 | 9.0 | 5.9 | 10.3 |

TABLE IV (G):
Calculated population coverage afforded by different HLA-supertype combinations

| | Phenotypic frequency | | | | | |
|---|---|---|---|---|---|---|
| HLA-supertypes | Caucasian | N.A Blacks | Japanese | Chinese | Hispanic | Average |
| A2, A3 and B7 | 83.0 | 86.1 | 87.5 | 88.4 | 86.3 | 86.2 |
| A2, A3, B7, A24, | 99.5 | 98.1 | 100.0 | 99.5 | 99.4 | 99.3 |

TABLE IV-continued (G):
Calculated population coverage afforded by different HLA-supertype combinations

| | Phenotypic frequency | | | | | |
|---|---|---|---|---|---|---|
| HLA-supertypes | Caucasian | N.A Blacks | Japanese | Chinese | Hispanic | Average |
| B44 and A1<br>A2, A3, B7, A24,<br>B44, A1, B27,<br>B62, and B58 | 99.9 | 99.6 | 100.0 | 99.8 | 99.9 | 99.8 |

Motifs indicate the residues defining supertype specificites. The motifs incorporate residues determined on the basis of published data to be recognized by multiple alleles within the supertype. Residues within brackets are additional residues also predicted to be tolerated by multiple alleles within the supertype.

TABLE V

Frequently Occurring Motifs

| Name | avrg. % identity | Description | Potential Function |
|---|---|---|---|
| zf-C2H2 | 34% | Zinc finger, C2H2 type | Nucleic acid-binding protein functions as transcription factor, nuclear location probable |
| cytochrome_b_N | 68% | Cytochrome b(N-terminal)/b6/petB | membrane bound oxidase, generate superoxide |
| lg | 19% | Immunoglobulin domain | domains are one hundred amino acids long and include a conserved intradomain disulfide bond. |
| WD40 | 18% | WD domain, G-beta repeat | tandem repeats of about 40 residues, each containing a Trp-Asp motif. Function in signal transduction and protein interaction |
| PDZ | 23% | PDZ domain | may function in targeting signaling molecules to sub-membranous sites |
| LRR | 28% | Leucine Rich Repeat | short sequence motifs involved in protein-protein interactions |
| Pkinase | 23% | Protein kinase domain | conserved catalytic core common to both serine/threonine and tyrosine protein kinases containing an ATP binding site and a catalytic site |
| PH | 16% | PH domain | pleckstrin homology involved in intracellular signaling or as constituents of the cytoskeleton |
| EGF | 34% | EGF-like domain | 30-40 amino-acid long found in the extracellular domain of membrane-bound proteins or in secreted proteins |
| Rvt | 49% | Reverse transcriptase (RNA-dependent DNA polymerase) | |
| Ank | 25% | Ank repeat | Cytoplasmic protein, associates integral membrane proteins to the cytoskeleton |
| Oxidored_q1 | 32% | NADH-Ubiquinone/plastoquinone (complex I), various chains | membrane associated. Involved in proton translocation across the membrane |
| Efhand | 24% | EF hand | calcium-binding domain, consists of a12 residue loop flanked on both sides by a 12 residue alpha-helical domain |
| Rvp | 79% | Retroviral aspartyl protease | Aspartyl or acid proteases, centered on a catalytic aspartyl residue |
| Collagen | 42% | Collagen triple helix repeat (20 copies) | extracellular structural proteins involved in formation of connective tissue. The sequence consists of the G-X-Y and the polypeptide chains forms a triple helix. |
| Fn3 | 20% | Fibronectin type III domain | Located in the extracellular ligand-binding region of receptors and is about 200 amino acid residues long with two pairs of cysteines involved in disulfide bonds |
| 7tm_1 | 19% | 7 transmembrane receptor (rhodopsin family) | seven hydrophobic transmembrane regions, with the N-terminus located extracellularly while the C-terminus is cytoplasmic. Signal through G proteins |

TABLE VI

| Motifs and Post-translational Modifications of 193P1E1B |
| --- |
| N-glycosylation site |
| Number of matches: 3 |
| 1 246-249 NKSE (SEQ ID NO:63) |
| 2 316-319 NSSS (SEQ ID NO:64) |
| 3 340-343 NLTD (SEQ ID NO:65) |
| cAMP- and cGMP-dependent protein kinase phosphorylation site |
| 107-110 KKNS (SEQ ID NO:66) |
| Protein kinase C phosphorylation site |
| Number of matches: 10 |
| 1 22-24 TAR |
| 2 53-55 TLK |
| 3 103-105 SPR |
| 4 152-154 SPR |
| 5 149-151 SEK |
| 6 103-105 SPR |
| 7 152-154 SPR |
| 8 203-205 TPK |
| 9 217-219 TPK |
| 10 203-205 TPK |
| Casein kinase II phosphorylation site |
| Number of matches: 12 |
| 1 16-19 STLD (SEQ ID NO:67) |
| 2 34-37 SDFE (SEQ ID NO:68) |
| 3 53-56 TLKD (SEQ ID NO:69) |
| 4 110-113 SVHE (SEQ ID NO:70) |
| 5 119-122 SDPE (SEQ ID NO:71) |
| 6 124-127 SNCE (SEQ ID NO:72) |
| 7 276-279 SDAE (SEQ ID NO:73) |
| 8 318-321 SSND (SEQ ID NO:74) |
| 9 336-339 TCFE (SEQ ID NO:75) |
| 10 350-353 SSYE (SEQ ID NO:76) |
| 11 360-363 TPPE (SEQ ID NO:77) |
| 12 408-411 SNKE (SEQ ID NO:78) |
| N-myristoylation site |
| 239-244 GLKNAR (SEQ ID NO:79) |

TABLE VII

Search Peptides variant 1:

9-mers, 10-mers and 15-mers (SEQ ID NO: 80)

MDPIRSFCGKLRSLASTLDCETARLQRALDGEESDFEDYPMRILYDLHSE

VQTLKDDVNIPELSNCENFQKTDVKDDLSDPPVASSCISGKSPRSPQLSD

FGLERYIVSQVLPNPPQAVNLLDKARLENQEGIDFIKATKVLMEKNSMDI

MKIREYFQKYGYSPRVKKNSVHEQEAINSDNYKEEPVIVTPPTKQSLVKV

LKTPKCALKMDDFECVTPKLEHFGISEYTMCLNEDYTMGLKNARNNKSEE

AIDTESRLNDNVFATPSPIIQQLEKSDAEYTNSPLVPTFCTPGLKIPSTK

NSIALVSTNYPLSKTNSSSNDLEVEDRTSLVLNSDTCFENLTDPSSPTIS

SYENLLRTPTPPEVTKIPEDILQLLSKYNSNLATPIAIKAVPPSKRFLKH

GQNIRDVSNKEN variant 5:

9-mers
PVASSCISEKSPRSPQL (SEQ ID NO: 81)

TABLE VII-continued

Search Peptides 10-mers
PPVASSCISEKSPRSPQLS (SEQ ID NO: 82)

15-mers
DDLSDPPVASSCISEKSPRSPQLSDFGLE (SEQ ID NO: 83)

Variant 6:

9-mers
NKSEEAIDAESRLND NV (SEQ ID NO: 84)

10-mers
NNKSEEAIDAESRLND NVF (SEQ ID NO: 85)

15-mers
LKNARNNKSEEAIDAESRLND NVFATPSP (SEQ ID NO: 86)

Variant 10:

9-mers
KIPEDILQKFQWIYPTQKLNKMR (SEQ ID NO: 87)

10-mers
TKIPEDILQKFQWIYPTQKLNKMR (SEQ ID NO: 88)

15-mers
TPPEVTKIPEDILQKFQWIYPTQKLNKMR (SEQ ID NO: 89)

Variant 12:

9-mers
RALDGEESLLSKYNSN (SEQ ID NO: 90)

10-mers
QRALDGEESLLSKYNSNL (SEQ ID NO: 91)

15-mers
ETARLQRALDGEESLLSKYNSNLATPIA (SEQ ID NO: 92)

Tables VIII-XXI:

TABLE VIII

| Start | Subsequence | Score |
| --- | --- | --- |
| V1-HLA-A1-9mers-193P1EIB<br>Each peptide is a portion of SEQ ID NO:3; each start position is specified, the length of peptide is 9 amino acids, and the end position for each peptide is the start position plus eight. | | |
| 19 | DCETARLQR | 45.000 |
| 98 | LSDFGLERY | 37.500 |
| 341 | LTDPSSPTI | 25.000 |
| 132 | GIDFIKATK | 20.000 |
| 78 | LSDPPVASS | 15.000 |
| 129 | NQEGIDFIK | 13.500 |
| 272 | QLEKSDAEY | 9.000 |
| 28 | ALDGEESDF | 5.000 |
| 253 | DTESRLNDN | 2.250 |
| 31 | GEESDFEDY | 2.250 |
| 33 | ESDFEDYPM | 1.500 |
| 306 | VSTNYPLSK | 1.500 |
| 63 | LSNCENFQK | 1.500 |
| 225 | ISEYTMCLN | 1.350 |
| 37 | EDYPMRILY | 1.250 |
| 228 | YTMCLNEDY | 1.250 |
| 319 | SNDLEVEDR | 1.250 |
| 71 | KTDVKDDLS | 1.250 |
| 232 | LNEDYTMGL | 1.125 |
| 358 | TPTPPEVTK | 1.000 |
| 215 | CVTPKLEHF | 1.000 |
| 389 | KAVPPSKRF | 1.000 |
| 17 | TLDCETARL | 1.000 |

TABLE VIII-continued

| Start | Subsequence | Score |
|---|---|---|
| 277 | DAEYTNSPL | 0.900 |
| 321 | DLEVEDRTS | 0.900 |
| 323 | EVEDRTSLV | 0.900 |
| 344 | PSSPTISSY | 0.750 |
| 349 | ISSYENLLR | 0.750 |
| 333 | NSDTCFENL | 0.750 |
| 275 | KSDAEYTNS | 0.750 |
| 48 | HSEVQTLKD | 0.675 |
| 233 | NEDYTMGLK | 0.500 |
| 382 | LATPIAIKA | 0.500 |
| 281 | TNSPLVPTF | 0.500 |
| 251 | AIDTESRLN | 0.500 |
| 370 | DILQLLSKY | 0.500 |
| 263 | FATPSPIIQ | 0.500 |
| 302 | SIALVSTNY | 0.500 |
| 97 | QLSDFGLER | 0.500 |
| 219 | KLEHFGISE | 0.450 |
| 381 | NLATPIAIK | 0.400 |
| 236 | YTMGLKNAR | 0.250 |
| 16 | STLDCETAR | 0.250 |
| 391 | VPPSKRFLK | 0.250 |
| 267 | SPIIQQLEK | 0.250 |
| 209 | KMDDFECVT | 0.250 |
| 121 | LLDKARLEN | 0.250 |
| 189 | VTPPTKQSL | 0.250 |
| 60 | IPELSNCEN | 0.225 |
| 367 | IPEDILQLL | 0.225 |
| 171 | VHEQEAINS | 0.225 |
| 35 | DFEDYPMRI | 0.225 |
| 142 | LMEKNSMDI | 0.225 |
| 182 | YKEEPVIVT | 0.225 |
| 175 | EAINSDNYK | 0.200 |
| 201 | LKTPKCALK | 0.200 |
| 110 | QVLPNPPQA | 0.200 |
| 83 | VASSCISGK | 0.200 |
| 102 | GLERYIVSQ | 0.180 |
| 146 | NSMDIMKIR | 0.150 |
| 173 | EQEAINSDN | 0.135 |
| 247 | KSEEAIDTE | 0.135 |
| 290 | CTPGLKIPS | 0.125 |
| 147 | SMDIMKIRE | 0.125 |
| 264 | ATPSPIIQQ | 0.125 |
| 30 | DGEESDFED | 0.113 |
| 86 | SCISGKSPR | 0.100 |
| 330 | LVLNSDTCF | 0.100 |
| 188 | IVTPPTKQS | 0.100 |
| 118 | AVNLLDKAR | 0.100 |
| 205 | KCALKMDDF | 0.100 |
| 160 | YGYSPRVKK | 0.100 |
| 137 | KATKVLMEK | 0.100 |
| 390 | AVPPSKRFL | 0.100 |
| 126 | RLENQEGID | 0.090 |
| 183 | KEEPVIVTP | 0.090 |
| 65 | NCENFQKTD | 0.090 |
| 212 | DFECVTPKL | 0.090 |
| 12 | RSLASTLDC | 0.075 |
| 178 | NSDNYKEEP | 0.075 |
| 5 | RSFCGKLRS | 0.075 |
| 316 | NSSSNDLEV | 0.075 |
| 350 | SSYENLLRT | 0.075 |
| 195 | QSLVKVLKT | 0.075 |
| 194 | KQSLVKVLK | 0.060 |
| 287 | PTFCTPGLK | 0.050 |
| 57 | DVNIPELSN | 0.050 |
| 112 | LPNPPQAVN | 0.050 |
| 280 | YTNSPLVPT | 0.050 |
| 106 | YIVSQVLPN | 0.050 |
| 224 | GISEYTMCL | 0.050 |
| 154 | REYFQKYGY | 0.050 |
| 257 | RLNDNVFAT | 0.050 |
| 369 | EDILQLLSK | 0.050 |
| 55 | KDDVNIPEL | 0.050 |
| 152 | KIREYFQKY | 0.050 |
| 366 | KIPEDILQL | 0.050 |
| 67 | ENFQKTDVK | 0.050 |
| 75 | KDDLSDPPV | 0.050 |
| 214 | ECVTPKLEH | 0.050 |

TABLE VIII-continued

| Start | Subsequence | Score |
|---|---|---|
| V5-HLA-A1-9mers-193P1E1B<br>Each peptide is a portion of SEQ ID NO:11; each start position is specified, the length of peptide is 9 amino acids, and the end position for each peptide is the start position plus eight. | | |
| 2 | VASSCISEK | 0.200 |
| 5 | SCISEKSPR | 0.100 |
| 6 | CISEKSPRS | 0.020 |
| 3 | ASSCISEKS | 0.015 |
| 7 | ISEKSPRSP | 0.014 |
| 9 | EKSPRSPQL | 0.010 |
| 4 | SSCISEKSP | 0.002 |
| 1 | PVASSCISE | 0.001 |
| 8 | SEKSPRSPQ | 0.000 |
| V6-HLA-A1-9mers-193P1E1B<br>Each peptide is a portion of SEQ ID NO:13; each start position is specified, the length of peptide is 9 amino acids, and the end position for each peptide is the start position plus eight. | | |
| 8 | DAESRLNDN | 0.900 |
| 6 | AIDAESRLN | 0.500 |
| 2 | KSEEAIDAE | 0.135 |
| 3 | SEEAIDAES | 0.090 |
| 5 | EAIDAESRL | 0.010 |
| 4 | EEAIDAESR | 0.050 |
| 1 | NKSEEAIDA | 0.003 |
| 7 | IDAESRLND | 0.000 |
| 9 | AESRLNDNV | 0.000 |
| V10-HLA-A1-9mers-193P1E1B<br>Each peptide is a portion of SEQ ID NO:21; each start position is specified, the length of peptide is 9 amino acids, and the end position for each peptide is the start position plus eight. | | |
| 2 | IPEDILQKF | 2.250 |
| 1 | KIPEDILQK | 1.000 |
| 12 | WIYPTQKLN | 0.100 |
| 13 | IYPTQKLNK | 0.050 |
| 6 | ILQKFQWIY | 0.050 |
| 5 | DILQKFQWI | 0.010 |
| 10 | FQWIYPTQK | 0.003 |
| 3 | PEDILQKFQ | 0.003 |
| 15 | PTQKLNKMR | 0.003 |
| 4 | EDILQKFQW | 0.003 |
| 14 | YPTQKLNKM | 0.003 |
| 8 | QKFQWIYPT | 0.001 |
| 9 | KFQWIYPTQ | 0.001 |
| 11 | QWIYPTQKL | 0.001 |
| 7 | LQKFQWIYP | 0.000 |
| V12-HLA-A1-9mers-193P1E1B<br>Each peptide is a portion of SEQ ID NO:25; each start position is specified, the length of peptide is 9 amino acids, and the end position for each peptide is the start position plus eight. | | |
| 4 | DGEESLLSK | 22.500 |
| 5 | GEESLLSKY | 2.250 |
| 2 | ALDGEESLL | 0.500 |
| 7 | ESLLSKYNS | 0.030 |
| 8 | SLLSKYNSN | 0.010 |
| 1 | RALDGEESL | 0.010 |
| 3 | LDGEESLLS | 0.003 |
| 6 | EESLLSKYN | 0.001 |

TABLE IX

| Start | Subsequence | Score |
|---|---|---|
| V1-HLA-A1-10mers-193P1EIB<br>Each peptide is a portion of SEQ ID NO:3; each start position is specified, the length of peptide is 10 amino acids, and the end position for each peptide is the start position plus nine. | | |
| 219 | KLEHFGISEY | 45.000 |
| 126 | RLENQEGIDF | 45.000 |
| 33 | ESDFEDYPMR | 15.000 |

TABLE IX-continued

| Start | Subsequence | Score |
|---|---|---|
| 341 | LTDPSSPTIS | 12.500 |
| 147 | SMDIMKIREY | 12.500 |
| 30 | DGEESDFEDY | 11.250 |
| 390 | AVPPSKRFLK | 10.000 |
| 78 | LSDPPVASSC | 7.500 |
| 173 | EQEAINSDNY | 6.750 |
| 36 | FEDYPMRILY | 6.250 |
| 323 | EVEDRTSLVL | 4.500 |
| 153 | IREYFQKYGY | 4.500 |
| 232 | LNEDYTMGLK | 4.500 |
| 60 | IPELSNCENF | 2.250 |
| 253 | DTESRLNDNV | 2.250 |
| 277 | DAEYTNSPLV | 1.800 |
| 247 | KSEEAIDTES | 1.350 |
| 367 | IPEDILQLLS | 1.125 |
| 357 | RTPTPPEVTK | 1.000 |
| 305 | LVSTNYPLSK | 1.000 |
| 62 | ELSNCENFQK | 1.000 |
| 19 | DCETARLQRA | 0.900 |
| 321 | DLEVEDRTSL | 0.900 |
| 65 | NCENFQKTDV | 0.900 |
| 301 | NSIALVSTNY | 0.750 |
| 333 | NSDTCFENLT | 0.750 |
| 178 | NSDNYKEEPV | 0.750 |
| 98 | LSDFGLERYI | 0.750 |
| 225 | ISEYTMCLNE | 0.675 |
| 129 | NQEGIDFIKA | 0.675 |
| 71 | KTDVKDDLSD | 0.625 |
| 17 | TLDCETARLQ | 0.500 |
| 263 | FATPSPIIQQ | 0.500 |
| 210 | MDDFECVTPK | 0.500 |
| 132 | GIDFIKATKV | 0.500 |
| 348 | TISSYENLLR | 0.500 |
| 289 | FCTPGLKIPS | 0.500 |
| 280 | YTNSPLVPTF | 0.500 |
| 97 | QLSDFGLERY | 0.500 |
| 248 | SEEAIDTESR | 0.450 |
| 368 | PEDILQLLSK | 0.250 |
| 190 | TPPTKQSLVK | 0.250 |
| 189 | VTPPTKQSLV | 0.250 |
| 128 | ENQEGIDFIK | 0.250 |
| 251 | AIDTESRLND | 0.250 |
| 46 | DLHSEVQTLK | 0.200 |
| 266 | PSPIIQQLEK | 0.150 |
| 85 | SSCISGKSPR | 0.150 |
| 15 | ASTLDCETAR | 0.150 |
| 318 | SSNDLEVEDR | 0.150 |
| 271 | QQLEKSDAEY | 0.150 |
| 48 | HSEVQTLKDD | 0.135 |
| 343 | DPSSPTISSY | 0.125 |
| 258 | LNDNVFATPS | 0.125 |
| 233 | NEDYTMGLKN | 0.125 |
| 319 | SNDLEVEDRT | 0.125 |
| 380 | SNLATPIAIK | 0.100 |
| 188 | IVTPPTKQSL | 0.100 |
| 185 | EPVIVTPPTK | 0.100 |
| 110 | QVLPNPPQAV | 0.100 |
| 214 | ECVTPKLEHF | 0.100 |
| 27 | RALDGEESDF | 0.100 |
| 131 | EGIDFIKATK | 0.100 |
| 382 | LATPIAIKAV | 0.100 |
| 329 | SLVLNSDTCF | 0.100 |
| 215 | CVTPKLEHFG | 0.100 |
| 117 | QAVNLLDKAR | 0.100 |
| 389 | KAVPPSKRFL | 0.100 |
| 102 | GLERYIVSQV | 0.090 |
| 272 | QLEKSDAEYT | 0.090 |
| 337 | CFENLTDPSS | 0.090 |
| 379 | NSNLATPIAI | 0.075 |
| 275 | KSDAEYTNSP | 0.075 |
| 94 | RSPQLSDFGL | 0.075 |
| 349 | ISSYENLLRT | 0.075 |
| 282 | NSPLVPTFCT | 0.075 |
| 291 | TPGLKIPSTK | 0.050 |
| 331 | VLNSDTCFEN | 0.050 |
| 54 | LKDDVNIPEL | 0.050 |
| 381 | NLATPIAIKA | 0.050 |

TABLE IX-continued

| Start | Subsequence | Score |
|---|---|---|
| 16 | STLDCETARL | 0.050 |
| 44 | LYDLHSEVQT | 0.050 |
| 236 | YTMGLKNARN | 0.050 |
| 28 | ALDGEESDFE | 0.050 |
| 112 | LPNPPQAVNL | 0.050 |
| 75 | KDDLSDPPVA | 0.050 |
| 286 | VPTFCTPGLK | 0.050 |
| 121 | LLDKARLENQ | 0.050 |
| 170 | SVHEQEAINS | 0.050 |
| 231 | CLNEDYTMGL | 0.050 |
| 141 | VLMEKNSMDI | 0.050 |
| 74 | VKDDLSDPPV | 0.050 |
| 150 | IMKIREYFQK | 0.050 |
| 120 | NLLDKARLEN | 0.050 |
| 209 | KMDDFECVTP | 0.050 |
| 290 | CTPGLKIPST | 0.050 |
| 136 | IKATKVLMEK | 0.050 |
| 183 | KEEPVIVTPP | 0.045 |
| 351 | SYENLLRTPT | 0.045 |
| 35 | DFEDYPMRIL | 0.045 |

V5-HLA-A1-10mers-193P1E1B
Each peptide is a portion of SEQ ID NO:11; each start position is specified, the length of peptide is 10 amino acids, and the end position for each peptide is the start position plus nine.

| Start | Subsequence | Score |
|---|---|---|
| 5 | SSCISEKSPR | 0.150 |
| 8 | ISEKSPRSPQ | 0.135 |
| 6 | SCISEKSPRS | 0.020 |
| 2 | PVASSCISEK | 0.020 |
| 3 | VASSCISEKS | 0.010 |
| 10 | EKSPRSPQLS | 0.005 |
| 4 | ASSCISEKSP | 0.002 |
| 7 | CISEKSPRSP | 0.001 |
| 1 | PPVASSCISE | 0.000 |
| 9 | SEKSPRSPQL | 0.000 |

V6-HLA-A1-10mers-193P1E1B
Each peptide is a portion of SEQ ID NO:13; each start position is specified, the length of peptide is 10 amino acids, and the end position for each peptide is the start position plus nine.

| Start | Subsequence | Score |
|---|---|---|
| 3 | KSEEAIDAES | 2.700 |
| 9 | DAESRLNDNV | 0.900 |
| 4 | SEEAIDAESR | 0.450 |
| 7 | AIDAESRLND | 0.250 |
| 6 | EAIDAESRLN | 0.010 |
| 1 | NNKSEEAIDA | 0.001 |
| 10 | AESRLNDNVF | 0.001 |
| 8 | IDAESRLNDN | 0.001 |
| 5 | EEAIDAESRL | 0.001 |
| 2 | NKSEEAIDAE | 0.000 |

V10-HLA-A1-10mers-193P1E1B
Each peptide is a portion of SEQ ID NO:21; each start position is specified, the length of peptide is 10 amino acids, and the end position for each peptide is the start position plus nine.

| Start | Subsequence | Score |
|---|---|---|
| 13 | WIYPTQKLNK | 10.000 |
| 1 | TKIPEDILQK | 0.500 |
| 6 | DILQKFQWIY | 0.500 |
| 3 | IPEDILQKFQ | 0.225 |
| 2 | KIPEDILQKF | 0.100 |
| 15 | YPTQKLNKMR | 0.025 |
| 4 | PEDILQKFQW | 0.013 |
| 10 | KFQWIYPTQK | 0.010 |
| 9 | QKFQWIYPTQ | 0.001 |
| 7 | ILQKFQWIYP | 0.001 |
| 14 | IYPTQKLNKM | 0.001 |
| 12 | QWIYPTQKLN | 0.001 |
| 5 | EDILQKFQWI | 0.001 |
| 8 | LQKFQWIYPT | 0.000 |
| 11 | FQWIYPTQKL | 0.000 |

V12-HLA-A1-10mers-193P1E1B
Each peptide is a portion of SEQ ID NO:25; each start position is specified, the length of peptide is 10 amino acids, and the end position for each peptide is the start position plus nine.

| Start | Subsequence | Score |
|---|---|---|
| 5 | DGEESLLSKY | 11.250 |
| 3 | ALDGEESLLS | 2.500 |

TABLE IX-continued

| Start | Subsequence | Score |
|---|---|---|
| 4 | LDGEESLLSK | 0.050 |
| 6 | GEESLLSKYN | 0.045 |
| 8 | ESLLSKYNSN | 0.015 |
| 9 | SLLSKYNSNL | 0.010 |
| 2 | RALDGEESLL | 0.010 |
| 7 | EESLLSKYNS | 0.001 |
| 1 | QRALDGEESL | 0.001 |

TABLE X

| Start | Subsequence | Score |
|---|---|---|
| V1-HLA-A0201-9mers-193P1E1B Each peptide is a portion of SEQ ID NO:3; each start position is specified, the length of peptide is 9 amino acids, and the end position for each peptide is the start position plus eight. | | |
| 43 | ILYDLHSEV | 1551.288 |
| 257 | RLNDNVFAT | 407.580 |
| 111 | VLPNPPQAV | 118.238 |
| 366 | KIPEDILQL | 96.947 |
| 209 | KMDDFECVT | 48.131 |
| 374 | LLSKYNSNL | 36.316 |
| 340 | NLTDPSSPT | 30.553 |
| 304 | ALVSTNYPL | 21.362 |
| 229 | TMCLNEDYT | 14.504 |
| 224 | GISEYTMCL | 12.043 |
| 17 | TLDCETARL | 8.545 |
| 10 | KLRSLASTL | 5.682 |
| 140 | KVLMEKNSM | 5.629 |
| 199 | KVLKTPKCA | 5.629 |
| 39 | YPMRILYDL | 5.459 |
| 295 | KIPSTKNSI | 5.021 |
| 278 | AEYTNSPLV | 4.328 |
| 46 | DLHSEVQTL | 3.685 |
| 261 | NVFATPSPI | 3.378 |
| 348 | TISSYENLL | 2.937 |
| 322 | LEVEDRTSL | 2.895 |
| 329 | SLVLNSDTC | 2.434 |
| 208 | LKMDDFECV | 2.319 |
| 383 | ATPIAIKAV | 2.222 |
| 390 | AVPPSKRFL | 2.056 |
| 110 | QVLPNPPQA | 1.608 |
| 350 | SSYENLLRT | 1.468 |
| 66 | CENFQKTDV | 1.352 |
| 200 | VLKTPKCAL | 1.271 |
| 280 | YTNSPLVPT | 1.095 |
| 283 | SPLVPTFCT | 1.044 |
| 314 | KTNSSSNDL | 1.038 |
| 207 | ALKMDDFEC | 1.009 |
| 119 | VNLLDKARL | 0.877 |
| 270 | IQQLEKSDA | 0.856 |
| 142 | LMEKNSMDI | 0.820 |
| 95 | SPQLSDFGL | 0.809 |
| 371 | ILQLLSKYN | 0.697 |
| 352 | YENLLRTPT | 0.667 |
| 254 | TESRLNDNV | 0.663 |
| 133 | IDFIKATKV | 0.608 |
| 145 | KNSMDIMKI | 0.548 |
| 52 | QTLKDDVNI | 0.536 |
| 189 | VTPPTKQSL | 0.504 |
| 231 | CLNEDYTMG | 0.458 |
| 316 | NSSSNDLEV | 0.454 |
| 190 | TPPTKQSLV | 0.454 |
| 195 | QSLVKVLKT | 0.414 |
| 373 | QLLSKYNSN | 0.414 |
| 103 | LERYIVSQV | 0.402 |
| 300 | KNSIALVST | 0.392 |
| 141 | VLMEKNSMD | 0.384 |
| 64 | SNCENFQKT | 0.379 |
| 114 | NPPQAVNLL | 0.321 |
| 265 | TPSPIIQQL | 0.321 |
| 378 | YNSNLATPI | 0.313 |
| 158 | QKYGYSPRV | 0.309 |

TABLE X-continued

| Start | Subsequence | Score |
|---|---|---|
| 380 | SNLATPIAI | 0.252 |
| 202 | KTPKCALKM | 0.242 |
| 307 | STNYPLSKT | 0.238 |
| 286 | VPTFCTPGL | 0.237 |
| 97 | QLSDFGLER | 0.232 |
| 223 | FGISEYTMC | 0.224 |
| 50 | EVQTLKDDV | 0.224 |
| 20 | CETARLQRA | 0.222 |
| 230 | MCLNEDYTM | 0.204 |
| 130 | QEGIDFIKA | 0.184 |
| 328 | TSLVLNSDT | 0.180 |
| 282 | NSPLVPTFC | 0.178 |
| 45 | YDLHSEVQT | 0.176 |
| 14 | LASTLDCET | 0.176 |
| 7 | FCGKLRSLA | 0.149 |
| 36 | FEDYPMRIL | 0.144 |
| 367 | IPEDILQLL | 0.143 |
| 331 | VLNSDTCFE | 0.139 |
| 75 | KDDLSDPPV | 0.135 |
| 131 | EGIDEIKAT | 0.131 |
| 128 | ENQEGIDFI | 0.130 |
| 58 | VNIPELSNC | 0.127 |
| 12 | RSLASTLDC | 0.120 |
| 323 | EVEDRTSLV | 0.120 |
| 382 | LATPIAIKA | 0.117 |
| 324 | VEDRTSLVL | 0.116 |
| 168 | KNSVHEQEA | 0.114 |
| 291 | TPGLKIPST | 0.112 |
| 135 | FIKATKVLM | 0.110 |
| 106 | YIVSQVLPN | 0.108 |
| 341 | LTDPSSPTI | 0.099 |
| 55 | KDDVNIPEL | 0.096 |
| 250 | EAIDTESRL | 0.091 |
| 9 | GKLRSLAST | 0.088 |
| 399 | KHGQNIRDV | 0.078 |
| 117 | QAVNLLDKA | 0.078 |
| 298 | STKNSIALV | 0.078 |
| 320 | NDLEVEDRT | 0.077 |
| 232 | LNEDYTMGL | 0.062 |
| 70 | QKTDVKDDL | 0.060 |
| 99 | SDFGLERYI | 0.059 |
| 354 | NLLRTPTPP | 0.055 |
| 237 | TMGLKNARN | 0.054 |
| X-V5-HLA-A0201-9mers-193P1E1B Each peptide is a portion of SEQ ID NO:11; each start position is specified, the length of peptide is 9 amino acids, and the end position for each peptide is the start position plus eight. | | |
| 6 | CISEKSPRS | 0.042 |
| 9 | EKSPRSPQL | 0.002 |
| 2 | VASSCISEK | 0.001 |
| 3 | ASSCISEKS | 0.000 |
| 5 | SCISEKSPR | 0.000 |
| 4 | SSCISEKSP | 0.000 |
| 1 | PVASSCISE | 0.000 |
| 8 | SEKSPRSPQ | 0.000 |
| 7 | ISEKSPRSP | 0.000 |
| V6-HLA-A0201-9mers-193P1E1B Each peptide is a portion of SEQ ID NO:13; each start position is specified, the length of peptide is 9 amino acids, and the end position for each peptide is the start position plus eight. | | |
| 9 | AESRLNDNV | 0.663 |
| 5 | EAIDAESRL | 0.091 |
| 1 | NKSEEAIDA | 0.028 |
| 6 | AIDAESRLN | 0.001 |
| 7 | IDAESRLND | 0.000 |
| 2 | KSEEAIDAE | 0.000 |
| 3 | SEEAIDAES | 0.000 |
| 8 | DAESRLNDN | 0.000 |
| 4 | EEAIDAESR | 0.000 |

TABLE X-continued

| Start | Subsequence | Score |
|---|---|---|
| V10-HLA-A0201-9mers-193P1E1B Each peptide is a portion of SEQ ID NO:21; each start position is specified, the length of peptide is 9 amino acids, and the end position for each peptide is the start position plus eight. | | |
| 5 | DILQKFQWI | 4.160 |
| 6 | ILQKFQWIY | 1.480 |
| 14 | YPTQKLNKM | 0.343 |
| 12 | WIYPTQKLN | 0.151 |
| 8 | QKFQWIYPT | 0.088 |
| 1 | KIPEDILQK | 0.068 |
| 10 | FQWIYPTQK | 0.058 |
| 11 | QWIYPTQKL | 0.003 |
| 7 | LQKFQWIYP | 0.001 |
| 2 | IPEDILQKF | 0.000 |
| 9 | KFQWIYPTQ | 0.000 |
| 4 | EDILQKFQW | 0.000 |
| 3 | PEDILQKFQ | 0.000 |
| 15 | PTQKLNKMR | 0.000 |
| 13 | IYPTQKLNK | 0.000 |
| V12-HLA-A0201-9mers-193P1E1B Each peptide is a portion of SEQ ID NO:25; each start position is specified, the length of peptide is 9 amino acids, and the end position for each peptide is the start position plus eight. | | |
| 2 | ALDGEESLL | 8.545 |
| 1 | RALDGEESL | 2.205 |
| 8 | SLLSKYNSN | 0.414 |
| 3 | LDGEESLLS | 0.001 |
| 6 | EESLLSKYN | 0.001 |
| 5 | GEESLLSKY | 0.000 |
| 7 | ESLLSKYNS | 0.000 |
| 4 | DGEESLLSK | 0.000 |

TABLE XI

| Start | Subsequence | Score |
|---|---|---|
| V1-HLA-A0201-10mers-193P1E1B Each peptide is a portion of SEQ ID NO:3; each start position is specified, the length of peptide is 10 amino acids, and the end position for each peptide is the start position plus nine. | | |
| 141 | VLMEKNSMDI | 269.051 |
| 366 | KIPEDILQLL | 96.947 |
| 231 | CLNEDYTMGL | 87.586 |
| 373 | QLLSKYNSNL | 79.041 |
| 340 | NLTDPSSPTI | 42.774 |
| 42 | RILYDLHSEV | 35.385 |
| 199 | KVLKTPKCAL | 24.206 |
| 110 | QVLPNPPQAV | 22.517 |
| 102 | GLERYIVSQV | 10.238 |
| 322 | LEVEDRTSLV | 9.426 |
| 355 | LLRTPTPPEV | 8.986 |
| 374 | LLSKYNSNLA | 8.446 |
| 13 | SLASTLDCET | 7.452 |
| 194 | KQSLVKVLKT | 6.082 |
| 381 | NLATPIAIKA | 4.968 |
| 228 | YTMCLNEDYT | 4.747 |
| 16 | STLDCETARL | 4.501 |
| 132 | GIDFIKATKV | 3.825 |
| 382 | LATPIAIKAV | 3.777 |
| 229 | TMCLNEDYTM | 3.588 |
| 188 | IVTPPTKQSL | 3.178 |
| 285 | LVPTFCTPGL | 3.178 |
| 207 | ALKMDDFECV | 2.266 |
| 127 | LENQEGIDFI | 2.138 |
| 162 | YSPRVKKNSV | 2.088 |
| 118 | AVNLLDKARL | 1.869 |
| 303 | IALVSTNYPL | 1.866 |
| 51 | VQTLKDDVNI | 1.798 |
| 189 | VTPPIKQSLV | 1.642 |
| 206 | CALKMDDFEC | 1.481 |
| 216 | VTPKLEHFGI | 1.429 |

TABLE XI-continued

| Start | Subsequence | Score |
|---|---|---|
| 261 | NVFATPSPII | 1.385 |
| 272 | QLEKSDAEYT | 1.285 |
| 130 | QEGIDFIKAT | 1.266 |
| 45 | YDLHSEVQTL | 1.161 |
| 269 | IIQQLEKSDA | 1.161 |
| 389 | KAVPPSKRFL | 1.142 |
| 157 | FQKYGYSPRV | 1.135 |
| 120 | NLLDKARLEN | 1.130 |
| 295 | KIPSTKNSIA | 0.980 |
| 332 | LNSDTCFENL | 0.905 |
| 94 | RSPQLSDFGL | 0.809 |
| 331 | VLNSDTCFEN | 0.735 |
| 264 | ATPSPIIQQL | 0.682 |
| 220 | LEHFGISEYT | 0.664 |
| 49 | SEVQTLKDDV | 0.663 |
| 223 | FGISEYTMCL | 0.641 |
| 109 | SQVLPNPPQA | 0.504 |
| 315 | TNSSSNDLEV | 0.454 |
| 208 | LKMDDFECVT | 0.416 |
| 97 | QLSDFGLERY | 0.344 |
| 282 | NSPLVPTFCT | 0.282 |
| 74 | VKDDLSDPPV | 0.269 |
| 290 | CTPGLKIPST | 0.238 |
| 5 | RSFCGKLRSL | 0.237 |
| 112 | LPNPPQAVNL | 0.237 |
| 296 | IPSTKNSIAL | 0.237 |
| 152 | KIREYFQKYG | 0.234 |
| 34 | SDFEDYPMRI | 0.220 |
| 54 | LKDDVNIPEL | 0.190 |
| 306 | VSTNYPLSKT | 0.190 |
| 349 | ISSYENLLRT | 0.190 |
| 142 | LMEKNSMDIM | 0.180 |
| 281 | TNSPLVPTFC | 0.178 |
| 69 | FQKTDVKDDL | 0.171 |
| 63 | LSNCENFQKT | 0.157 |
| 358 | TPTPPEVTKI | 0.157 |
| 99 | SDFGLERYIV | 0.147 |
| 371 | ILQLLSKYNS | 0.127 |
| 276 | SDAEYTNSPL | 0.122 |
| 168 | KNSVHEQEAI | 0.117 |
| 257 | RLNDNVFATP | 0.116 |
| 271 | QQLEKSDAEY | 0.115 |
| 304 | ALVSTNYPLS | 0.112 |
| 9 | GKLRSLASTL | 0.110 |
| 327 | RTSLVLNSDT | 0.104 |
| 321 | DLEVEDRTSL | 0.103 |
| 346 | SPTISSYENL | 0.102 |
| 224 | GISEYTMCLN | 0.097 |
| 178 | NSDNYKEEPV | 0.089 |
| 20 | CETARLQRAL | 0.083 |
| 133 | IDFIKATKVL | 0.077 |
| 398 | LKHGQNIRDV | 0.076 |
| 57 | DVNIPELSNC | 0.075 |
| 329 | SLVLNSDTCF | 0.075 |
| 333 | NSDTCFENLT | 0.074 |
| 372 | LQLLSKYNSN | 0.071 |
| 365 | TKIPEDILQL | 0.068 |
| 379 | NSNLATPIAI | 0.068 |
| 43 | ILYDLHSEVQ | 0.067 |
| 209 | KMDDFECVTP | 0.062 |
| 129 | NQEGIDFIKA | 0.061 |
| 378 | YNSNLATPIA | 0.061 |
| 328 | TSLVLNSDTC | 0.059 |
| 14 | LASTLDCETA | 0.057 |
| 354 | NLLRTPTPPE | 0.055 |
| 77 | DLSDPPVASS | 0.053 |
| 111 | VLPNPPQAVN | 0.052 |
| 256 | SRLNDNVFAT | 0.051 |
| 98 | LSDFGLERYI | 0.051 |
| V5-HLA-A0201-10mers-193P1E1B Each peptide is a portion of SEQ ID NO:11; each start position is specified, the length of peptide is 10 amino acids, and the end position for each peptide is the start position plus nine. | | |
| 9 | SEKSPRSPQL | 0.015 |
| 7 | CISEKSPRSP | 0.002 |
| 3 | VASSCISEKS | 0.001 |

TABLE XI-continued

| Start | Subsequence | Score |
|---|---|---|
| 6 | SCISEKSPRS | 0.000 |
| 5 | SSCISEKSPR | 0.000 |
| 4 | ASSCISEKSP | 0.000 |
| 2 | PVASSCISEK | 0.000 |
| 8 | ISEKSPRSPQ | 0.000 |
| 10 | EKSPRSPQLS | 0.000 |
| 1 | PPVASSCISE | 0.000 |
| V6-HLA-A0201-10mers-193P1E1B Each peptide is a portion of SEQ ID NO:13; each start position is specified, the length of peptide is 10 amino acids, and the end position for each peptide is the start position plus nine. | | |
| 5 | EEAIDAESRL | 0.031 |
| 9 | DAESRLNDNV | 0.002 |
| 8 | IDAESRLNDN | 0.002 |
| 1 | NNKSEEAIDA | 0.001 |
| 7 | AIDAESRLND | 0.001 |
| 10 | AESRLNDNVF | 0.001 |
| 3 | KSEEAIDAES | 0.000 |
| 2 | NKSEEAIDAE | 0.000 |
| 6 | EAIDAESRLN | 0.000 |
| 4 | SEEAIDAESR | 0.000 |
| V10-HLA-A0201-10mers-193P1E1B Each peptide is a portion of SEQ ID NO:21; each start position is specified, the length of peptide is 10 amino acids, and the end position for each peptide is the start position plus nine. | | |
| 11 | FQWIYPTQKL | 82.694 |
| 2 | KIPEDILQKF | 0.338 |
| 7 | ILQKFQWIYP | 0.237 |
| 8 | LQKFQWIYPT | 0.103 |
| 6 | DILQKFQWIY | 0.033 |
| 13 | WIYPTQKLNK | 0.030 |
| 5 | EDILQKFQWI | 0.011 |
| 14 | IYPTQKLNKM | 0.003 |
| 15 | YPTQKLNKMR | 0.000 |
| 3 | IPEDILQKFQ | 0.000 |
| 9 | QKFQWIYPTQ | 0.000 |
| 4 | PEDILQKFQW | 0.000 |
| 1 | TKIPEDILQK | 0.000 |
| 10 | KFQWIYPTQK | 0.000 |
| 12 | QWIYPTQKLN | 0.000 |
| V12-HLA-A0201-10mers-193P1E1B Each peptide is a portion of SEQ ID NO:25; each start position is specified, the length of peptide is 10 amino acids, and the end position for each peptide is the start position plus nine. | | |
| 9 | SLLSKYNSNL | 79.041 |
| 2 | RALDGEESLL | 4.501 |
| 3 | ALDGEESLLS | 0.030 |
| 1 | QRALDGEESL | 0.001 |
| 6 | GEESLLSKYN | 0.001 |
| 4 | LDGEESLLSK | 0.000 |
| 8 | ESLLSKYNSN | 0.000 |
| 7 | EESLLSKYNS | 0.000 |
| 5 | DGEESLLSKY | 0.000 |

TABLE XII

| Start | Subsequence | Score |
|---|---|---|
| V1-HLA-A3-9mers-193P1E1B Each peptide is a portion of SEQ ID NO:3; each start position is specified, the length of peptide is 9 amino acids, and the end position for each peptide is the start position plus eight. | | |
| 239 | GLKNARNNK | 60.000 |
| 381 | NLATPIAIK | 45.000 |
| 97 | QLSDFGLER | 24.000 |
| 152 | KIREYFQKY | 16.200 |
| 132 | GIDFIKATK | 9.000 |
| 129 | NQEGIDFIK | 4.050 |
| 397 | FLKHGQNIR | 4.000 |
| 272 | QLEKSDAEY | 4.000 |

TABLE XII-continued

| Start | Subsequence | Score |
|---|---|---|
| 387 | AIKAVPPSK | 3.000 |
| 28 | ALDGEESDF | 3.000 |
| 194 | KQSLVKVLK | 2.700 |
| 137 | KATKVLMEK | 2.700 |
| 304 | ALVSTNYPL | 2.700 |
| 197 | LVKVLKTPK | 2.000 |
| 374 | LLSKYNSNL | 1.800 |
| 10 | KLRSLASTL | 1.800 |
| 224 | GISEYTMCL | 1.620 |
| 142 | LMEKNSMDI | 1.200 |
| 43 | ILYDLHSEV | 1.000 |
| 209 | KMDDFECVT | 0.900 |
| 200 | VLKTPKCAL | 0.900 |
| 257 | RLNDNVFAT | 0.900 |
| 366 | KIPEDILQL | 0.810 |
| 267 | SPIIQQLEK | 0.600 |
| 207 | ALKMDDFEC | 0.600 |
| 306 | VSTNYPLSK | 0.600 |
| 391 | VPPSKRFLK | 0.600 |
| 302 | SIALVSTNY | 0.600 |
| 17 | TLDCETARL | 0.600 |
| 46 | DLHSEVQTL | 0.540 |
| 358 | TPTPPEVTK | 0.450 |
| 236 | YTMGLKNAR | 0.450 |
| 215 | CVTPKLEHF | 0.450 |
| 219 | KLEHFGISE | 0.360 |
| 186 | PVIVTPPTK | 0.300 |
| 83 | VASSCISGK | 0.300 |
| 111 | VLPNPPQAV | 0.300 |
| 63 | LSNCENFQK | 0.300 |
| 330 | LVLNSDTCF | 0.300 |
| 16 | STLDCETAR | 0.300 |
| 261 | NVFATPSPI | 0.300 |
| 228 | YTMCLNEDY | 0.300 |
| 329 | SLVLNSDTC | 3.000 |
| 2 | DPIRSFCGK | 0.270 |
| 102 | GLERYIVSQ | 0.270 |
| 370 | DILQLLSKY | 0.270 |
| 118 | AVNLLDKAR | 0.200 |
| 116 | PQAVNLLDK | 0.180 |
| 402 | QNIRDVSNK | 0.180 |
| 295 | KIPSTKNSI | 0.180 |
| 348 | TISSYENLL | 0.180 |
| 154 | REYFQKYGY | 0.180 |
| 160 | YGYSPRVKK | 0.150 |
| 287 | PTFCTPGLK | 0.150 |
| 340 | NLTDPSSPT | 0.150 |
| 149 | DIMKIREYF | 0.135 |
| 211 | DDFECVTPK | 0.135 |
| 157 | FQKYGYSPR | 0.120 |
| 31 | GEESDFEDY | 0.108 |
| 389 | KAVPPSKRF | 0.101 |
| 229 | TMCLNEDYT | 0.100 |
| 151 | MKIREYFQK | 0.090 |
| 140 | KVLMEKNSM | 0.090 |
| 314 | KTNSSSNDL | 0.090 |
| 205 | KCALKMDDF | 0.090 |
| 293 | GLKIPSTKN | 0.090 |
| 175 | EAINSDNYK | 0.090 |
| 39 | YPMRILYDL | 0.061 |
| 67 | ENFQKTDVK | 0.060 |
| 202 | KTPKCALKM | 0.060 |
| 150 | IMKIREYFQ | 0.060 |
| 86 | SCISGKSPR | 0.060 |
| 53 | TLKDDVNIP | 0.060 |
| 47 | LHSEVQTLK | 0.045 |
| 199 | KVLKTPKCA | 0.045 |
| 110 | QVLPNPPQA | 0.045 |
| 364 | VTKIPEDIL | 0.045 |
| 141 | VLME KNSMD | 0.045 |
| 52 | QTLKDDVNI | 0.045 |
| 189 | VTPPTKQSL | 0.045 |
| 341 | LTDPSSPTI | 0.045 |
| 349 | ISSYENLLR | 0.040 |
| 121 | LLDKARLEN | 0.040 |
| 147 | SMDIMKIRE | 0.040 |
| 191 | PPTKQSLVK | 0.040 |

TABLE XII-continued

| Start | Subsequence | Score |
|---|---|---|
| 196 | SLVKVLKTP | 0.034 |
| 146 | NSMDIMKIR | 0.034 |
| 201 | LKTPKCALK | 0.030 |
| 231 | CLNEDYTMG | 0.030 |
| 373 | QLLSKYNSN | 0.030 |
| 34 | SDFEDYPMR | 0.030 |
| 24 | RLQRALDGE | 0.030 |
| 98 | LSDFGLERY | 0.030 |
| 354 | NLLRTPTPP | 0.030 |
| 355 | LLRTPTPPE | 0.030 |
| 13 | SLASTLDCE | 0.030 |
| 363 | EVTKIPEDI | 0.027 |
| 369 | EDILQLLSK | 0.027 |
| 233 | NEDYTMGLK | 0.027 |
| 319 | SNDLEVEDR | 0.024 |
| V5-HLA-A3-9mers-193P1E1B<br>Each peptide is a portion of SEQ ID NO:11; each start position is specified, the length of pdptide is 9 amino acids, and the end position for each peptide is the start position plus eight. | | |
| 2 | VASSCISEK | 0.300 |
| 5 | SCISEKSPR | 0.060 |
| 6 | CISEKSPRS | 0.006 |
| 1 | PVASSCISE | 0.000 |
| 3 | ASSCISEKS | 0.000 |
| 9 | EKSPRSPQL | 0.000 |
| 8 | SEKSPRSPQ | 0.000 |
| 4 | SSCISEKSP | 0.000 |
| 7 | ISEKSPRSP | 0.000 |
| V6-HLA-A3-9mers-193P1E1B<br>Each peptide is a portion of SEQ ID NO:13; each start position is specified, the length of peptide is 9 amino acids, and the end position for each peptide is the start position plus eight. | | |
| 4 | EEAIDAESR | 0.004 |
| 5 | EAIDAESRL | 0.003 |
| 2 | KSEEAIDAE | 0.001 |
| 1 | NKSEEAIDA | 0.001 |
| 9 | AESRLNDNV | 0.001 |
| 6 | AIDAESRLN | 0.000 |
| 3 | SEEAIDAES | 0.000 |
| 8 | DAESRLNDN | 0.000 |
| 7 | IDAESRLND | 0.000 |
| V10-HLA-A3-9mers-193P1E1B<br>Each peptide is a portion of SEQ ID NO:21; each start position is specified, the length of peptide is 9 amino acids, and the end position for each peptide is the start position plus eight. | | |
| 6 | ILQKFQWIY | 36.000 |
| 1 | KIPEDILQK | 27.000 |
| 10 | FQWIYPTQK | 9.000 |
| 5 | DILQKFQWI | 0.081 |
| 2 | IPEDILQKF | 0.045 |
| 13 | IYPTQKLNK | 0.040 |
| 15 | PTQKLNKMR | 0.010 |
| 12 | WIYPTQKLN | 0.007 |
| 8 | QKFQWIYPT | 0.007 |
| 14 | YPTQKLNKM | 0.003 |
| 11 | QWIYPTQKL | 0.001 |
| 7 | LQKFQWIYP | 0.001 |
| 4 | EDILQKFQW | 0.000 |
| 9 | KFQWIYPTQ | 0.000 |
| 3 | PEDILQKFQ | 0.000 |
| V12-HLA-A3-9mers-193P1E1B<br>Each peptide is a portion of SEQ ID NO:25; each start position is specified, the length of peptide is 9 amino acids, and the end position for each peptide is the start position plus eight. | | |
| 2 | ALDGEESLL | 0.900 |
| 5 | GEESLLSKY | 0.054 |
| 8 | SLLSKYNSN | 0.030 |
| 4 | DGEESLLSK | 0.027 |
| 1 | RALDGEESL | 0.009 |
| 7 | ESLLSKYNS | 0.000 |
| 3 | LDGEESLLS | 0.000 |
| 6 | EESLLSKYN | 0.000 |

TABLE XIII

| Start | Subsequence | Score |
|---|---|---|
| V1-HLA-A3-10mers-193P1E1B<br>Each peptide is a portion of SEQ ID NO:3; each start position is specified, the length of peptide is 10 amino acids, and the end position for each peptide is the start position plus nine. | | |
| 150 | IMKIREYFQK | 60.000 |
| 196 | SLVKVLKTPK | 30.000 |
| 200 | VLKTPKCALK | 20.000 |
| 219 | KLEHFGISEY | 18.000 |
| 62 | ELSNCENFQK | 18.000 |
| 305 | LVSTNYPLSK | 12.000 |
| 46 | DLHSEVQTLK | 9.000 |
| 390 | AVPPSKRFLK | 9.000 |
| 97 | QLSDFGLERY | 6.000 |
| 231 | CLNEDYTMGL | 5.400 |
| 401 | GQNIRDVSNK | 5.400 |
| 126 | RLENQEGIDF | 4.000 |
| 329 | SLVLNSDTCF | 3.000 |
| 102 | GLERYIVSQV | 2.700 |
| 373 | QLLSKYNSNL | 2.700 |
| 141 | VLMEKNSMDI | 2.700 |
| 357 | RTPTPPEVTK | 1.500 |
| 348 | TISSYENLLR | 0.800 |
| 366 | KIPEDILQLL | 0.608 |
| 207 | ALKMDDFECV | 0.600 |
| 147 | SMDIMKI REY | 0.600 |
| 381 | NLATPIAIKA | 0.600 |
| 387 | AK AVPPSKR | 0.600 |
| 340 | NLTDPSSPTI | 0.600 |
| 229 | TMCLNEDYTM | 0.600 |
| 386 | IAIKAVPPSK | 0.450 |
| 261 | NVFATPSPII | 0.450 |
| 199 | KVLKTPKCAL | 0.405 |
| 190 | TPPTKQSLVK | 0.400 |
| 82 | PVASSCISGK | 0.300 |
| 291 | TPGLKIPSTK | 0.300 |
| 142 | LMEKNSMDIM | 0.300 |
| 280 | YTNSPLVPTF | 0.300 |
| 271 | QQLEKSDAEY | 0.270 |
| 355 | LLRTPTPPEV | 0.200 |
| 374 | LLSKYNSNLA | 0.200 |
| 321 | DLEVEDRTSL | 0.180 |
| 380 | SNLATPIAIK | 0.135 |
| 143 | MEKNSMDIMK | 0.120 |
| 371 | ILQLLSKYNS | 0.120 |
| 239 | GLKNARNNKS | 0.120 |
| 96 | PQLSDFGLER | 0.108 |
| 13 | SLASTLDCET | 0.100 |
| 43 | ILYDLHSEVQ | 0.100 |
| 272 | QLEKSDAEYT | 0.100 |
| 159 | KYGYSPRVKK | 0.090 |
| 136 | IKATKVLMEK | 0.090 |
| 216 | VTPKLEHFGI | 0.090 |
| 188 | IVTPPTKQSL | 0.090 |
| 257 | RLNDNVFATP | 0.900 |
| 185 | EPVIVTPPTK | 0.090 |
| 128 | ENQEGIDFIK | 0.081 |
| 264 | ATPSPIIQQL | 0.068 |
| 110 | QVLPNPPQAV | 0.068 |
| 1 | MDPIRSFCGK | 0.060 |
| 210 | MDDFECVTPK | 0.060 |
| 115 | PPQAVNLLDK | 0.060 |
| 304 | ALVSTNYPLS | 0.060 |
| 295 | KIPSTKNSIA | 0.060 |
| 293 | GLKIPSTKNS | 0.060 |
| 53 | TLKDDVNIPE | 0.060 |
| 118 | AVNLLDKARL | 0.600 |
| 132 | GIDFIKATKV | 0.060 |
| 331 | VLNSDTCFEN | 0.060 |
| 174 | QEAINSDNYK | 0.060 |
| 66 | CENFQKTDVK | 0.060 |
| 10 | KLRSLASTLD | 0.060 |
| 286 | VPTFCTPGLK | 0.060 |
| 285 | LVPTFCTPGL | 0.060 |
| 318 | SSNDLEVEDR | 0.060 |
| 209 | KMDDFECVTP | 0.060 |
| 120 | NLLDKARLEN | 0.060 |

TABLE XIII-continued

| Start | Subsequence | Score |
|---|---|---|
| 77 | DLSDPPVASS | 0.054 |
| 194 | KQSLVKVLKT | 0.054 |
| 129 | NQEGIDFIKA | 0.054 |
| 151 | MKIREYFQKY | 0.054 |
| 301 | NSIALVSTNY | 0.045 |
| 354 | NLLRTPTPPE | 0.045 |
| 16 | STLDCETARL | 0.045 |
| 287 | PTFCTPGLKI | 0.045 |
| 397 | FLKHGQNIRD | 0.040 |
| 323 | EVEDRTSLVL | 0.036 |
| 173 | EQEAINSDNY | 0.036 |
| 193 | TKQSLVKVLK | 0.030 |
| 238 | MGLKNARNNK | 0.030 |
| 28 | ALDGEESDFE | 0.030 |
| 42 | RILYDLHSEV | 0.030 |
| 117 | QAVNLLDKAR | 0.030 |
| 27 | RALDGEESDF | 0.030 |
| 111 | VLPNPPQAVN | 0.030 |
| 92 | SPRSPQLSDF | 0.030 |
| 121 | LLDKARLENQ | 0.030 |
| 358 | TPTPPEVTKI | 0.027 |
| 303 | IALVSTNYPL | 0.027 |
| 34 | SDFEDYPMRI | 0.027 |
| 363 | EVTKIPEDIL | 0.027 |
| 145 | KNSMDIMKIR | 0.027 |
| 69 | FQKTDVKDDL | 0.027 |
| 36 | FEDYPMRILY | 0.024 |
| 40 | PMRILYDLHS | 0.024 |
| V5-HLA-A3-10mers-193P1E1B Each peptide is a portion of SEQ ID NO:11; each start position is specified, the length of peptide is 10 amino acids, and the end position for each peptide is the start position plus nine. | | |
| 2 | PVASSCISEK | 0.300 |
| 5 | SSCISEKSPR | 0.020 |
| 9 | SEKSPRSPQL | 0.002 |
| 6 | SCISEKSPRS | 0.001 |
| 3 | VASSCISEKS | 0.001 |
| 7 | CISEKSPRSP | 0.000 |
| 8 | ISEKSPRSPQ | 0.000 |
| 1 | PPVASSCISE | 0.000 |
| 4 | ASSCISEKSP | 0.000 |
| 10 | EKSPRSPQLS | 0.000 |
| V6-HLA-A3-10mers-193P1E1B Each peptide is a portion of SEQ ID NO:13; each start position is specified, the length of peptide is 10 amino acids, and the end position for each peptide is the start position plus nine. | | |
| 4 | SEEAIDAESR | 0.012 |
| 10 | AESRLNDNVF | 0.006 |
| 7 | AIDAESRLND | 0.004 |
| 3 | KSEEAIDAES | 0.001 |
| 1 | NNKSEEAIDA | 0.001 |
| 9 | DAESRLNDNV | 0.001 |
| 5 | EEAIDAESRL | 0.001 |
| 8 | IDAESRLNDN | 0.000 |
| 2 | NKSEEAIDAE | 0.000 |
| 6 | EAIDAESRLN | 0.000 |
| V10-HLA-A3-10mers-193P1E1B Each peptide is a portion of SEQ ID NO:21; each start position is specified, the length of peptide is 10 amino acids, and the end position for each peptide is the start position plus nine. | | |
| 13 | WIYPTQKLNK | 30.000 |
| 2 | KIPEDILQKF | 2.025 |
| 6 | DILQKFQWIY | 1.620 |
| 10 | KFQWIYPTQK | 0.180 |
| 1 | TKIPEDILQK | 0.135 |
| 11 | FQWIYPTQKL | 0.135 |
| 8 | LQKFQWIYPT | 0.041 |
| 7 | ILQKFQWIYP | 0.040 |
| 15 | YPTQKLNKMR | 0.020 |
| 5 | EDILQKFQWI | 0.001 |
| 14 | IYPTQKLNKM | 0.000 |
| 4 | PEDILQKFQW | 0.000 |
| 9 | QKFQWIYPTQ | 0.000 |

TABLE XIII-continued

| Start | Subsequence | Score |
|---|---|---|
| 3 | IPEDILQKFQ | 0.000 |
| 12 | QWIYPTQKLN | 0.000 |
| V12-HLA-A3-10mers-193P1E1B Each peptide is a portion of SEQ ID NO:25; each start position is specified, the length of peptide is 10 amino acids, and the end position for each peptide is the start position plus nine. | | |
| 9 | SLLSKYNSNL | 2.700 |
| 3 | ALDGEESLLS | 0.120 |
| 4 | LDGEESLLSK | 0.090 |
| 2 | RALDGEESLL | 0.009 |
| 5 | DGEESLLSKY | 0.003 |
| 1 | QRALDGEESL | 0.001 |
| 7 | EESLLSKYNS | 0.000 |
| 6 | GEESLLSKYN | 0.000 |
| 8 | ESLLSKYNSN | 0.000 |

TABLE XIV

| Start | Subsequence | Score |
|---|---|---|
| V1-HLA-A1101-9mers-193P1E1B Each peptide is a portion of SEQ ID NO:3; each start position is specified, the length of peptide is 9 amino acids, and the end position for each peptide is the start position plus eight. | | |
| 197 | LVKVLKTPK | 2.000 |
| 194 | KQSLVKVLK | 1.800 |
| 129 | NQEGIDFIK | 1.800 |
| 239 | GLKNARNNK | 1.200 |
| 137 | KATKVLMEK | 1.200 |
| 132 | GIDFIKATK | 1.200 |
| 391 | VPPSKRFLK | 0.600 |
| 267 | SPIIQQLEK | 0.600 |
| 387 | AIKAVPPSK | 0.400 |
| 236 | YTMGLKNAR | 0.400 |
| 381 | NLATPIAIK | 0.400 |
| 186 | PVIVTPPTK | 0.300 |
| 16 | STLDCETAR | 0.300 |
| 118 | AVNLLDKAR | 0.200 |
| 287 | PTFCTPGLK | 0.200 |
| 358 | TPTPPEVTK | 0.200 |
| 83 | VASSCISGK | 0.200 |
| 97 | QLSDFGLER | 0.160 |
| 116 | PQAVNLLDK | 0.120 |
| 159 | KYGYSPRVK | 0.120 |
| 157 | FQKYGYSPR | 0.120 |
| 151 | MKIREYFQK | 0.090 |
| 140 | KVLMEKNSM | 0.090 |
| 175 | EAINSDNYK | 0.090 |
| 2 | DPIRSFCGK | 0.090 |
| 397 | FLKHGQNIR | 0.080 |
| 402 | QNIRDVSNK | 0.060 |
| 63 | LSNCENFQK | 0.060 |
| 202 | KTPKCALKM | 0.060 |
| 233 | NEDYTMGLK | 0.060 |
| 86 | SCISGKSPR | 0.060 |
| 199 | KVLKTPKCA | 0.045 |
| 160 | YGYSPRVKK | 0.040 |
| 191 | PPTKQSLVK | 0.040 |
| 306 | VSTNYPLSK | 0.040 |
| 261 | NVFATPSPI | 0.040 |
| 330 | LVLNSDTCF | 0.030 |
| 110 | QVLPNPPQA | 0.030 |
| 314 | KTNSSSNDL | 0.030 |
| 67 | ENFQKTDVK | 0.024 |
| 224 | GISEYTMCL | 0.024 |
| 19 | DCETARLQR | 0.024 |
| 366 | KIPEDILQL | 0.024 |
| 47 | LHSEVQTLK | 0.020 |
| 228 | YTMCLNEDY | 0.020 |
| 215 | CVTPKLEHF | 0.020 |
| 201 | LKTPKCALK | 0.020 |
| 369 | EDILQLLSK | 0.018 |
| 52 | QTLKDDVNI | 0.015 |

TABLE XIV-continued

| Start | Subsequence | Score |
|---|---|---|
| 295 | KIPSTKNSI | 0.012 |
| 144 | EKNSMDIMK | 0.012 |
| 211 | DDFECVTPK | 0.012 |
| 304 | ALVSTNYPL | 0.012 |
| 10 | KLRSLASTL | 0.012 |
| 152 | KIREYFQKY | 0.012 |
| 298 | STKNSIALV | 0.010 |
| 189 | VTPPTKQSL | 0.010 |
| 341 | LTDPSSPTI | 0.010 |
| 364 | VTKIPEDIL | 0.010 |
| 396 | RFLKHGQNI | 0.009 |
| 142 | LMEKNSMDI | 0.008 |
| 349 | ISSYENLLR | 0.008 |
| 34 | SDFEDYPMR | 0.008 |
| 319 | SNDLEVEDR | 0.008 |
| 43 | ILYDLHSEV | 0.008 |
| 39 | YPMRILYDL | 0.008 |
| 154 | REYFQKYGY | 0.007 |
| 323 | EVEDRTSLV | 0.006 |
| 165 | RVKKNSVHE | 0.006 |
| 50 | EVQTLKDDV | 0.006 |
| 363 | EVTKIPEDI | 0.006 |
| 205 | KCALKMDDF | 0.006 |
| 217 | TPKLEHFGI | 0.006 |
| 95 | SPQLSDFGL | 0.006 |
| 270 | IQQLEKSDA | 0.006 |
| 230 | MCLNEDYTM | 0.006 |
| 383 | ATPIAIKAV | 0.005 |
| 389 | KAVPPSKRF | 0.005 |
| 200 | VLKTPKCAL | 0.004 |
| 146 | NSMDIMKIR | 0.004 |
| 382 | LATPIAIKA | 0.004 |
| 222 | HFGISEYTM | 0.004 |
| 272 | QLEKSDAEY | 0.004 |
| 28 | ALDGEESDF | 0.004 |
| 111 | VLPNPPQAV | 0.004 |
| 288 | TFCTPGLKI | 0.004 |
| 135 | FIKATKVLM | 0.004 |
| 388 | IKAVPPSKR | 0.004 |
| 17 | TLDCETARL | 0.004 |
| 374 | LLSKYNSNL | 0.004 |
| 348 | TISSYENLL | 0.004 |
| 181 | NYKEEPVIV | 0.004 |
| 302 | SIALVSTNY | 0.004 |
| 257 | RLNDNVFAT | 0.004 |
| 249 | EEAIDTESR | 0.004 |
| 292 | PGLKIPSTK | 0.003 |
| 71 | KTDVKDDLS | 0.003 |
| 357 | RTPTPPEVT | 0.003 |
| 117 | QAVNLLDKA | 0.003 |
| 327 | RTSLVLNSD | 0.003 |
| V5-HLA-A1101-9mers-193P1E1B<br>Each peptide is a portion of SEQ ID NO:11; each start position is specified, the length of peptide is 9 amino acids, and the end position for each peptide is the start position plus eight. | | |
| 2 | VASSCISEK | 0.200 |
| 5 | SCISEKSPR | 0.060 |
| 1 | PVASSCISE | 0.000 |
| 6 | CISEKSPRS | 0.000 |
| 9 | EKSPRSPQL | 0.000 |
| 8 | SEKSPRSPQ | 0.000 |
| 3 | ASSCISEKS | 0.000 |
| 4 | SSCISEKSP | 0.000 |
| 7 | ISEKSPRSP | 0.000 |
| V6-HLA-A1101-9mers-193P1E1B<br>Each peptide is a portion of SEQ ID NO:13; each start position is specified, the length of peptide is 9 amino acids, and the end position for each peptide is the start position plus eight. | | |
| 4 | EEAIDAESR | 0.004 |
| 5 | EAIDAESRL | 0.001 |
| 9 | AESRLNDNV | 0.001 |
| 1 | NKSEEAIDA | 0.000 |
| 2 | KSEEAIDAE | 0.000 |
| 8 | DAESRLNDN | 0.000 |
| 3 | SEEAIDAES | 0.000 |

TABLE XIV-continued

| Start | Subsequence | Score |
|---|---|---|
| 7 | IDAESRLND | 0.000 |
| 6 | AIDAESRLN | 0.000 |
| V10-HLA-A1101-9mers-193P1E1B<br>Each peptide is a portion of SEQ ID NO:21; each start position is specified, the length of peptide is 9 amino acids, and the end position for each peptide is the start position plus eight. | | |
| 1 | KIPEDILQK | 2.400 |
| 10 | FQWIYPTQK | 1.200 |
| 13 | IYPTQKLNK | 0.800 |
| 15 | PTQKLNKMR | 0.010 |
| 6 | ILQKFQWIY | 0.008 |
| 14 | YPTQKLNKM | 0.002 |
| 2 | IPEDILQKF | 0.002 |
| 5 | DILQKFQWI | 0.002 |
| 7 | LQKFQWIYP | 0.001 |
| 9 | KFQWIYPTQ | 0.001 |
| 12 | WIYPTQKLN | 0.000 |
| 11 | QWIYPTQKL | 0.000 |
| 4 | EDILQKFQW | 0.000 |
| 8 | QKFQWIYPT | 0.000 |
| 3 | PEDILQKFQ | 0.000 |
| V12-HLA-A1101-9mers-193P1E1B<br>Each peptide is a portion of SEQ ID NO:25; each start position is specified, the length of peptide is 9 amino acids, and the end position for each peptide is the start position plus eight. | | |
| 4 | DGEESLLSK | 0.012 |
| 1 | RALDGEESL | 0.009 |
| 2 | ALDGEESLL | 0.004 |
| 5 | GEESLLSKY | 0.002 |
| 8 | SLLSKYNSN | 0.001 |
| 3 | LDGEESLLS | 0.000 |
| 7 | ESLLSKYNS | 0.000 |
| 6 | EESLLSKYN | 0.000 |

TABLE XV

| Start | Subsequence | Score |
|---|---|---|
| V1-HLA-A11-10mers-193P1E1B<br>Each peptide is a portion of SEQ ID NO:3; each start position is specified, the length of peptide is 10 amino acids, and the end position for each peptide is the start position plus nine. | | |
| 390 | AV PPSKRFLK | 6.000 |
| 305 | LVSTNYPLSK | 4.000 |
| 357 | TPTP PEVTK | 3.000 |
| 401 | GQNIRDVSNK | 1.800 |
| 159 | KYGYSPRVKK | 1.200 |
| 150 | IMKIREYFQK | 1.200 |
| 196 | SLVKVLKTPK | 0.600 |
| 200 | VLKTPKCALK | 0.400 |
| 190 | TPPTKQ SLVK | 0.400 |
| 62 | ELSNCENFQK | 0.360 |
| 386 | IAIKAVPPSK | 0.300 |
| 291 | TPGLKIPSTK | 0.200 |
| 286 | VPTFCTPGL K | 0.200 |
| 82 | PVASSCISGK | 0.200 |
| 396 | RFLKHGQ NIR | 0.180 |
| 348 | TISSYENLLR | 0.160 |
| 46 | DLHSEVQTLK | 0.120 |
| 143 | MEKNSMDIMK | 0.120 |
| 199 | KVLKTPKCAL | 0.090 |
| 185 | EPVIVTPPTK | 0.090 |
| 387 | AIKAVPPSKR | 0.080 |
| 380 | SNLATPIAIK | 0.060 |
| 174 | QEAI NSDNYK | 0.060 |
| 66 | CENFQKTDVK | 0.060 |
| 136 | IKATKVLMEK | 0.040 |
| 115 | PPQAVNLLDK | 0.040 |
| 156 | YFQKYGYSPR | 0.040 |
| 261 | NVFATPSPII | 0.040 |
| 232 | LNEDYTMGLK | 0.040 |

TABLE XV-continued

| Start | Subsequence | Score |
|---|---|---|
| 96 | PQLSDFGLER | 0.036 |
| 128 | ENQEGIDFIK | 0.036 |
| 238 | MGLKNARNNK | 0.030 |
| 110 | QVLPNPPQAV | 0.030 |
| 117 | QAVNLLDKAR | 0.030 |
| 216 | VTPKLEHFGI | 0.030 |
| 235 | DYTMGLKNAR | 0.024 |
| 126 | RLENQEGIDF | 0.024 |
| 188 | IVTPPTKQSL | 0.020 |
| 193 | TKQSLVKVLK | 0.020 |
| 1 | MDPIRSFCGK | 0.020 |
| 210 | MDDFECVTPK | 0.020 |
| 118 | AVNLLDKARL | 0.020 |
| 285 | LVPTFCTPGL | 0.020 |
| 42 | RILYDLHSEV | 0.018 |
| 141 | VLMEKNSMDI | 0.016 |
| 16 | STLDCETARL | 0.015 |
| 145 | KNSMDIMKIR | 0.012 |
| 129 | NQEGIDFIKA | 0.012 |
| 219 | KLEHFGISEY | 0.012 |
| 132 | GIDFIKATKV | 0.012 |
| 368 | PEDILQLLSK | 0.012 |
| 366 | KIPEDILQLL | 0.012 |
| 295 | KIPSTKNSIA | 0.012 |
| 323 | EVEDRTSLVL | 0.012 |
| 248 | SEEAIDTESR | 0.012 |
| 102 | GLERYIVSQV | 0.012 |
| 377 | KYNSNLATPI | 0.012 |
| 264 | ATPSPIIQQL | 0.010 |
| 280 | YTNSPLVPTF | 0.010 |
| 189 | VTPPT KQSLV | 0.010 |
| 27 | RALDGEESDF | 0.009 |
| 131 | EGIDFIKATK | 0.009 |
| 140 | KVLMEKNSMD | 0.009 |
| 109 | SQVLPNPPQA | 0.009 |
| 271 | QQLEKSDAEY | 0.009 |
| 231 | CLNEDYTMGL | 0.008 |
| 18 | LDCETARLQR | 0.008 |
| 381 | NLATPIAIKA | 0.008 |
| 229 | TMCLNEDYTM | 0.008 |
| 51 | VQTLKDDVNI | 0.006 |
| 373 | QLLSK YNSNL | 0.006 |
| 69 | FQKTDVKDDL | 0.006 |
| 303 | IALVSTNYPL | 0.006 |
| 329 | SLVLNSDTCF | 0.006 |
| 124 | KARLENQEGI | 0.006 |
| 363 | EVTKIPEDIL | 0.006 |
| 71 | KTDVKDDLSD | 0.006 |
| 157 | FQKYGYSPRV | 0.006 |
| 165 | RVKKNSVHEQ | 0.006 |
| 158 | QKYGYSPRVK | 0.004 |
| 266 | PSPIIQQLEK | 0.004 |
| 269 | IIQQLEKSDA | 0.004 |
| 287 | PTFCTPGLKI | 0.004 |
| 85 | SSCISGKSPR | 0.004 |
| 39 | YPMRILYDLH | 0.004 |
| 374 | LLSKYNSNLA | 0.004 |
| 355 | LLRTPTPPEV | 0.004 |
| 3 | PIRSFCGKLR | 0.004 |
| 296 | IPSTKNSIAL | 0.004 |
| 15 | ASTLDCETAR | 0.004 |
| 97 | QLSDFGLERY | 0.004 |
| 207 | ALKMDDFECV | 0.004 |
| 170 | SVHEQEAINS | 0.004 |
| 318 | SSNDLEVEDR | 0.004 |
| 142 | LMEKNSMDIM | 0.004 |
| 391 | VPPSKRFLKH | 0.004 |
| 340 | NLTDPSSPTI | 0.004 |
| 194 | KQSLVKVLKT | 0.004 |
| 105 | RYIVSQVLPN | 0.004 |
| 314 | KTNSSSNDLE | 0.003 |

TABLE XV-continued

| Start | Subsequence | Score |
|---|---|---|
| V5-HLA-A1101-10mers-193P1E1B Each peptide is a portion of SEQ ID NO:11, each start position is specified, the length of peptide is 10 amino acids, and the end position for each peptide is the start position plus nine. | | |
| 2 | PVASSCISEK | 0.200 |
| 5 | SSCISEKSPR | 0.004 |
| 9 | SEKSPRSPQL | 0.001 |
| 6 | SCISEKSPRS | 0.000 |
| 3 | VASSCISEKS | 0.000 |
| 1 | PPVASSCISE | 0.000 |
| 7 | CISEKSPRSP | 0.000 |
| 8 | ISEKSPRSPQ | 0.000 |
| 4 | ASSCISEKSP | 0.000 |
| 10 | EKSPRSPQLS | 0.000 |
| V6-HLA-A1101-10mers-193P1E1B Each peptide is a portion of SEQ ID NO:13, each start position is specified, the length of peptide is 10 amino acids, and the end position for each peptide is the start position plus nine. | | |
| 4 | SEEAIDAESR | 0.012 |
| 1 | NNKSEEAIDA | 0.001 |
| 7 | AIDAESRLND | 0.001 |
| 9 | DAESRLNDNV | 0.001 |
| 10 | AESRLNDNVF | 0.001 |
| 5 | EEAIDAESRL | 0.000 |
| 3 | KSEEAIDAES | 0.000 |
| 8 | IDAESRLNDN | 0.000 |
| 2 | NKSEEAIDAE | 0.000 |
| 6 | EAIDAESRLN | 0.000 |
| V10-HLA-A1101-10mers-193P1E1B Each peptide is a portion of SEQ ID NO:21; each start position is specified, the length of peptide is 10 amino acids, and the end position for each peptide is the start position plus nine. | | |
| 13 | WIYPTQKLNK | 1.600 |
| 10 | KFQWIYPTQK | 0.600 |
| 1 | TKIPEDILQK | 0.060 |
| 15 | YPTQKLNKMR | 0.020 |
| 2 | KIPEDILQKF | 0.012 |
| 11 | FQWIYPTQKL | 0.012 |
| 14 | IYPTQKLNKM | 0.004 |
| 6 | DILQKFQWIY | 0.004 |
| 8 | LQKFQWIYPT | 0.001 |
| 7 | ILQKFQWIYP | 0.001 |
| 4 | PEDILQKFQW | 0.000 |
| 3 | IPEDILQKFQ | 0.000 |
| 5 | EDILQKFQWI | 0.000 |
| 9 | QKFQWIYPTQ | 0.000 |
| 12 | QWIYPTQKLN | 0.000 |
| V12-HLA-A1101-10mers-193P1E1B Each peptide is a portion of SEQ ID NO:25; each start position is specified, the length of peptide is 10 amino acids, and the end position for each peptide is the start position plus nine. | | |
| 4 | LDGEESLLSK | 0.040 |
| 2 | RALDGEESLL | 0.009 |
| 9 | SLLSKYNSNL | 0.006 |
| 3 | ALDGEESLLS | 0.001 |
| 1 | QRALDGEESL | 0.000 |
| 6 | GEESLLSKYN | 0.000 |
| 5 | DGEESLLSKY | 0.000 |
| 7 | EESLLSKYNS | 0.000 |
| 8 | ESLLSKYNSN | 0.000 |

TABLE XVI

| Start | Subsequence | Score |
|---|---|---|
| V1-HLA-A24-9mers-193P1E1B Each peptide is a portion of SEQ ID NO:3; each start position is specified, the length of peptide is 9 amino acids, and the end position for each peptide is the start position plus eight. | | |
| 212 | DFECVTPKL | 46.200 |
| 134 | DFIKATKVL | 30.000 |

TABLE XVI-continued

| Start | Subsequence | Score |
|---|---|---|
| 6 | SFCGKLRSL | 20.000 |
| 396 | RFLKHGQNI | 18.000 |
| 366 | KIPEDILQL | 14.400 |
| 314 | KTNSSSNDL | 14.400 |
| 367 | IPEDILQLL | 12.096 |
| 10 | KLRSLASTL | 9.600 |
| 35 | DFEDYPMRI | 9.000 |
| 189 | VTPPTKQSL | 8.640 |
| 39 | YPMRILYDL | 8.400 |
| 265 | TPSPIIQQL | 8.064 |
| 309 | NYPLSKTNS | 7.500 |
| 114 | NPPQAVNLL | 7.200 |
| 250 | EAIDTESRL | 7.200 |
| 389 | KAVPPSKRF | 7.200 |
| 390 | AVPPSKRFL | 7.200 |
| 232 | LNEDYTMGL | 7.200 |
| 161 | GYSPRVKKN | 6.600 |
| 95 | SPQLSDFGL | 6.000 |
| 119 | VNLLDKARL | 6.000 |
| 304 | ALVSTNYPL | 6.000 |
| 277 | DAEYTNSPL | 6.000 |
| 181 | NYKEEPVIV | 6.000 |
| 288 | TFCTPGLKI | 5.500 |
| 235 | DYTMGLKNA | 5.000 |
| 262 | VFATPSPII | 5.000 |
| 155 | EYFQKYGYS | 5.000 |
| 224 | GISEYTMCL | 4.800 |
| 46 | DLHSEVQTL | 4.800 |
| 21 | ETARLQRAL | 4.800 |
| 333 | NSDTCFENL | 4.800 |
| 348 | TISSYENLL | 4.800 |
| 149 | DIMKIREYF | 4.200 |
| 200 | VLKTPKCAL | 4.000 |
| 286 | VPTFCTPGL | 4.000 |
| 364 | VTKIPEDIL | 4.000 |
| 17 | TLDCETARL | 4.000 |
| 205 | KCALKMDDF | 4.000 |
| 374 | LLSKYNSNL | 4.000 |
| 295 | KIPSTKNSI | 3.600 |
| 330 | LVLNSDTCF | 3.000 |
| 244 | RNNKSEEAI | 3.000 |
| 281 | TNSPLVPTF | 2.880 |
| 222 | HFGISEYTM | 2.500 |
| 215 | CVTPKLEHF | 2.400 |
| 255 | ESRLNDNVF | 2.400 |
| 145 | KNSMDIMKI | 2.200 |
| 28 | ALDGEESDF | 2.000 |
| 128 | ENQEGIDFI | 1.800 |
| 140 | KVLMEKNSM | 1.800 |
| 202 | KTPKCALKM | 1.650 |
| 380 | SNLATPIAI | 1.500 |
| 105 | RYIVSQVLP | 1.500 |
| 142 | LMEKNSMDI | 1.500 |
| 169 | NSVHEQEAI | 1.500 |
| 80 | DPPVASSCI | 1.500 |
| 52 | QTLKDDVNI | 1.500 |
| 377 | KYNSNLATP | 1.500 |
| 363 | EVTKIPEDI | 1.400 |
| 341 | LTDPSSPTI | 1.200 |
| 378 | YNSNLATPI | 1.200 |
| 180 | DNYKEEPVI | 1.000 |
| 217 | TPKLEHFGI | 1.000 |
| 159 | KYGYSPRVK | 1.000 |
| 261 | NVFATPSPI | 1.000 |
| 337 | CFENLTDPS | 0.900 |
| 351 | SYENLLRTP | 0.900 |
| 55 | KDDVNIPEL | 0.880 |
| 230 | MCLNEDYTM | 0.750 |
| 38 | DYPMRILYD | 0.750 |
| 322 | LEVEDRTSL | 0.720 |
| 193 | TKQSLVKVL | 0.720 |
| 113 | PNPPQAVNL | 0.720 |
| 104 | ERYIVSQVL | 0.672 |
| 70 | QKTDVKDDL | 0.672 |
| 227 | EYTMCLNED | 0.660 |
| 347 | PTISSYENL | 0.600 |
| 33 | ESDFEDYPM | 0.500 |

TABLE XVI-continued

| Start | Subsequence | Score |
|---|---|---|
| 44 | LYDLHSEVQ | 0.500 |
| 135 | FIKATKVLM | 0.500 |
| 279 | EYTNSPLVP | 0.500 |
| 100 | DFGLERYIV | 0.500 |
| 90 | GKSPRSPQL | 0.480 |
| 3 | PIRSFCGKL | 0.440 |
| 324 | VEDRTSLVL | 0.400 |
| 297 | PSTKNSIAL | 0.400 |
| 36 | FEDYPMRIL | 0.400 |
| 152 | KIREYFQKY | 0.380 |
| 91 | KSPRSPQLS | 0.360 |
| 257 | RLNDNVFAT | 0.360 |
| 199 | KVLKTPKCA | 0.300 |
| 357 | RTPTPPEVT | 0.300 |
| 12 | RSLASTLDC | 0.300 |
| 127 | LENQEGIDF | 0.300 |
| 168 | KNSVHEQEA | 0.264 |
| 209 | KMDDFECVT | 0.240 |
| 185 | EPVIVTPPT | 0.210 |
| 282 | NSPLVPTFC | 0.210 |
| 400 | HGQNIRDVS | 0.210 |

V5-HLA-A24-9mers-193P1E1B

Each peptide is a portion of SEQ ID NO:11; each start position is specified, the length of peptide is 9 amino acids, and the end position for each peptide is the start position plus eight.

| Start | Subsequence | Score |
|---|---|---|
| 9 | EKSPRSPQL | 0.480 |
| 3 | ASSCISEKS | 0.154 |
| 6 | CISEKSPRS | 0.120 |
| 7 | ISEKSPRSP | 0.015 |
| 5 | SCISEKSPR | 0.015 |
| 2 | VASSCISEK | 0.011 |
| 4 | SSCISEKSP | 0.010 |
| 8 | SEKSPRSPQ | 0.001 |
| 1 | PVASSCISE | 0.001 |

V6-HLA-A24-9mers-193P1E1B

Each peptide is a portion of SEQ ID NO:13; each start position is specified, the length of peptide is 9 amino acids, and the end position for each peptide is the start position plus eight.

| Start | Subsequence | Score |
|---|---|---|
| 5 | EAIDAESRL | 7.200 |
| 8 | DAESRLNDN | 0.180 |
| 6 | AIDAESRLN | 0.100 |
| 2 | KSEEAIDAE | 0.036 |
| 3 | SEEAIDAES | 0.023 |
| 9 | AESRLNDNV | 0.012 |
| 1 | NKSEEAIDA | 0.012 |
| 7 | IDAESRLND | 0.001 |
| 4 | EEAIDAESR | 0.001 |

V10-HLA-A24-9mers-193P1E1B

Each peptide is a portion of SEQ ID NO:21; each start position is specified, the length of peptide is 9 amino acids, and the end position for each peptide is the start position plus eight.

| Start | Subsequence | Score |
|---|---|---|
| 11 | QWIYPTQKL | 7.920 |
| 2 | IPEDILQKF | 6.653 |
| 5 | DILQKFQWI | 2.160 |
| 13 | IYPTQKLNK | 0.750 |
| 14 | YPTQKLNKM | 0.660 |
| 9 | KFQWIYPTQ | 0.210 |
| 6 | ILQKFQWIY | 0.150 |
| 12 | WIYPTQKLN | 0.120 |
| 1 | KIPEDILQK | 0.036 |
| 4 | EDILQKFQW | 0.015 |
| 7 | LQKFQWIYP | 0.010 |
| 8 | QKFQWIYPT | 0.010 |
| 10 | FQWIYPTQK | 0.010 |
| 15 | PTQKLNKMR | 0.002 |
| 3 | PEDILQKFQ | 0.000 |

V12-HLA-A24-9mers-193P1E1B

Each peptide is a portion of SEQ ID NO:25; each start position is specified, the length of peptide is 9 amino acids, and the end position for each peptide is the start position plus eight.

| Start | Subsequence | Score |
|---|---|---|
| 1 | RALDGEESL | 14.400 |
| 2 | ALDGEESLL | 4.000 |
| 8 | SLLSKYNSN | 0.180 |
| 7 | ESLLSKYNS | 0.150 |

TABLE XVI-continued

| Start | Subsequence | Score |
|---|---|---|
| 5 | GEESLLSKY | 0.020 |
| 4 | DGEESLLSK | 0.018 |
| 6 | EESLLSKYN | 0.012 |
| 3 | LDGEESLLS | 0.012 |

TABLE XVII

| Start | Subsequence | Score |
|---|---|---|
| V1-HLA-A24-10mers-193P1E1B Each peptide is a portion of SEQ ID NO:3; each start position is specified, the length of peptide is 10 amino acids, and the end position for each peptide is the start position plus nine. | | |
| 38 | DYPMRILYDL | 420.000 |
| 377 | KYNSNLATPI | 180.000 |
| 35 | DFEDYPMRIL | 36.000 |
| 366 | KIPEDILQLL | 24.192 |
| 105 | RYIVSQVLPN | 15.000 |
| 389 | KAVPPSKRFL | 14.400 |
| 94 | RSPQLSDFGL | 12.000 |
| 199 | KVLKTPKCAL | 12.000 |
| 264 | ATPSPIIQQL | 10.080 |
| 351 | SYENLLRTPT | 9.000 |
| 309 | NYPLSKTNSS | 9.000 |
| 161 | GYSPRVKKNS | 8.400 |
| 5 | RSFCGKLRSL | 8.000 |
| 231 | CLNEDYTMGL | 7.200 |
| 16 | STLDCETARL | 7.200 |
| 112 | LPNPPQAVNL | 7.200 |
| 323 | EV EDRTSLVL | 7.200 |
| 27 | RALDGEESDF | 7.200 |
| 2 | DPIRSFCGKL | 6.600 |
| 227 | EYTMCLNEDY | 6.000 |
| 181 | NYKEEPVIVT | 6.000 |
| 321 | DLEVEDRTSL | 6.000 |
| 118 | AVNLL DKARL | 6.000 |
| 373 | QLLSKYNSNL | 6.000 |
| 126 | RLENQ EGIDF | 6.000 |
| 285 | LVPTFCTPGL | 6.000 |
| 223 | FGISEYTMCL | 6.000 |
| 303 | IALVSTNYPL | 6.000 |
| 188 | IVTPPTKQSL | 5.760 |
| 332 | LNSDTCFENL | 5.760 |
| 69 | FQKTDVKDDL | 5.600 |
| 44 | LYDLHSEVQT | 5.000 |
| 279 | EYTNSPLVPT | 5.000 |
| 296 | IPSTKNSIAL | 4.000 |
| 363 | EVTKIPEDIL | 4.000 |
| 89 | SGKSPRSPQL | 4.000 |
| 346 | SPTISSYENL | 4.000 |
| 134 | DFIKATKVLM | 3.750 |
| 280 | YTNSPLVPTF | 3.600 |
| 60 | IPELSNCENF | 3.000 |
| 214 | ECVTPKLEHF | 3.000 |
| 329 | SLVLN SDTCF | 3.000 |
| 124 | KARL ENQEGI | 2.000 |
| 92 | SPRSPQLSDF | 2.000 |
| 168 | KNS VHEQEAI | 2.000 |
| 141 | VLMEKNSMDI | 1.800 |
| 260 | DNVFATPSPI | 1.500 |
| 379 | NSNLATPIAI | 1.500 |
| 216 | VTPKLEHFGI | 1.500 |
| 358 | TPTPPEVTKI | 1.320 |
| 340 | NLTDPSSPTI | 1.200 |
| 98 | LSDFGLERYI | 1.200 |
| 159 | KYGYSPRVKK | 1.100 |
| 51 | VQTLKDDVNI | 1.000 |
| 261 | NVFATPSPII | 1.000 |
| 113 | PNPPQAVNLL | 0.864 |
| 337 | CFENLTDPSS | 0.750 |
| 142 | LMEKNSMDIM | 0.750 |
| 211 | DDFECVTPKL | 0.739 |
| 9 | GKLRSLASTL | 0.720 |
| 365 | TKIPEDILQL | 0.720 |

TABLE XVII-continued

| Start | Subsequence | Score |
|---|---|---|
| 347 | PTISSYENLL | 0.720 |
| 45 | YDLHSEVQTL | 0.720 |
| 235 | DYTMGLKNAR | 0.720 |
| 103 | LERYIVSQVL | 0.672 |
| 6 | SFCGKLRSLA | 0.600 |
| 247 | KSEEAIDTES | 0.554 |
| 54 | LKDDVNIPEL | 0.528 |
| 155 | EYFQKYGYSP | 0.500 |
| 222 | HFGISEYTMC | 0.500 |
| 100 | DFGLERYIVS | 0.500 |
| 229 | TMCLNEDYTM | 0.500 |
| 276 | SDAEYTNSPL | 0.480 |
| 20 | CETARLQRAL | 0.480 |
| 192 | PTKQ SLVKVL | 0.480 |
| 313 | SKTNSSSNDL | 0.480 |
| 148 | MDIMKIREYF | 0.420 |
| 133 | IDFIKATKVL | 0.400 |
| 249 | EEAIDTESRL | 0.400 |
| 42 | RILYDLHSEV | 0.396 |
| 219 | KLEHFGISEY | 0.330 |
| 295 | KIPSTKNSIA | 0.300 |
| 137 | KATKVLMEKN | 0.264 |
| 300 | KNSIALVSTN | 0.240 |
| 254 | TESRLNDNVF | 0.240 |
| 395 | KRFLK HGQNI | 0.240 |
| 327 | RTSLVL NSDT | 0.240 |
| 63 | LSNCENFQKT | 0.238 |
| 194 | KQSLVKVLKT | 0.220 |
| 294 | LKIPSTKNSI | 0.216 |
| 110 | QVLPNPPQAV | 0.216 |
| 367 | IPEDILQLLS | 0.216 |
| 30 | DGEESDFEDY | 0.216 |
| 102 | GLERYIVSQV | 0.210 |
| 301 | NSIALVSTNY | 0.210 |
| 388 | IKAVPPSKRF | 0.200 |
| 271 | QQLEKSDAEY | 0.198 |
| 59 | NIPELSNCEN | 0.198 |
| 129 | NQEGIDFIKA | 0.198 |
| 120 | NLLDKARLEN | 0.198 |
| V5-HLA-A24-10mers-193P1E1B Each peptide is a portion of SEQ ID NO:11; each start position is specified, the length of peptide is 10 amino acids, and the end position for each peptide is the start position plus nine. | | |
| 9 | SEKSPRSPQL | 0.400 |
| 3 | VASSCISEKS | 0.154 |
| 6 | SCISEKSPRS | 0.150 |
| 8 | ISEKSPRSPQ | 0.015 |
| 10 | EKSPRSPQLS | 0.014 |
| 7 | CISEKSPRSP | 0.012 |
| 4 | ASSCISEKSP | 0.010 |
| 5 | SSCISEKSPR | 0.010 |
| 1 | PPVASSCISE | 0.002 |
| 2 | PVASSCISEK | 0.001 |
| V6-HLA-A24-10mers-193P1E1B Each peptide is a portion of SEQ ID NO:13; each start position is specified, the length of peptide is 10 amino acids, and the end position for each peptide is the start position plus nine. | | |
| 3 | KSEEAIDAES | 0.554 |
| 5 | EEAIDAESRL | 0.400 |
| 10 | AESRLNDNVF | 0.240 |
| 6 | EAIDAESRLN | 0.180 |
| 9 | DAESRLNDNV | 0.180 |
| 1 | NNKSEEAIDA | 0.100 |
| 8 | IDAESRLNDN | 0.014 |
| 7 | AIDAESRLND | 0.010 |
| 4 | SEEAIDAESR | 0.002 |
| 2 | NKSEEAIDAE | 0.001 |
| V10-HLA-A24-10mers-193P1E1B Each peptide is a portion of SEQ ID NO:21; each start position is specified, the length of peptide is 10 amino acids, and the end position for each peptide is the start position plus nine. | | |
| 14 | IYPTQKLNKM | 49.500 |
| 2 | KIPEDILQKF | 13.306 |
| 11 | FQWIYPTQKL | 5.280 |

TABLE XVII-continued

| Start | Subsequence | Score |
|---|---|---|
| 5 | EDILQKFQWI | 0.216 |
| 10 | KFQWIYPTQK | 0.150 |
| 6 | DILQKFQWIY | 0.150 |
| 12 | QWIYPTQKLN | 0.150 |
| 8 | LQKFQWIYPT | 0.100 |
| 3 | IPEDILQKFQ | 0.022 |
| 7 | ILQKFQWIYP | 0.015 |
| 15 | YPTQKLNKMR | 0.012 |
| 13 | WIYPTQKLNK | 0.012 |
| 1 | TKIPEDILQK | 0.002 |
| 9 | QKFQWIYPTQ | 0.001 |
| 4 | PEDILQKFQW | 0.001 |
| V12-HLA-A24-10mers-193P1E1B Each peptide is a portion of SEQ ID NO:25; each start position is specified, the length of peptide is 10 amino acids, and the end position for each peptide is the start position plus nine. | | |
| 2 | RALDGEESLL | 14.400 |
| 9 | SLLSKYNSNL | 6.000 |
| 1 | QRALDGEESL | 0.400 |
| 5 | DGEESLLSKY | 0.238 |
| 8 | ESLLSKYNSN | 0.180 |
| 3 | ALDGEESLLS | 0.100 |
| 6 | GEESLLSKYN | 0.018 |
| 7 | EESLLSKYNS | 0.010 |
| 4 | LDGEESLLSK | 0.001 |

TABLE XVIII

| Start | Subsequence | Score |
|---|---|---|
| V1-HLA-B7-9mers-193P1E1B Each peptide is a portion of SEQ ID NO:3; each start position is specified, the length of peptide is 9 amino acids, and the end position for each peptide is the start position plus eight. | | |
| 39 | YPMRILYDL | 240.000 |
| 265 | TPSPIIQQL | 80.000 |
| 114 | NPPQAVNLL | 80.000 |
| 95 | SPQLSDFGL | 80.000 |
| 286 | VPTFCTPGL | 80.000 |
| 390 | AVPPSKRFL | 60.000 |
| 10 | KLRSLASTL | 40.000 |
| 163 | SPRVKKNSV | 40.000 |
| 367 | IPEDILQLL | 24.000 |
| 304 | ALVSTNYPL | 12.000 |
| 250 | EAIDTESRL | 12.000 |
| 80 | DPPVASSCI | 8.000 |
| 217 | TPKLEHFGI | 8.000 |
| 200 | VLKTPKCAL | 6.000 |
| 364 | VTKIPEDIL | 6.000 |
| 140 | KVLMEKNSM | 5.000 |
| 189 | VTPPTKQSL | 4.000 |
| 3 | PIRSFCGKL | 4.000 |
| 314 | KTNSSSNDL | 4.000 |
| 374 | LLSKYNSNL | 4.000 |
| 224 | GISEYTMCL | 4.000 |
| 190 | TPPTKQSLV | 4.000 |
| 119 | VNLLDKARL | 4.000 |
| 366 | KIPEDILQL | 4.000 |
| 46 | DLHSEVQTL | 4.000 |
| 348 | TISSYENLL | 4.000 |
| 21 | ETARLQRAL | 4.000 |
| 277 | DAEYTNSPL | 3.600 |
| 92 | SPRSPQLSD | 3.000 |
| 283 | SPLVPTFCT | 3.000 |
| 185 | EPVIVTPPT | 2.000 |
| 261 | NVFATPSPI | 2.000 |
| 296 | IPSTKNSIA | 2.000 |
| 363 | EVTKIPEDI | 2.000 |
| 291 | TPGLKIPST | 2.000 |
| 232 | LNEDYTMGL | 1.200 |
| 17 | TLDCETARL | 1.200 |
| 333 | NSDTCFENL | 1.200 |

TABLE XVIII-continued

| Start | Subsequence | Score |
|---|---|---|
| 50 | EVQTLKDDV | 1.000 |
| 135 | FIKATKVLM | 1.000 |
| 230 | MCLNEDYTM | 1.000 |
| 202 | KTPKCALKM | 1.000 |
| 383 | ATPIAIKAV | 0.600 |
| 343 | DPSSPTISS | 0.600 |
| 112 | LPNPPQAVN | 0.600 |
| 322 | LEVEDRTSL | 0.600 |
| 110 | QVLPNPPQA | 0.500 |
| 199 | KVLKTPKCA | 0.500 |
| 22 | TARLQRALD | 0.450 |
| 113 | PNPPQAVNL | 0.400 |
| 70 | QKTDVKDDL | 0.400 |
| 297 | PSTKNSIAL | 0.400 |
| 145 | KNSMDIMKI | 0.400 |
| 169 | NSVHEQEAI | 0.400 |
| 347 | PTISSYENL | 0.400 |
| 90 | GKSPRSPQL | 0.400 |
| 134 | DFIKATKVL | 0.400 |
| 310 | YPLSKTNSS | 0.400 |
| 346 | SPTISSYEN | 0.400 |
| 378 | YNSNLATPI | 0.400 |
| 6 | SFCGKLRSL | 0.400 |
| 193 | TKQSLVKVL | 0.400 |
| 180 | DNYKEEPVI | 0.400 |
| 295 | KIPSTKNSI | 0.400 |
| 244 | RNNKSEEAI | 0.400 |
| 104 | ERYIVSQVL | 0.400 |
| 128 | ENQEGIDFI | 0.400 |
| 380 | SNLATPIAI | 0.400 |
| 52 | QTLKDDVNI | 0.400 |
| 323 | EVEDRTSLV | 0.300 |
| 117 | QAVNLLDKA | 0.300 |
| 15 | ASTLDCETA | 0.300 |
| 33 | ESDFEDYPM | 0.300 |
| 382 | LATPIAIKA | 0.300 |
| 242 | NARNNKSEE | 0.300 |
| 207 | ALKMDDFEC | 0.300 |
| 111 | VLPNPPQAV | 0.300 |
| 391 | VPPSKRFLK | 0.300 |
| 124 | KARLENQEG | 0.300 |
| 358 | TPTPPEVTK | 0.300 |
| 14 | LASTLDCET | 0.300 |
| 384 | TPIAIKAVP | 0.200 |
| 360 | TPPEVTKIP | 0.200 |
| 2 | DPIRSFCGK | 0.200 |
| 298 | STKNSIALV | 0.200 |
| 152 | KIREYFQKY | 0.200 |
| 43 | ILYDLHSEV | 0.200 |
| 203 | TPKCALKMD | 0.200 |
| 316 | NSSSNDLEV | 0.200 |
| 267 | SPIIQQLEK | 0.200 |
| 103 | LERYIVSQV | 0.200 |
| 255 | ESRLNDNVF | 0.200 |
| 36 | FEDYPMRIL | 0.180 |
| 355 | LLRTPTPPE | 0.150 |
| 280 | YTNSPLVPT | 0.150 |
| 57 | DVNIPELSN | 0.150 |
| 340 | NLTDPSSPT | 0.150 |
| 7 | FCGKLRSLA | 0.150 |
| 118 | AVNLLDKAR | 0.150 |
| 307 | STNYPLSKT | 0.150 |
| V5-HLA-B7-9mers-193P1E1B Each peptide is a portion of SEQ ID NO:11; each start position is specified, the length of peptide is 9 amino acids, and the end position for each peptide is the start position plus eight. | | |
| 9 | EKSPRSPQL | 0.400 |
| 3 | ASSCISEKS | 0.060 |
| 2 | VASSCISEK | 0.030 |
| 6 | CISEKSPRS | 0.020 |
| 5 | SCISEKSPR | 0.010 |
| 4 | SSCISEKSP | 0.010 |
| 1 | PVASSCISE | 0.005 |
| 7 | ISEKSPRSP | 0.003 |
| 8 | SEKSPRSPQ | 0.002 |

TABLE XVIII-continued

| Start | Subsequence | Score |
|---|---|---|
| V6-HLA-B7-9mers-193P1E1B Each peptide is a portion of SEQ ID NO:13; each start position is specified, the length of peptide is 9 amino acids, and the end position for each peptide is the start position plus eight. | | |
| 5 | EAIDAESRL | 12.000 |
| 9 | AESRLNDNV | 0.060 |
| 6 | AIDAESRLN | 0.018 |
| 8 | DAESRLNDN | 0.018 |
| 1 | NKSEEAIDA | 0.010 |
| 2 | KSEEAIDAE | 0.003 |
| 7 | IDAESRLND | 0.002 |
| 4 | EEAIDAESR | 0.001 |
| 3 | SEEAIDAES | 0.001 |
| V10-HLA-B7-9mers-193P1E1B Each peptide is a portion of SEQ ID NO:21; each start position is specified, the length of peptide is 9 amino acids, and the end position for each peptide is the start position plus eight. | | |
| 14 | YPTQKLNKM | 20.000 |
| 11 | QWIYPTQKL | 0.600 |
| 5 | DILQKFQWI | 0.400 |
| 2 | IPEDILQKF | 0.120 |
| 12 | WIYPTQKLN | 0.020 |
| 6 | ILQKFQWIY | 0.020 |
| 8 | QKFQWIYPT | 0.010 |
| 7 | LQKFQWIYP | 0.010 |
| 10 | FQWIYPTQK | 0.010 |
| 1 | KIPEDILQK | 0.010 |
| 4 | EDILQKFQW | 0.002 |
| 13 | IYPTQKLNK | 0.001 |
| 15 | PTQKLNKMR | 0.001 |
| 9 | KFQWIYPTQ | 0.001 |
| 3 | PEDILQKFQ | 0.000 |
| V12-HLA-B7-9mers-193P1E1B Each peptide is a portion of SEQ ID NO:25; each start position is specified, the length of peptide is 9 amino acids, and the end position for each peptide is the start position plus eight. | | |
| 1 | RALDGEESL | 12.000 |
| 2 | ALDGEESLL | 3.600 |
| 7 | ESLLSKYNS | 0.020 |
| 8 | SLLSKYNSN | 0.020 |
| 4 | DGEESLLSK | 0.003 |
| 3 | LDGEESLLS | 0.002 |
| 6 | EESLLSKYN | 0.002 |
| 5 | GEESLLSKY | 0.001 |

TABLE XIX

| Start | Subsequence | Score |
|---|---|---|
| V1-HLA-B7-10mers-193P1E1B Each peptide is a portion of SEQ ID NO:3; each start position is specified, the length of peptide is 10 amino acids, and the end position for each peptide is the start position plus nine. | | |
| 296 | IPSTKNSIAL | 80.000 |
| 2 | DPIRSFCGKL | 80.000 |
| 112 | LPNPPQAVNL | 80.000 |
| 346 | SPTISSYENL | 80.000 |
| 118 | AVNLLDKARL | 60.000 |
| 363 | EVTKIPEDIL | 30.000 |
| 199 | KVLKTPKCAL | 30.000 |
| 188 | IVTPPTKQSL | 20.000 |
| 285 | LVPTFCTPGL | 20.000 |
| 303 | IALVSTNYPL | 12.000 |
| 389 | KAVPPSKRFL | 12.000 |
| 264 | ATPSPIIQQL | 12.000 |
| 124 | KARLENQEGI | 12.000 |
| 358 | TPTPPEVTKI | 8.000 |
| 323 | EVEDRTSLVL | 6.000 |
| 231 | CLNEDYTMGL | 4.000 |
| 366 | KIPEDILQLL | 4.000 |

TABLE XIX-continued

| Start | Subsequence | Score |
|---|---|---|
| 103 | LERYIVSQVL | 4.000 |
| 69 | FQKTDVKDDL | 4.000 |
| 92 | SPRSPQLSDF | 4.000 |
| 94 | RSPQLSDFGL | 4.000 |
| 5 | RSFCGKLRSL | 4.000 |
| 223 | FGISEYTMCL | 4.000 |
| 332 | LNSDTCFENL | 4.000 |
| 16 | STLDCETARL | 4.000 |
| 89 | SGKSPRSPQL | 4.000 |
| 373 | QLLSKYNSNL | 4.000 |
| 261 | NVFATPSPII | 3.000 |
| 242 | NARNNKSEEA | 3.000 |
| 355 | LLRTPTPPEV | 2.000 |
| 163 | SPRVKKNSVH | 2.000 |
| 321 | DLEVEDRTSL | 1.800 |
| 110 | QVLPNPPQAV | 1.500 |
| 141 | VLMEKNSMDI | 1.200 |
| 255 | ESRLNDNVFA | 1.000 |
| 229 | TMCLNEDYTM | 1.000 |
| 207 | ALKMDDFECV | 0.600 |
| 382 | LATPIAIKAV | 0.600 |
| 39 | YPMRILYDLH | 0.600 |
| 57 | DVNIPELSNC | 0.500 |
| 197 | LVKVLKTPKC | 0.500 |
| 133 | IDFIKATKVL | 0.400 |
| 379 | NSNLATPIAI | 0.400 |
| 217 | TPKLEHFGIS | 0.400 |
| 191 | PPTKQSLVKV | 0.400 |
| 365 | TKIPEDILQL | 0.400 |
| 343 | DPSSPTISSY | 0.400 |
| 9 | GKLRSLASTL | 0.400 |
| 168 | KNSVHEQEAI | 0.400 |
| 276 | SDAEYTNSPL | 0.400 |
| 38 | DYPMRILYDL | 0.400 |
| 216 | VTPKLEHFGI | 0.400 |
| 211 | DDFECVTPKL | 0.400 |
| 45 | YDLHSEVQTL | 0.400 |
| 51 | VQTLKDDVNI | 0.400 |
| 20 | CETARLQRAL | 0.400 |
| 260 | DNVFATPSPI | 0.400 |
| 192 | PTKQSLVKVL | 0.400 |
| 313 | SKTNSSSNDL | 0.400 |
| 340 | NLTDPSSPTI | 0.400 |
| 267 | SPIIQQLEKS | 0.400 |
| 113 | PNPPQAVNLL | 0.400 |
| 249 | EEAIDTESRL | 0.400 |
| 80 | DPPVASSCIS | 0.400 |
| 347 | PTISSYENLL | 0.400 |
| 310 | YPLSKTNSSS | 0.400 |
| 228 | YTMCLNEDYT | 0.300 |
| 14 | LASTLDCETA | 0.300 |
| 22 | TARLQRALDG | 0.300 |
| 142 | LMEKNSMDIM | 0.300 |
| 206 | CALKMDDFEC | 0.300 |
| 390 | AVPPSKRFLK | 0.225 |
| 283 | SPLVPTFCTP | 0.200 |
| 25 | LQRALDGEES | 0.200 |
| 291 | TPGLKIPSTK | 0.200 |
| 265 | TPSPIIQQLE | 0.200 |
| 185 | EPVIVTPPTK | 0.200 |
| 180 | DNYKEEPVIV | 0.200 |
| 203 | TPKCALKMDD | 0.200 |
| 286 | VPTFCTPGLK | 0.200 |
| 403 | NIRDVSNKEN | 0.200 |
| 391 | VPPSKRFLKH | 0.200 |
| 189 | VTPPTKQSLV | 0.200 |
| 114 | NPPQAVNLLD | 0.200 |
| 384 | TPIAIKAVPP | 0.200 |
| 42 | RILYDLHSEV | 0.200 |
| 95 | SPQLSDFGLE | 0.200 |
| 315 | TNSSSNDLEV | 0.200 |
| 190 | TPPTKQSLVK | 0.200 |
| 157 | FQKYGYSPRV | 0.200 |
| 360 | TPPEVTKIPE | 0.200 |
| 162 | YSPRVKKNSV | 0.200 |
| 35 | DFEDYPMRIL | 0.180 |
| 277 | DAEYTNSPLV | 0.180 |

TABLE XIX-continued

| Start | Subsequence | Score |
|---|---|---|
| 306 | VSTNYPLSKT | 0.150 |
| 339 | ENLTDPSSPT | 0.150 |
| 282 | NSPLVPTFCT | 0.150 |
| 60 | IPELSNCENF | 0.120 |
| 243 | ARNNKSEEAI | 0.120 |
| 367 | IPEDILQLLS | 0.120 |
| V5-HLA-B7-10mers-193P1E1B Each peptide is a portion of SEQ ID NO:11; each start position is specified, the length of peptide is 10 amino acids, and the end position for each peptide is the start position plus nine. | | |
| 9 | SEKSPRSPQL | 0.400 |
| 3 | VASSCISEKS | 0.060 |
| 4 | ASSCISEKSP | 0.030 |
| 6 | SCISEKSPRS | 0.020 |
| 1 | PPVASSCISE | 0.020 |
| 5 | SSCISEKSPR | 0.010 |
| 7 | CISEKSPRSP | 0.010 |
| 8 | ISEKSPRSPQ | 0.007 |
| 2 | PVASSCISEK | 0.005 |
| 10 | EKSPRSPQLS | 0.002 |
| V6-HLA-B7-10mers-193P1E1B Each peptide is a portion of SEQ ID NO:13; each start position is specified, the length of peptide is 10 amino acids, and the end position for each peptide is the start position plus nine. | | |
| 5 | EEAIDAESRL | 0.400 |
| 9 | DAESRLNDNV | 0.180 |
| 1 | NNKSEEAIDA | 0.100 |
| 6 | EAIDAESRLN | 0.060 |
| 7 | AIDAESRLND | 0.013 |
| 10 | AESRLNDNVF | 0.006 |
| 3 | KSEEAIDAES | 0.006 |
| 8 | IDAESRLNDN | 0.002 |
| 2 | NKSEEAIDAE | 0.001 |
| 4 | SEEAIDAESR | 0.000 |
| V10-HLA-B7-10mers-193P1E1B Each peptide is a portion of SEQ ID NO:21; each start position is specified, the length of peptide is 10 amino acids, and the end position for each peptide is the start position plus nine. | | |
| 11 | FQWIYPTQKL | 6.000 |
| 15 | YPTQKLNKMR | 0.200 |
| 14 | IYPTQKLNKM | 0.100 |
| 8 | LQKFQWIYPT | 0.100 |
| 3 | IPEDILQKFQ | 0.060 |
| 5 | EDILQKFQWI | 0.040 |
| 6 | DILQKFQWIY | 0.020 |
| 2 | KIPEDILQKF | 0.020 |
| 13 | WIYPTQKLNK | 0.010 |
| 7 | ILQKFQWIYP | 0.010 |
| 12 | QWIYPTQKLN | 0.002 |
| 9 | QKFQWIYPTQ | 0.001 |
| 10 | KFQWIYPTQK | 0.001 |
| 1 | TKIPEDILQK | 0.001 |
| 4 | PEDILQKFQW | 0.000 |
| V12-HLA-B7-10mers-193P1E1B Each peptide is a portion of SEQ ID NO:25; each start position is specified, the length of peptide is 10 amino acids, and the end position for each peptide is the start position plus nine. | | |
| 2 | RALDGEESLL | 12.000 |
| 9 | SLLSKYNSNL | 4.000 |
| 1 | QRALDGEESL | 0.400 |
| 8 | ESLLSKYNSN | 0.020 |
| 3 | ALDGEESLLS | 0.018 |
| 5 | DGEESLLSKY | 0.006 |
| 7 | EESLLSKYNS | 0.002 |
| 4 | LDGEESLLSK | 0.001 |
| 6 | GEESLLSKYN | 0.001 |

TABLE XX

| Start | Subsequence | Score |
|---|---|---|
| V1-HLA-B3501-9mers-193P1E1B Each peptide is a portion of SEQ ID NO:3; each start position is specified, the length of peptide is 9 amino acids, and the end position for each peptide is the start position plus eight. | | |
| 217 | TPKLEHFGI | 36.000 |
| 152 | KIREYFQKY | 24.000 |
| 39 | YPMRILYDL | 20.000 |
| 95 | SPQLSDFGL | 20.000 |
| 114 | NPPQAVNLL | 20.000 |
| 286 | VPTFCTPGL | 20.000 |
| 265 | TPSPIIQQL | 20.000 |
| 255 | ESRLNDNVF | 15.000 |
| 163 | SPRVKKNSV | 12.000 |
| 367 | IPEDILQLL | 12.000 |
| 80 | DPPVASSCI | 8.000 |
| 250 | EAIDTESRL | 6.000 |
| 366 | KIPEDILQL | 6.000 |
| 140 | KVLMEKNSM | 6.000 |
| 135 | FIKATKVLM | 6.000 |
| 389 | KAVPPSKRF | 6.000 |
| 10 | KLRSLASTL | 6.000 |
| 33 | ESDFEDYPM | 4.500 |
| 202 | KTPKCALKM | 4.000 |
| 190 | TPPTKQSLV | 4.000 |
| 230 | MCLNED YTM | 3.000 |
| 364 | VTKIPEDIL | 3.000 |
| 98 | LSDFGLERY | 3.000 |
| 200 | VLKTPKCAL | 3.000 |
| 169 | NSVHEQEAI | 3.000 |
| 302 | SIALVSTNY | 2.000 |
| 283 | SPLVPTFCT | 2.000 |
| 296 | IPSTKNSIA | 2.000 |
| 112 | LPNPPQAVN | 2.000 |
| 310 | YPLSKTNSS | 2.000 |
| 370 | DILQLLSKY | 2.000 |
| 224 | GISEYTMCL | 2.000 |
| 185 | EPVIVTPPT | 2.000 |
| 228 | YTMCLNEDY | 2.000 |
| 314 | KTNSSSNDL | 2.000 |
| 346 | SPTISSYEN | 2.000 |
| 205 | KCALKMDDF | 2.000 |
| 291 | TPGLKIPST | 2.000 |
| 343 | DPSSPTISS | 2.000 |
| 312 | LSKTNSSSN | 1.500 |
| 46 | DLHSEVQTL | 1.500 |
| 119 | VNLLDKARL | 1.500 |
| 333 | NSDTCFENL | 1.500 |
| 375 | LSKYNSNLA | 1.500 |
| 145 | KNSMDIMKI | 1.200 |
| 5 | RSFCGKLRS | 1.000 |
| 215 | CVTPKLEHF | 1.000 |
| 390 | AVPPSKRFL | 1.000 |
| 304 | ALVSTNYPL | 1.000 |
| 189 | VTPPTKQSL | 1.000 |
| 350 | SSYENLLRT | 1.000 |
| 149 | DIMKIREYF | 1.000 |
| 374 | LLSKYNSNL | 1.000 |
| 316 | NSSSNDLEV | 1.000 |
| 330 | LVLNSDTCF | 1.000 |
| 344 | PSSPTISSY | 1.000 |
| 348 | TISSYENLL | 1.000 |
| 91 | KSPRSPQLS | 1.000 |
| 12 | RSLASTLDC | 1.000 |
| 281 | TNSPLVPTF | 1.000 |
| 21 | ETARLQRAL | 1.000 |
| 277 | DAEYTNSPL | 0.900 |
| 244 | RNNKSEEAI | 0.800 |
| 128 | ENQEGIDFI | 0.800 |
| 295 | KIPSTKNSI | 0.800 |
| 15 | ASTLDCETA | 0.750 |
| 272 | QLEKSDAEY | 0.600 |
| 60 | IPELSNCEN | 0.600 |
| 143 | MEKNSMDIM | 0.600 |
| 180 | DNYKEEPVI | 0.600 |
| 52 | QTLKDDVNI | 0.600 |
| 298 | STKNSIALV | 0.600 |

TABLE XX-continued

| Start | Subsequence | Score |
|---|---|---|
| 92 | SPRSPQLSD | 0.600 |
| 232 | LNEDYTMGL | 0.600 |
| 203 | TPKCALKMD | 0.600 |
| 379 | NSNLATPIA | 0.500 |
| 162 | YSPRVKKNS | 0.500 |
| 328 | TSLVLNSDT | 0.500 |
| 297 | PSTKNSIAL | 0.500 |
| 301 | NSIALVSTN | 0.500 |
| 282 | NSPLVPTFC | 0.500 |
| 195 | QSLVKVLKT | 0.500 |
| 84 | ASSCISGKS | 0.500 |
| 17 | TLDCETARL | 0.450 |
| 28 | ALDGEESDF | 0.450 |
| 207 | ALKMDDFEC | 0.450 |
| 275 | KSDAEYTNS | 0.450 |
| 380 | SNLATPIAI | 0.400 |
| 261 | NVFATPSPI | 0.400 |
| 154 | REYFQKYGY | 0.400 |
| 363 | EVTKIPEDI | 0.400 |
| 360 | TPPEVTKIP | 0.400 |
| 43 | ILYDLHSEV | 0.400 |
| 378 | YNSNLATPI | 0.400 |
| 257 | RLNDNVFAT | 0.400 |
| 386 | IAIKAVPPS | 0.300 |
| 8 | CGKLRSLAS | 0.300 |
| 117 | QAVNLLDKA | 0.300 |
| 14 | LASTLDCET | 0.300 |
| 3 | PIRSFCGKL | 0.300 |
| V5-HLA-B3501-9mers-193P1E1B<br>Each peptide is a portion of SEQ ID NO:11; each start position is specified, the length of peptide is 9 amino acids, and the end position for each peptide is the start position plus eight. | | |
| 3 | ASSCISEKS | 0.500 |
| 6 | CISEKSPRS | 0.200 |
| 9 | EKSPRSPQL | 0.100 |
| 4 | SSCISEKSP | 0.500 |
| 2 | VASSCISEK | 0.030 |
| 7 | ISEKSPRSP | 0.015 |
| 5 | SCISEKSPR | 0.015 |
| 8 | SEKSPRSPQ | 0.003 |
| 1 | PVASSCISE | 0.001 |
| V6-HLA-B3501-9mers-193P1E1B<br>Each peptide is a portion of SEQ ID NO:13; each start position is specified, the length of peptide is 9 amino acids, and the end position for each peptide is the start position plus eight. | | |
| 5 | EAIDAESRL | 6.000 |
| 8 | DAESRLNDN | 0.090 |
| 2 | KSEEAIDAE | 0.060 |
| 6 | AIDAESRLN | 0.045 |
| 1 | NKSEEAIDA | 0.030 |
| 9 | AESRLNDNV | 0.020 |
| 3 | SEEAIDAES | 0.003 |
| 7 | IDAESRLND | 0.002 |
| 4 | EEAIDAESR | 0.002 |
| V10-HLA-B3501-9mers-193P1E1B<br>Each peptide is a portion of SEQ ID NO:21; each start position is specified, the length of peptide is 9 amino acids, and the end position for each peptide is the start position plus eight. | | |
| 14 | YPTQKLNKM | 40.000 |
| 2 | IPEDILQKF | 12.000 |
| 6 | ILQKFQWIY | 2.000 |
| 5 | DILQKFQWI | 0.400 |
| 11 | QWIYPTQKL | 0.100 |
| 12 | WIYPTQKLN | 0.100 |
| 1 | KIPEDILQK | 0.060 |
| 4 | EDILQKFQW | 0.050 |
| 7 | LQKFQWIYP | 0.030 |
| 10 | FQWIYPTQK | 0.010 |
| 8 | QKFQWIYPT | 0.010 |
| 9 | KFQWIYPTQ | 0.002 |
| 13 | IYPTQKLNK | 0.001 |
| 15 | PTQKLNKMR | 0.001 |
| 3 | PEDILQKFQ | 0.000 |

TABLE XX-continued

| Start | Subsequence | Score |
|---|---|---|
| V12-HLA-B3501-9mers-193P1E1B<br>Each peptide is a portion of SEQ ID NO:25; each start position is specified, the length of peptide is 9 amino acids, and the end position for each peptide is the start position plus eight. | | |
| 1 | RALDGEESL | 12.000 |
| 7 | ESLLSKYNS | 0.500 |
| 2 | ALDGEESLL | 0.450 |
| 8 | SLLSKYNSN | 0.100 |
| 5 | GEESLLSKY | 0.060 |
| 3 | LDGEESLLS | 0.030 |
| 6 | EESLLSKYN | 0.010 |
| 4 | DGEESLLSK | 0.006 |

TABLE XXI

| Start | Subsequence | Score |
|---|---|---|
| V1-HLA-B3501-10mers-193P1E1B<br>Each peptide is a portion of SEQ ID NO:3; each start position is specified, the length of peptide is 10 amino acids, and the end position for each peptide is the start position plus nine. | | |
| 92 | SPRSPQLSDF | 60.000 |
| 343 | DPSSPTISSY | 40.000 |
| 346 | SPTISSYENL | 20.000 |
| 2 | DPIRSFCGKL | 20.000 |
| 296 | IPSTKNSIAL | 20.000 |
| 112 | LPNPPQAVNL | 20.000 |
| 27 | RALDGEESDF | 18.000 |
| 358 | TPTPPEVTKI | 12.000 |
| 301 | NSIALVSTNY | 10.000 |
| 94 | RSPQLSDFGL | 10.000 |
| 5 | RSFCGKLRSL | 10.000 |
| 124 | KARLENQEGI | 7.200 |
| 389 | KAVPPSKRFL | 6.000 |
| 217 | TPKLEHFGIS | 6.000 |
| 60 | IPELSNCENF | 6.000 |
| 271 | QQLEKSDAEY | 4.000 |
| 366 | KIPEDILQLL | 4.000 |
| 97 | QLSDFGLERY | 4.000 |
| 303 | IALVSTNYPL | 3.000 |
| 89 | SGKSPRSPQL | 3.000 |
| 69 | FQKTDVKDDL | 3.000 |
| 229 | TMCLNEDYTM | 3.000 |
| 16 | STLDCETARL | 3.000 |
| 255 | ESRLNDNVFA | 2.250 |
| 310 | YPLSKTNSSS | 2.000 |
| 199 | KVLKTPKCAL | 2.000 |
| 231 | CLNEDYTMGL | 2.000 |
| 332 | LNSDTCFENL | 2.000 |
| 379 | NSNLATPIAI | 2.000 |
| 80 | DPPVASSCIS | 2.000 |
| 267 | SPIIQQLEKS | 2.000 |
| 30 | DGEESDFEDY | 1.800 |
| 375 | LSKYNSNLAT | 1.500 |
| 118 | AVNLLDKARL | 1.500 |
| 168 | KNSVHEQEAI | 1.200 |
| 367 | IPEDILQLLS | 1.200 |
| 219 | KLEHFGISEY | 1.200 |
| 188 | IVTPPTKQSL | 1.000 |
| 280 | YTNSPLVPTF | 1.000 |
| 162 | YSPRVKKNSV | 1.000 |
| 329 | SLVLNSDTCF | 1.000 |
| 363 | EVTKIPEDIL | 1.000 |
| 264 | ATPSPIIQQL | 1.000 |
| 223 | FGISEYTMCL | 1.000 |
| 373 | QLLSKYNSNL | 1.000 |
| 285 | LVPTFCTPGL | 1.000 |
| 214 | ECVTPKLEHF | 1.000 |
| 126 | RLENQEGIDF | 0.900 |
| 207 | ALKMDDFECV | 0.900 |
| 242 | NARNNKSEEA | 0.900 |
| 250 | EAIDTESRLN | 0.900 |

TABLE XXI-continued

| Start | Subsequence | Score |
|---|---|---|
| 340 | NLTDPSSPTI | 0.800 |
| 141 | VLMEKNSMDI | 0.800 |
| 216 | VTPKLEHFGI | 0.600 |
| 323 | EVEDRTSLVL | 0.600 |
| 147 | SMDIMKIREY | 0.600 |
| 382 | LATPIAIKAV | 0.600 |
| 32 | EESDFEDYPM | 0.600 |
| 157 | FQKYGYSPRV | 0.600 |
| 203 | TPKCALKMDD | 0.600 |
| 51 | VQTLKDDVNI | 0.600 |
| 142 | LMEKNSMDIM | 0.600 |
| 137 | KATKVLMEKN | 0.600 |
| 403 | NIRDVSNKEN | 0.600 |
| 247 | KSEEAIDTES | 0.600 |
| 98 | LSDFGLERYI | 0.600 |
| 173 | EQEAINSDNY | 0.600 |
| 355 | LLRTPTPPEV | 0.600 |
| 163 | SPRVKKNSVH | 0.600 |
| 306 | VSTNYPLSKT | 0.500 |
| 282 | NSPLVPTFCT | 0.500 |
| 345 | SSPTISSYEN | 0.500 |
| 169 | NSVHEQEAIN | 0.500 |
| 328 | TSLVLNSDTC | 0.500 |
| 349 | ISSYENLLRT | 0.500 |
| 63 | LSNCENFQKT | 0.500 |
| 25 | LQRALDGEES | 0.450 |
| 245 | NNKSEEAIDT | 0.450 |
| 14 | LASTLDCETA | 0.450 |
| 206 | CALKMDDFEC | 0.450 |
| 321 | DLEVEDRTSL | 0.450 |
| 260 | DNVFATPSPI | 0.400 |
| 261 | NVFATPSPII | 0.400 |
| 42 | RILYDLHSEV | 0.400 |
| 191 | PPTKQSLVKV | 0.400 |
| 360 | TPPEVTKIPE | 0.400 |
| 138 | ATKVLMEKNS | 0.300 |
| 298 | STKNSIALVS | 0.300 |
| 180 | DNYKEEPVIV | 0.300 |
| 192 | PTKQSLVKVL | 0.300 |
| 170 | SVHEQEAINS | 0.300 |
| 197 | LVKVLKTPKC | 0.300 |
| 239 | GLKNARNNKS | 0.300 |
| 8 | CGKLRSLAST | 0.300 |
| 139 | TKVLMEKNSM | 0.300 |
| 103 | LERYIVSQVL | 0.300 |
| 178 | NSDNYKEEPV | 0.300 |
| 83 | VASSCISGKS | 0.300 |
| 95 | SPQLSDFGLE | 0.300 |
| 293 | GLKIPSTKNS | 0.300 |
| V5-HLA-B3501-10mers-193P1E1B Each peptide is a portion of SEQ ID NO:11; each start position is specified, the length of peptide is 10 amino acids, and the end position for each peptide is the start position plus nine. | | |
| 9 | SEKSPRSPQL | 0.300 |
| 3 | VASSCISEKS | 0.300 |
| 6 | SCISEKSPRS | 0.100 |
| 5 | SSCISEKSPR | 0.075 |
| 4 | ASSCISEKSP | 0.050 |
| 7 | CISEKSPRSP | 0.020 |
| 1 | PPVASSCISE | 0.020 |
| 8 | ISEKSPRSPQ | 0.015 |
| 10 | EKSPRSPQLS | 0.010 |
| 2 | PVASSCISEK | 0.001 |
| V6-HLA-B3501-10mers-193P1E1B Each peptide is a portion of SEQ ID NO:13; each start position is specified, the length of peptide is 10 amino acids, and the end position for each peptide is the start position plus nine. | | |
| 6 | EAIDAESRLN | 0.900 |
| 3 | KSEEAIDAES | 0.600 |
| 1 | NNKSEEAIDA | 0.450 |
| 9 | DAESRLNDNV | 0.180 |
| 5 | EEAIDAESRL | 0.100 |
| 10 | AESRLNDNVF | 0.100 |
| 8 | IDAESRLNDN | 0.020 |
| 7 | AIDAESRLND | 0.003 |
| 2 | NKSEEAIDAE | 0.002 |
| 4 | SEEAIDAESR | 0.000 |
| V10-HLA-B3501-10mers-193P1E1B Each peptide is a portion of SEQ ID NO:21; each start position is specified, the length of peptide is 10 amino acids, and the end position for each peptide is the start position plus nine. | | |
| 2 | KIPEDILQKF | 4.000 |
| 6 | DILQKFQWIY | 2.000 |
| 11 | FQWIYPTQKL | 1.000 |
| 8 | LQKFQWIYPT | 0.300 |
| 15 | YPTQKLNKMR | 0.200 |
| 14 | IYPTQKLNKM | 0.200 |
| 3 | IPEDILQKFQ | 0.120 |
| 5 | EDILQKFQWI | 0.040 |
| 7 | ILQKFQWIYP | 0.010 |
| 12 | QWIYPTQKLN | 0.010 |
| 13 | WIYPTQKLNK | 0.010 |
| 10 | KFQWIYPTQK | 0.002 |
| 4 | PEDILQKFQW | 0.002 |
| 1 | TKIPEDILQK | 0.002 |
| 9 | QKFQWIYPTQ | 0.001 |
| V12-HLA-B3501-10mers-193P1E1B Each peptide is a portion of SEQ ID NO:25; each start position is specified, the length of peptide is 10 amino acids, and the end position for each peptide is the start position plus nine. | | |
| 2 | RALDGEESLL | 18.000 |
| 5 | DGEESLLSKY | 1.200 |
| 9 | SLLSKYNSNL | 1.000 |
| 8 | ESLLSKYNSN | 0.500 |
| 1 | QRALDGEESL | 0.100 |
| 3 | ALDGEESLLS | 0.045 |
| 7 | EESLLSKYNS | 0.010 |
| 6 | GEESLLSKYN | 0.003 |
| 4 | LDGEESLLSK | 0.002 |

TABLE XII

V1-HLA-A1-9mers-193P1E1B
Each peptide is a portion of SEQ ID NO: 3; each start position is specified, the length of peptide is 9 amino acids, and the end position for each peptide is the start position plus eight.

| Pos | 123456789 | score |
|---|---|---|
| 98 | LSDFGLERY | 31 |
| 31 | GEESDFEDY | 28 |
| 37 | EDYPMRILY | 26 |
| 272 | QLEKSDAEY | 26 |
| 48 | HSEVQTLKD | 24 |
| 228 | YTMCLNEDY | 24 |
| 344 | PSSPTISSY | 23 |
| 152 | KIREYFQKY | 21 |
| 78 | LSDPPVASS | 20 |
| 341 | LTDPSSPTI | 20 |
| 182 | YKEEPVIVT | 19 |
| 302 | SIALVSTNY | 19 |
| 71 | KTDVKDDLS | 18 |
| 121 | LLDKARLEN | 18 |
| 324 | VEDRTSLVL | 18 |
| 368 | PEDILQLLS | 18 |
| 19 | DCETARLQR | 17 |
| 54 | LKDDVNIPE | 17 |
| 154 | REYFQKYGY | 17 |
| 220 | LEHFGISEY | 17 |
| 333 | NSDTCFENL | 17 |
| 370 | DILQLLSKY | 17 |
| 147 | SMDIMKIRE | 16 |
| 183 | KEEPVIVTP | 16 |
| 219 | KLEHFGISE | 16 |
| 225 | ISEYTMCLN | 16 |
| 253 | DTESRLNDN | 16 |
| 148 | MDIMKIREY | 15 |

TABLE XII-continued

V1-HLA-A1-9mers-193P1E1B
Each peptide is a portion of SEQ ID NO: 3; each start position is specified, the length of peptide is 9 amino acids, and the end position for each peptide is the start position plus eight.

| Pos | 123456789 | score |
|---|---|---|
| 171 | VHEQEAINS | 15 |
| 174 | QEAINSDNY | 15 |
| 178 | NSDNYKEEP | 15 |
| 258 | LNDNVFATP | 15 |

TABLE XXII

| Pos | 123456789 | score |
|---|---|---|
| V5-HLA-A1-9mers-193P1E1B Each peptide is a portion of SEQ ID NO: 11; each start position is specified, the length of peptide is 9 amino acids, and the end position for each peptide is the start position plus eight. | | |
| 7 | ISEKSPRSP | 14 |
| 3 | ASSCISEKS | 7 |
| 4 | SSCISEKSP | 6 |
| V6-HLA-A1-9mers-193P1E1B Each peptide is a portion of SEQ ID NO: 13; each start position is specified, the length of peptide is 9 amino acids, and the end position for each peptide is the start position plus eight. | | |
| 2 | KSEEAIDAE | 14 |
| 6 | AIDAESRLN | 13 |
| 3 | SEEAIDAES | 12 |
| 8 | DAESRLNDN | 10 |
| 7 | IDAESRLND | 7 |
| V10-HLA-A1-9mers-193P1E1B Each peptide is a portion of SEQ ID NO: 21; each start position is specified, the length of peptide is 9 amino acids, and the end position for each peptide is the start position plus eight. | | |
| 6 | ILQKFQWIY | 16 |
| 2 | IPEDILQKF | 12 |
| 3 | PEDILQKFQ | 10 |
| 13 | IYPTQKLNK | 8 |
| 15 | PTQKLNKMR | 8 |
| V12-HLA-A1-9mers-193P1E1B Each peptide is a portion of SEQ ID NO: 25; each start position is specified, the length of peptide is 9 amino acids, and the end position for each peptide is the start position plus eight. | | |
| 5 | GEESLLSKY | 27 |
| 4 | DGEESLLSK | 16 |
| 2 | ALDGEESLL | 15 |

TABLE XXIII

| Pos | 123456789 | score |
|---|---|---|
| V1-HLA-A0201-9mers-193P1E1B Each peptide is a portion of SEQ ID NO:3; each start position is specified, the length of peptide is 9 amino acids, and the end position for each peptide is the start position plus eight. | | |
| 43 | ILYDLHSEV | 27 |
| 366 | KIPEDILQL | 26 |
| 46 | DLHSEVQTL | 25 |
| 10 | KLRSLASTL | 24 |
| 17 | TLDCETARL | 24 |
| 224 | GISEYTMCL | 24 |
| 111 | VLPNPPQAV | 23 |
| 304 | ALVSTNYPL | 23 |
| 374 | LLSKYNSNL | 23 |
| 200 | VLKTPKCAL | 22 |
| 6 | SFCGKLRSL | 21 |
| 257 | RLNDNVFAT | 21 |

TABLE XXIII-continued

| Pos | 123456789 | score |
|---|---|---|
| 298 | STKNSIALV | 21 |
| 295 | KIPSTKNSI | 20 |
| 348 | TISSYENLL | 20 |
| 383 | ATPIAIKAV | 20 |
| 102 | GLERYIVSQ | 19 |
| 189 | VTPPTKQSL | 19 |
| 341 | LTDPSSPTI | 19 |
| 381 | NLATPIAIK | 19 |
| 3 | PIRSFCGKL | 18 |
| 13 | SLASTLDCE | 18 |
| 39 | YPMRILYDL | 18 |
| 55 | KDDVNIPEL | 18 |
| 192 | PTKQSLVKV | 18 |
| 280 | YTNSPLVPT | 18 |
| 390 | AVPPSKRFL | 18 |
| 142 | LMEKNSMDI | 17 |
| 196 | SLVKVLKTP | 17 |
| 307 | STNYPLSKT | 17 |
| 314 | KTNSSSNDL | 17 |
| 359 | PTPPEVTKI | 17 |
| 42 | RILYDLHSE | 16 |
| 52 | QTLKDDVNI | 16 |
| 133 | IDFIKATKV | 16 |
| 163 | SPRVKKNSV | 16 |
| 232 | LNEDYTMGL | 16 |
| 265 | TPSPIIQQL | 16 |
| 322 | LEVEDRTSL | 16 |
| 355 | LLRTPTPPE | 16 |
| 356 | LRTPTPPEV | 16 |
| 367 | IPEDILQLL | 16 |
| 370 | DILQLLSKY | 16 |
| 373 | QLLSKYNSN | 16 |
| 9 | GKLRSLAST | 15 |
| 21 | ETARLQRAL | 15 |
| 24 | RLQRALDGE | 15 |
| 53 | TLKDDVNIP | 15 |
| 97 | QLSDFGLER | 15 |
| 103 | LERYIVSQV | 15 |
| 106 | YIVSQVLPN | 15 |
| 114 | NPPQAVNLL | 15 |
| 117 | QAVNLLDKA | 15 |
| 119 | VNLLDKARL | 15 |
| 121 | LLDKARLEN | 15 |
| 125 | ARLENQEGI | 15 |
| 141 | VLMEKNSMD | 15 |
| 145 | KNSMDIMKI | 15 |
| 158 | QKYGYSPRV | 15 |
| 209 | KMDDFECVT | 15 |
| 340 | NLTDPSSPT | 15 |
| 364 | VTKIPEDIL | 15 |
| 399 | KHGQNIRDV | 15 |
| 28 | ALDGEESDF | 14 |
| 77 | DLSDPPVAS | 14 |
| 90 | GKSPRSPQL | 14 |
| 99 | SDFGLERYI | 14 |
| 120 | NLLDKARLE | 14 |
| 135 | FIKATKVLM | 14 |
| 140 | KVLMEKNSM | 14 |
| 152 | KIREYFQKY | 14 |
| 176 | AINSDNYKE | 14 |
| 193 | TKQSLVKVL | 14 |
| 195 | QSLVKVLKT | 14 |
| 208 | LKMDDFECV | 14 |
| 250 | EAIDTESRL | 14 |
| 278 | AEYTNSPLV | 14 |
| 329 | SLVLNSDTC | 14 |
| 331 | VLNSDTCFE | 14 |
| 350 | SSYENLLRT | 14 |
| 14 | LASTLDCET | 13 |
| 78 | LSDPPVASS | 13 |
| 95 | SPQLSDFGL | 13 |
| 110 | QVLPNPPQA | 13 |
| 128 | ENQEGIDFI | 13 |
| 179 | SDNYKEEPV | 13 |
| 181 | NYKEEPVIV | 13 |
| 207 | ALKMDDFEC | 13 |
| 212 | DFECVTPKL | 13 |

TABLE XXIII-continued

| Pos | 123456789 | score |
|---|---|---|
| 219 | KLEHFGISE | 13 |
| 231 | CLNEDYTMG | 13 |
| 261 | NVFATPSPI | 13 |
| 262 | VFATPSPII | 13 |
| 268 | PIIQQLEKS | 13 |
| 272 | QLEKSDAEY | 13 |
| 286 | VPTFCTPGL | 13 |
| 293 | GLKIPSTKN | 13 |
| 300 | KNSIALVST | 13 |
| 316 | NSSSNDLEV | 13 |
| 323 | EVEDRTSLV | 13 |
| 347 | PTISSYENL | 13 |
| 380 | SNLATPIAI | 13 |
| 382 | LATPIAIKA | 13 |
| 386 | IAIKAVPPS | 13 |
| 397 | FLKHGQNIR | 13 |
| 50 | EVQTLKDDV | 12 |
| 59 | NIPELSNCE | 12 |
| 75 | KDDLSDPPV | 12 |
| 87 | CISGKSPRS | 12 |
| 132 | GIDFIKATK | 12 |
| 134 | DFIKATKVL | 12 |
| 182 | YKEEPVIVT | 12 |
| 187 | VIVTPPTKQ | 12 |
| 202 | KTPKCALKM | 12 |
| 229 | TMCLNEDYT | 12 |
| 236 | YTMGLKNAR | 12 |
| 269 | IIQQLEKSD | 12 |
| 276 | SDAEYTNSP | 12 |
| 288 | TFCTPGLKI | 12 |
| 291 | TPGLKIPST | 12 |
| 302 | SIALVSTNY | 12 |
| 324 | VEDRTSLVL | 12 |
| 354 | NLLRTPTPP | 12 |
| 371 | ILQLLSKYN | 12 |
| 387 | AIKAVPPSK | 12 |
| 403 | NIRDVSNKE | 12 |

V5-HLA-A0201-9mers-193P1E1B Each peptide is a portion of SEQ ID NO:11; each start position is specified, the length of peptide is 9 amino acids, and the end position for each peptide is the start position plus eight.

| Pos | 123456789 | score |
|---|---|---|
| 6 | CISEKSPRS | 12 |
| 2 | VASSCISEK | 11 |
| 9 | EKSPRSPQL | 10 |
| 1 | PVASSCISE | 5 |

V6-HLA-A0201-9mers-193P1E1B Each peptide is a portion of SEQ ID NO:13; each start position is specified, the length of peptide is 9 amino acids, and the end position for each peptide is the start position plus eight.

| Pos | 123456789 | score |
|---|---|---|
| 5 | EAIDAESRL | 14 |
| 9 | AESRLNDNV | 13 |
| 6 | AIDAESRLN | 10 |
| 2 | KSEEAIDAE | 7 |
| 7 | IDAESRLND | 7 |
| 8 | DAESRLNDN | 7 |
| 1 | NKSEEAIDA | 6 |

V10-HLA-A0201-9mers-193P1E1B Each peptide is a portion is SEQ ID NO:21; each start position is specified, the length of peptide is 9 amino acids, and the end position for each peptide is the start position plus eight.

| Pos | 123456789 | score |
|---|---|---|
| 5 | DILQKFQWI | 18 |
| 1 | KIPEDILQK | 16 |
| 11 | QWIYPTQKL | 16 |
| 6 | ILQKFQWIY | 13 |
| 14 | YPTQKLNKM | 13 |
| 8 | QKFQWIYPT | 10 |
| 12 | WIYPTQKLN | 10 |
| 2 | IPEDILQKF | 8 |

TABLE XXIII-continued

V12-HLA-A0201-9mers-193P1E1B Each peptide is a portion of SEQ ID NO:25; each start position is specified, the length of peptide is 9 amino acids, and the end position for each peptide is the start position plus eight.

| Pos | 123456789 | score |
|---|---|---|
| 2 | ALDGEESLL | 24 |
| 1 | RALDGEESL | 21 |
| 8 | SLLSKYNSN | 18 |

TABLE XXIV

| Pos | 123456789 | score |
|---|---|---|
| V1-HLA-A0203-9mers-193P1E1B | | |
| NoResultsFound. | | |
| V5-HLA-A0203-9mers-193P1E1B | | |
| NoResultsFound. | | |
| V6-HLA-A0203-9mers-193P1E1B | | |
| NoResultsFound. | | |
| V10-HLA-A0203-9mers-193P1E1B | | |
| NoResultsFound. | | |
| V12-HLA-A0203-9mers-193P1E1B | | |
| NoResultsFound. | | |

TABLE XXV

V1-HLA-A3-9mers-193P1E1B
Each peptide is a portion of SEQ ID NO:3; each start position is specified, the length of peptide is 9 amino acids, and the end position for each peptide is the start position plus eight.

| Pos | 123456789 | score |
|---|---|---|
| 186 | PVIVTPPTK | 28 |
| 387 | AIKAVPPSK | 28 |
| 10 | KLRSLASTL | 26 |
| 132 | GIDFIKATK | 25 |
| 381 | NLATPIAIK | 24 |
| 97 | QLSDFGLER | 23 |
| 239 | GLKNARNNK | 23 |
| 28 | ALDGEESDF | 22 |
| 197 | LVKVLKTPK | 22 |
| 110 | QVLPNPPQA | 21 |
| 152 | KIREYFQKY | 21 |
| 272 | QLEKSDAEY | 21 |
| 358 | TPTPPEVTK | 21 |
| 402 | QNIRDVSNK | 21 |
| 43 | ILYDLHSEV | 20 |
| 292 | PGLKIPSTK | 20 |
| 102 | GLERYIVSQ | 19 |
| 118 | AVNLLDKAR | 19 |
| 151 | MKIREYFQK | 19 |
| 160 | YGYSPRVKK | 19 |
| 165 | RVKKNSVHE | 19 |
| 194 | KQSLVKVLK | 19 |
| 302 | SIALVSTNY | 19 |
| 369 | EDILQLLSK | 19 |
| 370 | DILQLLSKY | 19 |
| 159 | KYGYSPRVK | 18 |
| 188 | IVTPPTKQS | 18 |
| 215 | CVTPKLEHF | 18 |
| 219 | KLEHFGISE | 18 |
| 267 | SPIIQQLEK | 18 |
| 330 | LVLNSDTCF | 18 |
| 366 | KIPEDILQL | 18 |
| 385 | PIAIKAVPP | 18 |
| 24 | RLQRALDGE | 17 |

TABLE XXV-continued

| Pos | 123456789 | score |
|---|---|---|
| 77 | DLSDPPVAS | 17 |
| 120 | NLLDKARLE | 17 |
| 140 | KVLMEKNSM | 17 |
| 191 | PPTKQSLVK | 17 |
| 201 | LKTPKCALK | 17 |
| 284 | PLVPTFCTP | 17 |
| 306 | VSTNYPLSK | 17 |
| 354 | NLLRTPTPP | 17 |
| 373 | QLLSKYNSN | 17 |
| 397 | FLKHGQNIR | 17 |
| 2 | DPIRSFCGK | 16 |
| 42 | RILYDLHSE | 16 |
| 57 | DVNIPELSN | 16 |
| 126 | RLENQEGID | 16 |
| 141 | VLMEKNSMD | 16 |
| 196 | SLVKVLKTP | 16 |
| 199 | KVLKTPKCA | 16 |
| 257 | RLNDNVFAT | 16 |
| 261 | NVFATPSPI | 16 |
| 323 | EVEDRTSLV | 16 |
| 329 | SLVLNSDTC | 16 |
| 390 | AVPPSKRFL | 16 |
| 67 | ENFQKTDVK | 15 |
| 73 | DVKDDLSDP | 15 |
| 135 | FIKATKVLM | 15 |
| 137 | KATKVLMEK | 15 |
| 170 | SVHEQEAIN | 15 |
| 183 | KEEPVIVTP | 15 |
| 311 | PLSKTNSSS | 15 |
| 37 | EDYPMRILY | 14 |
| 46 | DLHSEVQTL | 14 |
| 116 | PQAVNLLDK | 14 |
| 121 | LLDKARLEN | 14 |
| 154 | REYFQKYGY | 14 |
| 175 | EAINSDNYK | 14 |
| 207 | ALKMDDFEC | 14 |
| 321 | DLEVEDRTS | 14 |
| 340 | NLTDPSSPT | 14 |
| 344 | PSSPTISSY | 14 |
| 17 | TLDCETARL | 13 |
| 23 | ARLQRALDG | 13 |
| 47 | LHSEVQTLK | 13 |
| 63 | LSNCENFQK | 13 |
| 79 | SDPPVASSC | 13 |
| 82 | PVASSCISG | 13 |
| 83 | VASSCISGK | 13 |
| 86 | SCISGKSPR | 13 |
| 107 | IVSQVLPNP | 13 |
| 111 | VLPNPPQAV | 13 |
| 149 | DIMKIREYF | 13 |
| 231 | CLNEDYTMG | 13 |
| 293 | GLKIPSTKN | 13 |
| 295 | KIPSTKNSI | 13 |
| 304 | ALVSTNYPL | 13 |
| 355 | LLRTPTPPE | 13 |
| 371 | ILQLLSKYN | 13 |
| 374 | LLSKYNSNL | 13 |
| 403 | NIRDVSNKE | 13 |
| V5-HLA-A3-9mers-193P1E1B<br>Each peptide is a portion of SEQ ID NO:11; each start position is specified, the length of peptide is 9 amino acids, and the end position for each peptide is the start position plus eight. | | |
| 1 | PVASSCISE | 13 |
| 2 | VASSCISEK | 13 |
| 5 | SCISEKSPR | 11 |
| 6 | CISEKSPRS | 10 |
| 9 | EKSPRSPQL | 8 |
| 8 | SEKSPRSPQ | 6 |
| V6-HLA-A3-9mers-193P1E1B<br>Each peptide is a portion of SEQ ID NO:13; each start position is specified, the length of peptide is 9 amino acids, and the end position for each peptide is the start position plus eight. | | |
| 6 | AIDAESRLN | 13 |
| 4 | EEAIDAESR | 11 |
| 7 | IDAESRLND | 8 |
| 5 | EAIDAESRL | 7 |
| 3 | SEEAIDAES | 6 |
| 9 | AESRLNDNV | 6 |
| V10-HLA-A3-9mers-193P1E1B<br>Each peptide is a portion of SEQ ID NO:21; each start position is specified, the length of peptide is 9 amino acids, and the end position for each peptide is the start position plus eight. | | |
| 1 | KIPEDILQK | 28 |
| 6 | ILQKFQWIY | 18 |
| 10 | FQWIYPTQK | 16 |
| 12 | WIYPTQKLN | 15 |
| 13 | IYPTQKLNK | 15 |
| V12-HLA-A3-9mers-193P1E1B<br>Each peptide is a portion of SEQ ID NO:25; each start position is specified, the length of peptide is 9 amino acids, and the end position for each peptide is the start position plus eight. | | |
| 2 | ALDGEESLL | 18 |
| 4 | DGEESLLSK | 16 |
| 8 | SLLSKYNSN | 16 |
| 1 | RALDGEESL | 11 |
| 5 | GEESLLSKY | 9 |

TABLE XXVI

| Pos | 123456789 | score |
|---|---|---|
| V1-HLA-A26-9mers-193P1E1B<br>Each peptide is a portion of SEQ ID NO:3; each start position is specified, the length of peptide is 9 amino acids, and the end position for each peptide is the start position plus eight. | | |
| 370 | DILQLLSKY | 29 |
| 21 | ETARLQRAL | 28 |
| 215 | CVTPKLEHF | 25 |
| 73 | DVKDDLSDP | 24 |
| 250 | EAIDTESRL | 24 |
| 363 | EVTKIPEDI | 23 |
| 37 | EDYPMRILY | 22 |
| 46 | DLHSEVQTL | 22 |
| 149 | DIMKIREYF | 22 |
| 323 | EVEDRTSLV | 22 |
| 50 | EVQTLKDDV | 21 |
| 253 | DTESRLNDN | 21 |
| 347 | PTISSYENL | 21 |
| 57 | DVNIPELSN | 20 |
| 131 | EGIDFIKAT | 20 |
| 134 | DFIKATKVL | 20 |
| 366 | KIPEDILQL | 20 |
| 369 | EDILQLLSK | 20 |
| 148 | MDIMKIREY | 19 |
| 228 | YTMCLNEDY | 19 |
| 255 | ESRLNDNVF | 19 |
| 390 | AVPPSKRFL | 19 |
| 104 | ERYIVSQVL | 18 |
| 189 | VTPPTKQSL | 18 |
| 211 | DDFECVTPK | 18 |
| 330 | LVLNSDTCF | 18 |
| 335 | DTCFENLTD | 18 |
| 152 | KIREYFQKY | 17 |
| 212 | DFECVTPKL | 17 |
| 265 | TPSPIIQQL | 17 |
| 277 | DAEYTNSPL | 17 |
| 314 | KTNSSSNDL | 17 |
| 344 | PSSPTISSY | 17 |
| 128 | ENQEGIDFI | 16 |
| 155 | EYFQKYGYS | 16 |
| 184 | EEPVIVTPP | 16 |
| 221 | EHFGISEYT | 16 |
| 281 | TNSPLVPTF | 16 |
| 326 | DRTSLVLNS | 16 |
| 364 | VTKIPEDIL | 16 |
| 3 | PIRSFCGKL | 15 |

TABLE XXVI-continued

| Pos | 123456789 | score |
|---|---|---|
| 6 | SFCGKLRSL | 15 |
| 67 | ENFQKTDVK | 15 |
| 186 | PVIVTPPTK | 15 |
| 193 | TKQSLVKVL | 15 |
| 214 | ECVTPKLEH | 15 |
| 220 | LEHFGISEY | 15 |
| 227 | EYTMCLNED | 15 |
| 261 | NVFATPSPI | 15 |
| 264 | ATPSPIIQQ | 15 |
| 302 | SIALVSTNY | 15 |
| 307 | STNYPLSKT | 15 |
| 322 | LEVEDRTSL | 15 |
| 367 | IPEDILQLL | 15 |
| 39 | YPMRILYDL | 14 |
| 56 | DDVNIPELS | 14 |
| 93 | PRSPQLSDF | 14 |
| 98 | LSDFGLERY | 14 |
| 106 | YIVSQVLPN | 14 |
| 107 | IVSQVLPNP | 14 |
| 175 | EAINSDNYK | 14 |
| 185 | EPVIVTPPT | 14 |
| 224 | GISEYTMCL | 14 |
| 325 | EDRTSLVLN | 14 |
| 348 | TISSYENLL | 14 |
| 359 | PTPPEVTKI | 14 |
| V5-HLA-A26-9mers-193P1E1B<br>Each peptide is a portion of SEQ ID NO:11; each start position is specified, the length of peptide is 9 amino acids, and the end position for each peptide is the start position plus eight. | | |
| 9 | EKSPRSPQL | 20 |
| 1 | PVASSCISE | 13 |
| V6-HLA-A26-9mers-193P1E1B<br>Each peptide is a portion of SEQ ID NO:13; each start position is specified, the length of peptide is 9 amino acids, and the end position for each peptide is the start position plus eight. | | |
| 5 | EAIDAESRL | 24 |
| 8 | DAESRLNDN | 13 |
| 4 | EEAIDAESR | 11 |
| V10-HLA-A26-9mers-193P1E1B<br>Each peptide is a portion of SEQ ID NO:21; each start position is specified, the length of peptide is 9 amino acids, and the end position for each peptide is the start position plus eight. | | |
| 2 | IPEDILQKF | 16 |
| 4 | EDILQKFQW | 15 |
| 5 | DILQKFQWI | 13 |
| 11 | QWIYPTQKL | 13 |
| 1 | KIPEDILQK | 12 |
| 6 | ILQKFQWIY | 10 |
| 15 | PTQKLNKMR | 10 |
| 8 | QKFQWIYPT | 8 |
| 14 | YPTQKLNKM | 7 |
| V12-HLA-A26-9mers-193P1E1B<br>Each peptide is a portion of SEQ ID NO:25; each start position is specified, the length of peptide is 9 amino acids, and the end position for each peptide is the start position plus eight. | | |
| 5 | GEESLLSKY | 18 |
| 4 | DGEESLLSK | 16 |
| 6 | EESLLSKYN | 11 |
| 1 | RALDGEESL | 10 |
| 7 | ESLLSKYNS | 10 |
| 2 | ALDGEESLL | 9 |

TABLE XXVII

| Pos | 123456789 | score |
|---|---|---|
| V1-HLA-B0702-9mers-193P1E1B<br>Each peptide is a portion of SEQ ID NO:3; each start position is specified, the length of peptide is 9 amino acids, and the end position for each peptide is the start position plus eight. | | |
| 265 | TPSPIIQQL | 23 |
| 286 | VPTFCTPGL | 22 |
| 39 | YPMRILYDL | 21 |
| 114 | NPPQAVNLL | 21 |
| 367 | IPEDILQLL | 21 |
| 95 | SPQLSDFGL | 20 |
| 185 | EPVIVTPPT | 20 |
| 283 | SPLVPTFCT | 20 |
| 296 | IPSTKNSIA | 19 |
| 163 | SPRVKKNSV | 18 |
| 291 | TPGLKIPST | 18 |
| 92 | SPRSPQLSD | 17 |
| 80 | DPPVASSCI | 16 |
| 112 | LPNPPQAVN | 16 |
| 190 | TPPTKQSLV | 16 |
| 217 | TPKLEHFGI | 16 |
| 343 | DPSSPTISS | 16 |
| 358 | TPTPPEVTK | 16 |
| 392 | PPSKRFLKH | 16 |
| 36 | FEDYPMRIL | 14 |
| 90 | GKSPRSPQL | 14 |
| 191 | PPTKQSLVK | 14 |
| 200 | VLKTPKCAL | 14 |
| 324 | VEDRTSLVL | 14 |
| 390 | AVPPSKRFL | 14 |
| 10 | KLRSLASTL | 13 |
| 17 | TLDCETARL | 13 |
| 21 | ETARLQRAL | 13 |
| 55 | KDDVNIPEL | 13 |
| 113 | PNPPQAVNL | 13 |
| 115 | PPQAVNLLD | 13 |
| 134 | DFIKATKVL | 13 |
| 224 | GISEYTMCL | 13 |
| 304 | ALVSTNYPL | 13 |
| 364 | VTKIPEDIL | 13 |
| 366 | KIPEDILQL | 13 |
| 374 | LLSKYNSNL | 13 |
| 384 | TPIAIKAVP | 13 |
| 3 | PIRSFCGKL | 12 |
| 6 | SFCGKLRSL | 12 |
| 104 | ERYIVSQVL | 12 |
| 193 | TKQSLVKVL | 12 |
| 212 | DFECVTPKL | 12 |
| 267 | SPIIQQLEK | 12 |
| 280 | YTNSPLVPT | 12 |
| 288 | TFCTPGLKI | 12 |
| 297 | PSTKNSIAL | 12 |
| 322 | LEVEDRTSL | 12 |
| 333 | NSDTCFENL | 12 |
| 348 | TISSYENLL | 12 |
| 2 | DPIRSFCGK | 11 |
| 28 | ALDGEESDF | 11 |
| 46 | DLHSEVQTL | 11 |
| 60 | IPELSNCEN | 11 |
| 81 | PPVASSCIS | 11 |
| 119 | VNLLDKARL | 11 |
| 182 | YKEEPVIVT | 11 |
| 189 | VTPPTKQSL | 11 |
| 232 | LNEDYTMGL | 11 |
| 250 | EAIDTESRL | 11 |
| 262 | VFATPSPII | 11 |
| 277 | DAEYTNSPL | 11 |
| 281 | TNSPLVPTF | 11 |
| 300 | KNSIALVST | 11 |
| 310 | YPLSKTNSS | 11 |
| 314 | KTNSSSNDL | 11 |
| 357 | RTPTPPEVT | 11 |
| 360 | TPPEVTKIP | 11 |
| 361 | PPEVTKIPE | 11 |
| 389 | KAVPPSKRF | 11 |
| 391 | VPPSKRFLK | 11 |

TABLE XXVII-continued

| Pos | 123456789 | score |
|---|---|---|
| V5-HLA-B0702-9mers-193P1E1B Each peptide is a portion of SEQ ID NO:11; each start position is specified, the length of peptide is 9 amino acids, and the end position for each peptide is the start position plus eight. | | |
| 9 | EKSPRSPQL | 15 |
| V6-HLA-B0702-9mers-193P1E1B Each peptide is a portion of SEQ ID NO:13; each start position is specified, the length of peptide is 9 amino acids, and the end position for each peptide is the start position plus eight. | | |
| 5 | EAIDAESRL | 11 |
| 9 | AESRLNDNV | 10 |
| 1 | NKSEEAIDA | 8 |
| 7 | IDAESRLND | 5 |
| V10-HLA-B0702-9mers-193P1E1B Each peptide is a portion of SEQ ID NO:21; each start position is specified, the length of peptide is 9 amino acids, and the end position for each peptide is the start position plus eight. | | |
| 2 | IPEDILQKF | 17 |
| 14 | YPTQKLNKM | 16 |
| 11 | QWIYPTQKL | 14 |
| V12-HLA-B0702-9mers-193P1E1B Each peptide is a portion of SEQ ID NO:25; each start position is specified, the length of peptide is 9 amino acids, and the end position for each peptide is the start position plus eight. | | |
| 2 | ALDGEESLL | 15 |
| 1 | RALDGEESL | 11 |

TABLE XXVIII

| Pos | 123456789 | score |
|---|---|---|
| V1-HLA-B08-9mers-193P1E1B Each peptide is a portion of SEQ ID NO:3; each start position is specified, the length of peptide is 9 amino acids, and the end position for each peptide is the start position plus eight. | | |
| 200 | VLKTPKCAL | 28 |
| 163 | SPRVKKNSV | 25 |
| 217 | TPKLEHFGI | 23 |
| 6 | SFCGKLRSL | 22 |
| 10 | KLRSLASTL | 22 |
| 364 | VTKIPEDIL | 21 |
| 3 | PIRSFCGKL | 20 |
| 8 | CGKLRSLAS | 20 |
| 141 | VLMEKNSMD | 20 |
| 90 | GKSPRSPQL | 19 |
| 95 | SPQLSDFGL | 19 |
| 150 | IMKIREYFQ | 19 |
| 122 | LDKARLENQ | 18 |
| 291 | TPGLKIPST | 18 |
| 296 | IPSTKNSIA | 18 |
| 46 | DLHSEVQTL | 17 |
| 53 | TLKDDVNIP | 17 |
| 114 | NPPQAVNLL | 17 |
| 203 | TPKCALKMD | 17 |
| 205 | KCALKMDDF | 17 |
| 207 | ALKMDDFEC | 17 |
| 224 | GISEYTMCL | 17 |
| 239 | GLKNARNNK | 17 |
| 265 | TPSPIIQQL | 17 |
| 286 | VPTFCTPGL | 17 |
| 293 | GLKIPSTKN | 17 |
| 304 | ALVSTNYPL | 17 |
| 366 | KIPEDILQL | 17 |
| 367 | IPEDILQLL | 17 |
| 374 | LLSKYNSNL | 17 |
| 391 | VPPSKRFLK | 17 |
| 397 | FLKHGQNIR | 17 |
| 17 | TLDCETARL | 16 |
| 39 | YPMRILYDL | 16 |

TABLE XXVIII-continued

| Pos | 123456789 | score |
|---|---|---|
| 120 | NLLDKARLE | 16 |
| 135 | FIKATKVLM | 16 |
| 190 | TPPTKQSLV | 16 |
| 215 | CVTPKLEHF | 16 |
| 250 | EAIDTESRL | 16 |
| 277 | DAEYTNSPL | 16 |
| 310 | YPLSKTNSS | 16 |
| 373 | QLLSKYNSN | 16 |
| 255 | ESRLNDNVF | 15 |
| 385 | PIAIKAVPP | 15 |
| 87 | CISGKSPRS | 14 |
| 92 | SPRSPQLSD | 14 |
| 348 | TISSYENLL | 14 |
| 387 | AIKAVPPSK | 14 |
| 392 | PPSKRFLKH | 14 |
| 21 | ETARLQRAL | 13 |
| 55 | KDDVNIPEL | 13 |
| 69 | FQKTDVKDD | 13 |
| 80 | DPPVASSCI | 13 |
| 124 | KARLENQEG | 13 |
| 166 | VKKNSVHEQ | 13 |
| 179 | SDNYKEEPV | 13 |
| 181 | NYKEEPVIV | 13 |
| 271 | QQLEKSDAE | 13 |
| 298 | STKNSIALV | 13 |
| V5-HLA-B08-9mers-193P1E1B Each peptide is a portion of SEQ ID NO:11; each start position is specified, the length of peptide is 9 amino acids, and the end position for each peptide is the start position plus eight. | | |
| 9 | EKSPRSPQL | 20 |
| 6 | CISEKSPRS | 16 |
| 8 | SEKSPRSPQ | 12 |
| V6-HLA-B08-9mers-193P1E1B Each peptide is a portion of SEQ ID NO:13; each start position is specified, the length of peptide is 9 amino acids, and the end position for each peptide is the start position plus eight. | | |
| 5 | EAIDAESRL | 16 |
| 8 | DAESRLNDN | 12 |
| V10-HLA-B08-9mers-193P1E1B Each peptide is a portion of SEQ ID NO:21; each start position is specified, the length of peptide is 9 amino acids, and the end position for each peptide is the start position plus eight. | | |
| 5 | DILQKFQWI | 20 |
| 14 | YPTQKLNKM | 16 |
| 2 | IPEDILQKF | 13 |
| 11 | QWIYPTQKL | 11 |
| 7 | LQKFQWIYP | 10 |
| V12-HLA-B08-9mers-193P1E1B Each peptide is a portion of SEQ ID NO:25; each start position is specified, the length of peptide is 9 amino acids, and the end position for each peptide is the start position plus eight. | | |
| 8 | SLLSKYNSN | 18 |
| 2 | ALDGEESLL | 16 |
| 1 | RALDGEESL | 14 |

TABLE XXIX

| Pos | 123456789 | score |
|---|---|---|
| V1-HLA-B1510-9mers-193P1E1B Each peptide is a portion of SEQ ID NO:3; each start position is specified, the length of peptide is 9 amino acids, and the end position for each peptide is the start position plus eight. | | |
| 21 | ETARLQRAL | 15 |
| 55 | KDDVNIPEL | 15 |
| 90 | GKSPRSPQL | 15 |
| 265 | TPSPIIQQL | 15 |
| 390 | AVPPSKRFL | 15 |
| 399 | KHGQNIRDV | 15 |

TABLE XXIX-continued

| Pos | 123456789 | score |
|---|---|---|
| 36 | FEDYPMRIL | 14 |
| 113 | PNPPQAVNL | 14 |
| 193 | TKQSLVKVL | 14 |
| 250 | EAIDTESRL | 14 |
| 367 | IPEDILQLL | 14 |
| 6 | SFCGKLRSL | 13 |
| 17 | TLDCETARL | 13 |
| 104 | ERYIVSQVL | 13 |
| 119 | VNLLDKARL | 13 |
| 134 | DFIKATKVL | 13 |
| 189 | VTPPTKQSL | 13 |
| 200 | VLKTPKCAL | 13 |
| 224 | GISEYTMCL | 13 |
| 281 | TNSPLVPTF | 13 |
| 297 | PSTKNSIAL | 13 |
| 46 | DLHSEVQTL | 12 |
| 47 | LHSEVQTLK | 12 |
| 70 | QKTDVKDDL | 12 |
| 114 | NPPQAVNLL | 12 |
| 171 | VHEQEAINS | 12 |
| 212 | DFECVTPKL | 12 |
| 221 | EHFGISEYT | 12 |
| 232 | LNEDYTMGL | 12 |
| 322 | LEVEDRTSL | 12 |
| 324 | VEDRTSLVL | 12 |
| 348 | TISSYENLL | 12 |
| 366 | KIPEDILQL | 12 |
| 374 | LLSKYNSNL | 12 |
| 10 | KLRSLASTL | 11 |
| 39 | YPMRILYDL | 11 |
| 277 | DAEYTNSPL | 11 |
| 286 | VPTFCTPGL | 11 |
| 364 | VTKIPEDIL | 11 |
| 389 | KAVPPSKRF | 11 |
| 3 | PIRSFCGKL | 10 |
| 95 | SPQLSDFGL | 10 |
| 255 | ESRLNDNVF | 10 |
| 304 | ALVSTNYPL | 10 |
| 314 | KTNSSSNDL | 10 |
| 333 | NSDTCFENL | 10 |
| 347 | PTISSYENL | 10 |
| 93 | PRSPQLSDF | 9 |
| 135 | FIKATKVLM | 9 |
| 149 | DIMKIREYF | 8 |
| 205 | KCALKMDDF | 8 |
| 215 | CVTPKLEHF | 8 |
| 28 | ALDGEESDF | 7 |
| 33 | ESDFEDYPM | 7 |
| 61 | PELSNCENF | 7 |
| 77 | DLSDPPVAS | 7 |
| 127 | LENQEGIDF | 7 |
| 140 | KVLMEKNSM | 7 |
| 143 | MEKNSMDIM | 7 |
| 182 | YKEEPVIVT | 7 |
| 183 | KEEPVIVTP | 7 |
| 202 | KTPKCALKM | 7 |
| 222 | HFGISEYTM | 7 |
| 230 | MCLNEDYTM | 7 |
| 358 | TPTPPEVTK | 7 |
| V5-HLA-B1510-9mers-193P1E1B<br>Each peptide is a portion of SEQ ID NO:11; each start position is specified, the length of peptide is 9 amino acids, and the end position for each peptide is the start position plus eight. | | |
| 9 | EKSPRSPQL | 15 |
| 7 | ISEKSPRSP | 7 |
| V6-HLA-B1510-9mers-193P1E1B<br>Each peptide is a portion of SEQ ID NO:13; each start position is specified, the length of peptide is 9 amino acids, and the end position for each peptide is the start position plus eight. | | |
| 5 | EAIDAESRL | 14 |

TABLE XXIX-continued

| Pos | 123456789 | score |
|---|---|---|
| V10-HLA-B1510-9mers-193P1E1B<br>Each peptide is a portion of SEQ ID NO:21; each start position is specified, the length of peptide is 9 amino acids, and the end position for each peptide is the start position plus eight. | | |
| 11 | QWIYPTQKL | 11 |
| 2 | IPEDILQKF | 10 |
| 14 | YPTQKLNKM | 8 |
| V12-HLA-B1510-9mers-193P1E1B<br>Each peptide is a portion of SEQ ID NO:25; each start position is specified, the length of peptide is 9 amino acids, and the end position for each peptide is the start position plus eight. | | |
| 1 | RALDGEESL | 12 |
| 2 | ALDGEESLL | 11 |

TABLE XXX

| Pos | 123456789 | score |
|---|---|---|
| V1-HLA-B2705-9mers-193P1E1B<br>Each peptide is a portion of SEQ ID NO:3; each start position is specified, the length of peptide is 9 amino acids, and the end position for each peptide is the start position plus eight. | | |
| 104 | ERYIVSQVL | 25 |
| 164 | PRVKKNSVH | 25 |
| 93 | PRSPQLSDF | 23 |
| 125 | ARLENQEGI | 22 |
| 4 | IRSFCGKLR | 21 |
| 137 | KATKVLMEK | 18 |
| 366 | KIPEDILQL | 18 |
| 389 | KAVPPSKRF | 18 |
| 395 | KRFLKHGQN | 18 |
| 23 | ARLQRALDG | 17 |
| 55 | KDDVNIPEL | 17 |
| 67 | ENFQKTDVK | 17 |
| 90 | GKSPRSPQL | 17 |
| 119 | VNLLDKARL | 17 |
| 132 | GIDFIKATK | 17 |
| 211 | DDFECVTPK | 17 |
| 292 | PGLKIPSTK | 17 |
| 370 | DILQLLSKY | 17 |
| 10 | KLRSLASTL | 16 |
| 47 | LHSEVQTLK | 16 |
| 86 | SCISGKSPR | 16 |
| 140 | KVLMEKNSM | 16 |
| 154 | REYFQKYGY | 16 |
| 160 | YGYSPRVKK | 16 |
| 194 | KQSLVKVLK | 16 |
| 202 | KTPKCALKM | 16 |
| 239 | GLKNARNNK | 16 |
| 265 | TPSPIIQQL | 16 |
| 267 | SPIIQQLEK | 16 |
| 330 | LVLNSDTCF | 16 |
| 369 | EDILQLLSK | 16 |
| 374 | LLSKYNSNL | 16 |
| 396 | RFLKHGQNI | 16 |
| 402 | QNIRDVSNK | 16 |
| 6 | SFCGKLRSL | 15 |
| 28 | ALDGEESDF | 15 |
| 34 | SDFEDYPMR | 15 |
| 41 | MRILYDLHS | 15 |
| 113 | PNPPQAVNL | 15 |
| 134 | DFIKATKVL | 15 |
| 148 | MDIMKIREY | 15 |
| 175 | EAINSDNYK | 15 |
| 191 | PPTKQSLVK | 15 |
| 220 | LEHFGISEY | 15 |
| 224 | GISEYTMCL | 15 |
| 236 | YTMGLKNAR | 15 |
| 250 | EAIDTESRL | 15 |
| 281 | TNSPLVPTF | 15 |

TABLE XXX-continued

| Pos | 123456789 | score |
|---|---|---|
| 302 | SIALVSTNY | 15 |
| 314 | KTNSSSNDL | 15 |
| 322 | LEVEDRTSL | 15 |
| 326 | DRTSLVLNS | 15 |
| 347 | PTISSYENL | 15 |
| 381 | NLATPIAIK | 15 |
| 388 | IKAVPPSKR | 15 |
| 397 | FLKHGQNIR | 15 |
| 11 | LRSLASTLD | 14 |
| 16 | STLDCETAR | 14 |
| 17 | TLDCETARL | 14 |
| 52 | QTLKDDVNI | 14 |
| 61 | PELSNCENF | 14 |
| 83 | VASSCISGK | 14 |
| 114 | NPPQAVNLL | 14 |
| 118 | AVNLLDKAR | 14 |
| 127 | LENQEGIDF | 14 |
| 129 | NQEGIDFIK | 14 |
| 145 | KNSMDIMKI | 14 |
| 151 | MKIREYFQK | 14 |
| 159 | KYGYSPRVK | 14 |
| 186 | PVIVTPPTK | 14 |
| 197 | LVKVLKTPK | 14 |
| 205 | KCALKMDDF | 14 |
| 212 | DFECVTPKL | 14 |
| 230 | MCLNEDYTM | 14 |
| 243 | ARNNKSEEA | 14 |
| 255 | ESRLNDNVF | 14 |
| 256 | SRLNDNVFA | 14 |
| 272 | QLEKSDAEY | 14 |
| 297 | PSTKNSIAL | 14 |
| 304 | ALVSTNYPL | 14 |
| 344 | PSSPTISSY | 14 |
| 349 | ISSYENLLR | 14 |
| 358 | TPTPPEVTK | 14 |
| 387 | AIKAVPPSK | 14 |
| 390 | AVPPSKRFL | 14 |
| 404 | IRDVSNKEN | 14 |
| 2 | DPIRSFCGK | 13 |
| 5 | RSFCGKLRS | 13 |
| 21 | ETARLQRAL | 13 |
| 39 | YPMRILYDL | 13 |
| 46 | DLHSEVQTL | 13 |
| 63 | LSNCENFQK | 13 |
| 95 | SPQLSDFGL | 13 |
| 98 | LSDFGLERY | 13 |
| 149 | DIMKIREYF | 13 |
| 152 | KIREYFQKY | 13 |
| 153 | IREYFQKYG | 13 |
| 157 | FQKYGYSPR | 13 |
| 180 | DNYKEEPVI | 13 |
| 189 | VTPPTKQSL | 13 |
| 193 | TKQSLVKVL | 13 |
| 201 | LKTPKCALK | 13 |
| 214 | ECVTPKLEH | 13 |
| 215 | CVTPKLEHF | 13 |
| 244 | RNNKSEEAI | 13 |
| 287 | PTFCTPGLK | 13 |
| 319 | SNDLEVEDR | 13 |
| 324 | VEDRTSLVL | 13 |
| 356 | LRTPTPPEV | 13 |
| 359 | PTPPEVTKI | 13 |
| 367 | IPEDILQLL | 13 |
| 392 | PPSKRFLKH | 13 |
| 3 | PIRSFCGKL | 12 |
| 19 | DCETARLQR | 12 |
| 26 | QRALDGEES | 12 |
| 37 | EDYPMRILY | 12 |
| 70 | QKTDVKDDL | 12 |
| 97 | QLSDFGLER | 12 |
| 99 | SDFGLERYI | 12 |
| 116 | PQAVNLLDK | 12 |
| 128 | ENQEGIDFI | 12 |
| 144 | EKNSMDIMK | 12 |
| 200 | VLKTPKCAL | 12 |
| 277 | DAEYTNSPL | 12 |

TABLE XXX-continued

| Pos | 123456789 | score |
|---|---|---|
| 306 | VSTNYPLSK | 12 |
| 333 | NSDTCFENL | 12 |
| V5-B2705-9mers-193P1E1B<br>Each peptide is a portion of SEQ ID NO:11; each start position is specified, the length of peptide is 9 amino acids, and the end position for each peptide is the start position plus eight. | | |
| 2 | VASSCISEK | 15 |
| 5 | SCISEKSPR | 15 |
| 9 | EKSPRSPQL | 14 |
| V6-B2705-9mers-193P1E1B<br>Each peptide is a portion of SEQ ID NO:13; each start position is specified, the length of peptide is 9 amino acids, and the end position for each peptide is the start position plus eight. | | |
| 5 | EAIDAESRL | 15 |
| 4 | EEAIDAESR | 12 |
| V10-B2705-9mers-193P1E1B<br>Each peptide is a portion of SEQ ID NO:21; each start position is specified, the length of peptide is 9 amino acids, and the end position for each peptide is the start positon plus eight. | | |
| 1 | KIPEDILQK | 18 |
| 2 | IPEDILQKF | 15 |
| 11 | QWIYPTQKL | 15 |
| 13 | IYPTQKLNK | 15 |
| 14 | YPTQKLNKM | 15 |
| 6 | ILQKFQWIY | 14 |
| 15 | PTQKLNKMR | 14 |
| 10 | FQWIYPTQK | 13 |
| 5 | DILQKFQWI | 11 |
| 8 | QKFQWIYPT | 9 |
| V12-B2705-9mers-193P1E1B<br>Each peptide is a portion of SEQ ID NO:25; each start position is specified, the length of peptide is 9 amino acids, and the end position for each peptide is the start position plus eight. | | |
| 1 | RALDGEESL | 19 |
| 5 | GEESLLSKY | 16 |
| 2 | ALDGEESLL | 15 |
| 4 | DGEESLLSK | 15 |

TABLE XXXI

| Pos | 123456789 | score |
|---|---|---|
| V1-HLA-B2709-9mers-193P1E1B<br>Each peptide is a portion of SEQ ID NO:3; each start position is specified, the length of peptide is 9 amino acids, and the end position for each peptide is the start position plus eight. | | |
| 104 | ERYIVSQVL | 22 |
| 125 | ARLENQEGI | 21 |
| 356 | LRTPTPPEV | 21 |
| 93 | PRSPQLSDF | 19 |
| 90 | GKSPRSPQL | 16 |
| 23 | ARLQRALDG | 15 |
| 326 | DRTSLVLNS | 15 |
| 366 | KIPEDILQL | 15 |
| 395 | KRFLKHGQN | 15 |
| 396 | RFLKHGQNI | 15 |
| 10 | KLRSLASTL | 14 |
| 113 | PNPPQAVNL | 14 |
| 119 | VNLLDKARL | 14 |
| 256 | SRLNDNVFA | 14 |
| 304 | ALVSTNYPL | 14 |
| 52 | QTLKDDVNI | 13 |
| 55 | KDDVNIPEL | 13 |
| 224 | GISEYTMCL | 13 |
| 265 | TPSPIIQQL | 13 |
| 314 | KTNSSSNDL | 13 |
| 347 | PTISSYENL | 13 |
| 389 | KAVPPSKRF | 13 |
| 39 | YPMRILYDL | 12 |
| 41 | MRILYDLHS | 12 |

TABLE XXXI-continued

| Pos | 123456789 | score |
|---|---|---|
| 46 | DLHSEVQTL | 12 |
| 61 | PELSNCENF | 12 |
| 133 | IDFIKATKV | 12 |
| 140 | KVLMEKNSM | 12 |
| 158 | QKYGYSPRV | 12 |
| 193 | TKQSLVKVL | 12 |
| 202 | KTPKCALKM | 12 |
| 244 | RNNKSEEAI | 12 |
| 250 | EAIDTESRL | 12 |
| 278 | AEYTNSPLV | 12 |
| 286 | VPTFCTPGL | 12 |
| 322 | LEVEDRTSL | 12 |
| 367 | IPEDILQLL | 12 |
| 390 | AVPPSKRFL | 12 |
| 3 | PIRSFCGKL | 11 |
| 4 | IRSFCGKLR | 11 |
| 17 | TLDCETARL | 11 |
| 26 | QRALDGEES | 11 |
| 43 | ILYDLHSEV | 11 |
| 70 | QKTDVKDDL | 11 |
| 75 | KDDLSDPPV | 11 |
| 103 | LERYIVSQV | 11 |
| 114 | NPPQAVNLL | 11 |
| 134 | DFIKATKVL | 11 |
| 145 | KNSMDIMKI | 11 |
| 153 | IREYFQKYG | 11 |
| 164 | PRVKKNSVH | 11 |
| 180 | DNYKEEPVI | 11 |
| 189 | VTPPTKQSL | 11 |
| 212 | DFECVTPKL | 11 |
| 230 | MCLNEDYTM | 11 |
| 243 | ARNNKSEEA | 11 |
| 281 | TNSPLVPTF | 11 |
| 295 | KIPSTKNSI | 11 |
| 297 | PSTKNSIAL | 11 |
| 324 | VEDRTSLVL | 11 |
| 333 | NSDTCFENL | 11 |
| 348 | TISSYENLL | 11 |
| 374 | LLSKYNSNL | 11 |
| 404 | IRDVSNKEN | 11 |
| 6 | SFCGKLRSL | 10 |
| 11 | LRSLASTLD | 10 |
| 21 | ETARLQRAL | 10 |
| 36 | FEDYPMRIL | 10 |
| 95 | SPQLSDFGL | 10 |
| 99 | SDFGLERYI | 10 |
| 200 | VLKTPKCAL | 10 |
| 205 | KCALKMDDF | 10 |
| 215 | CVTPKLEHF | 10 |
| 232 | LNEDYTMGL | 10 |
| 261 | NVFATPSPI | 10 |
| 277 | DAEYTNSPL | 10 |
| 316 | NSSSNDLEV | 10 |
| 330 | LVLNSDTCF | 10 |
| 341 | LTDPSSPTI | 10 |
| 359 | PTPPEVTKI | 10 |
| 363 | EVTKIPEDI | 10 |
| 364 | VTKIPEDIL | 10 |
| 380 | SNLATPIAI | 10 |
| 399 | KHGQNIRDV | 10 |
| V5-HLA-B2709-9mers-193P1E1B Each peptide is a portion of SEQ ID NO:11; each start position is specified, the length of peptide is 9 amino acids, and the end position for each peptide is the start position plus eight. | | |
| 9 | EKSPRSPQL | 13 |
| V6-HLA-B2709-9mers-193P1E1B Each peptide is a portion of SEQ ID NO:13; each start position is specified, the length of peptide is 9 amino acids, and the end position for each peptide is the start position plus eight. | | |
| 5 | EAIDAESRL | 12 |
| 9 | AESRLNDNV | 10 |

TABLE XXXI-continued

| Pos | 123456789 | score |
|---|---|---|
| V10-HLA-B2709-9mers-193P1E1B Each peptide is a portion of SEQ ID NO:21; each start position is specified, the length of peptide is 9 amino acids, and the end position for each peptide is the start position plus eight. | | |
| 11 | QWIYPTQKL | 11 |
| 2 | IPEDILQKF | 10 |
| 5 | DILQKFQWI | 10 |
| 14 | YPTQKLNKM | 9 |
| 1 | KIPEDILQK | 5 |
| V12-HLA-B2709-9mers-193P1E1B Each peptide is a portion of SEQ ID NO:25; each start position is specified, the length of peptide is 9 amino acids, and the end position for each peptide is the start position plus eight. | | |
| 1 | RALDGEESL | 16 |
| 2 | ALDGEESLL | 11 |

TABLE XXXII

| Pos | 123456789 | score |
|---|---|---|
| V1-HLA-B4402-9mers-193P1E1B Each peptide is a portion of SEQ ID NO:3; each start position is specified, the length of peptide is 9 amino acids, and the end position for each peptide is the start position plus eight. | | |
| 324 | VEDRTSLVL | 24 |
| 220 | LEHFGISEY | 23 |
| 36 | FEDYPMRIL | 22 |
| 61 | PELSNCENF | 22 |
| 31 | GEESDFEDY | 21 |
| 127 | LENQEGIDF | 21 |
| 174 | QEAINSDNY | 21 |
| 322 | LEVEDRTSL | 21 |
| 154 | REYFQKYGY | 20 |
| 183 | KEEPVIVTP | 19 |
| 265 | TPSPIIQQL | 19 |
| 37 | EDYPMRILY | 18 |
| 390 | AVPPSKRFL | 18 |
| 134 | DFIKATKVL | 17 |
| 148 | MDIMKIREY | 17 |
| 344 | PSSPTISSY | 17 |
| 366 | KIPEDILQL | 17 |
| 21 | ETARLQRAL | 16 |
| 55 | KDDVNIPEL | 16 |
| 90 | GKSPRSPQL | 16 |
| 113 | PNPPQAVNL | 16 |
| 250 | EAIDTESRL | 16 |
| 255 | ESRLNDNVF | 16 |
| 278 | AEYTNSPLV | 16 |
| 281 | TNSPLVPTF | 16 |
| 389 | KAVPPSKRF | 16 |
| 28 | ALDGEESDF | 15 |
| 93 | PRSPQLSDF | 15 |
| 114 | NPPQAVNLL | 15 |
| 184 | EEPVIVTPP | 15 |
| 6 | SFCGKLRSL | 14 |
| 32 | EESDFEDYP | 14 |
| 39 | YPMRILYDL | 14 |
| 49 | SEVQTLKDD | 14 |
| 145 | KNSMDIMKI | 14 |
| 172 | HEQEAINSD | 14 |
| 189 | VTPPTKQSL | 14 |
| 193 | TKQSLVKVL | 14 |
| 213 | FECVTPKLE | 14 |
| 215 | CVTPKLEHF | 14 |
| 297 | PSTKNSIAL | 14 |
| 333 | NSDTCFENL | 14 |
| 359 | PTPPEVTKI | 14 |
| 362 | PEVTKIPED | 14 |
| 367 | IPEDILQLL | 14 |
| 380 | SNLATPIAI | 14 |
| 10 | KLRSLASTL | 13 |

TABLE XXXII-continued

| Pos | 123456789 | score |
|---|---|---|
| 99 | SDFGLERYI | 13 |
| 103 | LERYIVSQV | 13 |
| 104 | ERYIVSQVL | 13 |
| 125 | ARLENQEGI | 13 |
| 128 | ENQEGIDFI | 13 |
| 130 | QEGIDFIKA | 13 |
| 131 | EGIDFIKAT | 13 |
| 149 | DIMKIREYF | 13 |
| 152 | KIREYFQKY | 13 |
| 200 | VLKTPKCAL | 13 |
| 226 | SEYTMCLNE | 13 |
| 233 | NEDYTMGLK | 13 |
| 249 | EEAIDTESR | 13 |
| 304 | ALVSTNYPL | 13 |
| 341 | LTDPSSPTI | 13 |
| 347 | PTISSYENL | 13 |
| 348 | TISSYENLL | 13 |
| 368 | PEDILQLLS | 13 |
| 370 | DILQLLSKY | 13 |
| 17 | TLDCETARL | 12 |
| 20 | CETARLQRA | 12 |
| 46 | DLHSEVQTL | 12 |
| 95 | SPQLSDFGL | 12 |
| 98 | LSDFGLERY | 12 |
| 119 | VNLLDKARL | 12 |
| 205 | KCALKMDDF | 12 |
| 212 | DFECVTPKL | 12 |
| 224 | GISEYTMCL | 12 |
| 232 | LNEDYTMGL | 12 |
| 248 | SEEAIDTES | 12 |
| 254 | TESRLNDNV | 12 |
| 261 | NVFATPSPI | 12 |
| 302 | SIALVSTNY | 12 |
| 314 | KTNSSSNDL | 12 |
| 330 | LVLNSDTCF | 12 |
| 352 | YENLLRTPT | 12 |
| 363 | EVTKIPEDI | 12 |
| 3 | PIRSFCGKL | 11 |
| 70 | QKTDVKDDL | 11 |
| 143 | MEKNSMDIM | 11 |
| 169 | NSVHEQEAI | 11 |
| 228 | YTMCLNEDY | 11 |
| 273 | LEKSDAEYT | 11 |
| 286 | VPTFCTPGL | 11 |
| 288 | TFCTPGLKI | 11 |
| 295 | KIPSTKNSI | 11 |
| 338 | FENLTDPSS | 11 |
| 374 | LLSKYNSNL | 11 |
| 378 | YNSNLATPI | 11 |
| 383 | ATPIAIKAV | 11 |
| V5-HLA-B4402-9mers-193P1E1B<br>Each peptide is a portion of SEQ ID NO:11; each start position is specified, the length of peptide is 9 amino acids, and the end position for each peptide is the start position plus eight. | | |
| 9 | EKSPRSPQL | 18 |
| 8 | SEKSPRSPQ | 12 |
| V6-HLA-B4402-9mers-193P1E1B<br>Each peptide is a portion of SEQ ID NO:13; each start position is specified, the length of peptide is 9 amino acids, and the end position for each peptide is the start position plus eight. | | |
| 5 | EAIDAESRL | 16 |
| 9 | AESRLNDNV | 15 |
| 4 | EEAIDAESR | 13 |
| 3 | SEEAIDAES | 12 |
| V10-HLA-B4402-9mers-193P1E1B<br>Each peptide is a portion of SEQ ID NO:21; each start position is specified, the length of peptide is 9 amino acids, and the end position for each peptide is the start position plus eight. | | |
| 4 | EDILQKFQW | 17 |
| 11 | QWIYPTQKL | 15 |
| 2 | IPEDILQKF | 14 |
| 3 | PEDILQKFQ | 13 |
| 5 | DILQKFQWI | 10 |
| 6 | ILQKFQWIY | 10 |

TABLE XXXII-continued

| Pos | 123456789 | score |
|---|---|---|
| V12-HLA-B4402-9mers-193P1E1B<br>Each peptide is a portion of SEQ ID NO:25; each start position is specified, the length of peptide is 9 amino acids, and the end position for each peptide is the start position plus eight. | | |
| 5 | GEESLLSKY | 22 |
| 2 | ALDGEESLL | 16 |
| 6 | EESLLSKYN | 16 |
| 1 | RALDGEESL | 12 |

TABLE XXXIII

| Pos | 123456789 | score |
|---|---|---|
| V1-HLA-B5101-9mers-193P1E1B<br>Each peptide is a portion of SEQ ID NO:3; each start position is specified, the length of peptide is 9 amino acids, and the end position for each peptide is the start position plus eight. | | |
| 80 | DPPVASSCI | 25 |
| 180 | DNYKEEPVI | 22 |
| 190 | TPPTKQSLV | 22 |
| 277 | DAEYTNSPL | 22 |
| 114 | NPPQAVNLL | 21 |
| 217 | TPKLEHFGI | 21 |
| 163 | SPRVKKNSV | 20 |
| 367 | IPEDILQLL | 20 |
| 39 | YPMRILYDL | 19 |
| 250 | EAIDTESRL | 19 |
| 35 | DFEDYPMRI | 18 |
| 265 | TPSPIIQQL | 18 |
| 95 | SPQLSDFGL | 17 |
| 286 | VPTFCTPGL | 17 |
| 360 | TPPEVTKIP | 17 |
| 2 | DPIRSFCGK | 16 |
| 133 | IDFIKATKV | 16 |
| 303 | IALVSTNYP | 16 |
| 310 | YPLSKTNSS | 16 |
| 359 | PTPPEVTKI | 16 |
| 380 | SNLATPIAI | 16 |
| 382 | LATPIAIKA | 16 |
| 43 | ILYDLHSEV | 15 |
| 101 | FGLERYIVS | 15 |
| 104 | ERYIVSQVL | 15 |
| 112 | LPNPPQAVN | 15 |
| 115 | PPQAVNLLD | 15 |
| 134 | DFIKATKVL | 15 |
| 158 | QKYGYSPRV | 15 |
| 160 | YGYSPRVKK | 15 |
| 191 | PPTKQSLVK | 15 |
| 261 | NVFATPSPI | 15 |
| 288 | TFCTPGLKI | 15 |
| 296 | IPSTKNSIA | 15 |
| 341 | LTDPSSPTI | 15 |
| 343 | DPSSPTISS | 15 |
| 384 | TPIAIKAVP | 15 |
| 386 | IAIKAVPPS | 15 |
| 392 | PPSKRFLKH | 15 |
| 46 | DLHSEVQTL | 14 |
| 52 | QTLKDDVNI | 14 |
| 60 | IPELSNCEN | 14 |
| 125 | ARLENQEGI | 14 |
| 137 | KATKVLMEK | 14 |
| 206 | CALKMDDFE | 14 |
| 212 | DFECVTPKL | 14 |
| 263 | FATPSPIIQ | 14 |
| 358 | TPTPPEVTK | 14 |
| 378 | YNSNLATPI | 14 |
| 14 | LASTLDCET | 13 |
| 27 | RALDGEESD | 13 |
| 30 | DGEESDFED | 13 |
| 99 | SDFGLERYI | 13 |
| 117 | QAVNLLDKA | 13 |
| 128 | ENQEGIDFI | 13 |

TABLE XXXIII-continued

| Pos | 123456789 | score |
|---|---|---|
| 142 | LMEKNSMDI | 13 |
| 145 | KNSMDIMKI | 13 |
| 181 | NYKEEPVIV | 13 |
| 192 | PTKQSLVKV | 13 |
| 193 | TKQSLVKVL | 13 |
| 203 | TPKCALKMD | 13 |
| 278 | AEYTNSPLV | 13 |
| 291 | TPGLKIPST | 13 |
| 295 | KIPSTKNSI | 13 |
| 391 | VPPSKRFLK | 13 |
| 396 | RFLKHGQNI | 13 |
| 81 | PPVASSCIS | 12 |
| 83 | VASSCISGK | 12 |
| 100 | DFGLERYIV | 12 |
| 103 | LERYIVSQV | 12 |
| 175 | EAINSDNYK | 12 |
| 185 | EPVIVTPPT | 12 |
| 208 | LKMDDFECV | 12 |
| 238 | MGLKNARNN | 12 |
| 244 | RNNKSEEAI | 12 |
| 262 | VFATPSPII | 12 |
| 283 | SPLVPTFCT | 12 |
| 292 | PGLKIPSTK | 12 |
| 324 | VEDRTSLVL | 12 |
| 356 | LRTPTPPEV | 12 |
| 361 | PPEVIKIPE | 12 |
| 363 | EVTKIPEDI | 12 |
| 389 | KAVPPSKRF | 12 |
| V5-HLA-B5101-9mers-193P1E1B<br>Each peptide is a portion of SEQ ID NO:11; each start position is specified, the length of peptide is 9 amino acids, and the end position for each peptide is the start position plus eight. | | |
| 2 | VASSCISEK | 12 |
| 7 | ISEKSPRSP | 6 |
| 9 | EKSPRSPQL | 6 |
| V6-HLA-B5101-9mers-193P1E1B<br>Each peptide is a portion of SEQ ID NO:13; each start position is specified, the length of peptide is 9 amino acids, and the end position for each peptide is the start position plus eight. | | |
| 5 | EAIDAESRL | 18 |
| 8 | DAESRLNDN | 16 |
| 9 | AESRLNDNV | 9 |
| V10-HLA-B5101-9mers-193P1E1B<br>Each peptide is a portion of SEQ ID NO:21; each start position is specified, the length of peptide is 9 amino acids, and the end position for each peptide is the start position plus eight. | | |
| 5 | DILQKFQWI | 18 |
| 14 | YPTQKLNKM | 17 |
| 2 | IPEDILQKF | 16 |
| 11 | QWIYPTQKL | 8 |
| V12-HLA-B5101-9mers-193P1E1B<br>Each peptide is a portion of SEQ ID NO:25; each start position is specified, the length of peptide is 9 amino acids, and the end position for each peptide is the start position plus eight. | | |
| 1 | RALDGEESL | 19 |
| 4 | DGEESLLSK | 15 |

TABLE XXXIV

| Pos | 1234567890 | score |
|---|---|---|
| V1-HLA-A1-10mers-193P1E1B<br>Each peptide is a portion of SEQ ID NO:3; each start position is specified, the length of peptide is 10 amino acids, and the end position for each peptide is the start position plus nine. | | |
| 36 | FEDYPMRILY | 33 |
| 30 | DGEESDFEDY | 28 |
| 147 | SMDIMKIREY | 27 |
| 219 | KLEHFGISEY | 26 |

TABLE XXXIV-continued

| Pos | 1234567890 | score |
|---|---|---|
| 153 | IREYFQKYGY | 25 |
| 173 | EQEAINSDNY | 25 |
| 71 | KTDVKDDLSD | 22 |
| 129 | NQEGIDFIKA | 20 |
| 151 | MKIREYFQKY | 20 |
| 225 | ISEYTMCLNE | 20 |
| 341 | LTDPSSPTIS | 20 |
| 233 | NEDYTMGLKN | 19 |
| 301 | NSIALVSTNY | 19 |
| 78 | LSDPPVASSC | 18 |
| 251 | AIDTESRLND | 18 |
| 367 | IPEDILQLLS | 18 |
| 253 | DTESRLNDNV | 17 |
| 323 | EVEDRTSLVL | 17 |
| 369 | EDILQLLSKY | 17 |
| 97 | QLSDFGLERY | 16 |
| 126 | RLENQEGIDF | 16 |
| 227 | EYTMCLNEDY | 16 |
| 333 | NSDTCFENLT | 16 |
| 368 | PEDILQLLSK | 16 |
| V5-HLA-A1-10mers-193P1E1B<br>Each peptide is a portion of SEQ ID NO:11; each start position is specified, the length of peptide is 10 amino acids, and the end position for each peptide is the start position plus nine. | | |
| 8 | ISEKSPRSPQ | 15 |
| V6-HLA-A1-10mers-193P1E1B<br>Each peptide is a portion of SEQ ID NO:13; each start position is specified, the length of peptide is 10 amino acids, and the end position for each peptide is the start position plus nine. | | |
| 7 | AIDAESRLND | 18 |
| 3 | KSEEAIDAES | 14 |
| 4 | SEEAIDAESR | 12 |
| 9 | DAESRLNDNV | 11 |
| V10-HLA-A1-10mers-193P1E1B<br>Each peptide is a portion of SEQ ID NO:21; each start position is specified, the length of peptide is 10 amino acids, and the end position for each peptide is the start position plus nine. | | |
| 6 | DILQKFQWIY | 15 |
| 1 | TKIPEDILQK | 10 |
| 3 | IPEDILQKFQ | 10 |
| 4 | PEDILQKFQW | 10 |
| 13 | WIYPTQKLNK | 10 |
| V12-HLA-A1-10mers-193P1E1B<br>Each peptide is a portion of SEQ ID NO:25; each start position is specified, the length of peptide is 10 amino acids, and the end position for each peptide is the start position plus nine. | | |
| 5 | DGEESLLSKY | 27 |
| 3 | ALDGEESLLS | 21 |

TABLE XXXV

| Pos | 1234567890 | score |
|---|---|---|
| V1-HLA-A0201-10mers-193P1E1B<br>Each peptide is a portion of SEQ ID NO:3; each start position is specified, the length of peptide is 10 amino acids, and the end position for each peptide is the start position plus nine. | | |
| 355 | LLRTPTPPEV | 25 |
| 366 | KIPEDILQLL | 25 |
| 102 | GLERYIVSQV | 24 |
| 231 | CLNEDYTMGL | 24 |
| 141 | VLMEKNSMDI | 22 |
| 373 | QLLSKYNSNL | 22 |
| 16 | STLDCETARL | 21 |
| 42 | RILYDLHSEV | 21 |
| 207 | ALKMDDFECV | 21 |
| 340 | NLTDPSSPTI | 21 |
| 382 | LATPIAIKAV | 21 |
| 13 | SLASTLDCET | 20 |

TABLE XXXV-continued

| Pos | 1234567890 | score |
|---|---|---|
| 45 | YDLHSEVQTL | 20 |
| 54 | LKDDVNIPEL | 20 |
| 132 | GIDFIKATKV | 20 |
| 264 | ATPSPIIQQL | 20 |
| 321 | DLEVEDRTSL | 20 |
| 110 | QVLPNPPQAV | 19 |
| 118 | AVNLLDKARL | 19 |
| 188 | IVTPPTKQSL | 19 |
| 303 | IALVSTNYPL | 19 |
| 365 | TKIPEDILQL | 19 |
| 77 | DLSDPPVASS | 18 |
| 199 | KVLKTPKCAL | 18 |
| 285 | LVPTFCTPGL | 18 |
| 381 | NLATPIAIKA | 18 |
| 398 | LKHGQNIRDV | 18 |
| 5 | RSFCGKLRSL | 17 |
| 112 | LPNPPQAVNL | 17 |
| 189 | VTPPTKQSLV | 17 |
| 290 | CTPGLKIPST | 17 |
| 294 | LKIPSTKNSI | 17 |
| 374 | LLSKYNSNLA | 17 |
| 389 | KAVPPSKRFL | 17 |
| 99 | SDFGLERYIV | 16 |
| 120 | NLLDKARLEN | 16 |
| 121 | LLDKARLENQ | 16 |
| 147 | SMDIMKIREY | 16 |
| 219 | KLEHFGISEY | 16 |
| 257 | RLNDNVFATP | 16 |
| 276 | SDAEYTNSPL | 16 |
| 9 | GKLRSLASTL | 15 |
| 97 | QLSDFGLERY | 15 |
| 106 | YIVSQVLPNP | 15 |
| 127 | LENQEGIDFI | 15 |
| 162 | YSPRVKKNSV | 15 |
| 211 | DDFECVTPKL | 15 |
| 229 | TMCLNEDYTM | 15 |
| 358 | TPTPPEVTKI | 15 |
| 28 | ALDGEESDFE | 14 |
| 38 | DYPMRILYDL | 14 |
| 43 | ILYDLHSEVQ | 14 |
| 113 | PNPPQAVNLL | 14 |
| 124 | KARLENQEGI | 14 |
| 191 | PPTKQSLVKV | 14 |
| 209 | KMDDFECVTP | 14 |
| 216 | VTPKLEHFGI | 14 |
| 261 | NVFATPSPII | 14 |
| 269 | IIQQLEKSDA | 14 |
| 280 | YTNSPLVPTF | 14 |
| 322 | LEVEDRTSLV | 14 |
| 331 | VLNSDTCFEN | 14 |
| 347 | PTISSYENLL | 14 |
| 2 | DPIRSFCGKL | 13 |
| 34 | SDFEDYPMRI | 13 |
| 74 | VKDDLSDPPV | 13 |
| 101 | FGLERYIVSQ | 13 |
| 111 | VLPNPPQAVN | 13 |
| 135 | FIKATKVLME | 13 |
| 142 | LMEKNSMDIM | 13 |
| 192 | PTKQSLVKVL | 13 |
| 223 | FGISEYTMCL | 13 |
| 239 | GLKNARNNKS | 13 |
| 256 | SRLNDNVFAT | 13 |
| 272 | QLEKSDAEYT | 13 |
| 287 | PTFCTPGLKI | 13 |
| 295 | KIPSTKNSIA | 13 |
| 296 | IPSTKNSIAL | 13 |
| 299 | TKNSIALVST | 13 |
| 302 | SIALVSTNYP | 13 |
| 304 | ALVSTNYPLS | 13 |
| 315 | TNSSSNDLEV | 13 |
| 332 | LNSDTCFENL | 13 |
| 354 | NLLRTPTPPE | 13 |
| 371 | ILQLLSKYNS | 13 |
| 14 | LASTLDCETA | 12 |
| 24 | RLQRALDGEE | 12 |
| 49 | SEVQTLKDDV | 12 |
| 59 | NIPELSNCEN | 12 |
| 79 | SDPPVASSCI | 12 |
| 87 | CISGKSPRSP | 12 |
| 89 | SGKSPRSPQL | 12 |
| 133 | IDFIKATKVL | 12 |
| 144 | EKNSMDIMKI | 12 |
| 176 | AINSDNYKEE | 12 |
| 180 | DNYKEEPVIV | 12 |
| 194 | KQSLVKVLKT | 12 |
| 196 | SLVKVLKTPK | 12 |
| 200 | VLKTPKCALK | 12 |
| 243 | ARNNKSEEAI | 12 |
| 253 | DTESRLNDNV | 12 |
| 277 | DAEYTNSPLV | 12 |
| 297 | PSTKNSIALV | 12 |
| 313 | SKTNSSSNDL | 12 |
| 323 | EVEDRTSLVL | 12 |
| 329 | SLVLNSDTCF | 12 |
| 385 | PIAIKAVPPS | 12 |
| V5-HLA-A0201-10mers-193P1E1B<br>Each peptide is a portion of SEQ ID NO:11; each start position is specified, the length of peptide is 10 amino acids, and the end position for each peptide is the start position plus nine. | | |
| 7 | CISEKSPRSP | 12 |
| 9 | SEKSPRSPQL | 12 |
| 2 | PVASSCISEK | 9 |
| 3 | VASSCISEKS | 7 |
| 6 | SCISEKSPRS | 5 |
| V6-HLA-A0201-10mers-193P1E1B<br>Each peptide is a portion of SEQ ID NO:13; each start position is specified, the length of peptide is 10 amino acids, and the end position for each peptide is the start position plus nine. | | |
| 9 | DAESRLNDNV | 12 |
| 7 | AIDAESRLND | 11 |
| 8 | IDAESRLNDN | 11 |
| 5 | EEAIDAESRL | 9 |
| 2 | NKSEEAIDAE | 7 |
| 3 | KSEEAIDAES | 6 |
| V10-HLA-A0201-10mers-193P1E1B<br>Each peptide is a portion of SEQ ID NO:21; each start position is specified, the length of peptide is 10 amino acids, and the end position for each peptide is the start position plus nine. | | |
| 2 | KIPEDILQKF | 17 |
| 11 | FQWIYPTQKL | 14 |
| 14 | IYPTQKLNKM | 13 |
| 7 | ILQKFQWIYP | 12 |
| 13 | WIYPTQKLNK | 12 |
| V12-HLA-A0201-10mers-193P1E1B<br>Each peptide is a portion of SEQ ID NO:25; each start position is specified, the length of peptide is 10 amino acids, and the end position for each peptide is the start position plus nine. | | |
| 9 | SLLSKYNSNL | 24 |
| 2 | RALDGEESLL | 17 |
| 3 | ALDGEESLLS | 15 |
| 1 | QRALDGEESL | 14 |
| 4 | LDGEESLLSK | 11 |

TABLE XXXVI

| Pos | 1234567890 | score |
|---|---|---|
| V1-HLA-A0203-10mers-193P1E1B<br>Each peptide is a portion of SEQ ID NO:3; each start position is specified, the length of peptide is 10 amino acids, and the end position for each peptide is the start position plus nine. | | |
| 6 | SFCGKLRSLA | 10 |
| 14 | LASTLDCETA | 10 |
| 19 | DCETARLQRA | 10 |
| 75 | KDDLSDPPVA | 10 |
| 109 | SQVLPNPPQA | 10 |

TABLE XXXVI-continued

| Pos | 1234567890 | score |
|---|---|---|
| 116 | PQAVNLLDKA | 10 |
| 129 | NQEGIDFIKA | 10 |
| 167 | KKNSVHEQEA | 10 |
| 198 | VKVLKTPKCA | 10 |
| 234 | EDYTMGLKNA | 10 |
| 242 | NARNNKSEEA | 10 |
| 255 | ESRLNDNVFA | 10 |
| 269 | IIQQLEKSDA | 10 |
| 295 | KIPSTKNSIA | 10 |
| 374 | LLSKYNSNLA | 10 |
| 378 | YNSNLATPIA | 10 |
| 381 | NLATPIAIKA | 10 |
| 7 | FCGKLRSLAS | 9 |
| 15 | ASTLDCETAR | 9 |
| 20 | CETARLQRAL | 9 |
| 76 | DDLSDPPVAS | 9 |
| 110 | QVLPNPPQAV | 9 |
| 117 | QAVNLLDKAR | 9 |
| 130 | QEGIDFIKAT | 9 |
| 168 | KNSVHEQEAI | 9 |
| 199 | KVLKTPKCAL | 9 |
| 235 | DYTMGLKNAR | 9 |
| 243 | ARNNKSEEAI | 9 |
| 256 | SRLNDNVFAT | 9 |
| 270 | IQQLEKSDAE | 9 |
| 296 | IPSTKNSIAL | 9 |
| 375 | LSKYNSNLAT | 9 |
| 379 | NSNLATPIAI | 9 |
| 382 | LATPIAIKAV | 9 |
| 8 | CGKLRSLAST | 8 |
| 16 | STLDCETARL | 8 |
| 21 | ETARLQRALD | 8 |
| 77 | DLSDPPVASS | 8 |
| 111 | VLPNPPQAVN | 8 |
| 118 | AVNLLDKARL | 8 |
| 131 | EGIDFIKATK | 8 |
| 169 | NSVHEQEAIN | 8 |
| 200 | VLKTPKCALK | 8 |
| 236 | YTMGLKNARN | 8 |
| 244 | RNNKSEEAID | 8 |
| 257 | RLNDNVFATP | 8 |
| 271 | QQLEKSDAEY | 8 |
| 297 | PSTKNSIALV | 8 |
| 376 | SKYNSNLATP | 8 |
| 380 | SNLATPIAIK | 8 |
| 383 | ATPIAIKAVP | 8 |
| | V5-HLA-A0203-10mers-193P1E1B | |
| | NoResultsFound. | |
| | V6-HLA-A0203-10mers-193P1E1B Each peptide is a portion of SEQ ID NO:13; each start position is specified, the length of peptide is 10 amino acids, and the end position for each peptide is the start position plus nine. | |
| 1 | NNKSEEAIDA | 10 |
| 2 | NKSEEAIDAE | 9 |
| 3 | KSEEAIDAES | 8 |
| | V10-HLA-A0203-10mers-193P1E1B | |
| | NoResultsFound. | |
| | V12-HLA-A0203-10mers-193P1E1B | |
| | NoResultsFound. | |

TABLE XXXVII

| Pos | 1234567890 | score |
|---|---|---|
| | V1-HLA-A3-10mers-193P1E1B Each peptide is a portion of SEQ ID NO:3; each start position is specified, the length of peptide is 10 amino acids, and the end position for each peptide is the start position plus nine. | |
| 390 | AVPPSKRFLK | 27 |
| 305 | LVSTNYPLSK | 26 |
| 62 | ELSNCENFQK | 24 |
| 82 | PVASSCISGK | 24 |
| 200 | VLKTPKCALK | 24 |
| 158 | QKYGYSPRVK | 23 |
| 126 | RLENQEGIDF | 22 |
| 196 | SLVKVLKTPK | 22 |
| 219 | KLEHFGISEY | 22 |
| 257 | RLNDNVFATP | 22 |
| 357 | RTPTPPEVTK | 22 |
| 387 | AIKAVPPSKR | 22 |
| 43 | ILYDLHSEVQ | 21 |
| 46 | DLHSEVQTLK | 21 |
| 131 | EGIDFIKATK | 21 |
| 97 | QLSDFGLERY | 19 |
| 102 | GLERYIVSQV | 19 |
| 110 | QVLPNPPQAV | 19 |
| 140 | KVLMEKNSMD | 19 |
| 291 | TPGLKIPSTK | 19 |
| 3 | PIRSFCGKLR | 18 |
| 24 | RLQRALDGEE | 18 |
| 111 | VLPNPPQAVN | 18 |
| 159 | KYGYSPRVKK | 18 |
| 323 | EVEDRTSLVL | 18 |
| 380 | SNLATPIAIK | 18 |
| 386 | IAIKAVPPSK | 18 |
| 10 | KLRSLASTLD | 17 |
| 42 | RILYDLHSEV | 17 |
| 118 | AVNLLDKARL | 17 |
| 120 | NLLDKARLEN | 17 |
| 150 | IMKIREYFQK | 17 |
| 188 | IVTPPTKQSL | 17 |
| 190 | TPPTKQSLVK | 17 |
| 329 | SLVLNSDTCF | 17 |
| 373 | QLLSKYNSNL | 17 |
| 77 | DLSDPPVASS | 16 |
| 185 | EPVIVTPPTK | 16 |
| 199 | KVLKTPKCAL | 16 |
| 368 | PEDILQLLSK | 16 |
| 9 | GKLRSLASTL | 15 |
| 28 | ALDGEESDFE | 15 |
| 115 | PPQAVNLLDK | 15 |
| 135 | FIKATKVLME | 15 |
| 152 | KIREYFQKYG | 15 |
| 163 | SPRVKKNSVH | 15 |
| 165 | RVKKNSVHEQ | 15 |
| 170 | SVHEQEAINS | 15 |
| 186 | PVIVTPPTKQ | 15 |
| 251 | AIDTESRLND | 15 |
| 272 | QLEKSDAEYT | 15 |
| 278 | AEYTNSPLVP | 15 |
| 311 | PLSKTNSSSN | 15 |
| 340 | NLTDPSSPTI | 15 |
| 348 | TISSYENLLR | 15 |
| 354 | NLLRTPTPPE | 15 |
| 27 | RALDGEESDF | 14 |
| 50 | EVQTLKDDVN | 14 |
| 57 | DVNIPELSNC | 14 |
| 66 | CENFQKTDVK | 14 |
| 136 | IKATKVLMEK | 14 |
| 174 | QEAINSDNYK | 14 |
| 193 | TKQSLVKVLK | 14 |
| 207 | ALKMDDFECV | 14 |
| 266 | PSPIIQQLEK | 14 |
| 271 | QQLEKSDAEY | 14 |
| 284 | PLVPTFCTPG | 14 |
| 295 | KIPSTKNSIA | 14 |
| 321 | DLEVEDRTSL | 14 |
| 355 | LLRTPTPPEV | 14 |
| 381 | NLATPIAIKA | 14 |
| 401 | GQNIRDVSNK | 14 |

TABLE XXXVII-continued

| Pos | 1234567890 | score |
|---|---|---|
| 17 | TLDCETARLQ | 13 |
| 87 | CISGKSPRSP | 13 |
| 107 | IVSQVLPNPP | 13 |
| 143 | MEKNSMDIMK | 13 |
| 215 | CVTPKLEHFG | 13 |
| 238 | MGLKNARNNK | 13 |
| 268 | PIIQQLEKSD | 13 |
| 269 | IIQQLEKSDA | 13 |
| 298 | STKNSIALVS | 13 |
| 304 | ALVSTNYPLS | 13 |
| 330 | LVLNSDTCFE | 13 |
| 369 | EDILQLLSKY | 13 |
| 371 | ILQLLSKYNS | 13 |
| 376 | SKYNSNLATP | 13 |
| V5-HLA-A3-10mers-193P1E1B Each peptide is a portion of SEQ ID NO:11; each start position is specified, the length of peptide is 10 amino acids, and the end position for each peptide is the start position plus nine. | | |
| 2 | PVASSCISEK | 24 |
| 7 | CISEKSPRSP | 12 |
| V6-HLA-A3-10mers-193P1E1B Each peptide is a portion of SEQ ID NO:13; each start position is specified, the length of peptide is 10 amino acids, and the end position for each peptide is the start position plus nine. | | |
| 7 | AIDAESRLND | 17 |
| 10 | AESRLNDNVF | 14 |
| 4 | SEEAIDAESR | 12 |
| 3 | KSEEAIDAES | |
| V10-HLA-A3-10mers-193P1E1B Each peptide is a portion of SEQ ID NO:21; each start position is specified, the length of peptide is 10 amino acids, and the end position for each peptide is the start position plus nine. | | |
| 13 | WIYPTQKLNK | 28 |
| 1 | TKIPEDILQK | 22 |
| 10 | KFQWIYPTQK | 18 |
| 2 | KIPEDILQKF | 16 |
| 6 | DILQKFQWIY | 16 |
| V12-HLA-A3-10mers-193P1E1B Each peptide is a portion of SEQ ID NO:25; each start position is specified, the length of peptide is 10 amino acids, and the end position for each peptide is the start position plus nine. | | |
| 3 | ALDGEESLLS | 18 |
| 4 | LDGEESLLSK | 16 |
| 9 | SLLSKYNSNL | 16 |
| 2 | RALDGEESLL | 10 |
| 5 | DGEESLLSKY | 10 |

TABLE XXXVIII

| Pos | 1234567890 | score |
|---|---|---|
| V1-HLA-A26-10mers-193P1E1B Each peptide is a portion of SEQ ID NO:3; each start position is specified, the length of peptide is 10 amino acids, and the end position for each peptide is the start position plus nine. | | |
| 323 | EVEDRTSLVL | 30 |
| 369 | EDILQLLSKY | 30 |
| 363 | EVTKIPEDIL | 29 |
| 214 | ECVTPKLEHF | 26 |
| 343 | DPSSPTISSY | 25 |
| 57 | DVNIPELSNC | 23 |
| 211 | DDFECVTPKL | 23 |
| 2 | DPIRSFCGKL | 22 |
| 264 | ATPSPIIQQL | 22 |
| 280 | YTNSPLVPTF | 22 |
| 188 | IVTPPTKQSL | 21 |
| 227 | EYTMCLNEDY | 21 |
| 347 | PTISSYENLL | 21 |
| 30 | DGEESDFEDY | 20 |

TABLE XXXVIII-continued

| Pos | 1234567890 | score |
|---|---|---|
| 38 | DYPMRILYDL | 20 |
| 50 | EVQTLKDDVN | 20 |
| 173 | EQEAINSDNY | 20 |
| 192 | PTKQSLVKVL | 20 |
| 335 | DTCFENLTDP | 20 |
| 365 | TKIPEDILQL | 20 |
| 73 | DVKDDLSDPP | 19 |
| 199 | KVLKTPKCAL | 19 |
| 249 | EEAIDTESRL | 19 |
| 16 | STLDCETARL | 18 |
| 21 | ETARLQRALD | 18 |
| 118 | AVNLLDKARL | 18 |
| 285 | LVPTFCTPGL | 18 |
| 366 | KIPEDILQLL | 18 |
| 5 | RSFCGKLRSL | 17 |
| 35 | DFEDYPMRIL | 17 |
| 253 | DTESRLNDNV | 17 |
| 321 | DLEVEDRTSL | 17 |
| 37 | EDYPMRILYD | 16 |
| 82 | PVASSCISGK | 16 |
| 131 | EGIDFIKATK | 16 |
| 144 | EKNSMDIMKI | 16 |
| 155 | EYFQKYGYSP | 16 |
| 67 | ENFQKTDVKD | 15 |
| 92 | SPRSPQLSDF | 15 |
| 97 | QLSDFGLERY | 15 |
| 147 | SMDIMKIREY | 15 |
| 151 | MKIREYFQKY | 15 |
| 175 | EAINSDNYKE | 15 |
| 185 | EPVIVTPPTK | 15 |
| 186 | PVIVTPPTKQ | 15 |
| 219 | KLEHFGISEY | 15 |
| 221 | EHFGISEYTM | 15 |
| 250 | EAIDTESRLN | 15 |
| 279 | EYTNSPLVPT | 15 |
| 287 | PTFCTPGLKI | 15 |
| 325 | EDRTSLVLNS | 15 |
| 326 | DRTSLVLNSD | 15 |
| 56 | DDVNIPELSN | 14 |
| 77 | DLSDPPVASS | 14 |
| 165 | RVKKNSVHEQ | 14 |
| 170 | SVHEQEAINS | 14 |
| 234 | EDYTMGLKNA | 14 |
| 261 | NVFATPSPII | 14 |
| 301 | NSIALVSTNY | 14 |
| V5-HLA-A26-10mers-193P1E1B Each peptide is a portion of SEQ ID NO:11; each start position is specified, the length of peptide is 10 amino acids, and the end position for each peptide is the start position plus nine. | | |
| 2 | PVASSCISEK | 16 |
| 9 | SEKSPRSPQL | 11 |
| 10 | EKSPRSPQLS | 11 |
| 7 | CISEKSPRSP | 7 |
| V6-HLA-A26-10mers-193P1E1B Each peptide is a portion of SEQ ID NO:13; each start position is specified, the length of peptide is 10 amino acids, and the end position for each peptide is the start position plus nine. | | |
| 5 | EEAIDAESRL | 19 |
| 6 | EAIDAESRLN | 15 |
| 9 | DAESRLNDNV | 9 |
| V10-HLA-A26-10mers-193P1E1B Each peptide is a portion of SEQ ID NO:21; each start position is specified, the length of peptide is 10 amino acids, and the end position for each peptide is the start position plus nine. | | |
| 6 | DILQKFQWIY | 22 |
| 2 | KIPEDILQKF | 19 |
| 5 | EDILQKFQWI | 14 |
| 1 | TKIPEDILQK | 12 |

TABLE XXXVIII-continued

| Pos | 1234567890 | score |
|---|---|---|
| V12-HLA-A26-10mers-193P1E1B Each peptide is a portion of SEQ ID NO:25; each start position is specified, the length of peptide is 10 amino acids, and the end position for each peptide is the start position plus nine. | | |
| 5 | DGEESLLSKY | 26 |

TABLE XXXIX

| Pos | 1234567890 | score |
|---|---|---|
| V1-HLA-B0702-10mers-193P1E1B Each peptide is a portion of SEQ ID NO:3; each start position is specified, the length of peptide is 10 amino acids, and the end position for each peptide is the start position plus nine. | | |
| 296 | IPSTKNSIAL | 24 |
| 112 | LPNPPQAVNL | 23 |
| 2 | DPIRSFCGKL | 20 |
| 346 | SPTISSYENL | 20 |
| 191 | PPTKQSLVKV | 19 |
| 358 | TPTPPEVTKI | 19 |
| 92 | SPRSPQLSDF | 18 |
| 60 | IPELSNCENF | 17 |
| 323 | EVEDRTSLVL | 14 |
| 384 | TPIAIKAVPP | 14 |
| 103 | LERYIVSQVL | 13 |
| 115 | PPQAVNLLDK | 13 |
| 118 | AVNLLDKARL | 13 |
| 133 | IDFIKATKVL | 13 |
| 163 | SPRVKKNSVH | 13 |
| 190 | TPPTKQSLVK | 13 |
| 199 | KVLKTPKCAL | 13 |
| 265 | TPSPIIQQLE | 13 |
| 332 | LNSDTCFENL | 13 |
| 365 | TKIPEDILQL | 13 |
| 367 | IPEDILQLLS | 13 |
| 389 | KAVPPSKRFL | 13 |
| 391 | VPPSKRFLKH | 13 |
| 392 | PPSKRFLKHG | 13 |
| 16 | STLDCETARL | 12 |
| 20 | CETARLQRAL | 12 |
| 54 | LKDDVNIPEL | 12 |
| 113 | PNPPQAVNLL | 12 |
| 114 | NPPQAVNLLD | 12 |
| 185 | EPVIVTPPTK | 12 |
| 188 | IVTPPTKQSL | 12 |
| 192 | PTKQSLVKVL | 12 |
| 194 | KQSLVKVLKT | 12 |
| 211 | DDFECVTPKL | 12 |
| 249 | EEAIDTESRL | 12 |
| 255 | ESRLNDNVFA | 12 |
| 264 | ATPSPIIQQL | 12 |
| 276 | SDAEYTNSPL | 12 |
| 285 | LVPTFCTPGL | 12 |
| 303 | IALVSTNYPL | 12 |
| 321 | DLEVEDRTSL | 12 |
| 343 | DPSSPTISSY | 12 |
| 363 | EVTKIPEDIL | 12 |
| 5 | RSFCGKLRSL | 11 |
| 39 | YPMRILYDLH | 11 |
| 45 | YDLHSEVQTL | 11 |
| 81 | PPVASSCISG | 11 |
| 89 | SGKSPRSPQL | 11 |
| 94 | RSPQLSDFGL | 11 |
| 95 | SPQLSDFGLE | 11 |
| 217 | TPKLEHFGIS | 11 |
| 223 | FGISEYTMCL | 11 |
| 231 | CLNEDYTMGL | 11 |
| 283 | SPLVPTFCTP | 11 |
| 291 | TPGLKIPSTK | 11 |
| 349 | ISSYENLLRT | 11 |
| 360 | TPPEVTKIPE | 11 |

TABLE XXXIX-continued

| Pos | 1234567890 | score |
|---|---|---|
| 361 | PPEVTKIPED | 11 |
| 366 | KIPEDILQLL | 11 |
| V5-HLA-B0702-10mers-193P1E1B Each peptide is a portion of SEQ ID NO:11; each start position is specified, the length of peptide is 10 amino acids, and the end position for each peptide is the start position plus nine. | | |
| 1 | PPVASSCISE | 11 |
| 9 | SEKSPRSPQL | 11 |
| V6-HLA-B0702-10mers-193P1E1B Each peptide is a portion of SEQ ID NO:13; each start position is specified, the length of peptide is 10 amino acids, and the end position for each peptide is the start position plus nine. | | |
| 5 | EEAIDAESRL | 12 |
| 10 | AESRLNDNVF | 11 |
| 7 | AIDAESRLND | 7 |
| 1 | NNKSEEAIDA | 6 |
| 9 | DAESRLNDNV | 6 |
| V10-HLA-B0702-10mers-193P1E1B Each peptide is a portion of SEQ ID NO:21; each start position is specified, the length of peptide is 10 amino acids, and the end position for each peptide is the start position plus nine. | | |
| 3 | IPEDILQKFQ | 12 |
| 11 | FQWIYPTQKL | 11 |
| 15 | YPTQKLNKMR | 10 |
| 5 | EDILQKFQWI | 8 |
| 2 | KIPEDILQKF | 7 |
| 8 | LQKFQWIYPT | 7 |
| 14 | IYPTQKLNKM | 7 |
| V12-HLA-B0702-10mers-193P1E1B Each peptide is a portion of SEQ ID NO:25; each start position is specified, the length of peptide is 10 amino acids, and the end position for each peptide is the start position plus nine. | | |
| 1 | QRALDGEESL | 11 |
| 2 | RALDGEESLL | 11 |
| 9 | SLLSKYNSNL | 10 |
| 3 | ALDGEESLLS | 7 |

TABLE XL

| Pos | 1234567890 | score |
|---|---|---|
| V1-HLA-B08-10mers-193P1E1B | | |
| NoResultsFound. | | |
| V5-HLA-B08-10mers-193P1E1B | | |
| NoResultsFound. | | |
| V6-HLA-B08-10mers-193P1E1B | | |
| NoResultsFound. | | |
| V10-HLA-B08-10mers-193P1E1B | | |
| NoResultsFound. | | |
| V12-HLA-B08-10mers-193P1E1B | | |
| NoResultsFound. | | |

TABLE XLI

| Pos | 1234567890 | score |
|---|---|---|
| V1-HLA-B1510-10mers-193P1E1B | | |
| NoResultsFound. | | |
| V5-HLA-B1510-10mers-193P1E1B | | |
| NoResultsFound. | | |
| V6-HLA-B1510-10mers-193P1E1B | | |
| NoResultsFound. | | |

TABLE XLI-continued

| Pos | 1234567890 | score |
|---|---|---|
| V10-HLA-B1510-10mers-193P1E1B | | |
| NoResultsFound. | | |
| V12-HLA-B1510-10mers-193P1E1B | | |
| NoResultsFound. | | |

TABLE XLII

| Pos | 1234567890 | score |
|---|---|---|
| V1-HLA-B2705-10mers-193P1E1B | | |
| NoResultsFound. | | |
| V5-HLA-B2705-10mers-193P1E1B | | |
| NoResultsFound. | | |
| V6-HLA-B2705-10mers-193P1E1B | | |
| NoResultsFound. | | |
| V10-HLA-B2705-10mers-193P1E1B | | |
| NoResultsFound. | | |
| V12-HLA-B2705-10mers-193P1E1B | | |
| NoResultsFound. | | |

TABLE XLIII

| Pos | 1234567890 | score |
|---|---|---|
| V1-HLA-B2709-10mers-193P1E1B | | |
| NoResultsFound. | | |
| V5-HLA-B2709-10mers-193P1E1B | | |
| NoResultsFound. | | |
| V6-HLA-B2709-10mers-193P1E1B | | |
| NoResultsFound. | | |
| V10-HLA-B2709-10mers-193P1E1B | | |
| NoResultsFound. | | |
| V12-HLA-B2709-10mers-193P1E1B | | |
| NoResultsFound. | | |

TABLE XLIV

| Pos | 1234567890 | score |
|---|---|---|
| V1-HLA-B4402-10mers-193P1E1B Each peptide is a portion of SEQ ID NO:3; each start position is specified, the length of peptide is 10 amino acids, and the end postion for each peptide is the start position plus nine. | | |
| 36 | FEDYPMRILY | 24 |
| 254 | TESRLNDNVF | 24 |
| 20 | CETARLQRAL | 23 |
| 249 | EEAIDTESRL | 22 |
| 103 | LERYIVSQVL | 21 |
| 127 | LENQEGIDFI | 21 |
| 365 | TKIPEDILQL | 21 |
| 362 | PEVTKIPEDI | 20 |
| 264 | ATPSPIIQQL | 18 |
| 369 | EDILQLLSKY | 18 |
| 113 | PNPPQAVNLL | 17 |
| 130 | QEGIDFIKAT | 17 |

TABLE XLIV-continued

| Pos | 1234567890 | score |
|---|---|---|
| 278 | AEYTNSPLVP | 17 |
| 133 | IDFIKATKVL | 16 |
| 147 | SMDIMKIREY | 16 |
| 151 | MKIREYFQKY | 16 |
| 2 | DPIRSFCGKL | 15 |
| 54 | LKDDVNIPEL | 15 |
| 112 | LPNPPQAVNL | 15 |
| 183 | KEEPVIVTPP | 15 |
| 294 | LKIPSTKNSI | 15 |
| 296 | IPSTKNSIAL | 15 |
| 323 | EVEDRTSLVL | 15 |
| 324 | VEDRTSLVLN | 15 |
| 347 | PTISSYENLL | 15 |
| 389 | KAVPPSKRFL | 15 |
| 5 | RSFCGKLRSL | 14 |
| 9 | GKLRSLASTL | 14 |
| 16 | STLDCETARL | 14 |
| 32 | EESDFEDYPM | 14 |
| 118 | AVNLLDKARL | 14 |
| 144 | EKNSMDIMKI | 14 |
| 148 | MDIMKIREYF | 14 |
| 184 | EEPVIVTPPT | 14 |
| 192 | PTKQSLVKVL | 14 |
| 199 | KVLKTPKCAL | 14 |
| 211 | DDFECVTPKL | 14 |
| 214 | ECVTPKLEHF | 14 |
| 219 | KLEHFGISEY | 14 |
| 223 | FGISEYTMCL | 14 |
| 226 | SEYTMCLNED | 14 |
| 233 | NEDYTMGLKN | 14 |
| 243 | ARNNKSEEAI | 14 |
| 301 | NSIALVSTNY | 14 |
| 343 | DPSSPTISSY | 14 |
| 366 | KIPEDILQLL | 14 |
| 379 | NSNLATPIAI | 14 |
| 45 | YDLHSEVQTL | 13 |
| 79 | SDPPVASSCI | 13 |
| 97 | QLSDFGLERY | 13 |
| 188 | IVTPPTKQSL | 13 |
| 285 | LVPTFCTPGL | 13 |
| 313 | SKTNSSSNDL | 13 |
| 332 | LNSDTCFENL | 13 |
| 352 | YENLLRTPTP | 13 |
| 358 | TPTPPEVTKI | 13 |
| 368 | PEDILQLLSK | 13 |
| 27 | RALDGEESDF | 12 |
| 34 | SDFEDYPMRI | 12 |
| 35 | DFEDYPMRIL | 12 |
| 38 | DYPMRILYDL | 12 |
| 61 | PELSNCENFQ | 12 |
| 66 | CENFQKTDVK | 12 |
| 89 | SGKSPRSPQL | 12 |
| 92 | SPRSPQLSDF | 12 |
| 126 | RLENQEGIDF | 12 |
| 143 | MEKNSMDIMK | 12 |
| 168 | KNSVHEQEAI | 12 |
| 173 | EQEAINSDNY | 12 |
| 227 | EYTMCLNEDY | 12 |
| 248 | SEEAIDTESR | 12 |
| 280 | YTNSPLVPTF | 12 |
| 287 | PTFCTPGLKI | 12 |
| 322 | LEVEDRTSLV | 12 |
| 329 | SLVLNSDTCF | 12 |
| 338 | FENLTDPSSP | 12 |
| 363 | EVTKIPEDIL | 12 |
| 388 | IKAVPPSKRF | 12 |
| 395 | KRFLKHGQNI | 12 |
| 30 | DGEESDFEDY | 11 |
| 49 | SEVQTLKDDV | 11 |
| 60 | IPELSNCENF | 11 |
| 69 | FQKTDVKDDL | 11 |
| 94 | RSPQLSDFGL | 11 |
| 174 | QEAINSDNYK | 11 |
| 213 | FECVTPKLEH | 11 |
| 231 | CLNEDYTMGL | 11 |
| 261 | NVFATPSPII | 11 |
| 271 | QQLEKSDAEY | 11 |

TABLE XLIV-continued

| Pos | 1234567890 | score |
|---|---|---|
| 273 | LEKSDAEYTN | 11 |
| 276 | SDAEYTNSPL | 11 |
| 303 | IALVSTNYPL | 11 |
| 321 | DLEVEDRTSL | 11 |
| 340 | NLTDPSSPTI | 11 |
| 346 | SPTISSYENL | 11 |
| 373 | QLLSKYNSNL | 11 |
| V5-HLA-B4402-10mers-193P1E1B Each peptide is a portion of SEQ ID NO:11; each start position is specified, the length of peptide is 10 amino acids, and the end position for each peptide is the start position plus nine. | | |
| 9 | SEKSPRSPQL | 22 |
| V6-HLA-B4402-10mers-193P1E1B Each peptide is a portion of SEQ ID NO:13; each start position is specified, the length of peptide is 10 amino acids, and the end position for each peptide is the start postion plus nine. | | |
| 10 | AESRLNDNVF | 27 |
| 5 | EEAIDAESRL | 22 |
| 4 | SEEAIDAESR | 12 |
| V10-HLA-B4402-10mers-193P1E1B Each peptide is a portion of SEQ ID NO:21; each start position is specified, the length of peptide is 10 amino acids, and the end position for each peptide is the start position plus nine. | | |
| 4 | PEDILQKFQW | 22 |
| 5 | EDILQKFQWI | 15 |
| 2 | KIPEDILQKF | 14 |
| 11 | FQWIYPTQKL | 12 |
| 1 | TKIPEDILQK | 11 |
| 6 | DILQKFQWIY | 11 |
| V12-HLA-B4402-10mers-193P1E1B Each peptide is a portion of SEQ ID NO:25; each start postition is specified, the length of peptide is 10 amino acids, and the end position for each peptide is the start position plus nine. | | |
| 7 | EESLLSKYNS | 14 |
| 2 | RALDGEESLL | 13 |
| 5 | DGEESLLSKY | 12 |
| 6 | GEESLLSKYN | 12 |
| 9 | SLLSKYNSNL | 12 |
| 1 | QRALDGEESL | 11 |
| 3 | ALDGEESLLS | 7 |

TABLE XLV

| Pos | 123456789012345 | score |
|---|---|---|
| V1-HLA-B5101-10mers-193P1E1B | | |
| NoResultsFound. | | |
| V5-HLA-B5101-10mers-193P1E1B | | |
| NoResultsFound. | | |
| V6-HLA-B5101-10mers-193P1E1B | | |
| NoResultsFound. | | |
| V10-HLA-B5101-10mers-193P1E1B | | |
| NoResultsFound. | | |
| V12-HLA-B5101-10mers-193P1E1B | | |
| NoResultsFound. | | |

TABLE XLVI

| Pos | 123456789012345 | score |
|---|---|---|
| V1-HLA-DRB1-0101-15mers-193P1E1B Each peptide is a portion of SEQ ID NO:3; each start position is specified, the length of peptide is 15 amino acids, and the end position for each peptide is the start position plus fourteen. | | |
| 130 | QEGIDFIKATKVLME | 33 |
| 124 | KARLENQEGIDFIKA | 31 |
| 168 | KNSVHEQEAINSDNY | 31 |
| 38 | DYPMRILYDLHSEVQ | 29 |
| 300 | KNSIALVSTNYPLSK | 29 |
| 105 | RYIVSQVLPNPPQAV | 28 |
| 375 | LSKYNSNLATPIAIK | 28 |
| 291 | TPGLKIPSTKNSIAL | 27 |
| 23 | ARLQRALDGEESDFE | 26 |
| 116 | PQAVNLLDKARLENQ | 26 |
| 153 | IREYFQKYGYSPRVK | 26 |
| 335 | DTCFENLTDPSSPTI | 26 |
| 8 | CGKLRSLASTLDCET | 25 |
| 229 | TMCLNEDYTMGLKNA | 25 |
| 267 | SPIIQQLEKSDAEYT | 25 |
| 307 | STNYPLSKTNSSSND | 25 |
| 361 | PPEVTKIPEDILQLL | 25 |
| 369 | EDILQLLSKYNSNLA | 25 |
| 379 | NSNLATPIAIKAVPP | 25 |
| 5 | RSFCGKLRSLASTLD | 24 |
| 185 | EPVIVTPPTKQSLVK | 24 |
| 195 | QSLVKVLKTPKCALK | 24 |
| 283 | SPLVPTFCTPGLKIP | 24 |
| 350 | SSYENLLRTPTPPEV | 24 |
| 353 | ENLLRTPTPPEVTKI | 24 |
| 372 | LQLLSKYNSNLATPI | 24 |
| 71 | KTDVKDDLSDPPVAS | 23 |
| 82 | PVASSCISGKSPRSP | 23 |
| 85 | SSCISGKSPRSPQLS | 23 |
| 104 | ERYIVSQVLPNPPQA | 23 |
| 210 | MDDFECVTPKLEHFG | 23 |
| 256 | SRLNDNVFATPSPII | 23 |
| 338 | FENLTDPSSPTISSY | 23 |
| 368 | PEDILQLLSKYNSNL | 23 |
| 41 | MRILYDLHSEVQTLK | 22 |
| 101 | FGLERYIVSQVLPNP | 22 |
| 108 | VSQVLPNPPQAVNLL | 22 |
| 139 | TKVLMEKNSMDIMKI | 22 |
| 259 | NDNVFATPSPIIQQL | 22 |
| 321 | DLEVEDRTSLVLNSD | 22 |
| 376 | SKYNSNLATPIAIKA | 22 |
| 382 | LATPIAIKAVPPSKR | 22 |
| 385 | PIAIKAVPPSKRFLK | 22 |
| 214 | ECVTPKLEHFGISEY | 21 |
| 77 | DLSDPPVASSCISGK | 20 |
| 132 | GIDFIKATKVLMEKN | 20 |
| 286 | VPTFCTPGLKIPSTK | 20 |
| 1 | MDPIRSFCGKLRSLA | 19 |
| 33 | ESDFEDYPMRILYDL | 19 |
| 36 | FEDYPMRILYDLHSE | 19 |
| 98 | LSDFGLERYIVSQVL | 19 |
| 159 | KYGYSPRVKKNSVHE | 19 |
| 327 | RTSLVLNSDTCFENL | 19 |
| 349 | ISSYENLLRTPTPPE | 19 |
| 383 | ATPIAIKAVPPSKRF | 19 |
| 4 | IRSFCGKLRSLASTL | 18 |
| 92 | SPRSPQLSDFGLERY | 18 |
| 131 | EGIDFIKATKVLMEK | 18 |
| 136 | IKATKVLMEKNSMDI | 18 |
| 140 | KVLMEKNSMDIMKIR | 18 |
| 145 | KNSMDIMKIREYFQK | 18 |
| 189 | VTPPTKQSLVKVLKT | 18 |
| 194 | KQSLVKVLKTPKCAL | 18 |
| 197 | LVKVLKTPKCALKMD | 18 |
| 199 | KVLKTPKCALKMDDF | 18 |
| 205 | KCALKMDDFECVTPK | 18 |
| 227 | EYTMCLNEDYTMGLK | 18 |
| 235 | DYTMGLKNARNNKSE | 18 |
| 237 | TMGLKNARNNKSEEA | 18 |
| 265 | TPSPIIQQLEKSDAE | 18 |
| 270 | IQQLEKSDAEYTNSP | 18 |

TABLE XLVI-continued

| Pos | 123456789012345 | score |
|---|---|---|
| 15 | ASTLDCETARLQRAL | 17 |
| 20 | CETARLQRALDGEES | 17 |
| 97 | QLSDFGLERYIVSQV | 17 |
| 102 | GLERYIVSQVLPNPP | 17 |
| 110 | QVLPNPPQAVNLLDK | 17 |
| 137 | KATKVLMEKNSMDIM | 17 |
| 178 | NSDNYKEEPVIVTPP | 17 |
| 186 | PVIVTPPTKQSLVKV | 17 |
| 196 | SLVKVLKTPKCALKM | 17 |
| 207 | ALKMDDFECVTPKLE | 17 |
| 255 | ESRLNDNVFATPSPI | 17 |
| 285 | LVPTFCTPGLKIPST | 17 |
| 296 | IPSTKNSIALVSTNY | 17 |
| 302 | SIALVSTNYPLSKTN | 17 |
| 306 | VSTNYPLSKTNSSSN | 17 |
| 319 | SNDLEVEDRTSLVLN | 17 |
| 393 | PSKRFLKHGQNIRDV | 17 |
| 7 | FCGKLRSLASTLDCE | 16 |
| 12 | RSLASTLDCETARLQ | 16 |
| 40 | PMRILYDLHSEVQTL | 16 |
| 48 | HSEVQTLKDDVNIPE | 16 |
| 57 | DVNIPELSNCENFQK | 16 |
| 72 | TDVKDDLSDPPVASS | 16 |
| 75 | KDDLSDPPVASSCIS | 16 |
| 100 | DFGLERYIVSQVLPN | 16 |
| 107 | IVSQVLPNPPQAVNL | 16 |
| 142 | LMEKNSMDIMKIREY | 16 |
| 147 | SMDIMKIREYFQKYG | 16 |
| 183 | KEEPVIVTPPTKQSL | 16 |
| 184 | EEPVIVTPPTKQSLV | 16 |
| 202 | KTPKCALKMDDFECV | 16 |
| 232 | LNEDYTMGLKNARNN | 16 |
| 240 | LKNARNNKSEEAIDT | 16 |
| 252 | IDTESRLNDNVFATP | 16 |
| 258 | LNDNVFATPSPIIQQ | 16 |
| 260 | DNVFATPSPIIQQLE | 16 |
| 290 | CTPGLKIPSTKNSIA | 16 |
| 293 | GLKIPSTKNSIALVS | 16 |
| 309 | NYPLSKTNSSSNDLE | 16 |
| 318 | SSNDLEVEDRTSLVL | 16 |
| 336 | TCFENLTDPSSPTIS | 16 |
| 351 | SYENLLRTPTPPEVT | 16 |
| 364 | VTKIPEDILQLLSKY | 16 |
| 371 | ILQLLSKYNSNLATP | 16 |
| 377 | KYNSNLATPIAIKAV | 16 |
| 380 | SNLATPIAIKAVPPS | 16 |
| | V5-HLA-DRB1-0101-15mers-193P1E1B Each peptide is a portion of SEQ ID NO:11; each start position is specified, the length of peptide is 15 amino acids, and the end position for each peptide is the start position plus fourteen. | |
| 10 | SSCISEKSPRSPQLS | 23 |
| 2 | DLSDPPVASSCISEK | 20 |
| 6 | PPVASSCISEKSPRS | 15 |
| 7 | PVASSCISEKSPRSP | 15 |
| 12 | CISEKSPRSPQLSDF | 15 |
| 3 | LSDPPVASSCISEKS | 14 |
| 9 | ASSCISEKSPRSPQL | 14 |
| 13 | ISEKSPRSPQLSDFG | 14 |
| | V6-HLA-DRB1-0101-15mers-193P1E1B Each peptide is a portion of SEQ ID NO:13; each start position is specified, the length of peptide is 15 amino acids, and the end position for each peptide is the start position plus fourteen. | |
| 4 | ARNNKSEEAIDAESR | 18 |
| 1 | LKNARNNKSEEAIDA | 16 |
| 13 | IDAESRLNDNVFATP | 16 |
| 7 | NKSEEAIDAESRLND | 14 |
| 8 | KSEEAIDAESRLNDN | 11 |
| 14 | DAESRLNDNVFATPS | 11 |
| 2 | KNARNNKSEEAIDAE | 9 |
| 6 | NNKSEEAIDAESRLN | 8 |
| 9 | SEEAIDAESRLNDNV | 8 |
| 10 | EEAIDAESRLNDNVF | 8 |
| 12 | AIDAESRLNDNVFAT | 8 |

TABLE XLVI-continued

| Pos | 123456789012345 | score |
|---|---|---|
| | V10-HLA-DRB1-0101-15mers-193P1E1B Each peptide is a portion of SEQ ID NO:21; each start position is specified, the length of peptide is 15 amino acids, and the end position for each peptide is the start position plus fourteen. | |
| 2 | PPEVTKIPEDILQKF | 25 |
| 13 | LQKFQWIYPTQKLNK | 23 |
| 10 | EDILQKFQWIYPTQK | 18 |
| 14 | QKFQWIYPTQKLNKM | 18 |
| 5 | VTKIPEDILQKFQWI | 17 |
| 1 | TPPEVTKIPEDILQK | 15 |
| 8 | IPEDILQKFQWIYPT | 15 |
| | V12-HLA-DRB1-0101-15mers-193P1E1B Each peptide is a portion of SEQ ID NO:25; each start position is specified, the length of peptide is 15 amino acids, and the end position for each peptide is the start position plus fourteen. | |
| 3 | ARLQRALDGEESLLS | 26 |
| 13 | ESLLSKYNSNLATPI | 24 |
| 6 | QRALDGEESLLSKYN | 23 |
| 10 | DGEESLLSKYNSNLA | 17 |
| 12 | EESLLSKYNSNLATP | 16 |
| 9 | LDGEESLLSKYNSNL | 15 |

TABLE XLVII

| Pos | 123456789012345 | score |
|---|---|---|
| | V1-HLA-DRB1-0301-15mers-193P1E1B Each peptide is a portion of SEQ ID NO:3; each start position is specified, the length of peptide is 15 amino acids, and the end position for each peptide is the start position plus fourteen. | |
| 364 | VTKIPEDILQLLSKY | 31 |
| 229 | TMCLNEDYTMGLKNA | 29 |
| 197 | LVKVLKTPKCALKMD | 28 |
| 371 | ILQLLSKYNSNLATP | 28 |
| 51 | VQTLKDDVNIPELSN | 27 |
| 186 | PVIVTPPTKQSLVKV | 27 |
| 116 | PQAVNLLDKARLENQ | 26 |
| 361 | PPEVTKIPEDILQLL | 26 |
| 67 | ENFQKTDVKDDLSDP | 25 |
| 247 | KSEEAIDTESRLNDN | 24 |
| 319 | SNDLEVEDRTSLVLN | 24 |
| 40 | PMRILYDLHSEVQTL | 23 |
| 71 | KTDVKDDLSDPPVAS | 22 |
| 205 | KCALKMDDFECVTPK | 22 |
| 174 | QEAINSDNYKEEPVI | 21 |
| 327 | RTSLVLNSDTCFENL | 21 |
| 329 | SLVLNSDTCFENLTD | 21 |
| 138 | ATKVLMEKNSMDIMK | 20 |
| 346 | SPTISSYENLLRTPT | 20 |
| 13 | SLASTLDCETARLQR | 19 |
| 95 | SPQLSDFGLERYIVS | 19 |
| 118 | AVNLLDKARLENQEG | 19 |
| 124 | KARLENQEGIDFIKA | 19 |
| 145 | KNSMDIMKIREYFQK | 19 |
| 213 | FECVTPKLEHFGISE | 19 |
| 217 | TPKLEHFGISEYTMC | 19 |
| 237 | TMGLKNARNNKSEEA | 19 |
| 249 | EEAIDTESRLNDNVF | 19 |
| 321 | DLEVEDRTSLVLNSD | 19 |
| 369 | EDILQLLSKYNSNLA | 19 |
| 388 | IKAVPPSKRFLKHGQ | 19 |
| 24 | RLQRALDGEESDFED | 18 |
| 44 | LYDLHSEVQTLKDDV | 18 |
| 57 | DVNIPELSNCENFQK | 18 |
| 109 | SQVLPNPPQAVNLLD | 18 |
| 150 | IMKIREYFQKYGYSP | 18 |
| 194 | KQSLVKVLKTPKCAL | 18 |
| 266 | PSPIIQQLEKSDAEY | 18 |

TABLE XLVII-continued

| Pos | 123456789012345 | score |
|---|---|---|
| 271 | QQLEKSDAEYTNSPL | 18 |
| 283 | SPLVPTFCTPGLKIP | 18 |
| 293 | GLKIPSTKNSIALVS | 18 |
| 315 | TNSSSNDLEVEDRTS | 18 |
| 345 | SSPTISSYENLLRTP | 18 |
| 394 | SKRFLKHGQNIRDVS | 18 |
| 18 | LDCETARLQRALDGE | 17 |
| 25 | LQRALDGEESDFEDY | 17 |
| 29 | LDGEESDFEDYPMRI | 17 |
| 33 | ESDFEDYPMRILYDL | 17 |
| 60 | IPELSNCENFQKTDV | 17 |
| 132 | GIDFIKATKVLMEKN | 17 |
| 225 | ISEYTMCLNEDYTMG | 17 |
| 267 | SPIIQQLEKSDAEYT | 17 |
| 387 | AIKAVPPSKRFLKHG | 17 |
| 395 | KRFLKHGQNIRDVSN | 17 |
| 4 | IRSFCGKLRSLASTL | 16 |
| 74 | VKDDLSDPPVASSCI | 16 |
| 108 | VSQVLPNPPQAVNLL | 16 |
| 146 | NSMDIMKIREYFQKY | 16 |
| 147 | SMDIMKIREYFQKYG | 16 |
| 206 | CALKMDDFECVTPKL | 16 |
| 301 | NSIALVSTNYPLSKT | 16 |
| 34 | SDFEDYPMRILYDLH | 15 |
| 117 | QAVNLLDKARLENQE | 15 |
| 274 | EKSDAEYTNSPLVPT | 15 |
| V5-HLA-DRB1-0301-15mers Each peptide is a portion of SEQ ID NO:11; each start position is specified, the length of peptide is 15 amino acids, and the end position for each peptide is the start position plus fourteen. | | |
| 10 | SSCISEKSPRSPQLS | 12 |
| 5 | DPPVASSCISEKSPR | 11 |
| 12 | CISEKSPRSPQLSDF | 10 |
| 15 | EKSPRSPQLSDFGLE | 10 |
| 14 | SEKSPRSPQLSDFGL | 8 |
| 7 | PVASSCISEKSPRSP | 7 |
| 8 | VASSCISEKSPRSPQ | 7 |
| 11 | SCISEKSPRSPQLSD | 7 |
| V6-HLA-DRB1-0301-15mers Each peptide is a portion of SEQ ID NO:13; each start position is specified, the length of peptide is 15 amino acids, and the end position for each peptide is the start position plus fourteen. | | |
| 8 | KSEEAIDAESRLNDN | 24 |
| 10 | EEAIDAESRLNDNVF | 19 |
| 15 | AESRLNDNVFATPSP | 13 |
| V10-HLA-DRB1-0301-15mers Each peptide is a portion of SEQ ID NO:21; each start position is specified, the length of peptide is 15 amino acids, and the end position for each peptide is the start position plus fourteen. | | |
| 5 | VTKIPEDILQKFQWI | 31 |
| 2 | PPEVTKIPEDILQKF | 26 |
| 9 | PEDILQKFQWIYPTQ | 26 |
| V12-HLA-DRB1-0301-15mers Each peptide is a portion of SEQ ID NO:25; each start position is specified, the length of peptide is 15 amino acids, and the end position for each peptide is the start position plus fourteen. | | |
| 12 | EESLLSKYNSNLATP | 28 |
| 4 | RLQRALDGEESLLSK | 26 |
| 5 | LQRALDGEESLLSKY | 18 |
| 6 | QRALDGEESLLSKYN | 13 |

TABLE XLVIII

| Pos | 123456789012345 | score |
|---|---|---|
| V1-HLA-DR1-0401-15mers-193P1E1B Each peptide is a portion of SEQ ID NO:3; each start position is specified, the length of peptide is 15 amino acids, and the end position for each peptide is the start position plus fourteen. | | |
| 349 | ISSYENLLRTPTPPE | 28 |
| 40 | PMRILYDLHSEVQTL | 26 |
| 41 | MRILYDLHSEVQTLK | 26 |
| 44 | LYDLHSEVQTLKDDV | 26 |
| 57 | DVNIPELSNCENFQK | 26 |
| 229 | TMCLNEDYTMGLKNA | 26 |
| 237 | TMGLKNARNNKSEEA | 26 |
| 283 | SPLVPTFCTPGLKIP | 26 |
| 319 | SNDLEVEDRTSLVLN | 26 |
| 368 | PEDILQLLSKYNSNL | 26 |
| 98 | LSDFGLERYIVSQVL | 22 |
| 132 | GIDFIKATKVLMEKN | 22 |
| 157 | FQKYGYSPRVKKNSV | 22 |
| 179 | SDNYKEEPVIVTPPT | 22 |
| 307 | STNYPLSKTNSSSND | 22 |
| 335 | DTCFENLTDPSSPTI | 22 |
| 8 | CGKLRSLASTLDCET | 20 |
| 15 | ASTLDCETARLQRAL | 20 |
| 26 | QRALDGEESDFEDYP | 20 |
| 38 | DYPMRILYDLHSEVQ | 20 |
| 48 | HSEVQTLKDDVNIPE | 20 |
| 51 | VQTLKDDVNIPELSN | 20 |
| 60 | IPELSNCENFQKTDV | 20 |
| 71 | KTDVKDDLSDPPVAS | 20 |
| 109 | SQVLPNPPQAVNLLD | 20 |
| 116 | PQAVNLLDKARLENQ | 20 |
| 119 | VNLLDKARLENQEGI | 20 |
| 130 | QEGIDFIKATKVLME | 20 |
| 138 | ATKVLMEKNSMDIMK | 20 |
| 147 | SMDIMKIREYFQKYG | 20 |
| 185 | EPVIVTPPTKQSLVK | 20 |
| 194 | KQSLVKVLKTPKCAL | 20 |
| 195 | QSLVKVLKTPKCALK | 20 |
| 205 | KCALKMDDFECVTPK | 20 |
| 249 | EEAIDTESRLNDNVF | 20 |
| 259 | NDNVFATPSPIIQQL | 20 |
| 267 | SPIIQQLEKSDAEYT | 20 |
| 291 | TPGLKIPSTKNSIAL | 20 |
| 293 | GLKIPSTKNSIALVS | 20 |
| 300 | KNSIALVSTNYPLSK | 20 |
| 309 | NYPLSKTNSSSNDLE | 20 |
| 329 | SLVLNSDTCFENLTD | 20 |
| 338 | FENLTDPSSPTISSY | 20 |
| 361 | PPEVTKIPEDILQLL | 20 |
| 364 | VTKIPEDILQLLSKY | 20 |
| 369 | EDILQLLSKYNSNLA | 20 |
| 372 | LQLLSKYNSNLATPI | 20 |
| 388 | IKAVPPSKRFLKHGQ | 20 |
| 5 | RSFCGKLRSLASTLD | 18 |
| 77 | DLSDPPVASSCISGK | 18 |
| 78 | LSDPPVASSCISGKS | 18 |
| 97 | QLSDFGLERYIVSQV | 18 |
| 101 | FGLERYIVSQVLPNP | 18 |
| 106 | YIVSQVLPNPPQAVN | 18 |
| 122 | LDKARLENQEGIDFI | 18 |
| 170 | SVHEQEAINSDNYKE | 18 |
| 182 | YKEEPVIVTPPTKQS | 18 |
| 214 | ECVTPKLEHFGISEY | 18 |
| 221 | EHFGISEYTMCLNED | 18 |
| 234 | EDYTMGLKNARNNKS | 18 |
| 264 | ATPSPIIQQLEKSDA | 18 |
| 280 | YTNSPLVPTFCTPGL | 18 |
| 290 | CTPGLKIPSTKNSIA | 18 |
| 320 | NDLEVEDRTSLVLNS | 18 |
| 325 | EDRTSLVLNSDTCFE | 18 |
| 337 | CFENLTDPSSPTISS | 18 |
| 343 | DPSSPTISSYENLLR | 18 |
| 365 | TKIPEDILQLLSKYN | 18 |
| 376 | SKYNSNLATPIAIKA | 18 |
| 392 | PPSKRFLKHGQNIRD | 18 |
| 4 | IRSFCGKLRSLASTL | 17 |
| 33 | ESDFEDYPMRILYDL | 16 |

TABLE XLVIII-continued

| Pos | 123456789012345 | score |
|---|---|---|
| 42 | RILYDLHSEVQTLKD | 16 |
| 103 | LERYIVSQVLPNPPQ | 16 |
| 210 | MDDFECVTPKLEHFG | 16 |
| 225 | ISEYTMCLNEDYTMG | 16 |
| 260 | DNVFATPSPIIQQLE | 16 |
| 277 | DAEYTNSPLVPTFCT | 16 |
| 375 | LSKYNSNLATPIAIK | 16 |
| 394 | SKRFLKHGQNIRDVS | 16 |
| 118 | AVNLLDKARLENQEG | 15 |
| 139 | TKVLMEKNSMDIMKI | 15 |
| 321 | DLEVEDRTSLVLNSD | 15 |
| 371 | ILQLLSKYNSNLATP | 15 |
| 1 | MDPIRSFCGKLRSLA | 14 |
| 11 | LRSLASTLDCETARL | 14 |
| 22 | TARLQRALDGEESDF | 14 |
| 75 | KDDLSDPPVASSCIS | 14 |
| 80 | DPPVASSCISGKSPR | 14 |
| 95 | SPQLSDFGLERYIVS | 14 |
| 100 | DFGLERYIVSQVLPN | 14 |
| 105 | RYIVSQVLPNPPQAV | 14 |
| 108 | VSQVLPNPPQAVNLL | 14 |
| 140 | KVLMEKNSMDIMKIR | 14 |
| 150 | IMKIREYFQKYGYSP | 14 |
| 163 | SPRVKKNSVHEQEAI | 14 |
| 168 | KNSVHEQEAINSDNY | 14 |
| 174 | QEAINSDNYKEEPVI | 14 |
| 184 | EEPVIVTPPTKQSLV | 14 |
| 186 | PVIVTPPTKQSLVKV | 14 |
| 197 | LVKVLKTPKCALKMD | 14 |
| 198 | VKVLKTPKCALKMDD | 14 |
| 207 | ALKMDDFECVTPKLE | 14 |
| 217 | TPKLEHFGISEYTMC | 14 |
| 222 | HFGISEYTMCLNEDY | 14 |
| 227 | EYTMCLNEDYTMGLK | 14 |
| 270 | IQQLEKSDAEYTNSP | 14 |
| 302 | SIALVSTNYPLSKTN | 14 |
| 303 | IALVSTNYPLSKTNS | 14 |
| 328 | TSLVLNSDTCFENLT | 14 |
| 346 | SPTISSYENLLRTPT | 14 |
| 352 | YENLLRTPTPPEVTK | 14 |
| 353 | ENLLRTPTPPEVTKI | 14 |
| 379 | NSNLATPIAIKAVPP | 14 |
| 385 | PIAIKAVPPSKRFLK | 14 |
| 395 | KRFLKHGQNIRDVSN | 14 |
| V5-HLA-DR1-0401-15mers-193P1E1B Each peptide is a portion of SEQ ID NO:11; each start position is specified, the length of peptide is 15 amino acids, and the end position for each peptide is the start position plus fourteen. | | |
| 2 | DLSDPPVASSCISEK | 18 |
| 3 | LSDPPVASSCISEKS | 18 |
| 9 | ASSCISEKSPRSPQL | 18 |
| 5 | DPPVASSCISEKSPR | 14 |
| 6 | PPVASSCISEKSPRS | 12 |
| 11 | SCISEKSPRSPQLSD | 12 |
| 12 | CISEKSPRSPQLSDF | 12 |
| V6-HLA-DR1-0401-15mers-193P1E1B Each peptide is a portion of SEQ ID NO:13; each start position is specified, the length of peptide is 15 amino acids, and the end position for each peptide is the start position plus fourteen. | | |
| 10 | EEAIDAESRLNDNVF | 20 |
| 9 | SEEAIDAESRLNDNV | 18 |
| 1 | LKNARNNKSEEAIDA | 12 |
| 4 | ARNNKSEEAIDAESR | 12 |
| 6 | NNKSEEAIDAESRLN | 12 |
| 8 | KSEEAIDAESRLNDN | 12 |
| 14 | DAESRLNDNVFATPS | 12 |
| 15 | AESRLNDNVFATPSP | 12 |

TABLE XLVIII-continued

| Pos | 123456789012345 | score |
|---|---|---|
| V10-HLA-DR1-0401-15mers-193P1E1B Each peptide is a portion of SEQ ID NO:21; each start position is specified, the length of peptide is 15 amino acids, and the end position for each peptide is the start position plus fourteen. | | |
| 13 | LQKFQWIYPTQKLNK | 22 |
| 15 | KFQWIYPTQKLNKMR | 22 |
| 2 | PPEVTKIPEDILQKF | 20 |
| 6 | TKIPEDILQKFQWIY | 18 |
| 5 | VTKIPEDILQKFQWI | 14 |
| 10 | EDILQKFQWIYPTQK | 14 |
| 4 | EVTKIPEDILQKFQW | 12 |
| 14 | QKFQWIYPTQKLNKM | 12 |
| V12-HLA-DR1-0401-15mers-193P1E1B Each peptide is a portion of SEQ ID NO:25; each start position is specified, the length of peptide is 15 amino acids, and the end position for each peptide is the start position plus fourteen. | | |
| 6 | QRALDGEESLLSKYN | 26 |
| 13 | ESLLSKYNSNLATPI | 20 |
| 9 | LDGEESLLSKYNSNL | 18 |
| 12 | EESLLSKYNSNLATP | 15 |
| 2 | TARLQRALDGEESLL | 14 |
| 3 | ARLQRALDGEESLLS | 12 |
| 4 | RLQRALDGEESLLSK | 12 |
| 7 | RALDGEESLLSKYNS | 12 |
| 10 | DGEESLLSKYNSNLA | 12 |
| 14 | SLLSKYNSNLATPIA | 12 |

TABLE XLIX

| Pos | 123456789012345 | score |
|---|---|---|
| V1-HLA-DRB1-1101-15mers-193P1E1B Each peptide is a portion of SEQ ID NO:3; each start position is specified, the length of peptide is 15 amino acids, and the end position for each peptide is the start position plus fourteen. | | |
| 159 | KYGYSPRVKKNSVHE | 26 |
| 267 | SPIIQQLEKSDAEYT | 26 |
| 369 | EDILQLLSKYNSNLA | 26 |
| 4 | IRSFCGKLRSLASTL | 25 |
| 349 | ISSYENLLRTPTPPE | 24 |
| 116 | PQAVNLLDKARLENQ | 22 |
| 335 | DTCFENLTDPSSPTI | 22 |
| 194 | KQSLVKVLKTPKCAL | 20 |
| 233 | NEDYTMGLKNARNNK | 20 |
| 306 | VSTNYPLSKTNSSSN | 20 |
| 132 | GIDFIKATKVLMEKN | 19 |
| 157 | FQKYGYSPRVKKNSV | 19 |
| 38 | DYPMRILYDLHSEVQ | 18 |
| 105 | RYIVSQVLPNPPQAV | 18 |
| 300 | KNSIALVSTNYPLSK | 18 |
| 98 | LSDFGLERYIVSQVL | 17 |
| 153 | IREYFQKYGYSPRVK | 17 |
| 191 | PPTKQSLVKVLKTPK | 17 |
| 210 | MDDFECVTPKLEHFG | 17 |
| 286 | VPTFCTPGLKIPSTK | 17 |
| 2 | DPIRSFCGKLRSLAS | 16 |
| 97 | QLSDFGLERYIVSQV | 16 |
| 144 | EKNSMDIMKIREYFQ | 16 |
| 186 | PVIVTPPTKQSLVKV | 16 |
| 287 | PTFCTPGLKIPSTKN | 16 |
| 307 | STNYPLSKTNSSSND | 16 |
| 19 | DCETARLQRALDGEE | 15 |
| 68 | NFQKTDVKDDLSDPP | 15 |
| 319 | SNDLEVEDRTSLVLN | 15 |
| 361 | PPEVTKIPEDILQLL | 15 |
| 381 | NLATPIAIKAVPPSK | 15 |
| 388 | IKAVPPSKRFLKHGQ | 15 |
| 397 | FLKHGQNIRDVSNKE | 15 |

TABLE XLIX-continued

| Pos | 123456789012345 | score |
|---|---|---|
| 40 | PMRILYDLHSEVQTL | 14 |
| 104 | ERYIVSQVLPNPPQA | 14 |
| 118 | AVNLLDKARLENQEG | 14 |
| 137 | KATKVLMEKNSMDIM | 14 |
| 160 | YGYSPRVKKNSVHEQ | 14 |
| 175 | EAINSDNYKEEPVIV | 14 |
| 195 | QSLVKVLKTPKCALK | 14 |
| 197 | LVKVLKTPKCALKMD | 14 |
| 213 | FECVTPKLEHFGISE | 14 |
| 214 | ECVTPKLEHFGISEY | 14 |
| 249 | EEAIDTESRLNDNVF | 14 |
| 255 | ESRLNDNVFATPSPI | 14 |
| 358 | TPTPPEVTKIPEDIL | 14 |
| 392 | PPSKRFLKHGQNIRD | 14 |
| 8 | CGKLRSLASTLDCET | 13 |
| 41 | MRILYDLHSEVQTLK | 13 |
| 48 | HSEVQTLKDDVNIPE | 13 |
| 85 | SSCISGKSPRSPQLS | 13 |
| 102 | GLERYIVSQVLPNPP | 13 |
| 127 | LENQEGIDFIKATKV | 13 |
| 130 | QEGIDFIKATKVLME | 13 |
| 136 | IKATKVLMEKNSMDI | 13 |
| 145 | KNSMDIMKIREYFQK | 13 |
| 237 | TMGLKNARNNKSEEA | 13 |
| 293 | GLKIPSTKNSIALVS | 13 |
| 302 | SIALVSTNYPLSKTN | 13 |
| 318 | SSNDLEVEDRTSLVL | 13 |
| 365 | TKIPEDILQLLSKYN | 13 |
| 372 | LQLLSKYNSNLATPI | 13 |
| 376 | SKYNSNLATPIAIKA | 13 |
| 379 | NSNLATPIAIKAVPP | 13 |
| 385 | PIAIKAVPPSKRFLK | 13 |
| 5 | RSFCGKLRSLASTLD | 12 |
| 12 | RSLASTLDCETARLQ | 12 |
| 23 | ARLQRALDGEESDFE | 12 |
| 33 | ESDFEDYPMRILYDL | 12 |
| 57 | DVNIPELSNCENFQK | 12 |
| 71 | KTDVKDDLSDPPVAS | 12 |
| 75 | KDDLSDPPVASSCIS | 12 |
| 82 | PVASSCISGKSPRSP | 12 |
| 121 | LLDKARLENQEGIDF | 12 |
| 147 | SMDIMKIREYFQKYG | 12 |
| 150 | IMKIREYFQKYGYSP | 12 |
| 165 | RVKKNSVHEQEAINS | 12 |
| 168 | KNSVHEQEAINSDNY | 12 |
| 181 | NYKEEPVIVTPPTKQ | 12 |
| 185 | EPVIVTPPTKQSLVK | 12 |
| 207 | ALKMDDFECVTPKLE | 12 |
| 225 | ISEYTMCLNEDYTMG | 12 |
| 232 | LNEDYTMGLKNARNN | 12 |
| 256 | SRLNDNVFATPSPII | 12 |
| 277 | DAEYTNSPLVPTFCT | 12 |
| 282 | NSPLVPTFCTPGLKI | 12 |
| 291 | TPGLKIPSTKNSIAL | 12 |
| 350 | SSYENLLRTPTPPEV | 12 |
| 368 | PEDILQLLSKYNSNL | 12 |
| 382 | LATPIAIKAVPPSKR | 12 |
| 383 | ATPIAIKAVPPSKRF | 12 |
| V5-HLA-DRB1-1101-15mers-193P1E1B<br>Each peptide is a portion of SEQ ID NO:11; each start position is specified, the length of peptide is 15 amino acids, and the end position for each peptide is the start position plus fourteen. | | |
| 10 | SSCISEKSPRSPQLS | 13 |
| 7 | PVASSCISEKSPRSP | 12 |
| 3 | LSDPPVASSCISEKS | 8 |
| 8 | VASSCISEKSPRSPQ | 8 |
| 9 | ASSCISEKSPRSPQL | 8 |
| 11 | SCISEKSPRSPQLSD | 8 |
| 6 | PPVASSCISEKSPRS | 7 |
| 13 | ISEKSPRSPQLSDFG | 7 |
| 2 | DLSDPPVASSCISEK | 6 |
| 5 | DPPVASSCISEKSPR | 6 |

TABLE XLIX-continued

| Pos | 123456789012345 | score |
|---|---|---|
| V6-HLA-DRB1-1101-15mers-193P1E1B<br>Each peptide is a portion of SEQ ID NO:13; each start position is specified, the length of peptide is 15 amino acids, and the end position for each peptide is the start position plus fourteen. | | |
| 10 | EEAIDAESRLNDNVF | 14 |
| 13 | IDAESRLNDNVFATP | 7 |
| 1 | LKNARNNKSEEAIDA | 6 |
| 4 | ARNNKSEEAIDAESR | 6 |
| 6 | NNKSEEAIDAESRLN | 6 |
| 7 | NKSEEAIDAESRLND | 6 |
| 14 | DAESRLNDNVFATPS | 6 |
| V10-HLA-DRB1-1101-15mers-193P1E1B<br>Each peptide is a portion of SEQ ID NO:21; each start position is specified, the length of peptide is 15 amino acids, and the end position for each peptide is the start position plus fourteen. | | |
| 13 | LQKFQWIYPTQKLNK | 16 |
| 2 | PPEVTKIPEDILQKF | 15 |
| 7 | KIPEDILQKFQWIYP | 14 |
| 10 | EDILQKFQWIYPTQK | 12 |
| 15 | KFQWIYPTQKLNKMR | 11 |
| 5 | VTKIPEDILQKFQWI | 7 |
| 9 | PEDILQKFQWIYPTQ | 7 |
| V12-HLA-DRB1-1101-15mers-193P1E1B<br>Each peptide is a portion of SEQ ID NO:25; each start position is specified, the length of peptide is 15 amino acids, and the end position for each peptide is the start position plus fourteen. | | |
| 10 | DGEESLLSKYNSNLA | 20 |
| 6 | QRALDGEESLLSKYN | 13 |
| 13 | ESLLSKYNSNLATPI | 13 |
| 3 | ARLQRALDGEESLLS | 12 |

TABLE L

Properties of 193P1E1B

| | Bioinformatic Program | Outcome |
|---|---|---|
| Variants 1, 5, 6 | | |
| ORF | ORF Finder | 805-2043 |
| Protein Length | n/a | 412 amino acids |
| Transmembrane region | TM Pred | No TM |
| | HMMTop | No TM |
| | Sosui | No TM, soluble |
| | TMHMM | No TM |
| Signal Peptide | Signal P | indicates no signal |
| pI | pI/MW tool | pI 5.03 |
| Molecular weight | pI/MW tool | 46.2 kDa |
| Localization | PSORT | Mitochondrial 48% |
| | PSORT II | Nuclear 60.9% |
| | iPSORT | No signal motif |
| Motifs | Pfam | No motif |
| | Prints | Rhodopsin |
| | Blocks | No motif |
| | Prosite | No motif |
| Variant 9 | | |
| ORF | ORF Finder | 989-1981 |
| Protein Length | n/a | 330 amino acids |
| Transmembrane region | TM Pred | No TM |
| | HMMTop | No TM |
| | Sosui | No TM, soluble |
| | TMHMM | No TM |
| Signal Peptide | Signal P | indicates no signal |
| pI | pI/MW tool | pI 5.17 |
| Molecular weight | pI/MW tool | 16.5 kDa |
| Localization | PSORT | Cytoplasmic 45% |
| | PSORT II | Nuclear 60.9% |
| | iPSORT | No signal motif |

TABLE L-continued

| Properties of 193P1E1B | Bioinformatic Program | Outcome |
|---|---|---|
| Motifs | Pfam | No motif |
| | Prints | No motif |
| | Blocks | No motif |
| | Prosite | No motif |
| Variant 10 | | |
| ORF | ORF Finder | 805-1971 |
| Protein Length | n/a | 388 amino acids |
| Transmembrane region | TM Pred | No TM |
| | HMMTop | No TM |
| | Sosui | No TM, soluble |
| | TMHMM | No TM |
| Signal Peptide | Signal P | indicates no signal |
| pI | pI/MW tool | pI 4.8 |
| Molecular weight | pI/MW tool | 34.5 kDa |
| Localization | PSORT | Mitochondrial 48% |
| | PSORT II | Nuclear 60.9% |
| | iPSORT | No signal motif |
| Motifs | Pfam | No motif |
| | Prints | No motif |
| | Blocks | No motif |

TABLE L-continued

| Properties of 193P1E1B | Bioinformatic Program | Outcome |
|---|---|---|
| | Prosite | No motif |
| Variant 12 | | |
| ORF | ORF Finder | 805-1026 |
| Protein Length | n/a | 73 amino acids |
| Transmembrane region | TM Pred | No TM |
| | HMMTop | No TM |
| | Sosui | No TM, soluble |
| | TMHMM | No TM |
| Signal Peptide | Signal P | indicates no signal |
| pI | pI/MW tool | pI 9.4 |
| Molecular weight | pI/MW tool | 8.1 kDa |
| Localization | PSORT | Mitochondrial 48% |
| | PSORT II | Nuclear 60.9% |
| | iPSORT | No signal motif |
| Motifs | Pfam | No motif |
| | Prints | No motif |
| | Blocks | No motif |
| | Prosite | No motif |

TABLE LI

Nucleotide sequence of transcript variant 193P1E1B v.9

```
                                                           (SEQ ID NO: 93)
   1 tatcatctgt gactgaggaa atccctatct tcctatcaga ctaatgaaac cacaggacag

  61 caattagact tttaagtatt ggggggttta gagctctaga tattcgatat gcagactact

 121 catgtttgtt tgttttaata aagactggtc caaaggctca ttttcacaca agctacagtt

 181 tttcagttcc aggaccaggt aaagatggtc agctccgtga tccataaaat ccaagggtga

 241 cgactcagga ttaggaccat ttcttggtga cattgagatg gtcgagctgg tccgcaatga

 301 atctatgcgg ggggaacttg gaagtggcgg ccgcctttat ggcctcgaag gcctccctcc

 361 tgcgcaccgc ggcgtggccg cgctcctgct cccgggtcat gtagggcatg ctcagccagt

 421 aatggttctc cgcctcgatc tccaggcggc ggatcatgtt ctgcttggcg cgcaacgaca

 481 cgaaccgcgg ccgccggtgc ttcccgatcc actgacggcc gggaatgcgg ccgcgccaga

 541 ggagcgcagt caggaacatg gtgcctgccg cgctgctcaa gactctgcgt ctccgcggcc

 601 gccagcagac gccgtggcgt aagcgcaccc gtctcgcggg gtctccgggg gcctcggcga

 661 gagacttcgg ctctcgcgag agaggactgc gcctgcgcag agccgaggac gcgtccggcg

 721 ccgagattca aactagtggc gggaggctgt gagctgagcg gtggggtctg cgtacgcctg

 781 gagtccttcc ccgctgtgct cagcatggac cctatccgga gcttctgcgg gaagctgcgg

 841 tctctggcca gcacgctgga ctgcgagacg gcccggctgc agcgagcgct ggacggagag

 901 gaaagcggat gatgttaata ttcttcttga taaagcaaga ttggaaaatc aagaaggcat

 961 tgatttcata aaggcaacaa aagtactaat ggaaaaaaat tcaatggata ttatgaaaat

1021 aagagagtat ttccagaagt atggatatag tccacgtgtc aagaaaaatt cagtacacga

1081 gcaagaagcc attaactctg acccagagtt gtctaattgt gaaaattttc agaagactga

1141 tgtgaaagat gatctgtctg atcctcctgt tgcaagcagt tgtatttctg ggaagtctcc

1201 acgtagtcca caactttcag attttggact tgagcggtac atcgtatccc aagttctacc

1261 aaaccctcca caggcagtga acaactataa ggaagagccc gtaattgtaa ccccacctac

1321 caaacaatca ctagtaaaag tactaaaaac tccaaaatgt gcactaaaaa tggatgattt
```

TABLE LI-continued

| Nucleotide sequence of transcript variant 193P1E1B v.9 |
|---|
| 1381 tgagtgtgta actcctaaat tagaacactt tggtatctct gaatatacta tgtgtttaaa |
| 1441 tgaagattac acaatgggac ttaaaaatgc gaggaataat aaaagtgagg aggccataga |
| 1501 tacagaatcc aggctcaatg ataatgtttt tgccactccc agccccatca tccagcagtt |
| 1561 ggaaaaaagt gatgccgaat ataccaactc tcctttggta cctacattct gtactcctgg |
| 1621 tttgaaaatt ccatctacaa agaacagcat agctttggta tccacaaatt acccattatc |
| 1681 aaaaacaaat agttcatcaa atgatttgga agttgaagat cgtacttcgt tggttttaaa |
| 1741 ttcagacaca tgctttgaga atttaacaga tccctcttca cctacgattt cttcttatga |
| 1801 gaatctgctc agaacaccta cacctccaga agtaactaaa attccagaag atattctcca |
| 1861 gcttttatca aaatacaact caaacctagc tactccaata gcaattaaag cagtgccacc |
| 1921 cagtaaaagg ttccttaaac atggacagaa catccgagat gtcagcaaca aagaaaactg |
| 1981 aaattccagt ggatctatcc aacacagaaa ctgaacaaaa tgagatgaaa gccgagctgg |
| 2041 accgatttta acattcacat tgccctgcct ctgtccccct ttaaacgttg acccatttta |
| 2101 aagacaaaca tgaacattaa catcataata tgctttttat gaagtttcaa taaggtttaa |
| 2161 ccttagtctt gttgacatgt agcccagtca ttcactcttt aaggactatt agtgtttcat |
| 2221 tgatactaaa ttacccagct taatcaacag aatggtttaa gtagtaccag gaagtaggac |
| 2281 aagtaatttc aaaaatataa aggtgtttgc tactcagatg aggccgcccc tgaccttctg |
| 2341 gccagagaga cattgctgcc agccagctct gccttcccat catctccttt caggaccgtc |
| 2401 ccacaccttt tacttgctca gtgctgtctg aagatgcagt tgctgtttgc aaacaacagg |
| 2461 aacaccagtt aaactaatta ggaaacagag ggagatttcc aggcctgggt aactatatac |
| 2521 tgtgaccatt ggcggttgag accggtcttc aaccagtgga accccgaact ctgctgtcag |
| 2581 ggtgtggact tcggtgctct tccaagtttt cacctggggg ggggagctaa ccccctatgt |
| 2641 tcacgccttc tattcccatt ggcgctgaac tcttaaggtc actctggtcg cttgtgaccc |
| 2701 cgtaaccctg atgtacccct ctaaaaggtg aggggc |

TABLE LII

Nuclerotide sequence alignment of 193P1E1B v.1 (SEQ ID NO: 94) and 193P1E1B v.9 (SEQ ID NO: 95)

Score = 1744 bits (907), Expect = 0.0Identities = 907/907 (100%) Strand = Plus/Plus

```
V. 1:   1 tatcatctgtgactgaggaaatccctatcttcctatcagactaatgaaaccacaggacag  60
          ||||||||||||||||||||||||||||||||||||||||||||||||||||||||||||
V. 9:   1 tatcatctgtgactgaggaaatccctatcttcctatcagactaatgaaaccacaggacag  60

V. 1:  61 caattagacttttaagtattgggggggtttagagctctagatattcgatatgcagactact 120
          ||||||||||||||||||||||||||||||||||||||||||||||||||||||||||||
V. 9:  61 caattagacttttaagtattgggggggtttagagctctagatattcgatatgcagactact 120

V. 1: 121 catgtttgtttgttttaataaagactggtccaaaggctcattttcacacaagctacagtt 180
          ||||||||||||||||||||||||||||||||||||||||||||||||||||||||||||
V. 9: 121 catgtttgtttgttttaataaagactggtccaaaggctcattttcacacaagctacagtt 180

V. 1: 181 tttcagttccaggaccaggtaaagatggtcagctccgtgatccataaaatccaagggtga 240
          ||||||||||||||||||||||||||||||||||||||||||||||||||||||||||||
V. 9: 181 tttcagttccaggaccaggtaaagatggtcagctccgtgatccataaaatccaagggtga 240
```

TABLE LII-continued

Nucleotide sequence alignment of 193P1E1B v.1 (SEQ ID NO: 94) and 193P1E1B v.9 (SEQ ID NO: 95)

```
V. 1: 241 cgactcaggattaggaccatttcttggtgacattgagatggtcgagctggtccgcaatga 300
          ||||||||||||||||||||||||||||||||||||||||||||||||||||||||||||
V. 9: 241 cgactcaggattaggaccatttcttggtgacattgagatggtcgagctggtccgcaatga 300

V. 1: 301 atctatgcggggggaacttggaagtggcggccgcctttatggcctcgaaggcctccctcc 360
          ||||||||||||||||||||||||||||||||||||||||||||||||||||||||||||
V. 9: 301 atctatgcggggggaacttggaagtggcggccgcctttatggcctcgaaggcctccctcc 360

V. 1: 361 tgcgcaccgcggcgtggccgcgctcctgctcccgggtcatgtagggcatgctcagccagt 420
          ||||||||||||||||||||||||||||||||||||||||||||||||||||||||||||
V. 9: 361 tgcgcaccgcggcgtggccgcgctcctgctcccgggtcatgtagggcatgctcagccagt 420

V. 1: 421 aatggttctccgcctcgatctccaggcggcggatcatgttctgcttggcgcgcaacgaca 480
          ||||||||||||||||||||||||||||||||||||||||||||||||||||||||||||
V. 9: 421 aatggttctccgcctcgatctccaggcggcggatcatgttctgcttggcgcgcaacgaca 480

V. 1: 481 cgaaccgcggccgccggtgcttcccgatccactgacggccgggaatgcggccgcgccaga 540
          ||||||||||||||||||||||||||||||||||||||||||||||||||||||||||||
V. 9: 481 cgaaccgcggccgccggtgcttcccgatccactgacggccgggaatgcggccgcgccaga 540

V. 1: 541 ggagcgcagtcaggaacatggtgcctgccgcgctgctcaagactctgcgtctccgcggcc 600
          ||||||||||||||||||||||||||||||||||||||||||||||||||||||||||||
V. 9: 541 ggagcgcagtcaggaacatggtgcctgccgcgctgctcaagactctgcgtctccgcggcc 600

V. 1: 601 gccagcagacgccgtggcgtaagcgcacccgtctcgcggggtctccgggggcctcggcga 660
          ||||||||||||||||||||||||||||||||||||||||||||||||||||||||||||
V. 9: 601 gccagcagacgccgtggcgtaagcgcacccgtctcgcggggtctccgggggcctcggcga 660

V. 1: 661 gagacttcggctctcgcgagagaggactgcgcctgcgcagagccgaggacgcgtccggcg 720
          ||||||||||||||||||||||||||||||||||||||||||||||||||||||||||||
V. 9: 661 gagacttcggctctcgcgagagaggactgcgcctgcgcagagccgaggacgcgtccggcg 720

V. 1: 721 ccgagattcaaactagtggcgggaggctgtgagctgagcggtggggtctgcgtacgcctg 780
          ||||||||||||||||||||||||||||||||||||||||||||||||||||||||||||
V. 9: 721 ccgagattcaaactagtggcgggaggctgtgagctgagcggtggggtctgcgtacgcctg 780

V. 1: 781 gagtccttccccgctgtgctcagcatggaccctatccggagcttctgcgggaagctgcgg 840
          ||||||||||||||||||||||||||||||||||||||||||||||||||||||||||||
V. 9: 781 gagtccttccccgctgtgctcagcatggaccctatccggagcttctgcgggaagctgcgg 840

V. 1: 841 tctctggccagcacgctggactgcgagacggcccggctgcagcgagcgctggacggagag 900
          ||||||||||||||||||||||||||||||||||||||||||||||||||||||||||||
V. 9: 841 tctctggccagcacgctggactgcgagacggcccqqctgcagcgagcgctggacggagag 900

V. 1: 901 gaaagcg                                                      907
          |||||||
V. 9: 901 gaaagcg                                                      907
```

Score = 3519 bits (1830), Expect = 0.0 Identities = 1830/1830 (100%) Strand = Plus/Plus

```
V. 1:  969 ggatgatgttaatattcttcttgataaagcaagattggaaaatcaagaaggcattgattt 1028
           ||||||||||||||||||||||||||||||||||||||||||||||||||||||||||||
V. 9:  907 ggatgatgttaatattcttcttgataaagcaagattggaaaatcaagaaggcattgattt  966

V. 1: 1029 cataaaggcaacaaaagtactaatggaaaaaaattcaatggatattatgaaaataagaga 1088
           ||||||||||||||||||||||||||||||||||||||||||||||||||||||||||||
V. 9:  967 cataaaggcaacaaaagtactaatggaaaaaaattcaatggatattatgaaaataagaga 1026

V. 1: 1089 gtatttccagaagtatggatatagtccacgtgtcaagaaaaaattcagtacacgagcaaga 1148
           ||||||||||||||||||||||||||||||||||||||||||||||||||||||||||||
V. 9: 1027 gtatttccagaagtatggatatagtccacgtgtcaagaaaaaattcagtacacgagcaaga 1086

V. 1: 1149 agccattaactctgacccagagttgtctaattgtgaaaattttcagaagactgatgtgaa 1208
           ||||||||||||||||||||||||||||||||||||||||||||||||||||||||||||
V. 9: 1087 agccattaactctgacccagagttgtctaattgtgaaaattttcagaagactgatgtgaa 1146
```

TABLE LII-continued

Nucleotide sequence alignment of 193P1E1B v.1 (SEQ ID NO: 94) and 193P1E1B v.9 (SEQ ID NO: 95)

```
V. 1: 1209 agatgatctgtctgatcctcctgttgcaagcagttgtatttctgggaagtctccacgtag 1268
           ||||||||||||||||||||||||||||||||||||||||||||||||||||||||||||
V. 9: 1147 agatgatctgtctgatcctcctgttgcaagcagttgtatttctgggaagtctccacgtag 1206

V. 1: 1269 tccacaactttcagatttttggacttgagcggtacatcgtatcccaagttctaccaaccc 1328
           ||||||||||||||||||||||||||||||||||||||||||||||||||||||||||||
V. 9: 1207 tccacaactttcagattttggacttgagcggtacatcgtatcccaagttctaccaaaccc 1266

V. 1: 1329 tccacaggcagtgaacaactataaggaagagcccgtaattgtaaccccacctaccaaaca 1388
           ||||||||||||||||||||||||||||||||||||||||||||||||||||||||||||
V. 9: 1267 tccacaggcagtgaacaactataaggaagagcccgtaattgtaacccacctaccaaaaca 1326

V. 1: 1389 atcactagtaaaagtactaaaaactccaaaatgtgcactaaaaatggatgattttgagtg 1448
           ||||||||||||||||||||||||||||||||||||||||||||||||||||||||||||
V. 9: 1327 atcactagtaaaagtactaaaaactccaaaatgtgcactaaaaatggatgattttgagtg 1386

V. 1: 1449 tgtaactcctaaattagaacactttggtatctctgaatatactatgtgtttaaatgaaga 1508
           ||||||||||||||||||||||||||||||||||||||||||||||||||||||||||||
V. 9: 1387 tgtaactcctaaattagaacactttggtatctctgaatatactatgtgtttaaatgaaga 1446

V. 1: 1509 ttacacaatgggacttaaaaatgcgaggaataataaaagtgaggaggccatagatacaga 1568
           ||||||||||||||||||||||||||||||||||||||||||||||||||||||||||||
V. 9: 1447 ttacacaatgggacttaaaaatgcgaggaataataaaagtgaggaggccatagatacaga 1506

V. 1: 1569 atccaggctcaatgataatgtttttgccactcccagccccatcatccagcagttggaaaa 1628
           ||||||||||||||||||||||||||||||||||||||||||||||||||||||||||||
V. 9: 1507 atccaggctcaatgataatgtttttgccactcccagccccatcatccagcagttggaaaa 1566

V. 1: 1629 aagtgatgccgaatataccaactctcctttggtacctacattctgtactcctggtttgaa 1688
           ||||||||||||||||||||||||||||||||||||||||||||||||||||||||||||
V. 9: 1567 aagtgatgccgaatataccaactctcctttggtacctacattctgtactcctggtttgaa 1626

V. 1: 1689 aattccatctacaaagaacagcatagctttggtatccacaaattacccattatcaaaaac 1748
           ||||||||||||||||||||||||||||||||||||||||||||||||||||||||||||
V. 9: 1627 aattccatctacaaagaacagcatagctttggtatccacaaattacccattatcaaaaac 1686

V. 1: 1749 aaatagttcatcaaatgatttggaagttgaagatcgtacttcgttggttttaaattcaga 1808
           ||||||||||||||||||||||||||||||||||||||||||||||||||||||||||||
V. 9: 1687 aaatagttcatcaaatgatttggaagttgaagatcgtacttcgttggttttaaattcaga 1746

V. 1: 1809 cacatgctttgagaatttaacagatccctcttcacctacgatttcttcttatgagaatct 1868
           ||||||||||||||||||||||||||||||||||||||||||||||||||||||||||||
V. 9: 1747 cacatgctttgagaatttaacagatccctcttcacctacgatttcttcttatgagaatct 1806

V. 1: 1869 gctcagaacacctacacctccagaagtaactaaaattccagaagatattctccagctttt 1928
           ||||||||||||||||||||||||||||||||||||||||||||||||||||||||||||
V. 9: 1807 gctcagaacacctacacctccagaagtaactaaaattccagaagatattctccagctttt 1866

V. 1: 1929 atcaaaatacaactcaaacctagctactccaatagcaattaaagcagtgccacccagtaa 1988
           ||||||||||||||||||||||||||||||||||||||||||||||||||||||||||||
V. 9: 1867 atcaaaatacaactcaaacctagctactccaatagcaattaaagcagtgccacccagtaa 1926

V. 1: 1989 aaggttccttaaacatggacagaacatccgagatgtcagcaacaaagaaaactgaaattc 2048
           ||||||||||||||||||||||||||||||||||||||||||||||||||||||||||||
V. 9: 1927 aaggttccttaaacatggacagaacatccgagatgtcagcaacaaagaaaactgaaattc 1986

V. 1: 2049 cagtggatctatccaacacagaaactgaacaaaatgagatgaaagccgagctggaccgat 2108
           ||||||||||||||||||||||||||||||||||||||||||||||||||||||||||||
V. 9: 1987 cagtggatctatccaacacagaaactgaacaaaatgagatgaaagccgagctggaccgat 2046

V. 1: 2109 tttaacattcacattgccctgcctctgtccccctttaaacgttgacccattttaaagaca 2168
           ||||||||||||||||||||||||||||||||||||||||||||||||||||||||||||
V. 9: 2047 tttaacattcacattgccctgcctctgtccccctttaaacgttgacccattttaaagaca 2106
```

TABLE LII-continued

Nucleotide sequence alignment of 193P1E1B v.1 (SEQ ID NO: 94) and 193P1E1B v.9 (SEQ ID NO: 95)

```
V. 1: 2169 aacatgaacattaacatcataatatgctttttatgaagtttcaataaggtttaaccttag 2228
           ||||||||||||||||||||||||||||||||||||||||||||||||||||||||||||
V. 9: 2107 aacatgaacattaacatcataatatgctttttatgaagtttcaataaggtttaaccttag 2166

V. 1: 2229 tcttgttgacatgtagcccagtcattcactctttaaggactattagtgtttcattgatac 2288
           ||||||||||||||||||||||||||||||||||||||||||||||||||||||||||||
V. 9: 2167 tcttgttgacatgtagcccagtcattcactctttaaggactattagtgtttcattgatac 2226

V. 1: 2289 taaattacccagcttaatcaacagaatggtttaagtagtaccaggaagtaggacaagtaa 2348
           ||||||||||||||||||||||||||||||||||||||||||||||||||||||||||||
V. 9: 2227 taaattacccagcttaatcaacagaatggtttaagtagtaccaggaagtaggacaagtaa 2286

V. 1: 2349 tttcaaaaatataaaggtgtttgctactcagatgaggccgcccctgaccttctggccaga 2408
           ||||||||||||||||||||||||||||||||||||||||||||||||||||||||||||
V. 9: 2287 tttcaaaaatataaaggtgtttgctactcagatgaggccgcccctgaccttctggccaga 2346

V. 1: 2409 gagacattgctgccagccagctctgccttcccatcatctcctttcaggaccgtcccacac 2468
           ||||||||||||||||||||||||||||||||||||||||||||||||||||||||||||
V. 9: 2347 gagacattgctgccagccagctctgccttcccatcatctcctttcaggaccgtcccacac 2406

V. 1: 2469 cttttacttgctcagtgctgtctgaagatgcagttgctgtttgcaaacaacaggaacacc 2528
           ||||||||||||||||||||||||||||||||||||||||||||||||||||||||||||
V. 9: 2407 cttttacttgctcagtgctgtctgaagatgcagttgctgtttgcaaacaacaggaacacc 2466

V. 1: 2529 agttaaactaattaggaaacagagggagatttccaggcctgggtaactatatactgtgac 2588
           ||||||||||||||||||||||||||||||||||||||||||||||||||||||||||||
V. 9: 2467 agttaaactaattaggaaacagagggagatttccaggcctgggtaactatatactgtgac 2526

V. 1: 2589 cattggcggttgagaccggtcttcaaccagtggaaccccgaactctgctgtcagggtgtg 2648
           ||||||||||||||||||||||||||||||||||||||||||||||||||||||||||||
V. 9: 2527 cattggcggttgagaccggtcttcaaccagtggaaccccgaactctgctgtcagggtgtg 2586

V. 1: 2649 gacttcggtgctcttccaagttttcacctgggggggggagctaacccccctatgttcacgc 2708
           ||||||||||||||||||||||||||||||||||||||||||||||||||||||||||||
V. 9: 2587 gacttcggtgctcttccaagttttcacctgggggggggagctaacccccctatgttcacgc 2646

V. 1: 2709 cttctattcccattggcgctgaactcttaaggtcactctggtcgcttgtgaccccgtaac 2768
           ||||||||||||||||||||||||||||||||||||||||||||||||||||||||||||
V. 9: 2647 cttctattcccattggcgctgaactcttaaggtcactctggtcgcttgtgaccccgtaac 2706

V. 1: 2769 cctgatgtacccctctaaaaggtgaggggc                               2798
           ||||||||||||||||||||||||||||||
V. 9: 2707 cctgatgtacccctctaaaaggtgaggggc                               2736
```

TABLE LIII

Peptide sequences of protein coded by 193P1E1B v.9

```
                                                       (SEQ ID NO: 96)
MEKNSMDIMK IREYFQKYGY SPRVKKNSVH EQEAINSDPE LSNCENFQKT DVKDDLSDPP  60

VASSCISGKS PRSPQLSDFG LERYIVSQVL PNPPQAVNNY KEEPVIVTPP TKQSLVKVLK 120

TPKCALKMDD FECVTPKLEH FGISEYTMCL NEDYTMGLKN ARNNKSEEAI DTESRLNDNV 180

FATPSPIIQQ LEKSDAEYTN SPLVPTFCTP GLKIPSTKNS IALVSTNYPL SKTNSSSNDL 240

EVEDRTSLVL NSDTCFENLT DPSSPTISSY ENLLRTPTPP EVTKIPEDIL QLLSKYNSNL 300

ATPIAIKAVP PSKRFLKHGQ NIRDVSNKEN                                 330
```

TABLE LIV

Amino acid sequence alignment of 193P1E1B v.1 (SEQ ID NO: 97) and 193P1E1B v.9 (SEQ ID NO: 98)

```
Score = 665 bits (1716), Expect = 0.0Identities = 330/330(100%),
Positives = 330/330 (100%)

v.1:   83 MEKNSMDIMKIREYFQKYGYSPRVKKNSVHEQEAINSDPELSNCENFQKTDVKDDLSDPP 142
          MEKNSMDIMKIREYFQKYGYSPRVKKNSVHEQEAINSDPELSNCENFQKTDVKDDLSDPP
v.9:    1 MEKNSMDIMKIREYFQKYGYSPRVKKNSVHEQEAINSDPELSNCENFQKTDVKDDLSDPP  60

v.1:  143 VASSCISGKSPRSPQLSDFGLERYIVSQVLPNPPQAVNNYKEEPVIVTPPTKQSLVKVLK 202
          VASSCISGKSPRSPQLSDFGLERYIVSQVLPNPPQAVNNYKEEPVIVTPPTKQSLVKVLK
v.9:   61 VASSCISGKSPRSPQLSDFGLERYIVSQVLPNPPQAVNNYKEEPVIVTPPTKQSLVKVLK 120

v.1:  203 TPKCALKMDDFECVTPKLEHFGISEYTMCLNEDYTMGLKNARNNKSEEAIDTESRLNDNV 262
          TPKCALKMDDFECVTPKLEHEGISEYTMCLNEDYTMGLKNARNNKSEEAIDTESRLNDNV
v.9:  121 TPKCALKMDDFECVTPKLEHFGISEYTMCLNEDYTMGLKNARNNKSEEAIDTESRLNDNV 180

v.1:  263 FATPSPIIQQLEKSDAEYTNSPLVPTFCTPGLKIPSTKNSIALVSTNYPLSKTNSSSNDL 322
          FATPSPIIQQLEKSDAEYTNSPLVPTFCTPGLKIPSTKNSIALVSTNYPLSKTNSSSNDL
v.9:  181 FATPSPIIQQLEKSDAEYTNSPLVPTFCTPGLKIPSTKNSIALVSTNYPLSKTNSSSNDL 240

v.1:  323 EVEDRTSLVLNSDTCFENLTDPSSPTISSYENLLRTPTPPEVTKIPEDILQLLSKYNSNL 382
          EVEDRTSLVLNSDTCFENLTDPSSPTISSYENLLRTPTPPEVTKIPEDILQLLSKYNSNL
v.9:  241 EVEDRTSLVLNSDTCFENLTDPSSPTISSYENLLRTPTPPEVTKIPEDILQLLSKYNSNL 300

v.1:  383 ATPIAIKAVPPSKRFLKHGQNIRDVSNKEN                               412
          ATPIAIKAVPPSKRFLKHGQNIRDVSNKEN
v.9:  301 ATPIAIKAVPPSKRELKHGQNIRDVSNKEN                               330
```

TABLE LV

Nucleotide sequence of transcript variant 193P1E1B v.10

```
                                                         (SEQ ID NO: 99)
   1 tatcatctgt gactgaggaa atccctatct tcctatcaga ctaatgaaac cacaggacag

  61 caattagact tttaagtatt ggggggttta gagctctaga tattcgatat gcagactact

 121 catgtttgtt tgttttaata aagactggtc caaaggctca ttttcacaca agctacagtt

 181 tttcagttcc aggaccaggt aaagatggtc agctccgtga tccataaaat ccaagggtga

 241 cgactcagga ttaggaccat ttcttggtga cattgagatg gtcgagctgg tccgcaatga

 301 atctatgcgg ggggaacttg gaagtggcgg ccgcctttat ggcctcgaag gcctccctcc

 361 tgcgcaccgc ggcgtggccg cgctcctgct cccgggtcat gtagggcatg ctcagccagt

 421 aatggttctc cgcctcgatc tccaggcggc ggatcatgtt ctgcttggcg cgcaacgaca

 481 cgaaccgcgg ccgccggtgc ttcccgatcc actgacggcc gggaatgcgg ccgcgccaga

 541 ggagcgcagt caggaacatg gtgcctgccg cgctgctcaa gactctgcgt ctccgcggcc

 601 gccagcagac gccgtggcgt aagcgcaccc gtctcgcggg gtctccgggg gcctcggcga

 661 gagacttcgg ctctcgcgag agaggactgc gcctgcgcag agccgaggac gcgtccggcg

 721 ccgagattca aactagtggc gggaggctgt gagctgagcg gtggggtctg cgtacgcctg

 781 gagtccttcc ccgctgtgct cagcatggac cctatccgga gcttctgcgg gaagctgcgg

 841 tctctggcca gcacgctgga ctgcgagacg gcccggctgc agcgagcgct ggacggagag

 901 gaaagcgact ttgaagatta tccaatgaga attttatatg accttcattc agaagttcag

 961 actctaaagg atgatgttaa tattcttctt gataaagcaa gattggaaaa tcaagaaggc

1021 attgatttca taaaggcaac aaaagtacta atggaaaaaa attcaatgga tattatgaaa

1081 ataagagagt atttccagaa gtatggatat agtccacgtg tcaagaaaaa ttcagtacac

1141 gagcaagaag ccattaactc tgacccagag ttgtctaatt gtgaaaattt tcagaagact

1201 gatgtgaaag atgatctgtc tgatcctcct gttgcaagca gttgtatttc tgggaagtct
```

TABLE LV-continued

| Nucleotide sequence of transcript variant 193P1E1B v.10 |
|---|
| 1261 ccacgtagtc cacaactttc agattttgga cttgagcggt acatcgtatc ccaagttcta |
| 1321 ccaaaccctc cacaggcagt gaacaactat aaggaagagc ccgtaattgt aaccccacct |
| 1381 accaaacaat cactagtaaa agtactaaaa actccaaaat gtgcactaaa aatggatgat |
| 1441 tttgagtgtg taactcctaa attagaacac tttggtatct ctgaatatac tatgtgttta |
| 1501 aatgaagatt acacaatggg acttaaaaat gcgaggaata ataaaagtga ggaggccata |
| 1561 gatacagaat ccaggctcaa tgataatgtt tttgccactc ccagccccat catccagcag |
| 1621 ttggaaaaaa gtgatgccga atataccaac tctcctttgg tacctacatt ctgtactcct |
| 1681 ggtttgaaaa ttccatctac aaagaacagc atagctttgg tatccacaaa ttacccatta |
| 1741 tcaaaaacaa atagttcatc aaatgatttg gaagttgaag atcgtacttc gttggtttta |
| 1801 aattcagaca catgctttga gaatttaaca gatccctctt cacctacgat ttcttcttat |
| 1861 gagaatctgc tcagaacacc tacacctcca gaagtaacta aaattccaga agatattctc |
| 1921 cagaaattcc agtggatcta tccaacacag aaactgaaca aaatgagatg aaagccgagc |
| 1981 tggaccgatt ttaacattca cattgccctg cctctgtccc cctttaaacg ttgacccatt |
| 2041 ttaaagacaa acatgaacat taacatcata atatgctttt tatgaagttt caataaggtt |
| 2101 taaccttagt cttgttgaca tgtagcccag tcattcactc tttaaggact attagtgttt |
| 2161 cattgatact aaattaccca gcttaatcaa cagaatggtt taagtagtac caggaagtag |
| 2221 gacaagtaat ttcaaaaata taaaggtgtt tgctactcag atgaggccgc ccctgacctt |
| 2281 ctggccagag agacattgct gccagccagc tctgccttcc catcatctcc tttcaggacc |
| 2341 gtcccacacc ttttacttgc tcagtgctgt ctgaagatgc agttgctgtt tgcaaacaac |
| 2401 aggaacacca gttaaactaa ttaggaaaca gagggagatt tccaggcctg ggtaactata |
| 2461 tactgtgacc attggcggtt gagaccggtc ttcaaccagt ggaaccccga actctgctgt |
| 2521 cagggtgtgg acttcggtgc tcttccaagt tttcacctgg ggggggggagc taacccccta |
| 2581 tgttcacgcc ttctattccc attggcgctg aactcttaag gtcactctgg tcgcttgtga |
| 2641 ccccgtaacc ctgatgtacc cctctaaaag gtgaggggc |

TABLE LVI

Nucleotide sequence alignment of 193P1E1B v.1 (SEQ ID NO: 100) and 193P1E1B v.10 (SEQ ID NO: 101)

Score = 3698 bits (1923), Expect = 0.0Identities = 1923/1923 (100%) Strand = Plus/Plus

```
V. 1:     1 tatcatctgtgactgaggaaatccctatcttcctatcagactaatgaaaccacaggacag   60
            ||||||||||||||||||||||||||||||||||||||||||||||||||||||||||||
V.10:     1 tatcatctgtgactgaggaaatccctatcttcctatcagactaatgaaaccacaggacag   60

V. 1:    61 caattagacttttaagtattggggggtttagagctctagatattcgatatgcagactact  120
            ||||||||||||||||||||||||||||||||||||||||||||||||||||||||||||
V.10:    61 caattagacttttaagtattggggggtttagagctctagatattcgatatgcagactact  120

V. 1:   121 catgtttgtttgttttaataaagactggtccaaaggctcattttcacacaagctacagtt  180
            ||||||||||||||||||||||||||||||||||||||||||||||||||||||||||||
V.10:   121 catgtttgtttgttttaataaagactggtccaaaggctcattttcacacaagctacagtt  180

V. 1:   181 tttcagttccaggaccaggtaaagatggtcagctccgtgatccataaaatccaagggtga  240
            ||||||||||||||||||||||||||||||||||||||||||||||||||||||||||||
V.10:   181 tttcagttccaggaccaggtaaagatggtcagctccgtgatccataaaatccaagggtga  240
```

TABLE LVI-continued

Nucleotide sequence alignment of 193P1E1B v.1 (SEQ ID NO: 100) and 193P1E1B v.10 (SEQ ID NO: 101)

```
V. 1:  241 cgactcaggattaggaccatttcttggtgacattgagatggtcgagctggtccgcaatga  300
           ||||||||||||||||||||||||||||||||||||||||||||||||||||||||||||
V.10:  241 cgactcaggattaggaccatttcttggtgacattgagatggtcgagctggtccgcaatga  300

V. 1:  301 atctatgcggggggaacttggaagtggcggccgcctttatggcctcgaaggcctccctcc  360
           ||||||||||||||||||||||||||||||||||||||||||||||||||||||||||||
V.10:  301 atctatgcggggggaacttggaagtggcggccgcctttatggcctcgaaggcctccctcc  360

V. 1:  361 tgcgcaccgcggcgtggccgcgctcctgctcccgggtcatgtagggcatgctcagccagt  420
           ||||||||||||||||||||||||||||||||||||||||||||||||||||||||||||
V.10:  361 tgcgcaccgcggcgtggccgcgctcctgctcccgggtcatgtagggcatgctcagccagt  420

V. 1:  421 aatggttctccgcctcgatctccaggcggcggatcatgttctgcttggcgcgcaacgaca  480
           ||||||||||||||||||||||||||||||||||||||||||||||||||||||||||||
V.10:  421 aatggttctccgcctcgatctccaggcggcggatcatgttctgcttggcgcgcaacgaca  480

V. 1:  481 cgaaccgcggccgccggtgcttcccgatccactgacggccgggaatgcggccgcgccaga  540
           ||||||||||||||||||||||||||||||||||||||||||||||||||||||||||||
V.10:  481 cgaaccgcggccgccggtgcttcccgatccactgacggccgggaatgcggccgcgccaga  540

V. 1:  541 ggagcgcagtcaggaacatggtgcctgccgcgctgctcaagactctgcgtctccgcggcc  600
           ||||||||||||||||||||||||||||||||||||||||||||||||||||||||||||
V.10:  541 ggagcgcagtcaggaacatggtgcctgccgcgctgctcaagactctgcgtctccgcggcc  600

V. 1:  601 gccagcagacgccgtggcgtaagcgcacccgtctcgcggggtctccgggggcctcggcga  660
           ||||||||||||||||||||||||||||||||||||||||||||||||||||||||||||
V.10:  601 gccagcagacgccgtggcgtaagcgcacccgtctcgcggggtctccgggggcctcggcga  660

V. 1:  661 gagacttcggctctcgcgagagaggactgcgcctgcgcagagccgaggacgcgtccggcg  720
           ||||||||||||||||||||||||||||||||||||||||||||||||||||||||||||
V.10:  661 gagacttcggctctcgcgagagaggactgcgcctgcgcagagccgaggacgcgtccggcg  720

V. 1:  721 ccgagattcaaactagtggcgggaggctgtgagctgagcggtggggtctgcgtacgcctg  780
           ||||||||||||||||||||||||||||||||||||||||||||||||||||||||||||
V.10:  721 ccgagattcaaactagtggcgggaggctgtgagctgagcggtggggtctgcgtacgcctg  780

V. 1:  781 gagtccttccccgctgtgctcagcatggaccctatccggagcttctgcgggaagctgcgg  840
           ||||||||||||||||||||||||||||||||||||||||||||||||||||||||||||
V.10:  781 gagtccttccccgctgtgctcagcatggaccctatccggagcttctgcgggaagctgcgg  840

V. 1:  841 tctctggccagcacgctggactgcgagacggcccggctgcagcgagcgctggacggagag  900
           ||||||||||||||||||||||||||||||||||||||||||||||||||||||||||||
V.10:  841 tctctggccagcacgctggactgcgagacggcccggctgcagcgagcgctggacggagag  900

V. 1:  901 gaaagcgactttgaagattatccaatgagaattttatatgaccttcattcagaagttcag  960
           ||||||||||||||||||||||||||||||||||||||||||||||||||||||||||||
V.10:  901 gaaagcgactttgaagattatccaatgagaattttatatgaccttcattcagaagttcag  960

V. 1:  961 actctaaaggatgatgttaatattcttcttgataaagcaagattggaaaatcaagaaggc 1020
           ||||||||||||||||||||||||||||||||||||||||||||||||||||||||||||
V.10:  961 actctaaaggatgatgttaatattcttcttgataaagcaagattggaaaatcaagaaggc 1020

V. 1: 1021 actctaaaggatgatgttaatattcttcttgataaagcaagattggaaaatcaagaaggc 1080
           ||||||||||||||||||||||||||||||||||||||||||||||||||||||||||||
V.10: 1021 actctaaaggatgatgttaatattcttcttgataaagcaagattggaaaatcaagaaggc 1080

V. 1: 1081 ataagagagtatttccagaagtatggatatagtccacgtgtcaagaaaaaattcagtacac 1140
           ||||||||||||||||||||||||||||||||||||||||||||||||||||||||||||
V.10: 1081 ataagagagtatttccagaagtatggatatagtccacgtgtcaagaaaaaattcagtacac 1140

V. 1: 1041 gagcaagaagccattaactctgacccagagttgtctaattgtgaaaattttcagaagact 1200
           ||||||||||||||||||||||||||||||||||||||||||||||||||||||||||||
V.10: 1041 gagcaagaagccattaactctgacccagagttgtctaattgtgaaaattttcagaagact 1200
```

TABLE LVI-continued

Nuclerotide sequence alignment of 193P1E1B v.1 (SEQ ID NO: 100) and 193P1E1B v.10 (SEQ ID NO: 101)

```
V. 1: 1201 gatgtgaaagatgatctgtctgatcctcctgttgcaagcagttgtatttctgggaagtct 1260
           ||||||||||||||||||||||||||||||||||||||||||||||||||||||||||||
V.10: 1201 gatgtgaaagatgatctgtctgatcctcctgttgcaagcagttgtatttctgggaagtct 1260

V. 1: 1261 ccacgtagtccacaactttcagattttggacttgagcggtacatcgtatcccaagttcta 1320
           ||||||||||||||||||||||||||||||||||||||||||||||||||||||||||||
V.10: 1261 ccacgtagtccacaactttcagattttggacttgagcggtacatcgtatcccaagttcta 1320

V. 1: 1321 ccaaaccctccacaggcagtgaacaactataaggaagagcccgtaattgtaaccccacct 1380
           ||||||||||||||||||||||||||||||||||||||||||||||||||||||||||||
V.10: 1321 ccaaaccctccacaggcagtgaacaactataaggaagagcccgtaattgtaaccccacct 1380

V. 1: 1381 accaaacaatcactagtaaaagtactaaaaactccaaaatgtgcactaaaaatggatgat 1440
           ||||||||||||||||||||||||||||||||||||||||||||||||||||||||||||
V.10: 1381 accaaacaatcactagtaaaagtactaaaaactccaaaatgtgcactaaaaatggatgat 1440

V. 1: 1441 tttgagtgtgtaactcctaaattagaacactttggtatctctgaatatactatgtgttta 1500
           ||||||||||||||||||||||||||||||||||||||||||||||||||||||||||||
V.10: 1441 tttgagtgtgtaactcctaaattagaacactttggtatctctgaatatactatgtgttta 1500

V. 1: 1501 aatgaagattacacaatgggacttaaaaatgcgaggaataataaaagtgaggaggccata 1560
           ||||||||||||||||||||||||||||||||||||||||||||||||||||||||||||
V.10: 1501 aatgaagattacacaatgggacttaaaaatgcgaggaataataaaagtgaggaggccata 1560

V. 1: 1561 gatacagaatccaggctcaatgataatgtttttgccactcccagccccatcatccagcag 1620
           ||||||||||||||||||||||||||||||||||||||||||||||||||||||||||||
V.10: 1561 gatacagaatccaggctcaatgataatgtttttgccactcccagccccatcatccagcag 1620

V. 1: 1621 ttggaaaaaagtgatgccgaatataccaactctcctttggtacctacattctgtactcct 1680
           ||||||||||||||||||||||||||||||||||||||||||||||||||||||||||||
V.10: 1621 ttggaaaaaagtgatgccgaatataccaactctcctttggtacctacattctgtactcct 1680

V. 1: 1681 ggtttgaaaattccatctacaaagaacagcatagctttggtatccacaaattacccatta 1740
           ||||||||||||||||||||||||||||||||||||||||||||||||||||||||||||
V.10: 1681 ggtttgaaaattccatctacaaagaacagcatagctttggtatccacaaattacccatta 1740

V. 1: 1741 tcaaaaacaaatagttcatcaaatgatttggaagttgaagatcgtacttcgttggtttta 1800
           ||||||||||||||||||||||||||||||||||||||||||||||||||||||||||||
V.10: 1741 tcaaaaacaaatagttcatcaaatgatttggaagttgaagatcgtacttcgttggtttta 1800

V. 1: 1801 aattcagacacatgctttgagaatttaacagatccctcttcacctacgatttcttcttat 1860
           ||||||||||||||||||||||||||||||||||||||||||||||||||||||||||||
V.10: 1801 aattcagacacatgctttgagaatttaacagatccctcttcacctacgatttcttcttat 1860

V. 1: 1861 gagaatctgctcagaacacctacacctccagaagtaactaaaattccagaagatattctc 1920
           ||||||||||||||||||||||||||||||||||||||||||||||||||||||||||||
V.10: 1861 gagaatctgctcagaacacctacacctccagaagtaactaaaattccagaagatattctc 1920

V. 1: 1921 cag                                                          1923
           |||
V.10: 1921 cag                                                          1923
```

Score = 1456 bits (757), Expect = 0.0 Identities = 757/757 (100%) Strand = Plus/Plus

```
V. 1: 2042 gaaattccagtggatctatccaacacagaaactgaacaaaatgagatgaaagccgagctg 2101
           ||||||||||||||||||||||||||||||||||||||||||||||||||||||||||||
V.10: 1923 gaaattccagtggatctatccaacacagaaactgaacaaaatgagatgaaagccgagctg 1982

V. 1: 2102 gaccgattttaacattcacattgccctgcctctgtccccctttaaacgttgacccatttt 2161
           ||||||||||||||||||||||||||||||||||||||||||||||||||||||||||||
V.10: 1983 gaccgattttaacattcacattgccctgcctctgtccccctttaaacgttgacccatttt 2042

V. 1: 2162 aaagacaaacatgaacattaacatcataatatgctttttatgaagtttcaataaggttta 2221
           ||||||||||||||||||||||||||||||||||||||||||||||||||||||||||||
V.10: 2043 aaagacaaacatgaacattaacatcataatatgctttttatgaagtttcaataaggttta 2102

V. 1: 2222 accttagtcttgttgacatgtagcccagtcattcactctttaaggactattagtgtttca 2281
           ||||||||||||||||||||||||||||||||||||||||||||||||||||||||||||
V.10: 2103 accttagtcttgttgacatgtagcccagtcattcactctttaaggactattagtgtttca 2162
```

TABLE LVI-continued

Nucleotide sequence alignment of 193P1E1B v.1 (SEQ ID NO: 100) and 193P1E1B v.10 (SEQ ID NO: 101)

```
V. 1: 2282 ttgatactaaattacccagcttaatcaacagaatggtttaagtagtaccaggaagtagga 2281
           ||||||||||||||||||||||||||||||||||||||||||||||||||||||||||||
V.10: 2163 ttgatactaaattacccagcttaatcaacagaatggtttaagtagtaccaggaagtagga 2222

V. 1: 2342 caagtaatttcaaaaatataaaggtgtttgctactcagatgaggccgcccctgaccttct 2401
           ||||||||||||||||||||||||||||||||||||||||||||||||||||||||||||
V.10: 2223 caagtaatttcaaaaatataaaggtgtttgctactcagatgaggccgcccctgaccttct 2282

V. 1: 2402 ggccagagagacattgctgccagccagctctgccttcccatcatctcctttcaggaccgt 2461
           ||||||||||||||||||||||||||||||||||||||||||||||||||||||||||||
V.10: 2283 ggccagagagacattgctgccagccagctctgccttcccatcatctcctttcaggaccgt 2342

V. 1: 2462 cccacaccttttacttgctcagtgctgtctgaagatgcagttgctgtttgcaaacaacag 2521
           ||||||||||||||||||||||||||||||||||||||||||||||||||||||||||||
V.10: 2343 cccacaccttttacttgctcagtgctgtctgaagatgcagttgctgtttgcaaacaacag 2402

V. 1: 2522 gaacaccagttaaactaattaggaaacagagggagatttccaggcctgggtaactatata 2581
           ||||||||||||||||||||||||||||||||||||||||||||||||||||||||||||
V.10: 2403 gaacaccagttaaactaattaggaaacagagggagatttccaggcctgggtaactatata 2462

V. 1: 2582 ctgtgaccattggcggttgagaccggtcttcaaccagtggaaccccgaactctgctgtca 2641
           ||||||||||||||||||||||||||||||||||||||||||||||||||||||||||||
V.10: 2463 ctgtgaccattggcggttgagaccggtcttcaaccagtggaaccccgaactctgctgtca 2522

V. 1: 2642 gggtgtggacttcggtgctcttccaagttttcacctgggggggggagctaacccccctatg 2701
           ||||||||||||||||||||||||||||||||||||||||||||||||||||||||||||
V.10: 2523 gggtgtggacttcggtgctcttccaagttttcacctgggggggggagctaacccccctatg 2582

V. 1: 2702 ttcacgccttctattcccattggcgctgaactcttaaggtcactctggtcgcttgtgacc 2761
           ||||||||||||||||||||||||||||||||||||||||||||||||||||||||||||
V.10: 2583 ttcacgccttctattcccattggcgctgaactcttaaggtcactctggtcgcttgtgacc 2642

V. 1: 2762 ccgtaaccctgatgtacccctctaaaaggtgaggggc                        2798
           |||||||||||||||||||||||||||||||||||||
V.10: 2643 ccgtaaccctgatgtacccctctaaaaggtgaggggc                        2679
```

TABLE LVII

Peptide sequences of protein coded by 193P1E1B v.10

```
                                                     (SEQ ID NO: 102)
MDPIRSFCGK LRSLASTLDC ETARLQRALD GEESDFEDYP MRILYDLHSE VQTLKDDVNI  60

LLDKARLENQ EGIDFIKATK VLMEKNSMDI MKIREYFQKY GYSPRVKKNS VHEQEAINSD 120

PELSNCENFQ KTDVKDDLSD PPVASSCISG KSPRSPQLSD FGLERYIVSQ VLPNPPQAVN 180

NYKEEPVIVT PPTKQSLVKV LKTPKCALKM DDFECVTPKL EHFGISEYTM CLNEDYTMGL 240

KNARNNKSEE AIDTESRLND NVFATPSPII QQLEKSDAEY TNSPLVPTFC TPGLKIPSTK 300

NSIALVETNY PLSKTNSSSN DLEVEDRTSL VLNSDTCFEN LTDPSSPTIS SYENLLRTPT 360

PPEVTKIPED ILQKFQWIYP TQKLNKMR                                   388
```

TABLE LVIII

Amino acid sequence alignment of 193P1E1B v.1 (SEQ ID NO: 103) and 193P1E1B v.10 (SEQ ID NO: 104)

```
Score = 749 bits (1935), Expect = 0.0Identities = 373/373 (100%),
Positives = 373/373(100%)

v.1:     1 MDPIRSFCGKLRSLASTLDCETARLQRALDGEESDFEDYPMRILYDLHSEVQTLKDDVNI  60
             MDPIRSFCGKLRSLASTLDCETARLQRALDGEESDFEDYPMRILYDLHSEVQTLKDDVNI
v.10:    1 MDPIRSFCGKLRSLASTLDCETARLQRALDGEESDFEDYPMRILYDLHSEVQTLKDDVNI  60

v.1:    61 LLDKARLENQEGIDFIKATKVLMEKNSMDIMKIREYFQKYGYSPRVKKNSVHEQEAINSD 120
           LLDKARLENQEGIDFIKATKVLMEKNSMDIMKIREYFQKYGYSPRVKKNSVHEQEAINSD
v.10:   61 LLDKARLENQEGIDFIKATKVLMEKNSMDIMKIREYFQKYGYSPRVKKNSVHEQEAINSD 120
```

TABLE LVIII-continued

Amino acid sequence alignment of 193P1E1B v.1 (SEQ ID NO: 103) and 193P1E1B v.10 (SEQ ID NO: 104)

```
v.1:  121 PELSNCENFQKTDVKDDLSDPPVASSCISGKSPRSPQLSDFGLERYIVSQVLPNPPQAVN 180
          PELSNCENFQKTDVKDDLSDPPVASSCISGKSPRSPQLSDFGLERYIVSQVLPNPPQAVN
v.10: 121 PELSNCENFQKTDVKDDLSDPPVASSCISGKSPRSPQLSDFGLERYIVSQVLPNPPQAVN 180

v.1:  181 NYKEEPVIVTPPTKQSLVKVLKTPKCALKMDDFECVTPKLEHFGISEYTMCLNEDYTMGL 240
          NYKEEPVIVTPPTKQSLVKVLKTPKCALKMDDFECVTPKLEHFGISEYTMCLNEDYTMGL
v.10: 181 NYKEEPVIVTPPTKQSLVKVLKTPKCALKMDDFECVTPKLEHFGISEYTMCLNEDYTMGL 240

v.1:  241 KNARNNKSEEAIDTESRLNDNV-
FATPSPIIQQLEKSDAEYTNSPLVPT-
FCTPGLKIPSTK                                             300
          KNARNNKSEEAIDTESRLNDNVFATPSPIIQQLEKSDAEYTNSPLVPTFCTPGLKIPSTK
v.10: 241 KNARNNKSEEAIDTESRLNDNV-
FATPSPIIQQLEKSDAEYTNSPLVPT-
FCTPGLKIPSTK                                               300

v.1:  301 NSIALVSTNYPLSKTNSSSNDLEVEDRTSLVLNSDTCFENLTDPSSPTISSYENLLRTPT 360
          NSIALVSTNYPLSKTNSSSNDLEVEDRTSLVLNSDTCFENLTDPSSPTISSYENLLRTPT
v.10: 301 NSIALVSTNYPLSKTNSSSNDLEVEDRTSLVLNSDTCFENLTDPSSPTTSSYENLLRTPT 360

v.1:  361 PPEVTKIPEDILQ 373
          PPEVTKIPEDILQ
v.10: 361 PPEVTKIPEDILQ 373
```

TABLE LIX

Nucleotide sequence of transcript variant 193P1E1Bv.11

```
                                                      (SEQ ID NO: 105)
   1 tatcatctgt gactgaggaa atccctatct tcctatcaga ctaatgaaac cacaggacag

  61 caattagact tttaagtatt ggggggttta gagctctaga tattcgatat gcagactact

 121 catgtttgtt tgttttaata aagactggtc caaaggctca ttttcacaca agctacagtt

 181 tttcagttcc aggaccaggt aaagatggtc agctccgtga tccataaaat ccaagggtga

 241 cgactcagga ttaggaccat ttcttggtga cattgagatg gtcgagctgg tccgcaatga

 301 atctatgcgg ggggaacttg gaagtggcgg ccgcctttat ggcctcgaag gcctccctcc

 361 tgcgcaccgc ggcgtggccg cgctcctgct cccgggtcat gtagggcatg ctcagccagt

 421 aatggttctc cgcctcgatc tccaggcggc ggatcatgtt ctgcttggcg cgcaacgaca

 481 cgaaccgcgg ccgccggtgc ttcccgatcc actgacggcc gggaatgcgg ccgcgccaga

 541 ggagcgcagt caggaacatg gtgcctgccg cgctgctcaa gactctgcgt ctccgcggcc

 601 gccagcagac gccgtggcgt aagcgcaccc gtctcgcggg gtctccgggg gcctcggcga

 661 gagacttcgg ctctcgcgag agaggactgc gcctgcgcag agccgaggac gcgtccggcg

 721 ccgagattca aactagtggc gggaggctgt gagctgagcg gtggggtctg cgtacgcctg

 781 gagtccttcc ccgctgtgct cagcatggac catatccgga gcttctgcgg gaagctgcgg

 841 tctctggcca gcacgctgga ctgcgagacg gcccggctgc agcgagcgct ggacggagag

 901 gaaagcggat gatgttaata ttcttcttga taaagcaaga ttggaaaatc aagaaggcat

 961 tgatttcata aaggcaacaa aagtactaat ggaaaaaaat tcaatggata ttatgaaaat

1021 aagagagtat ttccagaagt atggatatag tccacgtgtc aagaaaaatt cagtacacga

1081 gcaagaagcc attaactctg acccagagtt gtctaattgt gaaaattttc agaagactga

1141 tgtgaaagat gatctgtctg atcctcctgt tgcaagcagt tgtatttctg ggaagtctcc

1201 acgtagtcca caactttcag attttggact tgagcggtac atcgtatccc aagttctacc

1261 aaaccctcca caggcagtga acaactataa ggaagagccc gtaattgtaa ccccacctac
```

TABLE LIX-continued

| Nucleotide sequence of transcript variant 193P1E1Bv.11 |
|---|
| 1321 caaacaatca ctagtaaaag tactaaaaac tccaaaatgt gcactaaaaa tggatgattt |
| 1381 tgagtgtgta actcctaaat tagaacactt tggtatctct gaatatacta tgtgtttaaa |
| 1441 tgaagattac acaatgggac ttaaaaatgc gaggaataat aaaagtgagg aggccataga |
| 1501 tacagaatcc aggctcaatg ataatgtttt tgccactccc agccccatca tccagcagtt |
| 1561 ggaaaaaagt gatgccgaat ataccaactc tcctttggta cctacattct gtactcctgg |
| 1621 tttgaaaatt ccatctacaa agaacagcat agctttggta tccacaaatt acccattatc |
| 1681 aaaaacaaat agttcatcaa atgatttgga agttgaagat cgtacttcgt tggttttaaa |
| 1741 ttcagacaca tgctttgaga atttaacaga tccctcttca cctacgattt cttcttatga |
| 1801 gaatctgctc agaacaccta cacctccaga agtaactaaa attccagaag atattctcca |
| 1861 gaaattccag tggatctatc caacacagaa actgaacaaa atgagatgaa agccgagctg |
| 1921 gaccgatttt aacattcaca ttgccctgcc tctgtccccc tttaaacgtt gacccatttt |
| 1981 aaagacaaac atgaacatta acatcataat atgcttttta tgaagtttca ataaggttta |
| 2041 accttagtct tgttgacatg tagcccagtc attcactctt taaggactat tagtgtttca |
| 2101 ttgatactaa attacccagc ttaatcaaca gaatggttta agtagtacca ggaagtagga |
| 2161 caagtaattt caaaaatata aaggtgtttg ctactcagat gaggccgccc ctgaccttct |
| 2221 ggccagagag acattgctgc cagccagctc tgccttccca tcatctcctt tcaggaccgt |
| 2281 cccacacctt ttacttgctc agtgctgtct gaagatgcag ttgctgtttg caaacaacag |
| 2341 gaacaccagt taaactaatt aggaaacaga gggagatttc caggcctggg taactatata |
| 2401 ctgtgaccat tggcggttga gaccggtctt caaccagtgg aaccccgaac tctgctgtca |
| 2461 gggtgtggac ttcggtgctc ttccaagttt tcacctgggg gggggagcta accccctatg |
| 2521 ttcacgcctt ctattcccat tggcgctgaa ctcttaaggt cactctggtc gcttgtgacc |
| 2581 ccgtaaccct gatgtacccc tctaaaaggt gaggggc |

TABLE LX

Nucteotide sequence alignment of 193P1E1B v.1 (SEQ ID NO: 106) and 193P1E1B v.11 (SEQ ID NO: 107)

```
Score = 1744 bits (907), Expect = 0.0Identities = 907/907 (100%) Strand =
Plus/Plus

V. 1:    1 tatcatctgtgactgaggaaatccctatcttcctatcagactaatgaaaccacaggacag   60
           ||||||||||||||||||||||||||||||||||||||||||||||||||||||||||||
V.11:    1 tatcatctgtgactgaggaaatccctatcttcctatcagactaatgaaaccacaggacag   60
V. 1:   61 caattagacttttaagtattgggggggtttagagctctagatattcgatatgcagagtact  120
           ||||||||||||||||||||||||||||||||||||||||||||||||||||||||||||
V.11:   61 caattagacttttaagtattgggggggtttagagctctagatattcgatatgcagagtact  120
V. 1:  121 catgtttgtttgttttaataaagactggtccaaaggctcattttcacacaagctacagtt  180
           ||||||||||||||||||||||||||||||||||||||||||||||||||||||||||||
V.11:  121 catgtttgtttgttttaataaagactggtccaaaggctcattttcacacaagctacagtt  180
V. 1:  181 tttcagttccaggaccaggtaaagatggtcagctccgtgatccataaaatccaagggtga  240
           ||||||||||||||||||||||||||||||||||||||||||||||||||||||||||||
V.11:  181 tttcagttccaggaccaggtaaagatggtcagctccgtgatccataaaatccaagggtga  240
```

TABLE LX-continued

Nucteotide sequence alignment of 193P1E1B v.1 (SEQ ID NO: 106) and 193P1E1B v.11 (SEQ ID NO: 107)

```
V.1 :  241 cgactcaggattaggaccatttcttggtgacattgagatggtcgagctggtccgcaatga  300
           ||||||||||||||||||||||||||||||||||||||||||||||||||||||||||||
V.11:  241 cgactcaggattaggaccatttcttggtgacattgagatggtcgagctggtccgcaatga  300

V.1 :  301 atctatgcggggggaacttggaagtggcggccgcctttatggcctcgaaggcctccctcc  360
           ||||||||||||||||||||||||||||||||||||||||||||||||||||||||||||
V.11:  301 atctatgcggggggaacttggaagtggcggccgcctttatggcctcgaaggcctccctcc  360

V.1 :  361 tgcgcaccgcggcgtggccgcgctcctgctcccgggtcatgtagggcatgctcagccagt  420
           ||||||||||||||||||||||||||||||||||||||||||||||||||||||||||||
V.11:  361 tgcgcaccgcggcgtggccgcgctcctgctcccgggtcatgtagggcatgctcagccagt  420

V.1 :  421 aatggttctccgcctcgatctccaggcggcggatcatgttctgcttggcgcgcaacgaca  480
           ||||||||||||||||||||||||||||||||||||||||||||||||||||||||||||
V.11:  421 aatggttctccgcctcgatctccaggcggcggatcatgttctgcttggcgcgcaacgaca  480

V.1 :  481 cgaaccgcggccgccggtgcttcccgatccactgacggccgggaatgcggccgcgccaga  540
           ||||||||||||||||||||||||||||||||||||||||||||||||||||||||||||
V.11:  481 cgaaccgcggccgccggtgcttcccgatccactgacggccgggaatgcggccgcgccaga  540

V.1 :  541 ggagcgcagtcaggaacatggtgcctgccgcgctgctcaagactctgcgtctccgcggcc  600
           ||||||||||||||||||||||||||||||||||||||||||||||||||||||||||||
V.11:  541 ggagcgcagtcaggaacatggtgcctgccgcgctgctcaagactctgcgtctccgcggcc  600

V.1 :  601 gccagcagacgccgtggcgtaagcgcacccgtctcgcggggtctccgggggcctcggcga  660
           ||||||||||||||||||||||||||||||||||||||||||||||||||||||||||||
V.11:  601 gccagcagacgccgtggcgtaagcgcacccgtctcgcggggtctccgggggcctcggcga  660

V.1 :  661 gagacttcggctctcgcgagagaggactgcgcctgcgcagagccgaggacgcgtccggcg  720
           ||||||||||||||||||||||||||||||||||||||||||||||||||||||||||||
V.11:  661 gagacttcggctctcgcgagagaggactgcgcctgcgcagagccgaggacgcgtccggcg  720

V.1 :  721 ccgagattcaaactagtggcgggaggctgtgagctgagcggtggggtctgcgtacgcctg  780
           ||||||||||||||||||||||||||||||||||||||||||||||||||||||||||||
V.11:  721 ccgagattcaaactagtggcgggaggctgtgagctgagcggtggggtctgcgtacgcctg  780

V.1 :  781 gagtccttccccgctgtgctcagcatggaccctatccggagcttctgcgggaagctgcgg  840
           ||||||||||||||||||||||||||||||||||||||||||||||||||||||||||||
V.11:  781 gagtccttccccgctgtgctcagcatggaccctatccggagcttctgcgggaagctgcgg  840

V.1 :  841 tctctggccagcacgctggactgcgagacggcccggctgcagcgagcgctggacggagag  900
           ||||||||||||||||||||||||||||||||||||||||||||||||||||||||||||
V.11:  841 tctctggccagcacgctggactgcgagacggcccggctgcagcgagcgctggacggagag  900

V.1 :  901 gaaagcg                                                       907
           |||||||
V.11:  901 gaaagcg                                                       907
```

Score = 1836 bits (955), Expect = 0.0Identities = 955/955 (100%) Strand = Plus/Plus

```
V.1 :  969 ggatgatgttaatattcttcttgataaagcaagattggaaaatcaagaaggcattgattt 1028
           ||||||||||||||||||||||||||||||||||||||||||||||||||||||||||||
V.11:  907 ggatgatgttaatattcttcttgataaagcaagattggaaaatcaagaaggcattgattt  966

V.1 : 1029 cataaaggcaacaaaagtactaatggaaaaaaattcaatggatattatgaaaataagaga 1088
           ||||||||||||||||||||||||||||||||||||||||||||||||||||||||||||
V.11:  967 cataaaggcaacaaaagtactaatggaaaaaaattcaatggatattatgaaaataagaga 1026

V.1 : 1089 gtatttccagaagtatggatatagtccacgtgtcaagaaaaattcagtacacgagcaaga 1148
           ||||||||||||||||||||||||||||||||||||||||||||||||||||||||||||
V.11: 1027 gtatttccagaagtatggatatagtccacgtgtcaagaaaaattcagtacacgagcaaga 1086

V.1 : 1149 agccattaactctgacccagagttgtctaattgtgaaaattttcagaagactgatgtgaa 1208
           ||||||||||||||||||||||||||||||||||||||||||||||||||||||||||||
V.11: 1087 agccattaactctgacccagagttgtctaattgtgaaaattttcagaagactgatgtgaa 1146

V.1 : 1209 agatgatctgtctgatcctcctgttgcaagcagttgtatttctgggaagtctccacgtag 1268
           ||||||||||||||||||||||||||||||||||||||||||||||||||||||||||||
V.11: 1147 agatgatctgtctgatcctcctgttgcaagcagttgtatttctgggaagtctccacgtag 1206

V.1 : 1269 tccacaactttcagattttggacttgagcggtacatcgtatcccaagttctaccaaaccc 1328
           ||||||||||||||||||||||||||||||||||||||||||||||||||||||||||||
V.11: 1207 tccacaactttcagattttggacttgagcggtacatcgtatcccaagttctaccaaaccc 1266

V.1 : 1329 tccacaggcagtgaacaactataaggaagagcccgtaattgtaaccccacctaccaaaca 1388
           ||||||||||||||||||||||||||||||||||||||||||||||||||||||||||||
V.11: 1267 tccacaggcagtgaacaactataaggaagagcccgtaattgtaaccccacctaccaaaca 1326

V.1 : 1389 atcactagtaaaagtactaaaaactccaaaatgtgcactaaaaatggatgattttgagtg 1448
           ||||||||||||||||||||||||||||||||||||||||||||||||||||||||||||
V.11: 1327 atcactagtaaaagtactaaaaactccaaaatgtgcactaaaaatggatgattttgagtg 1386
```

TABLE LX-continued

Nucteotide sequence alignment of 193P1E1B v.1 (SEQ ID NO: 106) and 193P1E1B v.11 (SEQ ID NO: 107)

```
V.1 : 1449 tgtaactcctaaattagaacactttggtatctctgaatatactatgtgtttaaatgaaga 1508
           ||||||||||||||||||||||||||||||||||||||||||||||||||||||||||||
V.11: 1387 tgtaactcctaaattagaacactttggtatctctgaatatactatgtgtttaaatgaaga 1446

V.1 : 1509 ttacacaatgggacttaaaaatgcgaggaataataaaagtgaggaggccatagatacaga 1568
           ||||||||||||||||||||||||||||||||||||||||||||||||||||||||||||
V.11: 1447 ttacacaatgggacttaaaaatgcgaggaataataaaagtgaggaggccatagatacaga 1506

V.1 : 1569 atccaggctcaatgataatgtttttgccactcccagccccatcatccagcagttggaaaa 1628
           ||||||||||||||||||||||||||||||||||||||||||||||||||||||||||||
V.11: 1507 atccaggctcaatgataatgtttttgccactcccagccccatcatccagcagttggaaaa 1566

V.1 : 1629 aagtgatgccgaatataccaactctcctttggtacctacattctgtactcctggtttgaa 1688
           ||||||||||||||||||||||||||||||||||||||||||||||||||||||||||||
V.11: 1567 aagtgatgccgaatataccaactctcctttggtacctacattctgtactcctggtttgaa 1626

V.1 : 1689 aattccatctacaaagaacagcatagctttggtatccacaaattacccattatcaaaaac 1748
           ||||||||||||||||||||||||||||||||||||||||||||||||||||||||||||
V.11: 1627 aattccatctacaaagaacagcatagctttggtatccacaaattacccattatcaaaaac 1686

V.1 : 1749 aaatagttcatcaaatgatttggaagttgaagatcgtacttcgttggttttaaattcaga 1808
           ||||||||||||||||||||||||||||||||||||||||||||||||||||||||||||
V.11: 1687 aaatagttcatcaaatgatttggaagttgaagatcgtacttcgttggttttaaattcaga 1746

V.1 : 1809 cacatgctttgagaatttaacagatccctcttcacctacgatttcttcttatgagaatct 1868
           ||||||||||||||||||||||||||||||||||||||||||||||||||||||||||||
V.11: 1747 cacatgctttgagaatttaacagatccctcttcacctacgatttcttcttatgagaatct 1806

V.1 : 1869 gctcagaacacctacacctccagaagtaactaaaattccagaagatattctccag      1923
           |||||||||||||||||||||||||||||||||||||||||||||||||||||||
V.11: 1807 gctcagaacacctacacctccagaagtaactaaaattccagaagatattctccag      1861
```

Score = 1456 bits (757), Expect = 0.0Identities = 757/757 (100%) Strand = Plus/Plus

```
V.1 : 2042 gaaattccagtggatctatccaacacagaaactgaacaaaatgagatgaaagccgagctg 2101
           ||||||||||||||||||||||||||||||||||||||||||||||||||||||||||||
V.11: 1861 gaaattccagtggatctatccaacacagaaactgaacaaaatgagatgaaagccgagctg 1920

V.1 : 2102 gaccgattttaacattcacattgccctgcctctctccccctttaaacgttgacccatttt 2161
           ||||||||||||||||||||||||||||||||||||||||||||||||||||||||||||
V.11: 1921 gaccgattttaacattcacattgccctgcctctctccccctttaaacgttgacccatttt 1980

V.1 : 2162 aaagacaaacatgaagattaacatcataatatgctttttatgaagtttcaataaggttta 2221
           ||||||||||||||||||||||||||||||||||||||||||||||||||||||||||||
V.11: 1981 aaagacaaacatgaagattaacatcataatatgctttttatgaagtttcaataaggttta 2040

V.1 : 2222 accttagtcttgttgacatgtagcccagtcattcactctttaaggactattagtgtttca 2281
           ||||||||||||||||||||||||||||||||||||||||||||||||||||||||||||
V.11: 2041 accttagtcttgttgacatgtagcccagtcattcactctttaaggactattagtgtttca 2100

V.1 : 2282 ttgatactaaattacccagcttaatcaacagaatggtttaagtagtaccaggaagtagga 2341
           ||||||||||||||||||||||||||||||||||||||||||||||||||||||||||||
V.11: 2101 ttgatactaaattacccagcttaatcaacagaatggtttaagtagtaccaggaagtagga 2160

V.1 : 2342 caagtaatttcaaaaatataaaggtgtttgctactcagatgaggccgcccctgaccttct 2401
           ||||||||||||||||||||||||||||||||||||||||||||||||||||||||||||
V.11: 2161 caagtaatttcaaaaatataaaggtgtttgctactcagatgaggccgcccctgaccttct 2220

V.1 : 2402 ggccagagagacattgctgccagccagctctgccttcccatcatctcctttcaggaccgt 2461
           ||||||||||||||||||||||||||||||||||||||||||||||||||||||||||||
V.11: 2221 ggccagagagacattgctgccagccagctctgccttcccatcatctcctttcaggaccgt 2280

V.1 : 2462 cccacaccttttacttgctcagtgctgtctgaagatgcagttgctgtttgcaaacaacag 2521
           ||||||||||||||||||||||||||||||||||||||||||||||||||||||||||||
V.11: 2281 cccacaccttttacttgctcagtgctgtctgaagatgcagttgctgtttgcaaacaacag 2340

V.1 : 2522 gaacaccagttaaactaattaggaaacagagggagatttccaggcctccctaactatata 2581
           ||||||||||||||||||||||||||||||||||||||||||||||||||||||||||||
V.11: 2341 gaacaccagttaaactaattaggaaacagagggagatttccaggcctccctaactatata 2400

V.1 : 2582 ctgtgaccattggcggttgagaccggtcttcaaccagtggaaccccgaactctgctgtca 2641
           ||||||||||||||||||||||||||||||||||||||||||||||||||||||||||||
V.11: 2401 ctgtgaccattggcggttgagaccggtcttcaaccagtggaaccccgaactctgctgtca 2460

V.1 : 2642 gggtgtggacttcggtgctcttccaagttttcacctgggggggggagctaacccccctatg 2701
           ||||||||||||||||||||||||||||||||||||||||||||||||||||||||||||
V.11: 2461 gggtgtggacttcggtgctcttccaagttttcacctgggggggggagctaacccccctatg 2520

V.1 : 2702 ttcacgccttctattcccattggcgctgaactcttaaggtcactctggtcgcttgtgacc 2761
           ||||||||||||||||||||||||||||||||||||||||||||||||||||||||||||
V.11: 2521 ttcacgccttctattcccattggcgctgaactcttaaggtcactctggtcgcttgtgacc 2580

V.1 : 2762 ccgtaaccctgatgtacccctctaaaaggtgaggggc                        2798
           |||||||||||||||||||||||||||||||||||||
V.11: 2581 ccgtaaccctgatgtacccctctaaaaggtgaggggc                        2617
```

TABLE LXI

| Peptide sequences of protein coded by 193P1E1B v.11 |
|---|
| (SEQ ID NO: 108) |
| MEKNSMDIMK IREYFQKYGY SPRVKKNSVH EQEATNSDPE LSNCENFQKT DVKDDLSDPP 60 |
| VASSCISGKS PRSPQLSDFG LERYIVSQVL PNPPQAVNNY KEEPVIVTPP TKQSLVKVLK 120 |
| TPKCALKMDD FECVTPKLEH FGISEYTMCL NEDYTMGLKN ARNNKSEEAI DTESRLNDNV 180 |
| FATPSPIIQQ LEKSDAEYTN SPLVPTFCTP GLKIPSTKNS IALVSTNYPL SKTNSSSNDL 240 |
| EVEDRTSLVL NSDTCFENLT DPSSPTISSY ENLLRTPTPP EVTKIPEDIL QKFQWIYPTQ 300 |
| KLNKMR 306 |

TABLE LXII

Amino acid sequence alignment of 193P1E1B v.1 (SEQ ID NO: 109) and 193P1E1B v.11 (SEQ ID NO: 110)

```
Score = 589 bits (1518), Expect = e-167Identities = 291/291 (100%),
Positives = 291/291 (100%)

v.1:   83 MEKNSMDIMKIREYFQKYGYSPRVKKNSVHEQEAINSDPELSNCENFQKTDVKDDLSDPP 142
          MEKNSMDIMKIREYFQKYGYSPRVKKNSVHEQEAINSDPELSNCENFQKTDVKDDLSDPP
v.11:   1 MEKNSMDIMKIREYFQKYGYSPRVKKNSVHEQEAINSDPELSNCENFQKTDVKDDLSDPP  60

v.1:  143 VASSCISGKSPRSPQLSDFGLERYIVSQVLPNPPQAVNNYKEEPVIVTPPTKQSLVKVLK 202
          VASSCISGKSPRSPQLSDFGLERYIVSQVLPNPPQAVNNYKEEPVIVTPPTKQSLVKVLK
v.11:  61 VASSCISGKSPRSPQLSDFGLERYIVSQVLPNPPQAVNNYKEEPVIVTPPTKQSLVKVLK 120

v.1:  203 TPKCALKMDDFECVTPKLEHFGISEYTMCLNEDYTMGLKNARNNKSEEAIDTESRLNDNV 262
          TPKCALKMDDFECVTPKLEHFGISEYTMCLNEDYTMGLKNARNNKSEEAIDTESRLNDNV
v.11: 121 TPKCALKMDDFECVTPKLEHFGTSEYTMCLNEDYTMGLKNARNNKSEEAIDTESRLNDNV 180

v.1:  263 FATPSPIIQQLEKSDAEYTNSPLVPTFCTPGLKIPSTKNSIALVSTNYPLSKTNSSSNDL 322
          FATPSPIIQQLEKSDAEYTNSPLVPTFCTPGLKTPSTKNSIALVSTNYPLSKTNSSSNDL
v.11: 181 FATPSPIIQQLEKSDAEYTNSPLVPTFCTPGLKIPSTKNSIALVSTNYPLSKTNSSSNDL 240

v.1:  323 EVEDRTSLVLNSDTCFENLTDPSSPTISSYENLLRTPTPPEVTKIPEDILQ         373
          EVEDRTSLVLNSDTCFENLTDPSSPTISSYENLLRTPTPPEVTKIPEDILQ
v.11: 241 EVEDRTSLVLNSDTCFENLTDPSSPTISSYENLLITPTPPEVTKIPEDILQ         291
```

TABLE LXIII

| Nucleotide sequence of transcript variant 193P1E1B v.12 |
|---|
| (SEQ ID NO: 111) |
| 1 tatcatctgt gactgaggaa atccctatct tcctatcaga ctaatgaaac cacaggacag |
| 61 caattagact tttaagtatt ggggggttta gagctctaga tattcgatat gcagactact |
| 121 catgtttgtt tgttttaata aagactggtc caaaggctca ttttcacaca agctacagtt |
| 181 tttcagttcc aggaccaggt aaagatggtc agctccgtga tccataaaat ccaagggtga |
| 241 cgactcagga ttaggaccat ttcttggtga cattgagatg gtcgagctgg tccgcaatga |
| 301 atctatgcgg ggggaacttg gaagtggcgg ccgcctttat ggcctcgaag gcctccctcc |
| 361 tgcgcaccgc ggcgtggccg cgctcctgct cccgggtcat gtagggcatg ctcagccagt |
| 421 aatggttctc cgcctcgatc tccaggcggc ggatcatgtt ctgcttggcg cgcaacgaca |
| 481 cgaaccgcgg ccgccggtgc ttcccgatcc actgacggcc gggaatgcgg ccgcgccaga |
| 541 ggagcgcagt caggaacatg gtgcctgccg cgctgctcaa gactctgcgt ctccgcggcc |
| 601 gccagcagac gccgtggcgt aagcgcaccc gtctcgcggg gtctccgggg gcctcggcga |
| 661 gagacttcgg ctctcgcgag agaggactgc gcctgcgcag agccgaggac gcgtccggcg |
| 721 ccgagattca aactagtggc gggaggctgt gagctgagcg gtggggtctg cgtacgcctg |

TABLE LXIII-continued

| Nucleotide sequence of transcript variant 193P1E1B v.12 |
|---|
| 781 gagtccttcc ccgctgtgct cagcatggac cctatccgga gcttctgcgg gaagctgcgg |
| 841 tctctggcca gcacgctgga ctgcgagacg gcccggctgc agcgagcgct ggacggagag |
| 901 gaaagccttt tatcaaaata caactcaaac ctagctactc caatagcaat taaagcagtg |
| 961 ccacccagta aaaggttcct taaacatgga cagaacatcc gagatgtcag caacaaagaa |
| 1021 aactgaaatt ccagtggatc tatccaacac agaaactgaa caaaatgaga tgaaagccga |
| 1081 gctggaccga ttttaacatt cacattgccc tgcctctgtc cccctttaaa cgttgaccca |
| 1141 ttttaaagac aaacatgaac attaacatca taatatgctt tttatgaagt ttcaataagg |
| 1201 tttaacctta gtcttgttga catgtagccc agtcattcac tctttaagga ctattagtgt |
| 1261 ttcattgata ctaaattacc cagcttaatc aacagaatgg tttaagtagt accaggaagt |
| 1321 aggacaagta atttcaaaaa tataaaggtg tttgctactc agatgaggcc gcccctgacc |
| 1381 ttctggccag agagacattg ctgccagcca gctctgcctt cccatcatct cctttcagga |
| 1441 ccgtcccaca ccttttactt gctcagtgct gtctgaagat gcagttgctg tttgcaaaca |
| 1501 acaggaacac cagttaaact aattaggaaa cagagggaga tttccaggcc tgggtaacta |
| 1561 tatactgtga ccattggcgg ttgagaccgg tcttcaacca gtggaacccc gaactctgct |
| 1621 gtcagggtgt ggacttcggt gctcttccaa gttttcacct gggggggga gctaaccccc |
| 1681 tatgttcacg ccttctattc ccattggcgc tgaactctta aggtcactct ggtcgcttgt |
| 1741 gaccccgtaa ccctgatgta cccctctaaa aggtgagggg c |

TABLE LXIV

Nucleotide sequence alignment of 193P1E1B v.1 (SEQ ID NO: 112) and 193P1E1B v.12 (SEQ ID NO: 113)

Score = 1742 bits (906), Expect = 0.0Identities = 906/906 (100%) Strand = Plus/Plus

```
V. 1:    1 tatcatctgtgactgaggaaatccctatcttcctatcagactaatgaaaccacaggacag   60
           ||||||||||||||||||||||||||||||||||||||||||||||||||||||||||||
V.12:    1 tatcatctgtgactgaggaaatccctatcttcctatcagactaatgaaaccacaggacag   60
V. 1:   61 caattagacttttaagtattgggggtttagagctctagatattcgatatgcagactact  120
           ||||||||||||||||||||||||||||||||||||||||||||||||||||||||||||
V.12:   61 caattagacttttaagtattgggggtttagagctctagatattcgatatgcagactact  120
V. 1:  121 catgtttgtttgttttaataaagactggtccaaaggctcattttcacacaagctacagtt  180
           ||||||||||||||||||||||||||||||||||||||||||||||||||||||||||||
V.12:  121 catgtttgtttgttttaataaagactggtccaaaggctcattttcacacaagctacagtt  180
V. 1:  181 tttcagttccaggaccaggtaaagatggtcagctccgtgatccataaaatccaagggtga  240
           ||||||||||||||||||||||||||||||||||||||||||||||||||||||||||||
V.12:  181 tttcagttccaggaccaggtaaagatggtcagctccgtgatccataaaatccaagggtga  240

V. 1:  241 cgactcaggattaggaccatttcttggtgacattgagatggtcgagctggtccgcaatga  300
           ||||||||||||||||||||||||||||||||||||||||||||||||||||||||||||
V.12:  241 cgactcaggattaggaccatttcttggtgacattgagatggtcgagctggtccgcaatga  300
V. 1:  301 atctatgcgggggaacttggaagtggcggccgcctttatggcctcgaaggcctccctcc  360
           ||||||||||||||||||||||||||||||||||||||||||||||||||||||||||||
V.12:  301 atctatgcgggggaacttggaagtggcggccgcctttatggcctcgaaggcctccctcc  360
V. 1:  361 tgcgcaccgcggcgtggccgcgctcctgctcccgggtcatgtagggcatgctcagccagt  420
           ||||||||||||||||||||||||||||||||||||||||||||||||||||||||||||
V.12:  361 tgcgcaccgcggcgtggccgcgctcctgctcccgggtcatgtagggcatgctcagccagt  420
V. 1:  421 aatggttctccgcctcgatctccaggcggcggatcatgttctgcttggcgcgcaacgaca  480
           ||||||||||||||||||||||||||||||||||||||||||||||||||||||||||||
V.12:  421 aatggttctccgcctcgatctccaggcggcggatcatgttctgcttggcgcgcaacgaca  480
```

TABLE LXIV-continued

Nucleotide sequence alignment of 193P1E1B v.1 (SEQ ID NO: 112) and 193P1E1B v.12 (SEQ ID NO: 113)

```
V. 1:  481 cgaaccgcggccgccggtgcttcccgatccactgacggccgggaatgcggccgcgccaga  540
           ||||||||||||||||||||||||||||||||||||||||||||||||||||||||||||
V.12:  481 cgaaccgcggccgccggtgcttcccgatccactgacggccgggaatgcggccgcgccaga  540

V. 1:  541 ggagcgcagtcaggaacatggtgcctgccgcgctgctcaagactctgcgtctccgcggcc  600
           ||||||||||||||||||||||||||||||||||||||||||||||||||||||||||||
V.12:  541 ggagcgcagtcaggaacatggtgcctgccgcgctgctcaagactctgcgtctccgcggcc  600

V. 1:  601 gccagcagacgccgtggcgtaagcgcacccgtctcgcggggtctccgggggcctcggcga  660
           ||||||||||||||||||||||||||||||||||||||||||||||||||||||||||||
V.12:  601 gccagcagacgccgtggcgtaagcgcacccgtctcgcggggtctccgggggcctcggcga  660

V. 1:  661 gagacttcggctctcgcgagagaggactgcgcctgcgcagagccgaggacgcgtccggcg  720
           ||||||||||||||||||||||||||||||||||||||||||||||||||||||||||||
V.12:  661 gagacttcggctctcgcgagagaggactgcgcctgcgcagagccgaggacgcgtccggcg  720

V. 1:  721 ccgagattcaaactagtggcgggaggctgtgagctgagcggtggggtctgcgtacgcctg  780
           ||||||||||||||||||||||||||||||||||||||||||||||||||||||||||||
V.12:  721 ccgagattcaaactagtggcgggaggctgtgagctgagcggtggggtctgcgtacgcctg  780

V. 1:  781 gagtccttccccgctgtgctcagcatggaccctatccggagcttctgcgggaagctgcgg  840
           ||||||||||||||||||||||||||||||||||||||||||||||||||||||||||||
V.12:  781 gagtccttccccgctgtgctcagcatggaccctatccggagcttctgcgggaagctgcgg  840

V. 1:  841 tctctggccagcacgctggactgcgagacggcccggctgcagcgagcgctggacggagag  900
           ||||||||||||||||||||||||||||||||||||||||||||||||||||||||||||
V.12:  841 tctctggccagcacgctggactgcgagacggcccggctgcagcgagcgctggacggagag  900

V. 1:  901 gaaagc                                                        906
           ||||||
V.12:  901 gaaagc                                                        906
```

Score = 1683 bits (875), Expect = 0.0Identities = 875/875 (100%) Strand = Plus/Plus

```
V. 1: 1924 cttttatcaaaatacaactcaaacctagctactccaatagcaattaaagcagtgccaccc 1983
           ||||||||||||||||||||||||||||||||||||||||||||||||||||||||||||
V.12:  907 cttttatcaaaatacaactcaaacctagctactccaatagcaattaaagcagtgccaccc  966

V. 1: 1984 agtaaaaggttccttaaacatggacagaacatccgagatgtcagcaacaaagaaaactga 2043
           ||||||||||||||||||||||||||||||||||||||||||||||||||||||||||||
V.12:  967 agtaaaaggttccttaaacatggacagaacatccgagatgtcagcaacaaagaaaactga 1026

V. 1: 2044 aattccagtggatctatccaacacagaaactgaacaaaatgagatgaaagccgagctgga 2103
           ||||||||||||||||||||||||||||||||||||||||||||||||||||||||||||
V.12: 1027 aattccagtggatctatccaacacagaaactgaacaaaatgagatgaaagccgagctgga 1086

V. 1: 2104 ccgattttaacattcacattgccctgcctctgtccccctttaaacgttgacccattttaa 2163
           ||||||||||||||||||||||||||||||||||||||||||||||||||||||||||||
V.12: 1087 ccgattttaacattcacattgccctgcctctgtccccctttaaacgttgacccattttaa 1146

V. 1: 2164 agacaaacatgaacattaacatcataatatgcttttatgaagtttcaataaggtttaac 2223
           ||||||||||||||||||||||||||||||||||||||||||||||||||||||||||||
V.12: 1147 agacaaacatgaacattaacatcataatatgcttttatgaagtttcaataaggtttaac 1206

V. 1: 2224 cttagtcttgttgacatgtagcccagtcattcactctttaaggactattagtgtttcatt 2283
           ||||||||||||||||||||||||||||||||||||||||||||||||||||||||||||
V.12: 1207 cttagtcttgttgacatgtagcccagtcattcactctttaaggactattagtgtttcatt 1266

V. 1: 2284 gatactaaattacccagcttaatcaacagaatggtttaagtagtaccaggaagtaggaca 2343
           ||||||||||||||||||||||||||||||||||||||||||||||||||||||||||||
V.12: 1267 gatactaaattacccagcttaatcaacagaatggtttaagtagtaccaggaagtaggaca 1326

V. 1: 2344 agtaatttcaaaaatataaaggtgtttgctactcagatgaggccgcccctgaccttctgg 2403
           ||||||||||||||||||||||||||||||||||||||||||||||||||||||||||||
V.12: 1327 agtaatttcaaaaatataaaggtgtttgctactcagatgaggccgcccctgaccttctgg 1386

V. 1: 2404 ccagagagacattgctgccagccagctctgccttcccatcatctcctttcaggaccgtcc 2463
           ||||||||||||||||||||||||||||||||||||||||||||||||||||||||||||
V.12: 1387 ccagagagacattgctgccagccagctctgccttcccatcatctcctttcaggaccgtcc 1446

V. 1: 2464 cacaccttttacttgctcagtgctgtctgaagatgcagttgctgtttgcaaacaacagga 2523
           ||||||||||||||||||||||||||||||||||||||||||||||||||||||||||||
V.12: 1447 cacaccttttacttgctcagtgctgtctgaagatgcagttgctgtttgcaaacaacagga 1506

V. 1: 2524 acaccagttaaactaattaggaaacagagggagatttccaggcctgggtaactatatact 2583
           ||||||||||||||||||||||||||||||||||||||||||||||||||||||||||||
V.12: 1507 acaccagttaaactaattaggaaacagagggagatttccaggcctgggtaactatatact 1566

V. 1: 2584 gtgaccattggcggttgagaccggtcttcaaccagtggaaccccgaactctgctgtcagg 2643
           ||||||||||||||||||||||||||||||||||||||||||||||||||||||||||||
V.12: 1567 gtgaccattggcggttgagaccggtcttcaaccagtggaaccccgaactctgctgtcagg 1626
```

TABLE LXIV-continued

Nucleotide sequence alignment of 193P1E1B v.1 (SEQ ID NO: 112) and 193P1E1B v.12 (SEQ ID NO: 113)

```
V. 1: 2644 gtgtggacttcggtgctcttccaagttttcacctgggggggggagctaaccccctatgtt 2703
           ||||||||||||||||||||||||||||||||||||||||||||||||||||||||||||
V.12: 1627 gtgtggacttcggtgctcttccaagttttcacctgggggggggagctaaccccctatgtt 1686
V. 1: 2704 cacgccttctattcccattggcgctgaactcttaaggtcactctggtcgcttgtgacccc 2763
           ||||||||||||||||||||||||||||||||||||||||||||||||||||||||||||
V.12: 1687 cacgccttctattcccattggcgctgaactcttaaggtcactctggtcgcttgtgacccc 1746
V. 1: 2764 gtaaccctgatgtacccctctaaaaggtgaggggc                          2798
           |||||||||||||||||||||||||||||||||||
V.12: 1747 gtaaccctgatgtacccctctaaaaggtgaggggc                          1781
```

TABLE LXV

Peptide sequences of protein coded by 193P1E1B v.12

```
                                                      (SEQ ID NO: 114)
MDPIRSFCGK LRSLASTLDC ETARLQRALD GEESLLSKYN SNLATPIAIK AVPPSKRFLK 60

HGQNIRDVSN
KEN                                                              73
```

TABLE LXVI

Amino acid sequence alignment of 193P1E1B v.1 (SEQ ID NO: 115) and 193P1E1B v.12 (SEQ ID NO: 116)

```
Score = 72.0 bits (175), Expect = 2e-12Identities = 35/39
(89%), Positives = 35/39 (89%)

v.1:        1      MDPIRSFCGKLRSLASTLDCETARLQRALDGEESDFEDY 39
                   MDPIRSECGKLRSLASTLDCETARLQRALDGEES    Y
v.12:       1      MDPIRSFCGKLRSLASTLDCETARLQRALDGEESLLSKY 39

Score = 80.9 bits (198), Expect = 4e-15Identities = 39/39
(100%), Positives = 39/39 (100%)

v.1:      374      LLSKYNSNLATPIAIKAVPPSKRFLKHGQNIRDVSNKEN 412
                   LLSKYNSNLATPIAIKAVPPSKRFLKHGQNIRDVSNKEN
v.12:      35      LLSKYNSNLATPIAIKAVPPSKRFLKHGQNIRDVSNKEN  73
```

TABLE LXVII

Nucleotide sequence of transcript variant 193P1E1B v.13

```
                                                          (SEQ ID NO: 117)
  1 tatcatctgt gactgaggaa atccctatct tcctatcaga ctaatgaaac cacaggacag

 61 caattagact tttaagtatt ggggggttta gagctctaga tattcgatat gcagactact

121 catgtttgtt tgttttaata aagactggtc caaaggctca ttttcacaca agctacagtt

181 tttcagttcc aggaccaggt aaagatggtc agctccgtga tccataaaat ccaagggtga

241 cgactcagga ttaggaccat ttcttggtga cattgagatg gtcgagctgg tccgcaatga

301 atctatgcgg ggggaacttg gaagtggcgg ccgcctttat ggcctcgaag gcctccctcc

361 tgcgcaccgc ggcgtggccg cgctcctgct cccgggtcat gtagggcatg ctcagccagt

421 aatggttctc cgcctcgatc tccaggcggc ggatcatgtt ctgcttggcg cgcaacgaca

481 cgaaccgcgg ccgccggtgc ttcccgatcc actgacggcc gggaatgcgg ccgcgccaga

541 ggagcgcagt caggaacatg gtgcctgccg cgctgctcaa gactctgcgt ctccgcggcc

601 gccagcagac gccgtggcgt aagcgcaccc gtctcgcggg gtctccgggg gcctcggcga

661 gagacttcgg ctctcgcgag agaggactgc gcctgcgcag agccgaggac gcgtccggcg
```

TABLE LXVII-continued

| Nucleotide sequence of transcript variant 193P1E1B v.13 |
| --- |
| 721 ccgagattca aactagtggc gggaggctgt gagctgagcg gtggggtctg cgtacgcctg |
| 781 gagtccttcc ccgctgtgct cagcatggac cctatccgga gcttctgcgg gaagctgcgg |
| 841 tctctggcca gcacgctgga ctgcgagacg gcccggctgc agcgagcgct ggacggagag |
| 901 gaaagcggtg cgtgaggcgg gcggccaggg cacgactttg aagattatcc aatgagaatt |
| 961 ttatatgacc ttcattcaga agttcagact ctaaaggatg atgttaatat tcttcttgat |
| 1021 aaagcaagat tggaaaatca agaaggcatt gatttcataa aggcaacaaa agtactaatg |
| 1081 gaaaaaaatt caatggatat tatgaaaata agagagtatt tccagaagta tggatatagt |
| 1141 ccacgtgtca agaaaaattc agtacacgag caagaagcca ttaactctga cccagagttg |
| 1201 tctaattgtg aaaattttca gaagactgat gtgaaagatg atctgtctga tcctcctgtt |
| 1261 gcaagcagtt gtatttctgg gaagtctcca cgtagtccac aactttcaga ttttggactt |
| 1321 gagcggtaca tcgtatccca agttctacca aaccctccac aggcagtgaa caactataag |
| 1381 gaagagcccg taattgtaac cccacctacc aaacaatcac tagtaaaagt actaaaaact |
| 1441 ccaaaatgtg cactaaaaat ggatgatttt gagtgtgtaa ctcctaaatt agaacacttt |
| 1501 ggtatctctg aatatactat gtgtttaaat gaagattaca caatgggact taaaaatgcg |
| 1561 aggaataata aaagtgagga ggccatagat acagaatcca ggctcaatga taatgttttt |
| 1621 gccactccca gccccatcat ccagcagttg gaaaaaagtg atgccgaata taccaactct |
| 1681 cctttggtac ctacattctg tactcctggt ttgaaaattc catctacaaa gaacagcata |
| 1741 gctttggtat ccacaaatta cccattatca aaaacaaata gttcatcaaa tgatttggaa |
| 1801 gttgaagatc gtacttcgtt ggttttaaat tcagacacat gctttgagaa tttaacagat |
| 1861 ccctcttcac ctacgatttc ttcttatgag aatctgctca gaacacctac acctccagaa |
| 1921 gtaactaaaa ttccagaaga tattctccag cttttatcaa aatacaactc aaacctagct |
| 1981 actccaatag caattaaagc agtgccaccc agtaaaaggt tccttaaaca tggacagaac |
| 2041 atccgagatg tcagcaacaa agaaaactga aattccagtg gatctatcca acacagaaac |
| 2101 tgaacaaaat gagatgaaag ccgagctgga ccgattttaa cattcacatt gccctgcctc |
| 2161 tgtcccccttt taaacgttga cccattttaa agacaaacat gaacattaac atcataatat |
| 2221 gctttttatg aagtttcaat aaggtttaac cttagtcttg ttgacatgta gcccagtcat |
| 2281 tcactcttta aggactatta gtgtttcatt gatactaaat tacccagctt aatcaacaga |
| 2341 atggtttaag tagtaccagg aagtaggaca agtaatttca aaaatataaa ggtgtttgct |
| 2401 actcagatga ggccgcccct gaccttctgg ccagagagac attgctgcca gccagctctg |
| 2461 ccttcccatc atctcctttc aggaccgtcc cacacctttt acttgctcag tgctgtctga |
| 2521 agatgcagtt gctgtttgca aacaacagga acaccagtta aactaattag gaaacagagg |
| 2581 gagatttcca ggcctgggta actatatact gtgaccattg gcggttgaga ccggtcttca |
| 2641 accagtggaa ccccgaactc tgctgtcagg gtgtggactt cggtgctctt ccaagttttc |
| 2701 acctgggggg gggagctaac cccctatgtt cacgccttct attcccattg gcgctgaact |
| 2761 cttaaggtca ctctggtcgc ttgtgacccc gtaaccctga tgtacccctc taaaaggtga |
| 2821 ggggc |

TABLE LXVIII

Nucleotide sequence alignment of 193P1E1B v.1 (SEQ ID NO: 118) and 193P1E1B v.13 (SEQ ID NO: 119)

Score 1744 bits (907), Expect = 0.0Identities = 907/907 (100%) Strand = Plus/Plus

```
V. 1:    1 tatcatctgtgactgaggaaatccctatcttcctatcagactaatgaaaccacaggacag   60
           ||||||||||||||||||||||||||||||||||||||||||||||||||||||||||||
V.13:    1 tatcatctgtgactgaggaaatccctatcttcctatcagactaatgaaaccacaggacag   60
V. 1:   61 caattagacttttaagtattggggggtttagagctctagatattcgatatgcagactact  120
           ||||||||||||||||||||||||||||||||||||||||||||||||||||||||||||
V.13:   61 caattagacttttaagtattggggggtttagagctctagatattcgatatgcagactact  120
V. 1:  121 catgtttgtttgttttaataaagactggtccaaaggctcattttcacacaagctacagtt  180
           ||||||||||||||||||||||||||||||||||||||||||||||||||||||||||||
V.13:  121 catgtttgtttgttttaataaagactggtccaaaggctcattttcacacaagctacagtt  180
V. 1:  181 tttcagttccaggaccaggtaaagatggtcagctccgtgatccataaaatccaagggtga  240
           ||||||||||||||||||||||||||||||||||||||||||||||||||||||||||||
V.13:  181 tttcagttccaggaccaggtaaagatggtcagctccgtgatccataaaatccaagggtga  240

V. 1:  241 cgactcaggattaggaccatttcttggtgacattgagatggtcgagctggtccgcaatga  300
           ||||||||||||||||||||||||||||||||||||||||||||||||||||||||||||
V.13:  241 cgactcaggattaggaccatttcttggtgacattgagatggtcgagctggtccgcaatga  300
V. 1:  301 atctatgcgggggaacttggaagtggcggccgcctttatggcctcgaaggcctccctcc  360
           ||||||||||||||||||||||||||||||||||||||||||||||||||||||||||||
V.13:  301 atctatgcgggggaacttggaagtggcggccgcctttatggcctcgaaggcctccctcc  360
V. 1:  361 tgcgcaccgcggcgtggccgcgctcctgctcccgggtcatgtagggcatgctcagccagt  420
           ||||||||||||||||||||||||||||||||||||||||||||||||||||||||||||
V.13:  361 tgcgcaccgcggcgtggccgcgctcctgctcccgggtcatgtagggcatgctcagccagt  420
V. 1:  421 aatggttctccgcctcgatctccaggcggcggatcatgttctgcttggcgcgcaacgaca  480
           ||||||||||||||||||||||||||||||||||||||||||||||||||||||||||||
V.13:  421 aatggttctccgcctcgatctccaggcggcggatcatgttctgcttggcgcgcaacgaca  480

V. 1:  481 cgaaccgcggccgccggtgcttcccgatccactgacggccgggaatgcggccgcgccaga  540
           ||||||||||||||||||||||||||||||||||||||||||||||||||||||||||||
V.13:  481 cgaaccgcggccgccggtgcttcccgatccactgacggccgggaatgcggccgcgccaga  540
V. 1:  541 ggagcgcagtcaggaacatggtgcctgccgcgctgctcaagactctgcgtctccgcggcc  600
           ||||||||||||||||||||||||||||||||||||||||||||||||||||||||||||
V.13:  541 ggagcgcagtcaggaacatggtgcctgccgcgctgctcaagactctgcgtctccgcggcc  600
V. 1:  601 gccagcagacgccgtggcgtaagcgcacccgtctcgcggggtctccgggggcctcggcga  660
           ||||||||||||||||||||||||||||||||||||||||||||||||||||||||||||
V.13:  601 gccagcagacgccgtggcgtaagcgcacccgtctcgcggggtctccgggggcctcggcga  660
V. 1:  661 gagacttcggctctcgcgagagaggactgcgcctgcgcagagccgaggacgcgtccggcg  720
           ||||||||||||||||||||||||||||||||||||||||||||||||||||||||||||
V.13:  661 gagacttcggctctcgcgagagaggactgcgcctgcgcagagccgaggacgcgtccggcg  720

V. 1:  721 ccgagattcaaactagtggcgggaggctgtgagctgagcggtggggtctgcgtacgcctg  780
           ||||||||||||||||||||||||||||||||||||||||||||||||||||||||||||
V.13:  721 ccgagattcaaactagtggcgggaggctgtgagctgagcggtggggtctgcgtacgcctg  780
V. 1:  781 gagtccttccccgctgtgctcagcatggaccctatccggagcttctgcgggaagctgcgg  840
           ||||||||||||||||||||||||||||||||||||||||||||||||||||||||||||
V.13:  781 gagtccttccccgctgtgctcagcatggaccctatccggagcttctgcgggaagctgcgg  840
V. 1:  841 tctctggccagcacgctggactgcgagacggcccggctgcagcgagcgctggacggagag  900
           ||||||||||||||||||||||||||||||||||||||||||||||||||||||||||||
V.13:  841 tctctggccagcacgctggactgcgagacggcccggctgcagcgagcgctggacggagag  900
V. 1:  901 gaaagcg                                                       907
           |||||||
V.13:  901 gaaagcg                                                       907
```

Score = 3640 bits (1893), Expect = 0.0Identities = 1893/1893 (100%) Strand = Plus/Plus

```
V. 1:  906 cagctttgaagattatccaatgagaattttatatgaccttcattcagaagttcagactct  965
           ||||||||||||||||||||||||||||||||||||||||||||||||||||||||||||
V.13:  933 cagctttgaagattatccaatgagaattttatatgaccttcattcagaagttcagactct  992
V. 1:  966 aaaggatgatgttaatattcttcttgataaagcaagattggaaaatcaagaaggcattga 1025
           ||||||||||||||||||||||||||||||||||||||||||||||||||||||||||||
V.13:  993 aaaggatgatgttaatattcttcttgataaagcaagattggaaaatcaagaaggcattga 1052
V. 1: 1026 tttcataaaggcaacaaaagtactaatggaaaaaaattcaatggatattatgaaaataag 1085
           ||||||||||||||||||||||||||||||||||||||||||||||||||||||||||||
V.13: 1053 tttcataaaggcaacaaaagtactaatggaaaaaaattcaatggatattatgaaaataag 1112
V. 1: 1086 agagtatttccagaagtatggatatagtccacgtgtcaagaaaaattcagtacacgagca 1145
           ||||||||||||||||||||||||||||||||||||||||||||||||||||||||||||
V.13: 1113 agagtatttccagaagtatggatatagtccacgtgtcaagaaaaattcagtacacgagca 1172
```

TABLE LXVIII-continued

Nucleotide sequence alignment of 193P1E1B v.1 (SEQ ID NO: 118) and 193P1E1B v.13 (SEQ ID NO: 119)

```
V. 1: 1146 agaagccattaactctgacccagagttgtctaattgtgaaaattttcagaagactgatgt 1205
           ||||||||||||||||||||||||||||||||||||||||||||||||||||||||||||
V.13: 1173 agaagccattaactctgacccagagttgtctaattgtgaaaattttcagaagactgatgt 1232

V. 1: 1206 gaaagatgatctgtctgatcctcctgttgcaagcagttgtatttctgggaagtctccacg 1265
           ||||||||||||||||||||||||||||||||||||||||||||||||||||||||||||
V.13: 1233 gaaagatgatctgtctgatcctcctgttgcaagcagttgtatttctgggaagtctccacg 1292

V. 1: 1266 tagtccacaactttcagattttggacttgagcggtacatcgtatcccaagttctaccaaa 1325
           ||||||||||||||||||||||||||||||||||||||||||||||||||||||||||||
V.13: 1293 tagtccacaactttcagattttggacttgagcggtacatcgtatcccaagttctaccaaa 1352

V. 1: 1326 ccctccacaggcagtgaacaactataaggaagagcccgtaattgtaaccccacctaccaa 1385
           ||||||||||||||||||||||||||||||||||||||||||||||||||||||||||||
V 13: 1353 ccctccacaggcagtgaacaactataaggaagagcccgtaattgtaaccccacctaccaa 1412


V. 1: 1386 acaatcactagtaaaagtactaaaaactccaaaatgtgcactaaaaatggatgattttga 1445
           ||||||||||||||||||||||||||||||||||||||||||||||||||||||||||||
V 13: 1413 acaatcactagtaaaagtactaaaaactccaaaatgtgcactaaaaatggatgattttga 1472

V. 1: 1446 gtgtgtaactcctaaattagaacactttggtatctctgaatatactatgtgtttaaatga 1505
           ||||||||||||||||||||||||||||||||||||||||||||||||||||||||||||
V 13: 1473 gtgtgtaactcctaaattagaacactttggtatctctgaatatactatgtgtttaaatga 1532

V. 1: 1506 agattacacaatgggacttaaaaatgcgaggaataataaaagtgaggaggccatagatac 1565
           ||||||||||||||||||||||||||||||||||||||||||||||||||||||||||||
V.13: 1533 agattacacaatgggacttaaaaatgcgaggaataataaaagtgaggaggccatagatac 1592

V. 1: 1566 agaatccaggctcaatgataatgtttttgccactcccagccccatcatccagcagttgga 1625
           ||||||||||||||||||||||||||||||||||||||||||||||||||||||||||||
V.13: 1593 agaatccaggctcaatgataatgtttttgccactcccagccccatcatccagcagttgga 1652


V. 1: 1626 aaaaagtgatgccgaatataccaactctcctttggtacctacattctgtactcctggttt 1685
           ||||||||||||||||||||||||||||||||||||||||||||||||||||||||||||
V.13: 1653 aaaaagtgatgccgaatataccaactctcctttggtacctacattctgtactcctggttt 1712

V. 1: 1686 gaaaattccatctacaaagaacagcatagctttggtatccacaaattacccattatcaaa 1745
           ||||||||||||||||||||||||||||||||||||||||||||||||||||||||||||
V.13: 1713 gaaaattccatctacaaagaacagcatagctttggtatccacaaattacccattatcaaa 1772

V. 1: 1746 aacaaatagttcatcaaatgatttggaagttgaagatcgtacttcgttggttttaaattc 1805
           ||||||||||||||||||||||||||||||||||||||||||||||||||||||||||||
V.13: 1773 aacaaatagttcatcaaatgatttggaagttgaagatcgtacttcgttggttttaaattc 1832

V. 1: 1806 agacacatgctttgagaatttaacagatccctcttcacctacgatttcttcttatgagaa 1865
           ||||||||||||||||||||||||||||||||||||||||||||||||||||||||||||
V.13: 1833 agacacatgctttgagaatttaacagatccctcttcacctacgatttcttcttatgagaa 1892


V. 1: 1866 tctgctcagaacacctacacctccagaagtaactaaaattccagaagatattctccagct 1925
           ||||||||||||||||||||||||||||||||||||||||||||||||||||||||||||
V.13: 1893 tctgctcagaacacctacacctccagaagtaactaaaattccagaagatattctccagct 1952

V. 1: 1926 tttatcaaaatacaactcaaacctagctactccaatagcaattaaagcagtgccacccag 1985
           ||||||||||||||||||||||||||||||||||||||||||||||||||||||||||||
V.13: 1953 tttatcaaaatacaactcaaacctagctactccaatagcaattaaagcagtgccacccag 2012

V. 1: 1986 taaaaggttccttaaacatggacagaacatccgagatgtcagcaacaaagaaaactgaaa 2045
           ||||||||||||||||||||||||||||||||||||||||||||||||||||||||||||
V.13: 2013 taaaaggttccttaaacatggacagaacatccgagatgtcagcaacaaagaaaactgaaa 2072

V. 1: 2046 ttccagtggatctatccaacacagaaactgaacaaaatgagatgaaagccgagctggacc 2105
           ||||||||||||||||||||||||||||||||||||||||||||||||||||||||||||
V.13: 2073 ttccagtggatctatccaacacagaaactgaacaaaatgagatgaaagccgagctggacc 2132


V. 1: 2106 gattttaacattcacattgccctgcctctgtccccctttaaacgttgacccattttaaag 2165
           ||||||||||||||||||||||||||||||||||||||||||||||||||||||||||||
V.13: 2133 gattttaacattcacattgccctgcctctgtccccctttaaacgttgacccattttaaag 2192

V. 1: 2166 acaaacatgaacattaacatcataatatgctttttatgaagtttcaataaggtttaacct 2225
           ||||||||||||||||||||||||||||||||||||||||||||||||||||||||||||
V.13: 2193 acaaacatgaacattaacatcataatatgctttttatgaagtttcaataaggtttaacct 2252

V. 1: 2226 tagtcttgttgacatgtagcccagtcattcactctttaaggactattagtgtttcattga 2285
           ||||||||||||||||||||||||||||||||||||||||||||||||||||||||||||
V.13: 2253 tagtcttgttgacatgtagcccagtcattcactctttaaggactattagtgtttcattga 2312

V. 1: 2286 tactaaattacccagcttaatcaacagaatggtttaagtagtaccaggaagtaggacaag 2345
           ||||||||||||||||||||||||||||||||||||||||||||||||||||||||||||
V.13: 2313 tactaaattacccagcttaatcaacagaatggtttaagtagtaccaggaagtaggacaag 2372
```

TABLE LXVIII-continued

Nucleotide sequence alignment of 193P1E1B v.1 (SEQ ID NO: 118) and 193P1E1B v.13 (SEQ ID NO: 119)

```
V. 1: 2346 taatttcaaaaatataaaggtgtttgctactcagatgaggccgcccctgaccttctggcc 2405
           ||||||||||||||||||||||||||||||||||||||||||||||||||||||||||||
V.13: 2373 taatttcaaaaatataaaggtgtttgctactcagatgaggccgcccctgaccttctggcc 2432
V. 1: 2406 agagagacattgctgccagccagctctgccttcccatcatctcctttcaggaccgtccca 2465
           ||||||||||||||||||||||||||||||||||||||||||||||||||||||||||||
V.13: 2433 agagagacattgctgccagccagctctgccttcccatcatctcctttcaggaccgtccca 2492
V. 1: 2466 caccttttacttgctcagtgctgtctgaagatgcagttgctgtttgcaaacaacaggaac 2525
           ||||||||||||||||||||||||||||||||||||||||||||||||||||||||||||
V.13: 2493 caccttttacttgctcagtgctgtctgaagatgcagttgctgtttgcaaacaacaggaac 2552
V. 1: 2526 accagttaaactaattaggaaacagagggagatttccaggcctgggtaactatatactgt 2585
           ||||||||||||||||||||||||||||||||||||||||||||||||||||||||||||
V.13: 2553 accagttaaactaattaggaaacagagggagatttccaggcctgggtaactatatactgt 2612


V. 1: 2586 gaccattggcggttgagaccggtcttcaaccagtggaaccccgaactctgctgtcagggt 2645
           ||||||||||||||||||||||||||||||||||||||||||||||||||||||||||||
V 13: 2613 gaccattggcggttgagaccggtcttcaaccagtggaaccccgaactctgctgtcagggt 2672
V. 1: 2646 gtggacttcggtgctcttccaagttttcacctgggggggggagctaacccccctatgttca 2705
           ||||||||||||||||||||||||||||||||||||||||||||||||||||||||||||
V 13: 2673 gtggacttcggtgctcttccaagttttcacctgggggggggagctaacccccctatgttca 2732
V. 1: 2706 cgccttctattcccattggcgctgaactcttaaggtcactctggtcgcttgtgaccccgt 2765
           ||||||||||||||||||||||||||||||||||||||||||||||||||||||||||||
V 13: 2733 cgccttctattcccattggcgctgaactcttaaggtcactctggtcgcttgtgaccccgt 2792
V. 1: 2766 aaccctgatgtacccctctaaaaggtgaggggc                            2798
           |||||||||||||||||||||||||||||||||
V 13: 2793 aaccctgatgtacccctctaaaaggtgaggggc                            2825
```

Score = 1744 bits (907), Expect = 0.0Identities = 907/907 (100%) Strand = Plus/Plus

```
V. 1:    1 tatcatctgtgactgaggaaatccctatcttcctatcagactaatgaaaccacaggacag   60
           ||||||||||||||||||||||||||||||||||||||||||||||||||||||||||||
V.13:    1 tatcatctgtgactgaggaaatccctatcttcctatcagactaatgaaaccacaggacag   60
V. 1:   61 caattagacttttaagtattgggggtttagagctctagatattcgatatgcagactact  120
           ||||||||||||||||||||||||||||||||||||||||||||||||||||||||||||
V.13:   61 caattagacttttaagtattgggggtttagagctctagatattcgatatgcagactact  120
V. 1:  121 catgtttgtttgttttaataaagactggtccaaaggctcattttcacacaagctacagtt  180
           ||||||||||||||||||||||||||||||||||||||||||||||||||||||||||||
V.13:  121 catgtttgtttgttttaataaagactggtccaaaggctcattttcacacaagctacagtt  180
V. 1:  181 tttcagttccaggaccaggtaaagatggtcagctccgtgatccataaaatccaagggtga  240
           ||||||||||||||||||||||||||||||||||||||||||||||||||||||||||||
V.13:  181 tttcagttccaggaccaggtaaagatggtcagctccgtgatccataaaatccaagggtga  240


V. 1:  241 cgactcaggattaggaccatttcttggtgacattgagatggtcgagctggtccgcaatga  300
           ||||||||||||||||||||||||||||||||||||||||||||||||||||||||||||
V.13:  241 cgactcaggattaggaccatttcttggtgacattgagatggtcgagctggtccgcaatga  300
V. 1:  301 atctatgcgggggaacttggaagtggcggccgcctttatggcctcgaaggcctccctcc  360
           ||||||||||||||||||||||||||||||||||||||||||||||||||||||||||||
V.13:  301 atctatgcgggggaacttggaagtggcggccgcctttatggcctcgaaggcctccctcc  360
V. 1:  361 tgcgcaccgcggcgtggccgcgctggtgctcccgggtcatgtagggcatgctcagccagt  420
           ||||||||||||||||||||||||||||||||||||||||||||||||||||||||||||
V.13:  361 tgcgcaccgcggcgtggccgcgctggtgctcccgggtcatgtagggcatgctcagccagt  420
V. 1:  421 aatggttctccgcctcgatctccaggcggcggatcatgttctgcttggcgcgcaacgaca  480
           ||||||||||||||||||||||||||||||||||||||||||||||||||||||||||||
V.13:  421 aatggttctccgcctcgatctccaggcggcggatcatgttctgcttggcgcgcaacgaca  480


V. 1:  481 cgaaccgcggccgccggtgcttcccgatccactgacggccgggaatgcggccgcgccaga  540
           ||||||||||||||||||||||||||||||||||||||||||||||||||||||||||||
V.13:  481 cgaaccgcggccgccggtgcttcccgatccactgacggccgggaatgcggccgcgccaga  540
V. 1:  541 ggagcgcagtcaggaacatggtgcctgccgcgctgctcaagactctgcgtctccgcggcc  600
           ||||||||||||||||||||||||||||||||||||||||||||||||||||||||||||
V.13:  541 ggagcgcagtcaggaacatggtgcctgccgcgctgctcaagactctgcgtctccgcggcc  600
V. 1:  601 gccagcagacgccgtggcgtaagcgcacccgtctcgcggggtctccgggggcctcggcga  660
           ||||||||||||||||||||||||||||||||||||||||||||||||||||||||||||
V.13:  601 gccagcagacgccgtggcgtaagcgcacccgtctcgcggggtctccgggggcctcggcga  660
V. 1:  661 gagacttcggctctcgcgagagaggactgcgcctgcgcagagccgaggacgcgtccggcg  720
           ||||||||||||||||||||||||||||||||||||||||||||||||||||||||||||
V.13:  661 gagacttcggctctcgcgagagaggactgcgcctgcgcagagccgaggacgcgtccggcg  720
```

TABLE LXVIII-continued

Nucleotide sequence alignment of 193P1E1B v.1 (SEQ ID NO: 118) and 193P1E1B v.13 (SEQ ID NO: 119)

```
V. 1:  721 ccgagattcaaactagtggcgggaggctgtgagctgagcggtggggtctgcgtacgcctg  780
           ||||||||||||||||||||||||||||||||||||||||||||||||||||||||||||
V.13:  721 ccgagattcaaactagtggcgggaggctgtgagctgagcggtggggtctgcgtacgcctg  780
V. 1:  781 gagtccttccccgctgtgctcagcatggaccctatccggagcttctgcgggaagctgcgg  840
           ||||||||||||||||||||||||||||||||||||||||||||||||||||||||||||
V.13:  781 gagtccttccccgctgtgctcagcatggaccctatccggagcttctgcgggaagctgcgg  840
V. 1:  841 tctctggccagcacgctggactgcgagacggcccggctgcagcgagcgctggacggagag  900
           ||||||||||||||||||||||||||||||||||||||||||||||||||||||||||||
V.13:  841 tctctggccagcacgctggactgcgagacggcccggctgcagcgagcgctggacggagag  900
V. 1:  901 gaaagcg                                                       907
           |||||||
V.13:  901 gaaagcg                                                       907
```

TABLE LXIX

Peptide sequences of protein coded by 193P1E1B v.13

```
                                                           (SEQ ID NO:120)
MRILYDLHSE VQTLKDDVNI LLDKARLENQ EGIDFIKATK VLMEKNSMDI MKIREYFQKY   60

GYSPRVKKNS VHEQEAINSD PELSNCENFQ KTDVKDDLSD PPVASSCISG KSPRSPQLSD  120

FGLERYIVSQ VLPNPPQAVN NYKEEPVIVT PPTKQSLVKV LKTPKCALKM DDFECVTPKL  180

EHFGISEYTM CLNEDYTMGL KNARNNKSEE AIDTESRLND NVFATPSPII QQLEKSDAEY  240

TNSPLVPTFC TPGLKIPSTK NSIALVSTNY PLSKTNSSSN DLEVEDRTSL VLNSDTCFEN  300

LTDPSSPTIS SYENLLRTPT PPEVTKIPED ILQLLSKYNS NLATPIAIKA VPPSKRFLKH  360

GQNIRDVSNK EN                                                      372
```

TABLE LXX

Amino acid sequence alignment of 193P1E1B v.1 (SEQ ID NO:121) and 193P1E1B v.13 (SEQ ID NO:122)

```
Score = 745 bits (1923), Expect = 0.0Identities = 372/372 (100%),
Positives = 372/372 (100%)
V.1:     41 MRILYDLHSEVQTLKDDVNILLDKARLENQEGIDFIKATKVLMEKNSMDIMKIREYFQKY  100
            MRILYDLHSEVQTLKDDVNILLDKARLENQEGIDFIKATKVLMEKNSMDIMKIREYFQKY
V.13:     1 MRILYDLHSEVQTLKDDVNILLDKARLENQEGIDFIKATKVLMEKNSMDIMKIREYFQKY   60

V.1:    101 GYSPRVKKNSVHEQEAINSDPELSNCENFQKTDVKDDLSDPPVASSCISGKSPRSPQLSD  160
            GYSPRVKKNSVHEQEAINSDPELSNCENFQKTDVKDDLSDPPVASSCISGKSPRSPQLSD
V.13:    61 GYSPRVKKNSVHEQEAINSDPELSNCENFQKTDVKDDLSDPPVASSCISGKSPRSPQLSD  120

V.1:    161 FGLERYIVSQVLPNPPQAVNNYKEEPVIVTPPTKQSLVKVLKTPKCALKMDDFECVTPKL  220
            FGLERYIVSQVLPNPPQAVNNYKEEPVIVTPPTKQSLVKVLKTPKCALKMDDFECVTPKL
V.13:   121 FGLERYIVSQVLPNPPQAVNNYKEEPVIVTPPTKQSLVKVLKTPKCALKMDDFECVTPKL  180

V.1:    221 EHFGISEYTMCLNEDYTMGLKNARNNKSEEAIDTESRLNDNVFATPSPIIQQLEKSDAEY  280
            EHFGISEYTMCLNEDYTMGLKNARNNKSEEAIDTESRLNDNVFATPSPIIQQLEKSDAEY
V.13:   181 EHFGISEYTMCLNEDYTMGLKNARNNKSEEAIDTESRLNDNVFATPSPIIQQLEKSDAEY  240

V.1:    281 TNSPLVPTFCTPGLKIPSTKNSIALVSTNYPLSKTNSSSNDLEVEDRTSLVLNSDTCFEN  340
            TNSPLVPTFCTPGLKIPSTKNSIALVSTNYPLSKTNSSSNDLEVEDRTSLVLNSDTCFEN
V.13:   241 TNSPLVPTFCTPGLKIPSTKNSIALVSTNYPLSKTNSSSNDLEVEDRTSLVLNSDTCFEN  300

V.1:    341 LTDPSSPTISSYENLLRTPTPPEVTKIPEDILQLLSKYNSNLATPIAIKAVPPSKRFLKH  400
            LTDPSSPTISSYENLLRTPTPPEVTKIPEDILQLLSKYNSNLATPIAIKAVPPSKRFLKH
V.13:   301 LTDPSSPTISSYENLLRTPTPPEVTKIPEDILQLLSKYNSNLATPIAIKAVPPSKRFLKH  360

V.1:    401 GQNIRDVSNKEN                                                  412
            GQNIRDVSNKEN
V.13:   361 GQNIRDVSNKEN                                                  372
```

We claim:

1. A method for detecting, in a sample, the presence of a protein, comprising:

contacting the sample with an antibody or fragment thereof that specifically binds to a protein comprising the amino acid sequence of SEQ ID NO:3, SEQ ID NO: 11 or SEQ ID NO: 13; and, detecting the formation and/or presence of a complex comprising the antibody and the protein, wherein the protein comprises an amino acid sequence, and wherein the amino acid sequence is selected from group consisting of SEQ ID NO:3, SEQ ID NO: 11, and SEQ ID NO: 13.

2. The method of claim 1, wherein the protein comprises the amino acid sequence of SEQ ID NO: 11 or SEQ ID NO: 13.

* * * * *

UNITED STATES PATENT AND TRADEMARK OFFICE
CERTIFICATE OF CORRECTION

PATENT NO. : 7,615,379 B2
APPLICATION NO. : 10/313972
DATED : November 10, 2009
INVENTOR(S) : Raitano et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 998 days.

Signed and Sealed this

Twenty-eighth Day of September, 2010

David J. Kappos
*Director of the United States Patent and Trademark Office*